(12) United States Patent
Cyr et al.

(10) Patent No.: US 11,247,989 B2
(45) Date of Patent: Feb. 15, 2022

(54) THERAPEUTIC COMPOUNDS AND USES THEREOF

(71) Applicants: GENENTECH, INC., South San Francisco, CA (US); CONSTELLATION PHARMACEUTICALS, INC., Cambridge, MA (US)

(72) Inventors: Patrick Cyr, South San Francisco, CA (US); Sarah Bronner, South San Francisco, CA (US); F. Anthony Romero, South San Francisco, CA (US); Steven Magnuson, South San Francisco, CA (US); Vickie Hsiao-Wei Tsui, South San Francisco, CA (US); Jeremy M. Murray, South San Francisco, CA (US); John Wai, Shanghai (CN); Kwong Wah Lai, Shanghai (CN); Fei Wang, Shanghai (CN); Kevin X. Chen, Shanghai (CN)

(73) Assignees: GENENTECH, INC., South San Francisco, CA (US); CONSTELLATION PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/198,581

(22) Filed: Nov. 21, 2018

(65) Prior Publication Data

US 2019/0241558 A1  Aug. 8, 2019

Related U.S. Application Data

(63) Continuation of application No. PCT/US2017/034326, filed on May 24, 2017.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................. C07D 471/04
USPC .................................. 546/119, 120; 514/303
See application file for complete search history.

(56) References Cited

U.S. PATENT DOCUMENTS

| 4,500,525 | A | 2/1985 | Winters et al. |
| 9,763,922 | B2 | 9/2017 | Adler et al. |
| 2015/0366939 | A1 | 12/2015 | Pendurthi et al. |

FOREIGN PATENT DOCUMENTS

| CN | 101812063 A | 8/2010 |
| EP | 2239264 A1 | 10/2010 |
| EP | 2993174 A1 | 3/2016 |
| WO | 2004013144 A1 | 2/2004 |
| WO | 2004014374 A1 | 2/2004 |
| WO | 2004080457 A1 | 9/2004 |
| WO | 2007068619 A1 | 6/2007 |
| WO | 2007099166 A1 | 9/2007 |
| WO | 2009138440 A1 | 11/2009 |
| WO | 2009158394 A1 | 12/2009 |
| WO | 2013037389 A1 | 3/2013 |
| WO | 2013097052 A1 | 7/2013 |
| WO | 2013148114 A1 | 10/2013 |

OTHER PUBLICATIONS

Wells et al., "The dormancy, etc.," Cancer Res.,3811-3816. (Year: 2013).*
Chambers et al, "Dissemination and Growth, etc.," Nature Reviews, vol. 2, pp. 663-672, (Year: 2002).*
Klein, "Bromodomain protein, etc.," RMD Open, 4:e000744.doi:10.1136/imopen. (Year: 2018).*
Klein et al., "Evaulating the bromdomain, etc," Scientific Reports 8:11125, 1-7. (Year: 2018).*
Zaware et al, "Bromodomain biology, etc," Nature Structural $ Molecular Biology,26, 870-879, (Year: 2019).*
White et al., "Emerging roles, etc.," Cellular Immunology 337, 48-53. (Year: 2019).*
Basheer et al., "BET bromodomain, etc.," Experimental Hematology, 43, 718-731. (Year: 2015).*

(Continued)

*Primary Examiner* — Patricia L Morris
(74) *Attorney, Agent, or Firm* — Viksnins Harris Padys Malen LLP

(57) ABSTRACT

The present invention relates to a compound formula (I):

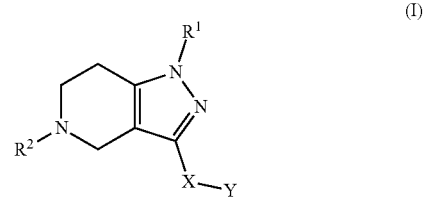

and to salts thereof, wherein $R^1$, $R^2$ X, and Y have any of the values defined herein, and compositions and uses thereof. The compounds are useful as inhibitors of CBP and/or EP300. Also included are pharmaceutical compositions comprising a compound of formula (I) or a pharmaceutically acceptable salt thereof, and methods of using such compounds and salts in the treatment of various CBP and/or EP300-mediated disorders.

8 Claims, No Drawings
Specification includes a Sequence Listing.

(56) References Cited

OTHER PUBLICATIONS

Stathis et al., "BET proteins, etc,.," Cancer Discovery, 24-36. (Year: 2018).*
Simone, Oncology: Introduction, Cecil Textbook of Medicine, ed Bennett et al. W.B. Saunders CO. 20th ed. vol. 1, pp. 1004-1010. (Year: 1996).*
Gura, Systems for Identifying New Drugs Are Often Faulty, Cancer Models, Science, vol. 278. No. 5340, pp. 1041-1042,. (Year: 1997).*
Johnson et al., Relationships between drug activity in NCI preclinical in vitro and in vivo and early clinical trials, British Journal of Cancer 64(10): 1424-1431. (Year: 2001).*
Golub et al., "Molecular Classification, etc.," Science, 286, 531-537. (Year: 1999).*
Pearce et al., "Failure modes in, etc.," Cancer Drug Design and Discovery, ed by Stephen Neidle, Chapter 18, pp. 424-435. (Year: 2008).*
Amaroju, S , et al., "Identification and development of pyrazolo[4,3-c]pyridine carboxamides as *Mycobacterium tuberculosis* pantothenate synthetase inhibitors", New Journal of Chemistry 41(1), 347-357 (2016).
Andres, M , et al., "2-(1H-Pyrazol-1-yl)acetic acids as chemoattractant receptor-homologous molecule expressed on Th2 lymphocytes (CRTh2) antagonists", European Journal of Medicinal Chemistry 71, 168-184 (2013).
Crawford, T , et al., "Discovery of a Potent and Selective in Vivo Probe (GNE-272) for the Bromodomains of CBP/EP300", Journal of Medicinal Chemistry 59(23), 10549-10563 (2016).
Filippakopoulos, Panagis , et al., "Selective inhibition of BET bromodomain", Nature, vol. 468, No. 7327, pp. 1067-1073, XP055104608, (2010).
Genin, M , et al., "Imidazopyridine and Pyrazolopiperidine Derivatives as Novel Inhibitors of Serine Palmitoyl Transferase", Journal of Medicinal Chemistry 59(12), 5904-5910 (2016).
Gustin, D , et al., "Discovery and SAR studies of a novel series of noncovalent cathepsin S inhibitors", Bioorganic & Medicinal Chemistry Letters 15(6), 1687-1691 (2005).
Hay , et al., "Discovery and optimization of small-molecule ligands for the CBP/p300 bromodomains", Journal of the American Chemical Society 136(26), 9308-9319 (2014).
Jeanmougin, F., "The bromodomain revisited", Trends Biochem Sci 22(5), 151-153 (1997).
Muller, S. , et al., "Bromodomains as therapeutic targets", Expert Rev Mol Med 13 (29), 1-21 (2011).
Patent Cooperation Treaty , International Searching Authority, Search Report for PCT/US2017/034326, 6 pages, dated Sep. 13, 2017.
Prinjha, RK , et al., "Place your BETs: the therapeutic potential of bromodomains". Trends Pharm Sci 33(3), 146-153 (2012).
Struhl, K. , "Histone acetylation and transcriptional regulatory mechanisms", Genes Dev 12 (5), 599-606 (1989).
Famkun, JW , et al., "brahma: a regulator of *Drosophila homeotic* genes structurally related to the yeast transcriptional activator SNF2/SWI2", Cell 68, 561-572 (1992).
Winters, G , et al., "Synthesis, in vitro [3H]prazosin displacement, and in vivo activity of 3-aryl-4,5,6,7-tetrahydropyrazolo[4,3-c]pyridines, a new class of antihypertensive agents", Journal of Medicinal Chemistry 28, 934-940 (1985).
CHEMCATS , RN 1349159-92-7, 1 page (Dec. 5, 2011).
CHEMCATS , RN 1350101-01-7, 1 page (Dec. 7, 2011).
CHEMCATS , RN 1367868-74-3, 1 page (Apr. 13, 2012).
CHEMCATS , RN 1789047-56-8, 1 page (Jun. 26, 2015).
CHEMCATS , RN 1790521-91-3, 1 page (Jun. 28, 2015).
CHEMCATS , RN 1790521-98-0, 1 page (Jun. 28, 2015).
CHEMCATS , RN 1790625-75-0, 1 page (Jun. 28, 2015).

* cited by examiner

SEQUENCE LISTING

```
<160> NUMBER OF SEQ ID NOS: 3

<210> SEQ ID NO 1
<211> LENGTH: 381
<212> TYPE: PRT
<213> ORGANISM: Homo sapiens

<400> SEQUENCE: 1

Glu Asn Lys Phe Ser Ala Lys Arg Leu Gln Thr Thr Arg Leu Gly Asn
1               5                   10                  15

His Leu Glu Asp Arg Val Asn Lys Phe Leu Arg Arg Gln Asn His Pro
            20                  25                  30

Glu Ala Gly Glu Val Phe Val Arg Val Val Ala Ser Ser Asp Lys Thr
        35                  40                  45

Val Glu Val Lys Pro Gly Met Lys Ser Arg Phe Val Asp Ser Gly Glu
    50                  55                  60

Met Ser Glu Ser Phe Pro Tyr Arg Thr Lys Ala Leu Phe Ala Phe Glu
65                  70                  75                  80

Glu Ile Asp Gly Val Asp Val Cys Phe Phe Gly Met His Val Gln Glu
                85                  90                  95

Tyr Gly Ser Asp Cys Pro Pro Asn Thr Arg Arg Val Tyr Ile Ser
            100                 105                 110

Tyr Leu Asp Ser Ile His Phe Phe Arg Pro Arg Cys Leu Arg Thr Ala
        115                 120                 125

Val Tyr His Glu Ile Leu Ile Gly Tyr Leu Glu Tyr Val Lys Lys Leu
    130                 135                 140

Gly Tyr Val Thr Gly His Ile Trp Ala Cys Pro Pro Ser Glu Gly Asp
145                 150                 155                 160

Asp Tyr Ile Phe His Cys His Pro Pro Asp Gln Lys Ile Pro Lys Pro
                165                 170                 175
```

Lys Arg Leu Gln Glu Trp Tyr Lys Met Leu Asp Lys Ala Phe Ala
            180                 185                 190

Glu Arg Ile Ile His Asp Tyr Lys Asp Ile Phe Lys Gln Ala Thr Glu
            195                 200                 205

Asp Arg Leu Thr Ser Ala Lys Glu Leu Pro Tyr Phe Glu Gly Asp Phe
        210                 215                 220

Trp Pro Asn Val Leu Glu Ser Ile Lys Glu Leu Glu Gln Glu Glu
225                 230                 235                 240

Glu Glu Arg Lys Lys Glu Ser Thr Ala Ala Ser Glu Thr Thr Glu
                245                 250                 255

Gly Ser Gln Gly Asp Ser Lys Asn Ala Lys Lys Asn Asn Lys Lys
            260                 265                 270

Thr Asn Lys Asn Lys Ser Ser Ile Ser Arg Ala Asn Lys Lys Pro
            275                 280                 285

Ser Met Pro Asn Val Ser Asn Asp Leu Ser Gln Lys Leu Tyr Ala Thr
            290                 295                 300

Met Glu Lys His Lys Glu Val Phe Phe Val Ile His Leu His Ala Gly
305                 310                 315                 320

Pro Val Ile Asn Thr Leu Pro Pro Ile Val Asp Pro Asp Pro Leu Leu
                325                 330                 335

Ser Cys Asp Leu Met Asp Gly Arg Asp Ala Phe Leu Thr Leu Ala Arg
            340                 345                 350

Asp Lys His Trp Glu Phe Ser Ser Leu Arg Arg Ser Lys Trp Ser Thr
            355                 360                 365

Leu Cys Met Leu Val Glu Leu His Thr Gln Gly Gln Asp
            370                 375                 380

<210> SEQ ID NO 2
<211> LENGTH: 380
<212> TYPE: PRT
<213> ORGANISM: Homo sapiens

<400> SEQUENCE: 2

Glu Asn Lys Phe Ser Ala Lys Arg Leu Pro Ser Thr Arg Leu Gly Thr
1               5                   10                  15

Phe Leu Glu Asn Arg Val Asn Asp Phe Leu Arg Arg Gln Asn His Pro
            20                  25                  30

Glu Ser Gly Glu Val Thr Val Arg Val Val His Ala Ser Asp Lys Thr
        35                  40                  45

Val Glu Val Lys Pro Gly Met Lys Ala Arg Phe Val Asp Ser Gly Glu
    50                  55                  60

Met Ala Glu Ser Phe Pro Tyr Arg Thr Lys Ala Leu Phe Ala Phe Glu
65                  70                  75                  80

Glu Ile Asp Gly Val Asp Leu Cys Phe Phe Gly Met His Val Gln Glu
                85                  90                  95

Tyr Gly Ser Asp Cys Pro Pro Asn Gln Arg Arg Val Tyr Ile Ser
            100                 105                 110

Tyr Leu Asp Ser Val His Phe Phe Arg Pro Lys Cys Leu Arg Thr Ala
            115                 120                 125

Val Tyr His Glu Ile Leu Ile Gly Tyr Leu Glu Tyr Val Lys Lys Leu
        130                 135                 140

Gly Tyr Thr Thr Gly His Ile Trp Ala Cys Pro Pro Ser Glu Gly Asp
145                 150                 155                 160

Asp Tyr Ile Phe His Cys His Pro Pro Asp Gln Lys Ile Pro Lys Pro
            165                 170                 175

Lys Arg Leu Gln Glu Trp Tyr Lys Lys Met Leu Asp Lys Ala Val Ser
            180                 185                 190

Glu Arg Ile Val His Asp Tyr Lys Asp Ile Phe Lys Gln Ala Thr Glu
            195                 200                 205

Asp Arg Leu Thr Ser Ala Lys Glu Leu Pro Tyr Phe Glu Gly Asp Phe
            210                 215                 220

Trp Pro Asn Val Leu Glu Glu Ser Ile Lys Glu Leu Glu Gln Glu Glu
225                 230                 235                 240

Glu Glu Arg Lys Arg Glu Glu Asn Thr Ser Asn Glu Ser Thr Asp Val
            245                 250                 255

Thr Lys Gly Asp Ser Lys Asn Ala Lys Lys Lys Asn Asn Lys Lys Thr
            260                 265                 270

Ser Lys Asn Lys Ser Ser Leu Ser Arg Gly Asn Lys Lys Pro Gly
            275                 280                 285

Met Pro Asn Val Ser Asn Asp Leu Ser Gln Lys Leu Tyr Ala Thr Met
            290                 295                 300

Glu Lys His Lys Glu Val Phe Phe Val Ile Arg Leu Ile Ala Gly Pro
305                 310                 315                 320

Ala Ala Asn Ser Leu Pro Pro Ile Val Asp Pro Asp Pro Leu Ile Pro
            325                 330                 335

Cys Asp Leu Met Asp Gly Arg Asp Ala Phe Leu Thr Leu Ala Arg Asp
            340                 345                 350

Lys His Leu Glu Phe Ser Ser Leu Arg Arg Ala Gln Trp Ser Thr Met
            355                 360                 365

Cys Met Leu Val Glu Leu His Thr Gln Ser Gln Asp
            370                 375                 380

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

THERAPEUTIC COMPOUNDS AND USES THEREOF

PRIORITY OF INVENTION

This application is a continuation of International Application No. PCT/US2017/034326, filed 24 May 2017, which claims priority to International Patent Application PCT/CN2016/083118, filed 24 May 2016. The entire content of the applications referenced above are hereby incorporated by reference.

SEQUENCE LISTING

The instant application contains a Sequence Listing which has been filed electronically in ASCII format and is hereby incorporated by reference in its entirety. Said ASCII copy, created on Feb. 27, 2019, is named 01076_032US1_SL.txt and is 7,162 bytes in size.

TECHNICAL FIELD OF THE INVENTION

The present invention relates to compounds useful as inhibitors of CBP/EP300 and methods of treating cancer using such inhibitors.

BACKGROUND OF THE INVENTION

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification. These modifications include acetylation, methylation, phosphorylation, ubiquitinylation, and SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Of all classes of proteins, histones are amongst the most susceptible to post-translational modification. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl K., *Genes Dev.*, 1989, 12, 5, 599-606).

Bromodomains, which are approximately 110 amino acids long, are found in a large number of chromatin-associated proteins and have been identified in approximately 70 human proteins, often adjacent to other protein motifs (Jeanmougin F., et al., *Trends Biochem. Sci.*, 1997, 22, 5, 151-153; and Tamkun J. W., et al., *Cell*, 1992, 7, 3, 561-572). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al., *Trends Pharm. Sci.*, 33(3):146-153 (2012) and Muller et al., *Expert Rev.*, 13(29): 1-20 (September 2011).

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. This is highlighted by the observation that mutations in bromodomain-containing proteins are linked to cancer, as well as immune and neurologic dysfunction. Hence, the selective inhibition of bromodomains across a specific family, such as the selective inhibition of a bromodomain of CBP/EP300, creates varied opportunities as novel therapeutic agents in human dysfunction.

There is a need for treatments for cancer, immunological disorders, and other CBP/EP300 bromodomain related diseases.

SUMMARY OF THE INVENTION

Compounds of Formula (I)

One aspect is a compound of formula (I):

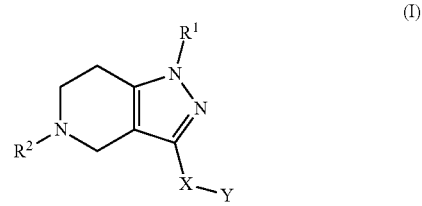

or a salt thereof, wherein:

$R^1$ is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^1$ is optionally substituted with one or more groups $R^d$;

$R^2$ is —C(O)—N($R^e$)$_2$, —S(O)—N($R^e$)$_2$, —S(O)$_2$—N($R^e$)$_2$, —C(O)—$R^e$, —C(O)—O—$R^e$, —S(O)—$R^e$, or —S(O)$_2$—$R^e$,

X is absent, —C(=O)—, or $C_{1-3}$alkyl; and Y is phenyl, a 9-membered bicyclic carbocycle, a 10-membered bicyclic carbocycle, a 9-membered bicyclic heterocycle, or a 10-membered bicyclic heterocycle, wherein Y is optionally substituted with $R^a$ and wherein Y is further optionally substituted with one or more groups $R^b$;

or wherein —X—Y taken together is selected from the group consisting of:
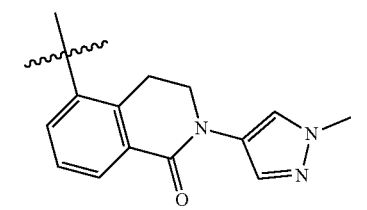
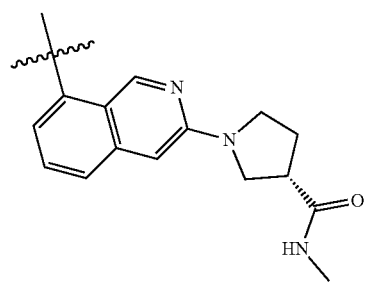
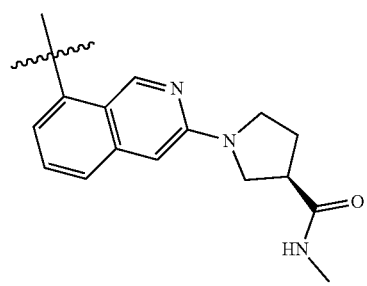
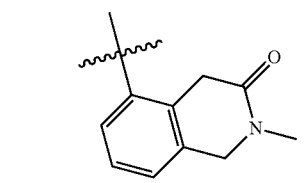
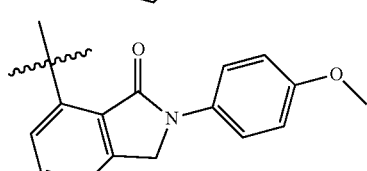
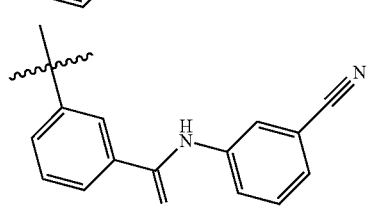
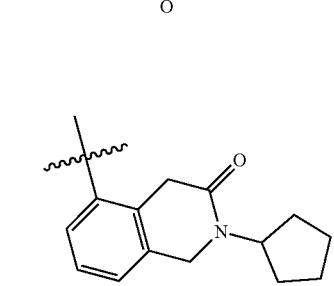
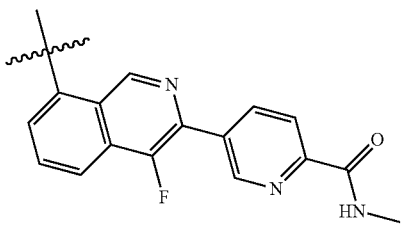
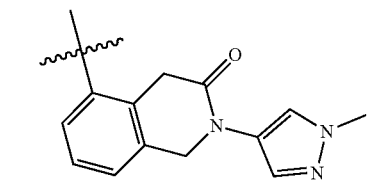
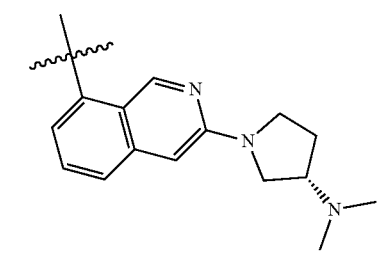
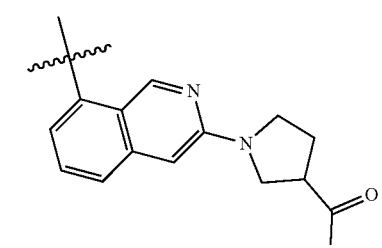
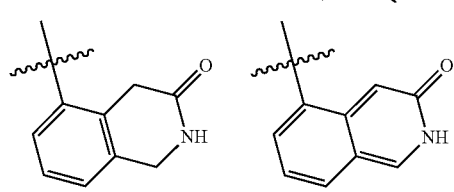
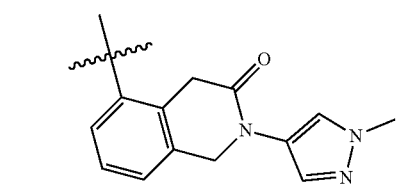
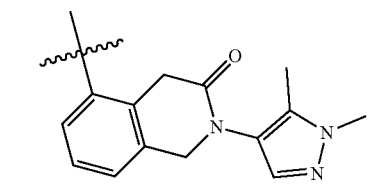
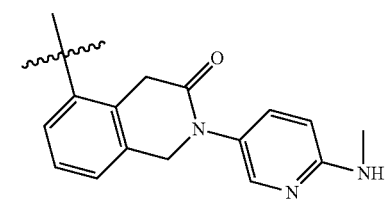

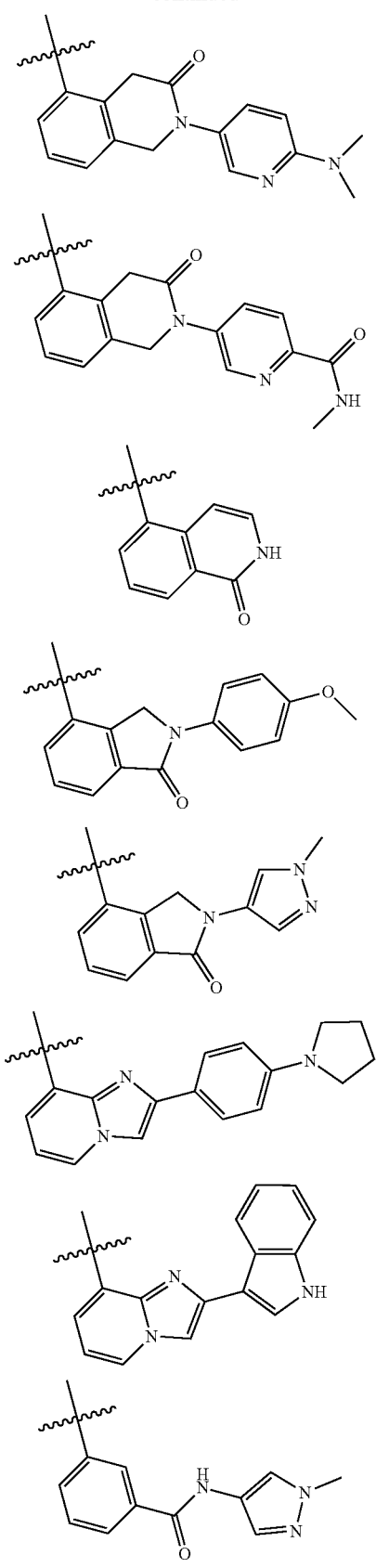
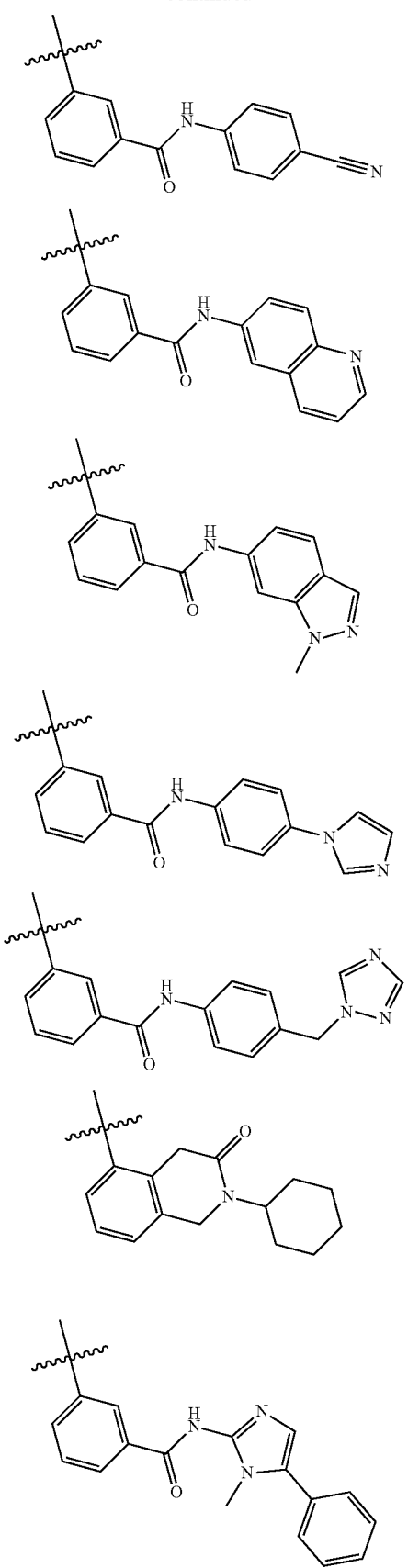

-continued

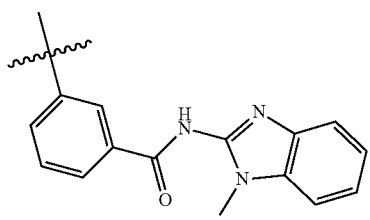
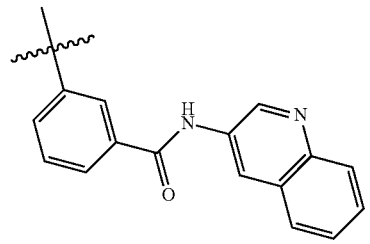
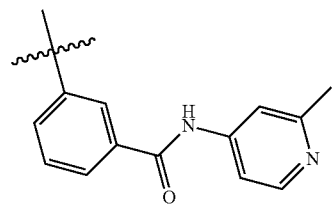
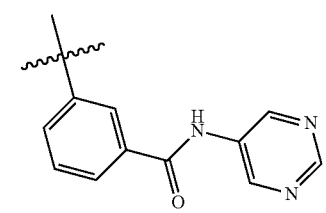
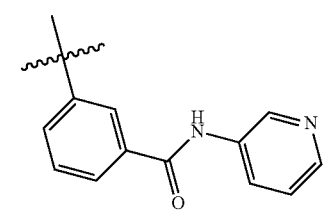
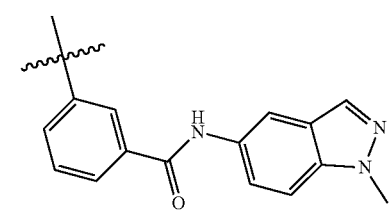
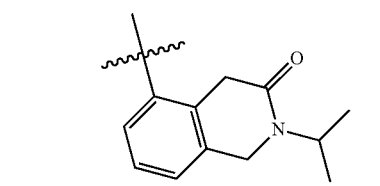
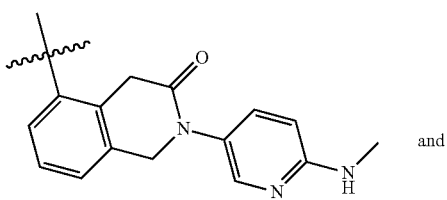

and

-continued

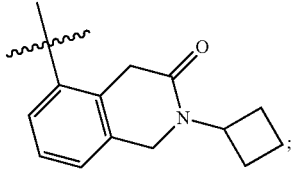
;

each $R^a$ is independently selected from the group consisting of a 5-membered carbocycle, a 6-membered carbocycle, a 5-membered heterocycle, and a 6-membered heterocycle, which a 5-membered carbocycle, 6-membered carbocycle, 5-membered heterocycle, and 6-membered heterocycle are optionally substituted with one or more groups $R^c$;

each $R^b$ is independently selected from the group consisting of a 5-membered amino, $C_{1-4}$alkyl, $C_{2-4}$alkenyl, $C_{2-4}$alkynyl, $C_{2-6}$cycloalkyl, $(C_{2-6}$cycloalkyl) $C_{1-4}$alkyl, $C_{1-4}$alkoxy, $C_{1-4}$alkoxycarbonyl, $C_{1-4}$alkanoyl, —C(O)—N$(R^f)_2$, —N($R^f$)C(O)—$R^f$, and $C_{1-4}$alkanoyloxy, wherein each $C_{1-4}$alkyl, $C_{2-4}$alkenyl, $C_{2-4}$alkynyl, $C_{2-6}$cycloalkyl, $(C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo;

each $R^c$ is independently selected from the group consisting of halo, cyano, hydroxy, amino, $C_{1-4}$alkyl, $C_{2-4}$alkenyl, $C_{2-4}$alkynyl, $C_{2-6}$cycloalkyl, $(C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, wherein each $C_{1-4}$alkyl, $C_{2-4}$alkenyl, $C_{2-4}$alkynyl, $C_{2-6}$cycloalkyl, $(C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo;

each $R^d$ is independently selected from the group consisting of oxo, halo, cyano, hydroxy, amino, $C_{1-4}$alkyl, $C_{2-4}$alkenyl, $C_{2-4}$alkynyl, $C_{2-6}$cycloalkyl, $(C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, wherein each $C_{1-4}$alkyl, $C_{2-4}$alkenyl, $C_{2-4}$alkynyl, $C_{2-6}$cycloalkyl, $(C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo;

each $R^e$ is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo; and each $R^f$ is independently selected from hydrogen and $C_{1-4}$alkyl;

or a compound selected from the group consisting of:

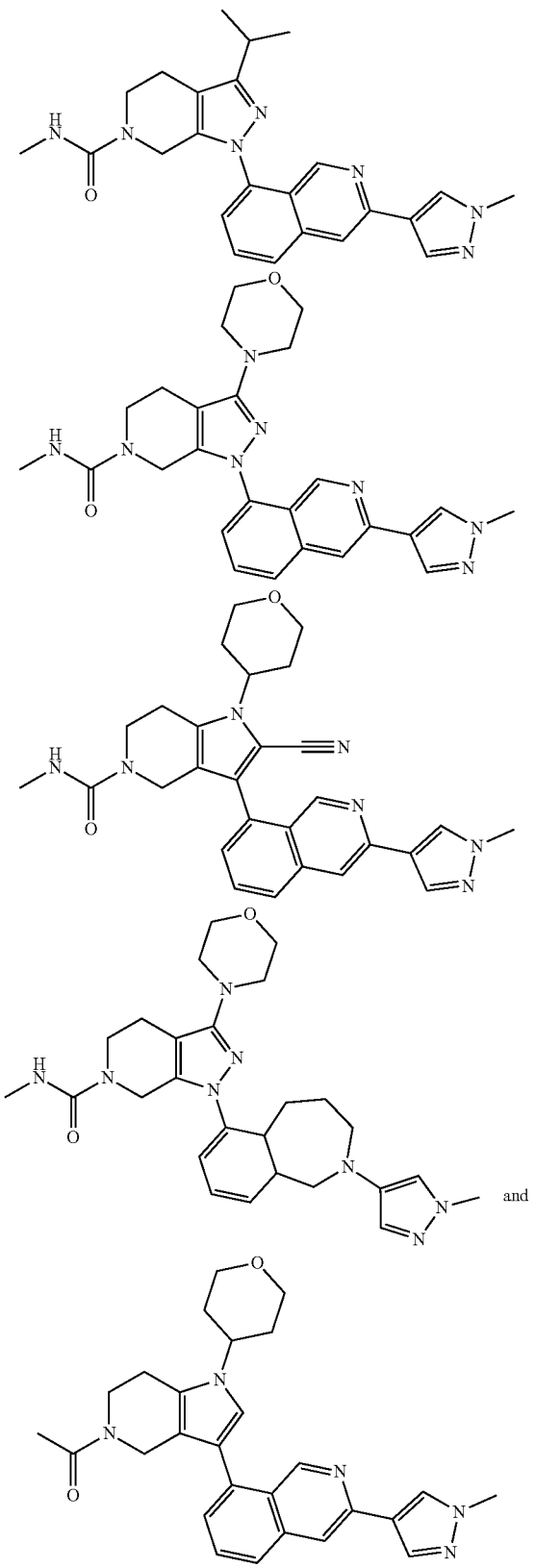

and or a salt thereof.

Another aspect is a compound of formula (I):

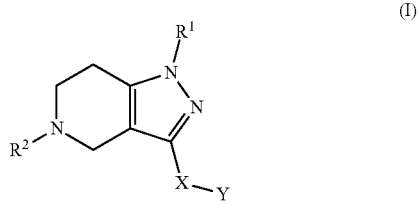

or a salt thereof, wherein:

$R^1$ is $C_{1-12}$alkyl, $C_{2-12}$alkenyl, $C_{2-12}$alkynyl, 3-12 membered carbocycle, and 3-12 membered heterocycle, wherein each $C_{1-12}$alkyl, $C_{2-12}$alkenyl, $C_{2-12}$alkynyl, 3-12 membered carbocycle, and 3-12 membered heterocycle of $R^1$ is optionally substituted with one or more groups $R^d$;

$R^2$ is —C(O)—N($R^e$)$_2$, —S(O)—N($R^e$)$_2$, —S(O)$_2$—N($R^e$)$_2$, —C(O)—$R^e$, —C(O)—O—$R^e$, —S(O)—$R^e$, or —S(O)$_2$—$R^e$,

X is absent, —C(=O)—, or $C_{1-3}$alkyl;

Y is phenyl, a 9-membered bicyclic carbocycle, a 10-membered bicyclic carbocycle, a 9-membered bicyclic heterocycle, or a 10-membered bicyclic heterocycle, wherein Y is optionally substituted with $R^a$ and wherein Y is further optionally substituted with one or more groups $R^b$;

each $R^a$ is independently selected from the group consisting of a 5-membered carbocycle, a 6-membered carbocycle, a 5-membered heterocycle, and a 6-membered heterocycle, which a 5-membered carbocycle, 6-membered carbocycle, 5-membered heterocycle, and 6-membered heterocycle are optionally substituted with one or more groups $R^c$;

each $R^b$ is independently selected from the group consisting of halo, cyano, hydroxy, amino, $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, —C(O)—N($R^f$)$_2$, —N($R^f$)C(O)—$R^f$, and $C_{1-4}$alkanoyloxy, wherein each $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo;

each $R^c$ is independently selected from the group consisting of halo, cyano, hydroxy, amino, $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, wherein each $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo;

each $R^d$ is independently selected from the group consisting of oxo, halo, cyano, hydroxy, amino, $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, wherein each $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo;

each $R^e$ is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo; and each $R^f$ is independently selected from hydrogen and $C_{1-4}$alkyl.

Another aspect includes a composition comprising a compound of formula (I) or a pharmaceutically acceptable salt thereof, and a pharmaceutically acceptable adjuvant, carrier, or vehicle.

Another aspect includes a method for treating a CBP and/or EP300-mediated disorder in an animal comprising administering a compound of formula (I) or a pharmaceutically acceptable salt thereof to the animal.

Another aspect includes a method for treating a CBP and/or EP300-mediated disorder in an animal, wherein the disorder is cancer, comprising administering a compound of formula (I) or a pharmaceutically acceptable salt thereof to the animal.

Another aspect includes a method for treating a CBP and/or EP300-mediated disorder in an animal, wherein the disorder is a fibrotic disease, comprising administering a compound of formula (I) or a pharmaceutically acceptable salt thereof to the animal.

Another aspect includes a method for treating a CBP and/or EP300-mediated disorder in an animal, wherein the disorder is a fibrotic lung disease, comprising administering a compound of formula (I) or a pharmaceutically acceptable salt thereof to the animal.

Another aspect includes a compound of formula (I) or a pharmaceutically acceptable salt thereof for use in medical therapy.

Another aspect includes a compound of formula (I) or a pharmaceutically acceptable salt thereof for the prophylactic or therapeutic treatment of a CBP and/or EP300-mediated disorder.

Another aspect includes the use of a compound of formula (I) or a pharmaceutically acceptable salt thereof to prepare a medicament for treating a CBP and/or EP300-mediated disorder in an animal (e.g. a mammal such as a human).

Another aspect includes compounds for the study of CBP and/or EP300.

Another aspect includes synthetic intermediates and synthetic processes disclosed herein that are useful for preparing a compound of formula (I) or a salt thereof.

DETAILED DESCRIPTION

Compounds and Definitions

Definitions and terms are described in more detail below. Chemical elements are identified in accordance with the Periodic Table of the Elements, CAS version, *Handbook of Chemistry and Physics*, 75th Ed.

Unless otherwise stated, compounds of formula (I) include enantiomeric, diastereomeric and geometric (or conformational) isomeric forms of a given structure. For example, the R and S configurations for each asymmetric center, Z and E double bond isomers, Z and E conformational isomers, single stereochemical isomers, as well as enantiomeric, diastereomeric, and geometric (or conformational) mixtures are included. Unless otherwise stated, all tautomeric forms of structures depicted herein are included.

Additionally, unless otherwise stated, structures depicted herein are also meant to include compounds that differ only in the presence of one or more isotopically enriched atoms. For example, compounds of formula (I), wherein the independent replacement or enrichment of one or more hydrogen by deuterium or tritium, carbon by $^{13}$C- or $^{14}$C carbon, nitrogen by a $^{15}$N nitrogen, sulfur by a $^{33}$S, $^{34}$S or $^{36}$S sulfur, oxygen by a $^{17}$O or $^{18}$O oxygen, or fluorine by a $^{18}$F are included. Such compounds are useful, for example, as analytical tools, as probes in biological assays, or as therapeutic agents.

Where a particular enantiomer is described, it may, in certain embodiments be provided substantially free of the corresponding enantiomer, and may also be referred to as "optically enriched." "Optically-enriched," as used herein, means that the mixture of enantiomers is made up of a significantly greater proportion of one enantiomer, and may be described by enantiomeric excess (ee %). In certain embodiments, the mixture of enantiomers is made up of at least about 90% by weight of a given enantiomer (about 90% ee). In other embodiments, the mixture of enantiomers is made up of at least about 95%, 98% or 99% by weight of a given enantiomer (about 95%, 98% or 99% ee). Enantiomers and diastereomers may be isolated from racemic mixtures by any method known to those skilled in the art, including recrystallization from solvents in which one stereoisomer is more soluble than the other, chiral high pressure liquid chromatography (HPLC), supercritical fluid chromatography (SFC), the formation and crystallization of chiral salts, which are then separated by any of the above methods, or prepared by asymmetric syntheses and optionally further enriched. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

The term "heteroatom" means any atom independently selected from an atom other than carbon or hydrogen, for example, one or more of oxygen, sulfur, nitrogen, phosphorus or silicon (including any oxidized form of nitrogen, sulfur, phosphorus or silicon; and the quaternized form of any nitrogen).

The terms "halo" and "halogen" as used herein refer to an atom selected from fluorine (fluoro, —F), chlorine (chloro, —Cl), bromine (bromo, —Br) and iodine (iodo, —I).

The term "oxo" refers to =O.

The term "amino" includes —NH$_2$, —NH(C$_1$-C$_3$alkyl), and —N(C$_1$-C$_3$alkyl)$_2$.

The term "unsaturated", as used herein, means that a moiety has one or more units of unsaturation.

The term "carbocyclyl" used alone or as part of a larger moiety, refers to a saturated, partially unsaturated, or aromatic ring system having 3 to 20 carbon atoms. In one embodiment, carbocyclyl includes 3 to 12 carbon atoms (C$_3$-C$_{12}$). In another embodiment, carbocyclyl includes C$_3$-C$_8$, C$_3$-C$_{10}$ or C$_5$-C$_{10}$. In other embodiment, carbocyclyl, as a monocycle, includes C$_3$-C$_8$, C$_3$-C$_6$ or C$_5$-C$_6$. In another embodiment, carbocyclyl, as a bicycle, includes C$_7$-C$_{12}$. In another embodiment, carbocyclyl, as a spiro system, includes C$_5$-C$_{12}$. Examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, for example bicyclo[2.2.1]heptane, bicyclo[2.2.2]octane, naphthalene, and bicyclo[3.2.2]nonane; and spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g. saturated or partially unsaturated mono-, bi-, or spiro-carbocycles).

The term "alkyl," as used herein, refers to a saturated linear or branched-chain hydrocarbon radical. In one embodiment, the alkyl radical is one to eighteen carbon atoms ($C_1$-$C_{18}$). In other embodiments, the alkyl radical is $C_0$-$C_6$, $C_0$-$C_5$, $C_0$-$C_3$, $C_1$-$C_{12}$, $C_1$-$C_{10}$, $C_1$-$C_8$, $C_1$-$C_6$, $C_1$-$C_5$, $C_1$-$C_4$ or $C_1$-$C_3$. $C_0$ alkyl refers to a bond. Examples of alkyl groups include methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), heptyl, octyl, nonyl, decyl, undecyl and dodecyl.

The term "alkenyl," as used herein, denotes a linear or branched-chain hydrocarbon radical with at least one carbon-carbon double bond. An alkenyl includes radicals having "cis" and "trans" orientations, or alternatively, "E" and "Z" orientations. In one example, the alkenyl radical is two to eighteen carbon atoms ($C_2$-$C_{18}$). In other examples, the alkenyl radical is $C_2$-$C_{12}$, $C_2$-$C_{10}$, $C_2$-$C_8$, $C_2$-$C_6$ or $C_2$-$C_3$. Examples include, but are not limited to, ethenyl or vinyl (—CH=$CH_2$), prop-1-enyl (—CH=$CHCH_3$), prop-2-enyl (—$CH_2$CH=$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl and hexa-1,3-dienyl.

The term "alkynyl," as used herein, refers to a linear or branched hydrocarbon radical with at least one carbon-carbon triple bond. In one example, the alkynyl radical is two to eighteen carbon atoms ($C_2$-$C_{18}$). In other examples, the alkynyl radical is $C_2$-$C_{12}$, $C_2$-$C_{10}$, $C_2$-$C_8$, $C_2$-$C_6$ or $C_2$-$C_3$. Examples include, but are not limited to, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

The term "alkoxy" refers to a linear or branched radical represented by the formula —OR in which R is alkyl, alkenyl, alkynyl or carbocycyl. Alkoxy groups include methoxy, ethoxy, propoxy, isopropoxy, and cyclopropoxy.

The term "haloalkyl," as used herein, refers to an alkyl as defined herein that is substituted with one or more (e.g. 1, 2, 3, or 4) halo groups.

The term "aryl" used alone or as part of a larger moiety as in "arylalkyl", "arylalkoxy", or "aryloxyalkyl", refers to a monocyclic, bicyclic or tricyclic, carbon ring system, that includes fused rings, wherein at least one ring in the system is aromatic. The term "aryl" may be used interchangeably with the term "aryl ring". In one embodiment, aryl includes groups having 6-20 carbon atoms ($C_6$-$C_{20}$ aryl). In another embodiment, aryl includes groups having 6-10 carbon atoms ($C_6$-$C_{10}$ aryl). Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, and the like, which may be substituted or independently substituted by one or more substituents described herein. A particular aryl is phenyl. In another embodiment aryl includes an aryl ring fused to one or more carbocyclic rings, such as indanyl, dihydrophenanthryl, or tetrahydronaphthyl, and the like, where the radical or point of attachment is on an aromatic ring.

The term "heteroaryl" used alone or as part of a larger moiety, e.g., "heteroarylalkyl", or "heteroarylalkoxy", refers to a monocyclic, bicyclic or tricyclic ring system having 5 to 14 ring atoms, wherein at least one ring is aromatic and contains at least one heteroatom. In one embodiment, heteroaryl includes 4-6 membered monocyclic aromatic groups where one or more ring atoms is nitrogen, sulfur or oxygen that is independently optionally substituted. In another embodiment, heteroaryl includes 5-6 membered monocyclic aromatic groups where one or more ring atoms is nitrogen, sulfur or oxygen that is independently optionally substituted. In some embodiments, the heteroaryl group is a $C_1$-$C_{20}$ heteroaryl group, where the heteroaryl ring contains 1-20 carbon atoms and the remaining ring atoms include one or more nitrogen, sulfur, or oxygen atoms. Example heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, triazinyl, tetrazinyl, tetrazolo[1,5-b]pyridazinyl, imidazol[1,2-a]pyrimidinyl, purinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, pyrid-2-yl N-oxide, and pyrazolo[4,3-c]pyridinyl. The terms "heteroaryl" also includes groups in which a heteroaryl is fused to one or more aryl, carbocyclyl, or heterocyclyl rings, where the radical or point of attachment is on the heteroaryl ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi- or tri-cyclic.

As used herein, the term "heterocyclyl" or "heterocycle" refers to a "carbocyclyl" as defined herein, wherein one or more (e.g. 1, 2, 3, or 4) carbon atoms have been replaced with a heteroatom (e.g. O, N, or S). In some embodiments, a heterocyclyl or heterocycle refers to a saturated ring system, such as a 3 to 12 membered saturated heterocyclyl ring system. In some embodiments, a heterocyclyl or heterocycle refers to a heteroaryl ring system, such as a 5 to 14 membered heteroaryl ring system. A heterocyclyl or heterocycle can optionally be substituted with one or more substituents independently selected from those defined herein.

In one example, heterocyclyl or heterocycle includes 3-12 ring atoms and includes monocycles, bicycles, tricycles and spiro ring systems, wherein the ring atoms are carbon, and one to five ring atoms is a heteroatom selected from nitrogen, sulfur or oxygen, which is independently optionally substituted by one or more groups. In one example, heterocyclyl or heterocycle includes 1 to 4 heteroatoms. In another example, heterocyclyl or heterocycle includes 3- to 7-membered monocycles having one or more heteroatoms selected from nitrogen, sulfur or oxygen. In another example, heterocyclyl or heterocycle includes 4- to 6-membered monocycles having one or more heteroatoms selected from nitrogen, sulfur or oxygen. In another example, heterocyclyl or heterocycle includes 3-membered monocycles. In another example, heterocyclyl or heterocycle includes 4-membered monocycles. In another example, heterocyclyl or heterocycle includes 5-6 membered monocycles. In one example, the heterocyclyl or heterocycle group includes 0 to 3 double bonds. Any nitrogen or sulfur heteroatom may optionally be oxidized (e.g. NO, SO, $SO_2$), and any nitrogen heteroatom may optionally be quaternized (e.g. $[NR_4]^+Cl^-$, $[NR_4]^+OH^-$). Example heterocyclyls or heterocycles include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydrofuranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls or heterocycles containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls or heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Example benzo-fused 5-membered heterocyclyls or heterocycles are benzoxazol-2-yl, benzthiazol-2-yl and benzimidazol-2-yl. Example 6-membered heterocyclyls or heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are other example heterocyclyl groups.

The term "heterocyclyl" or "heterocycle" also includes groups in which a heterocyclyl is fused to one or more aryl, carbocyclyl, or heterocyclyl rings, where the radical or point of attachment is on the heterocyclyl ring. Nonlimiting examples include tetrahydroquinolinyl and tetrahydroisoquinolinyl.

As used herein, the term "partially unsaturated" refers to a ring moiety that includes at least one double or triple bond between ring atoms but the ring moiety is not aromatic.

As used herein, the term "inhibitor" refers to a compound that binds to and inhibits the bromodomain of CBP and/or EP300 with measurable affinity and activity. In certain embodiments, an inhibitor has an $IC_{50}$ or binding constant of less about 20 μM, less than about 1 μM, less than about 500 nM, less than about 100 nM, or less than about 10 nM.

The terms "measurable affinity" and "measurably inhibit," as used herein, refer to a measurable reduction in activity (e.g., reduction in recognition of lysine acetyl recognition of chromatin) of the bromodomain of CBP and/or EP300 between: (i) a sample comprising a compound of formula (I) or composition thereof and such bromodomain, and (ii) an equivalent sample comprising such bromodomain, in the absence of said compound, or composition thereof.

"Pharmaceutically acceptable salts" include both acid and base addition salts. It is to be understood that when a compound or Example herein is shown as a specific salt, the corresponding free-base, as well as other salts of the corresponding free-base (including pharmaceutically acceptable salts of the corresponding free-base) are contemplated.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids may be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, benzenesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly base addition salts are the ammonium, potassium, sodium, calcium and magnesium salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, tromethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particular organic non-toxic bases are isopropylamine, diethylamine, ethanolamine, tromethamine, dicyclohexylamine, choline, and caffeine.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A "solvate" refers to an association or complex of one or more solvent molecules and a compound of the present invention. Examples of solvents include water, isopropanol, ethanol, methanol, DMSO, ethyl acetate, acetic acid and ethanolamine. The term "hydrate" refers to the complex where the solvent molecule is water.

"Therapeutically effective amount" refers to an amount of a compound of the present invention that (i) treats the particular disease, condition or disorder, (ii) attenuates, ameliorates or eliminates one or more symptoms of the particular disease, condition, or disorder, or (iii) delays the onset of one or more symptoms of the particular disease, condition or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. For cancer therapy, efficacy can, for example, be measured by assessing the time to disease progression (TTP) and/or determining the response rate (RR). In the case of immunological disorders, the therapeutic effective amount is an amount sufficient to decrease or alleviate an allergic disorder, the symptoms of an autoimmune and/or inflammatory disease, or the symptoms of an acute inflammatory reaction (e.g. asthma).

"Treatment" (and variations such as "treat" or "treating") refers to clinical intervention in an attempt to alter the natural course of the individual or cell being treated, and can be performed either for prophylaxis or during the course of clinical pathology. Desirable effects of treatment include one or more of preventing recurrence of disease, alleviation of symptoms, diminishment of any direct or indirect pathological consequences of the disease, stabilized (i.e., not worsening) state of disease, preventing metastasis, decreasing the rate of disease progression, amelioration or palliation of the disease state, prolonging survival as compared to expected survival if not receiving treatment and remission or improved prognosis. In certain embodiments, a compound of formula (I) is used to delay development of a disease or disorder or to slow the progression of a disease or disorder. Those individuals in need of treatment include those already with the condition or disorder as well as those prone to have the condition or disorder, (for example, through a genetic mutation or abberent expression of a gene or protein).

"CBP/EP300 bromodomain inhibitor" or "CBP and/or EP300 bromodomain inhibitor" refers to a compound that binds to the CBP bromodomain and/or EP300 bromodomain and inhibits and/or reduces a biological activity of CBP and/or EP300. In some embodiments, CBP/EP300 bromodomain inhibitor binds to the CBP and/or EP300 primarily (e.g., solely) through contacts and/or interactions with the CBP bromodomain and/or EP300 bromodomain. In some embodiments, CBP/EP300 bromodomain inhibitor binds to the CBP and/or EP300 through contacts and/or interactions with the CBP bromodomain and/or EP300 bromodomain as well as additional CBP and/or EP300 residues and/or domains. In some embodiments, CBP/EP300 bromodomain inhibitor substantially or completely inhibits the biological activity of the CBP and/or EP300. In some embodiments, the biological activity is binding of the bromodomain of CBP and/or EP300 to chromatin (e.g., histones associated with DNA) and/or another acetylated protein. In certain embodiments, the CBP/EP300 bromodomain inhibitor blocks CBP/EP300 activity so as to restore a functional response by T-cells (e.g., proliferation, cytokine production, target cell killing) from a dysfunctional state to antigen stimulation. In some embodiments, the CBP/EP300 bromodomain inhibitor binds to and inhibits CBP bromodomain. In some embodiments, the CBP/EP300 bromodomain inhibitor binds to and inhibits EP300 bromodomain.

As used herein, "a" or "an" means one or more, unless clearly indicated otherwise. As used herein, "another" means at least a second or more.

Exemplary Values for Compounds of Formula (I)

In certain embodiments the compound is a compound of formula (Id):

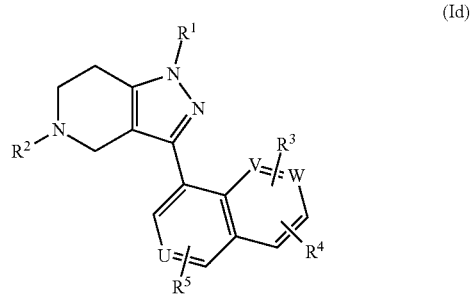

(Id)

or a salt thereof, wherein:
U is CH or N; V is CH; and W is CH or N; or
U is CH or N; V is N; and W is CH; and
one of $R^3$, $R^4$, and $R^5$ is selected from the group consisting of hydrogen and $R^a$ and the remainder of $R^3$, $R^4$, and $R^5$ $R^b$ are independently selected from the group consisting of hydrogen, halo, cyano, hydroxy, amino, $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, wherein each $C_{1-4}$alkyl, $C_{2-4}$alkenyl, $C_{2-4}$alkynyl, $C_{2-6}$cycloalkyl, ($C_{2-6}$cycloalkyl) $C_{1-4}$alkyl, $C_{1-4}$alkoxy, $C_{1-4}$alkoxycarbonyl, $C_{1-4}$alkanoyl, and $C_{1-4}$alkanoyloxy, is optionally substituted with one or more groups independently selected from oxo, halo, amino, hydroxy, $C_{1-3}$alkoxy, and $C_1$-$C_3$ alkyl that is optionally substituted with one or more groups independently selected from halo.

In certain embodiments the compound is a compound of formula (Ia):

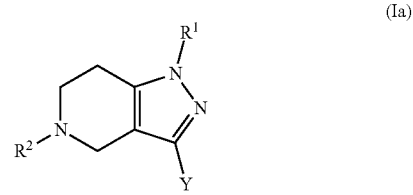

(Ia)

or a salt thereof.

In certain embodiments the compound is a compound of formula (Ib):

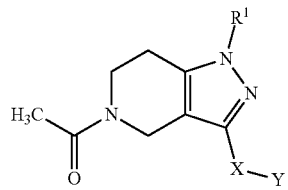
(Ib)

or a salt thereof.

In certain embodiments the compound is a compound of formula (Ic):

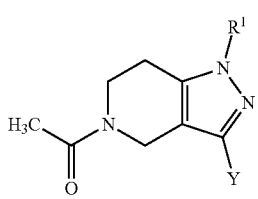
(Ic)

or a salt thereof.

In certain embodiments $R^1$ is $C_{1-12}$alkyl or 3-12 membered heterocycle, wherein each $C_{1-12}$alkyl and 3-12 membered heterocycle of $R^1$ is optionally substituted with one or more groups $R^d$.

In certain embodiments $R^1$ is $C_{1-3}$alkyl or 3-6 membered heterocycle, wherein each $C_{1-3}$alkyl or 3-6 membered heterocycle of $R^1$ is optionally substituted with one or more groups $R^d$.

In certain embodiments $R^1$ is $C_{1-3}$alkyl or 3-6 membered heterocycle, wherein each $C_{1-3}$alkyl or 3-6 membered heterocycle of $R^1$ is optionally substituted with one or more groups independently selected from the group consisting of oxo, halo, $C_{2-6}$cycloalkyl, and $C_{1-4}$alkoxy.

In certain embodiments $R^1$ is selected from the group consisting of: methyl,

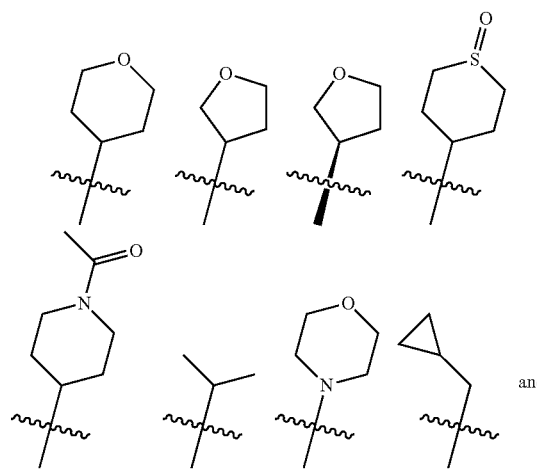

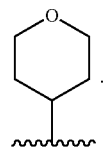

In certain embodiments $R^1$ is:

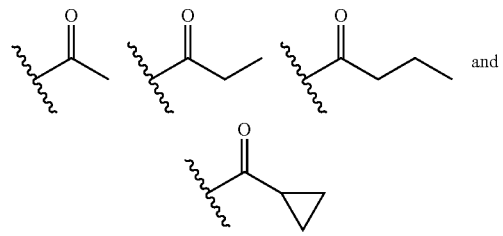

In certain embodiments $R^2$ is $C_{1-4}$alkanoyl

In certain embodiments $R^2$ is selected from the group consisting of:

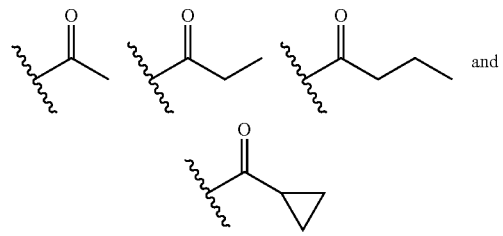

and

In certain embodiments $R^2$ is —C(=O)CH$_3$.

In certain embodiments Y is phenyl, wherein Y is optionally substituted with $R^a$ and wherein Y is further optionally substituted with one or more groups $R^b$.

In certain embodiments Y is 9-membered bicyclic carbocycle or a 10-membered bicyclic carbocycle, wherein Y is optionally substituted with $R^a$ and wherein Y is further optionally substituted with one or more groups $R^b$.

In certain embodiments Y is a 9-membered bicyclic heterocycle or a 10-membered bicyclic heterocycle, wherein Y is optionally substituted with $R^a$ and wherein Y is further optionally substituted with one or more groups $R^b$.

In certain embodiments —X—Y is selected from the group consisting of:

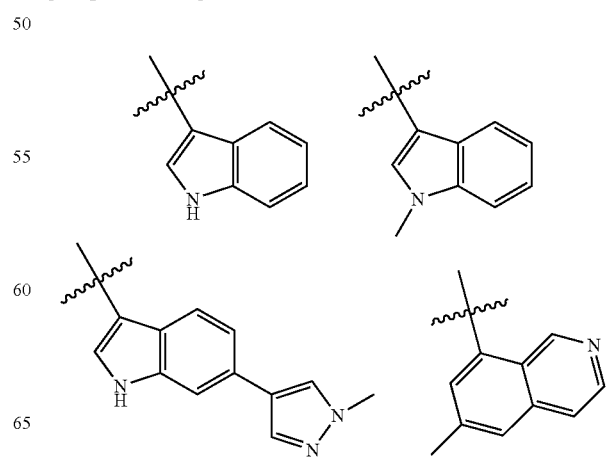

-continued
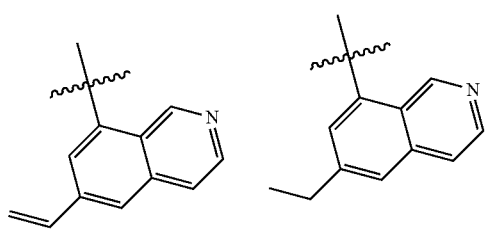
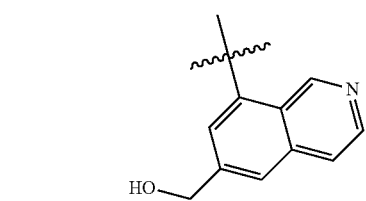
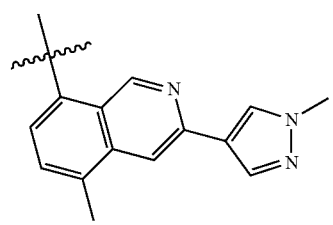
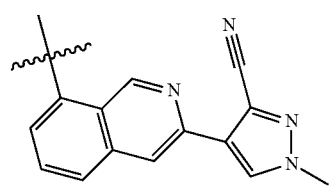
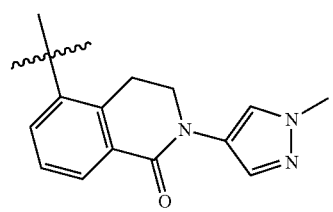
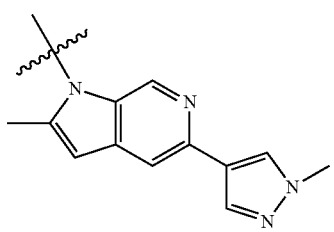
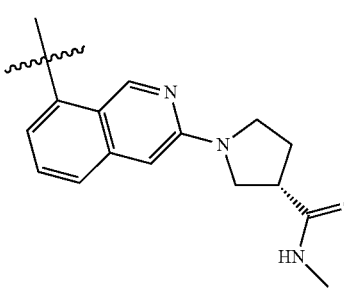
-continued
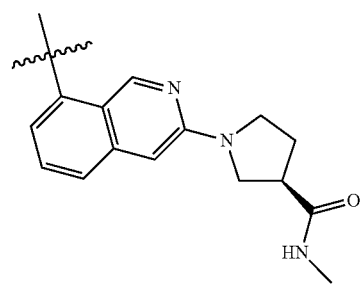
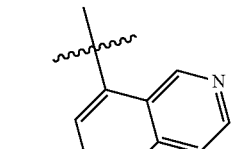
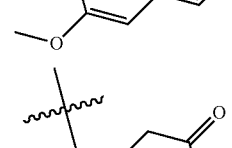
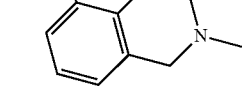
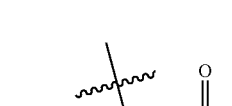
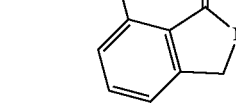
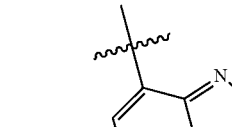

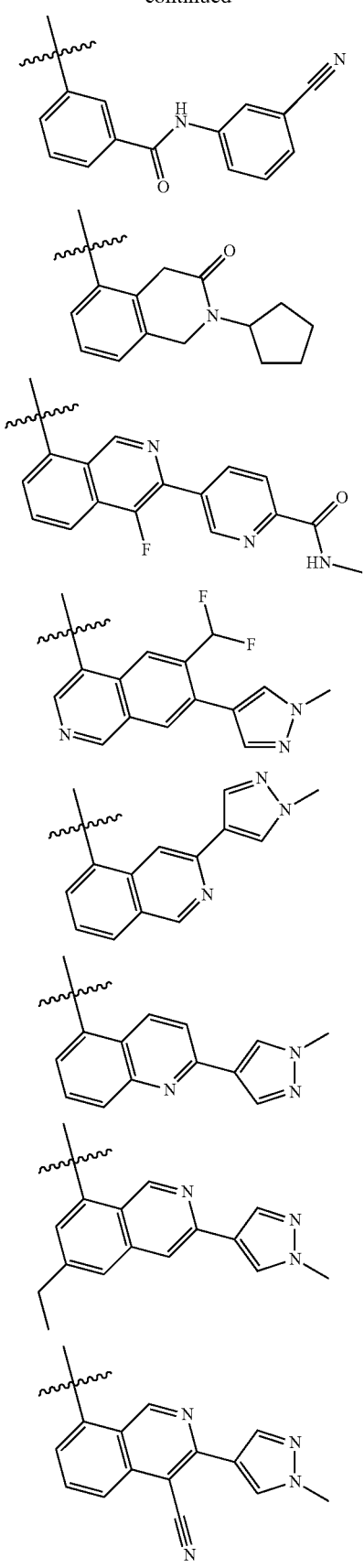
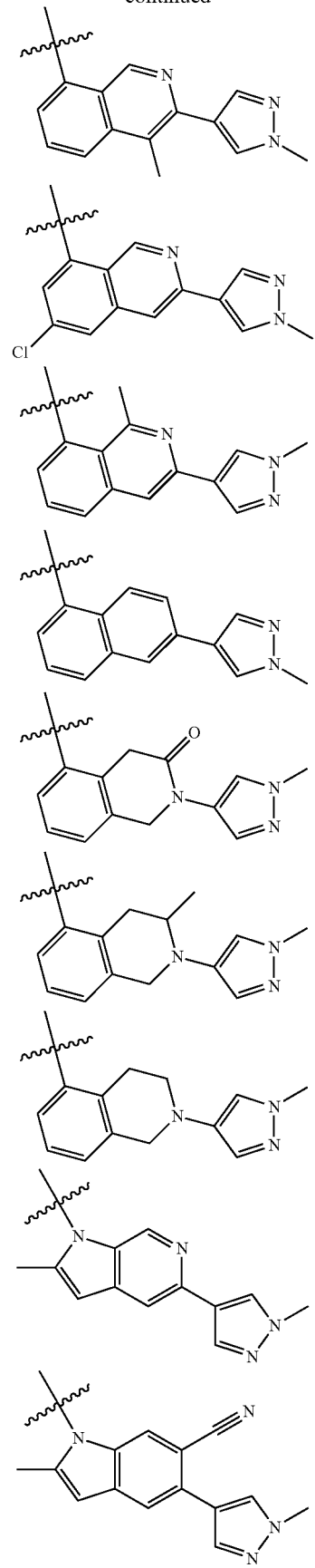

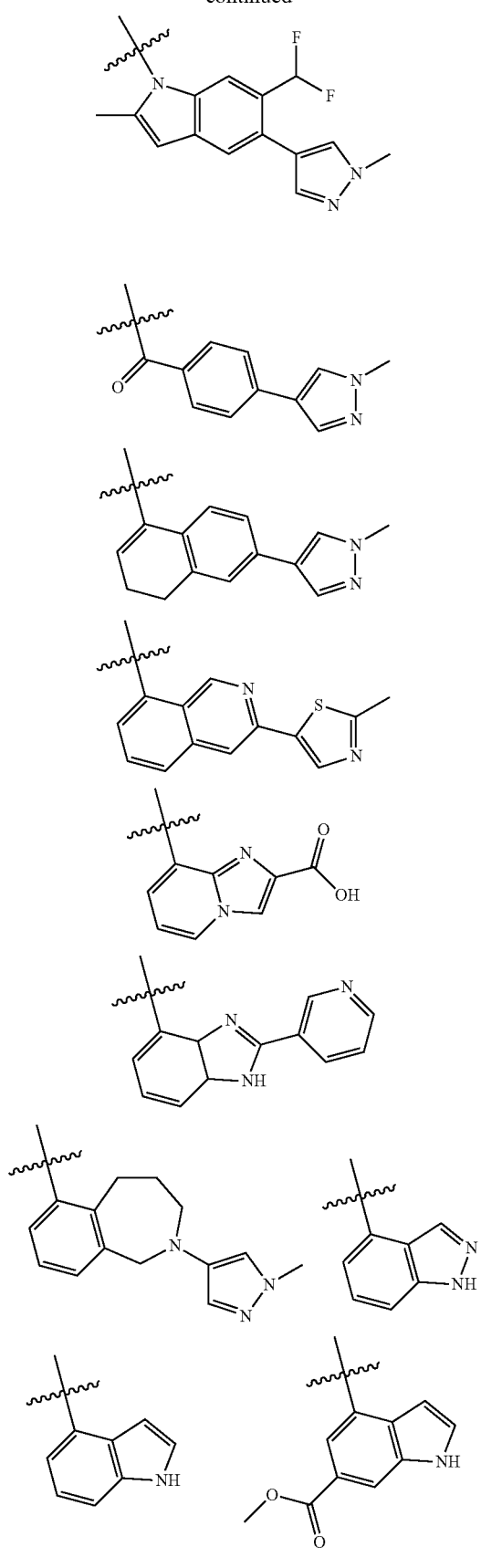
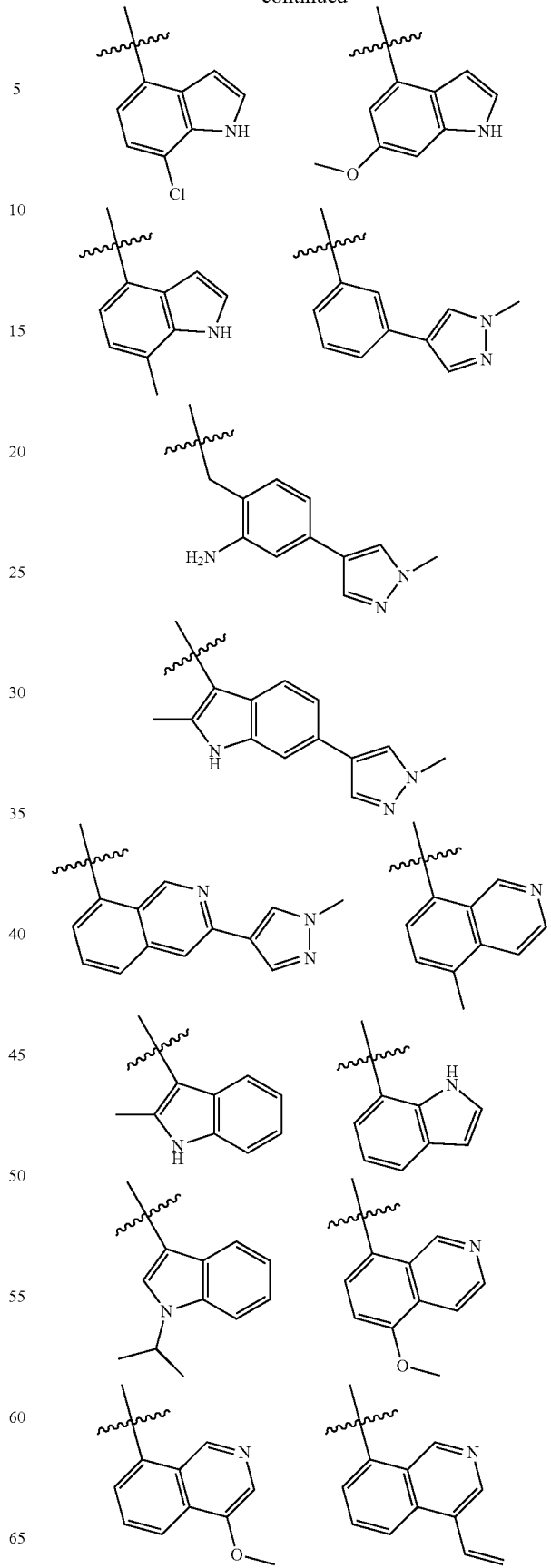

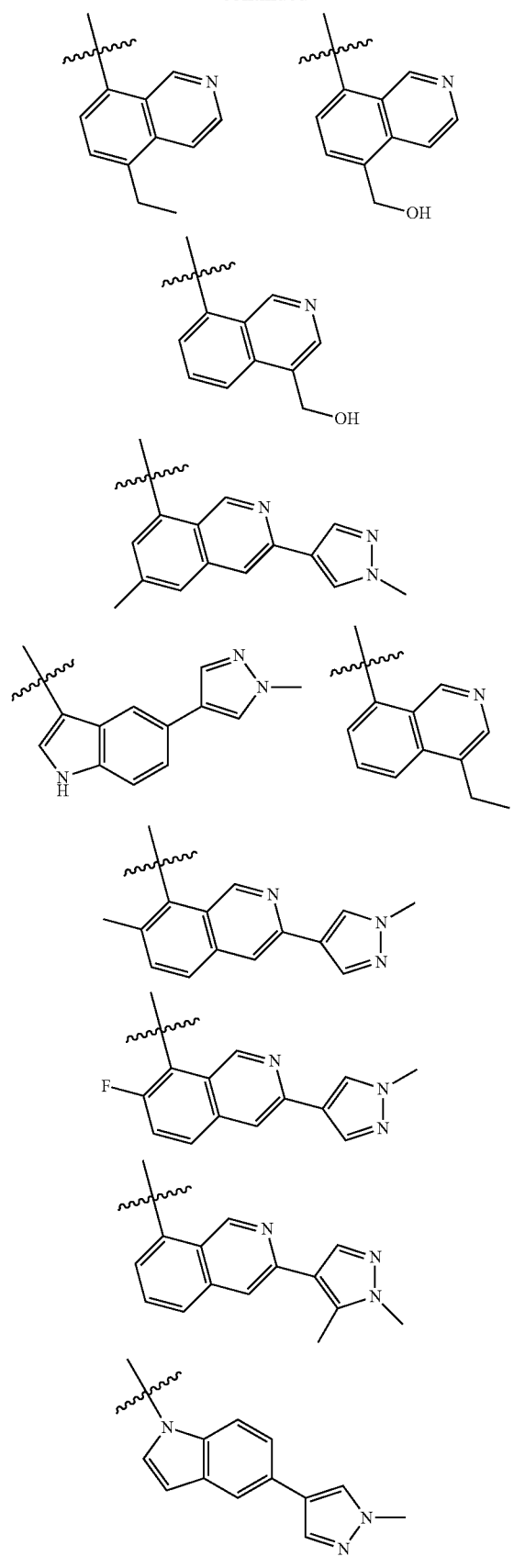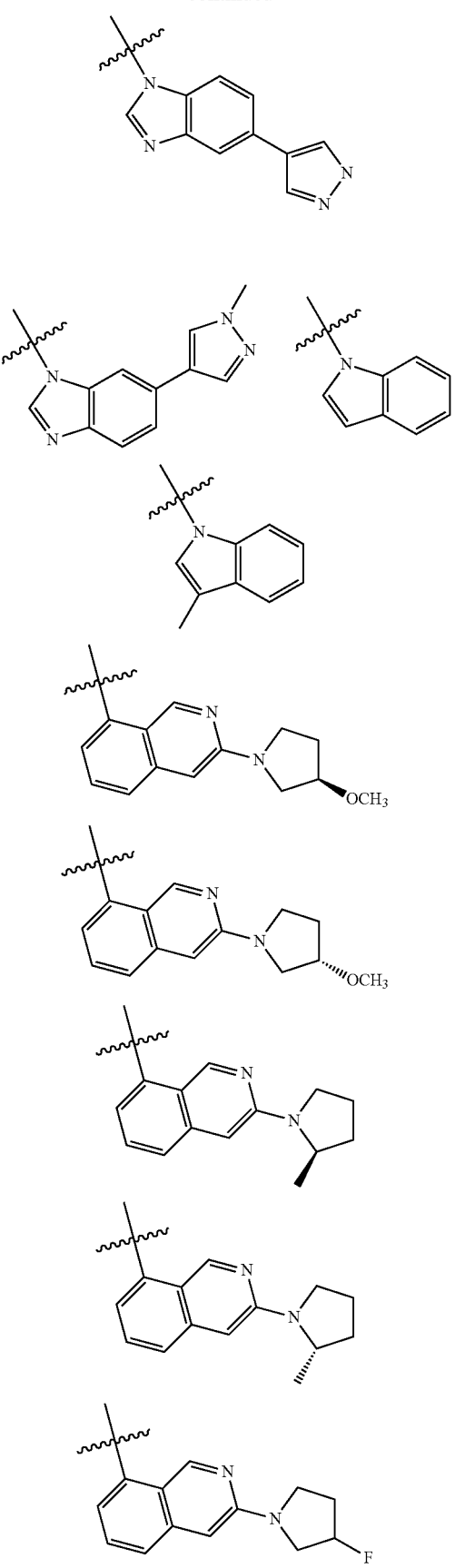

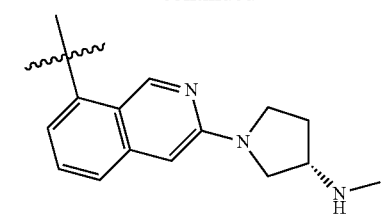
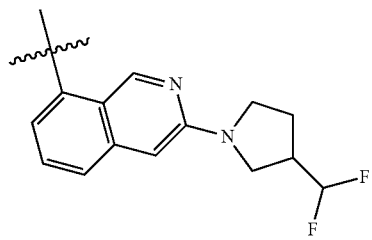
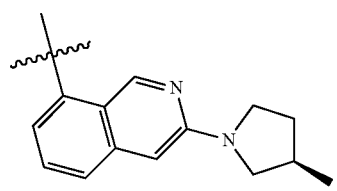
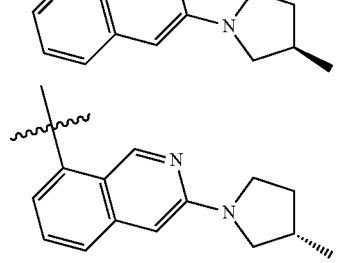
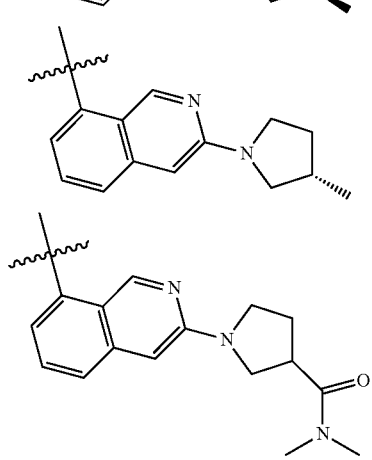
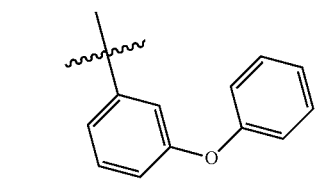
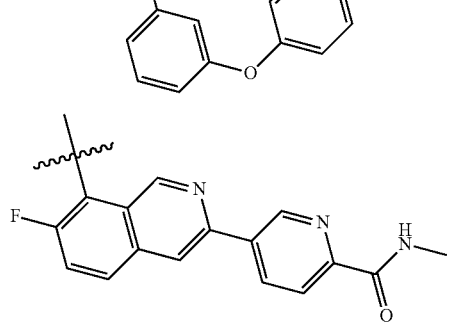
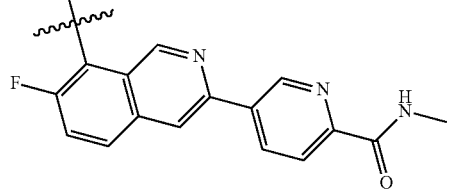
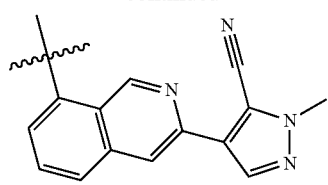
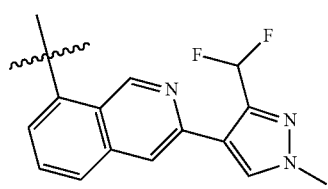
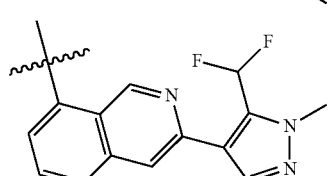
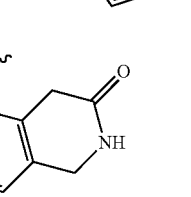
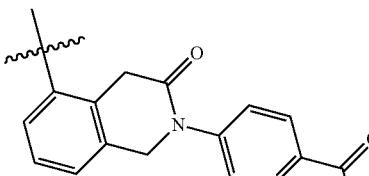
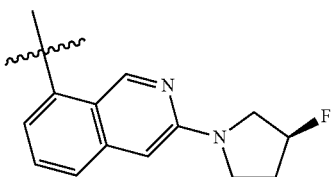
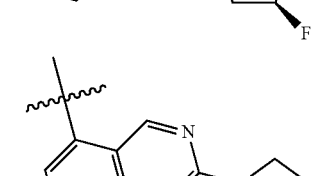
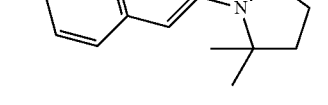

-continued
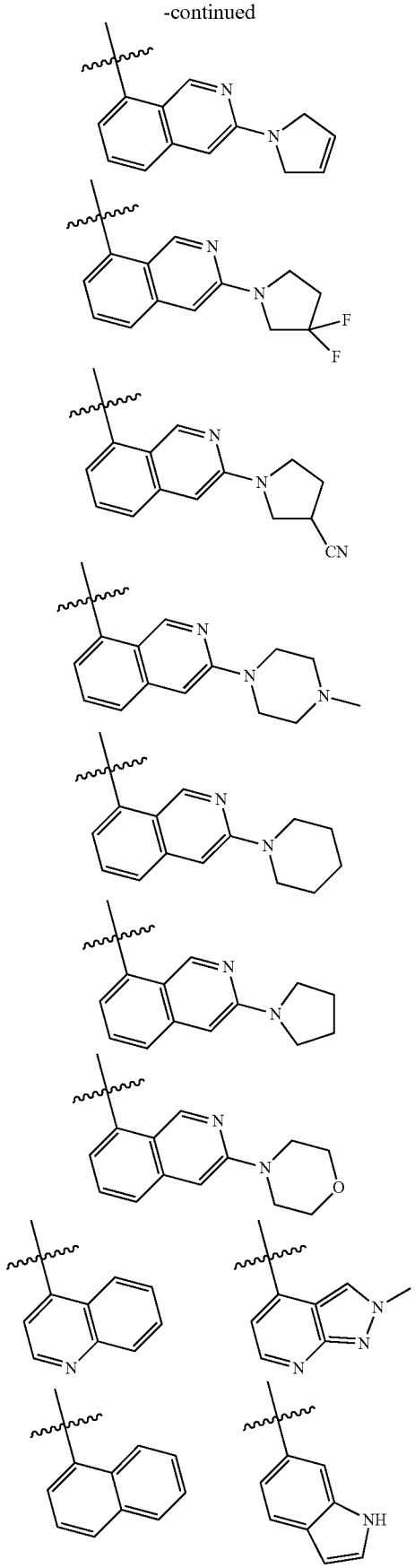
-continued
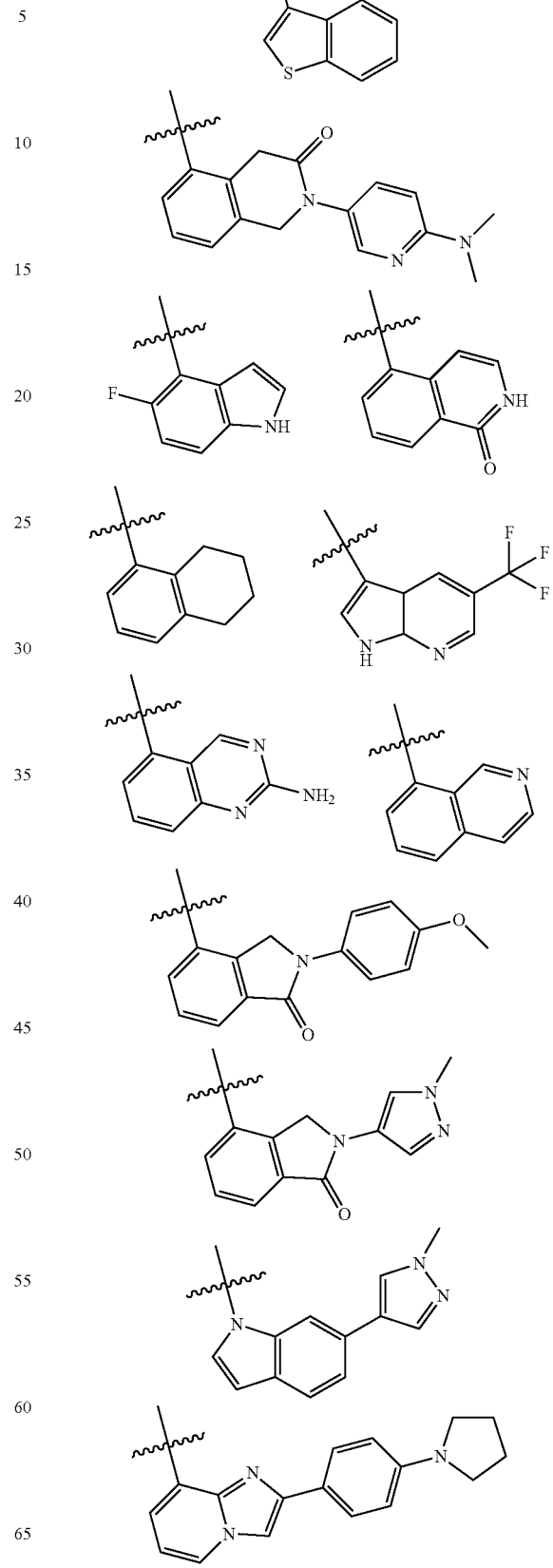

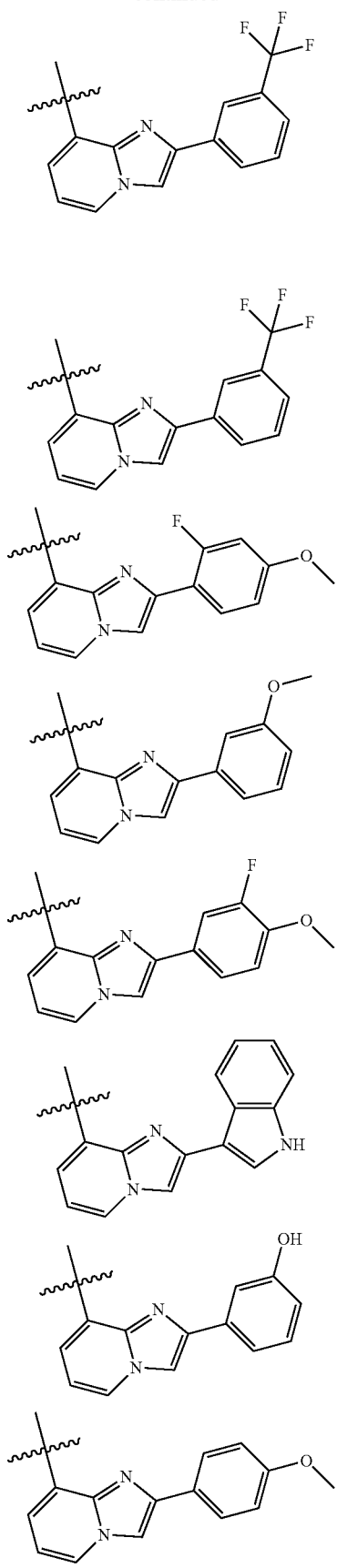
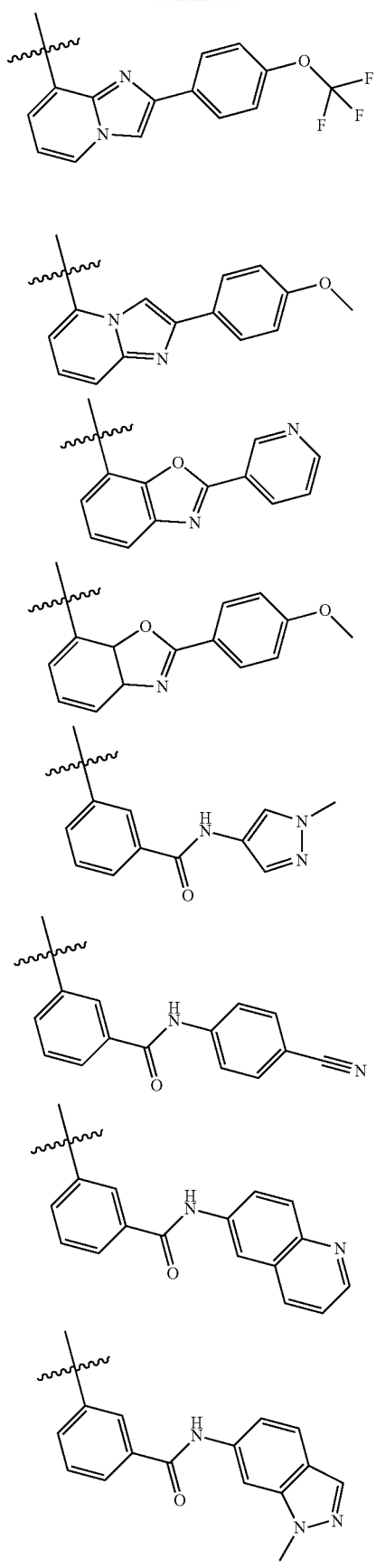

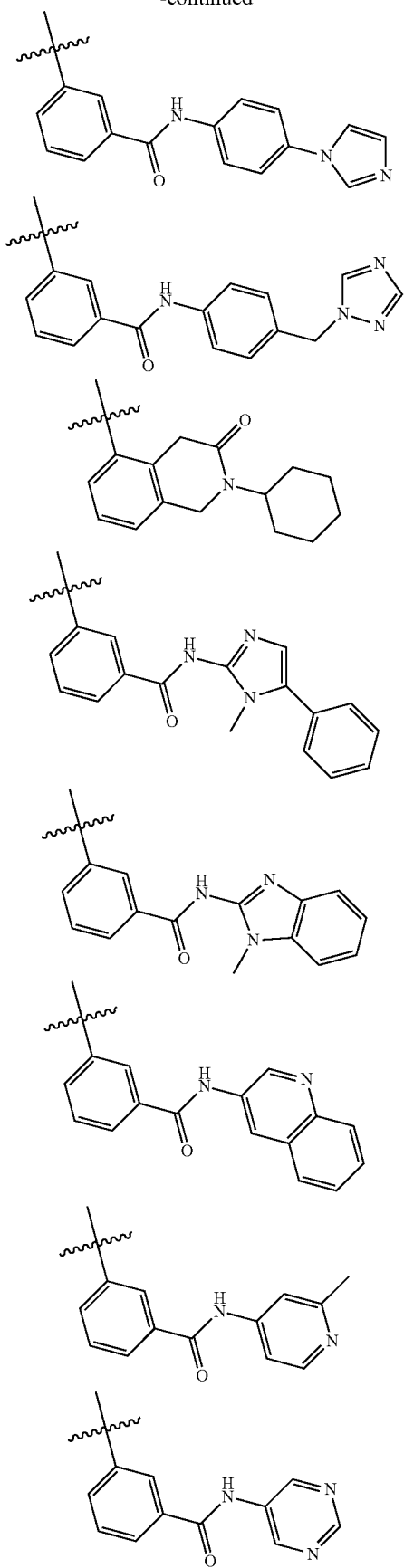
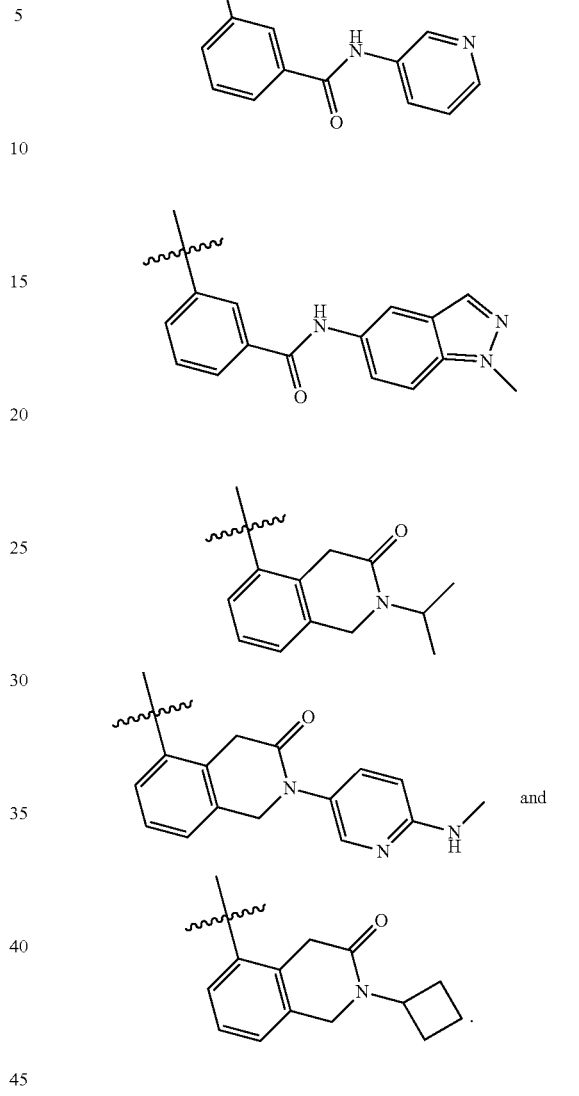
In certain embodiments Y is selected from the group consisting of:
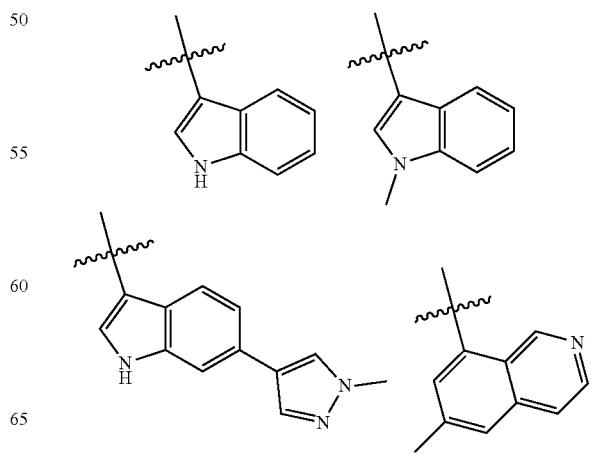

-continued
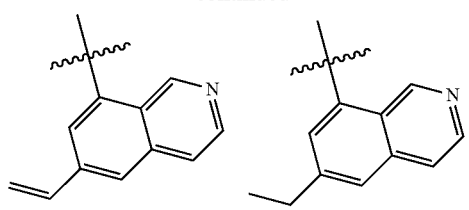
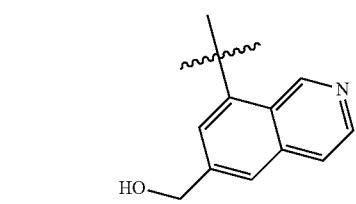
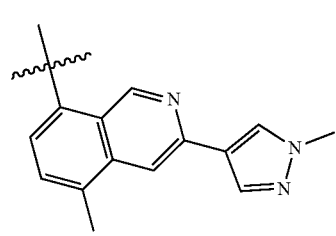
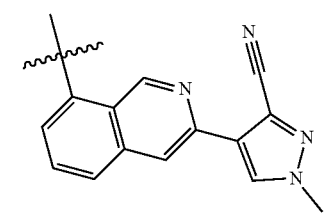
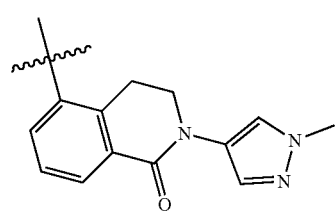
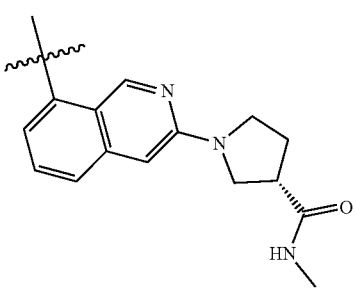
-continued
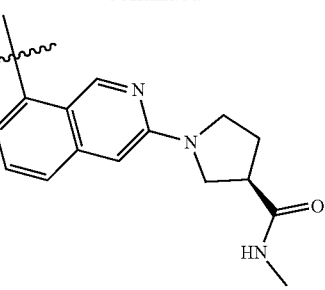
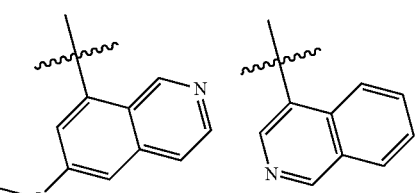
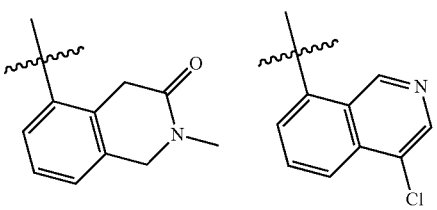
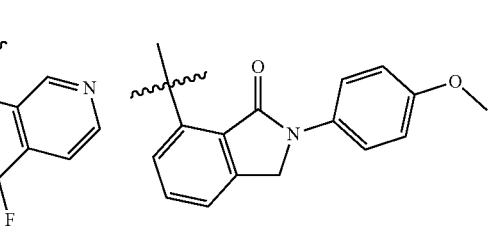
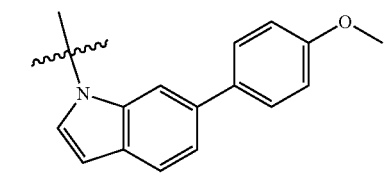
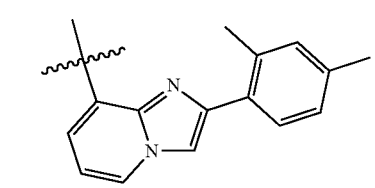
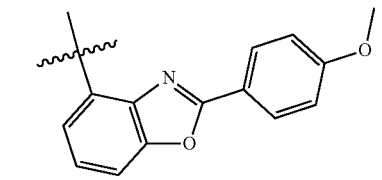
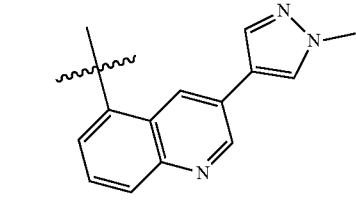

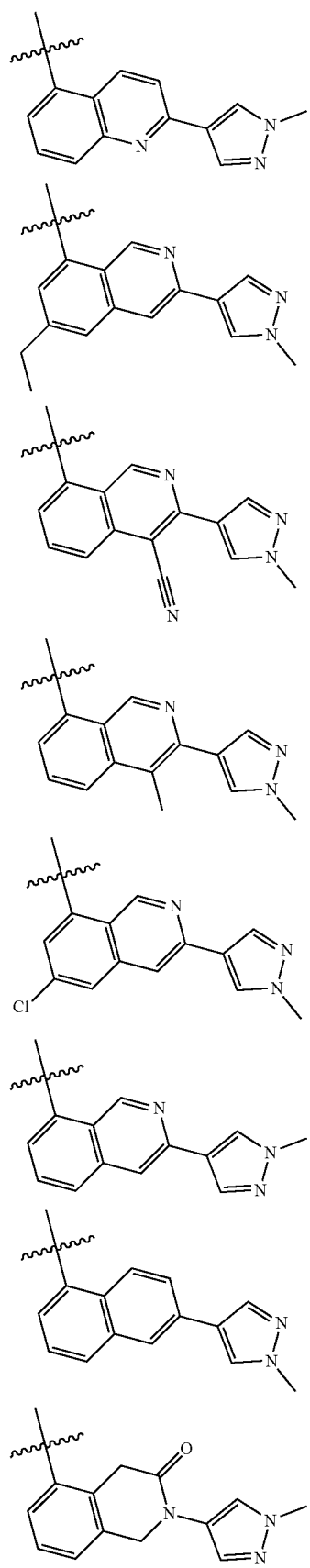
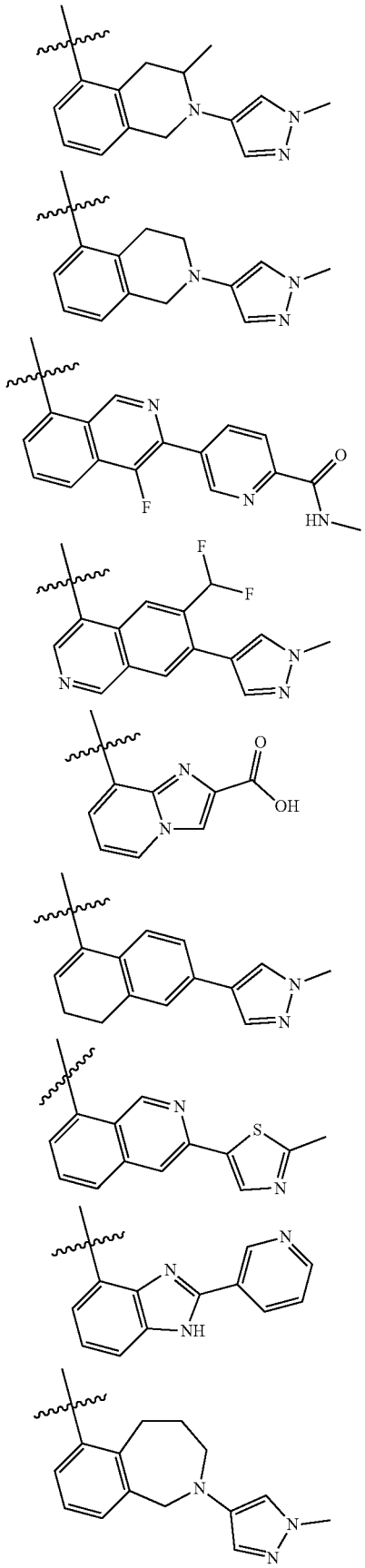

-continued
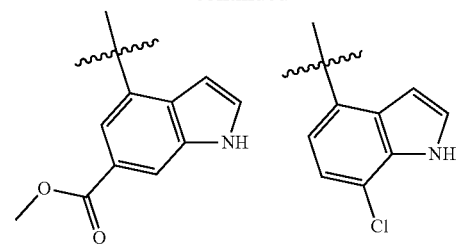
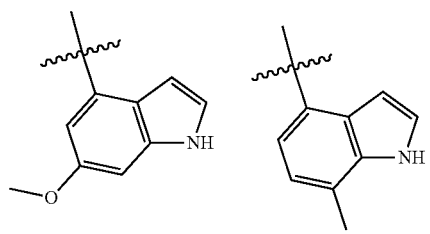
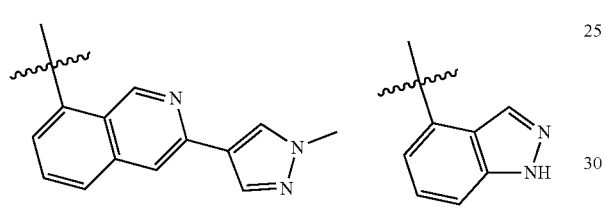
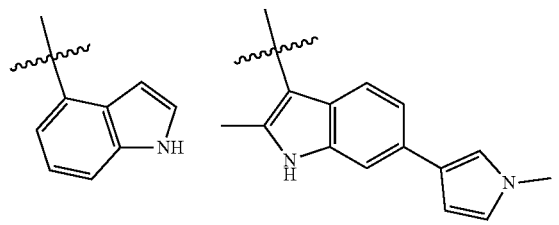
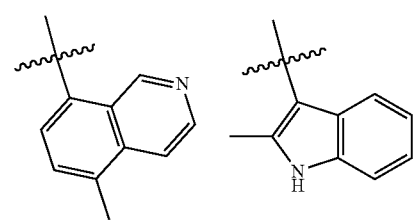
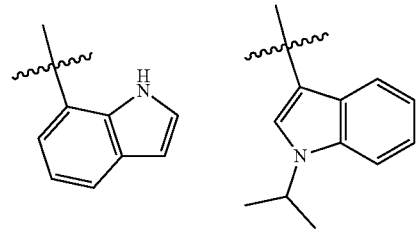
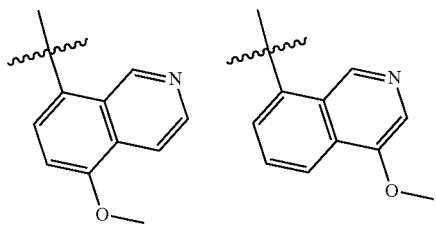
-continued
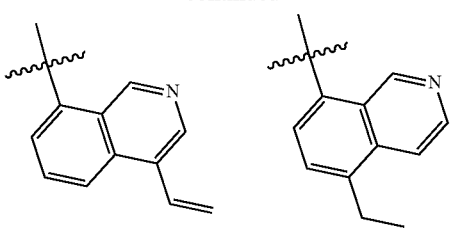
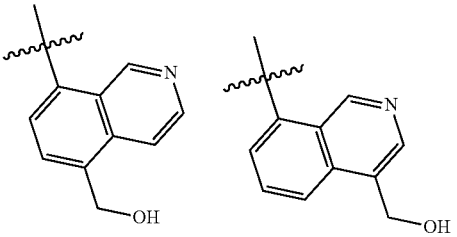
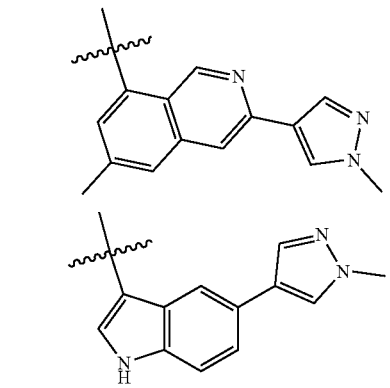
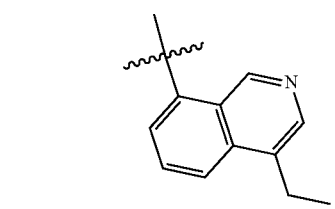
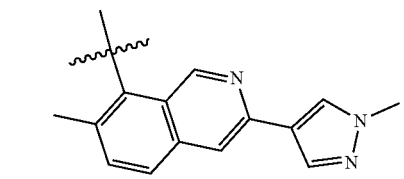
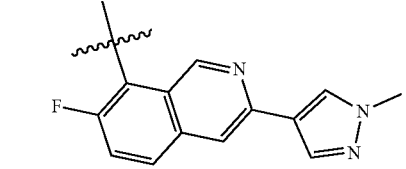
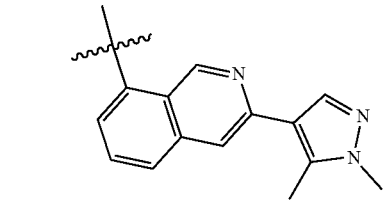

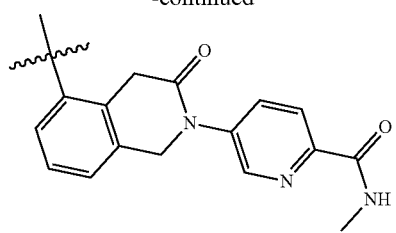
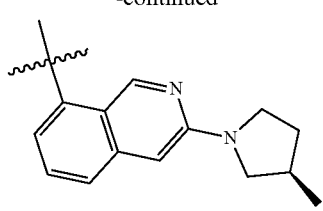
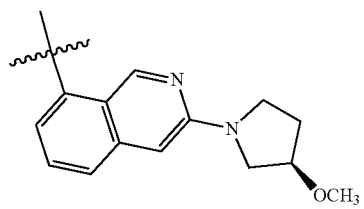
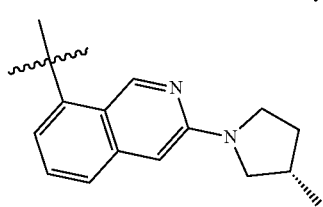

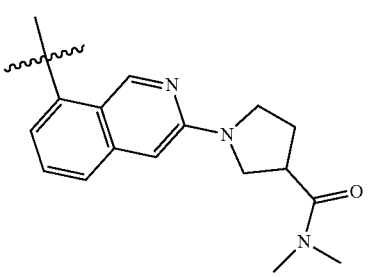
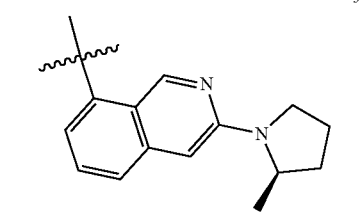
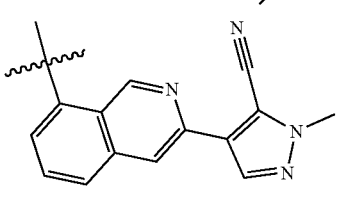
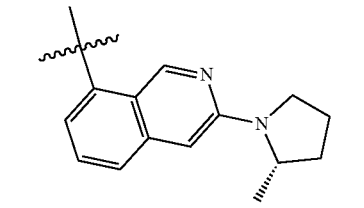
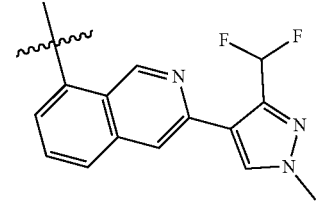
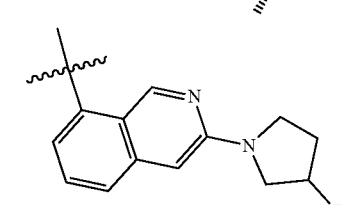
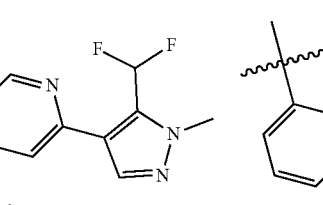
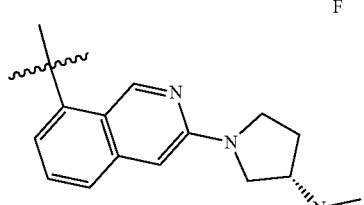
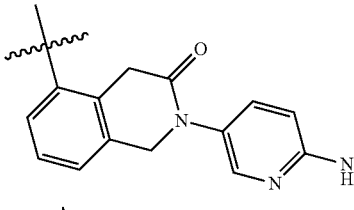
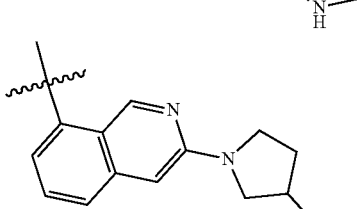
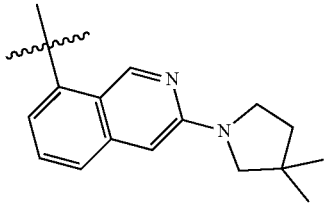
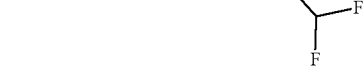

-continued
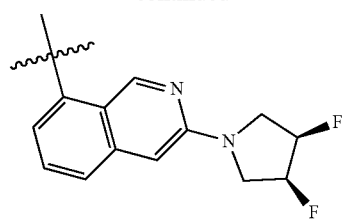
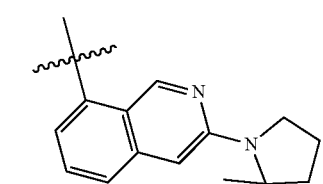
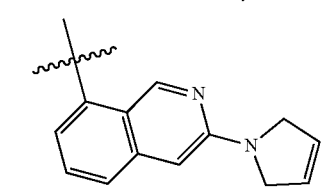
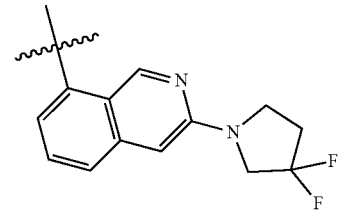
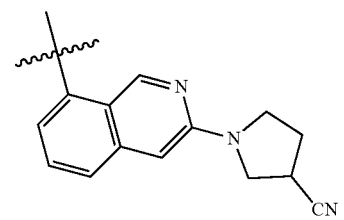
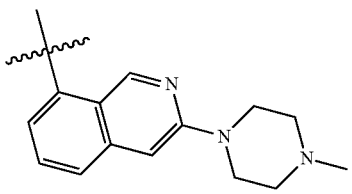
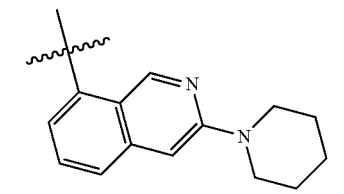
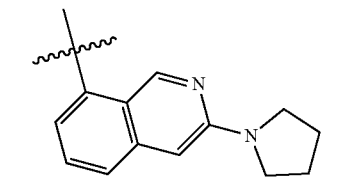
-continued
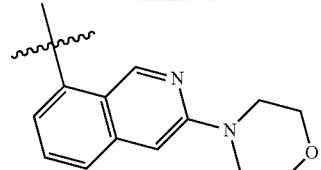
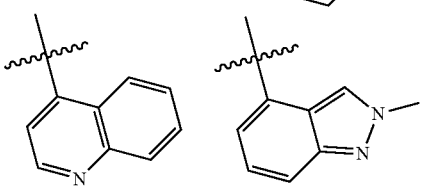
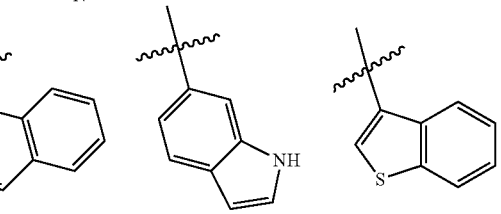
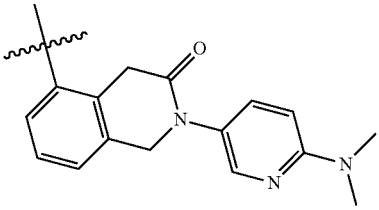
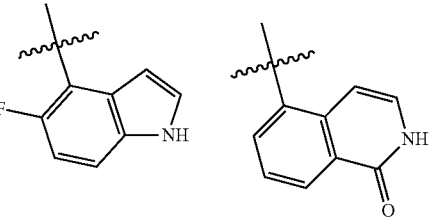
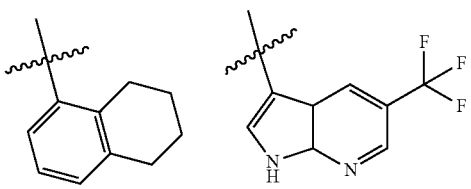
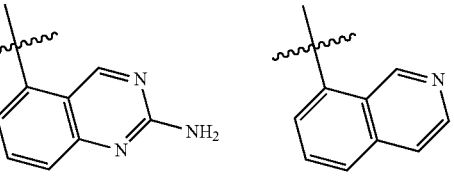
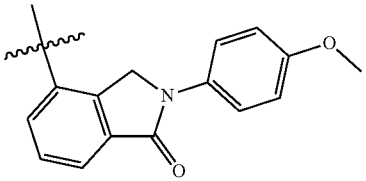
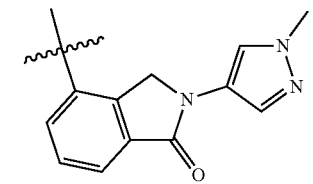

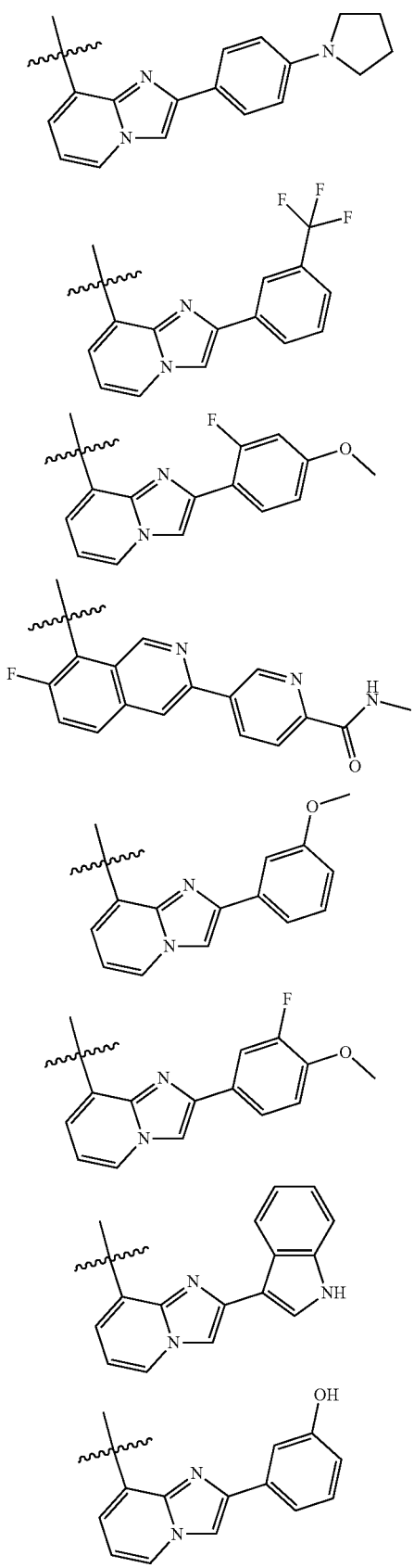
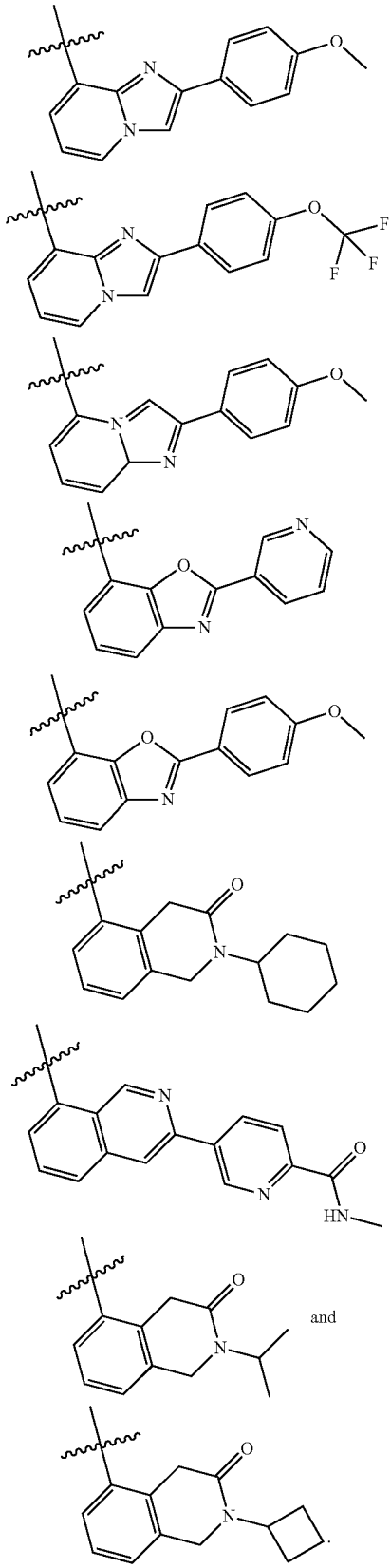
In certain embodiments —X—Y is selected from the group consisting of:

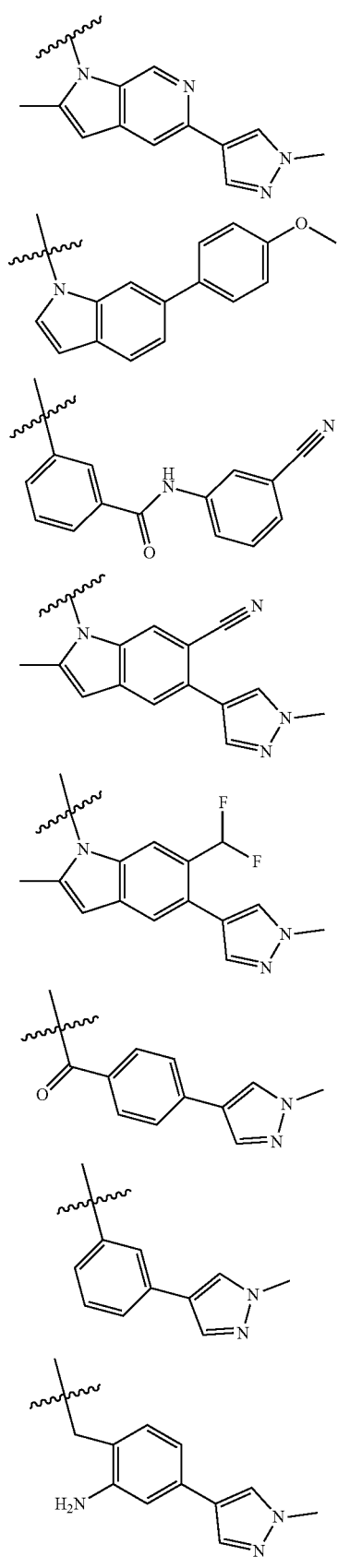
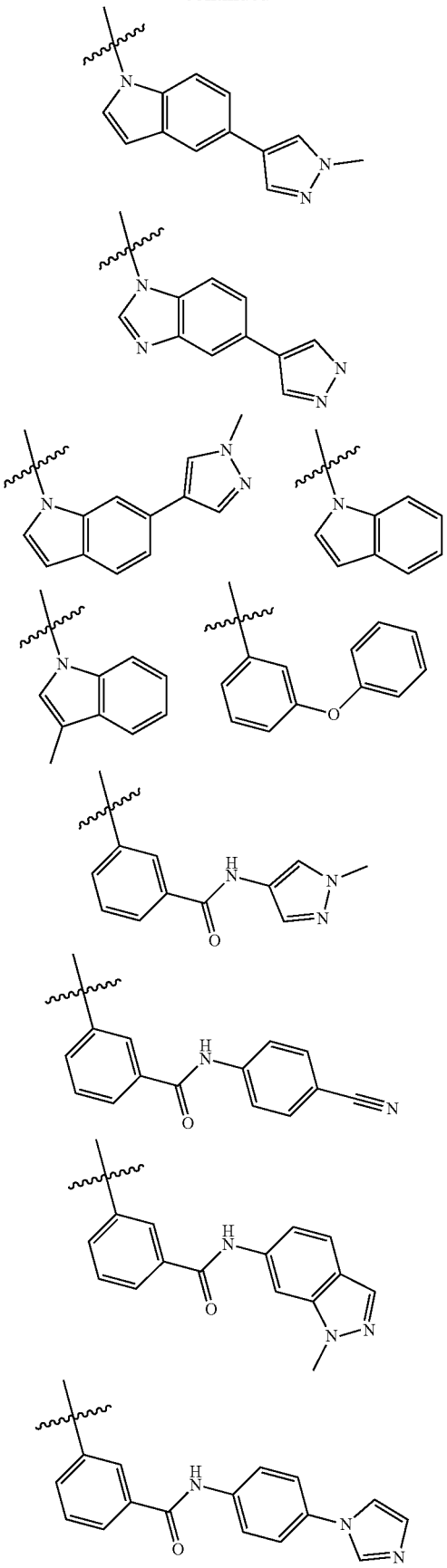

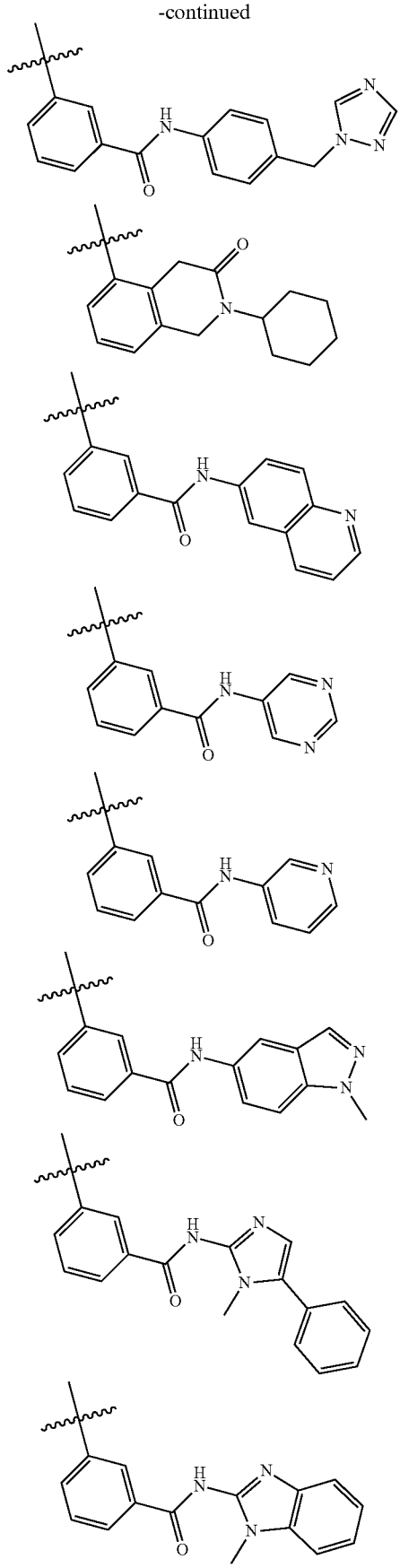
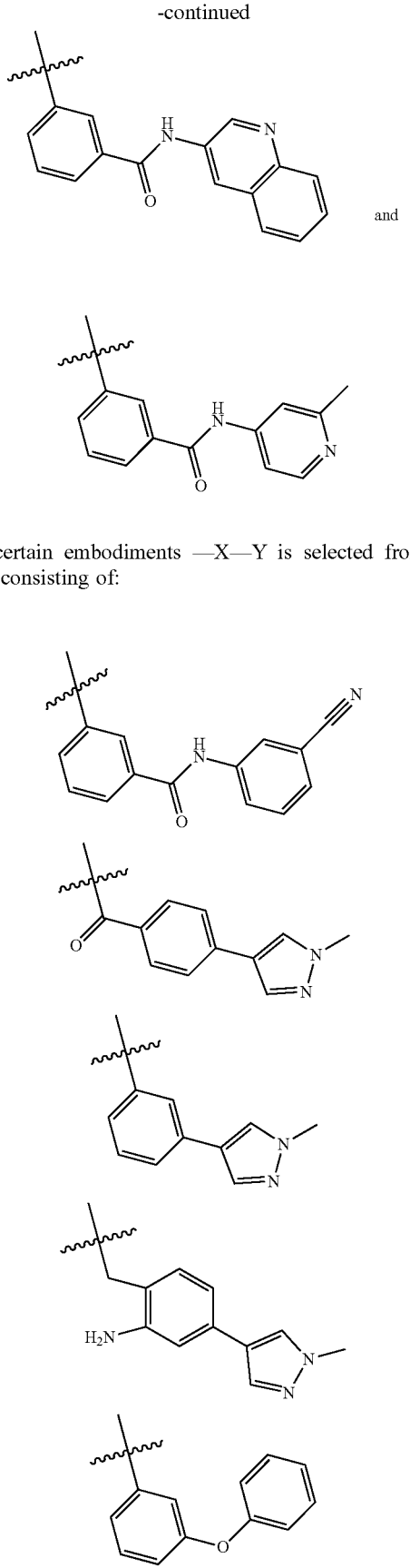
In certain embodiments —X—Y is selected from the group consisting of:

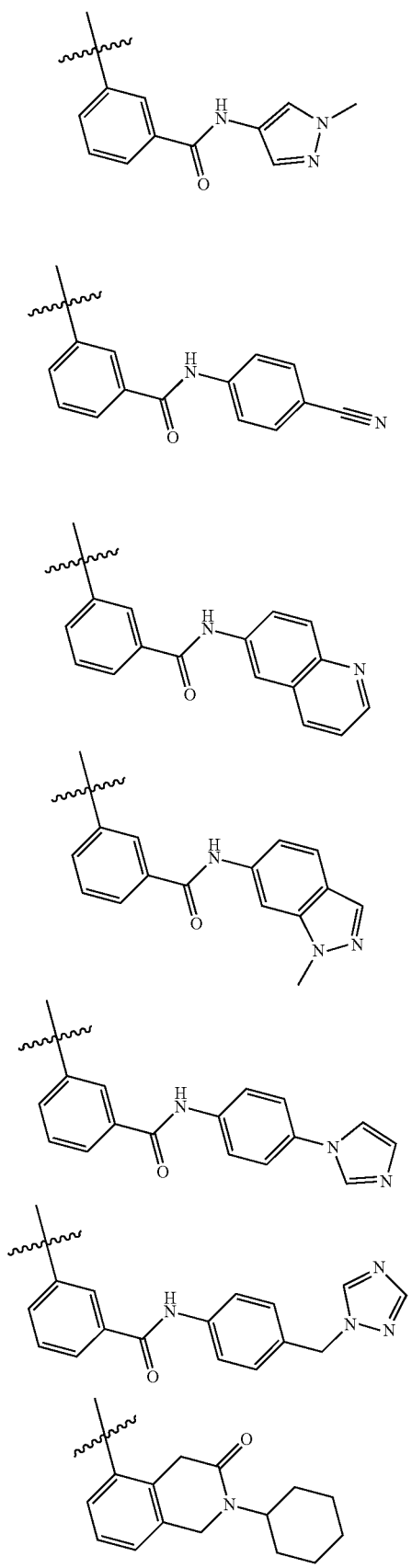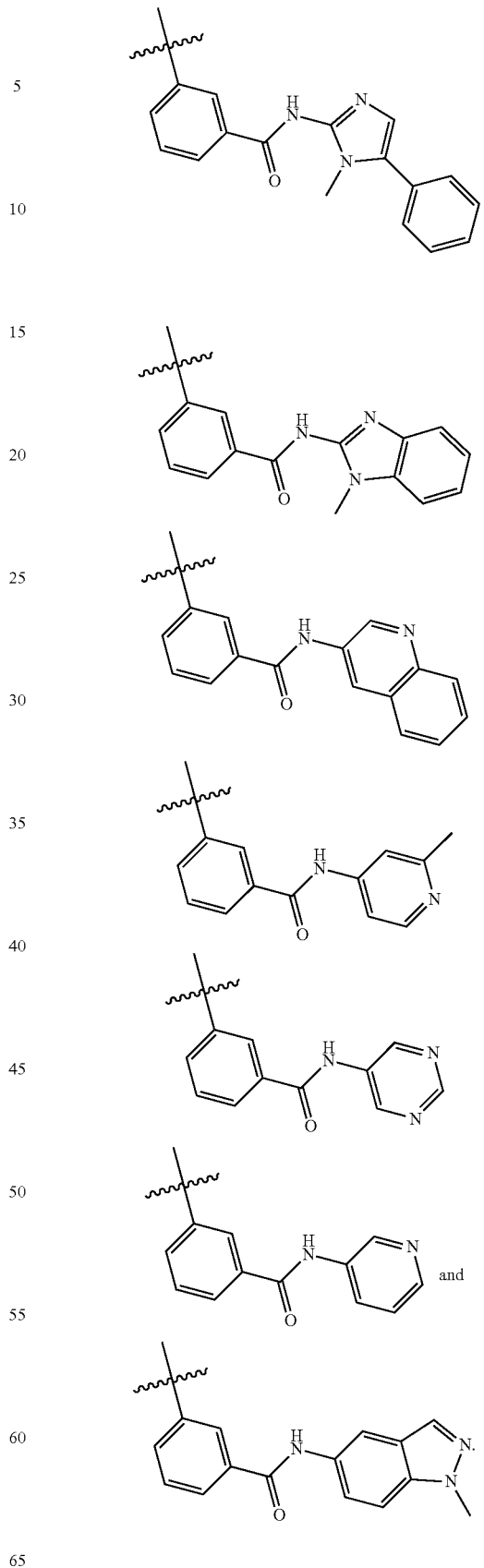
In certain embodiments —X—Y is selected from the group consisting of:

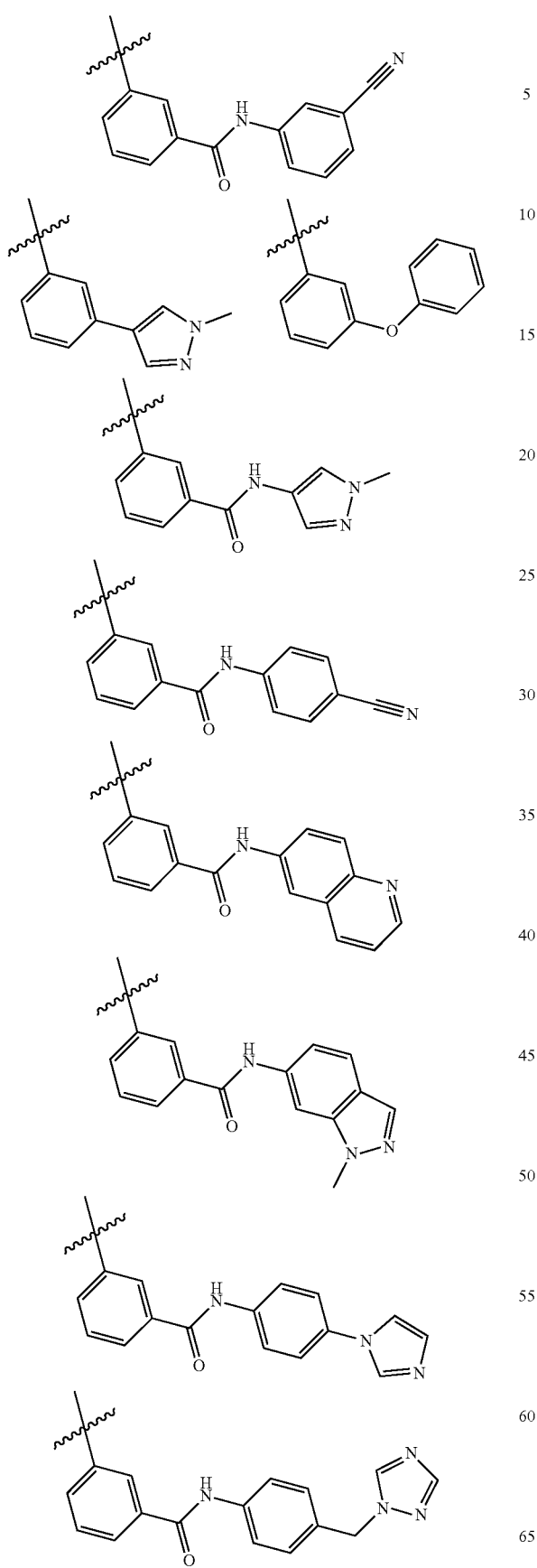
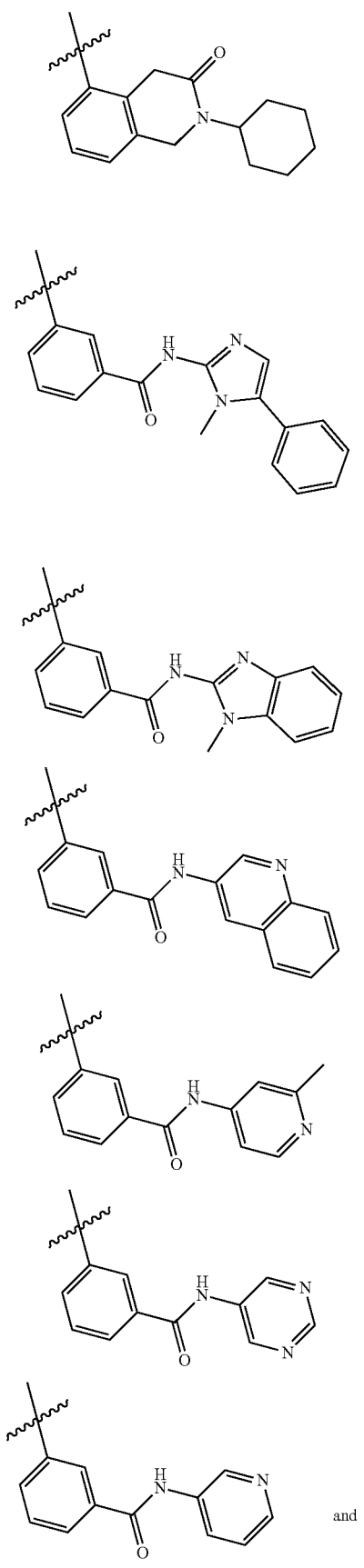

57
-continued
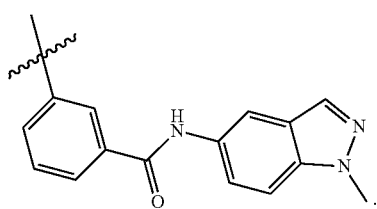
In certain embodiments Y is selected from the group consisting of:
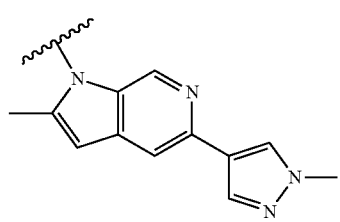
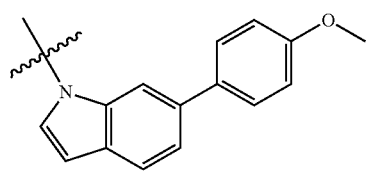
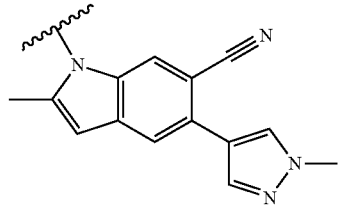
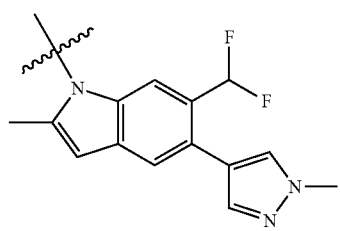
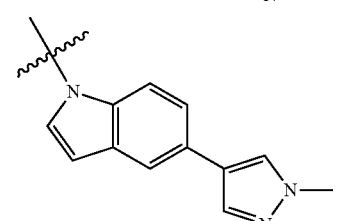
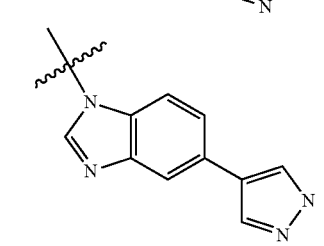
58
-continued
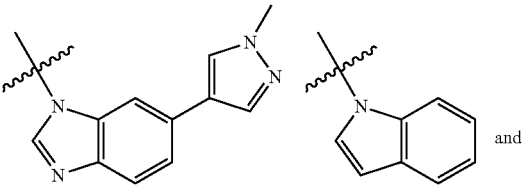
and
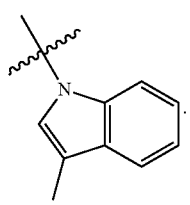
In certain embodiments —X—Y is selected from the group consisting of:
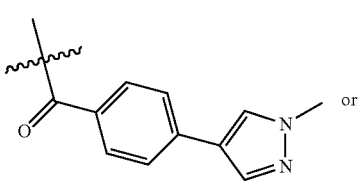
or
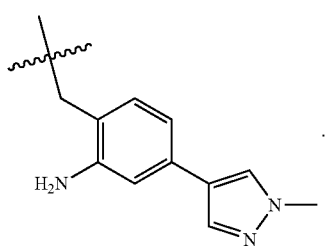
In certain embodiments the compound or salt is selected from the group consisting of:
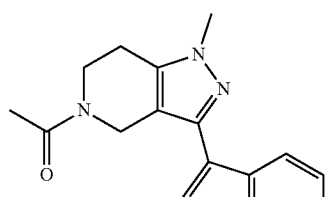
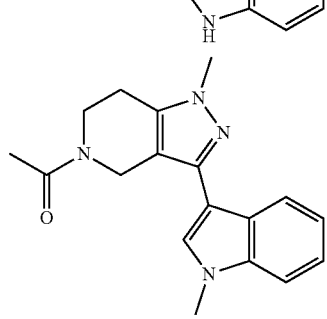

59
-continued
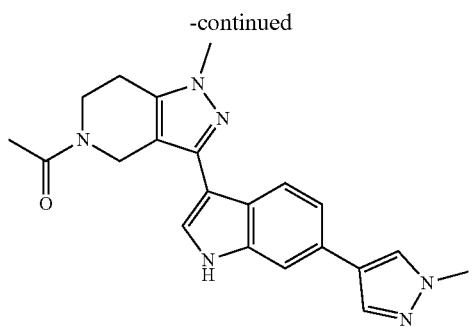
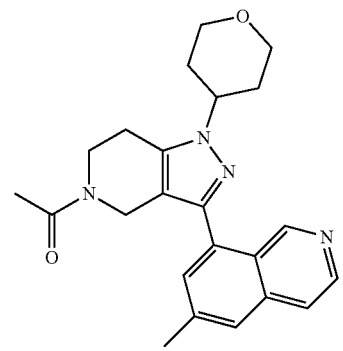
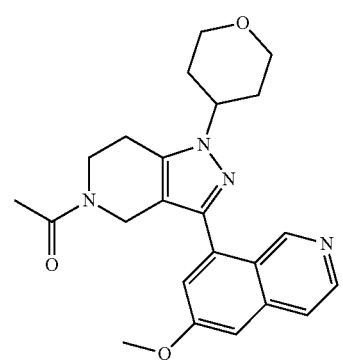
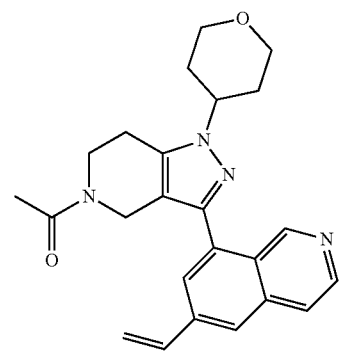
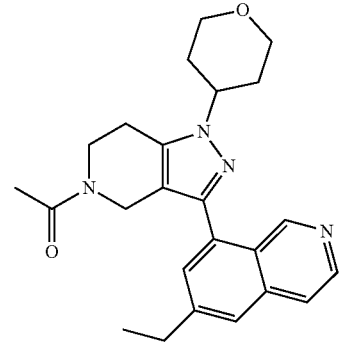
60
-continued
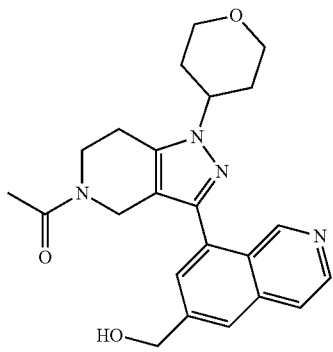
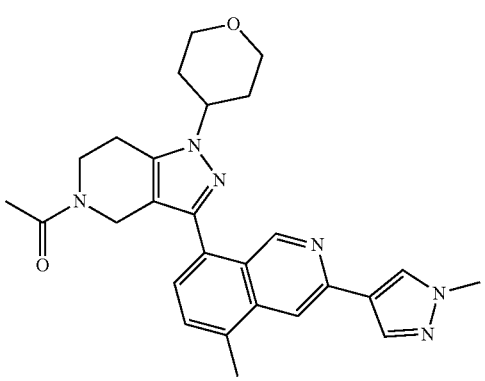
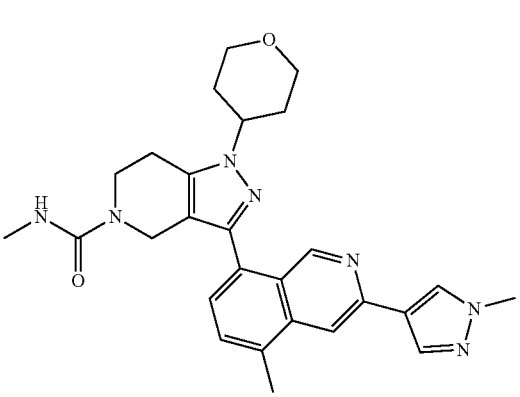
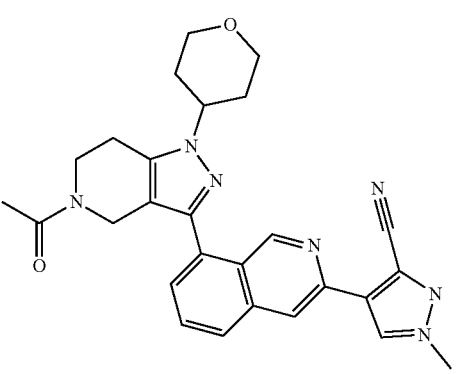

61
-continued
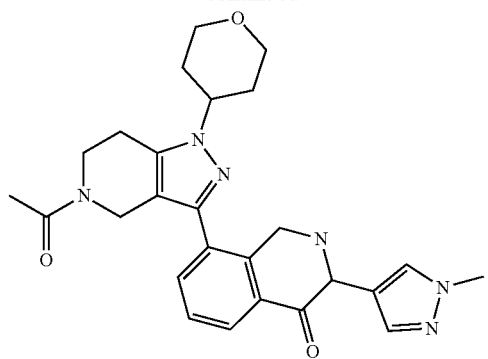
62
-continued
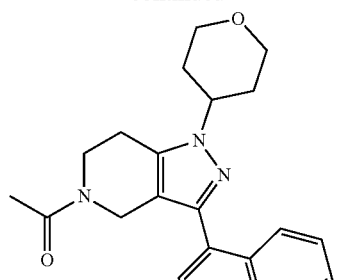
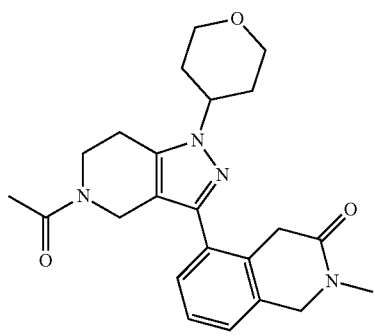
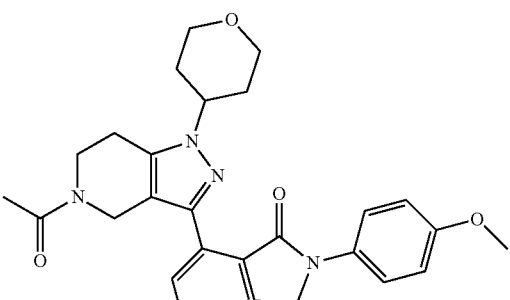
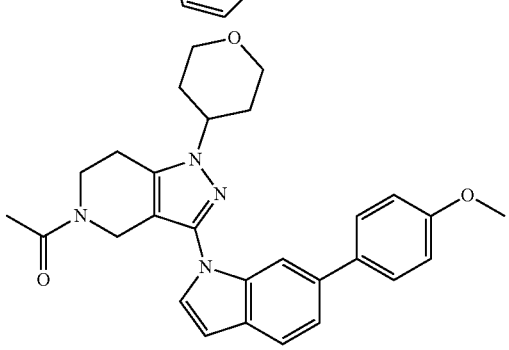
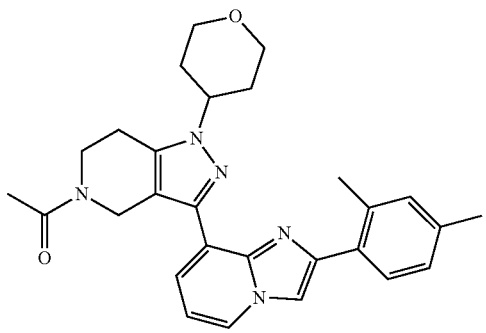

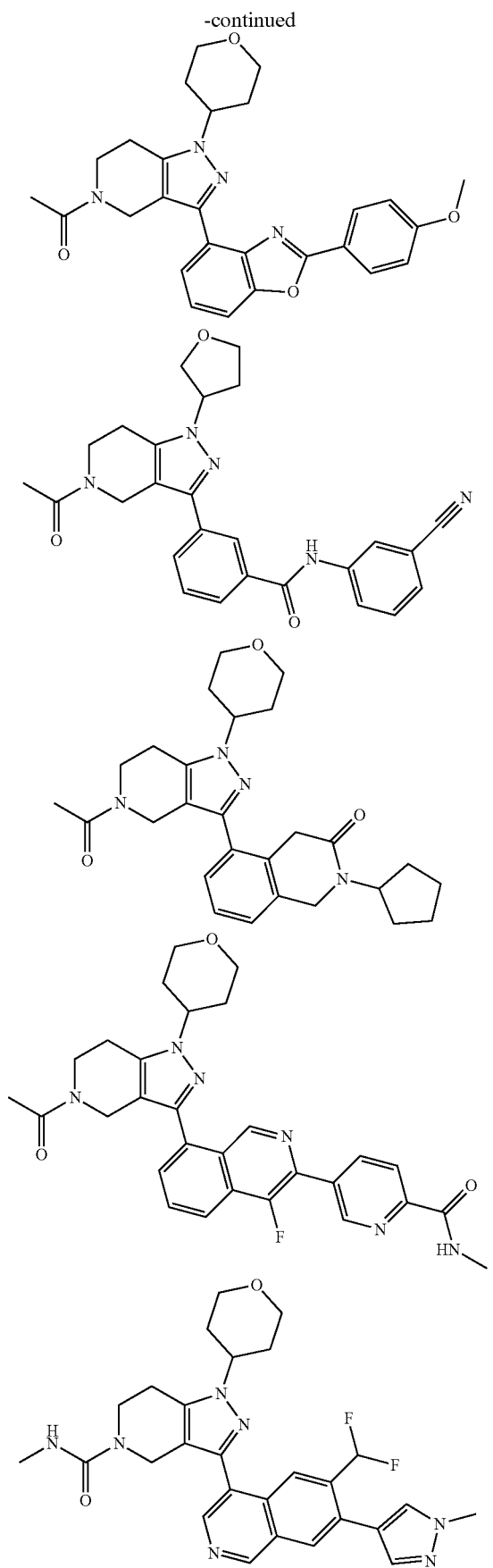
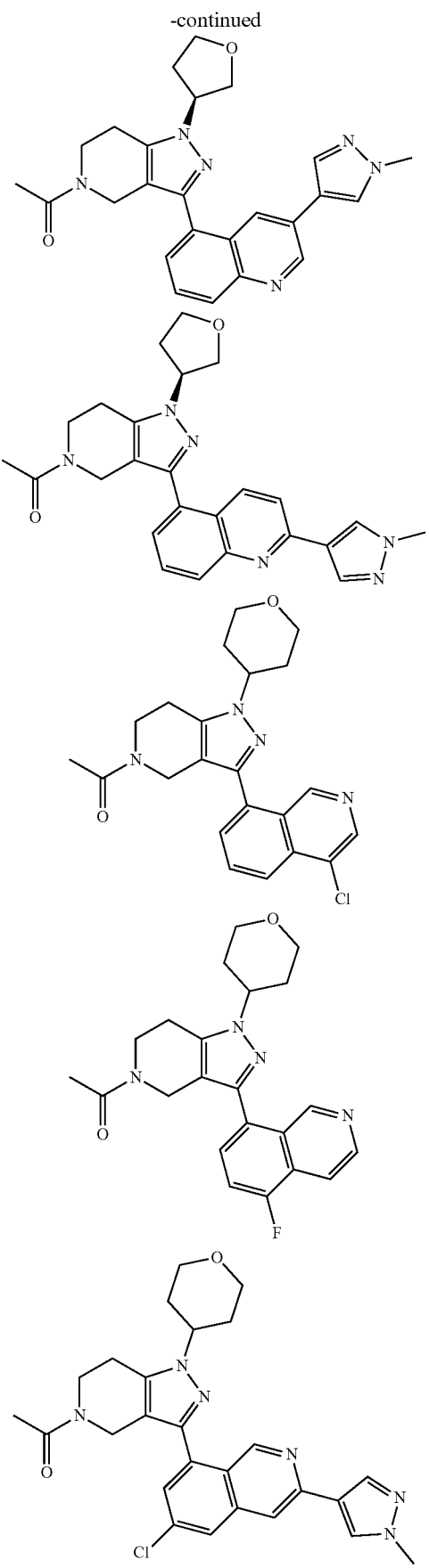

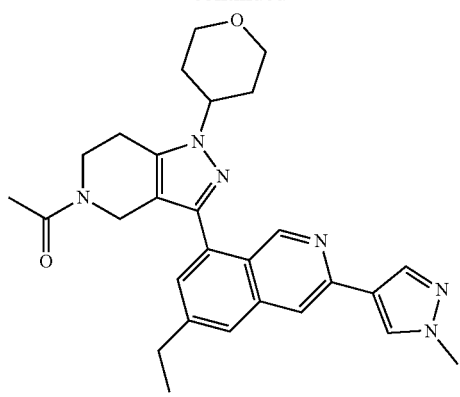
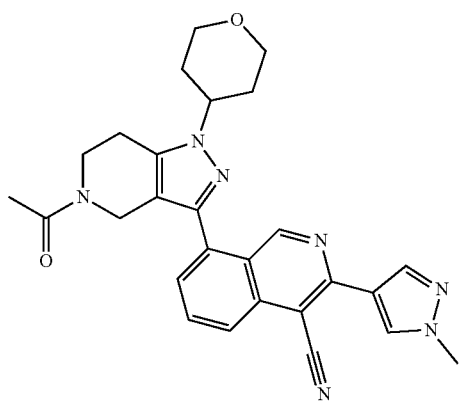
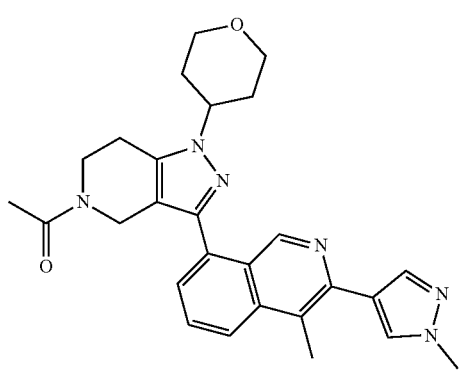
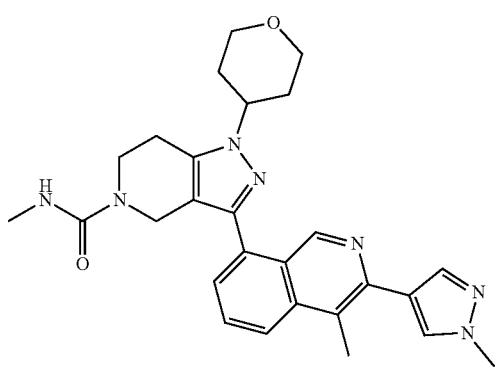
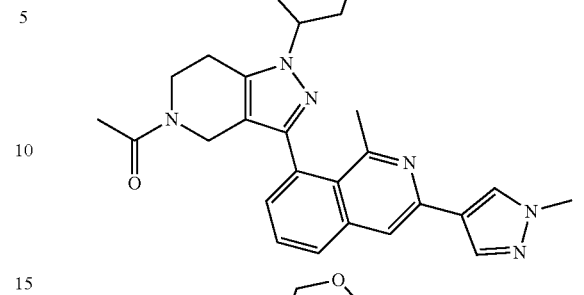
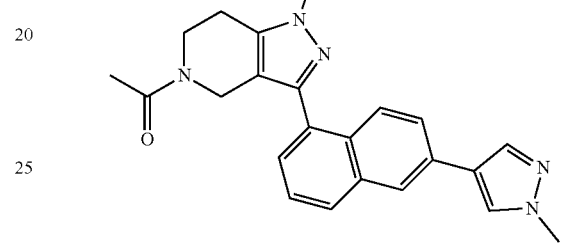
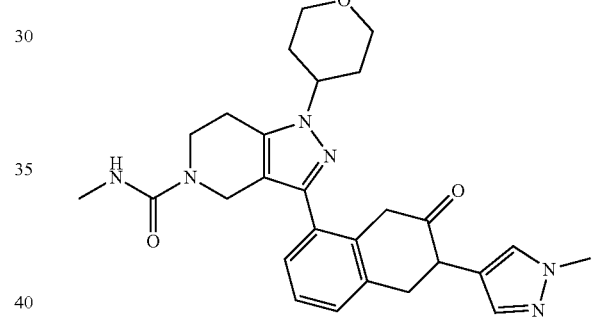
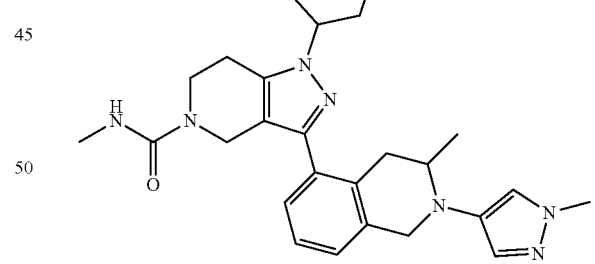
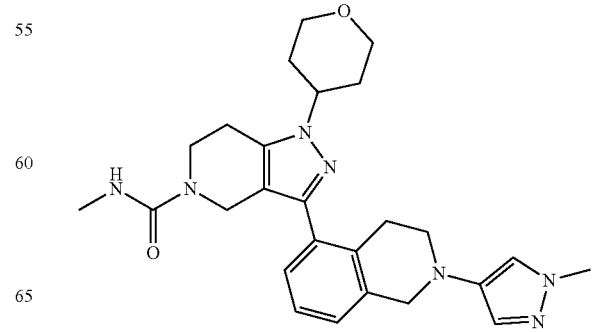

-continued
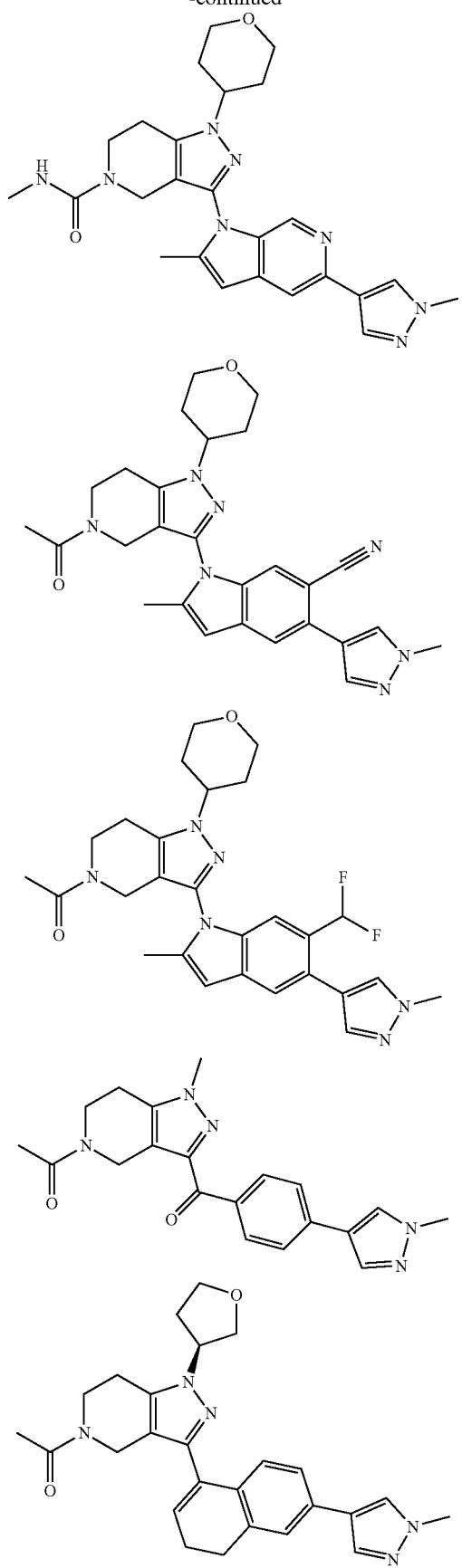
-continued
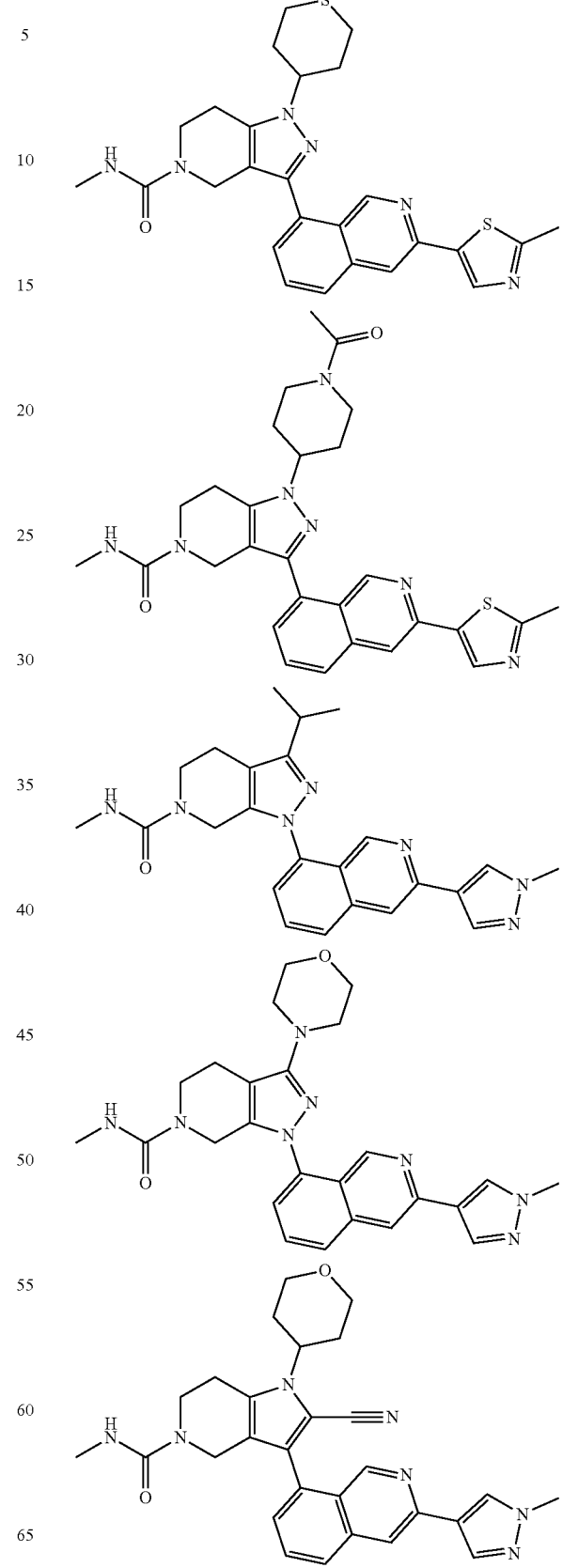

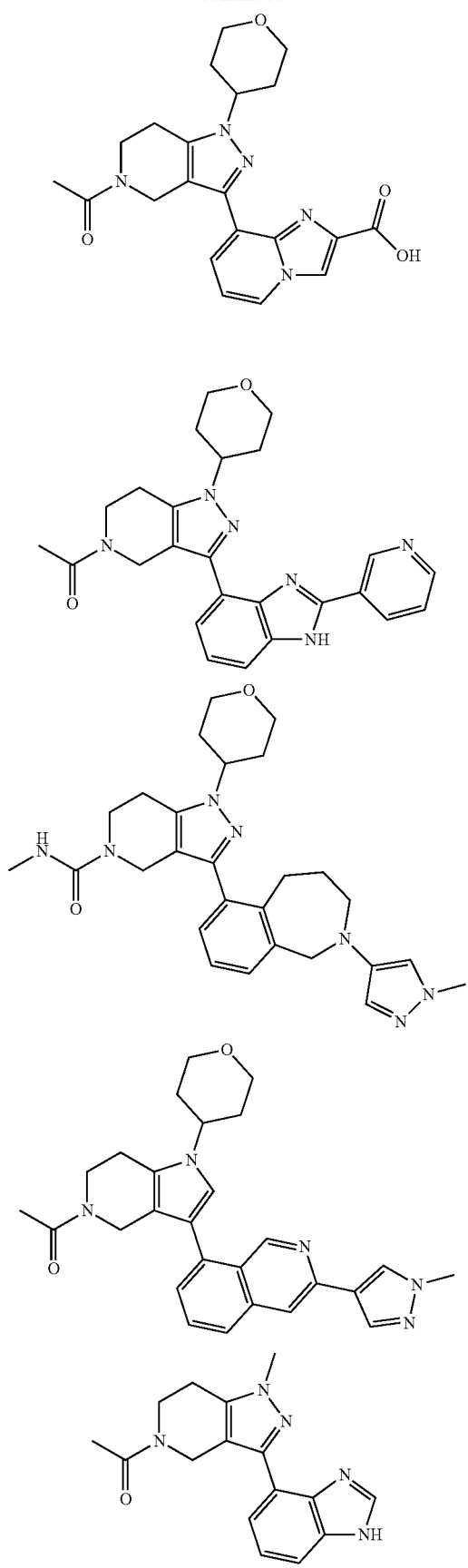
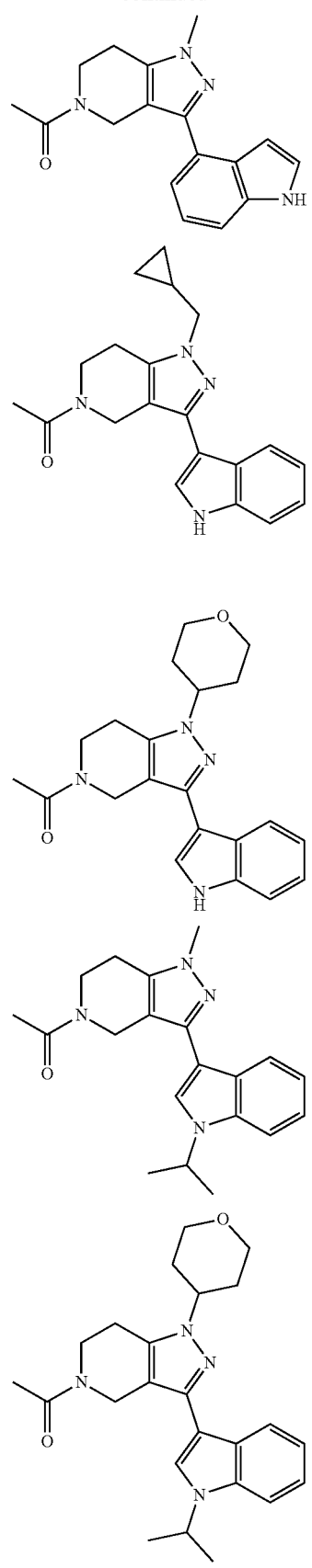

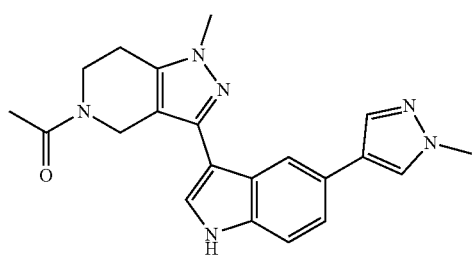
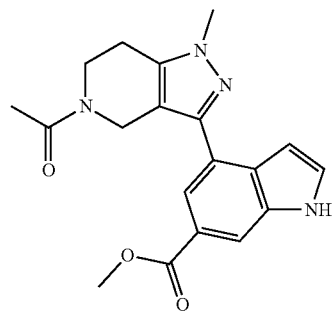
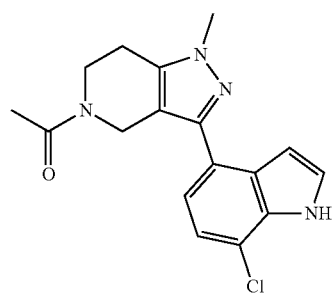
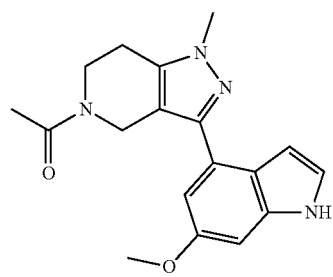
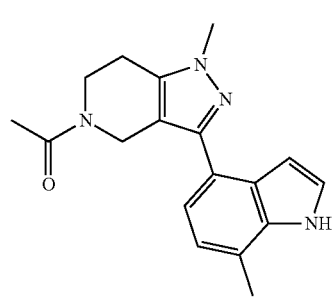
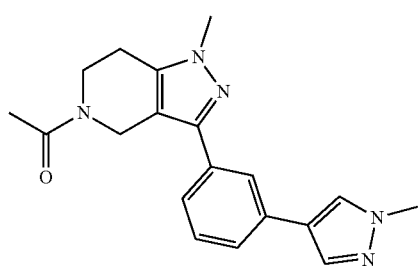
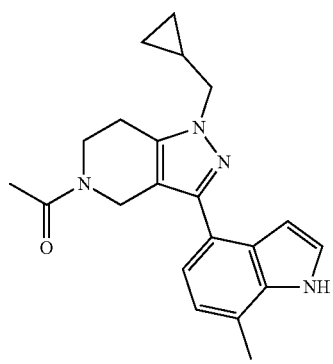
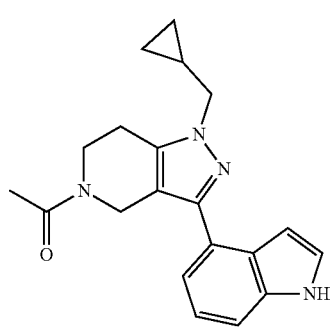
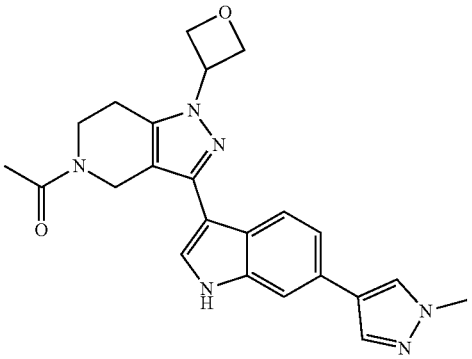
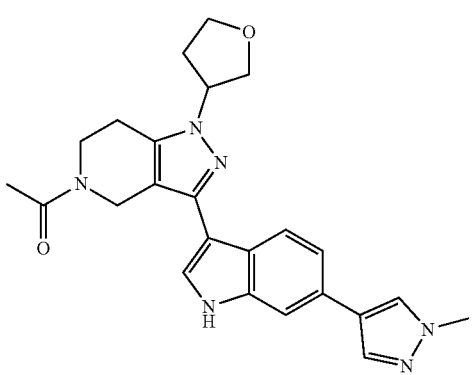

73
-continued
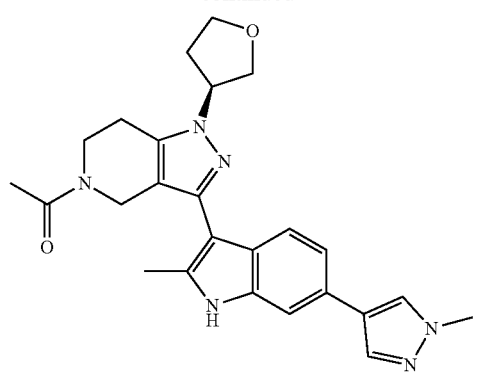
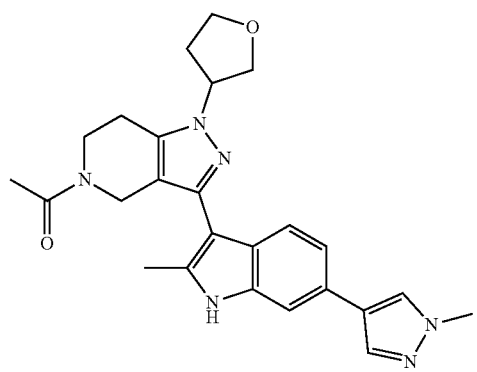
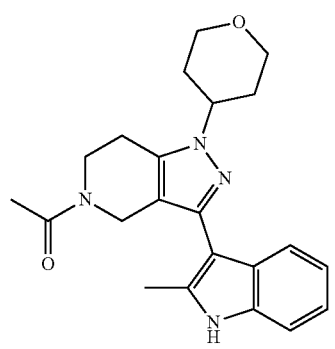
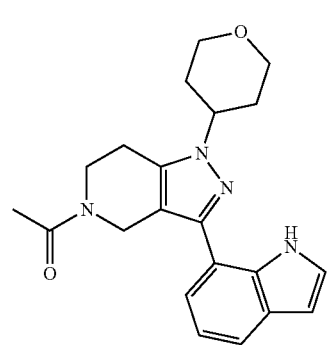
74
-continued
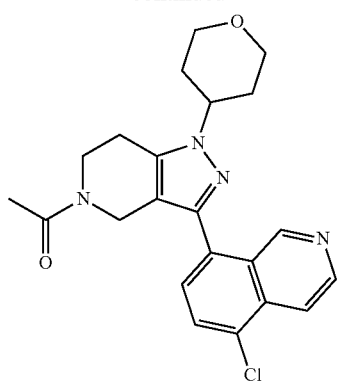
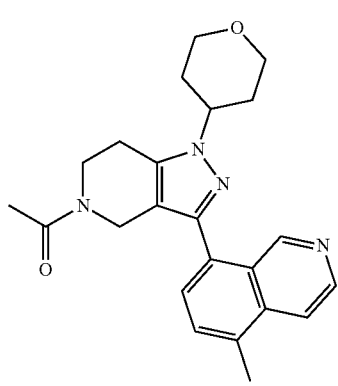
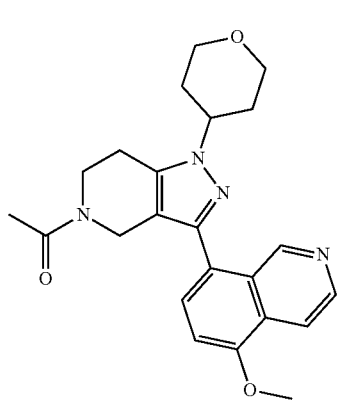
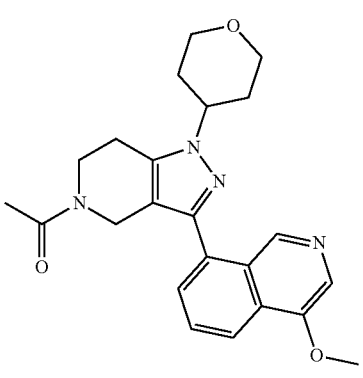

75
-continued
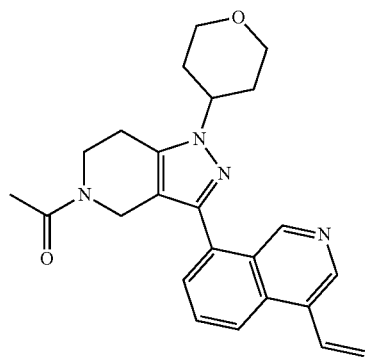
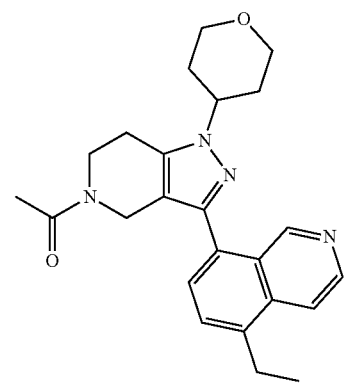
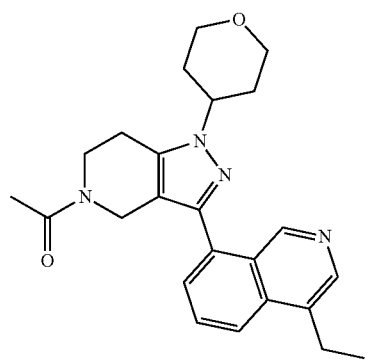
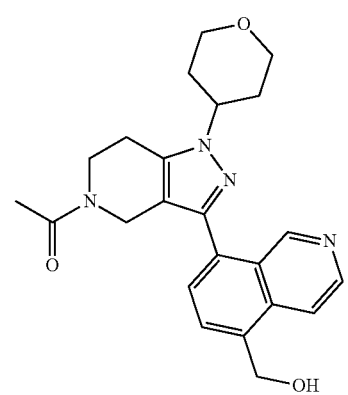
76
-continued
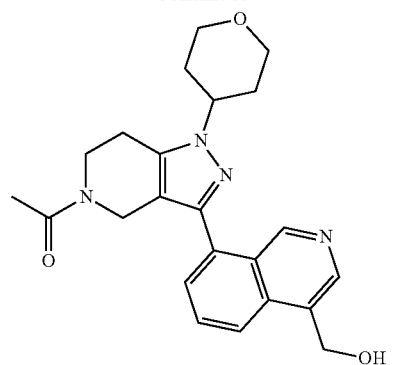
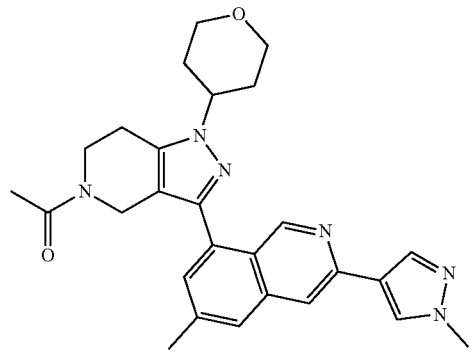
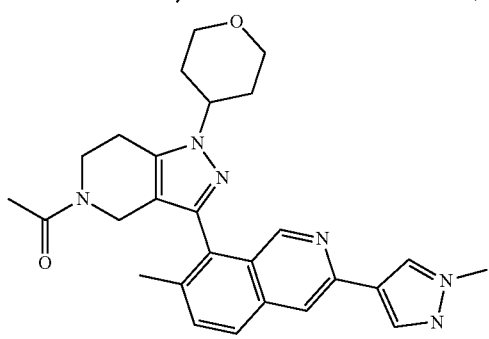
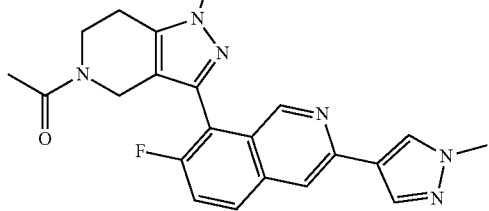
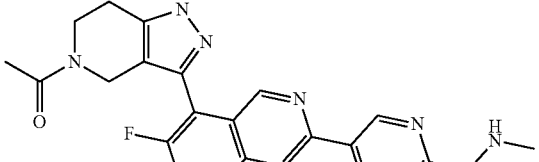

77
-continued
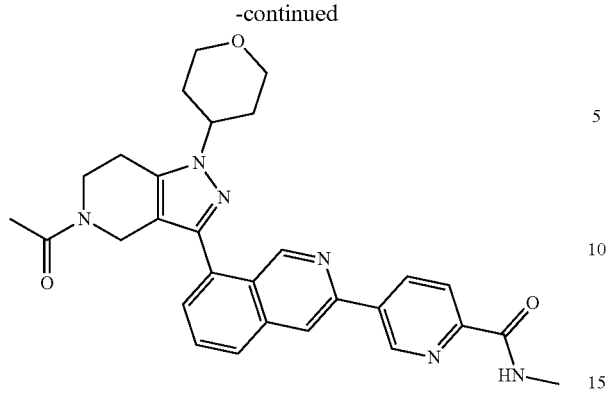
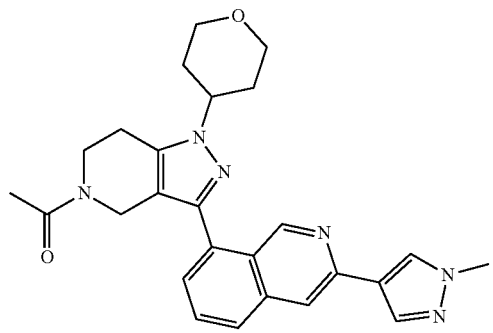
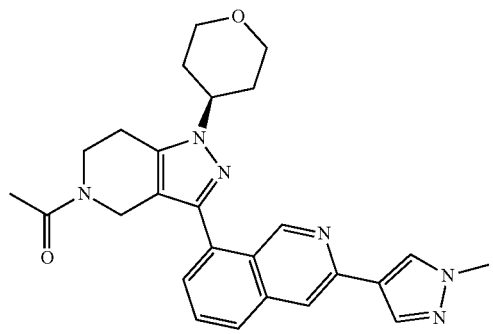
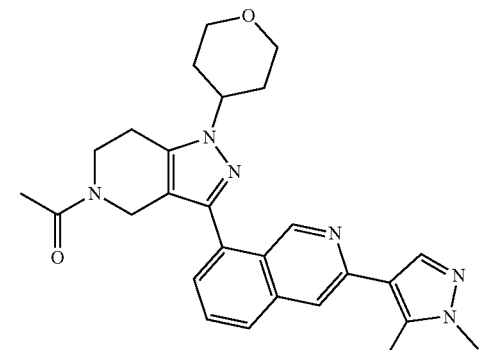
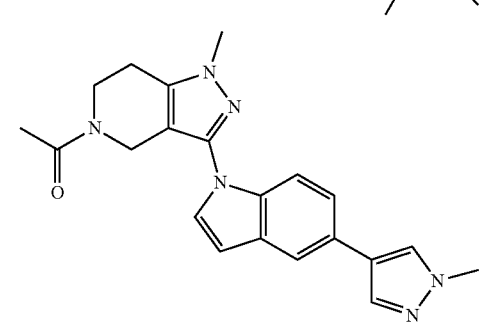
78
-continued
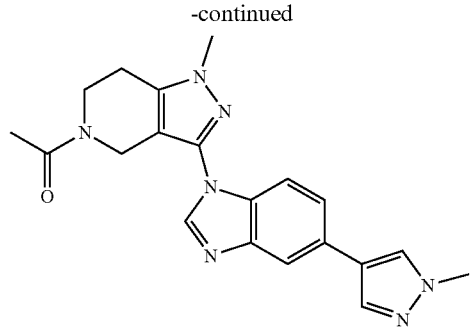
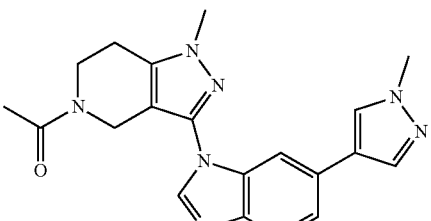
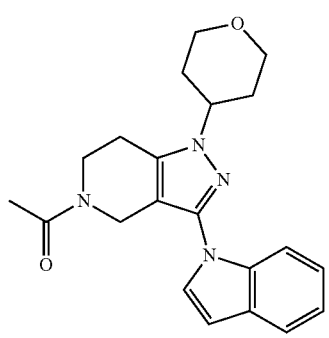
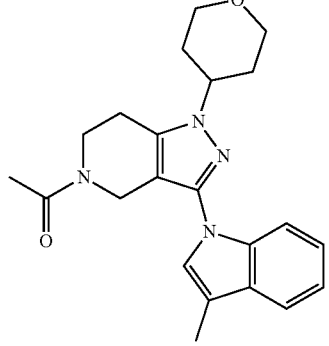
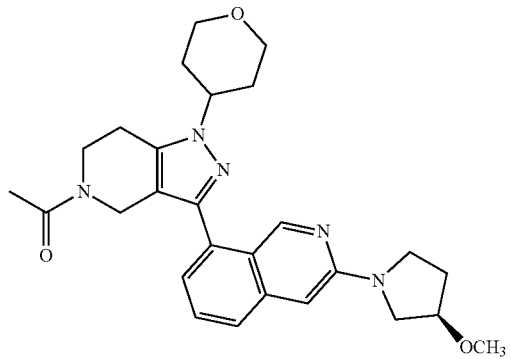

79
-continued
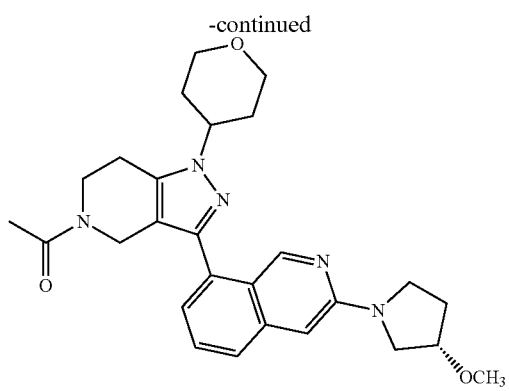
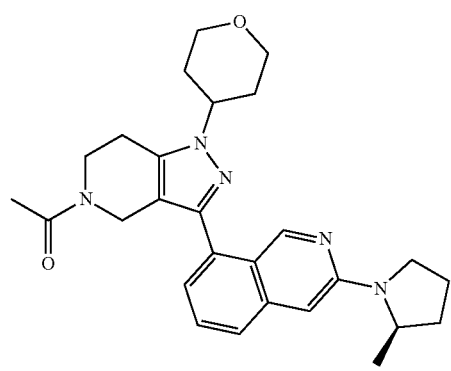
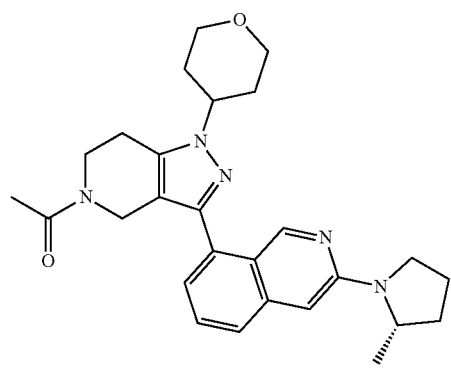
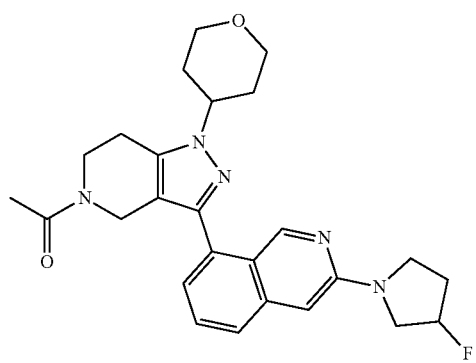
80
-continued
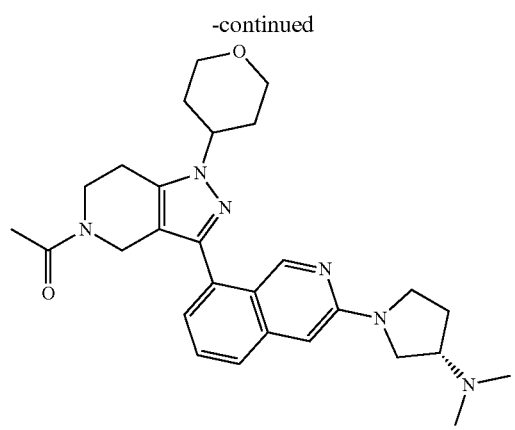
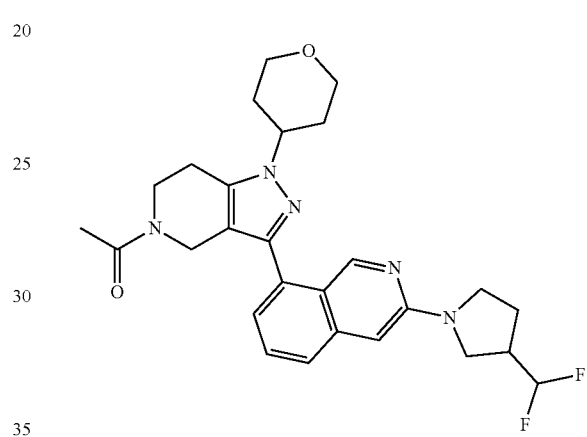
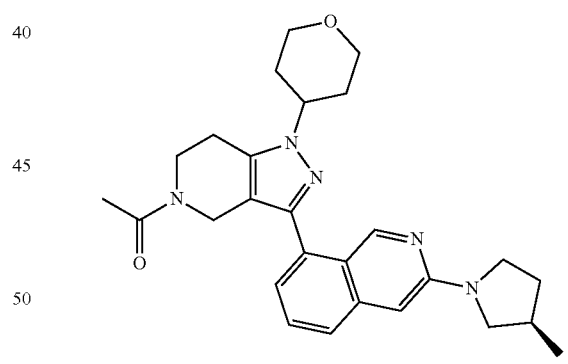
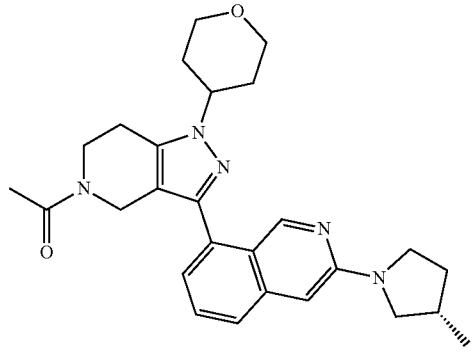

-continued
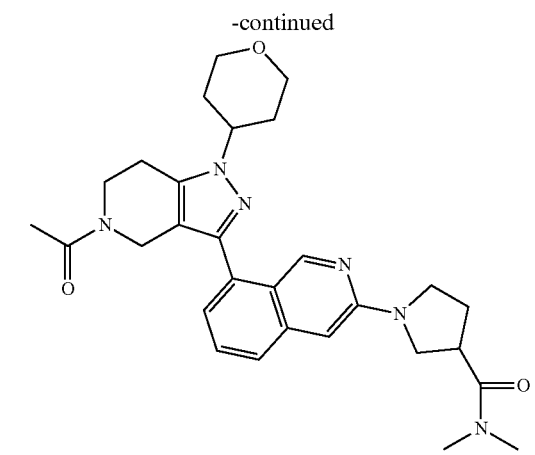
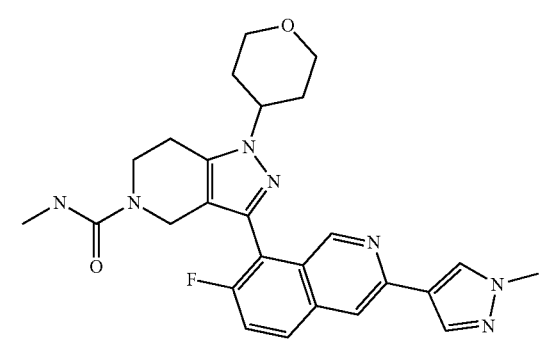
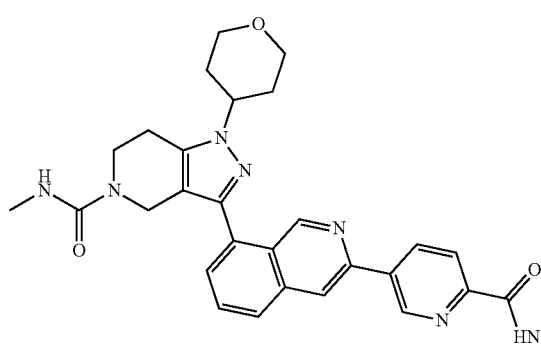
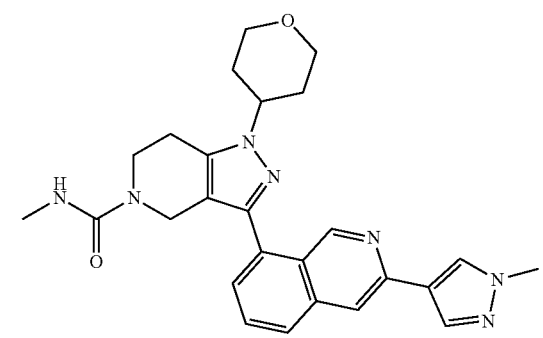
-continued
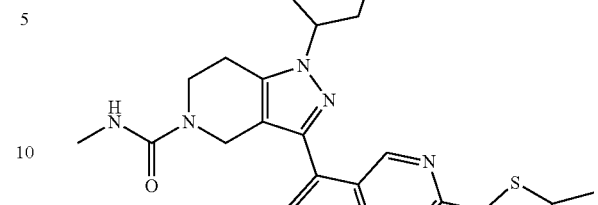
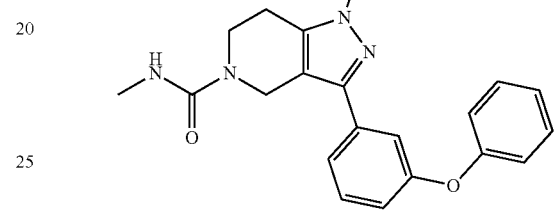
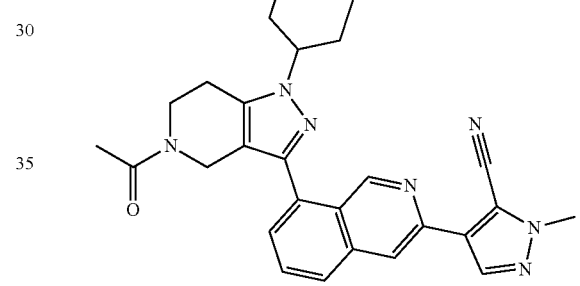
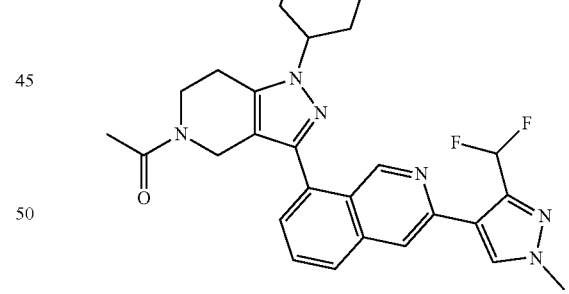
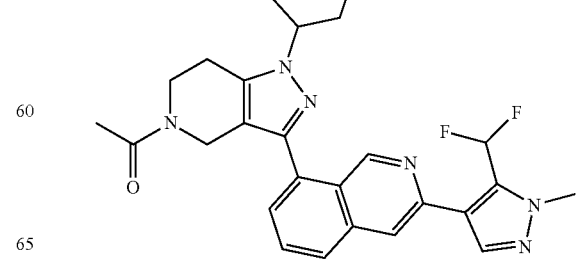

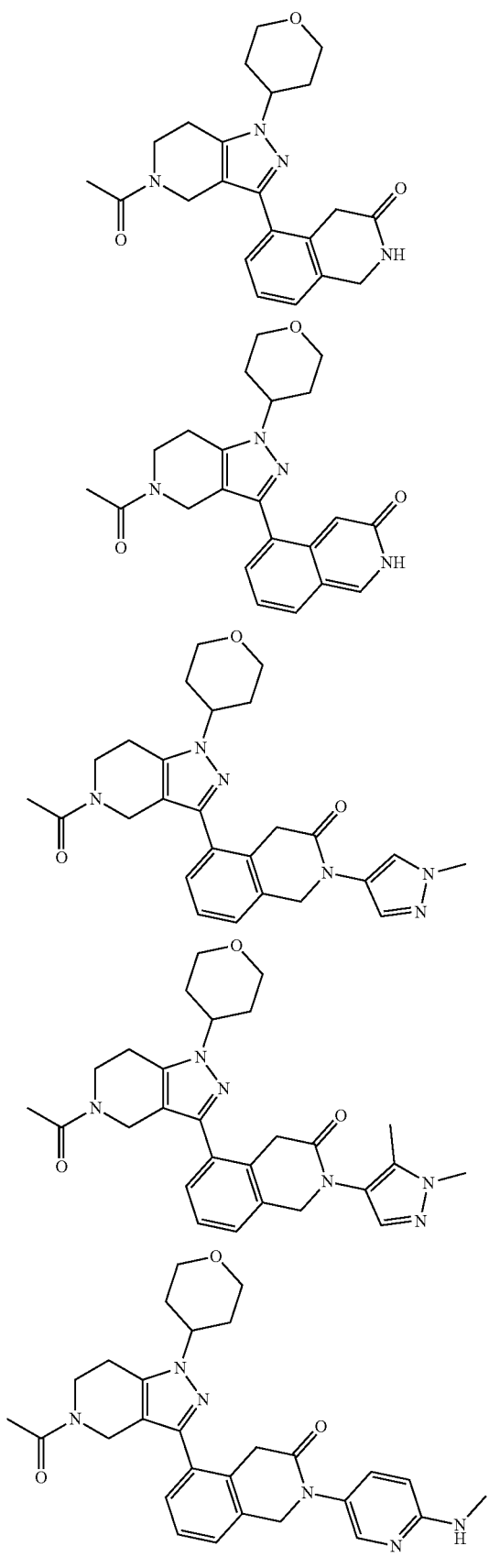
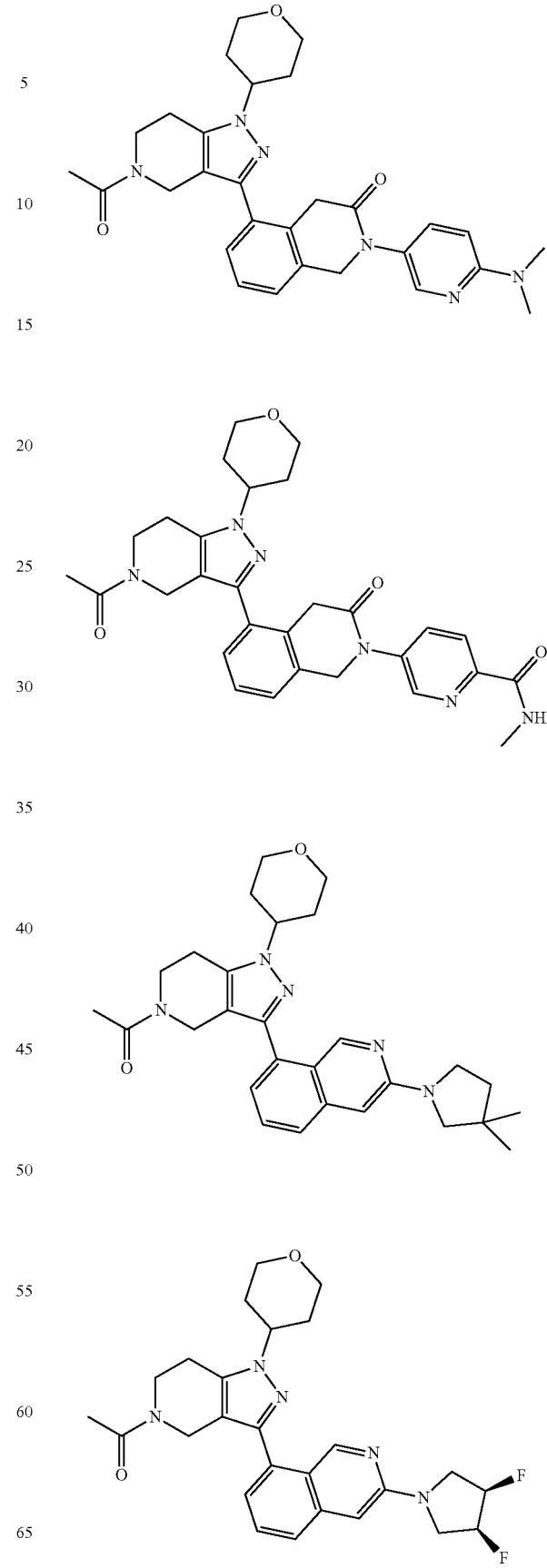

-continued

-continued
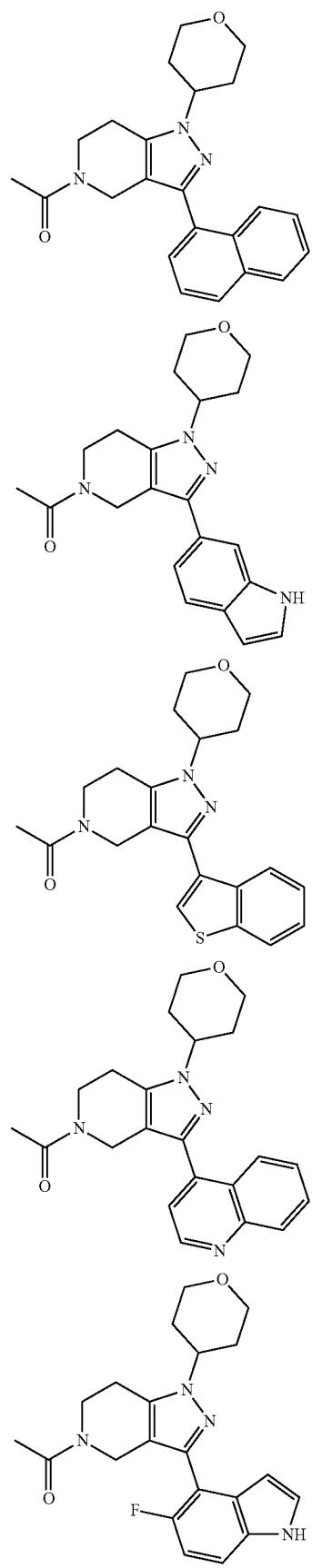
-continued
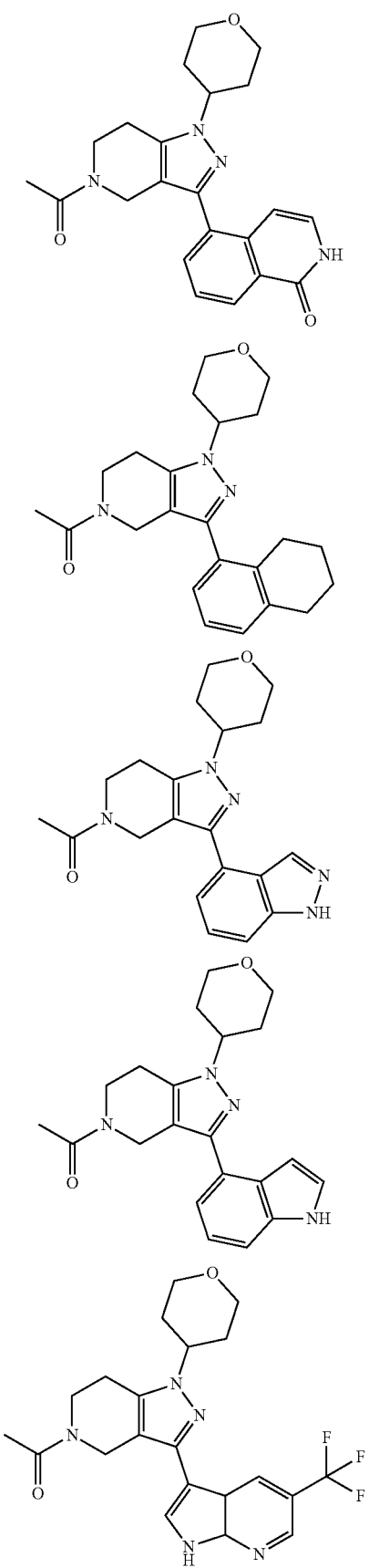

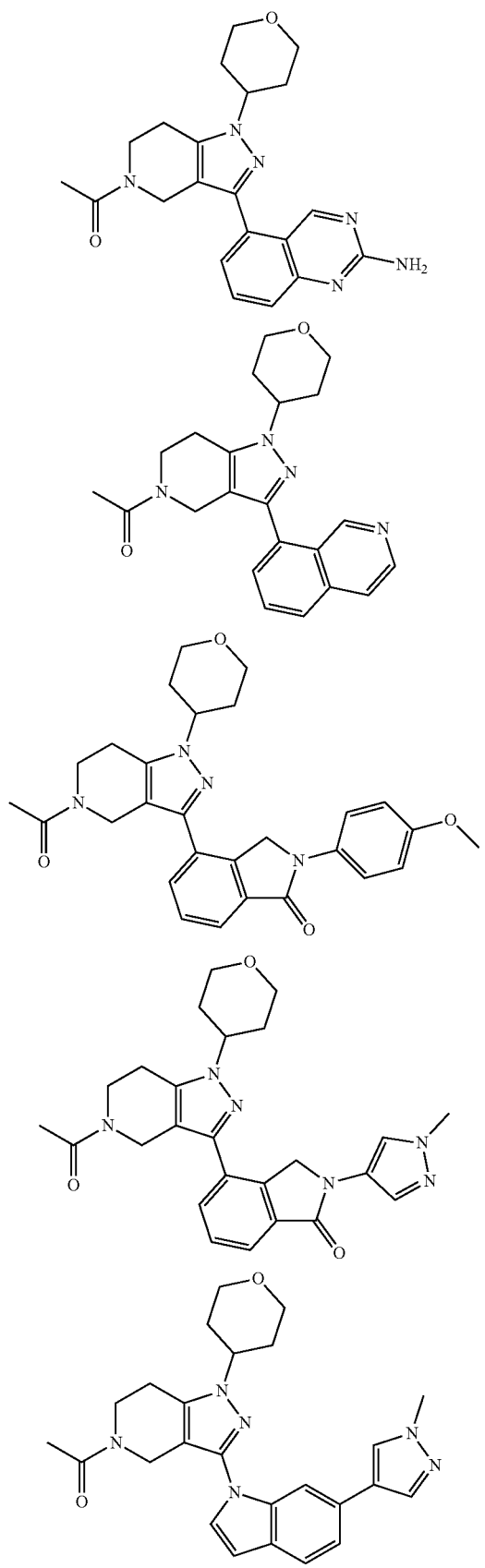
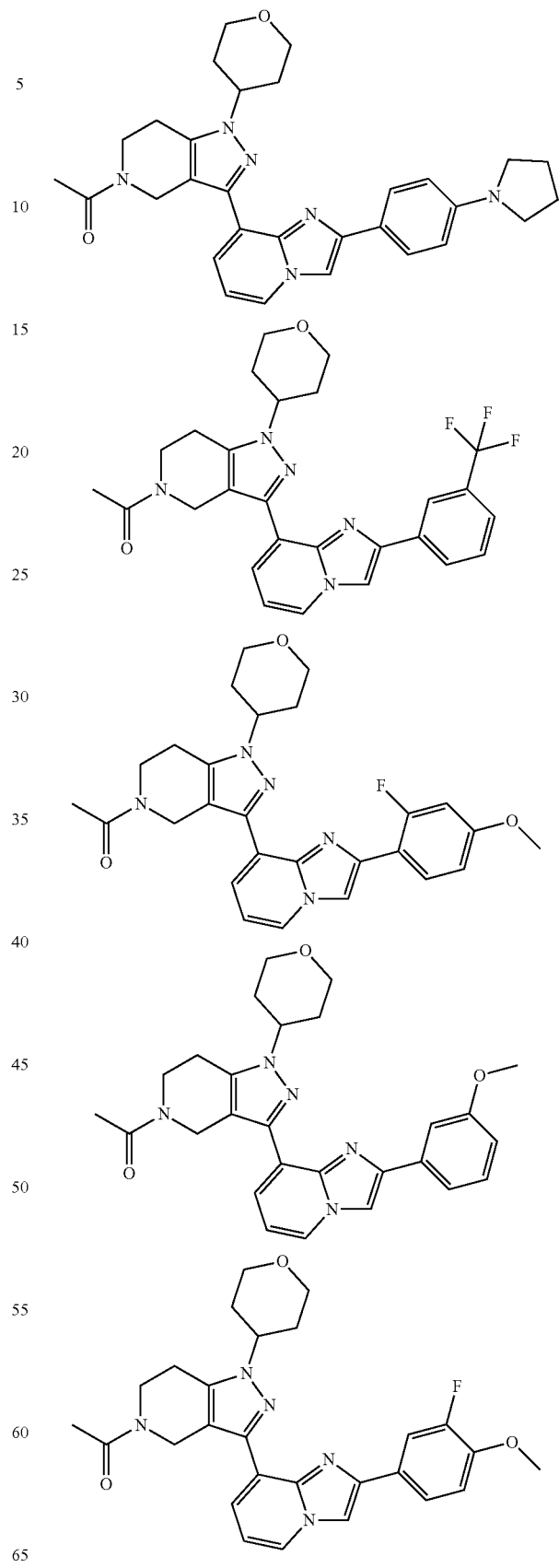

91
-continued
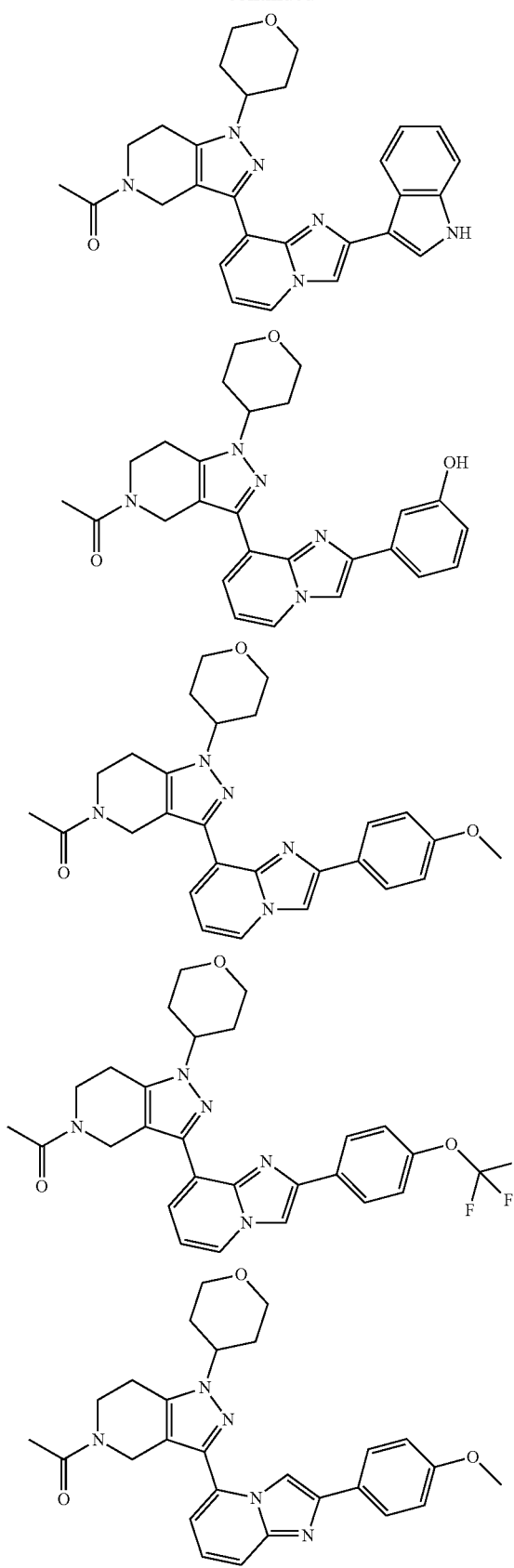
92
-continued
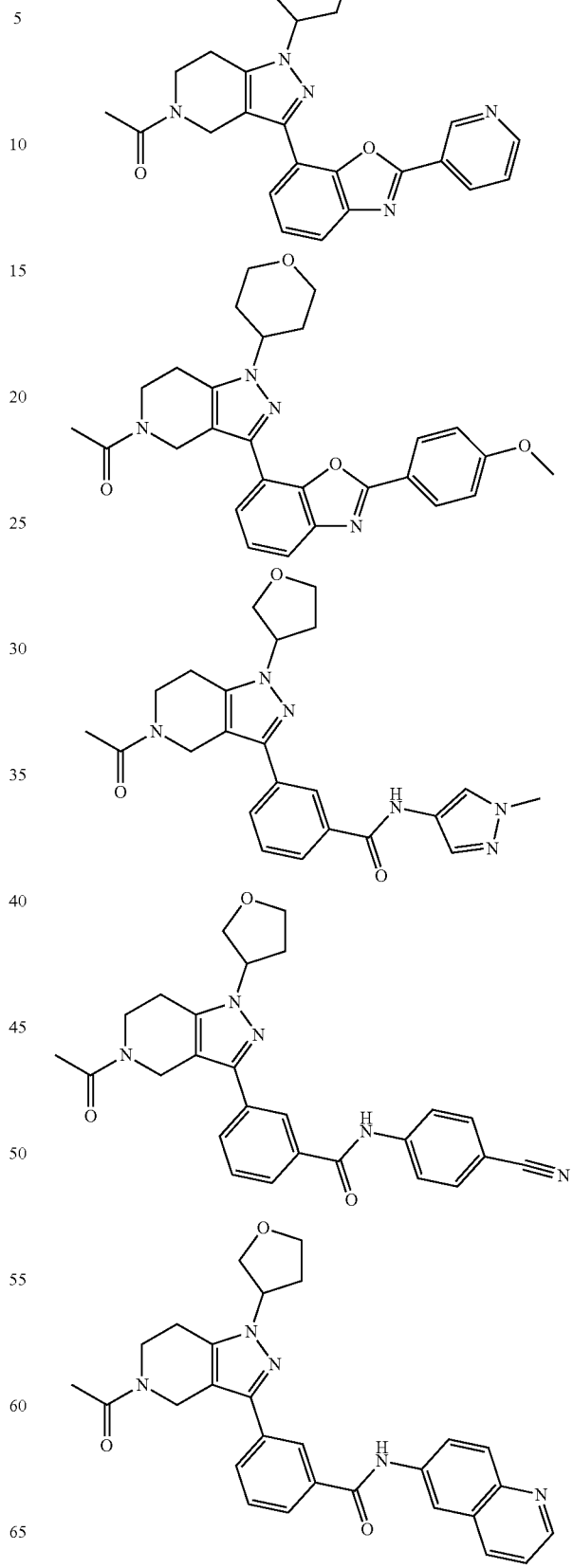

-continued
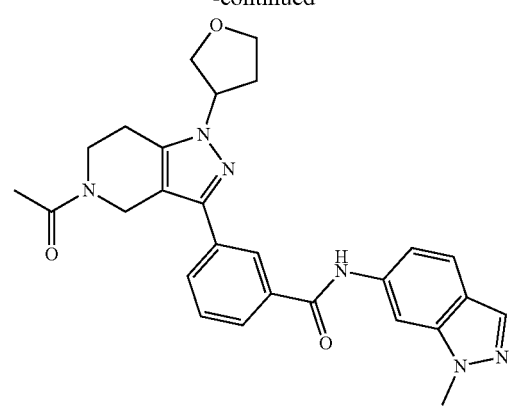
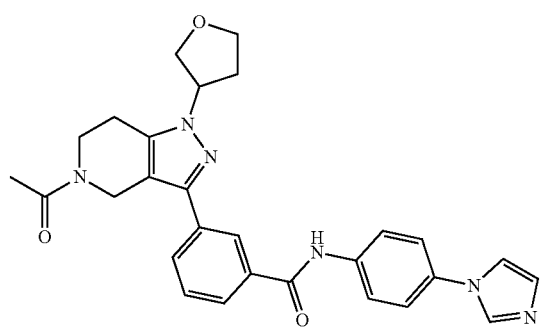
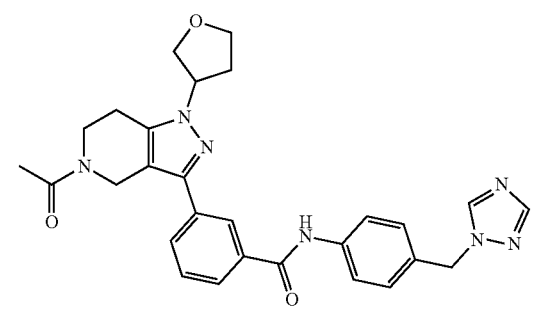
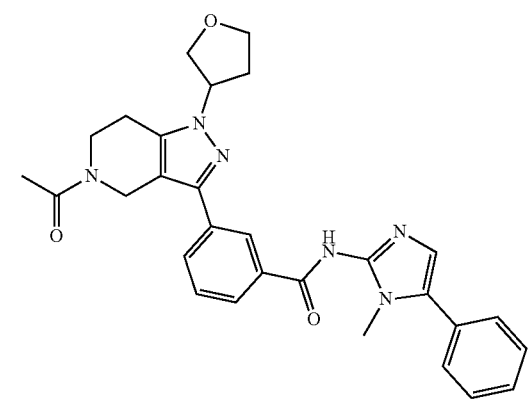
-continued
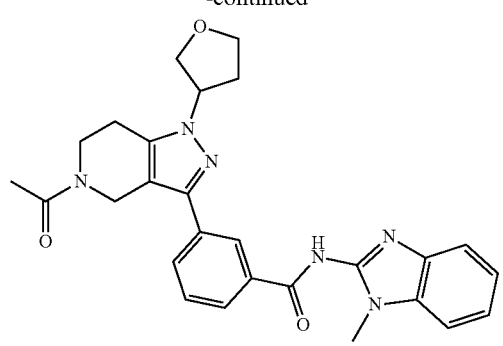
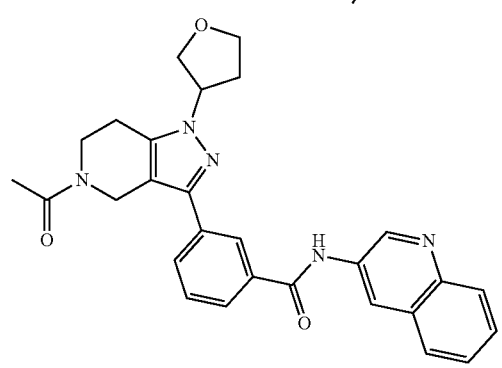
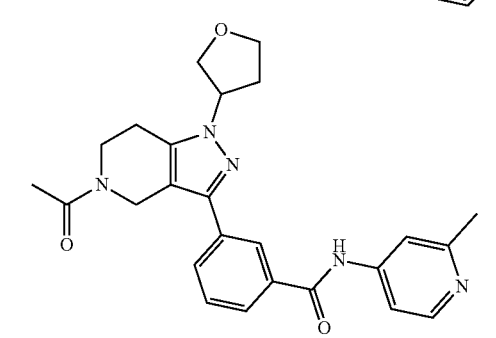
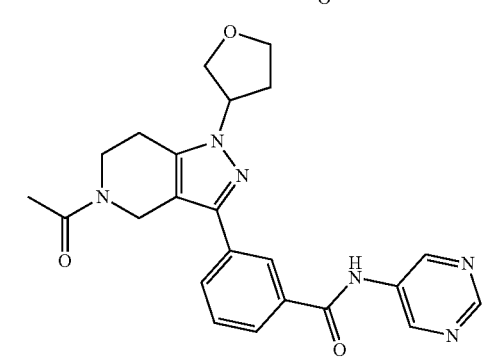
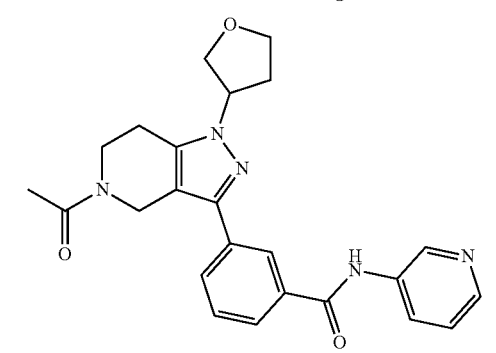

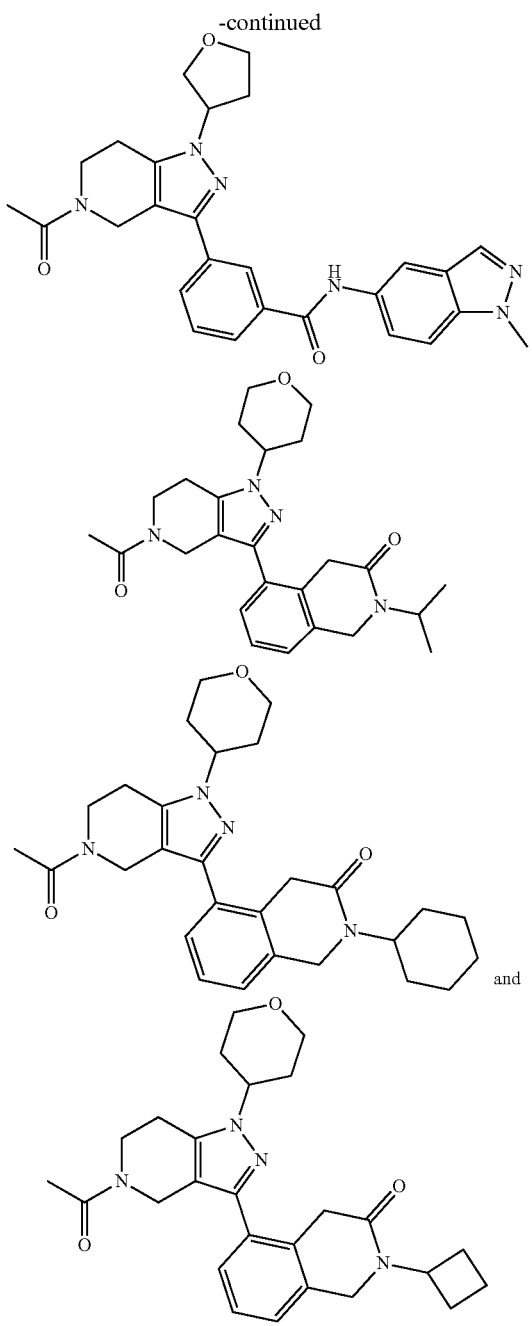

and salts thereof.

Uses, Formulation and Administration of Compounds of Formula (I)

Pharmaceutically Acceptable Compositions

Another aspect includes a pharmaceutical composition comprising a compound of formula (I) or a pharmaceutically acceptable salt thereof. In one embodiment, the composition further comprises a pharmaceutically acceptable carrier, adjuvant, or vehicle. In another embodiment, the composition further comprises an amount of the compound effective to measurably inhibit a bromodomain of CBP and/or EP300. In certain embodiments, the composition is formulated for administration to a patient in need thereof.

The term "patient" or "individual" as used herein, refers to an animal, such as a mammal, such as a human. In one embodiment, patient or individual refers to a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions comprising a compound of formula (I) or salt thereof may be administered orally, parenterally, by inhalation spray, topically, transdermally, rectally, nasally, buccally, sublingually, vaginally, intraperitoneal, intrapulmonary, intradermal, epidural or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

In one embodiment, the composition comprising a compound of formula (I) or salt thereof is formulated as a solid dosage form for oral administration. Solid dosage forms for oral administration include capsules, tablets, pills, powders, and granules. In certain embodiments, the solid oral dosage form comprising a compound of formula (I) or a salt thereof further comprises one or more of (i) an inert, pharmaceutically acceptable excipient or carrier, such as sodium citrate or dicalcium phosphate, and (ii) filler or extender such as starches, lactose, sucrose, glucose, mannitol, or silicic acid, (iii) binders such as carboxymethylcellulose, alginates, gelatin, polyvinylpyrrolidinone, sucrose or acacia, (iv) humectants such as glycerol, (v) disintegrating agent such as agar, calcium carbonate, potato or tapioca starch, alginic acid, certain silicates or sodium carbonate, (vi) solution retarding agents such as paraffin, (vii) absorption accelerators such as quaternary ammonium salts, (viii) a wetting agent such as cetyl alcohol or glycerol monostearate, (ix) absorbent such as kaolin or bentonite clay, and (x) lubricant such as talc, calcium stearate, magnesium stearate, polyethylene glycols or sodium lauryl sulfate. In certain embodiments, the solid oral dosage form is formulated as capsules, tablets or pills. In certain embodiments, the solid oral dosage form further comprises buffering agents. In certain embodiments, such compositions for solid oral dosage forms may be formulated as fillers in soft and hard-filled gelatin capsules comprising one or more excipients such as lactose or milk sugar, polyethylene glycols and the like.

In certain embodiments, tablets, dragees, capsules, pills and granules of the compositions comprising a compound of formula (I) or salt thereof optionally comprise coatings or shells such as enteric coatings. They may optionally comprise opacifying agents and can also be of a composition that they release the active ingredient(s) only, or preferentially, in a certain part of the intestinal tract, optionally, in a delayed manner. Examples of embedding compositions include polymeric substances and waxes, which may also be employed as fillers in soft and hard-filled gelatin capsules using such excipients as lactose or milk sugar as well as high molecular weight polyethylene glycols and the like.

In another embodiment, a composition comprises microencapsulated compound of formula (I) or salt thereof, and optionally, further comprises one or more excipients.

In another embodiment, compositions comprise liquid dosage formulations comprising a compound of formula (I) or salt thereof for oral administration, and optionally further comprise one or more of pharmaceutically acceptable emulsions, microemulsions, solutions, suspensions, syrups and elixirs. In certain embodiments, the liquid dosage form optionally, further comprise one or more of an inert diluent such as water or other solvent, a solubilizing agent, and an emulsifier such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols or fatty acid esters of sorbitan, and mixtures thereof. In certain embodiments, liquid oral compositions optionally further comprise one or more adjuvant, such as a wetting agent, a suspending agent, a sweetening agent, a flavoring agent and a perfuming agent.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula (I), it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

In certain embodiments, the composition for rectal or vaginal administration are formulated as suppositories which can be prepared by mixing a compound of formula (I) or a salt thereof with suitable non-irritating excipients or carriers such as cocoa butter, polyethylene glycol or a suppository wax, for example those which are solid at ambient temperature but liquid at body temperature and therefore melt in the rectum or vaginal cavity and release the compound of formula (I).

Example dosage forms for topical or transdermal administration of a compound of formula (I) include ointments, pastes, creams, lotions, gels, powders, solutions, sprays, inhalants or patches. The compound of formula (I) or a salt thereof is admixed under sterile conditions with a pharmaceutically acceptable carrier, and optionally preservatives or buffers. Additional formulation examples include an ophthalmic formulation, ear drops, eye drops, transdermal patches. Transdermal dosage forms can be made by dissolving or dispensing the compound of formula (I) or a salt thereof in medium, for example ethanol or dimethylsulfoxide. Absorption enhancers can also be used to increase the flux of the compound across the skin. The rate can be controlled by either providing a rate controlling membrane or by dispersing the compound in a polymer matrix or gel.

Nasal aerosol or inhalation formulations of a compound of formula (I) or a salt thereof may be prepared as solutions in saline, employing benzyl alcohol or other suitable preservatives, absorption promotors to enhance bioavailability, fluorocarbons, and/or other conventional solubilizing or dispersing agents.

In certain embodiments, pharmaceutical compositions may be administered with or without food. In certain embodiments, pharmaceutically acceptable compositions are administered without food. In certain embodiments, pharmaceutically acceptable compositions of this invention are administered with food.

Specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound of formula (I) or salt thereof in the composition will also depend upon the particular compound in the composition.

In one embodiment, the therapeutically effective amount of the compound of the invention administered parenterally per dose will be in the range of about 0.01-100 mg/kg, alternatively about 0.1 to 20 mg/kg of patient body weight per day, with the typical initial range of compound used being 0.3 to 15 mg/kg/day. In another embodiment, oral unit dosage forms, such as tablets and capsules, contain from about 5 to about 100 mg of the compound of the invention.

An example tablet oral dosage form comprises about 2 mg, 5 mg, 25 mg, 50 mg, 100 mg, 250 mg or 500 mg of a compound of formula (I) or salt thereof, and further comprises about 5-30 mg anhydrous lactose, about 5-40 mg sodium croscarmellose, about 5-30 mg polyvinylpyrrolidone (PVP) K30 and about 1-10 mg magnesium stearate. The process of formulating the tablet comprises mixing the powdered ingredients together and further mixing with a solution of the PVP. The resulting composition can be dried, granulated, mixed with the magnesium stearate and compressed to tablet form using conventional equipment. An example of an aerosol formulation can be prepared by dissolving about 2-500 mg of a compound of formula (I) or salt thereof, in a suitable buffer solution, e.g. a phosphate buffer, and adding a tonicifier, e.g. a salt such sodium chloride, if desired. The solution may be filtered, e.g. using a 0.2 micron filter, to remove impurities and contaminants.

Uses of Compounds and Pharmaceutically Acceptable Compositions

Another aspect includes the use of a compound of formula (I) or a salt thereof for the inhibition of a bromodomain (in vitro or in vivo) (e.g., in vitro or in vivo inhibition of the bromodomain of CBP/EP300).

Another embodiment includes a method for treating a bromodomain-mediated disorder (e.g., CBP/EP300 bromodomain-mediated disorder) in an animal comprising administering a compound of formula (I), or a pharmaceutically acceptable salt thereof to the animal. CBP/EP300-mediated disorders include, but are not limited to those disorders described herein.

Another embodiment includes a method of increasing efficacy of a cancer treatment comprising a cytotoxic agent in an animal comprising administering to the animal an effective amount of a compound of formula (I) or a pharmaceutically acceptable salt thereof.

Another embodiment includes a method of extending the duration of response to a cancer therapy in an animal, comprising administering to an animal undergoing the cancer therapy a compound of formula (I) or a pharmaceutically acceptable salt thereof, wherein the duration of response to the cancer therapy when the compound of formula (I) or the pharmaceutically acceptable salt thereof is administered is extended over the duration of response to the cancer therapy in the absence of the administration of the compound of formula (I) or the pharmaceutically acceptable salt thereof.

Another embodiment includes a method of treating cancer in an individual comprising administering to the individual (a) a compound of formula (I) or a pharmaceutically acceptable salt thereof, and (b) a cytotoxic agent. In one embodiment the cytotoxic agent is selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine or a pharmaceutically acceptable salt thereof (e.g., erlotinib). In one embodiment the cytotoxic agent is a RAF inhibitor. In one embodiment the RAF inhibitor is a BRAF or CRAF inhibitor. In one embodiment the RAF inhibitor is vemurafenib. In one embodiment the cytotoxic agent is a PI3K inhibitor.

In certain embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the CBP/EP300 bromodomain inhibitor interferes with the associating of CBP and/or EP300 with histones, in particular acetylated lysines in histones. In some embodiments, the CBP/EP300 bromodomain inhibitor inhibits binding of CBP and/or EP300 to chromatin (e.g., histone associated DNA). In some embodiments, the CBP/EP300 bromodomain inhibitor inhibits and/or reduces binding of the CBP bromodomain and/or EP300 bromodomain to chromatin (e.g., histone associated DNA).

In some embodiments, the CBP/EP300 bromodomain inhibitor does not affect association of other domains of CBP and/or EP300 to chromatin. In some embodiments, CBP/EP300 bromodomain inhibitor binds to the CBP and/or EP300 primarily (e.g., solely) through contacts and/or interactions with the CBP bromodomain and/or EP300 bromodomain. In some embodiments, CBP/EP300 bromodomain inhibitor binds to the CBP and/or EP300 through contacts and/or interactions with the CBP bromodomain and/or EP300 bromodomain as well as additional CBP and/or EP300 residues and/or domains. Methods of assaying association with chromatin are known in the art and include, but are not limited to, chromatin fractionation, BRET assay (Promega), FRAP assay, Chromatin Immunoprecipitation (ChIP), biophysical binding assay, and/or Histone Association Assay. See, e.g., Das et al., *BioTechniques* 37:961-969 (2004).

In some embodiments, the CBP/EP300 bromodomain inhibitor does not affect effector function in CD8 cells (i.e., effector function is substantially the same in the presence and/or absence of the CBP/EP300 bromodomain inhibitor). In some embodiments, the CBP/EP300 bromodomain inhibitor does not affect expression levels of perforin, granzyme, and/or EOMES (i.e., expression levels of one or more perforin, granzyme, and/or EOMES are substantially the same in the presence and/or absence of the CBP/EP300 bromodomain inhibitor). In some embodiments, the CBP/EP300 bromodomain inhibitor does not affect expression levels of effector cytokines IFN-γ and/or TNFα (i.e., expression levels of effector cytokines IFN-γ and/or TNFα are substantially the same in the presence and/or absence of the CBP/EP300 bromodomain inhibitor). In some embodiments, the CBP/EP300 bromodomain inhibitor enhances naïve T cell responsiveness to CD3/CD28 stimulation in the presence of Treg cells.

In some embodiments, the CBP/EP300 bromodomain inhibitor does not substantially bind to (e.g., does not bind to) the HAT domain of CBP and/or EP300. In some embodiments, the CBP/EP300 bromodomain inhibitor does not substantially bind to (e.g., does not bind to) the HAT domain of CBP and/or EP300 as identified in Delvecchio et al., *Nat. Struct. & Mol. Biol.* 20:1040-1046 (2013), which is incorporated by reference in its entirety. In some embodiments, the CBP/EP300 bromodomain inhibitor does not substantially bind to one or more residues of the amino acid sequence ENKFSAKRLQTTR LGNHLEDRVNKFLRRQNHPEAGEVFVRV-VASSDKTVEVKPGMKSRFVDSGEMSESFPY RTKAL-FAFEEIDGVDVCFFGMHVQEYGSDCPPPNTRRVYIS YLDSIHFFRPRcLRTAVYH EILIGY-LEYVKKLGYVTGHIWACPPSEGD-DYIFHCHPPDQKIPKPKRLQEWYKKMLDKA FAER-IIHDYKDIFKQATEDRLTSAKELPYFEGDFWPNVLE ESIKELEQEEEERKKEESTAA SETTEGSQGD-SKNAKKKNNKKTNKNKSSIS-RANKKKPSMPNVSNDLSQKLYATMEKH KEV-FFVIHLHAGPVINTLPPIVDPDPLLSCDLMDGRDAFLT-LARDKHWEFSSLRRSKWST LCMLVELHTQGQD (amino acid residues 1321-1701 of UniProt No. Q92793 (SEQ ID NO: 1)). In some embodiments, the CBP/EP300 bromodomain inhibitor does not substantially bind to one or more residues of the amino acid sequence ENKFSAKRLP-STRLGTFLENRVNDFLRRQNHPESGEVTVRVVH-ASDKTVEVKPGMKAR FVDSGEMAESFPYRTKALFA-FEEIDGVDLCFFGMHVQEYGSDCPPPNQRRVYISYL DSV HFFRPKCLRTAVYHEILIGYLEYVKKLGYTTGHI- WACPPSEGDDYIFHCHPPDQKIPKPK
RLQEWYKKMLDKAVSERIVHDYKDIFKQATEDRLT-
SAKELPYFEGDFWPNVLEESIKEL EQEEEER-
KREENTSNESTDVTKGDSKNAKK-
KNNKKTSKNKSSLSRGNKKKPGMPNVSN
DLSQKLYATMEKHKEVFFVIRLIAGPAANSLPPIV-
DPDPLIPCDLMDGRDAFLTLARDKH LEFSSLR-
RAQWSTMCMLVELHTQSQD (amino acid residues 1285-1664 of UniProt No. Q09472 (SEQ ID NO:2)). In some embodiments, the CBP/EP300 bromodomain inhibitor does not inhibit the histone acetyltransferase (HAT) catalytic activity of CBP and/or EP300.

Compounds that are CBP/EP300 bromodomain inhibitors are expected to have improved and/or distinct properties over other compounds, such as "HAT" inhibitor compounds. HAT inhibition is expected to result in a global reduction in protein acetylation (histone and non-histone), likely affecting cell viability in a significant way. In some embodiments, CBP/EP300 bromodomain inhibition preserves the HAT activity of these proteins while resulting in the reduction of transcriptional activity of a relatively small subset of target genes.

In some embodiments, provided are methods of enhancing immune function in an individual having cancer comprising administering an effective amount of any CBP/EP300 bromodomain inhibitors disclosed herein. In some embodiments of any of the methods, the CD8 T cells in the individual have enhanced priming, activation, proliferation, and/or cytolytic activity relative to prior to the administration of the CBP/EP300 bromodomain inhibitor. In some embodiments, the number of CD8 T cells is elevated relative to prior to administration of the CBP/EP300 bromodomain inhibitors. In some embodiments, the CD8 T cells have reduced levels of expression of one or more of the following biomarkers: IFNA17, IGF1, FSCN1, SUMO2, C1orf129, EIF2S2, TDGF1, AIDA, CCR4, CD160, MC4R, KRTAP2-2, MTIJP, OR4N2, KRTAP4-5, MTIL//MTIL, ILI3, LCEID, KIR2DL2, LOC158696, LIF, 1L28A, TAS2R13, CTLA4, and/or FOXP3 relative to prior to administration of the CBP/EP300 bromodomain inhibitor. In some embodiments, the CD8 T cells have reduced levels of expression of CD160 and/or KIR2DL2 relative to prior to administration of the CBP/EP300 bromodomain inhibitor.

In some embodiments of the methods of enhancing immune function, the enhanced immune function is characterized by Treg cells in the individual (e.g., at the tumor site(s)) have reduced levels of expression of one or more of the following markers: 1L28A, GPR87, ANKRD37, CABLES1, RAPGEF2, TRIM69, MT1L//MT1L, FAM1138, FOXP3, CSF2, OCM2, GLIPR1, FGFBP2, CTLA4, CST7, GOLGA6L1, IFIT3, FAMI3A, APOD, AK2, CLDN1, HSD11B1, DNAJC12, PHEX, IL2, FOXD4L3, GNA15, ZBTB32, RDH10, OR52E5, CYP2A6, GZMH, CCL20, ADM, LOC100131541, RNF122, FAM36A, AMY2B, GPR183, MYOF, IL29, AIDA, SPRYI, ENOPH1, IL1RN, SLAMF1, PGM2L1, SSBP3, MMP23B, HISTIH3J, MYO1B, BENDS, S1PR1, CDK6, GPR56, ZC3HIZA, DOK5, DUSPI, CYB5R2, KCNAB2, LAG3, KLF10, GK, SHC4, IL12RB2, CD109, HAVCR2 (TIM-3), LTA, FAM40B, HMGCSI, HSPA1A, ZNF705A, CMAH, KIF3A, CHN1, KBTBD8, TNF, MOP-1, RASGRP4, INSIG1, SLAMF7, OR10H4, LPL, HIST1H2BJ, LIF, IGF1, ILI8RAP, OR52N4, OR1D2, CCR4, CXCR5, IL1R1, MICAL2, NRN1, PICALM, B3GNT5, IFI44L, CXCR3, ICOS, IFIT2, NCR3, HSPA1B, CD80, GNG2, C7orf68, GPRl71, RPSl0P7, IL23A, LOC283174, PLK2, EMP1, FNBP1L, CD226, RBMS3, IL23R, PTGER4, GZMB, F5, and/or HIST1H2BK relative to prior to administration of CBP/EP300 bromodomain inhibitor. In some embodiments, the Treg cell biomarker is one or more of LAG3, CTLA4, and/or FOXP3. In some embodiments of the methods of enhancing immune function, the enhanced immune function is characterized by enhanced naive T cell responsiveness to CD3/CD28 stimulation in the presence of Treg cells. In some embodiments, the CD8 T cell priming is characterized by increased T cell proliferation and/or enhanced cytolytic activity in CD8 T cells. In some embodiments, the CD8 T cell activation is characterized by an elevated frequency of T-IFN$^+$ CD8 T cells. In some embodiments, the CD8 T cell is an antigen-specific T-cell. In some embodiments, the immune evasion is inhibited.

In some embodiments, the methods provided herein are useful in treating conditions where enhanced immunogenicity is desired such as increasing tumor immunogenicity for the treatment of cancer. For example, provided herein are CBP/EP300 bromodomain inhibitors for use to enhance T-cell function to upregulate cell-mediated immune responses and for the treatment of T cell dysfunctional disorders, tumor immunity. In some embodiments, the CBP/EP300 bromodomain inhibitors promote anti-tumor immunity by inhibiting the suppressive function of regulatory T (Treg) cells and/or relieving T cell exhaustion on chronically stimulated CD8$^+$ T cells. CBP/EP300 bromodomain inhibitors are further useful in reducing FOXP3 expression during extra-thymic Treg cell differentiation. Continual FOXP3 expression is essential to maintain suppressive activity in Treg cells. In some embodiments, reduced FOXP3 expression through CBP/EP300 bromodomain inhibition impairs Treg cells suppressive activity and promotes tumor antiimmunity. Treg cells are highly enriched in tumors derived from multiple cancer indications, including melanoma, NSCLC, renal, ovarian, colon, pancreatic, hepatocellular, and breast cancer. In a subset of these indications, increased intratumoral Treg cell densities are associated with poor patient prognosis. These indications include NSCLC, ovarian, pancreatic, hepatocellular, and breast cancer. CBP/EP300 bromodomain inhibitors are predicted to impair intratumoral Treg cell function in these cancer indications to enhance effector T cell activity. In other embodiments, the CBP/EP300 bromodomain inhibitors may be used to treat infectious diseases, where some pathogens may have evolved to manipulate regulatory T (Treg) cells to immunosuppress the host to ensure survival, such as in retroviral infections (e.g., HIV), mycobacterial infections (e.g., tuberculosis), and parasitic infections (e.g., Leishmania and malaria).

In some embodiments, the methods provided herein are useful in treating a CBP and/or EP300-mediated disorder involving fibrosis. In some embodiments, the CBP and/or EP300-mediated disorder is a fibrotic disease. Certain fibrotic diseases may include, for example, pulmonary fibrosis, silicosis, cystic fibrosis, renal fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, systemic sclerosis or arthro fibrosis.

In other embodiments, the CBP and/or EP300-mediated disorder is a fibrotic lung disease. Fibrotic lung diseases may include, for example, idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD), or pulmonary arterial hypertension. In certain embodiments, the fibrotic lung disease is idiopathic pulmonary fibrosis.

CBP and/or EP300-Mediated Disorders

A "CBP and/or EP300-mediated disorder" is characterized by the participation of the bromodomains of CBP and/or EP300 in the inception, manifestation of one or more symptoms or disease markers, severity, or progression of a disorder. In one embodiment the bromodomain-mediated disorder is a CBP bromodomain-mediated disorder. In one embodiment the bromodomain-mediated disorder is an EP300 bromodomain-mediated disorder.

CBP and/or EP300 bromodomain-mediated disorders include cancers, including, but not limited to acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstr6m's macroglobulinemia, testicular tumors, uterine cancer and Wilms' tumor.

In certain embodiments, the cancer is lung cancer, breast cancer, pancreatic cancer, colorectal cancer, and/or melanoma. In certain embodiments, the cancer is lung. In certain embodiments, the lung cancer is NSCLC. In certain embodiments, the cancer is breast cancer.

In certain embodiments, the cancer is melanoma.

CBP and/or EP300-mediated disorders also include inflammatory diseases, inflammatory conditions, and autoimmune diseases, including, but not limited to: Addison's disease, acute gout, ankylosing spondylitis, asthma, atherosclerosis, Behcet's disease, bullous skin diseases, chronic obstructive pulmonary disease (COPD), Crohn's disease, dermatitis, eczema, giant cell arteritis, glomerulonephritis, hepatitis, hypophysitis, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

CBP and/or EP300-mediated disorders also include AIDS; chronic kidney diseases, including, but are not limited to diabetic nephropathy, hypertensive nephropathy, HIV-associated nephropathy, glomerulonephritis, lupus nephritis, IgA nephropathy, focal segmental glomerulosclerosis, membranous glomerulonephritis, minimal change disease, polycystic kidney disease and tubular interstitial nephritis; acute kidney injury or disease or condition including, but are not limited to ischemia-reperfusion induced, cardiac and major surgery induced, percutaneous coronary intervention induced, radio-contrast agent induced, sepsis induced, pneumonia induced, and drug toxicity induced; obesity; dyslipidemia; hypercholesterolemia; Alzheimer's disease; metabolic syndrome; hepatic steatosis; type II diabetes; insulin resistance; and diabetic retinopathy.

CBP and/or EP300 inhibitors may also be used to provide male contraception.

CBP and/or EP300-mediated disorders also include fibrotic diseases. Certain fibrotic diseases may include, for example, pulmonary fibrosis, silicosis, cystic fibrosis, renal fibrosis, liver fibrosis, liver cirrhosis, primary sclerosing cholangitis, primary biliary cirrhosis, endomyocardial fibrosis, mediastinal fibrosis, myelofibrosis, retroperitoneal fibrosis, progressive massive fibrosis, nephrogenic systemic fibrosis, Crohn's disease, keloid, myocardial infarction, systemic sclerosis or arthro fibrosis.

CBP and/or EP300-mediated disorders also include fibrotic lung diseases. Fibrotic lung diseases may include, for example, idiopathic pulmonary fibrosis, fibrotic interstitial lung disease, interstitial pneumonia, fibrotic variant of non-specific interstitial pneumonia, cystic fibrosis, lung fibrosis, chronic obstructive pulmonary lung disease (COPD), or pulmonary arterial hypertension. In certain embodiments, the fibrotic lung disease is idiopathic pulmonary fibrosis.

Co-Administration of Compounds and Other Agents

The compounds of formula (I) or salts thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound of formula (I) or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula (I), an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound of formula (I) or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signaling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin;

phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4 Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166

((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6 [5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin; podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; famesyltransferase inhibitors such as lonafamib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lomoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound of the present invention is administered in combination with a biologic agent, such as bevacizumab or panitumumab.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®), glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin. Additionally, chemotherapeutic agents include pharmaceutically acceptable salts, acids or derivatives of any of chemotherapeutic agents, described herein, as well as combinations of two or more of them.

In another embodiment, provided are methods of using CBP/EP300 bromodomain inhibitors to treat and/or delay progression of cancer in combination with a PD-1 axis binding antagonist. Further provided herein are methods of enhancing immune function in an individual having cancer comprising administering to the individual an effective amount of a CBP/EP300 bromodomain inhibitor and an effective amount of a PD-1 axis binding antagonist. A PD-1 axis binding antagonist includes a PD-1 binding antagonist, a PD-L1 binding antagonist and a PD-L2 binding antagonist.

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PDL1, PDL2. In some embodiments, the PD-1 binding antagonist is a molecule that inhibits the binding of PD-1 to its binding partners. In a specific aspect, the PD-1 binding antagonist inhibits the binding of PD-1 to PDL1 and/or PDL2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PDL1 and/or PDL2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody.

In a specific aspect, a PD-1 binding antagonist is nivolumab described herein (also known as MDX-1106-04, MDX-1106, ONO-4538, BMS-936558, and OPDIVO®). In another specific aspect, a PD-1 binding antagonist is pembrolizumab described herein (also known as MK-3475, Merck 3475, KEYTRUDA®, and SCH-900475). In another specific aspect, a PD-1 binding antagonist is CT-011 described herein (also known as hBAT or hBAT-1). In yet another specific aspect, a PD-1 binding antagonist is AMP-224 (also known as B7-DCIg) described herein.

The term "PDL1 binding antagonists" is a molecule that decreases, blocks, inhibits, abrogates or interferes with signal transduction resulting from the interaction of PDL1 with either one or more of its binding partners, such as PD-1, B7-1. In some embodiments, a PDL1 binding antagonist is a molecule that inhibits the binding of PDL1 to its binding partners. In a specific aspect, the PDL1 binding antagonist inhibits binding of PDL1 to PD-1 and/or B7-1. In some embodiments, the PDL1 binding antagonists include anti-PDL1 antibodies, antigen binding fragments thereof, immunoadhesins, fusion proteins, oligopeptides and other molecules that decrease, block, inhibit, abrogate or interfere with signal transduction resulting from the interaction of PDL1 with one or more of its binding partners, such as PD-1, B7-1. In one embodiment, a PDL1 binding antagonist reduces the negative co-stimulatory signal mediated by or through cell surface proteins expressed on T lymphocytes mediated signaling through PDL1 so as to render a dysfunctional T-cell less dysfunctional (e.g., enhancing effector responses to antigen recognition). In some embodiments, a PDL1 binding antagonist is an anti-PDL1 antibody. In a specific aspect, an anti-PDL1 antibody is YW243.55.S70 described herein. In another specific aspect, an anti-PDL1 antibody is MDX-1105 described herein (also known as BMS-936559). In still another specific aspect, an anti-PDL1 antibody is MPDL3280A described herein. In still another specific aspect, an anti-PDL1 antibody is MEDI4736 described herein.

The term "PDL2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

Alternative names for "PD-1" include CD279 and SLEB2. Alternative names for "PD-L1" include B7-H 1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide. In some embodiment, the PD-1 binding antagonist is an anti-PD-1 antibody (e.g., a human antibody, a humanized antibody, or a chimeric antibody). In some embodiments, the anti-PD-1 antibody is selected from the group consisting of MDX-1 106, Merck 3475 (also known as: pembrolizumab, lambrolizumab, or MK-3475), nivolumab (BMS-936558), CT-011, and MPDL3280A. In some embodiments, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-1 binding antagonist is AMP-224. In some embodiments, the PD-L1 binding antagonist is anti-PD-L1 antibody. In some embodiments, the anti-PD-L1 binding antagonist is selected from the group consisting of YW243.55.S70, MPDL3280A and MDX-1 105. MDX-1 105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 described in WO 2010/077634 A1. MDX-1 106, also known as MDX-1 106-04, ONO-4538 or BMS-936558, is an anti-PD-1 antibody described in WO2006/121168. Merck 3745, also known as MK-3475 or SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO201 1/066342. In some embodiments, the anti-PD-1 antibody is MDX-1 106. Alternative names for "MDX-1106" include MDX-1 106-04, ONO-4538, BMS-936558 or Nivolumab. In some embodiments, the anti-PD-1 antibody is Nivolumab (CAS Registry Number: 946414-94-4). In some embodiments, the cancer is melanoma, NSCLC, and renal cell carcinoma.

For treating an inflammatory disease or an autoimmune disease, a compound of formula (I) or a pharmaceutically acceptable salt thereof may be co-administered with methotrexate, tofacitinib, 6-mercaptopurine, azathioprine sulphasalazine, mesalazine, olsalazine chloroquinine/hydroxychloroquinine, penicillamine, aurothiomalate (intramuscular and oral), azathioprine, cochicine, corticosteroids (oral, inhaled, and local injection), a beta-2 adrenoreceptor agonist (salbutamol, terbutaline, salmeteral), a xanthine (theophylline, aminophylline), cromoglycate, nedocromil, ketotifen, ipratropium and oxitropium, cyclosporin, FK506, rapamycin, mycophenolate mofetil, leflunomide, an NSAID (e.g. ibuprofen), a corticosteroid (e. g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-1 (e.g., a NIK, IKK, p38 or MAP kinase inhibitor), an IL-1 converting enzyme inhibitor, a T-cell signalling inhibitor (e.g. a kinase inhibitor), a metalloproteinase inhibitor, sulfasalazine, a 6-mercaptopurine, an angiotensin converting enzyme inhibitor, a soluble cytokine receptor (e.g. soluble p55 or p75 TNF receptors and the derivatives p75TNFRigG (etanercept) and p55TNFRigG (Lenercept), siL-1RI, siL-1RII, siL-6R), an antiinflammatory cytokine (e.g. IL-4, IL-1 0, IL-11, IL-13 and TGF), celecoxib, folic acid, hydroxychloroquine sulfate, rofecoxib, etanercept, infliximab, adalimumab, certolizumab, tocilizumab, abatacept, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, cortisone, betamethasone, morphine sulfate, lidocaine hydrochloride, indomethacin, glucosamine sulf/chondroitin, amitriptyline HCl, sulfadiazine, oxycodone HCVacetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL1S, BIRB-796, SCIO-469, VX-702, AMG-548, VX-740, Roflumilast, IC-485, CDC-801, S1PI agonists (such as FTY720), a PKC family inhibitor (e.g. Ruboxistaurin or AEB-071) or Mesopram. In certain embodiments, a compound of formula (I) or a pharmaceutically acceptable salt thereof may be co-administered with methotrexate or leflunomide. In moderate or severe Rheumatoid arthritis cases, a compound of formula (I) or a pharmaceutically acceptable salt thereof may be co-administered with cyclosporine and anti-TNF antibodies as noted above. A compound of formula (I) or a pharmaceutically acceptable salt thereof may also be co-administered with: budenoside; epidermal growth factor; a corticosteroid; cyclosporin, sulfasalazine; an aminosalicylate; 6-mercaptopurine; azathioprine; metronidazole; a lipoxygenase inhibitor; mesalamine; olsalazine; balsalazide; an antioxidant; a thromboxane inhibitor; an IL-1 receptor antagonist; an anti-IL-1 monoclonal antibody; an anti-IL-6 monoclonal antibody; a growth factor; an elastase inhibitor; a pyridinyl-imidazole compound; an antibody to or antagonist of other human cytokines or growth factors (e.g. TNF, LT, IL-1, IL-2, IL-6, IL-7, IL-8, IL-12, IL-15, IL-16, IL-23, EMAP-II, GM-CSF, FGF, and PDGF); a cell surface molecule (e.g. CD2, CD3, CD4, CD8, CD25, CD28, CD30, CD40, CD45, CD69, or CD90 or their ligands); methotrexate; cyclosporine; FK506; rapamycin; mycophenolate mofetil; leflunomide; an NSAID (e.g. ibuprofen); a corticosteroid (e.g. prednisolone); a phosphodiesterase inhibitor; an adenosine agonist; an antithrombotic agent; a complement inhibitor; an adrenergic agent; an agent that interferes with signalling by proinflammatory cytokines such as TNF 5 or IL-1 (e.g. a NIK, IKK, or MAP kinase inhibitor); an IL-1 converting enzyme inhibitor; a TNF converting enzyme inhibitor; a T-cell signalling inhibitor such as kinase inhibitors; a metalloproteinase inhibitor; sulfasalazine; azathioprine; a 6-mercaptopurine; an angiotensin converting enzyme inhibitor; a soluble cytokine receptor (e.g. soluble p55 or p75 TNF receptors, siL-1RI, siL-1RII, siL-6R), and an antiinflammatory cytokine (e.g. IL-4, IL-l 0, IL-11, IL-13 or TGF).

For treating Crohn's disease, a compound of formula (I) or a pharmaceutically acceptable salt thereof may be co-administered with a TNF antagonist (e.g. an anti-TNF antibody), D2E7 (adalimumab), CA2 (infliximab), CDP 571, a TNFR-Ig construct, (p75TNFRigG (etanercept)), a p55TNFRigG (LENERCEPT™) inhibitor, or a PDE4 inhibitor.

For treating inflammatory bowel disease, a compound of formula (I) or a pharmaceutically acceptable salt thereof may be co-administered with a corticosteroid (e.g. budenoside or dexamethasone); sulfasalazine, 5-aminosalicylic acid; olsalazine; an agent that interferes with synthesis or action of proinflammatory cytokines such as IL-1 (e.g. an IL-1 converting enzyme inhibitor or IL-lra); a T cell signaling inhibitor (e.g. a tyrosine kinase inhibitor); 6-mercaptopurine; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab or interferon-gamma.

For treating multiple sclerosis, a compound of formula (I) or a pharmaceutically acceptable salt thereof may be co-administered with a corticosteroid; prednisolone; methylprednisolone; azathioprine; cyclophosphamide; cyclosporine; methotrexate; 4-aminopyridine; tizanidine; interferon-la (AVONEX®; Biogen); interferon-1b (BETASERON®; Chiron/Berlex); interferon-n3) (Interferon Sciences/Fujimoto), interferon-(Alfa Wassermann/J&J), interferon 1A-IF (Serono/Inhale Therapeutics), Peginterferon 2b (Enzon/Schering-Plough), Copolymer 1 (Cop-1; COPAXONE®; Teva Pharmaceutical Industries, Inc.); hyperbaric oxygen; intravenous immunoglobulin; cladribine; an antibody to or antagonist of other human cytokines or growth factors and their receptors (e.g. TNF, LT, IL-1, IL-2, IL-6, IL-7, IL-8, IL-12, IL-23, IL-15, IL-16, EMAP-II, GM-CSF, FGF, or PDGF).

For treating AIDS a compound of formula (I) or a pharmaceutically acceptable salt thereof may be co-administered with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) or a pharmaceutically acceptable salt thereof may also be co-administered with methotrexate, cyclosporine, FK506, rapamycin, mycophenolate mofetil, leflunomide, an S1P1 agonist, an NSAID (e.g. ibuprofen), a corticosteroid (e.g. prednisolone), a phosphodiesterase inhibitor, an adensosine agonist, an antithrombotic agent, a complement inhibitor, an adrenergic agent, an agent that interferes with signalling by proinflammatory cytokines such as TNF or IL-l (e.g., a NIK, IKK, p38 or MAP kinase inhibitor), an IL-1 converting enzyme inhibitor, a TACE inhibitor, a T-cell signaling inhibitor (e. g. a kinase inhibitor), a metalloproteinase inhibitor, sulfasalazine, azathioprine, a 6-mercaptopurine, an angiotensin converting enzyme inhibitor, a soluble cytokine receptor (e. g. soluble p55 or p75 TNF receptors, siL-1RI, siL-1RII, or siL-6R), or an antiinflammatory cytokine (e.g. IL-4, IL-l 0, IL-13 or TGF).

A compound of formula (I) or a pharmaceutically acceptable salt thereof may also be co-administered with agents, such as alemtuzumab, dronabinol, daclizumab, mitoxantrone, xaliproden hydrochloride, fampridine, glatiramer acetate, natalizumab, sinnabidol, immunokine NNS03, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, an anti-IL-6 receptor antibody, neurovax, pirfenidone allotrap 1258 (RDP-1258), sTNF-R1, talampanel, teriflunomide, TGF-beta2, tiplimotide, a VLA-4 antagonist (e.g. TR-14035, VLA4 Ultrahaler, or Antegran-ELAN/Biogen), an interferon gamma antagonist, or an IL-4 agonist.

For treating ankylosing spondylitis a compound of formula (I) or a pharmaceutically acceptable salt thereof may be co-administered with ibuprofen, diclofenac, misoprostol, naproxen, meloxicam, indomethacin, diclofenac, celecoxib, rofecoxib, sulfasalazine, methotrexate, azathioprine, minocyclin, prednisone, an anti-TNF antibody, D2E7 (HUMIRA®), CA2 (infliximab), CDP 571, a TNFR-Ig construct, (p75TNFRigG (ENBREL®), or p55TNFRigG (LENERCEPT®).

For treating asthma a compound of formula (I) or a pharmaceutically acceptable salt thereof may be co-administered with albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, cromolyn sodium, fexofenadine hydrochloride, flunisolide/menthol, amoxicillin/clavulanate, levofloxacin, guaifenesin, dexamethasone sodium phosphate, moxifloxacin HCl, doxycycline hyclate, guaifenesin/d-methorphan, p-ephedrine/cod/-chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, an anti-IL-13 antibody, or metaproterenol sulfate.

For treating COPD a compound of formula (I) or a pharmaceutically acceptable salt thereof may be co-administered with albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, cilomilast, or roflumilast.

For treating psoriasis, a compound of formula (I) or a pharmaceutically acceptable salt thereof may be co-administered with calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, he/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 or ustekinamab.

For treating psoriatic arthritis, a compound of formula (I) or a pharmaceutically acceptable salt thereof may be co-administered with methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, D2E7 (adalimumab), or efalizumab.

For treating lupus, a compound of formula (I) or a pharmaceutically acceptable salt thereof may be co-administered with an NSAID (e.g. diclofenac, naproxen, ibuprofen, piroxicam, or indomethacin); a COX2 inhibitor (e.g. celecoxib, rofecoxib, or valdecoxib); an anti-malarial (e.g. hydroxychloroquine); a steroid (e.g. prednisone, prednisolone, budenoside, or dexamethasone); a cytotoxic (e.g. azathioprine, cyclophosphamide, mycophenolate mofetil, or methotrexate); an inhibitor of PDE4, or a purine synthesis inhibitor (e.g. Cellcept®). For example, a compound of formula (I) or a pharmaceutically acceptable salt thereof may be co-administered with sulfasalazine, 5-aminosalicylic acid, olsalazine, Imuran®, an agent that interferes with the synthesis, production, or action of a proinflammatory cytokine (e.g. IL-l), or a caspase inhibitor (e.g. a IL-l converting enzyme inhibitor or IL-lra).

A compound of formula (I) or a pharmaceutically acceptable salt thereof may also be co-administered with a T cell signaling inhibitor (e.g. a tyrosine kinase inhibitor), or a molecule that targets T cell activation (e.g. CTLA-4-IgG, an anti-B7 family antibody, or an anti-PD-1 family antibody).

A compound of formula (I) or a pharmaceutically acceptable salt thereof can also be co-administered with an IL-11 antibody, an anti-cytokine antibody (e.g. fonotolizumab (anti-IFNg antibody)), or an anti-receptor receptor antibodies (e.g. an anti-IL-6 receptor antibody or an antibody to a B-cell surface molecule).

A compound of formula (I) or a pharmaceutically acceptable salt thereof can also be co-administered with LJP 394 (abetimus), an agent that depletes or inactivates B-cells (e.g. Rituximab (anti-CD20 antibody) or lymphostat-B (anti-BlyS antibody)), a TNF antagonist (e.g. an anti-TNF antibody), D2E7 (adalimumab), CA2 (infliximab), CDP 571, a TNFR-Ig construct, (p75TNFRigG (etanercept), or p55TNFRigG (LENERCEPT™).

A compound of formula (I) or a pharmaceutically acceptable salt thereof can also be co-administered with one or more agents used in the prevention or treatment of AIDS: an HIV reverse transcriptase inhibitor, an HIV protease inhibitor, an immunomodulator, or another retroviral drug. Examples of reverse transcriptase inhibitors include, but are not limited to, abacavir, adefovir, didanosine, dipivoxil delavirdine, efavirenz, emtricitabine, lamivudine, nevirapine, rilpivirine, stavudine, tenofovir, zalcitabine, and zidovudine. Examples of protease inhibitors include, but are not limited to, amprenavir, atazanavir, darunavir, indinavir, fosamprenavir, lopinavir, nelfinavir, ritonavir, saquinavir, and tipranavir. Examples of other retroviral drugs include, but are not limited to, elvitegravir, enfuvirtide, maraviroc and raltegravir.

For treating type II diabetes, hepatic steatosis, insulin resistance, metabolic syndrome or a related disorder, a compound of formula (I) or a pharmaceutically acceptable salt thereof may be co-administered with insulin or insulins that have been modified to improve the duration of action in the body; agents that stimulate insulin secretion such as acetohexamide, chlorpropamide, glyburide, glimepiride, glipizide, glicazide, glycopyramide, gliquidone, rapaglinide, nataglinide, tolazamide or tolbutamide; agents that are glucagon-like peptide agonists such as exanatide, liraglutide or taspoglutide; agents that inhibit dipeptidyl-peptidase IV such as vildagliptin, sitagliptin, saxagliptin, linagliptin, allogliptin or septagliptin; agents that bind to the peroxisome proliferator-activated receptor gamma such as rosiglitazone or pioglitazone; agents that decrease insulin resistance such as metformin; or agents that reduce glucose absorbance in the small intestine such as acarbose, miglitol or voglibose.

For treating acute kidney disorders or a chronic kidney disease, a compound of formula (I) or a pharmaceutically acceptable salt thereof may be co-administered with dopamine, a diuretic (e.g. furosemide), bumetanide, thiazide, mannitol, calcium gluconate, sodium bicarbonate, albuterol, paricalcitol, doxercalciferol, cinacalcet, or bardoxalone methyl.

The amount of both the compound of formula (I) or salt thereof and additional agent (in those compositions which comprise an additional therapeutic agent as described above) that may be combined with the carrier materials to produce a single dosage form will vary depending upon the host treated and the particular mode of administration. In certain embodiments, compositions of this invention are formulated such that a dosage of between 0.01-100 mg/kg body weight/day of an inventive can be administered.

The additional therapeutic agent and the compound of formula (I) may act synergistically. Therefore, the amount of additional therapeutic agent in such compositions may be less than that required in a monotherapy utilizing only that therapeutic agent, or there may be fewer side effects for the patient given that a lower dose is used. In certain embodiments, in such compositions a dosage of between 0.01-1,000 µg/kg body weight/day of the additional therapeutic agent can be administered.

Provided herein are methods of extending the duration of response to a cytotoxic agent in an individual with cancer comprising administering to the individual (a) an effective amount of a compound of formula (I) or a pharmaceutically acceptable salt thereof and (b) an effective amount of the cytotoxic agent.

In certain embodiments of any of the methods, the cytotoxic agent is a targeted therapy. In certain embodiments, the targeted therapy is one or more of an EGFR antagonist, RAF inhibitor, and/or PI3K inhibitor.

In certain embodiments of any of the methods, the targeted therapy is an EGFR antagonist. In certain embodiments of any of the methods, the EGFR antagonist is N-(3-ethynylphenyl)-6,7-bis(2-methoxyethoxy)-4-quinazolinamine and/or a pharmaceutical acceptable salt thereof. In certain embodiments, the EGFR antagonist is N-(3-ethynylphenyl)-6,7-bis(2-methoxyethoxy)-4-quinazolinamine.

In certain embodiments, the EGFR antagonist is N-(4-(3-fluorobenzyloxy)-3-chlorophenyl)-6-(5-((2-(methylsulfonyl)ethylamino)methyl)furan-2-yl)quinazolin-4-amine, di4-methylbenzenesulfonate or a pharmaceutically acceptable salt thereof (e.g., lapatinib).

In certain embodiments of any of the methods, targeted therapy is a RAF inhibitor. In certain embodiments, the RAF inhibitor is a BRAF inhibitor. In certain embodiments, the RAF inhibitor is a CRAF inhibitor.

In certain embodiments, the BRAF inhibitor is vemurafenib. In certain embodiments, the RAF inhibitor is 3-(2-cyanopropan-2-yl)-N-(4-methyl-3-(3-methyl-4-oxo-3,4-dihydroquinazolin-6-ylamino)phenyl)benzamide or a pharmaceutically acceptable salt thereof (e.g., AZ628 (CAS #878739-06-1)).

In certain embodiments of any of the methods, the targeted therapy is a PI3K inhibitor.

In certain embodiments of any of the methods, the cytotoxic agent is chemotherapy. In certain embodiments of any of the methods, the chemotherapy is a taxane. In certain embodiments, the taxane is paclitaxel. In certain embodiments, the taxane is docetaxel.

In certain embodiments of any of the methods, the cytotoxic agent is a platinum agent. In certain embodiments, the platinum agent is carboplatin. In certain embodiments, the platinum agent is cisplatin. In certain embodiments of any of the methods, the cytotoxic agent is a taxane and a platinum agent. In certain embodiments, the taxane is paclitaxel. In certain embodiments, the taxane is docetaxel. In certain embodiments, the platinum agent is carboplatin. In certain embodiments, the platinum agent is cisplatin.

In certain embodiments of any of the methods, the cytotoxic agent is a vinca alkyloid. In certain embodiments, the vinca alkyloid is vinorelbine. In certain embodiments of any of the methods, the chemotherapy is a nucleoside analog. In certain embodiments, the nucleoside analog is gemcitabine.

In certain embodiments of any of the methods, the cytotoxic agent is radiotherapy.

In certain embodiments of any of the methods, the compound of formula (I) or a pharmaceutically acceptable salt thereof is concomitantly administered with the cytotoxic agent (e.g., targeted therapy, chemotherapy, and/or radiotherapy). In certain embodiments, the compound of formula (I) or a pharmaceutically acceptable salt thereof is administered prior to and/or concurrently with the cytotoxic agent (e.g., targeted therapy, chemotherapy, and/or radiotherapy).

Exemplification of Compounds of Formula (I)

As depicted in the Examples of Compounds of Formula (I), below, in certain exemplary embodiments, compounds of Formula (I) are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Scheme 1

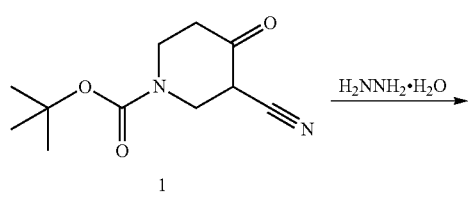
1

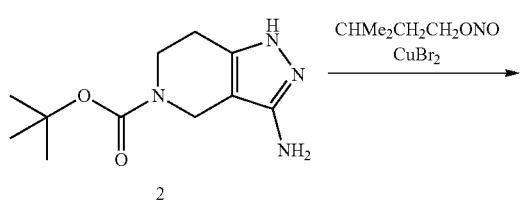
2

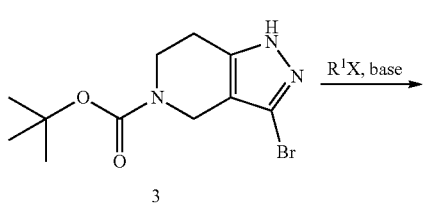
3

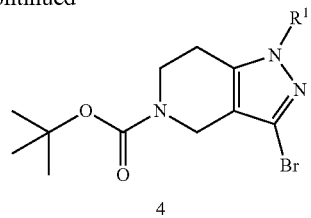
4

Compounds of formula (4) may be prepared by general synthetic methods as shown in Scheme 1.

Reaction between cyano-ketone (1) and hydrazine in a suitable solvent such as ethanol at a temperature ranging from about room temperature to reflux and for a time varying from about 30 minutes to about 2 hours, can readily produce bicycle-pyrazole (2). The bromo pyrazole (3) can be formed by converting the amino pyrazole (2) using a nitrite such as, but not limited to, isoamylnitrite, sodium nitrite, or tert-butyl nitrite and a copper salt such as, but not limited to, copper(II) bromide in organic an solvent such as, but not limited to, acetonitrile at a temperature of about 20° C. to about 60° C. for a time of about 5 hours. The alkylation of pyrazole $N^1$ nitrogen of (2) can be carried out using an alkyl iodide/bromide/mesylate/triflate in the presence of an inorganic base such as, but not limited to, sodium hydride or cesium carbonate in a suitable organic solvent such as, but not limited to, N,N-dimethylformamide (DMF) or tetrahydrofuran (THF) at a temperature ranging from about 0° C. to 120° C. and for a time varying from about 30 minutes to about 16 hours to form compounds of formula (4).

Scheme 2

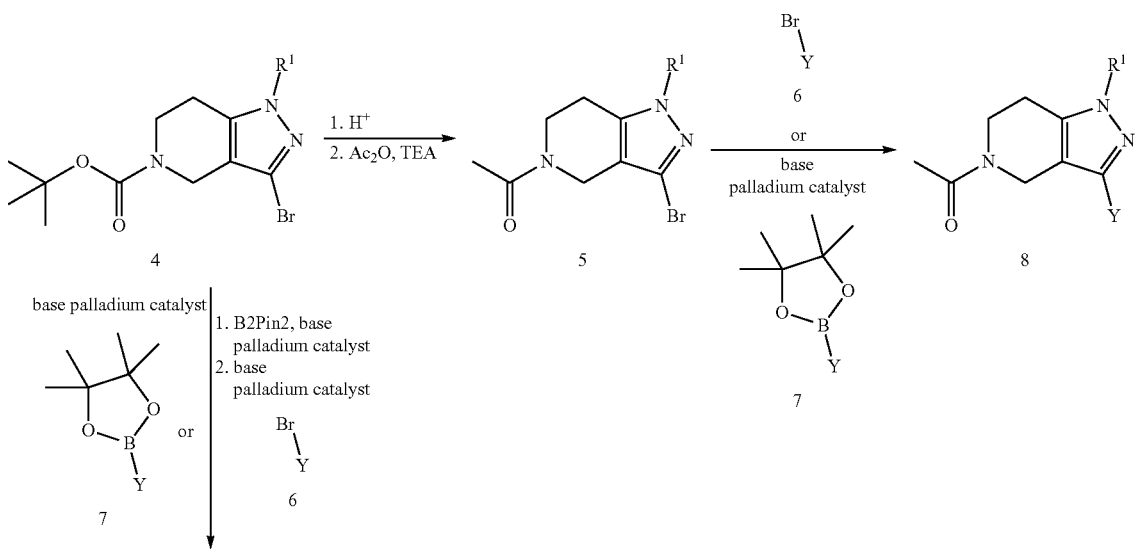

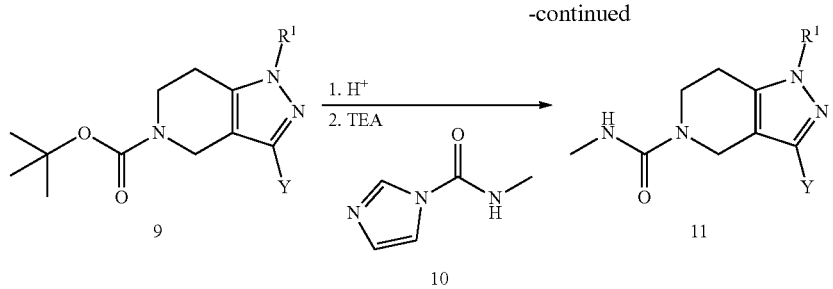

Compounds of formula (8) and (11) may be prepared by general synthetic methods as shown in Scheme 2.

Deprotection of N-tert-butoxycarbonyl (Boc) group using a protic acid such as, but not limited to, trifluoroacetic acid or hydrochloric acid, and subsequent N-acetylation using acetic anhydride in the presence of a base such as, but not limited to, triethylamine (TEA) can readily afford compounds of formula (5). Compounds of formula (8) can be prepared from the bromide (5) upon treatment with aryl, heteroaryl or heterocyclic boronic acids or boronate esters (7) under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature. Alternatively, reaction between bromide (5) and 4,4,4',4',5,5,5',5'-octamethyl-2,2'-bi(1,3,2-dioxaborolane) in the presence of base such as, but not limited to, potassium acetate or potassium 2-ethyl heanoate, under palladium catalyst conditions such as, but not limited to, [1,1'-bis(diphenylphosphino)ferrocene] dichloropalladium (II) in the presence of an organic solvent such as, but not limited to, 1,4-dioxane or dimethylformamide, can produce the corresponding boronate ester that upon treatment with aryl, heteroaryl or heterocyclic halides under the analogous palladium catalyst conditions can also yield compounds of formula (8). To access compounds of formula (11), Boc-protected (4) can be directly elaborated to compounds of formula (9) using either coupling procedure described above. Subjection of piperidine (9) to the protic conditions described above, followed by treatment with a base such as, but not limited to, triethylamine (TEA), and urea (10) provides compounds of formula (11).

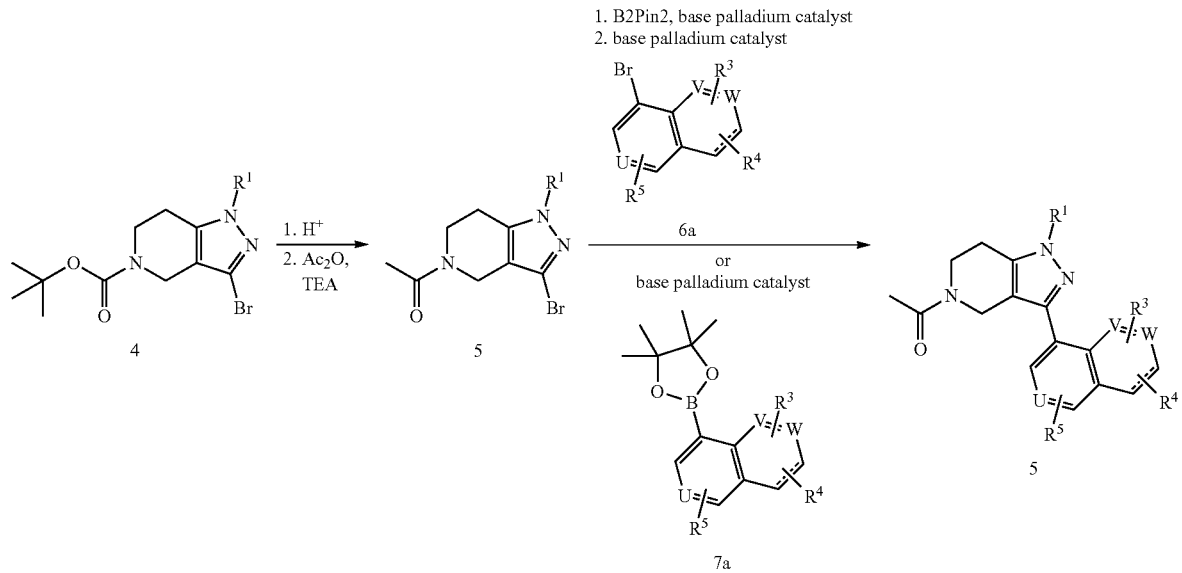

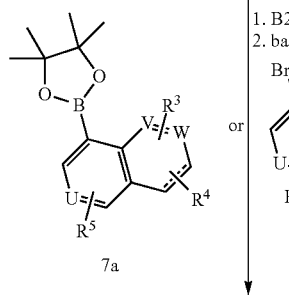
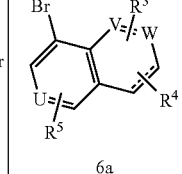

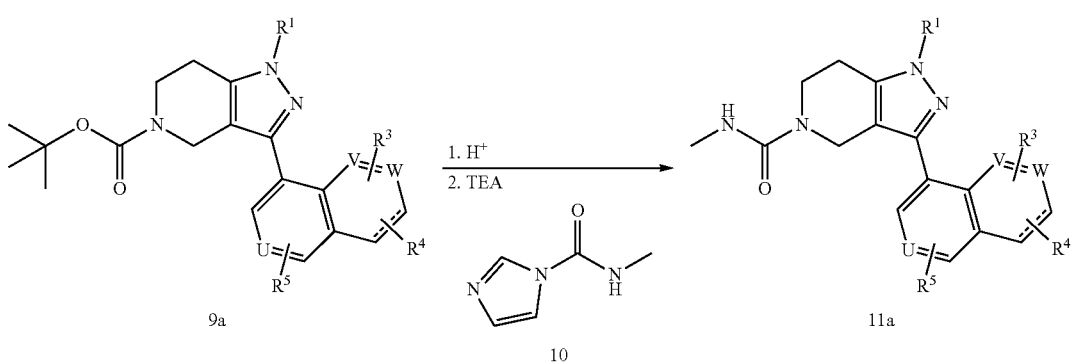

Compounds of formula (8a) and (11a) may be prepared by general synthetic methods as shown in Scheme 3.

Deprotection of N-tert-butoxycarbonyl (Boc) group using a protic acid such as, but not limited to, trifluoroacetic acid or hydrochloric acid, and subsequent N-acetylation using acetic anhydride in the presence of a base such as, but not limited to, triethylamine (TEA) can readily afford compounds of formula (5). Compounds of formula (8a) can be prepared from the bromide (5) upon treatment with aryl, heteroaryl or heterocyclic boronic acids or boronate esters (7a) under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature. Alternatively, reaction between bromide (5) and 4,4,4',4',5,5,5',5'-octamethyl-2,2'-bi(1,3,2-dioxaborolane) in the presence of base such as, but not limited to, potassium acetate or potassium 2-ethyl heanoate, under palladium catalyst conditions such as, but not limited to, [1,1'-bis(diphenylphosphino)ferrocene] dichloropalladium (II) in the presence of an organic solvent such as, but not limited to, 1,4-dioxane or dimethylformamide, can produce the corresponding boronate ester that upon treatment with aryl, heteroaryl or heterocyclic halides under the analogous palladium catalyst conditions can also yield compounds of formula (8a). To access compounds of formula (11a), Boc-protected (4) can be directly elaborated to compounds of formula (9a) using either coupling procedure described above. Subjection of piperidine (9a) to the protic conditions described above, followed by treatment with a base such as, but not limited to, triethylamine (TEA), and urea (10) provides compounds of formula (11a).

Scheme 4

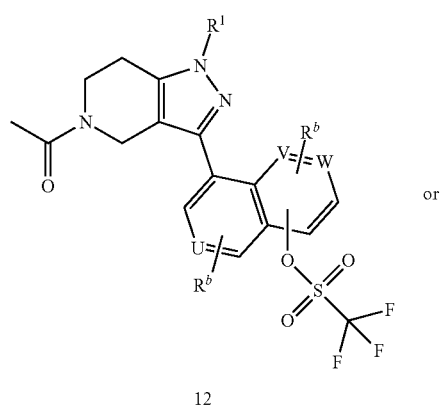

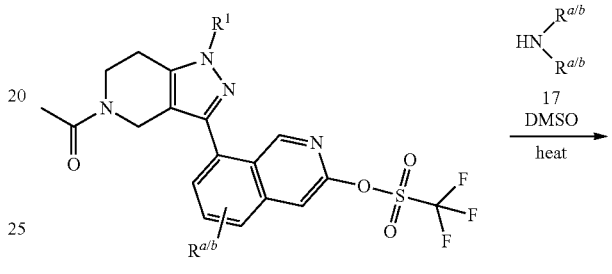

catalyst conditions such as, but not limited to, [1,1'-bis(diphenylphosphino)ferrocene]dichloropalladium(II) or chloro(2-dicyclohexylphosphino-2',4',6'-tri-i-propyl-1,1'-biphenyl)(2'-amino-1,1'-biphenyl-2-yl) palladium(II) in the presence of water and an inorganic base such as, but not limited to, sodium carbonate in an organic solvent such as, but not limited to, 1,4-dioxane at an elevated temperature. Alternatively, reaction between triflate (12) under the analogous palladium catalyst conditions can also yield compounds of formula (15).

Scheme 5

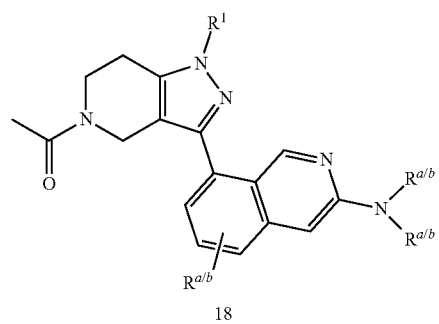

Compounds of formula (15) may be prepared by general synthetic methods as shown in Scheme 4.

Compounds of formula (15) can be prepared from the bromide (13) upon treatment with aryl, heteroaryl or heterocyclic boronic acids or boronate esters under palladium Compounds of formula (18) may be prepared by general synthetic methods as shown in Scheme 5.

Compounds of formula (18) can be prepared from the triflate (16) upon treatment with amines (17) in the presence of an organic solvent such as, but not limited to, dimethyl sulfoxide (DMSO) under microwave irradiation. When the salt form of amines (17) were utilized, a base such as, but not limited to, triethylamine was added to the reaction conditions.

Scheme 6

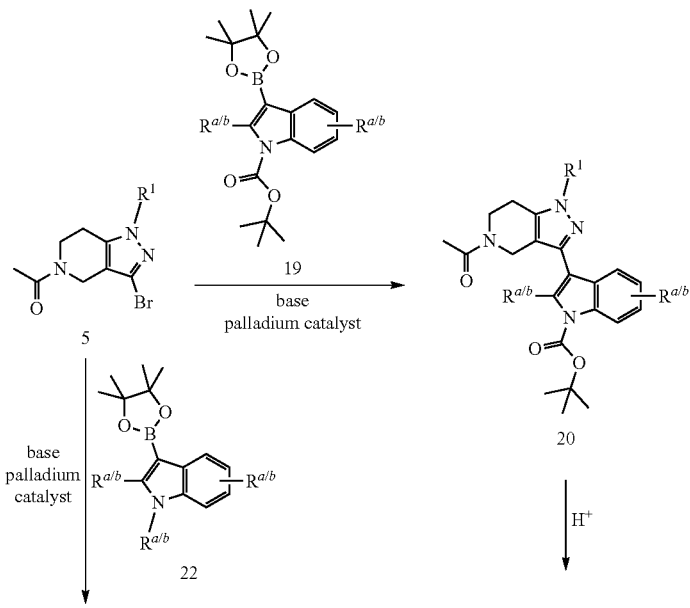

Compounds of formulas (21) and (23) may be prepared by general synthetic methods as shown in Scheme 6.

Compounds of formula (23) can be prepared from the bromide (5) upon treatment with indole or azaindole boronic acids or boronate esters (22) under palladium catalyst conditions such as, but not limited to, [1,1'-bis(diphenylphosphino)ferrocene] dichloropalladium(II) in the presence of water and an inorganic base such as, but not limited to, sodium carbonate, potassium carbonate, or potassium phosphate in an organic solvent such as, but not limited to, 1,4-dioxane at an elevated temperature. Alternatively, reaction between bromide (5) and indole or azaindole boronic acids or boronate esters (19) under the analogous palladium catalyst conditions, followed by deprotection of N-tert-butoxycarbonyl (Boc) group using a protic acid such as, but not limited to, trifluoroacetic acid or hydrochloric acid yields compounds of formula (21).

Scheme 7

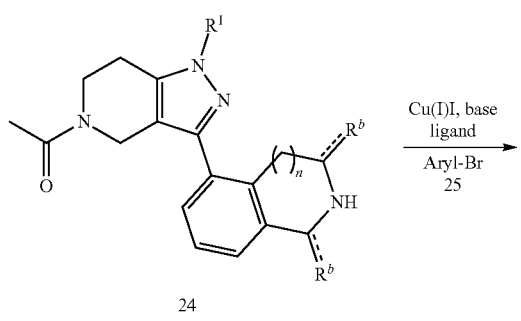

-continued

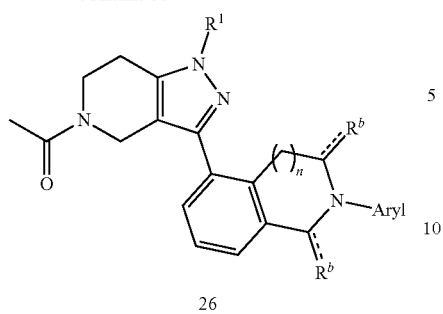

Compounds of formula (26) may be prepared by general synthetic methods as shown in Scheme 7.

Compounds of formula (26) can be prepared from (24) upon treatment with aryl, heteroaryl, or heterocyclic iodides or bromides (25) under copper catalyst conditions such as, but not limited to, copper (I) iodide in the presence of an inorganic base such as, but not limited to, potassium carbonate or potassium phosphate and a ligand such as, but not limited to, N,N'-dimethylethylenediame or (1R,2R)-cyclohexane-1,2-diamine in an organic solvent such as, but not limited to, 1,4-dioxane at an elevated temperature.

Scheme 8

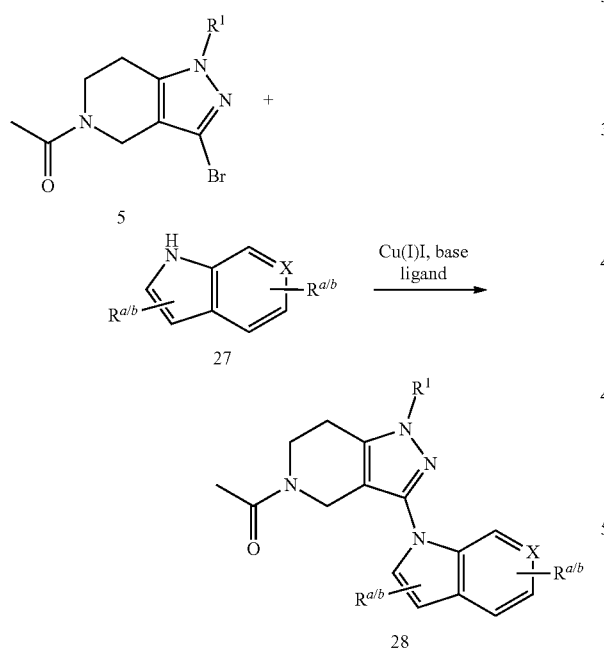

Compounds of formula (28) may be prepared by general synthetic methods as shown in Scheme 8.

Compounds of formula (28) can be prepared from the bromide (5) upon treatment with indoles or azaindoles (27) under copper catalyst conditions such as, but not limited to, copper (I) iodide in the presence of an inorganic base such as, but not limited to, potassium phosphate and a ligand such as, but not limited to, (1R,2R)-cyclohexane-1,2-diamine in an organic solvent such as, but not limited to, toluene at an elevated temperature.

Scheme 9

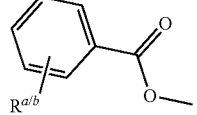

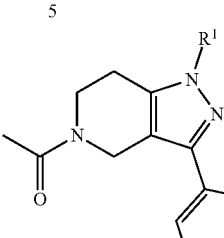

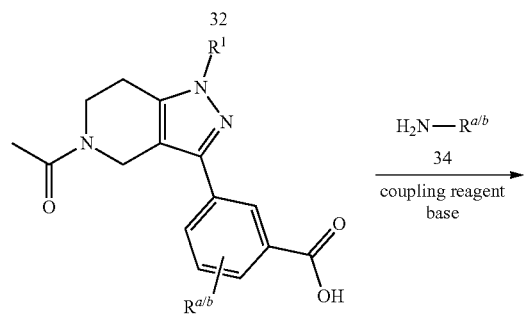

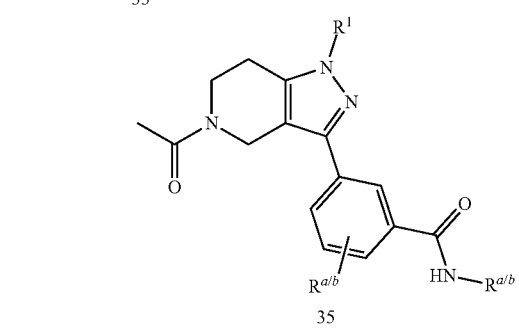

Compounds of formula (34) may be prepared by general synthetic methods as shown in Scheme 9.

Compounds of formula (32) can be prepared from the bromide (5) upon treatment with boronic esters or boronate acids (31) under palladium catalyst conditions such as, but not limited to, [1,1'-bis(diphenylphosphino)ferrocene]dichloropalladium(II) in the presence of water and an inorganic base such as, but not limited to, sodium carbonate, in an organic solvent such as, but not limited to, 1,4-dioxane at an elevated temperature. Treatment of the ester (32) with hydroxide sources such as, but not limited to, lithium hydroxide in the presence of water and organic solvents such as, but not limited to, methanol and/or tetrahydrofuran yields carboxylic acids of formula (33). Reaction of carboxylic acids (33) with a coupling reagent such as, but not limited to, 1-[bis(dimethylamino)methylene]-1H-1,2,3-triazolo[4,5-b]pyridinium 3-oxide hexafluorophosphate, a base such as, but not limited to, diisopropylethylamine, and an amine (34) provides amides of formula (35).

General Procedure for Intermediates a & B

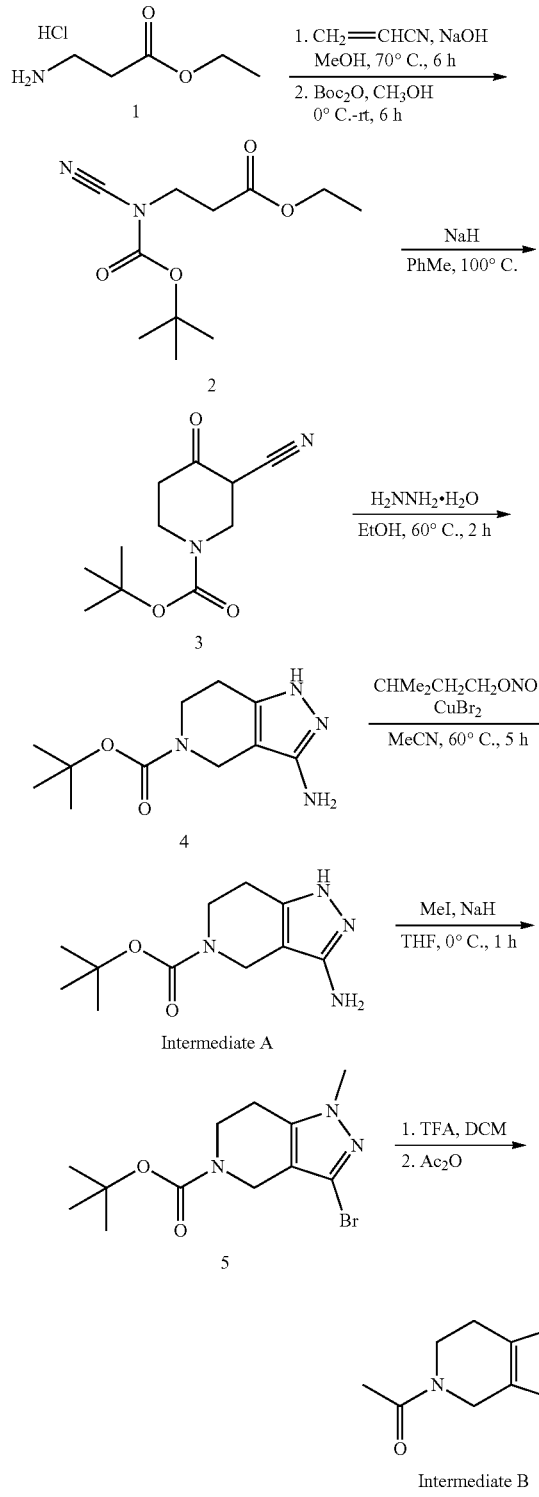

Step 1: ethyl 3-((tert-butoxycarbonyl)(2-cyanoethyl)amino)propanoate

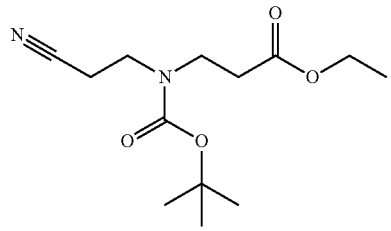 [SMILES: CCOC(=O)CCN(CCC#N)C(=O)OC(C)(C)C]

To a solution of ethyl 3-aminopropanoate hydrochloride (366.5 g, 2.39 mol) in MeOH (1.2 L) at room temperature was added NaOH (95.6 g, 2.39 mol) in portions. The mixture was heated to 70° C., acrylonitrile (158 g, 2.98 mol) was added dropwise and the reaction mixture stirred for 6 h. The solution was cooled to 0° C. before (Boc)$_2$O (521 g, 2.39 mol) was added. The reaction was stirred at room temperature for 6 h, filtered, and washed with MeOH (200 mL). The filtrate was concentrated in vacuo to give a yellow oil residue that was re-dissolved in EtOAc and water (500 mL). The aqueous layer was extracted with EtOAc (800 mL). The combined organic layers were dried over anhydrous Na$_2$SO$_4$, filtered and concentrated in vacuo to give the title compound (638 g) as light yellow oil that required no further purification. $^1$H NMR (400 MHz, CDCl$_3$) δ 4.17 (q, J=7.2 Hz, 2H), 3.68-3.62 (m, 4H), 2.57-2.53 (m, 4H), 1.49 (s, 9H), 1.29 (t, J=7.2 Hz, 3H).

Step 2: tert-butyl 3-cyano-4-oxopiperidine-1-carboxylate

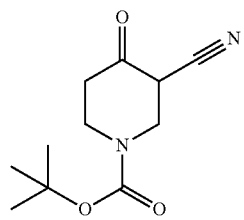 [SMILES: CC(C)(C)OC(=O)N1CCC(=O)C(C#N)C1]

To toluene (2.7 L) at 25° C. was added NaH (80 g, 2.0 mol) portion-wise and the suspension was heated to 80° C. Ethyl 3-((tert-butoxycarbonyl)(2-cyanoethyl)amino)propanoate (270 g, crude) in anhydrous toluene (270 mL) was added dropwise. The mixture was heated to 100° C. and stirred for 5 hours. The mixture was cooled to room temperature, quenched with sat. aq. ammonium chloride (800 mL) and washed with hexanes (800 mL). The aqueous phase was acidified with HCl (2 N) to pH 6 and then extracted with EtOAc (1 L×2). The combined organic layers were dried over anhydrous Na$_2$SO$_4$, filtered and concentrated in vacuo to give the title compound (310 g) as yellow oil that required no further purification. $^1$H NMR (400 MHz, CDCl$_3$) δ 4.17-4.14 (m, 1H), 3.59-3.56 (m, 2H), 3.43-3.41 (m, 2H), 2.70-2.66 (m, 2H), 1.51 (s, 9H).

Step 3: tert-butyl 3-amino-6,7-dihydro-1H-pyrazolo[4,3-c]pyridine-5(4H)-carboxylate

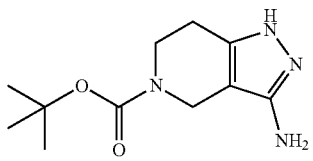 [SMILES: CC(C)(C)OC(=O)N1CCc2[nH]nc(N)c2C1]

A mixture of tert-butyl 3-cyano-4-oxopiperidine-1-carboxylate (310 g, 1.38 mol) and hydrazine mono-hydrate (140 mL, 2.08 mol) in EtOH (1.5 L) was heated to 60° C. for 2 h. The mixture was concentrated in vacuo to give the crude product that was dissolved in EtOAc (1 L) and washed with water (1 L×2). The organic layer was dried over anhydrous Na$_2$SO$_4$, filtered and concentrated in vacuo to afford the title compound (230 g, 70%) as a colorless solid. $^1$H NMR (400 MHz, CD$_3$OD) δ 4.28 (s, 2H), 3.66-3.63 (m, 2H), 2.62-2.59 (m, 2H), 1.49 (s, 9H).

Step 4: tert-butyl 3-bromo-6,7-dihydro-1H-pyrazolo[4,3-c]pyridine-5(4H)-carboxylate

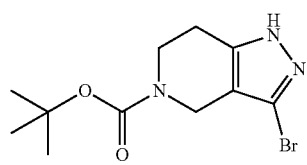 [SMILES: CC(C)(C)OC(=O)N1CCc2[nH]nc(Br)c2C1]

To a stirred mixture of tert-butyl 3-amino-6,7-dihydro-1H-pyrazolo[4,3-c]pyridine-5(4H)-carboxylate (120 g, 503.6 mmol), CuBr$_2$ (112.5 g, 503.6 mmol) and MeCN (1.2 L) at 0° C. was added isopentyl nitrite (76.7 g, 654.7 mmol) and the reaction mixture stirred for 20 min. The temperature was raised to 60° C. and the reaction mixture was stirred for an additional 5 h. After cooling the reaction to room temperature, the reaction mixture was quenched with water (1 L) and the mixture was extracted with EtOAc (1 L×2). The combined organic layers were dried over anhydrous Na$_2$SO$_4$, filtered and concentrated in vacuo. The crude residue was purified by silica gel chromatography (petroleum ether/EtOAc=4:1) to afford the title compound (Intermediate A, 52 g, 34%) as light yellow solid. LCMS M/Z (M+H) 302.

Step 5: tert-butyl 3-bromo-1-methyl-6,7-dihydro-1H-pyrazolo[4,3-c]pyridine-5(4H)-carboxylate

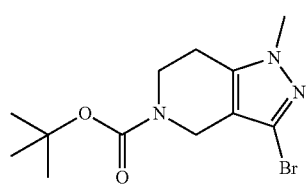 [SMILES: Cn1nc(Br)c2c1CCN(C(=O)OC(C)(C)C)C2]

To a stirred solution of tert-butyl 3-bromo-6,7-dihydro-1H-pyrazolo[4,3-c]pyridine-5(4H)-carboxylate (Intermediate A, 32 g, 105.9 mmol) in THF at 0° C. (350 mL) was added NaH (5.08 g, 127.1 mmol) and the mixture was stirred for 30 min. Methyliodide (18.05 g, 127.1 mmol) was added dropwise and the mixture stirred for an additional 2 h. The mixture was quenched with water and extracted with EtOAc (300 mL×2). The combined organic layers were dried over anhydrous Na$_2$SO$_4$, filtered and concentrated in vacuo. The crude residue was purified by silica gel chromatography (petroleum ether/EtOAc=8:1) to afford the title compound (16 g, 48%) as a colorless oil. $^1$H NMR (400 MHz, CD$_3$OD) δ 4.24 (s, 2H), 3.70 (s, 3H), 3.69-3.67 (m, 2H), 2.70-2.67 (m, 2H), 1.47 (s, 9H).

Step 6: 1-(3-bromo-1-methyl-6,7-dihydro-1H-pyrazolo[4,3-c]pyridin-5(4H)-yl)ethanone

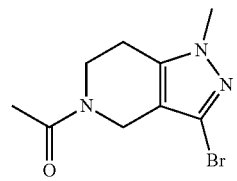

A mixture of tert-butyl 3-bromo-1-methyl-6,7-dihydro-1H-pyrazolo[4,3-c]pyridine-5(4H)-carboxylate (12 g, 38.0 mmol) and trifluoroacetic acid (40 mL) in DCM (80 mL) was stirred at room temperature for 2 h. The mixture was concentrated in vacuo and the residue was re-dissolved in DCM (120 mL). The mixture was cooled to 0° C. before TEA (12.1 g, 120 mmol) and acetic anhydride (5.3 g, 52 mmol) were added dropwise. The mixture stirred at room temperature for an additional 2 h before water (100 mL) was added. The organic layer was dried over anhydrous Na$_2$SO$_4$, filtered and concentrated in vacuo. The crude residue was purified by silica gel chromatography (DCM/MeOH=20:1) to afford the title compound (Intermediate B, 8.5 g, 87%) as white solid. H NMR (400 MHz, CD$_3$OD) δ 4.40-4.39 (m, 2H), 3.88-3.78 (m, 2H), 3.72 (s, 3H), 2.83-2.70 (m, 2H), 2.20-2.17 (m, 3H).

General Procedure for Intermediate C

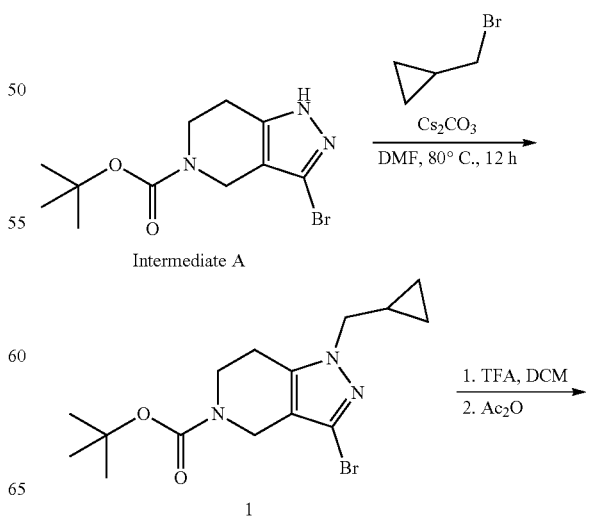

Step 1: tert-butyl 3-bromo-1-(cyclopropylmethyl)-6,7-dihydro-1H-pyrazolo[4,3-c]pyridine-5(4H)-carboxylate

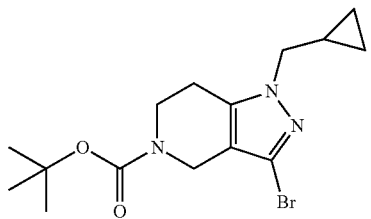 [SMILES: CC(C)(C)OC(=O)N1CCc2c(c(Br)nn2CC2CC2)C1]

To a stirred solution of tert-butyl 3-bromo-6,7-dihydro-1H-pyrazolo[4,3-c]pyridine-5(4H)-carboxylate (Intermediate A, 6.0 g, 19.8 mmol) in DMF (40 mL) was added Cs$_2$CO$_3$ (9.70 g, 29.8 mmol) and (bromomethyl)cyclopropane (4.0 g, 29.8 mmole). The reaction mixture was heated to 80° C. for 12 h. The mixture was diluted with EtOAc (200 mL), washed with brine (100 mL×3), dried over Na$_2$SO$_4$, filtered and concentrated in vacuo. The crude residue was purified by silica gel chromatography (eluent gradient from petroleum ether to petroleum ether/tert-butyl methyl ether/THF=10:1:1) to give the title compound (3.0 g, 42%) as a white solid. $^1$H NMR (400 MHz, CDCl$_3$) δ 4.29 (s, 2H), 3.85 (d, J=3.4 Hz, 2H), 3.71 (t, J=5.2 Hz, 2H), 2.67 (t, J=5.2 Hz, 2H), 1.49 (s, 9H), 1.25-1.18 (m, 1H), 0.61-0.55 (m, 2H), 0.35-0.31 (m, 2H).

Step 2: 1-(3-bromo-1-(cyclopropylmethyl)-6,7-dihydro-1H-pyrazolo[4,3-c]pyridin-5(4H)-yl)ethanone

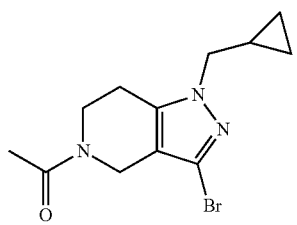 [SMILES: CC(=O)N1CCc2c(c(Br)nn2CC2CC2)C1]

A mixture of tert-butyl 3-bromo-1-(cyclopropylmethyl)-6,7-dihydro-1H-pyrazolo[4,3-c]pyridine-5(4H)-carboxylate (3.0 g, 8.4 mmol) and trifluoroacetic acid (30 mL) in DCM (30 mL) was stirred at room temperature for 2 h. The solvent was concentrated in vacuo and the crude product was re-dissolved in DCM (120 mL). The solution was cooled to 0° C. before TEA (2.49 g, 24.6 mmol) and acetic anhydride (1.26 g, 12.3 mmol) were added dropwise. The reaction mixture was stirred at room temperature for additional 2 h before it was quenched with water. The organic layer was dried over anhydrous Na$_2$SO$_4$, filtered and concentrated in vacuo. The crude residue was purified by silica gel chromatography (DCM/MeOH=20:1) to afford the title compound (2.40 g, 96%) as a white solid. $^1$H NMR (400 MHz, CDCl$_3$) δ 4.49-4.33 (m, 3H), 3.90-3.70 (m, 4H), 2.77-2.67 (m, 2H), 2.23-2.19 (m, 3H), 1.28-1.18 (m, 1H), 0.63-0.58 (m, 2H), 0.36-0.32 (m, 2H).

General Procedure for Intermediate D

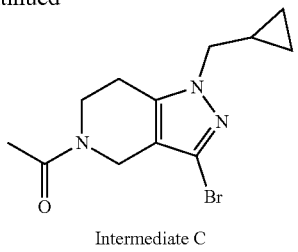

Intermediate C

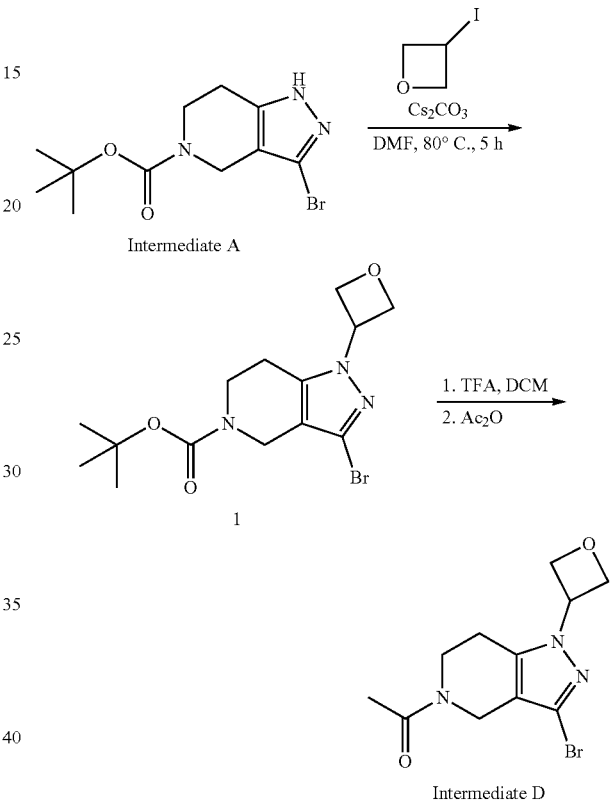

Intermediate D

Step 1: tert-butyl 3-bromo-1-(oxetan-3-yl)-6,7-dihydro-1H-pyrazolo[4,3-c]pyridine-5(4H)-carboxylate

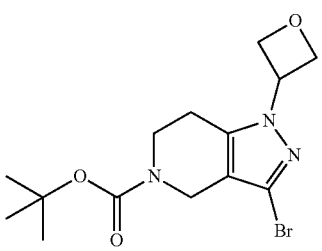 [SMILES: CC(C)(C)OC(=O)N1CCc2c(c(Br)nn2C2COC2)C1]

To a solution of tert-butyl 3-bromo-6,7-dihydro-1H-pyrazolo[4,3-c]pyridine-5(4H)-carboxylate (Intermediate A, 40.0 g, 132 mmol) in DMF (500 mL) was added Cs$_2$CO$_3$ (87 g, 264 mmol) and 3-iodooxetane (27 g, 146 mmol). The mixture was heated to 60° C. for 12 h before 3-iodooxetane (5 g, 27.0 mmol) was added and the mixture was stirred at 60° C. for an additional 6 h. After cooling the reaction to room temperature, the mixture was filtered, washed with EtOAc (500 mL) and concentrated in vacuo. The crude residue was purified by silica gel chromatography (petroleum ether:tert-butyl methyl ether:THF=from 100:1:1 to 5:1:1) to give the title compound (30 g, 64%) as a white solid. $^1$H NMR (400 MHz, CDCl$_3$) δ 5.30-5.25 (m 1H), 5.18-5.14 (m, 2H), 4.95-4.91 (m, 2H), 4.28 (s, 2H), 3.73-3.66 (m, 2H), 2.64 (t, J=5.6 Hz, 2H), 1.48 (s, 9H).

Step 2: 1-(3-bromo-1-(oxetan-3-yl)-6,7-dihydro-1H-pyrazolo[4,3-c]pyridin-5(4H)-yl)ethanone

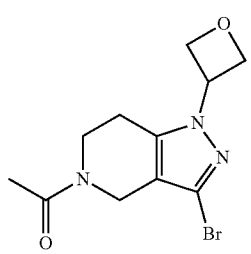 [SMILES: CC(=O)N1CCc2c(c(Br)nn2C2COC2)C1]

To a solution of tert-butyl 3-bromo-1-(oxetan-3-yl)-6,7-dihydro-1H-pyrazolo[4,3-c]pyridine-5(4H)-carboxylate (25.0 g, 70.0 mmol) in DCM (50 mL) was added trifluoroacetic acid (50 mL) dropwise at 0° C. The mixture was stirred at room temperature for 2 h. The mixture was concentrated in vacuo and the residue was re-dissolved in DCM (500 mL). The mixture was cooled to 0° C. before triethylamine (48.8 mL, 350 mmol) and acetic anhydride (7.2 g, 70.0 mmol) were added dropwise. The mixture was stirred at room temperature for additional 2 h. The reaction was quenched with water. The organic layer was dried over anhydrous Na$_2$SO$_4$, filtered and concentrated in vacuo. The crude residue was purified by silica gel chromatography (DCM/MeOH=80:1) to give the title compound (Intermediate D, 17.0 g, 81%) as a light yellow solid. $^1$H NMR (400 MHz, CDCl$_3$) δ 5.32-5.27 (m 1H), 5.16-5.13 (m, 2H), 4.95-4.91 (m, 2H), 4.47-4.31 (m, 2H), 3.88-3.70 (m, 2H), 2.75-2.63 (m, 2H), 2.17 (s, 3H).

General Procedure for Intermediate E

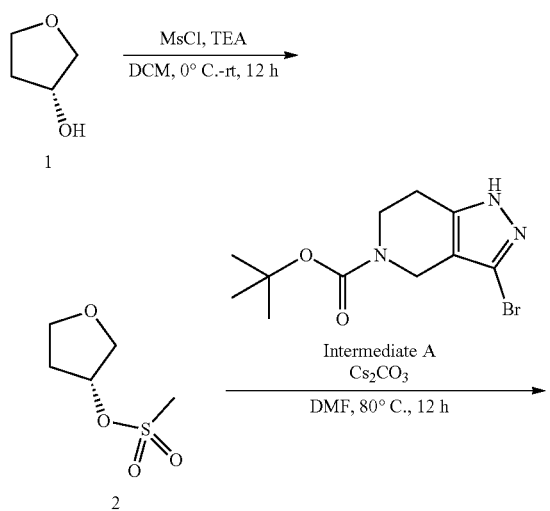

Intermediate E

Step 1: (R)-tetrahydrofuran-3-yl methanesulfonate

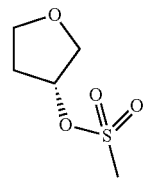

To a solution of (R)-tetrahydrofuran-3-ol (25 g, 253.7 mmol) in DCM (250 mL) at 0° C. was added triethylamine (119 mL, 851.2 mmol) and mesyl chloride (39 g, 340.48 mmol) dropwise. The mixture was stirred at room temperature for 12 h. The reaction was quenched with water (100 mL) and extracted with DCM (100 mL×2). The combined organic layers were dried over anhydrous Na$_2$SO$_4$, filtered and concentrated in vacuo to give the title compound (47 g, 99%) as a brown oil. $^1$H NMR (400 MHz, CDCl$_3$) δ 5.35-5.27 (m, 1H), 4.05-3.83 (m, 4H), 3.04 (s, 3H), 2.28-2.20 (m, 2H).

Step 2: (S)-tert-butyl 3-bromo-1-(tetrahydrofuran-3-yl)-6,7-dihydro-1H-pyrazolo[4,3-c]pyridine-5(4H)-carboxylate

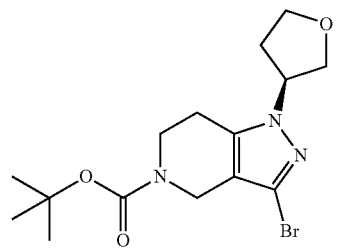 [SMILES: CC(C)(C)OC(=O)N1CCc2c(c(Br)nn2[C@H]2CCOC2)C1]

To a solution of tert-butyl 3-bromo-6,7-dihydro-1H-pyrazolo[4,3-c]pyridine-5(4H)-carboxylate (Intermediate A, 24.8 g, 82 mmol) in DMF (200 mL) was added Cs$_2$CO$_3$ (79 g, 246 mmol) and (R)-tetrahydrofuran-3-yl methanesulfonate (17.4 g, 98 mmol). The mixture was heated to 80° C. for 12 h. After cooling the reaction to room temperature, the mixture was concentrated in vacuo. The crude residue was purified by silica gel chromatography (petroleum ether/EtOAc=from 10:1 to 3:1) to give the title compound (50 g, 71%) as a yellow oil. $^1$H NMR (400 MHz, DMSO-d$_6$) δ 4.97-4.78 (m, 1H), 4.13 (s, 2H), 3.98-3.86 (m, 2H), 3.81-3.67 (m, 2H), 3.56 (t, J=5.6 Hz, 2H), 2.68 (t, J=5.6 Hz, 2H), 2.33-2.08 (m, 2H), 1.38 (s, 9H).

Step 3: (S)-1-(3-bromo-1-(tetrahydrofuran-3-yl)-6,7-dihydro-1H-pyrazolo[4,3-c]pyridin-5(4H)-yl)ethanone

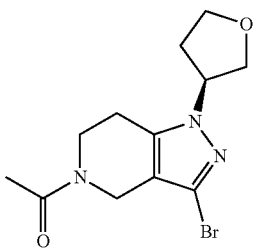 [SMILES: CC(=O)N1CCc2c(c(Br)nn2[C@H]2CCOC2)C1]

To a solution of (S)-tert-butyl 3-bromo-1-(tetrahydrofuran-3-yl)-6,7-dihydro-1H-pyrazolo[4,3-c]pyridine-5(4H)-carboxylate (29 g, 78 mmol) in DCM (300 mL) was added trifluroacetic acid (70 mL) dropwise. The mixture was stirred at room temperature for 2 h. The solvent was concentrated in vacuo and the crude residue was re-dissolved in DMF (100 mL). The mixture was cooled to 0° C. before triethylamine (22 mL, 156 mmol) and acetic anhydride (8.7 g, 86 mmol) were added dropwise. The mixture was stirred at room temperature for an additional 2 h. The reaction was quenched with water (200 mL) at 0° C. and extracted with EtOAc (150 mL×3). The combined organic layers were dried over anhydrous Na$_2$SO$_4$, filtered and concentrated in vacuo. The crude residue was purified by silica gel chromatography (DCM/MeOH=30:1) to give the title compound (Intermediate E, 21.3 g, 87%) as a white solid. $^1$H NMR (400 MHz, CDCl$_3$) δ 4.78-4.67 (m, 1H), 4.45-4.29 (m, 2H), 4.15-4.06 (m, 2H), 3.96-3.92 (m, 2H), 3.88-3.70 (m, 2H), 2.71-2.67 (m, 2H), 2.38-2.34 (m, 2H), 2.16 (s, 3H).

General Procedure for Intermediate F

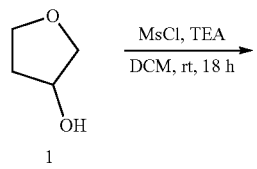

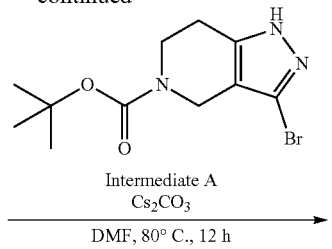

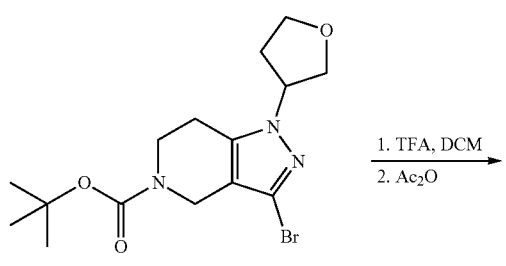

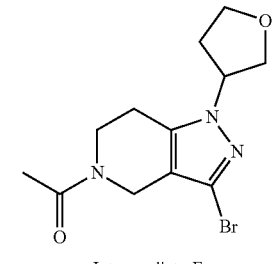

Intermediate F

Step 1: tetrahydrofuran-3-yl methanesulfonate

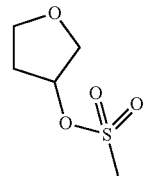

To a solution of tetrahydrofuran-3-ol (10 g, 113.5 mmol) in DCM (150 mL) was added MsCl (15.6 g, 136.2 mmol) and TEA (23 g, 227 mmol). The reaction mixture was stirred at room temperature for 18 h. Water (100 mL) was added and the mixture was extracted with DCM (100 mL×2). The combined organic layers was dried over anhydrous Na$_2$SO$_4$, filtered and concentrated in vacuo to give the title compound (16 g, 85%) as a brown oil. $^1$H NMR (400 MHz, CDCl$_3$) δ 5.27-5.25 (m, 1H), 4.00-3.83 (m, 4H), 3.01 (s, 3H), 2.23-2.18 (m, 2H).

143

Step 2: tert-butyl 3-bromo-1-(tetrahydrofuran-3-yl)-6,7-dihydro-1H-pyrazolo[4,3-c]pyridine-5(4H)-carboxylate

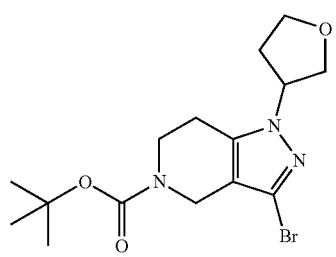 [SMILES: CC(C)(C)OC(=O)N1CCc2c(c(Br)nn2C2CCOC2)C1]

To a solution of tert-butyl 3-bromo-6,7-dihydro-1H-pyrazolo[4,3-c]pyridine-5(4H)-carboxylate (Intermediate A, 20.0 g, 66.0 mmol) in DMF (100 mL) was added Cs$_2$CO$_3$ (40.0 g, 123 mmol) and tetrahydrofuran-3-yl methanesulfonate (16.0 g, 98.0 mmol). The mixture was heated to 80° C. for 12 h. The solution was concentrated in vacuo and the crude residue was purified by silica gel chromatography (eluent from petroleum ether/EtOAc=10:1 to 3:1) to give the title compound (17 g, 69%) as a yellow oil. $^1$H NMR (400 MHz, CDCl$_3$) δ 4.78-4.69 (m, 1H), 4.26 (s, 2H), 4.18-3.86 (m, 4H), 3.72 (s, 2H), 2.72-2.62 (m, 2H), 2.44-2.22 (m, 2H), 1.48 (s, 9H).

Step 3: 1-(3-bromo-1-(tetrahydrofuran-3-yl)-6,7-dihydro-1H-pyrazolo[4,3-]pyridin-5(4H)-yl)ethanone

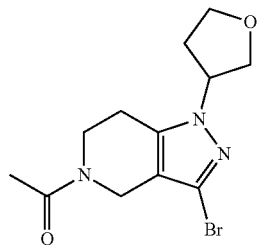 [SMILES: CC(=O)N1CCc2c(c(Br)nn2C2CCOC2)C1]

To a solution of tert-butyl 3-bromo-1-(tetrahydrofuran-3-yl)-6,7-dihydro-1H-pyrazolo [4,3-c]pyridine-5(4H)-carboxylate (17.0 g, 45.0 mmol) in DCM (60 mL) was added TFA (30 mL) dropwise. The reaction solution was stirred at room temperature for 2 h. The solvent was removed by evaporation and the crude product was re-dissolved in DMF (50 mL). The mixture was cooled to 0° C. before TEA (41.0 g, 40.5 mmol) and acetic anhydride (7.0 g, 68.0 mmol) were added dropwise. The ice bath was removed and the reaction was stirred at room temperature for additional 2 h. Water (50 mL) was added and the solution was extracted with EtOAc (150 mL×3). The combined organic layers were dried over anhydrous Na$_2$SO$_4$, filtered and concentrated in vacuo. The crude residue was purified by silica gel chromatography (DCM/MeOH=30:1) to give the title compound (Intermediate F, 12.0 g, 82%) as a white solid. $^1$H NMR (400 MHz, DMSO-d$_6$) δ 4.96-4.92 (m 1H), 4.28 (s, 2H), 3.99-3.95 (m, 2H), 3.80-3.68 (m, 4H), 2.82-2.70 (m, 2H), 2.29-2.19 (m, 2H), 2.10-2.08 (m, 3H).

144

General Procedure for Intermediates G & H

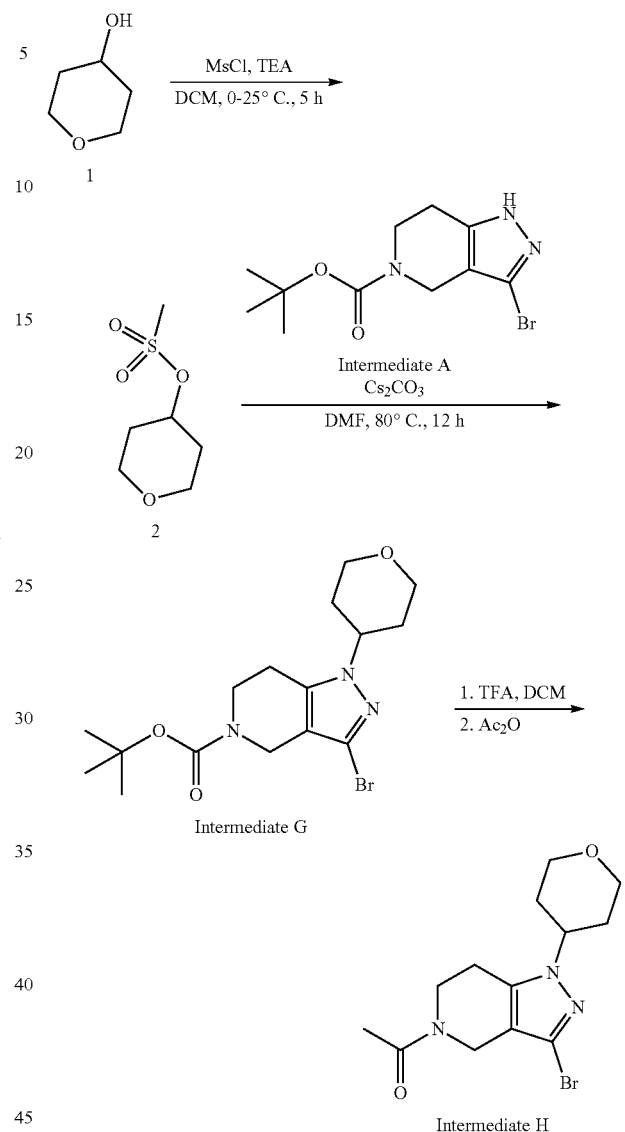

Step 1: tetrahydro-2H-pyran-4-yl methanesulfonate

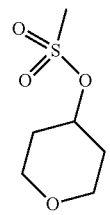

To a solution of tetrahydro-2H-pyran-4-ol (5 g, 49.0 mmol) and triethylamine (8.2 mL, 58.7 mmol) in DCM (100 mL) was added mesyl chloride (16.8 g, 146.9 mmol) dropwise at 0° C. under a nitrogen atmosphere. The mixture was stirred at room temperature for 5 h. Water (100 mL) was added and extracted with DCM (100 mL×2). The combined organic layers were dried over anhydrous Na₂SO₄, filtered and concentrated in vacuo to give the title compound (4 g, 45%) as a yellow solid. ¹H NMR (400 MHz, CDCl₃) δ 4.85-4.81 (m 1H), 3.90-3.87 (m, 2H), 3.52-3.46 (m, 2H), 2.99 (s, 3H), 2.01-1.97 (m, 2H), 1.83-1.80 (m, 2H).

Step 2: tert-butyl 3-bromo-1-(tetrahydro-2H-pyran-4-yl)-6,7-dihydro-1H-pyrazolo[4,3-c]pyridine-5(4H)-carboxylate

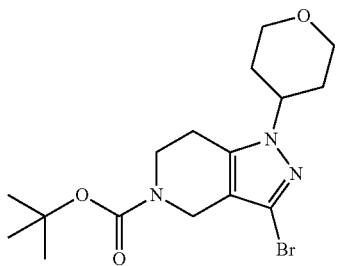 [SMILES: CC(C)(C)OC(=O)N1CCc2c(c(Br)nn2C2CCOCC2)C1]

To a solution of tert-butyl 3-bromo-6,7-dihydro-1H-pyrazolo[4,3-c]pyridine-5(4H)-carboxylate (Intermediate A, 6 g, 19.8 mmol) in DMF (40 mL) was added Cs₂CO₃ (19.5 g, 59.6 mmol) and tetrahydro-2H-pyran-4-yl methanesulfonate (3.9 g, 21.8 mmol). The mixture was heated to 80° C. for 12 h under a nitrogen atmosphere. After cooling the reaction to room temperature, the mixture was filtered. The mixture was diluted with EtOAc (100 mL) and washed with brine (100 mL×2). The organic layer was concentrated in vacuo. The crude residue was purified by silica gel chromatography (petroleum ether:tert-butyl methyl ether:THF=from 10:1:1 to 2:1:1) to give the title compound (Intermediate G, 3.2 g, 47%) as a clear oil. ¹H NMR (400 MHz, DMSO-d₆) δ 4.35-4.25 (m, 1H), 4.17 (s, 2H), 3.95-3.93 (m, 2H), 3.62-3.57 (m, 2H), 3.42 (t, J=11.2 Hz, 2H), 2.74-2.73 (m, 2H), 1.98-1.89 (m, 2H), 1.80-1.77 (m, 2H), 1.41 (s, 9H).

Step 3: 1-(3-bromo-1-(tetrahydro-2H-pyran-4-yl)-6,7-dihydro-1H-pyrazolo[4,3-c]pyridin-5(4H)-yl)ethanone

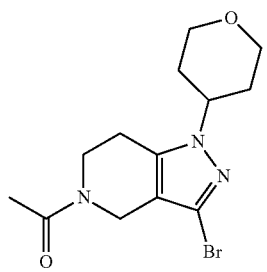 [SMILES: CC(=O)N1CCc2c(c(Br)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 3.2 g, 8.3 mmol) in DCM (20 mL) was added trifluoroacetic acid (20 mL) dropwise at 0° C. The mixture was stirred at room temperature for 2 h. The mixture was concentrated in vacuo and the residue was re-dissolved in DCM (30 mL). The mixture was cooled to 0° C. before triethylamine (2.9 mL, 21 mmol) and acetic anhydride (0.93 g, 9.1 mmol) were added dropwise. The mixture was stirred at room temperature for an additional 0.5 h. The reaction was quenched with water (60 mL). The organic layer was dried over anhydrous Na₂SO₄, filtered and concentrated in vacuo. The crude residue was purified by silica gel chromatography (DCM/MeOH=50:1) to give the title compound (Intermediate H, 2.1 g, 77%) as a light yellow solid. ¹H NMR (400 MHz, DMSO-d₆) δ 4.33-4.29 (m, 1H), 4.28 (s 2H), 3.95-3.92 (m, 2H), 3.70-3.67 (m, 2H), 3.43-3.36 (m, 2H), 2.84-2.69 (m, 2H), 2.09-2.08 (m, 3H), 1.96-1.91 (m, 2H), 1.80-1.76 (m, 2H).

General Procedure for Intermediate I

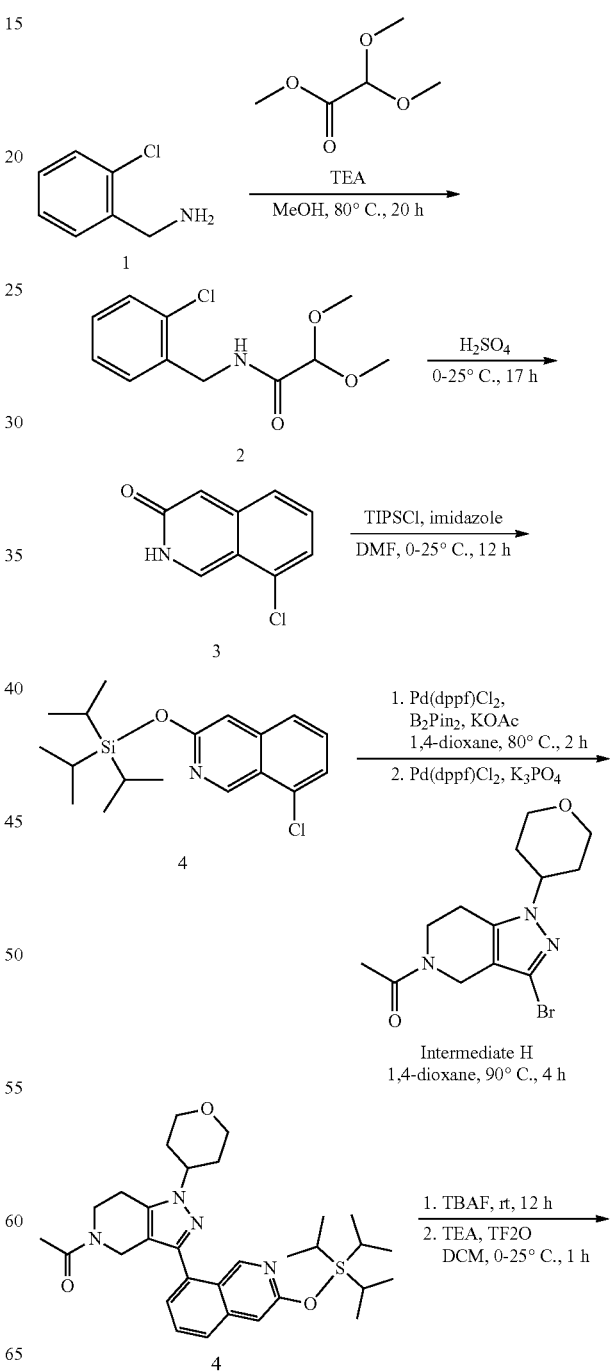

-continued

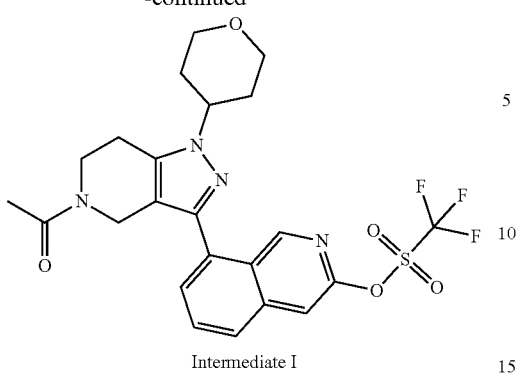

Intermediate I

Step 1: N-(2-chlorobenzyl)-2,2-dimethoxyacetamide

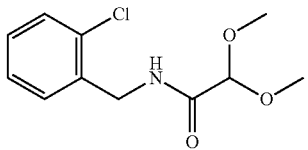 [SMILES: COC(OC)C(=O)NCc1ccccc1Cl]

To a solution of 2-chlorobenzylamine (30.0 g, 212 mmol) in MeOH (200 mL) was added triethylamine (36.7 mL, 265 mmol) and methyl dimethoxyacetate (31.0 g, 233 mmol). The reaction was heated to 80° C. for 20 h. After cooling to room temperature, the reaction was concentrated in vacuo. EtOAc (300 ml) was added, washed with 1N HCl (300 mL×2) and sat. aq. NaHCO$_3$ (300 mL×2). The organic layer was dried over anhydrous Na$_2$SO$_4$, filtered and concentrated in vacuo to give the title compound (40.0 g, crude) as colorless oil that required no further purification. $^1$H NMR (400 MHz, CDCl$_3$) δ 7.39-7.33 (m, 2H), 7.24-7.21 (m, 2H), 4.73 (s, 1H), 4.56 (d, J=6.0 Hz, 2H), 3.38 (s, 6H).

Step 2: 8-chloroisoquinolin-3(2H)-one

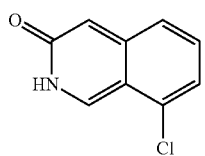 [SMILES: O=c1cc2cccc(Cl)c2c[nH]1]

To a solution of concentrated sulfuric acid (100 mL) at 0° C. was added N-(2-chlorobenzyl)-2,2-dimethoxyacetamide (40.0 g, 164 mmol). The reaction was stirred at room temperature for 16 h. The reaction was poured into ice water and the mixture was basified with ammonium hydroxide to pH 8. The yellow precipitate was filtered off, washed with water, and dried in vacuo to give the title compound (20.0 g, crude) as a yellow solid that required no further purification. $^1$H NMR (400 MHz, CDCl$_3$) δ 9.11 (s, 1H), 7.72 (d, J=8.4 Hz, 1H), 7.56-7.52 (m, 1H), 7.45 (d, J=7.6 Hz, 1H), 7.00 (s, 1H).

Step 3:
8-chloro-3-((triisopropylsilyl)oxy)isoquinoline

To a solution of 8-chloroisoquinolin-3(2H)-one (12.0 g, 66.8 mmol) in DMF (15 mL) at 0° C. was added imidazole (13.6 g, 200.5 mmol) and chlorotriisopropylsilane (17.2 mL, 80.2 mmol). The reaction was stirred at room temperature for 12 h. The reaction mixture was concentrated in vacuo. The crude residue was dissolved in EtOAc (70 mL) and washed with H$_2$O (40 mL×2). The organic layer was dried over anhydrous Na$_2$SO$_4$, filtered and concentrated in vacuo. The crude residue was purified by silica gel column chromatography (petroleum ether) to give the title compound (13.0 g, 62%) as colourless oil. $^1$H NMR (400 MHz, DMSO-d$_6$) δ 9.16 (s, 1H), 7.79 (d, J=8.4 Hz, 1H), 7.65-7.56 (m, 1H), 7.55-7.47 (m, 1H), 7.23 (s, 1H), 1.46-1.30 (m, 3H), 1.06 (d, J=7.6 Hz, 18H).

Step 4: 8-(4,4,5,5-tetramethyl-1,3,2-dioxaborolan-2-yl)-3-((triisopropylsilyl)-oxy)isoquinoline

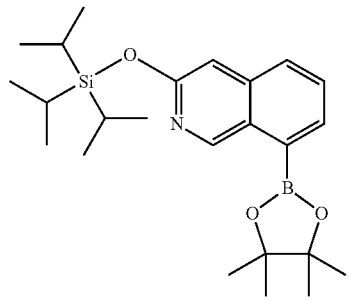 [SMILES: CC(C)[Si](Oc1cc2cccc(B3OC(C)(C)C(C)(C)O3)c2cn1)(C(C)C)C(C)C]

To a solution of 8-chloro-3-((triisopropylsilyl)oxy)isoquinoline (13.0 g, 38.7 mmol) in 1,4-dioxane (10 mL) was added [1,1'-bis(diphenylphosphino)ferrocene]dichloropalladium(II) (913 mg, 1.2 mmol), 4,4,4',4',5,5,5',5'-octamethyl-2,2'-bi(1,3,2-dioxaborolane) (19.6 g, 77.4 mmol) and KOAc (11.4 g, 116.1 mmol). The mixture was heated to 80° C. for 2 h under a nitrogen atmosphere. After cooling the reaction to room temperature, the reaction mixture was used to the next step directly without further purification. LCMS M/Z (M-TIPS+H) 272.

Step 5: 1-(1-(tetrahydro-2H-pyran-4-yl)-3-(3-((tri-isopropylsilyl)oxy)isoquinolin-8-yl)-6,7-dihydro-1H-pyrazolo[4,3-c]pyridin-5(4H)-yl)ethanone

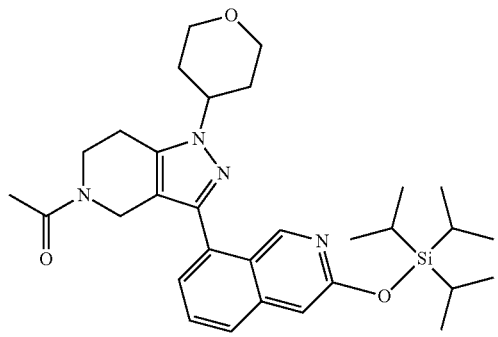 [SMILES: CC(=O)N1CCc2c(c(-c3cccc4cc(O[Si](C(C)C)(C(C)C)C(C)C)ncc34)nn2C2CCOCC2)C1]

To the above step cooled solution was added 1-(3-bromo-1-(tetrahydro-2H-pyran-4-yl)-6,7-dihydro-1H-pyrazolo[4,3-c]pyridin-5(4H)-yl)ethanone (Intermediate H, 8.9 g, 27.0 mmol), [1,1'-bis(diphenylphosphino)ferrocene]dichloropalladium(II) (1.2 g, 1.5 mmol) and K₃PO₄ (20.5 g, 96.5 mmol), 1,4-dioxane (5 mL) and water (3 mL). The reaction mixture was heated to 90° C. for 4 h under a nitrogen atmosphere. After cooling to room temperature, the mixture was filtered and concentrated in vacuo. DCM (60 mL) was added and washed with water (50 mL×2). The organic layer was dried over anhydrous Na₂SO₄, filtered and concentrated in vacuo. The crude residue was purified by silica gel chromatography (DCM/MeOH=20:1) to give the title compound (6.0 g, 28%) as a brown solid. LCMS M/Z (M-TIPS+H) 393.

Step 6: 1-(3-(3-hydroxyisoquinolin-8-yl)-1-(tetrahydro-2H-pyran-4-yl)-6,7-dihydro-1H-pyrazolo[4,3-c]pyridin-5(4H)-yl)ethanone

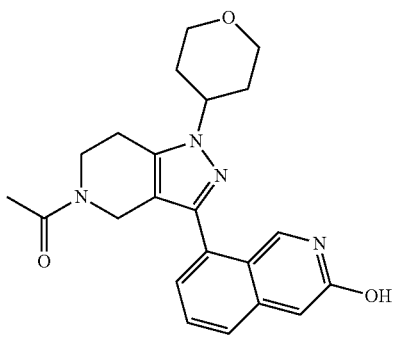 [SMILES: CC(=O)N1CCc2c(c(-c3cccc4cc(O)ncc34)nn2C2CCOCC2)C1]

To a solution of 1-(1-(tetrahydro-2H-pyran-4-yl)-3-(3-(((triisopropylsilyl)oxy)isoquinolin-8-yl)-6,7-dihydro-1H-pyrazolo[4,3-c]pyridin-5(4H)-yl)ethanone (6.0 g, 10.9 mmol) in THF (10 mL) at 20° C. was added TBAF (54.7 ml, 54.7 mmol, 1 M in THF). The reaction was stirred at room temperature for 12 h. The reaction mixture was concentrated in vacuo. The crude residue was dissolved in DCM (50 mL) and washed with H₂O (150 mL×2). The organic layer was dried over anhydrous Na₂SO₄, filtered and concentrated in vacuo. The crude residue was purified by silica gel chromatography (DCM/MeOH=10:1) to give the title compound (5.0 g, 86% purity) as a brown solid. LCMS M/Z (M+H) 393.

Step 7: 8-(5-acetyl-1-(tetrahydro-2H-pyran-4-yl)-4,5,6,7-tetrahydro-1H-pyrazolo[4,3-c]pyridin-3-yl)isoquinolin-3-yl trifluoromethanesulfonate

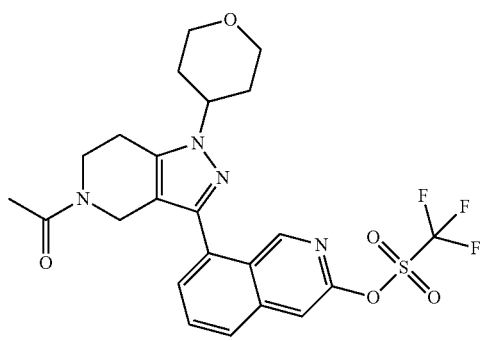 [SMILES: CC(=O)N1CCc2c(c(-c3cccc4cc(OS(=O)(=O)C(F)(F)F)ncc34)nn2C2CCOCC2)C1]

To a solution of 1-(3-(3-hydroxyisoquinolin-8-yl)-1-(tetrahydro-2H-pyran-4-yl)-6,7-dihydro-1H-pyrazolo[4,3-c]pyridin-5(4H)-yl)ethanone (5.0 g, 12.7 mmol) in DCM (10 mL) at 0° C. was added triethylamine (5.3 mL, 38.2 mmol) and trifluoromethanesulfonic anhydride (3.2 mL, 19.1 mmol). The reaction was stirred at room temperature for 1 h. DCM (100 mL) was added and washed with water (80 mL×2). The organic layer was dried over anhydrous Na₂SO₄, filtered and concentrated in vacuo. The crude residue was purified by silica gel chromatography (EtOAc) to give the title compound (Intermediate I, 1.7 g, 23%) as a white solid. ¹H NMR (400 MHz, DMSO-d₆) δ 9.84-9.74 (m, 1H), 8.21 (s, 1H), 8.16 (d, J=8.4 Hz, 1H), 8.05-7.95 (m, 1H), 7.84-7.72 (m, 1H), 4.59 (s, 2H), 4.50-4.45 (m, 1H), 4.05-3.98 (m, 2H), 3.89-3.74 (m, 2H), 3.51 (d, J=12.0 Hz, 1H), 3.01-2.80 (m, 2H), 2.20-2.00 (m, 5H), 1.99-1.88 (m, 2H).

Example 1 (Procedure A)

1-(3-(1H-indol-3-yl)-1-methyl-6,7-dihydro-1H-pyrazolo[4,3-c]pyridin-5(4H)-yl)ethanone

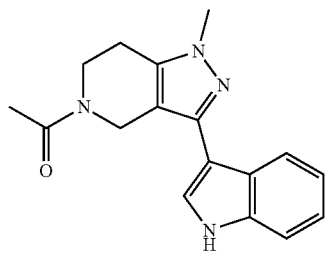

Step 1: tert-butyl 3-(5-acetyl-1-methyl-4,5,6,7-tetra-hydro-1H-pyrazolo[4,3-c]pyridin-3-yl)-1H-indole-1-carboxylate

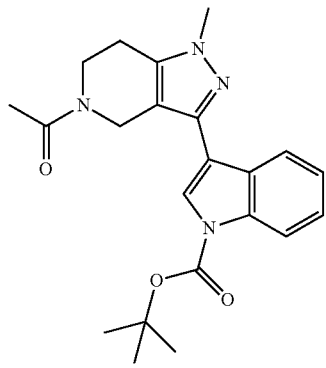 [SMILES: CC(=O)N1CCc2c(c(-c3cn(C(=O)OC(C)(C)C)c4ccccc34)nn2C)C1]

To a solution of 1-(3-bromo-1-methyl-6,7-dihydro-1H-pyrazolo[4,3-c]pyridin-5(4H)-yl)ethanone (Intermediate B, 500 mg, 1.92 mmol) in 1,4-dioxane (8 mL) and water (2 mL) was added [1,1'-bis(diphenylphosphino)ferrocene]dichloropalladium(II) (146 mg, 0.2 mmol), $Na_2CO_3$ (408 mg, 3.84 mmol) and (1-(tert-butoxycarbonyl)-1H-indol-3-yl)boronic acid (552 mg, 2.1 mmol). The mixture was heated to 110° C. for 18 h under a nitrogen atmosphere. After cooling the reaction to room temperature, the mixture was filtered and concentrated in vacuo. The crude residue was purified by silica gel chromatography (DCM/MeOH=20:1) to give the title compound (400 mg, 53%) as a brown solid.

Step 2: 1-(3-(1H-indol-3-yl)-1-methyl-6,7-dihydro-1H-pyrazolo[4,3-c]pyridin-5(4H)-yl)ethanone

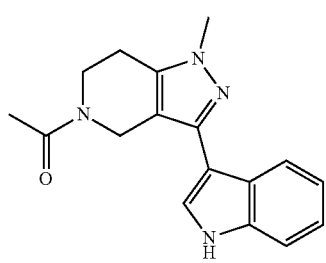 [SMILES: CC(=O)N1CCc2c(c(-c3c[nH]c4ccccc34)nn2C)C1]

To a solution of tert-butyl 3-(5-acetyl-1-methyl-4,5,6,7-tetrahydro-1H-pyrazolo[4,3-c]pyridin-3-yl)-1H-indole-1-carboxylate (200 mg, 0.51 mmol) in DCM (2 mL) at 0° C. was added trifluoroacetic acid (2 mL, 3.4 mmol). The mixture was stirred at room temperature for 2 h and concentrated in vacuo. The crude residue was purified by reverse phase chromatography (acetonitrile 30-60%/0.1% $NH_4OH$ in water) to give the title compound (15 mg, 10%) as a white solid. $^1$H NMR (400 MHz, DMSO-$d_6$) δ 11.23 (s, 1H), 8.26-8.21 (m, 1H), 7.52-7.40 (m, 2H), 7.15-7.06 (m, 2H), 4.58 (s, 2H), 3.85-3.68 (m, 5H), 2.80-2.68 (m, 2H), 2.12 (s, 3H). LCMS M/Z (M+H) 295.

Example 2 (Procedure B)

1-(1-methyl-3-(1-methyl-1H-indol-3-yl)-6,7-dihydro-1H-pyrazolo[4,3-c]pyridin-5(4H)-yl)ethanone

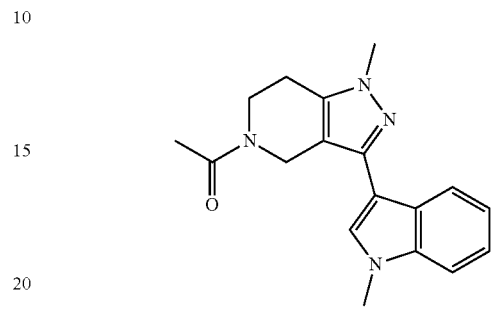

To a solution of 1-(3-(1H-indol-3-yl)-1-methyl-6,7-dihydro-1H-pyrazolo[4,3-c]pyridin-5(4H)-yl)ethanone (Example 1, 150 mg, 0.51 mmol) in DMF (2 mL) at 0° C. was added sodium hydride (60%, 41 mg, 1.02 mmol) by portionwise. The mixture was stirred at room temperature for 0.5 h. Iodomethane (0.073 mL, 1.02 mmol) was added dropwise and the mixture stirred at room temperature for an additional 1 h. The mixture was quenched with water (20 mL) and extracted with EtOAc (20 mL×3). The combined organic layers were dried over anhydrous $Na_2SO_4$, filtered and concentrated in vacuo. The crude residue was purified by reverse phase chromatography (acetonitrile 36-66%/0.1% $NH_4OH$ in water) to give the title compound (47 mg, 29%) as a white solid. $^1$H NMR (400 MHz, DMSO-$d_6$) δ 8.28-8.24 (m, 1H), 7.55-7.42 (m, 2H), 7.22-7.18 (m, 1H), 7.12-7.08 (m, 1H), 4.61-4.54 (m, 2H), 3.85 (s, 1H), 3.79-3.72 (m, 5H), 2.82-2.67 (m, 2H), 2.13-2.07 (m, 3H). LCMS M/Z (M+H) 309.

Example 3 (Procedure C)

1-(1-methyl-3-(6-(1-methyl-1H-pyrazol-4-yl)-1H-indol-3-yl)-6,7-dihydro-H-pyrazolo[4,3-c]pyridin-5(4H)-yl)ethanone

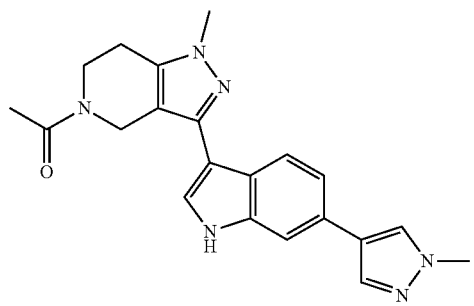 [SMILES: CC(=O)N1CCc2c(c(-c3c[nH]c4cc(-c5cnn(C)c5)ccc34)nn2C)C1]

Step 1: tert-butyl 6-bromo-1H-indole-1-carboxylate

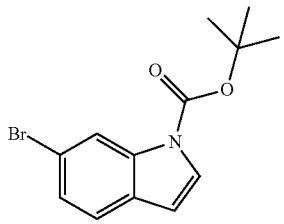 [SMILES: CC(C)(C)OC(=O)n1ccc2ccc(Br)cc21]

To a solution of 6-bromo-1H-indole (10.0 g, 51.0 mmol) in DCM (100 mL) was added di-tert-butyl dicarbonate (13.4 g, 61.2 mmol), DMAP (623 mg, 5.1 mmol) and triethylamine (21.2 mL, 153.0 mmol). The mixture was stirred at 20° C. for 16 h under a nitrogen atmosphere. The mixture was concentrated in vacuo. The crude residue was purified by silica gel chromatography (petroleum ether/EtOAc=10:1) to give the title compound (14.5 g, 96%) as a yellow solid.

Step 2: tert-butyl 6-(1-methyl-1H-pyrazol-4-yl)-1H-indole-1-carboxylate

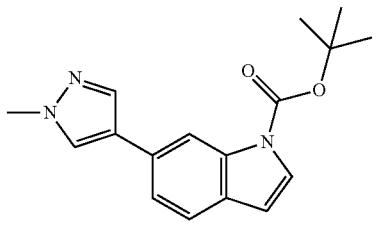 [SMILES: Cn1cc(-c2ccc3ccn(C(=O)OC(C)(C)C)c3c2)cn1]

To a solution of tert-butyl 6-bromo-1H-indole-1-carboxylate (10.0 g, 33.8 mmol) in 1,4-dioxane (90 mL) and water (30 mL) was added [1,1'-is(diphenylphosphino)ferrocene]-dichloropalladium (II) (2.0 g, 3.4 mmol), Na$_2$CO$_3$ (10.7 g, 101.3 mmol) and 1-methyl-4-(4,4,5,5-tetramethyl-1,3,2-dioxaborolan-2-yl)-1H-pyrazole (8.4 g, 40.5 mmol). The mixture was heated to 110° C. for 16 h under a nitrogen atmosphere. After cooling the reaction to room temperature, water (100 mL) was added and extracted with EtOAc (100 mL×3). The combined organic layers were dried over anhydrous Na$_2$SO$_4$, filtered and concentrated in vacuo. The crude residue was purified by silica gel chromatography (petroleum ether/EtOAc=2:1) to give the title compound (9.0 g, 90%) as a light brown solid.

Step 3: tert-butyl 3-bromo-6-(1-methyl-1H-pyrazol-4-yl)-1H-indole-1-carboxylate

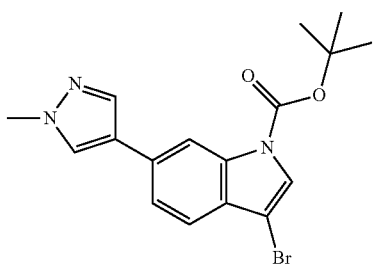 [SMILES: Cn1cc(-c2ccc3c(Br)cn(C(=O)OC(C)(C)C)c3c2)cn1]

To a solution of tert-butyl 6-(1-methyl-1H-pyrazol-4-yl)-1H-indole-1-carboxylate (7.5 g, 25.2 mmol) in DCM (80 mL) was added N-bromosuccinimide (4.49 g, 25.2 mmol). The mixture was stirred at 40° C. for 16 h under a nitrogen atmosphere. Water (120 mL) was added and the mixture was extracted with DCM (120 mL×2). The combined organic layers were dried over anhydrous Na$_2$SO$_4$, filtered and concentrated in vacuo to give the title compound (7.0 g, 74%) as brown oil that required no further purification.

Step 4: tert-butyl 6-(1-methyl-1H-pyrazol-4-yl)-3-(4,4,5,5-tetramethyl-1,3,2-dioxaborolan-2-yl)-1H-indole-1-carboxylate

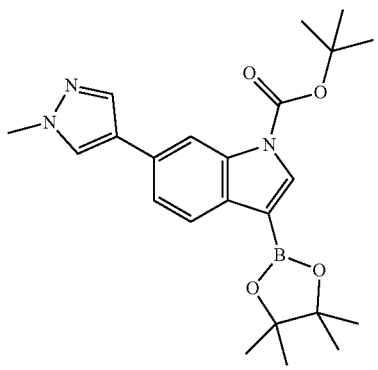 [SMILES: Cn1cc(-c2ccc3c(B4OC(C)(C)C(C)(C)O4)cn(C(=O)OC(C)(C)C)c3c2)cn1]

To a solution of tert-butyl 3-bromo-6-(1-methyl-1H-pyrazol-4-yl)-1H-indole-1-carboxylate (7.0 g, 18.6 mmol) in DMF (40 mL) was added [1,1'-bis(diphenylphosphino)ferrocene]dichloropalladium(II) (1.4 g, 1.9 mmol), KOAc (5.5 g, 55.8 mmol) and 4,4,4',4',5,5,5',5'-octamethyl-2,2'-bi(1,3,2-dioxaborolane) (7.0 g, 27.9 mmol). The mixture was heated to 70° C. for 12 h under a nitrogen atmosphere. After cooling the reaction to room temperature, the mixture was concentrated in vacuo. The crude residue was purified by silica gel chromatography (petroleum ether/EtOAc=5:1) to give the title compound (3.0 g, 38%) as a yellow oil.

Step 5: tert-butyl 3-(5-acetyl-1-methyl-4,5,6,7-tetrahydro-1H-pyrazolo[4,3-c]pyridin-3-yl)-6-(1-methyl-1H-pyrazol-4-yl)-1H-indole-1-carboxylate

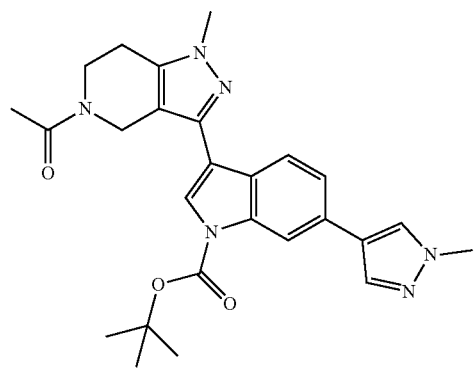 [SMILES: CC(=O)N1CCc2c(c(-c3cn(C(=O)OC(C)(C)C)c4cc(-c5cnn(C)c5)ccc34)nn2C)C1]

To a solution of 1-(3-bromo-1-methyl-6,7-dihydro-1H-pyrazolo[4,3-c]pyridin-5(4H)-yl)ethanone (Intermediate B, 838 mg, 3.25 mmol) in 1,4-dioxane (15 mL) and water (5 mL) was added [1,1'-bis(diphenylphosphino)ferrocene]dichloropalladium(II) (238 mg, 0.33 mmol), K$_2$CO$_3$ (898 mg, 6.50 mmol) and tert-butyl 6-(1-methyl-1H-pyrazol-4-yl)-3-(4,4,5,5-tetramethyl-1,3,2-dioxaborolan-2-yl)-1H-indole-1-carboxylate (2.5 g, 3.25 mmol). The mixture was heated to 70° C. for 16 h under a nitrogen atmosphere. After cooling the reaction to room temperature, water (50 mL) was added and extracted with EtOAc (60 mL×3). The combined organic layers were dried over anhydrous Na$_2$SO$_4$, filtered and concentrated in vacuo. The crude residue was purified by silica gel chromatography (DCM/MeOH=20:1) to give the title compound (1.0 g, 65%) as a brown solid.

Step 6: 1-(1-methyl-3-(6-(1-methyl-1H-pyrazol-4-yl)-1H-indol-3-yl)-6,7-dihydro-1H-pyrazolo[4,3-c]pyridin-5(4H)-yl)ethanone

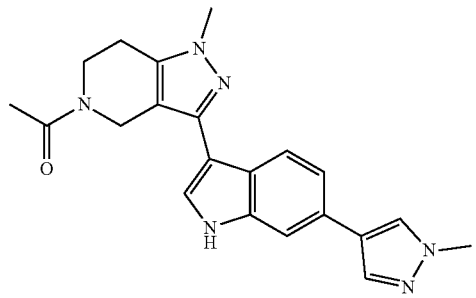 [SMILES: CC(=O)N1CCc2c(c(-c3c[nH]c4cc(-c5cnn(C)c5)ccc34)nn2C)C1]

To a solution of tert-butyl 3-(5-acetyl-1-methyl-4,5,6,7-tetrahydro-1H-pyrazolo[4,3-c]pyridin-3-yl)-6-(1-methyl-1H-pyrazol-4-yl)-1H-indole-1-carboxylate (700 mg, 1.48 mmol) in DCM (7 mL) was added trifluoroacetic acid (7 mL). The mixture was stirred at 20° C. for 3 h under a nitrogen atmosphere. The mixture was concentrated in vacuo to give the crude residue that was dissolved in EtOAc (50 mL), washed with sat. aq. NaHCO$_3$ (50 mL×2) and brine (50 mL×2), dried over anhydrous Na$_2$SO$_4$, filtered and concentrated in vacuo. The crude residue was purified by recrystallization to give the title compound (202 mg, 36%) as a white solid. $^1$H NMR (400 MHz, DMSO-d$_6$) δ 11.21 (s, 1H), 8.21-8.15 (m, 1H), 8.08 (s, 1H), 7.83 (s, 1H), 7.52 (s, 1H), 7.47-7.37 (m, 1H), 7.28-7.26 (m, 1H), 4.57 (s, 2H), 3.86 (s, 3H), 3.80-3.68 (m, 5H), 2.80-2.67 (m, 2H), 2.11 (s, 3H). LCMS M/Z (M+H) 375.

Example 4 (Procedure D)

1-(3-(6-methylisoquinolin-8-yl)-1-(tetrahydro-2H-pyran-4-yl)-6,7-dihydro-1H-pyrazolo[4,3-c]pyridin-5(4H)-yl)ethanone

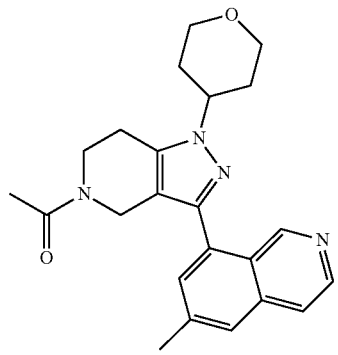 [SMILES: CC(=O)N1CCc2c(c(-c3cc(C)cc4ccncc34)nn2C2CCOCC2)C1]

Step 1: N-(2-bromo-4-chlorobenzylidene)-2,2-dimethoxyethanamine

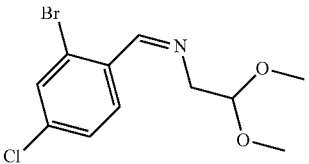 [SMILES: COC(C/N=C\c1ccc(Cl)cc1Br)OC]

To a solution of 2-bromo-4-chlorobenzaldehyde (40.0 g, 182.27 mmol) in toluene (100 mL) was added 2,2-dimethoxyethanamine (19.16 g, 182.27 mmol). The mixture was heated to 110° C. for 16 h under a nitrogen atmosphere. After cooling the reaction to room temperature, the mixture was concentrated in vacuo to give the title compound (59.0 g, crude) as colorless oil that required no further purification. $^1$H NMR (400 MHz, CDCl$_3$) δ 8.57 (s, 1H), 7.96 (d, J=8.4 Hz, 1H), 7.57 (s, 1H), 7.31-7.28 (m, 1H), 4.67 (t, J=5.2 Hz, 1H), 3.80 (d, J=4.4 Hz, 2H), 3.41 (s, 6H).

Step 2: N-(2-bromo-4-chlorobenzyl)-2,2-dimethoxyethanamine

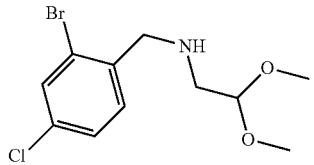 [SMILES: COC(CNCc1ccc(Cl)cc1Br)OC]

To a solution of N-(2-bromo-4-chlorobenzylidene)-2,2-dimethoxyethanamine (59.0 g, 192.45 mmol) in MeOH (200 mL) at 0° C. was added sodium borohydride (5.82 g, 153.96 mmol) portionwise. The mixture was stirred at 28° C. for 2 h under a nitrogen atmosphere and concentrated in vacuo. Water (200 mL) was added and extracted with DCM (200 mL×3). The combined organic layers were dried over anhy- Step 3: N-(2-bromo-4-chlorobenzyl)-N-(2,2-dimethoxyethyl)-4-methylbenzenesulfonamide

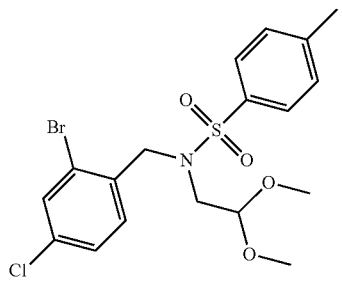 [SMILES: COC(CN(Cc1ccc(Cl)cc1Br)S(=O)(=O)c1ccc(C)cc1)OC]

To a solution of N-(2-bromo-4-chlorobenzyl)-2,2-dimethoxyethanamine (60.0 g, 194.43 mmol) in DCM (300 mL) at 0° C. was added 4-methylbenzene-1-sulfonyl chloride (37.0 g, 194.43 mmol), N,N-dimethylpyridin-4-amine (1.19 g, 9.72 mmol) and triethylamine (53.9 mL, 388.85 mmol). The mixture was stirred at 28° C. for 10 h under a nitrogen atmosphere. Water (300 mL) was added and extracted with DCM (300 mL×3). The combined organic layers were dried over anhydrous Na$_2$SO$_4$, filtered and concentrated in vacuo. The crude residue was purified by silica gel chromatography (petroleum ether/EtOAc=5:1) to give the title compound (70 g, 78%) as a white solid. $^1$H NMR (400 MHz, CDCl$_3$) δ 7.72 (d, J=7.6 Hz, 1H), 7.52 (s, 1H), 7.45 (d, J=8.4 Hz, 1H), 7.35-7.27 (m, 3H), 4.48 (s, 2H), 4.36 (t, J=5.2 Hz, 1H), 3.29 (d, J=5.2 Hz, 2H), 3.23 (s, 6H), 2.45 (s, 3H). LCMS M/Z (M+H) 462.

Step 4: 8-bromo-6-chloroisoquinoline

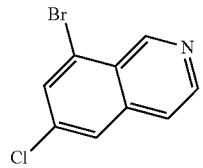 [SMILES: Clc1cc(Br)c2cnccc2c1]

To a solution of aluminum trichloride (43.22 g, 324.12 mmol) in 1,2-dichloroethane (200 mL) at 0° C. was added N-(2-bromo-4-chlorobenzyl)-N-(2,2-dimethoxyethyl)-4-methylbenzenesulfonamide (30.0 g, 64.82 mmol) in 1,2-dichloroethane (200 mL) dropwise. The mixture was stirred at 28° C. for 16 h under a nitrogen atmosphere and concentrated in vacuo. The crude residue was purified by silica gel chromatography (petroleum ether/EtOAc=10:1) to give the title compound (6.2 g, 39%) as a yellow solid. LCMS M/Z (M+H) 242.

Step 5: 6-chloro-8-(4,4,5,5-tetramethyl-1,3,2-dioxaborolan-2-yl)isoquinoline

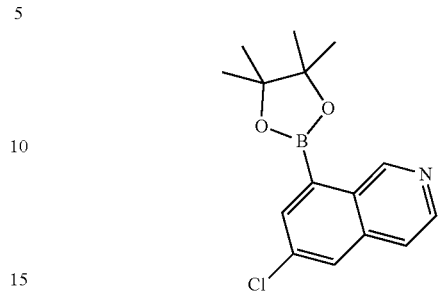

To a solution of 8-bromo-6-chloroisoquinoline (3.0 g, 12.37 mmol) in 1,4-dioxane (50 mL) was added [1,1'-bis(diphenylphosphino)ferrocene]dichloropalladium(II) (905 mg, 1.24 mmol), potassium 2-ethylhexanoate (3.38 g, 18.56 mmol) and 4,4,4',4',5,5,5',5'-octamethyl-2,2'-bi(1,3,2-dioxaborolane) (4.71 g, 18.56 mmol). The mixture was heated to 80° C. for 1 h under a nitrogen atmosphere. After cooling the reaction to room temperature, the reaction mixture was used to the next step directly without further purification. LCMS M/Z (M+H) 290.

Step 6: 1-(3-(6-chloroisoquinolin-8-yl)-1-(tetrahydro-2H-pyran-4-yl)-6,7-dihydro-1H-pyrazolo[4,3-c]pyridin-5(4H)-yl)ethanone

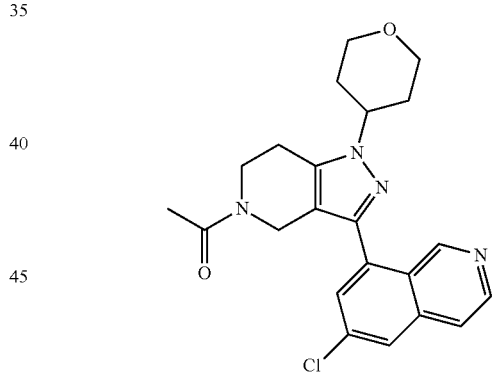

To the above step cooled solution was added 1-(3-bromo-1-(tetrahydro-2H-pyran-4-yl)-6,7-dihydro-1H-pyrazolo[4,3-c]pyridin-5(4H)-yl)ethanone (Intermediate H, 6.12 g, 18.65 mmol), [1,1'-bis(diphenylphosphino)ferrocene]dichloropalladium(II) (758 mg, 1.04 mmol) and K$_3$PO$_4$ (4.40 g, 20.72 mmol), 1,4-dioxane (30 mL) and water (20 mL). The reaction mixture was heated to 80° C. for 8 h under nitrogen atmosphere. After cooling to room temperature, the mixture was filtered and concentrated in vacuo. EtOAc (200 mL) was added and washed with water (120 mL×2). The organic layer was dried over anhydrous Na$_2$SO$_4$, filtered and concentrated in vacuo. The crude residue was purified by silica gel chromatography (DCM/MeOH=30:1) to give the title compound (1.6 g, 31%) as a brown solid. $^1$H NMR (400 MHz, DMSO-d$_6$) δ 9.78-9.70 (m, 1H), 8.58 (d, J=5.6 Hz, 1H), 8.15 (s, 1H), 7.88 (d, J=5.6 Hz, 1H), 7.68-7.55 (m, 1H), 4.55 (s, 2H), 4.54-4.42 (m, 1H), 4.06-3.96 (m, 2H), 3.87-

3.77 (m, 2H), 3.51 (t, J=12.0 Hz, 2H), 3.01-2.80 (m, 2H), 2.15-2.00 (m, 5H), 1.98-1.87 (m, 2H). LCMS M/Z (M+H) 411.

Step 7: 1-(3-(6-methylisoquinolin-8-yl)-1-(tetrahydro-2H-pyran-4-yl)-6,7-dihydro-1H-pyrazolo[4,3-c]pyridin-5(4H)-yl)ethanone

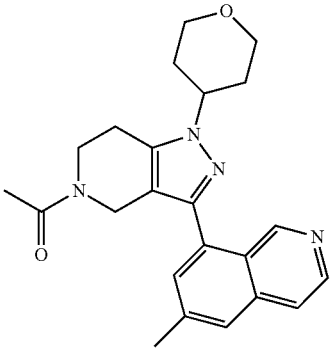 [SMILES: CC(=O)N1CCc2c(c(-c3cc(C)cc4ccncc34)nn2C2CCOCC2)C1]

To a solution of 1-(3-(6-chloroisoquinolin-8-yl)-1-(tetrahydro-2H-pyran-4-yl)-6,7-dihydro-1H-pyrazolo[4,3-c]pyridin-5(4H)-yl)ethanone (200 mg, 0.49 mmol) in toluene (10 mL) and water (2 mL) was added potassium methyltrifluoroborate (59 mg, 0.49 mmol), butyl di-1-adamantylphosphine (175 mg, 0.49 mmol), palladium(II) acetate (109 mg, 0.49 mmol) and $Cs_2CO_3$ (159 mg, 0.49 mmol). The mixture was heated to 80° C. for 16 h under a nitrogen atmosphere. After cooling the reaction to room temperature, EtOAc (100 mL) was added and washed with water (100 mL×3) and brine (100 mL). The organic phase was dried over anhydrous $Na_2SO_4$, filtered and concentrated in vacuo. The crude residue was purified by reverse phase chromatography (acetonitrile 30-60%/0.05% $NH_4OH$ in water) to give the title compound (15 mg, 8%) as a white solid. $^1H$ NMR (400 MHz, DMSO-$d_6$) δ 9.66 (s, 1H), 8.48 (d, J=6.0 Hz, 1H), 7.81-7.73 (m, 2H), 7.54-7.42 (m, 1H), 4.52 (s, 2H), 4.51-4.40 (s, 1H), 4.08-3.95 (m, 2H), 3.87-3.76 (m, 2H), 3.52 (t, J=12.0 Hz, 2H), 3.00-2.81 (m, 2H), 2.56 (s, 3H), 2.13-2.03 (m, 5H), 2.01-1.94 (m, 2H). LCMS M/Z (M+H) 391.

Example 5 (Procedure E)

1-(3-(6-methoxyisoquinolin-8-yl)-1-(tetrahydro-2H-pyran-4-yl)-6,7-dihydro-1H-pyrazolo[4,3-c]pyridin-5(4H)-yl)ethanone

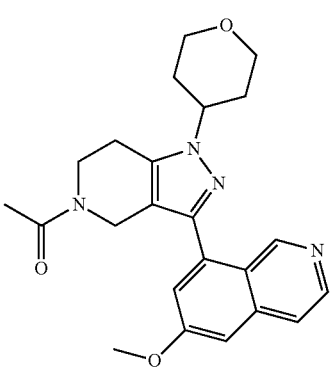 [SMILES: COc1cc(-c2nn(C3CCOCC3)c3c2CN(C(C)=O)CC3)c2cnccc2c1]

To a solution of 1-(3-(6-chloroisoquinolin-8-yl)-1-(tetrahydro-2H-pyran-4-yl)-6,7-dihydro-1H-pyrazolo[4,3-c]pyridin-5(4H)-yl)ethanone (200 mg, 0.49 mmol) in 1,4-dioxane (6 mL) was added 2-(dicyclohexylphosphino)-2',4',6'-triisopropylbiphenyl (46 mg, 0.10 mmol), methanesulfonato(2-dicyclohexylphosphino-2',4',6'-tri-i-propyl-1,1'-biphenyl)(2'-amino-1,1'-biphenyl-2-yl)palladium(II) (82 mg, 0.10 mmol), t-BuONa (65 mg, 0.68 mmol) and MeOH (0.1 mL, 2.43 mmol). The mixture was heated to 50° C. for 20 h under a nitrogen atmosphere. After cooling the reaction to room temperature, the mixture was filtered and concentrated in vacuo. The crude residue was purified by reverse phase chromatography (acetonitrile 15-45%/0.05% $NH_4OH$ in water) to give the title compound (30 mg, 90% purity) which was further separated by using chiral SFC (SFC 80; Chiralpak AS 250×30 mm I.D, 5 um; Supercritical $CO_2$/MeOH+$NH_3.H_2O$=30/30; 60 ml/min) to give the title compound (18 mg, 9%) as a white solid. $^1H$ NMR (400 MHz, DMSO-$d_6$) δ 9.66-9.59 (m, 1H), 8.41 (d, J=5.6 Hz, 1H), 7.75 (d, J=5.6 Hz, 1H), 7.36 (d, J=2.4 Hz, 1H), 7.24-7.14 (m, 1H), 4.51 (s, 2H), 4.50-4.39 (m, 1H), 4.05-3.95 (m, 2H), 3.94 (s, 3H), 3.86-3.76 (m, 2H), 3.51 (t, J=12.0 Hz, 2H), 3.00-2.79 (m, 2H), 2.16-2.00 (m, 5H), 1.99-1.87 (m, 2H). LCMS M/Z (M+H) 407.

Example 6 (Procedure F)

1-(1-(tetrahydro-2H-pyran-4-yl)-3-(6-vinylisoquinolin-8-yl)-6,7-dihydro-1H-pyrazolo[4,3-c]pyridin-5(4H)-yl)ethanone

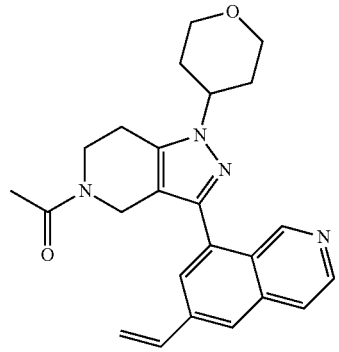 [SMILES: C=Cc1cc(-c2nn(C3CCOCC3)c3c2CN(C(C)=O)CC3)c2cnccc2c1]

To a solution of 1-(3-(6-chloroisoquinolin-8-yl)-1-(tetrahydro-2H-pyran-4-yl)-6,7-dihydro-1H-pyrazolo[4,3-c]pyridin-5(4H)-yl)ethanone (3.0 g, 7.3 mmol) in THF (30 mL) and water (6 mL) was added 2-(dicyclohexylphosphino)-2',4',6'-triisopropylbiphenyl (348 mg, 0.73 mmol) and chloro(2-dicyclohexylphosphino-2',4',6'-tri-i-propyl-1,1'-biphenyl)(2'-amino-1,1'-biphenyl-2-yl) palladium(II) (574 mg, 0.73 mmol), $Na_2CO_3$ (1.55 g, 14.6 mmol) and 4,4,5,5-tetramethyl-2-vinyl-1,3,2-dioxaborolane (1.46 g, 9.49 mmol). The mixture was heated to 60° C. for 16 h under a nitrogen atmosphere. After cooling the reaction to room temperature, the mixture was filtered and concentrated in vacuo. The crude residue was purified by silica gel chromatography (DCM/MeOH=30:1) to give the title compound (1.5 g, 51%) as a yellow solid. $^1H$ NMR (400 MHz, DMSO-$d_6$) δ 9.70-9.64 (m, 1H), 8.50 (d, J=5.6 Hz, 1H), 7.96 (s, 1H), 7.83 (d, J=6.0 Hz, 1H), 7.74 (s, 1H), 7.04-6.92 (m, 1H), 6.12 (d, J=17.6 Hz, 1H), 5.51 (d, J=11.2 Hz, 1H), 4.53 (s, 2H), 4.48-4.38 (m, 1H), 4.04-3.95 (m, 2H), 3.87-3.76 (m, 2H), 3.50 (t, J=11.6 Hz, 2H), 3.00-2.79 (m, 2H), 2.13-1.98 (m, 5H), 1.97-1.92 (m, 2H). LCMS M/Z (M+H) 403.

Example 7 (Procedure G)

1-(3-(6-ethylisoquinolin-8-yl)-1-(tetrahydro-2H-pyran-4-yl)-6,7-dihydro-1H-pyrazolo[4,3-c]pyridin-5(4H)-yl)ethanone

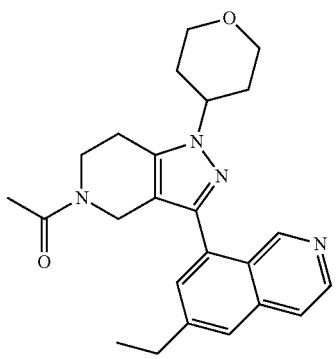 [SMILES: CCc1cc(-c2nn(C3CCOCC3)c3c2CN(C(C)=O)CC3)c2cnccc2c1]

To a solution of 1-(1-(tetrahydro-2H-pyran-4-yl)-3-(6-vinylisoquinolin-8-yl)-6,7-dihydro-1H-pyrazolo[4,3-c]pyridin-5(4H)-yl)ethanone (Example 6, 200 mg, 0.50 mmol) in MeOH (5 mL) was added 10% Pd/C (53 mg). The mixture was stirred at room temperature for 24 h under a hydrogen atmosphere (15 Psi). The mixture was filtered and the filtrate was concentrated in vacuo. The crude residue was purified by reverse phase chromatography (acetonitrile 15-45%/0.05% NH$_4$OH in water) to give the title compound (14 mg, 7%) as a white solid. $^1$H NMR (400 MHz, DMSO-d$_6$) δ 9.67 (s, 1H), 8.48 (d, J=6.0 Hz, 1H), 7.80 (d, J=5.6 Hz, 1H), 7.77 (s, 1H), 7.59-7.45 (m, 1H), 4.52 (s, 2H), 4.50-4.39 (m, 1H), 4.05-3.93 (m, 2H), 3.88-3.74 (m, 2H), 3.51 (t, J=11.6 Hz, 2H), 2.99-2.77 (m, 2H), 2.86 (q, J=7.6 Hz, 2H), 2.19-2.00 (m, 5H), 1.99-1.88 (m, 2H), 1.31 (t, J=7.6 Hz, 2H). LCMS M/Z (M+1) 405.

Example 8 (Procedure H)

1-(3-(6-(hydroxymethyl)isoquinolin-8-yl)-1-(tetrahydro-2H-pyran-4-yl)-6,7-dihydro-1H-pyrazolo[4,3-c]pyridin-5(4H)-yl)ethanone

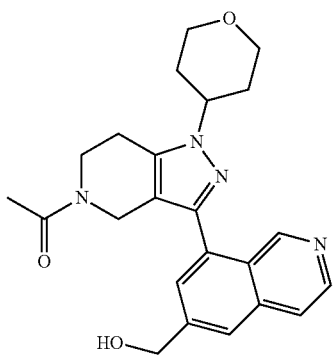 [SMILES: CC(=O)N1CCc2c(c(-c3cc(CO)cc4ccncc34)nn2C2CCOCC2)C1]

Step 1: 8-(5-acetyl-1-(tetrahydro-2H-pyran-4-yl)-4,5,6,7-tetrahydro-1H-pyrazolo[4,3-c]pyridin-3-yl)isoquinoline-6-carbaldehyde

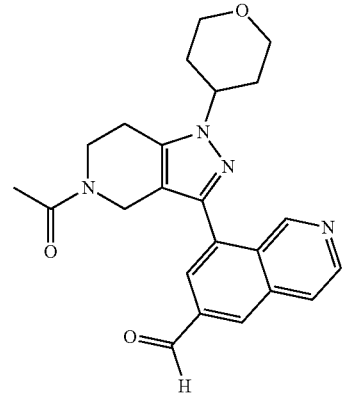 [SMILES: CC(=O)N1CCc2c(c(-c3cc(C=O)cc4ccncc34)nn2C2CCOCC2)C1]

To a solution of 1-(1-(tetrahydro-2H-pyran-4-yl)-3-(6-vinylisoquinolin-8-yl)-6,7-dihydro-1H-pyrazolo[4,3-c]pyridin-5(4H)-yl)ethanone (Example 6, 300 mg, 0.75 mmol) in THF (3 mL) and water (3 mL) was added osmium(VIII) oxide (500 mg, 1.97 mmol). The mixture was stirred at room temperature for 0.5 h. Sodium periodate (294 mg, 1.37 mmol) was added and the mixture stirred for an additional 2 h. Water (30 mL) was added and the mixture was extracted with EtOAc (30 mL×3). The combined organic layers were dried over anhydrous Na$_2$SO$_4$, filtered and concentrated in vacuo to give the title compound (300 mg, crude) as a yellow solid that required no further purification. LCMS M/Z (M+H) 405.

Step 2: 1-(3-(6-(hydroxymethyl)isoquinolin-8-yl)-1-(tetrahydro-2H-pyran-4-yl)-6,7-dihydro-1H-pyrazolo[4,3-c]pyridin-5(4H)-yl)ethanone

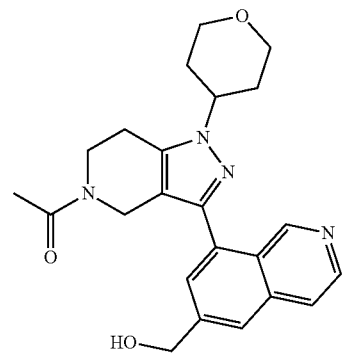 [SMILES: CC(=O)N1CCc2c(c(-c3cc(CO)cc4ccncc34)nn2C2CCOCC2)C1]

To a solution of 8-(5-acetyl-1-(tetrahydro-2H-pyran-4-yl)-4,5,6,7-tetrahydro-1H-pyrazolo[4,3-c]pyridin-3-yl)isoquinoline-6-carbaldehyde (300 mg, 0.74 mmol) in MeOH (5 mL) at 0° C. was added sodium borohydride (84 mg, 2.23 mmol). The mixture was stirred at room temperature for 1 h under a nitrogen atmosphere. The reaction was concentrated in vacuo. Water (30 mL) was added and extracted with EtOAc (30 mL×3). The combined organic layers were dried over anhydrous Na$_2$SO$_4$, filtered and concentrated in vacuo. The crude residue was purified by reverse phase chromatography (acetonitrile 13-43%/0.05% NH₄OH in water) to give the title compound (13 mg, 4%) as a white solid. ¹H NMR (400 MHz, DMSO-d₆) δ 9.70 (s, 1H), 8.51 (d, J=5.6 Hz, 1H), 7.91-7.82 (m, 2H), 7.60-7.53 (m, 1H), 5.53 (t, J=5.6 Hz, 2H), 7.75 (d, J=5.2 Hz, 1H), 4.61-4.41 (m, 1H), 4.51 (s, 2H), 4.06-3.95 (m, 2H), 3.88-3.76 (m, 2H), 3.52 (t, J=12.0 Hz, 2H), 3.03-2.79 (m, 2H), 2.19-2.00 (m, 5H), 1.99-1.95 (m, 2H). LCMS M/Z (M+1) 407.

Example 9 (Procedure I)

1-(3-(5-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

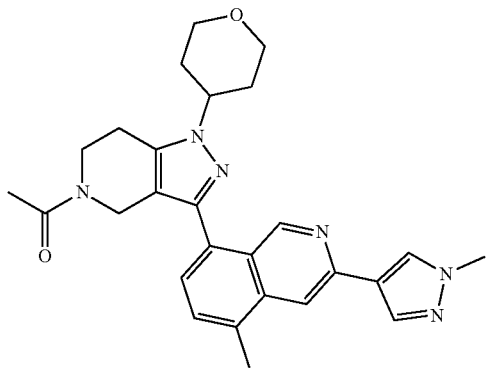 [SMILES: CC(=O)N1CCc2c(c(-c3ccc(C)c4cc(-c5cnn(C)c5)ncc34)nn2C2CCOCC2)C1]

Step 1: (2-chloro-5-methylphenyl)methanamine

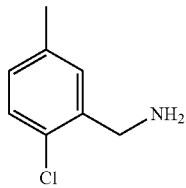

To a solution of 2-chloro-5-methyl-benzonitrile (9.0 g, 59.4 mmol) in anhydrous THF (90 mL) at 0° C. was added BH₃-THF (1.0 M, 178 mL, 178 mmol) dropwise under a nitrogen atmosphere. The mixture was stirred at room temperature for 12 h. The reaction was quenched with 2N HCl (110 mL) at 0° C. and then heated to 70° C. for 1 h. After cooling the reaction to room temperature, the solution was washed with DCM (150 mL). The aqueous phase was basified with 1N NaOH to pH 8 and then extracted with DCM (150 mL×3). The combined organic layers were dried over anhydrous Na₂SO₄, filtered and concentrated in vacuo to give the title compound (5.8 g, 63%) as yellow oil. ¹H NMR (400 MHz, CDCl₃) δ 7.22 (d, J=8.0 Hz, 1H), 7.17 (s, 1H), 6.99 (d, J=8.0 Hz, 1H), 3.88 (s, 2H), 2.32 (s, 3H).

Step 2: N-(2-chloro-5-methylbenzyl)-2,2-dimethoxyacetamide

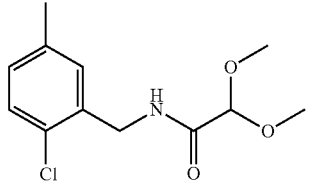 [SMILES: COC(OC)C(=O)NCc1cc(C)ccc1Cl]

To a solution of (2-chloro-5-methylphenyl)methanamine (4.6 g, 29.6 mmol) in MeOH (40 mL) was added triethylamine (5.2 mL, 37.2 mmol) and methyl dimethoxyacetate (4.4 g, 33.1 mmol). The mixture was heated to 80° C. for 16 h in sealed tube. After cooling the reaction to room temperature, the mixture was concentrated in vacuo. EtOAc (100 mL) was added and washed with 1N HCl (50 mL), WATER (50 mL), brine (50 mL). The organic layer was dried over anhydrous Na₂SO₄, filtered and concentrated in vacuo to give the title compound (4.1 g, 54%) as colorless oil. ¹H NMR (400 MHz, DMSO-d₆) δ 8.47-8.37 (m, 1H), 7.28 (d, J=8.4 Hz, 1H), 7.09-7.05 (s, 2H), 4.74 (s, 1H), 4.31 (d, J=6.4 Hz, 2H), 3.32 (s, 6H), 2.25 (s, 3H).

Step 3: 8-chloro-5-methylisoquinolin-3(2H)-one

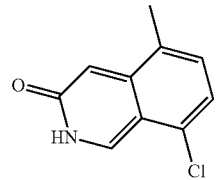

To a solution of sulfuric acid (40 mL) at 0° C. was added N-(2-chloro-5-methylbenzyl)-2,2-dimethoxyacetamide (5.0 g, 19.4 mmol). The reaction was stirred at room temperature for 16 h. The reaction was poured into ice water (100 mL) and the mixture was basified with ammonium hydroxide to pH 8. The yellow precipitate was filtered off, washed with MeOH (10 mL), Et₂O (10 mL), and dried in vacuo to give the title compound (3.8 g, crude) as a yellow solid that required no further purification. ¹H NMR (400 MHz, DMSO-d₆) δ 9.07 (s, 1H), 7.37-7.30 (m, 2H), 6.93 (s, 1H), 2.48 (s, 3H).

Step 4: 8-chloro-5-methylisoquinolin-3-yl trifluoromethanesulfonate

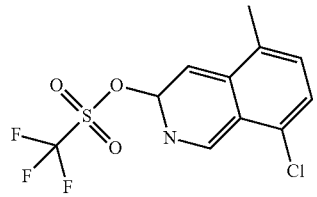 [SMILES: Cc1ccc(Cl)c2c1=CC(OS(=O)(=O)C(F)(F)F)NC=2]

To a solution of 8-chloro-5-methylisoquinolin-3(2H)-one (1 g, 5.16 mmol) in DCM (10 mL) at 0° C. was added triethylamine (4.3 mL, 31 mmol) and trifluoromethanesulfonic anhydride (1.3 mL, 7.75 mmol). The reaction was stirred at room temperature for 1 h. DCM (50 mL) was added and washed with ice water (40 mL×2). The organic layer was dried over anhydrous $Na_2SO_4$, filtered and concentrated in vacuo to give the title compound (2 g, crude) as dark brown oil that required no further purification.

Step 5: 8-chloro-5-methyl-3-(1-methyl-1H-pyrazol-4-yl)isoquinoline

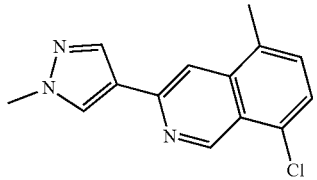 [SMILES: Cc1ccc(Cl)c2cnc(-c3cnn(C)c3)cc12]

To a solution of 8-chloro-5-methylisoquinolin-3-yl trifluoromethanesulfonate (2 g, crude) in 1,4-dioxane (10 mL) and water (2 mL) was added [1,1'-bis(diphenylphosphino)ferrocene]dichloropalladium(II) (449 mg, 0.6 mmol), $Na_2CO_3$ (1.95 g, 18.4 mmol) and 1-methyl-4-(4,4,5,5-tetramethyl-1,3,2-dioxaborolan-2-yl)-1H-pyrazole (1.4 g, 6.7 mmol). The mixture was irradiated in a microwave at 90° C. for 0.5 h. EtOAc (100 mL) was added and washed with water (60 mL×2), brine (60 mL). The organic layer was dried over anhydrous $Na_2SO_4$, filtered and concentrated in vacuo. The crude residue was purified by silica gel chromatography (petroleum ether/EtOAc=1:1) to give the title compound (770 mg) as a white solid. $^1$H NMR (400 MHz, DMSO-$d_6$) δ 9.48 (s, 1H), 8.45 (s, 1H), 8.19 (s, 1H), 8.10 (s, 1H), 7.59-7.53 (m. 2H), 3.92 (s, 3H), 2.66 (s, 3H).

Step 6: 1-(1-(tetrahydro-2H-pyran-4-yl)-3-(4,4,5,5-tetramethyl-1,3,2-dioxaborolan-2-yl)-6,7-dihydro-1H-pyrazolo[4,3-c]pyridin-5(4H)-yl)ethanone

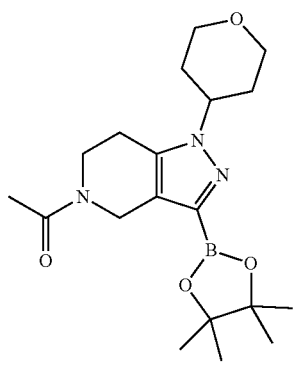 [SMILES: CC(=O)N1CCc2c(c(B3OC(C)(C)C(C)(C)O3)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 200 mg, 0.6 mmol) in 1,4-dioxane (4 mL) was added 2-(dicyclohexylphosphino)-2',4',6'-triisopropylbiphenyl (17 mg, 0.04 mmol), chloro(2-dicyclohexylphosphino-2',4',6'-tri-i-propyl-1,1'-biphenyl)(2'-amino-1,1'-biphenyl-2-yl) palladium(II) (14 mg, 0.02 mmol), KOAc (179 mg, 1.8 mmol) and 4,4,4',4',5,5,5',5'-octamethyl-2,2'-bi(1,3,2-dioxaborolane) (309 mg, 1.2 mmol). The mixture was heated to 80° C. for 2 h under a nitrogen atmosphere. After cooling the reaction to room temperature, the reaction mixture was used to the next step directly without further purification. LCMS M/Z (M+H) 376.

Step 7: 1-(3-(5-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

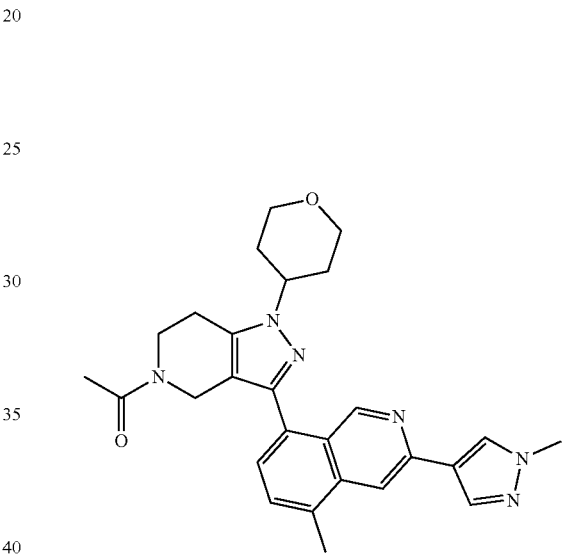

To the above step cooled solution was added 8-chloro-5-methyl-3-(1-methyl-1H-pyrazol-4-yl)isoquinoline (94 mg, 0.36 mmol), chloro(2-dicyclohexylphosphino-2',4',6'-tri-i-propyl-1,1'-biphenyl)(2'-amino-1,1'-biphenyl-2-yl) palladium(II) (19 mg, 0.02 mmol), $K_3PO_4$ (322 mg, 1.5 mmol), 1,4-dioxane (1 mL) and water (1 mL). The reaction mixture was heated to 90° C. for 1 h under a nitrogen atmosphere. After cooling to room temperature, the mixture was filtered and concentrated in vacuo. DCM (50 mL) was added and washed with water (40 mL×2). The organic layer was dried over anhydrous $Na_2SO_4$, filtered and concentrated in vacuo. The crude residue was purified by reverse phase chromatography (acetonitrile 20-50%/0.2% formic acid in water) to give the title compound (50 mg, 17%) as a yellow solid. $^1$H NMR (400 MHz, $CDCl_3$) δ 9.66-9.62 (m, 1H), 8.08-8.06 (m, 2H), 7.92-7.90 (m, 1H), 7.55-7.50 (m, 1H), 7.44-7.32 (m, 1H), 4.62-4.45 (m, 2H), 4.34-4.21 (m, 1H), 4.19-4.14 (m, 2H), 4.09-3.77 (m, 2H), 4.00 (s, 3H), 3.59-3.53 (m, 2H), 2.96-2.81 (m, 2H), 2.76-2.70 (m, 3H), 2.48-2.37 (m, 2H), 2.24-2.02 (m, 3H), 2.00-1.88 (m, 2H). LCMS M/Z (M+H) 471.

Example 10 (Procedure J)

N-methyl-3-(5-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxamide

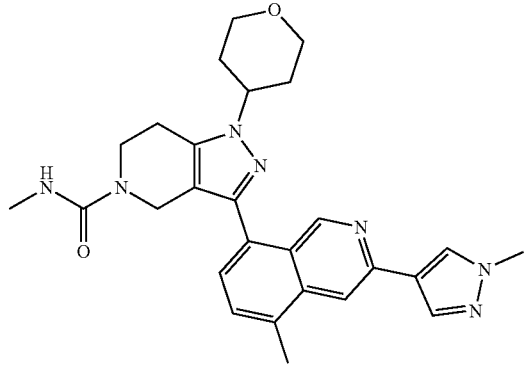

Step 1: tert-butyl 1-(tetrahydro-2H-pyran-4-yl)-3-(4,4,5,5-tetramethyl-1,3,2-dioxaborolan-2-yl)-6,7-dihydro-1H-pyrazolo[4,3-c]pyridine-5(4H)-carboxylate

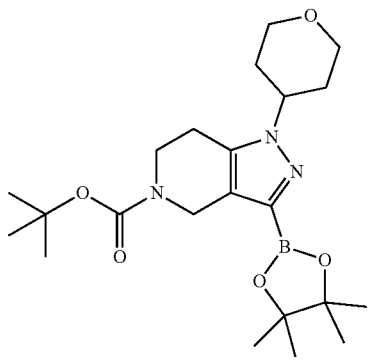 [SMILES: CC(C)(C)OC(=O)N1CCc2c(c(B3OC(C)(C)C(C)(C)O3)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 400 mg, 1.04 mmol) in 1,4-dioxane (10 mL) was added 2-(dicyclohexylphosphino)-2',4',6'-triisopropylbiphenyl (30 mg, 0.06 mmol), chloro(2-dicyclohexylphosphino-2',4',6'-tri-i-propyl-1,1'-biphenyl)(2'-amino-1,1'-biphenyl-2-yl) palladium(II) (25 mg, 0.03 mmol), KOAc (300 mg, 3.12 mmol) and 4,4,4',4',5,5,5',5'-octamethyl-2,2'-bi(1,3,2-dioxaborolane) (526 mg, 2.08 mmol). The mixture was heated to 80° C. for 2 h under a nitrogen atmosphere. After cooling the reaction to room temperature, the reaction mixture was used to the next step directly without further purification. LCMS M/Z (M+H) 434.

Step 2: tert-butyl 3-(5-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxylate

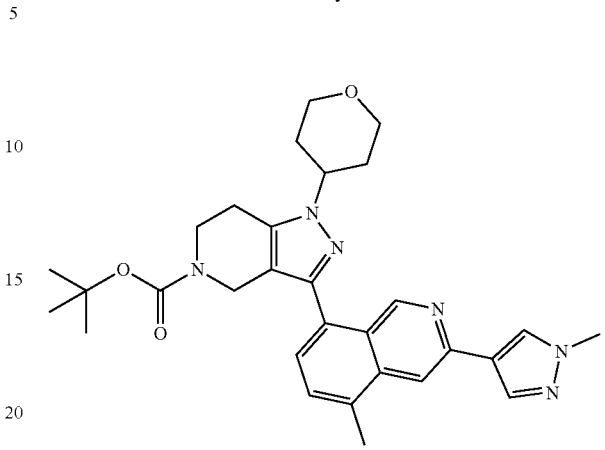

To the above step cooled solution was added 8-chloro-5-methyl-3-(1-methyl-1H-pyrazol-4-yl)isoquinoline (160 mg, 0.62 mmol), chloro(2-dicyclohexylphosphino-2',4',6'-tri-i-propyl-1,1'-biphenyl)(2'-amino-1,1'-biphenyl-2-yl) palladium(II) (25 mg, 0.03 mmol), $K_3PO_4$ (661 mg, 3.12 mmol), 1,4-dioxane (5 mL) and water (3 mL). The reaction mixture was heated to 90° C. for 12 h under a nitrogen atmosphere. After cooling to room temperature, the mixture was filtered and concentrated in vacuo. DCM (20 mL) was added and washed with water (15 mL×2), brine (20 mL). The organic layer was dried over anhydrous $Na_2SO_4$, filtered and concentrated in vacuo. The crude residue was purified by silica gel chromatography (DCM/MeOH=20:1) to give the title compound (180 mg, 37%) as a yellow solid. LCMS M/Z (M+H) 529.

Step 3: 5-methyl-3-(1-methyl-1H-pyrazol-4-yl)-8-(1-(tetrahydro-2H-pyran-4-yl)-4,5,6,7-tetrahydro-1H-pyrazolo[4,3-c]pyridin-3-yl)isoquinoline

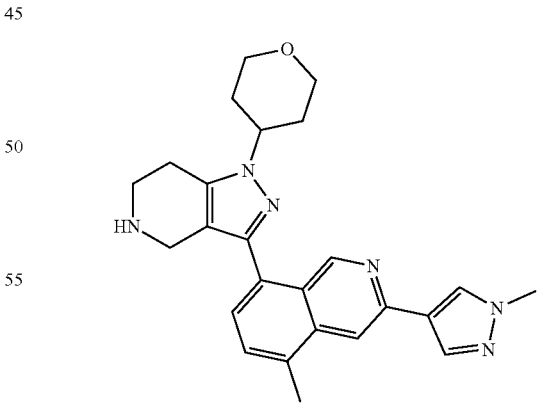

To a solution of tert-butyl 3-(5-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxylate (180 mg, 0.34 mmol) in DCM (3 mL) was added trifluoroacetic acid (0.27 mL, 3.6 mmol). The mixture was stirred at room temperature for 1 h and concentrated in vacuo to give the title compound (100 mg, crude) as yellow oil that required no further purification. LCMS M/Z (M+H) 429.

Step 4: N-methyl-3-(5-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxamide

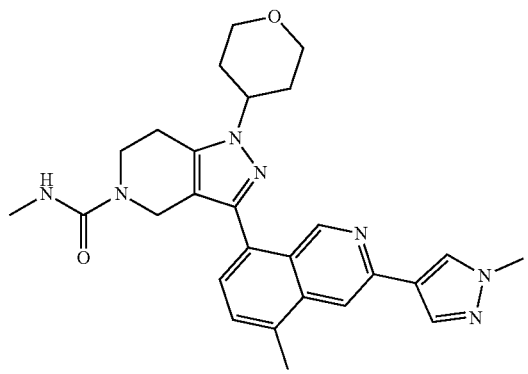

To a solution of 5-methyl-3-(1-methyl-1H-pyrazol-4-yl)-8-(1-(tetrahydro-2H-pyran-4-yl)-4,5,6,7-tetrahydro-1H-pyrazolo[4,3-c]pyridin-3-yl)isoquinoline (100 mg, 0.23 mmol) in DCM (2 mL) was added triethylamine (0.1 mL, 0.70 mmol) and N-methyl-1H-imidazole-1-carboxamide (58 mg, 0.47 mmol). The reaction was stirred at room temperature for 12 h and concentrated in vacuo. The crude residue was purified by reverse phase chromatography (acetonitrile 23-53%/0.05% NH$_4$OH in water) to give the title compound (12 mg, 10%) as a light yellow solid. $^1$H NMR (400 MHz, CDCl$_3$) δ 9.58 (s, 1H), 8.08-8.05 (m, 2H), 7.91 (s, 1H), 7.56-7.49 (m, 1H), 7.41-7.36 (m, 1H), 4.47-4.39 (m, 1H), 4.35-4.21 (m, 3H), 4.20-4.12 (m, 2H), 4.00 (s, 3H), 3.90-3.84 (m, 2H), 3.62-3.51 (m, 2H), 2.89-2.83 (m, 2H), 2.78 (d, J=4.4 Hz, 3H), 2.73 (s, 3H), 2.50-2.36 (m, 2H), 2.00-1.91 (m, 2H). LCMS M/Z (M+H) 486.

Example 11 (Procedure K)

4-(8-(5-acetyl-1-(tetrahydro-2H-pyran-4-yl)-4,5,6,7-tetrahydro-1H-pyrazolo[4,3-c]pyridin-3-yl)isoquinolin-3-yl)-1-methyl-1H-pyrazole-3-carbonitrile

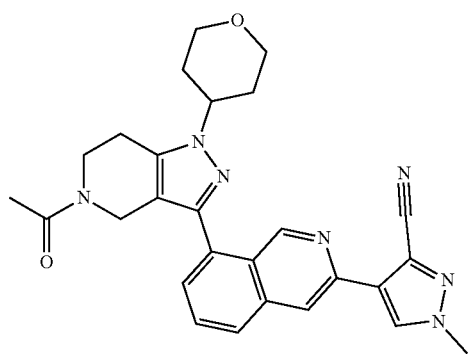 [SMILES: CC(=O)N1CCc2c(c(-c3cccc4cc(-c5cn(C)nc5C#N)ncc34)nn2C2CCOCC2)C1]

Step 1: 1-methyl-4-(4,4,5,5-tetramethyl-1,3,2-dioxaborolan-2-yl)-1H-pyrazole-3-carbonitrile

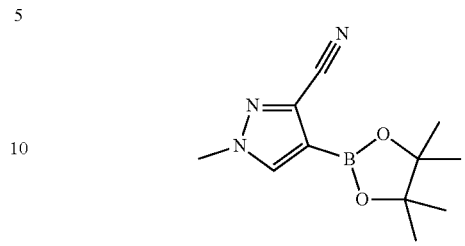

To a solution of 4-bromo-1-methyl-1H-pyrazole-3-carbonitrile (150 mg, 0.81 mmol) in 1,4-dioxane (4 mL) was added (dicyclohexylphosphino)-2',4',6'-triisopropylbiphenyl (38 mg, 0.08 mmol) and chloro(2-dicyclohexylphosphino-2',4',6'-tri-i-propyl-1,1'-biphenyl)(2'-amino-1,1'-biphenyl-2-yl) palladium(II) (63 mg, 0.08 mmol), 4,4,4',4',5,5,5',5'-octamethyl-2,2'-bi(1,3,2-dioxaborolane) (225 mg, 0.88 mmol) and KOAc (237 mg, 2.42 mmol). The mixture was heated to 90° C. for 12 h under a nitrogen atmosphere. After cooling the reaction to room temperature, the reaction mixture was used to the next step directly without further purification. LCMS M/Z (M+H) 234.

Step 2: 4-(8-(5-acetyl-1-(tetrahydro-2H-pyran-4-yl)-4,5,6,7-tetrahydro-1H-pyrazolo[4,3-c]pyridin-3-yl)isoquinolin-3-yl)-1-methyl-1H-pyrazole-3-carbonitrile

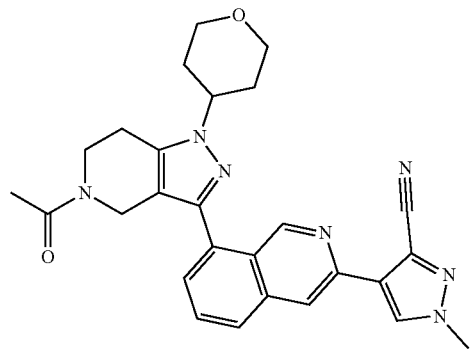 [SMILES: CC(=O)N1CCc2c(c(-c3cccc4cc(-c5cn(C)nc5C#N)ncc34)nn2C2CCOCC2)C1]

To the above step cooled solution was added 8-(5-acetyl-1-(tetrahydro-2H-pyran-4-yl)-4,5,6,7-tetrahydro-1H-pyrazolo[4,3-c]pyridin-3-yl)isoquinolin-3-yl trifluoromethanesulfonate (Intermediate I, 100 mg, 0.19 mmol), (dicyclohexylphosphino)-2',4',6'-triisopropylbiphenyl (9 mg, 0.02 mmol) and chloro(2-dicyclohexylphosphino-2',4',6'-tri-i-propyl-1,1'-biphenyl)(2'-amino-1,1'-biphenyl-2-yl) palladium(II) (15 mg, 0.02 mmol) and Na$_2$CO$_3$ (40 mg, 0.38 mmol), 1,4-dioxane (1 mL) and water (1 mL). The reaction mixture was heated to 60° C. for 16 h under a nitrogen atmosphere. After cooling to room temperature, the mixture was filtered and concentrated in vacuo. The crude residue was purified by reverse phase chromatography (acetonitrile 25-55%/0.2% formic acid in water) to give the title compound (25 mg, 6%) as a white solid. $^1$H NMR (400 MHz, DMSO-d$_6$) δ 9.86 (s, 1H), 8.68 (s, 1H), 8.22 (s, 1H), 7.98 (d, J=8.0 Hz, 1H), 7.91-7.83 (m, 1H), 7.71-7.60 (m, 1H), 4.55 (s, 2H), 4.52-4.42 (m, 1H), 4.07-3.97 (m, 2H), 4.03 (s, 1H), 3.88-3.78 (m, 2H), 3.52 (d, J=12.0 Hz, 2H), 3.02-2.82 (m, 2H), 2.17-2.01 (m, 5H), 2.00-1.89 (m, 2H). LCMS M/Z (M+H) 482.

Example 12 (Procedure L)

5-(5-acetyl-1-(tetrahydro-2H-pyran-4-yl)-4,5,6,7-tetrahydro-1H-pyrazolo[4,3-c]pyridin-3-yl)-2-(1-methyl-1H-pyrazol-4-yl)-3,4-dihydroisoquinolin-1(2H)-one

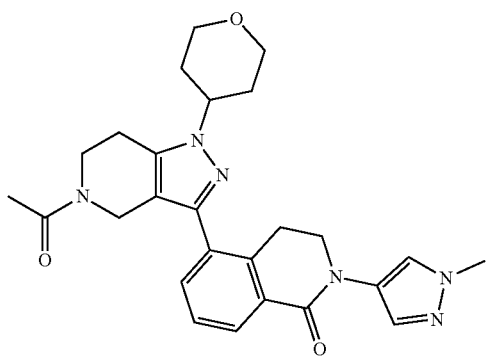 [SMILES: CC(=O)N1CCc2c(c(-c3cccc4c3CCN(c3cnn(C)c3)C4=O)nn2C2CCOCC2)C1]

Step 1: 1-(1-(tetrahydro-2H-pyran-4-yl)-3-(4,4,5,5-tetramethyl-1,3,2-dioxaborolan-2-yl)-6,7-dihydro-1H-pyrazolo[4,3-c]pyridin-5(4H)-yl)ethanone

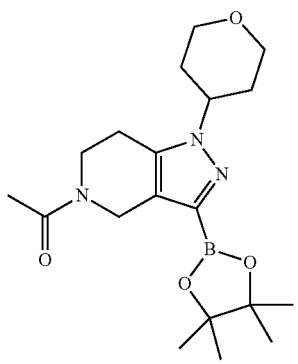 [SMILES: CC(=O)N1CCc2c(c(B3OC(C)(C)C(C)(C)O3)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 600 mg, 1.83 mmol) in 1,4-dioxane (4 mL) was added 2-(dicyclohexylphosphino)-2',4',6'-triisopropylbiphenyl (52 mg, 0.11 mmol), chloro(2-dicyclohexylphosphino-2',4',6'-tri-i-propyl-1,1'-biphenyl)(2'-amino-1,1'-biphenyl-2-yl) palladium(II) (43 mg, 0.05 mmol), KOAc (538 mg, 5.48 mmol) and 4,4,4',4',5,5,5',5'-octamethyl-2,2'-bi(1,3,2-dioxaborolane) (928 mg, 3.66 mmol). The mixture was heated to 80° C. for 3 h under a nitrogen atmosphere. After cooling the reaction to room temperature, the reaction mixture was used to the next step directly without further purification. LCMS M/Z (M+H) 376.

Step 2: 5-(5-acetyl-1-(tetrahydro-2H-pyran-4-yl)-4,5,6,7-tetrahydro-1H-pyrazolo[4,3-c]pyridin-3-yl)-3,4-dihydroisoquinolin-1(2H)-one

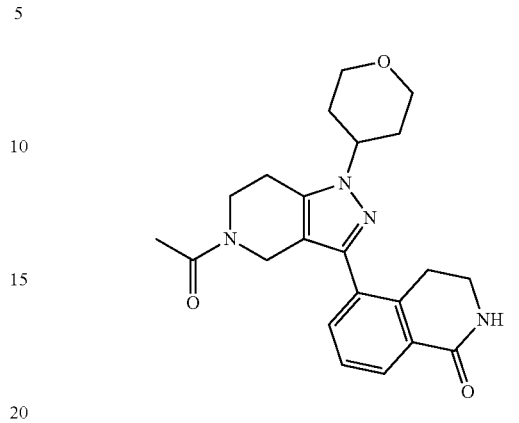

To the above step cooled solution was added 5-bromo-3,4-dihydroisoquinolin-1(2H)-one (238 mg, 1.06 mmol), chloro(2-dicyclohexylphosphino-2',4',6'-tri-i-propyl-1,1'-biphenyl)(2'-amino-1,1'-biphenyl-2-yl) palladium(II) (47 mg, 0.06 mmol), $K_3PO_4$ (509 mg, 2.4 mmol), 1,4-dioxane (1 mL) and water (1 mL). The reaction mixture was heated to 90° C. for 1 h under a nitrogen atmosphere. After cooling to room temperature, the mixture was filtered and concentrated in vacuo. Water (100 mL) was added and extracted with EtOAc (50 mL×3). The combined organic layers were washed with brine (50 mL×2), dried over anhydrous $Na_2SO_4$, filtered and concentrated in vacuo. The crude residue was purified by silica gel chromatography (DCM/MeOH=30:1) to give the title compound (250 mg, 35%) as a white solid. $^1$H NMR (400 MHz, CDCl$_3$) δ 8.15-8.11 (m, 1H), 7.46-7.39 (m, 2H), 6.29-6.22 (m, 1H), 4.58-4.42 (m, 2H), 4.26-4.10 (m, 3H), 3.97-3.80 (m, 2H), 3.61-3.45 (m, 4H), 3.20-3.09 (m, 2H), 2.86-2.80 (m, 2H), 2.38-2.27 (m, 2H), 2.20-2.11 (m, 3H), 1.94-1.85 (m, 2H). LCMS M/Z (M+H) 395.

Step 3: 5-(5-acetyl-1-(tetrahydro-2H-pyran-4-yl)-4,5,6,7-tetrahydro-1H-pyrazolo[4,3-c]pyridin-3-yl)-2-(1-methyl-1H-pyrazol-4-yl)-3,4-dihydroisoquinolin-1(2H)-one

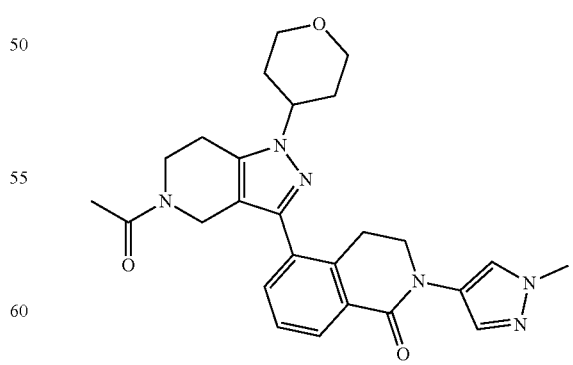

To a solution of 5-(5-acetyl-1-(tetrahydro-2H-pyran-4-yl)-4,5,6,7-tetrahydro-1H-pyrazolo[4,3-c]pyridin-3-yl)-3,4-dihydroisoquinolin-1(2H)-one (100 mg, 0.25 mmol) in 1,4-dioxane (10 mL) was added copper(I) iodide (2 mg, 0.01 mmol), (1R,2R)-cyclohexane-1,2-diamine (6 mg, 0.05 mmol), K₃PO₄ (161 mg, 0.76 mmol) and 4-iodo-1-methyl-1H-pyrazole (79 mg, 0.38 mmol). The reaction mixture was heated to 100° C. for 12 h under a nitrogen atmosphere. After cooling to room temperature, the mixture was filtered and concentrated in vacuo. Water (50 mL) was added and extracted with DCM (30 mL×3). The combined organic layers were dried over anhydrous Na₂SO₄, filtered and concentrated in vacuo. The crude residue was purified by reverse phase chromatography (acetonitrile 26-56%/0.2% formic acid in water) to give the title compound (37 mg, 31%) as a yellow solid. ¹H NMR (400 MHz, CDCl₃) δ 8.20-8.10 (m, 2H), 7.54 (d, J=5.2 Hz, 1H), 7.49-7.36 (m, 2H), 4.61-4.45 (m, 2H), 4.27-4.11 (m, 3H), 4.02-3.78 (m, 4H), 3.93 (s, 3H), 3.61-3.50 (m, 2H), 3.36-3.28 (m, 2H), 2.90-2.77 (m, 2H), 2.40-2.27 (m, 2H), 2.20-2.11 (m, 3H), 1.95-1.86 (m, 2H). LCMS M/Z (M+H) 475.

Example 13 (Procedure M)

1-(3-(2-methyl-5-(1-methyl-1H-pyrazol-4-yl)-1H-pyrrolo[2,3-c]pyridin-1-yl)-1-(tetrahydro-2H-pyran-4-yl)-6,7-dihydro-1H-pyrazolo[4,3-c]pyridin-5(4H)-yl)ethanone

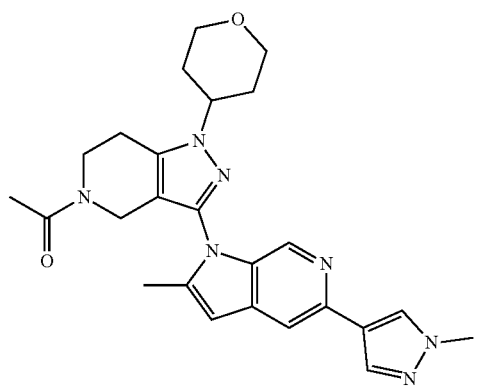 [SMILES: CC(=O)N1CCc2c(c(-n3c(C)cc4cc(-c5cnn(C)c5)ncc43)nn2C2CCOCC2)C1]

Step 1: 2-methyl-5-(1-methyl-H-pyrazol-4-yl)-1H-pyrrolo[2,3-c]pyridine

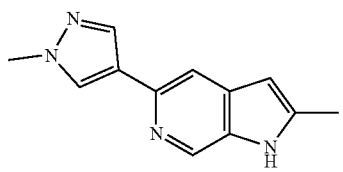

To a solution of 5-chloro-2-methyl-1H-pyrrolo[2,3-c]pyridine (900 mg, 5.4 mmol) in 1,4-dioxane (50 mL) and water (10 mL) was added 2-(dicyclohexylphosphino)-2',4',6'-triisopropylbiphenyl (258 mg, 0.54 mmol) and chloro(2-dicyclohexylphosphino-2',4',6'-tri-i-propyl-1,1'-biphenyl)(2'-amino-1,1'-biphenyl-2-yl) palladium(II) (425 mg, 0.54 mmol), Na₂CO₃ (1.72 g, 16.2 mmol) and 1-methyl-4-(4,4,5,5-tetramethyl-1,3,2-dioxaborolan-2-yl)-1H-pyrazole (1.35 g, 6.48 mmol). The mixture was heated to 100° C. for 16 h under a nitrogen atmosphere. After cooling the reaction to room temperature, the mixture was filtered and concentrated in vacuo. The crude residue was purified by silica gel chromatography (DCM/MeOH=10:1) to give the title compound (700 mg, 61%) as a white solid. LCMS M/Z (M+H) 213.

Step 2: 1-(3-(2-methyl-5-(1-methyl-1H-pyrazol-4-yl)-1H-pyrrolo[2,3-c]pyridin-1-yl)-1-(tetrahydro-2H-pyran-4-yl)-6,7-dihydro-1H-pyrazolo[4,3-c]pyridin-5(4H)-yl)ethanone

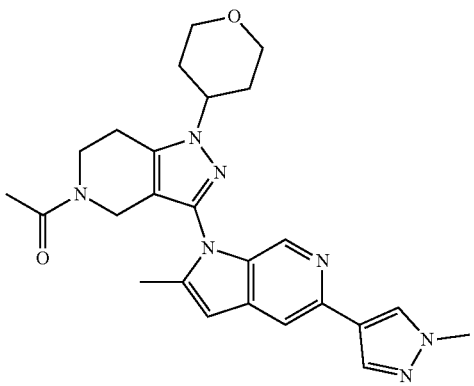 [SMILES: CC(=O)N1CCc2c(c(-n3c(C)cc4cc(-c5cnn(C)c5)ncc43)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 250 mg, 0.76 mmol) in toluene (10 mL) was added copper(I) iodide (7 mg, 0.04 mmol), K₃PO₄ (646 mg, 3.05 mmol), (1R,2R)-cyclohexane-1,2-diamine (17 mg, 0.15 mmol) and 2-methyl-5-(1-methyl-1H-pyrazol-4-yl)-1H-pyrrolo[2,3-c]pyridine (162 mg, 0.76 mmol). The mixture was heated to 120° C. for 12 h under a nitrogen atmosphere. After cooling the reaction to room temperature, the mixture was filtered and concentrated in vacuo. Water (100 mL) was added and extracted with EtOAc (50 mL×3). The combined organic layers were washed with brine (30 mL), dried over anhydrous Na₂SO₄, filtered and concentrated in vacuo. The crude residue was purified by reverse phase chromatography (acetonitrile 20-50%/0.05% NH₄OH in water) to give the title compound (6 mg, 2%) as a white solid. ¹H NMR (400 MHz, CDCl₃) δ 8.38-8.34 (m, 1H), 7.95 (s, 1H), 7.89-7.86 (m, 1H), 7.64-7.60 (m, 1H), 6.40-6.36 (m, 1H), 4.40-4.19 (m, 3H), 4.17-4.12 (m, 2H), 4.06-3.81 (m, 2H), 3.96 (s, 3H), 3.56 (t, J=12.0 Hz, 2H), 2.95-2.81 (m, 2H), 2.42-2.27 (m, 5H), 2.19-2.04 (m, 3H), 1.95-1.92 (m, 2H). LCMS M/Z (M+H) 460.

Examples 14 & 15 (Procedure N)

(S)-1-[8-(5-acetyl-1-tetrahydropyran-4-yl-6,7-dihydro-4H-pyrazolo[4,3-c]pyridin-3-yl)-3-isoquinolyl]-N-methyl-pyrrolidine-3-carboxamide and (R)-1-[8-(5-acetyl-1-tetrahydropyran-4-yl-6,7-dihydro-4H-pyrazolo[4,3-c]pyridin-3-yl)-3-isoquinolyl]-N-methyl-pyrrolidine-3-carboxamide

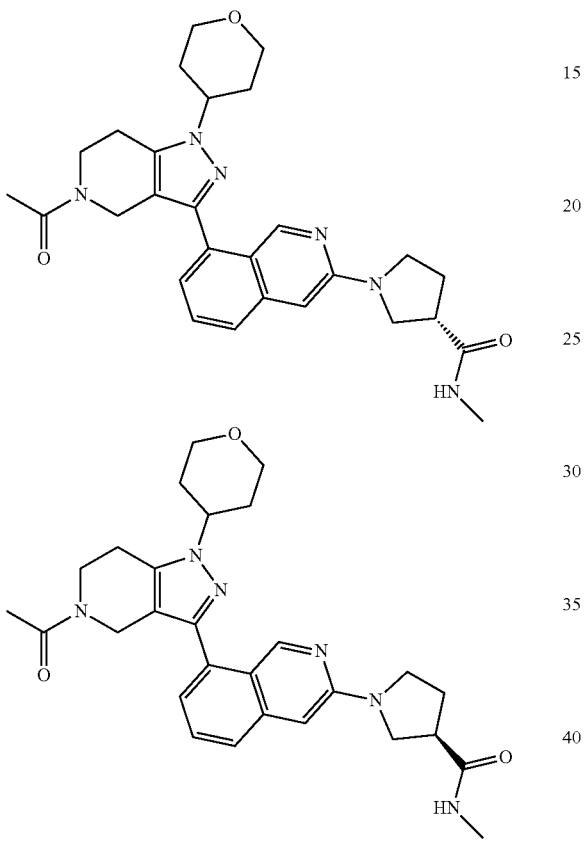

To a microwave vial was added [8-(5-acetyl-1-tetrahydropyran-4-yl-6,7-dihydro-4H-pyrazolo[4,3-c]pyridin-3-yl)-3-isoquinolyl] trifluoromethanesulfonate (Intermediate I, 40.0 mg, 0.0763 mmol), N-methylpyrrolidine-3-carboxamide (39.1 mg, 0.305 mmol), and then DMSO (1.0 mL). The mixture was heated to 130° C. for 0.5 h under microwave conditions. After cooling to room temperature, the crude mixture was purified by reverse phase preparative HPLC (acetonitrile 5-50%/0.1% ammonium hydroxide in water) to give racemic 1-[8-(5-acetyl-1-tetrahydropyran-4-yl-6,7-dihydro-4H-pyrazolo[4,3-c]pyridin-3-yl)-3-isoquinolyl]-N-methyl-pyrrolidine-3-carboxamide (18.6 mg, 49%) as a yellow solid that was separated by chiral SFC (Chiralpak AD 150×21.2 mm I.D., 5 µm); Supercritical $CO_2$/MeOH (0.1% $NH_3H_2O$)=60:40 at 70 mL/min) to give (S)-1-[8-(5-acetyl-1-tetrahydropyran-4-yl-6,7-dihydro-4H-pyrazolo[4,3-c]pyridin-3-yl)-3-isoquinolyl]-N-methyl-pyrrolidine-3-carboxamide (6.7 mg, first peak) and (R)-1-[8-(5-acetyl-1-tetrahydropyran-4-yl-6,7-dihydro-4H-pyrazolo[4,3-c]pyridin-3-yl)-3-isoquinolyl]-N-methyl-pyrrolidine-3-carboxamide (7.4 mg, seconds peak). Absolute configuration was arbitrarily assigned to each diastereomer. Example 14: $^1$H NMR (400 MHz, DMSO-$d_6$) δ 9.44 (t, J=0.9 Hz, 1H), 7.95 (d, J=4.8 Hz, 1H), 7.61 (dt, J=8.6, 1.0 Hz, 1H), 7.53 (ddd, J=8.7, 7.0, 2.1 Hz, 1H), 7.21-7.07 (m, 1H), 6.63 (d, J=1.1 Hz, 1H), 4.50 (s, 2H), 4.48-4.37 (m, 1H), 4.07-3.95 (m, 2H), 3.87-3.75 (m, 2H), 3.75-3.67 (m, 1H), 3.65-3.60 (m, 1H), 3.56-3.42 (m, 4H), 3.12-3.02 (m, 1H), 2.99-2.78 (m, 2H), 2.62 (d, J=4.6 Hz, 3H), 2.21-2.00 (m, 7H), 1.98-1.88 (m, 2H). LCMS M/Z (M+H) 503.3. Example 15: $^1$H NMR (400 MHz, DMSO-$d_6$) δ 9.44 (d, J=1.0 Hz, 1H), 7.95 (d, J=4.8 Hz, 1H), 7.61 (dt, J=8.5, 1.1 Hz, 1H), 7.53 (ddd, J=8.9, 7.0, 2.1 Hz, 1H), 7.19-7.08 (m, 1H), 6.67-6.59 (m, 1H), 4.50 (s, 2H), 4.46-4.47 (m, 1H), 4.01 (dd, J=10.9, 4.8 Hz, 2H), 3.87-3.77 (m, 2H), 3.73-3.66 (m, 1H), 3.65-3.58 (m, 1H), 3.54-3.42 (m, 4H), 3.11-3.03 (m, 1H), 2.94 (t, J=5.6 Hz, 2H), 2.62 (d, J=4.6 Hz, 3H), 2.18-2.00 (m, 7H), 1.96-1.88 (m, 2H). LCMS M/Z (M+H) 503.3.

Example 16 (Procedure O)

1-(3-(isoquinolin-4-yl)-1-(tetrahydro-2H-pyran-4-yl)-1,4,6,7-tetrahydro-5H-pyrazolo[4,3-c]pyridin-5-yl)ethan-1-one

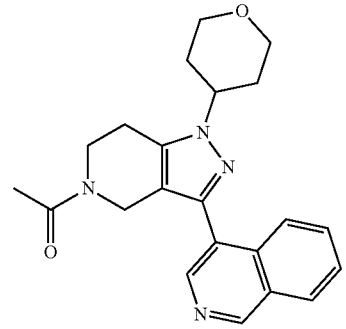 [SMILES: CC(=O)N1CCc2c(c(-c3cncc4ccccc34)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 35 mg, 0.11 mmol) and 4-isoquinolylboronic acid (37 mg, 0.21 mmol) in dioxane (0.7 mL) and water (0.2 mL) was added $K_3PO_4.H_2O$ (63 mg, 0.27 mmol), (2-dicyclohexylphosphino-2',4',6'-triisopropyl-1,1'-biphenyl)[2-(2'-amino-1,1'-biphenyl)]palladium(II) methanesulfonate (4.8 mg, 0.0053 mmol) and 2-(dicyclohexylphosphino)-2',4',6'-triisopropylbiphenyl (2.6 mg, 0.0053 mmol). The mixture was stirred at 100° C. for 5 h under a nitrogen atmosphere. The reaction mixture was then cooled to room temperature and concentrated in vacuo. The crude residue was dissolved in dichloromethane (5 mL), dried over anhydrous $MgSO_4$, filtered through celite and concentrated in vacuo. The mixture obtained was purified by reverse phase chromatography (acetonitrile 5-50%/0.1% ammonium hydroxide in water) to give the title compound (38.2 mg, 90%) as a white solid. $^1$H NMR (400 MHz, DMSO-$d_6$) δ 9.32 (s, 1H), 8.50-8.42 (m, 2H), 8.20 (d, J=8.0 Hz, 1H), 7.89-7.80 (m, 1H), 7.77-7.71 (m, 1H), 4.56-4.49 (m, 2H), 4.49-4.38 (m, 1H), 4.06-3.97 (m, 2H), 3.88-3.77 (m, 2H), 3.58-3.46 (m, 2H), 3.00-2.78 (m, 2H), 2.20-2.05 (m, 4H), 2.01 (s, 1H), 1.98-1.88 (m, 2H). LCMS M/Z (M+H) 377.

Example 17 (Procedure P)

5-(5-acetyl-1-(tetrahydro-2H-pyran-4-yl)-4,5,6,7-tetrahydro-1H-pyrazolo[4,3-c]pyridin-3-yl)-2-methyl-1,4-dihydroisoquinolin-3(2H)-one

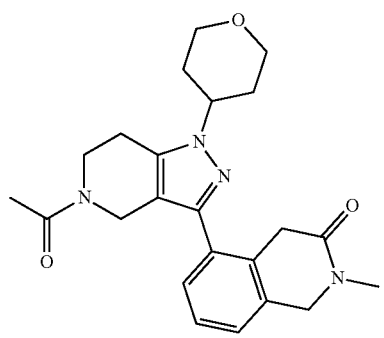 [SMILES: CC(=O)N1CCc2c(c(-c3cccc4c3CC(=O)N(C)C4)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 80 mg, 0.24 mmol) and bis(pinacolato)diboron (124 mg, 0.488 mmol) in dioxane (1.2 mL) was added KOAc (72 mg, 0.73 mmol), (2-dicyclohexylphosphino-2',4',6'-triisopropyl-1,1'-biphenyl)[2-(2'-amino-1,1'-biphenyl)]palladium(II) methanesulfonate (5.9 mg, 0.0073 mmol) and 2-(dicyclohexylphosphino)-2',4',6'-triisopropylbiphenyl (7.1 mg, 0.015 mmol). The mixture was stirred at 80° C. for 16 h under a nitrogen atmosphere. The reaction mixture was cooled to room temperature and 5-chloro-2-methyl-1,4-dihydroisoquinolin-3-one (26 mg, 0.13 mmol), $K_3PO_4 \cdot H_2O$ (78 mg, 0.33 mmol), water (0.3 mL) and (2-dicyclohexylphosphino-2',4',6'-triisopropyl-1,1'-biphenyl)[2-(2'-amino-1,1'-biphenyl)]palladium(II) methanesulfonate (5.9 mg, 0.0073 mmol) were added. The reaction mixture was stirred at 90° C. for 4 h under a nitrogen atmosphere. The reaction mixture was then cooled to room temperature and concentrated in vacuo. The crude residue was dissolved in dichloromethane (5 mL), dried over anhydrous $MgSO_4$, filtered through celite and concentrated in vacuo. The mixture obtained was purified by SFC (Supercritical $CO_2$ 5-40%/MeOH (0.1% $NH_3H_2O$)) to give the title compound (28.3 mg, 28%) as a white solid. $^1$H NMR (400 MHz, DMSO-$d_6$) δ 7.37-7.19 (m, 3H), 4.55 (s, 2H), 4.42 (s, 2H), 4.40-4.31 (m, 1H), 4.02-3.94 (m, 2H), 3.78 (dt, J=14.7, 5.8 Hz, 2H), 3.65 (d, J=3.9 Hz, 2H), 3.54-3.43 (m, 2H), 2.96 (s, 3H), 2.93-2.73 (m, 2H), 2.13-1.98 (m, 5H), 1.87 (dd, J=12.7, 5.2 Hz, 2H). LCMS M/Z (M+H) 409.

Example 18 (Procedure Q)

7-(5-acetyl-1-(tetrahydro-2H-pyran-4-yl)-4,5,6,7-tetrahydro-1H-pyrazolo[4,3-c]pyridin-3-yl)-2-(4-methoxyphenyl)isoindolin-1-one

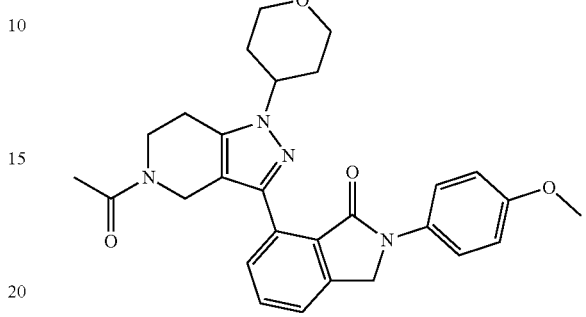

Step 1: 7-(5-acetyl-1-(tetrahydro-2H-pyran-4-yl)-4,5,6,7-tetrahydro-1H-pyrazolo[4,3-c]pyridin-3-yl)isoindolin-1-one To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 350 mg, 1.07 mmol) and bis(pinacolato)diboron (542 mg, 2.13 mmol) in dioxane (5.3 mL) was added KOAc (314 mg, 3.20 mmol), (2-dicyclohexylphosphino-2',4',6'-triisopropyl-1,1'-biphenyl)[2-(2'-amino-1,1'-biphenyl)]palladium(II) methanesulfonate (26 mg, 0.032 mmol) and 2-(dicyclohexylphosphino)-2',4',6'-triisopropylbiphenyl (31 mg, 0.064 mmol). The mixture was stirred at 80° C. for 16 h under a nitrogen atmosphere. The reaction mixture was cooled to room temperature and 7-bromoisoindolin-1-one (113 mg, 0.533 mmol), $K_3PO_4 \cdot H_2O$ (313 mg, 1.33 mmol), water (1.3 mL) and (2-dicyclohexylphosphino-2',4',6'-triisopropyl-1,1'-biphenyl)[2-(2'-amino-1,1'-biphenyl)]palladium(II) methanesulfonate (26 mg, 0.032 mmol) were added. The reaction mixture was stirred at 90° C. for 4 h under a nitrogen atmosphere. The reaction mixture was then cooled to room temperature and concentrated in vacuo. The crude residue was dissolved in dichloromethane (20 mL), dried over anhydrous $MgSO_4$, filtered through celite and concentrated in vacuo. The mixture obtained was purified by silica gel chromatography (MeOH/iPrOAc=1:10 to 1:3) to give the title compound (144 mg, 36%) as a white solid. $^1$H NMR (400 MHz, DMSO-$d_6$, 23/24 H) δ 7.66-7.40

(m, 3H), 6.06-5.94 (m, 1H), 4.48 (d, J=9.5 Hz, 2H), 4.62-4.41 (m, 1H), 4.18 (dd, J=36.7, 11.6 Hz, 2H), 3.99-3.77 (m, 2H), 3.59-3.47 (m, 3H), 2.82 (dt, J=24.3, 5.9 Hz, 2H), 2.43-2.30 (m, 2H), 2.17-2.06 (m, 3H), 1.93 (d, J=13.2 Hz, 2H). LCMS M/Z (M+H) 381.

Step 2: 7-(5-acetyl-1-(tetrahydro-2H-pyran-4-yl)-4,5,6,7-tetrahydro-1H-pyrazolo[4,3-c]pyridin-3-yl)-2-(4-methoxyphenyl)isoindolin-1-one

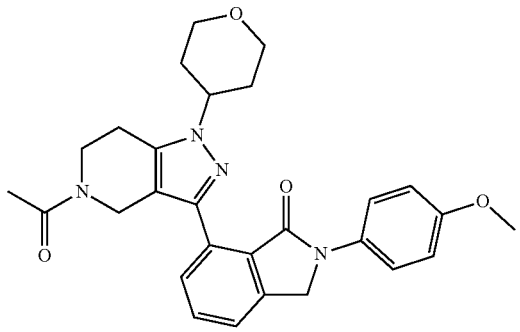 [SMILES: COc1ccc(N2Cc3cccc(-c4nn(C5CCOCC5)c5c4CN(C(C)=O)CC5)c3C2=O)cc1]

To a solution of 7-(5-acetyl-1-(tetrahydro-2H-pyran-4-yl)-4,5,6,7-tetrahydro-1H-pyrazolo[4,3-c]pyridin-3-yl)isoindolin-1-one (30 mg, 0.079 mmol) in dioxane (0.46 mL) was added 4-bromoanisole (14 mg, 0.075 mmol), N,N'-dimethylethylenediame (1.0 µL, 0.0095 mmol), copper(I) iodide (1.8 mg, 0.0095 mmol) and K₂CO₃ (44 mg, 0.32 mmol). The mixture was stirred at 101° C. for 24 h under a nitrogen atmosphere. The reaction mixture was then cooled to room temperature, diluted with dichloromethane (5 mL), filtered through celite and concentrated in vacuo. The mixture obtained was purified by reverse phase chromatography (acetonitrile 20-60%/0.1% formic acid in water) to give the title compound (32.1 mg, 84%) as a white solid. ¹H NMR (400 MHz, DMSO-d₆) δ 7.80-7.70 (m, 2H), 7.72-7.61 (m, 2H), 7.43 (ddd, J=11.2, 6.7, 1.9 Hz, 1H), 7.04-6.96 (m, 2H), 5.00 (s, 2H), 4.40 (s, 1H), 4.38-4.31 (m, 2H), 4.02-3.94 (m, 2H), 3.77 (s, 3H), 3.73 (t, J=6.1 Hz, 2H), 3.48 (dd, J=13.7, 10.4 Hz, 2H), 2.94-2.72 (m, 2H), 2.16-2.03 (m, 4H), 1.98 (s, 1H), 1.88 (d, J=12.9 Hz, 2H). LCMS M/Z (M+H) 487.

Example 19 (Procedure R)

1-(3-(6-(4-methoxyphenyl)-1H-indol-1-yl)-1-(tetrahydro-2H-pyran-4-yl)-1,4,6,7-tetrahydro-5H-pyrazolo[4,3-c]pyridin-5-yl)ethan-1-one

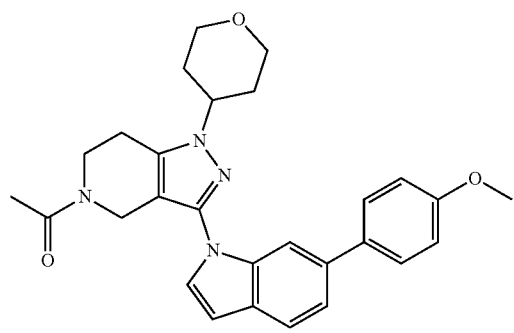 [SMILES: COc1ccc(-c2ccc3ccn(-c4nn(C5CCOCC5)c5c4CN(C(C)=O)CC5)c3c2)cc1]

Step 1: 6-(4-methoxyphenyl)-1H-indole

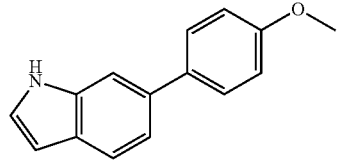 [SMILES: COc1ccc(-c2ccc3cc[nH]c3c2)cc1]

To a solution of 6-bromo-1H-indole (150 mg, 0.765 mmol) and (4-methoxyphenyl)boronic acid (151 mg, 0.995 mmol) in dioxane (2.6 mL) and water (0.6 mL) was added K₃PO₄·H₂O (545 mg, 2.30 mmol), (2-dicyclohexylphosphino-2',4',6'-triisopropyl-1,1'-biphenyl)[2-(2'-amino-1,1'-biphenyl)]palladium(II) methanesulfonate (25 mg, 0.031 mmol) and 2-(dicyclohexylphosphino)-2',4',6'-triisopropylbiphenyl (15 mg, 0.031 mmol). The reaction mixture was stirred at 85° C. for 16 h under a nitrogen atmosphere. The reaction mixture was then cooled to room temperature and concentrated in vacuo. The crude residue was dissolved in dichloromethane (10 mL), dried over anhydrous MgSO₄, filtered through celite and concentrated in vacuo. The mixture obtained was purified by silica gel chromatography (iPrOAc/Heptane=1:19 to 1:9) to give the title compound (134 mg, 78%) as a white solid. ¹H NMR (400 MHz, DMSO-d₆) δ 8.17 (s, 1H), 7.67 (d, J=8.2 Hz, 1H), 7.62-7.48 (m, 3H), 7.34 (dd, J=8.2, 1.6 Hz, 1H), 7.22 (dd, J=3.2, 2.4 Hz, 1H), 7.03-6.94 (m, 2H), 6.56 (ddd, J=3.2, 2.1, 1.0 Hz, 1H), 3.86 (s, 3H). LCMS M/Z (M+H) 224.

Step 2: 1-(3-(6-(4-methoxyphenyl)-1H-indol-1-yl)-1-(tetrahydro-2H-pyran-4-yl)-1,4,6,7-tetrahydro-5H-pyrazolo[4,3-c]pyridin-5-yl)ethan-1-one

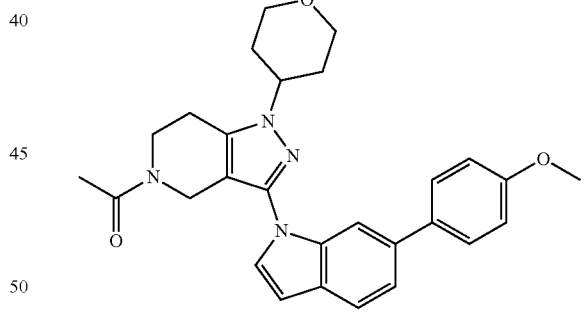

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 50 mg, 0.15 mmol) in toluene (0.76 mL) was added 6-(4-methoxyphenyl)-1H-indole (51 mg, 0.23 mmol), K₃PO₄ (77 mg, 0.35 mmol), copper(I) iodide (29 mg, 0.15 mmol) and (trans)-1,2-diaminocyclohexane (18 mg, 0.15 mmol). The mixture was stirred at 110° C. for 16 h under a nitrogen atmosphere. The reaction mixture was then cooled to room temperature, diluted with dichloromethane (5 mL), filtered through celite and concentrated in vacuo. The mixture obtained was purified by reverse phase chromatography (acetonitrile 30-70%/0.1% ammonium hydroxide in water) to give the title compound (49.6 mg, 69%) as a white solid. ¹H NMR (400 MHz, DMSO-d₆) δ 8.05-7.90 (m, 1H), 7.69 (dd, J=8.2, 2.1 Hz, 1H), 7.62-7.54

(m, 2H), 7.58-7.47 (m, 1H), 7.40 (dd, J=8.2, 1.6 Hz, 1H), 7.08-6.98 (m, 2H), 6.73-6.67 (m, 1H), 4.52 (d, J=11.4 Hz, 2H), 4.41 (tt, J=11.0, 4.5 Hz, 1H), 4.00 (ddd, J=9.3, 4.8, 2.5 Hz, 2H), 3.86-3.77 (m, 5H), 3.50 (td, J=12.0, 2.4 Hz, 2H), 2.95-2.75 (m, 2H), 2.12 (s, 2H), 2.10-1.99 (m, 3H), 1.93 (dd, J=12.8, 4.2 Hz, 2H). LCMS M/Z (M+H) 471.

Example 20 (Procedure S)

1-(3-(2-(2,4-dimethylphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one

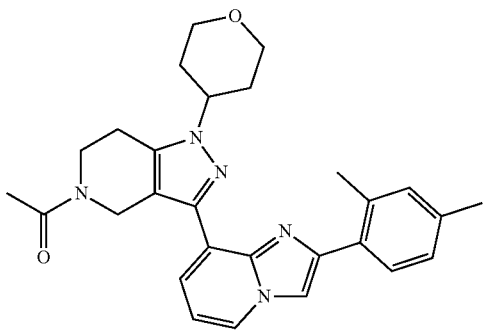 [SMILES: CC(=O)N1CCc2c(c(-c3cccn4cc(-c5ccc(C)cc5C)nc34)nn2C2CCOCC2)C1]

Step 1: 8-bromo-2-(2,4-dimethylphenyl)imidazo[1,2-a]pyridine

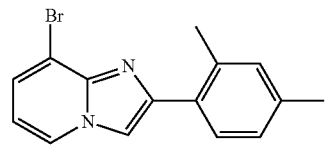 [SMILES: Cc1ccc(-c2cn3cccc(Br)c3n2)c(C)c1]

To a solution of 3-bromopyridin-2-amine (200 mg, 1.16 mmol) in 2-propanol (2.3 mL) was added 2-bromo-1-(2,4-dimethylphenyl)ethanone (315 mg, 1.39 mmol). The mixture was stirred at 75° C. for 72 h. The reaction mixture was then cooled to room temperature and concentrated in vacuo. The crude residue was partitioned between DCM (50 mL) and saturated aqueous NaHCO$_3$ solution (50 mL) and the two phases were separated. The aqueous layer was extracted with DCM (2×50 mL). The combined organic layers were dried over anhydrous MgSO$_4$, filtered and concentrated in vacuo. The mixture obtained was purified by silica gel chromatography (iPrOAc/Heptane=1:9) to give the title compound (242 mg, 70%) as a pale yellow solid. $^1$H NMR (400 MHz, DMSO-d$_6$) δ 8.12 (dd, J=6.7, 1.1 Hz, 1H), 7.84-7.77 (m, 1H), 7.74 (s, 1H), 7.43 (dd, J=7.3, 1.0 Hz, 1H), 7.13-7.06 (m, 2H), 6.66 (dd, J=7.3, 6.7 Hz, 1H), 2.52 (s, 3H), 2.36 (s, 3H). LCMS M/Z (M+H) 301.

Step 2: 1-(3-(2-(2,4-dimethylphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one

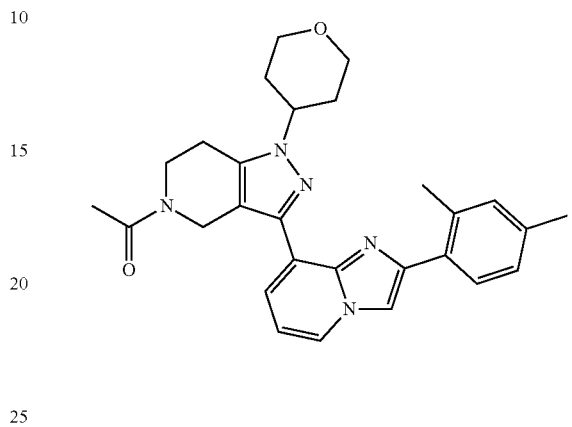

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 50 mg, 0.15 mmol) and bis(pinacolato)diboron (77 mg, 0.30 mmol) in dioxane (0.76 mL) was added KOAc (45 mg, 0.46 mmol), (2-dicyclohexylphosphino-2',4',6'-triisopropyl-1,1'-biphenyl)[2-(2'-amino-1,1'-biphenyl)]palladium(II) methanesulfonate (3.7 mg, 0.0046 mmol) and 2-(dicyclohexylphosphino)-2',4',6'-triisopropyl-biphenyl (4.4 mg, 0.0091 mmol). The mixture was stirred at 80° C. for 16 h under a nitrogen atmosphere. The reaction mixture was cooled to room temperature and 8-bromo-2-(2,4-dimethylphenyl)imidazo[1,2-a]pyridine (23 mg, 0.076 mmol), K$_3$PO$_4$.H$_2$O (38 mg, 0.17 mmol), water (0.3 mL) and (2-dicyclohexylphosphino-2',4',6'-triisopropyl-1,1'-biphenyl)[2-(2'-amino-1,1'-biphenyl)]palladium(II) methanesulfonate (3.7 mg, 0.0046 mmol) were added. The reaction mixture was stirred at 90° C. for 4 h under a nitrogen atmosphere. The reaction mixture was then cooled to room temperature and concentrated in vacuo. The crude residue was dissolved in dichloromethane (5 mL), dried over anhydrous MgSO$_4$, filtered through celite and concentrated in vacuo. The mixture obtained was purified by reverse phase chromatography (acetonitrile 20-60%/0.1% ammonium hydroxide in water) to give the title compound (21.3 mg, 30%) as a white solid. $^1$H NMR (400 MHz, DMSO-d$_6$) δ 8.58 (ddd, J=6.7, 3.2, 1.2 Hz, 1H), 8.25 (s, 1H), 8.06-7.81 (m, 1H), 7.50-7.36 (m, 1H), 7.14-7.05 (m, 2H), 6.97 (q, J=7.0 Hz, 1H), 4.87 (s, 1H), 4.76 (s, 1H), 4.39 (tq, J=10.7, 4.6 Hz, 1H), 4.00 (dd, J=10.3, 4.6 Hz, 2H), 3.79 (dt, J=8.9, 5.7 Hz, 2H), 3.50 (tt, J=11.8, 1.8 Hz, 2H), 2.95-2.75 (m, 2H), 2.52 (s, 3H), 2.31 (s, 3H), 2.19-2.03 (m, 4H), 1.96-1.84 (m, 3H). LCMS M/Z (M+H) 470.

Example 21 (Procedure T)

1-(3-(2-(4-methoxyphenyl)benzo[d]oxazol-4-yl)-1-(tetrahydro-2H-pyran-4-yl)-1,4,6,7-tetrahydro-5H-pyrazolo[4,3-c]pyridin-5-yl)ethan-1-one

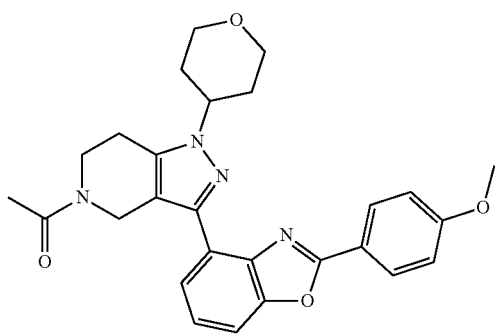 [SMILES: COc1ccc(-c2nc3c(-c4nn(C5CCOCC5)c5c4CN(C(C)=O)CC5)cccc3o2)cc1]

Step 1: 4-bromo-2-(4-methoxyphenyl)benzo[d]oxazole

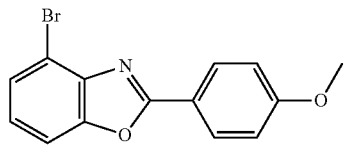 [SMILES: COc1ccc(-c2nc3c(Br)cccc3o2)cc1]

To a solution of 3-bromo-2-nitro-phenol (120 mg, 0.550 mmol) in toluene (1.4 mL) was added (4-methoxyphenyl)methanol (190 mg, 1.38 mmol) and 1,1'-bis(diphenylphosphino)ferrocene (9.2 mg, 0.016 mmol). The mixture was stirred at 150° C. for 24 h in a sealed vial under a nitrogen atmosphere. The reaction mixture was then cooled to room temperature, diluted with dichloromethane (10 mL), filtered through celite and concentrated in vacuo. The mixture obtained was purified by silica gel chromatography (acetone/heptane=1:19 to 1:9) to give the title compound (69.2 mg, 41%) as a pink solid. $^1$H NMR (400 MHz, DMSO-d$_6$) δ 8.29-8.20 (m, 2H), 7.50 (d, J=8.0 Hz, 2H), 7.19 (t, J=8.0 Hz, 1H), 7.07-6.98 (m, 2H), 3.90 (s, 3H). LCMS M/Z (M+H) 305.

Step 2: 1-(3-(2-(4-methoxyphenyl)benzo[d]oxazol-4-yl)-1-(tetrahydro-2H-pyran-4-yl)-1,4,6,7-tetrahydro-5H-pyrazolo[4,3-c]pyridin-5-yl)ethan-1-one

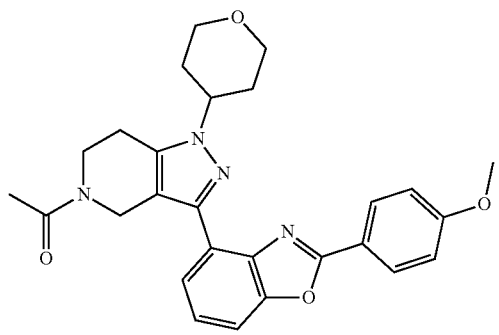 [SMILES: COc1ccc(-c2nc3c(-c4nn(C5CCOCC5)c5c4CN(C(C)=O)CC5)cccc3o2)cc1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 50 mg, 0.15 mmol) and bis(pinacolato)diboron (77 mg, 0.30 mmol) in dioxane (0.76 mL) was added KOAc (45 mg, 0.46 mmol), (2-dicyclohexylphosphino-2',4',6'-triisopropyl-1,1'-biphenyl)[2-(2'-amino-1,1'-biphenyl)]palladium(II) methanesulfonate (3.7 mg, 0.0046 mmol) and 2-(dicyclohexylphosphino)-2',4',6'-triisopropyl-biphenyl (4.4 mg, 0.0091 mmol). The mixture was stirred at 80° C. for 16 h under a nitrogen atmosphere. The reaction mixture was cooled to room temperature and 4-bromo-2-(4-methoxyphenyl)-1,3-benzoxazole (27 mg, 0.088 mmol), K$_3$PO$_4$.H$_2$O (47 mg, 0.20 mmol), water (0.3 mL) and (2-dicyclohexylphosphino-2',4',6'-triisopropyl-1,1'-biphenyl)[2-(2'-amino-1,1'-biphenyl)]palladium(II) methanesulfonate (3.7 mg, 0.0046 mmol) were added. The reaction mixture was stirred at 90° C. for 4 h under a nitrogen atmosphere. The reaction mixture was then cooled to room temperature and concentrated in vacuo. The crude residue was dissolved in dichloromethane (5 mL), dried over anhydrous MgSO$_4$, filtered through celite and concentrated in vacuo. The mixture obtained was purified by reverse phase chromatography (acetonitrile 30-70%/0.1% formic acid in water) to give the title compound (28.9 mg, 40%) as a white solid. $^1$H NMR (400 MHz, DMSO-d$_6$) δ 8.29-8.15 (m, 2H), 7.73 (ddd, J=8.1, 4.8, 1.1 Hz, 1H), 7.63 (td, J=7.9, 1.0 Hz, 1H), 7.44 (td, J=8.0, 4.4 Hz, 1H), 7.22-7.12 (m, 2H), 4.86 (d, J=10.1 Hz, 2H), 4.40 (td, J=11.2, 4.5 Hz, 1H), 4.05-3.96 (m, 2H), 3.88 (d, J=1.3 Hz, 3H), 3.83 (dt, J=12.0, 5.7 Hz, 2H), 3.50 (tt, J=11.5, 1.8 Hz, 2H), 2.95-2.75 (m, 2H), 2.20-2.03 (m, 5H), 1.94-1.85 (m, 2H). LCMS M/Z (M+H) 473.

Example 22 (Procedure U)

3-(5-acetyl-1-tetrahydrofuran-3-yl-6,7-dihydro-4H-pyrazolo[4,3-c]pyridin-3-yl)-N-(3-cyanophenyl)benzamide

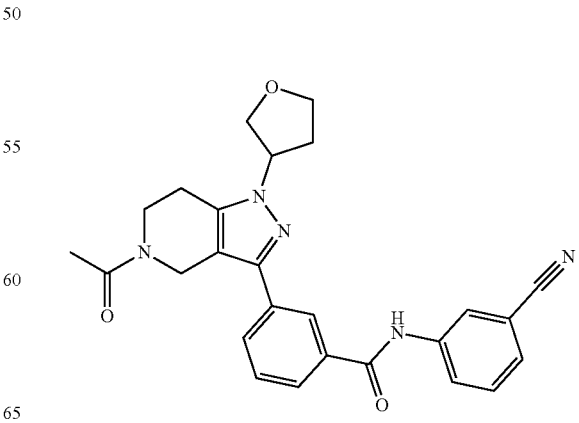

Step 1: methyl 3-(5-acetyl-1-tetrahydrofuran-3-yl-6,7-dihydro-4H-pyrazolo[4,3-c]pyridin-3-yl)benzoate

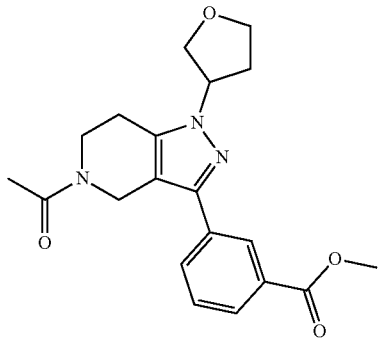 [SMILES: COC(=O)c1cccc(-c2nn(C3CCOC3)c3c2CN(C(C)=O)CC3)c1]

A solution of 1-(3-bromo-1-(tetrahydrofuran-3-yl)-6,7-dihydro-1H-pyrazolo[4,3-c]pyridin-5(4H)-yl)ethanone (Intermediate F, 2.3 g, 7.3 mmol) and (3-(methoxycarbonyl)phenyl)boronic acid (2.0 g, 11 mmol) in dioxane (20 mL) was charged with aqueous sodium carbonate solution (1.0 M, 20 mL) and heated at 120° C. for 20 minutes. The mixture was then diluted with ethyl acetate and water and the layers were partitioned and separated. The organic layer was washed once with water, dried over anhydrous magnesium sulfate, filtered and concentrated in vacuo. The crude residue was purified by silica gel chromatography (dichloromethane/methanol=100:1 to 10:1) to give the title compound (2.6 g, 7.0 mmol, 96% yield). LCMS M/Z (M+H) 370.

Step 2: 3-(5-acetyl-1-tetrahydrofuran-3-yl-6,7-dihydro-4H-pyrazolo[4,3-c]pyridin-3-yl)benzoic acid

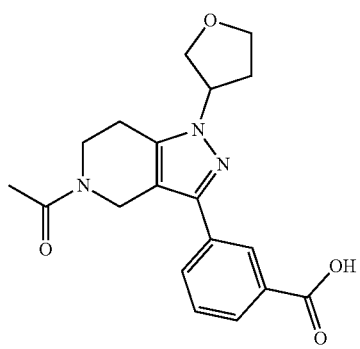 [SMILES: CC(=O)N1CCc2c(c(-c3cccc(C(=O)O)c3)nn2C2CCOC2)C1]

A solution of methyl 3-(5-acetyl-1-tetrahydrofuran-3-yl-6,7-dihydro-4H-pyrazolo[4,3-c]pyridin-3-yl)benzoate (3.2 g, 8.7 mmol) in THF (20 mL) and MeOH (10 mL) was charged with aqueous lithium hydroxide solution (2.0 M, 10 mL) and stirred at room temperature overnight. The mixture was then concentrated in vacuo to remove the organic solvents. The pH of the resulting aqueous mixture was adjusted to pH=4 by titration with aqueous hydrochloric acid solution (1.0 M). The precipitate was then collected by filtration, washed with water, and dried under vacuum to afford the title compound (2.9 g, 8.2 mmol, 92% yield). LCMS M/Z (M+H) 356.

Step 3: 3-(5-acetyl-1-tetrahydrofuran-3-yl-6,7-dihydro-4H-pyrazolo[4,3-c]pyridin-3-yl)-N-(3-cyanophenyl)benzamide

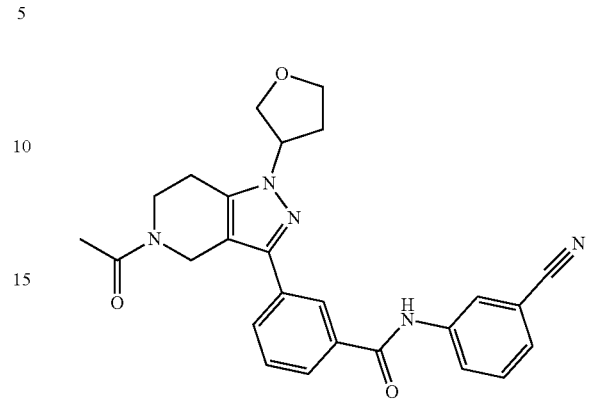

A solution of 3-(5-acetyl-1-tetrahydrofuran-3-yl-6,7-dihydro-4H-pyrazolo[4,3-c]pyridin-3-yl)benzoic acid (20 mg, 0.056 mmol) in DMF (0.5 mL) was charged with 1-[bis(dimethylamino)methylene]-1H-1,2,3-triazolo[4,5-b]pyridinium 3-oxide hexafluorophosphate (44 mg, 0.11 mmol) and diisopropylethylamine (15 mg, 0.11 mmol), then stirred at room temperature for 5 min. To the mixture was added 3-aminobenzonitrile (13 mg, 0.11 mmol). After stirring at room temperature for an additional 1 h, the reaction mixture was purified by reverse phase preparative HPLC (acetonitrile 5-50%/0.1% ammonium hydroxide in water) to give the title compound (23 mg, 0.055 mmol, 90%). $^1$H NMR (400 MHz, DMSO-d$_6$) δ 10.65 (s, 1H), 8.27 (ddd, J=2.8, 2.3, 1.1 Hz, 1H), 8.21-8.13 (m, 1H), 8.11-8.02 (m, 1H), 7.95-7.87 (m, 1H), 7.86-7.79 (m, 1H), 7.68-7.55 (m, 3H), 5.07-4.93 (m, 1H), 4.71 (d, J=2.6 Hz, 2H), 4.16-3.99 (m, 2H), 3.97-3.71 (m, 4H), 2.95-2.84 (m, 1H), 2.77 (d, J=6.0 Hz, 1H), 2.42-2.30 (m, 2H), 2.17-2.00 (m, 3H). LCMS M/Z (M+H) 456.2.

Example 23 (Procedure V)

5-(5-acetyl-1-(tetrahydro-2H-pyran-4-yl)-4,5,6,7-tetrahydro-1H-pyrazolo[4,3-c]pyridin-3-yl)-2-cyclopentyl-1,2-dihydroisoquinolin-3(4H)-one

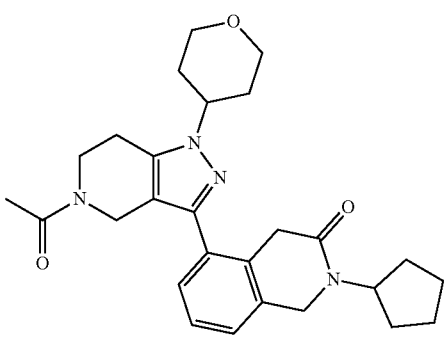 [SMILES: CC(=O)N1CCc2c(c(-c3cccc4c3CC(=O)N(C3CCCC3)C4)nn2C2CCOCC2)C1]

Step 1: 2-(2-chlorophenyl)-N-cyclopentylacetamide

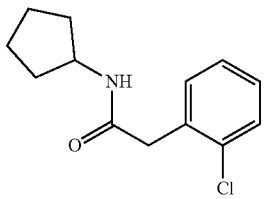 [SMILES: O=C(Cc1ccccc1Cl)NC1CCCC1]

To a solution of 2-(2-chlorophenyl)acetic acid (17.5 g, 102.59 mmol) in DMF (100 mL) was added HATU (58.51 g, 153.88 mmol), N,N-diisopropylethylamine (50.86 mL, 307.76 mmol) and cyclopentylamine (12.06 mL, 123.1 mmol). The reaction mixture was stirred at room temperature for 16 h under a nitrogen atmosphere. The reaction solution was poured into water (200 mL) and extracted with EtOAc (150 mL×3). The combined organic layers were washed with brine (200 mL×2), dried over anhydrous Na₂SO₄, filtered and concentrated in vacuo. The crude residue was purified by silica gel chromatography (petroleum ether/EtOAc=3:1) to give the title compound (20 g, 82%) as a white solid.

Step 2: 5-chloro-2-cyclopentyl-1,2-dihydroisoquinolin-3(4H)-one

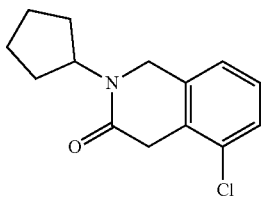 [SMILES: O=C1Cc2c(Cl)cccc2CN1C1CCCC1]

A mixture of 2-(2-chlorophenyl)-N-cyclopentylacetamide (3 g, 12.62 mmol), paraformaldehyde (1.89 g, 63.1 mmol), methanesulfonic acid (25 mL, 384.98 mmol) and phosphorus pentoxide (3.0 g, 21.14 mmol) was heated to 80° C. for 2 h. The reaction mixture was poured into ice water (150 mL), neutralized with Na₂CO₃, and then extracted with EtOAc (100 mL×3). The combined organic layers were washed with brine (100 mL×3), dried over anhydrous Na₂SO₄, filtered and concentrated in vacuo. The crude residue was purified by silica gel chromatography (petroleum ether/EtOAc=4:1) to give the title compound (600 mg, 19%) as a green solid. LCMS M/Z (M+H) 250.

Step 3: 1-(1-(tetrahydro-2H-pyran-4-yl)-3-(4,4,5,5-tetramethyl-1,3,2-dioxaborolan-2-yl)-6,7-dihydro-1H-pyrazolo[4,3-c]pyridin-5(4H)-yl)ethanone

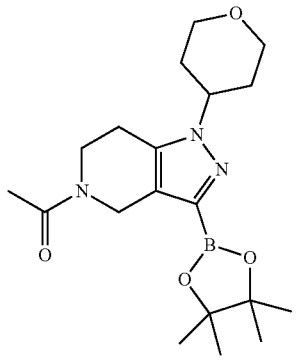 [SMILES: CC(=O)N1CCc2c(c(B3OC(C)(C)C(C)(C)O3)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 300 mg, 0.91 mmol) in 1,4-dioxane (4 mL) was added 2-(dicyclohexylphosphino)-2',4',6'-triisopropylbiphenyl (26 mg, 0.05 mmol), chloro(2-dicyclohexylphosphino-2',4',6'-tri-i-propyl-1,1'-biphenyl)(2'-amino-1,1'-biphenyl-2-yl) palladium(II) (22 mg, 0.03 mmol), KOAc (269 mg, 2.74 mmol) and 4,4,4',4',5,5,5',5'-octamethyl-2,2'-bi(1,3,2-dioxaborolane) (464 mg, 1.83 mmol). The mixture was heated to 80° C. for 3 h under a nitrogen atmosphere. After cooling the reaction to room temperature, the reaction mixture was used to the next step directly without further purification. LCMS M/Z (M+H) 376.

Step 4: 5-(5-acetyl-1-(tetrahydro-2H-pyran-4-yl)-4,5,6,7-tetrahydro-1H-pyrazolo[4,3-c]pyridin-3-yl)-2-cyclopentyl-1,2-dihydroisoquinolin-3(4H)-one

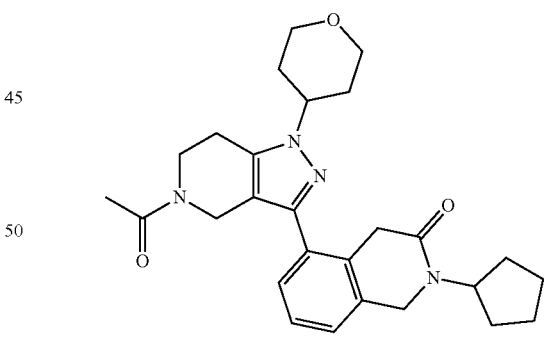

To the above step cooled solution was added 5-chloro-2-cyclopentyl-1,2-dihydroisoquinolin-3(4H)-one (113 mg, 0.45 mmol), chloro(2-dicyclohexylphosphino-2',4',6'-tri-i-propyl-1,1'-biphenyl)(2'-amino-1,1'-biphenyl-2-yl) palladium(II) (23 mg, 0.03 mmol), K₃PO₄ (240 mg, 1.13 mmol), 1,4-dioxane (1 mL) and water (1 mL). The reaction mixture was heated to 90° C. for 1 h under a nitrogen atmosphere. After cooling to room temperature, the mixture was filtered and concentrated in vacuo. Water (100 mL) was added and extracted with EtOAc (50 mL×3). The combined organic layers were washed with brine (50 mL×2), dried over anhydrous Na₂SO₄, filtered and concentrated in vacuo. The crude residue was purified by reverse phase chromatography (acetonitrile 30-60%/0.05% NH₄OH in water) to give the title compound (86 mg, 20%) as a white solid. ¹H NMR (400 MHz, DMSO-d₆) δ 7.40 (d, J=8.0 Hz, 1H), 7.34-7.29 (m, 1H), 7.24 (d, J=6.8 Hz, 1H), 4.88-4.78 (m, 1H), 4.47-4.31 (m, 5H), 4.04-3.95 (m, 2H), 3.83-3.73 (m, 2H), 3.71-3.65 (m, 2H), 3.49 (t, J=12.0 Hz, 2H), 2.94-2.75 (m, 2H), 2.12-2.01 (m, 5H), 1.92-1.83 (m, 2H), 1.80-1.64 (m, 4H), 1.62-1.52 (m, 4H). LCMS M/Z (M+H) 463.

Example 24

5-(8-(5-acetyl-1-(tetrahydro-2H-pyran-4-yl)-4,5,6,7-tetrahydro-1H-pyrazolo[4,3-c]pyridin-3-yl)-4-fluoroisoquinolin-3-yl)-N-methylpicolinamide

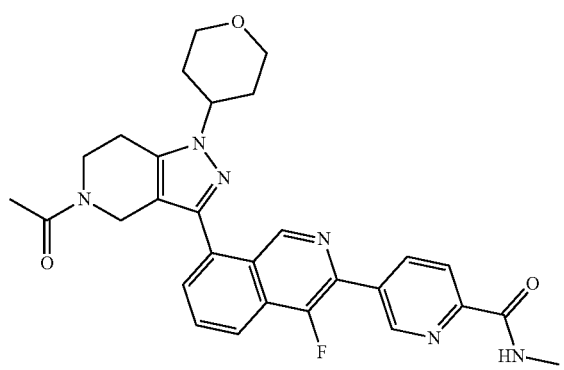 [SMILES: CNC(=O)c1ccc(-c2ncc3c(-c4nn(C5CCOCC5)c5c4CN(C(C)=O)CC5)cccc3c2F)cn1]

Step 1: 8-chloro-4-fluoroisoquinolin-3(2H)-one

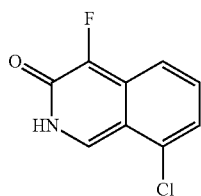 [SMILES: O=c1[nH]cc2c(Cl)cccc2c1F]

To a solution of 8-chloroisoquinolin-3(2H)-one (600 mg, 3.34 mmol) in THF (10 mL) was added 1-chloromethyl-4-fluoro-1,4-diazoniabicyclo[2.2.2]octane bis(tetrafluoroborate) (1.36 g, 3.84 mmol). The reaction was stirred at room temperature for 16 h. DCM (80 mL) was added and washed with water (20 mL×2). The organic layer was dried over anhydrous Na₂SO₄, filtered and concentrated in vacuo to give the title compound (650 mg, crude) as a yellow solid that required no further purification. LCMS M/Z (M+H) 198.

Step 2: 8-chloro-4-fluoroisoquinolin-3-yl trifluoromethanesulfonate

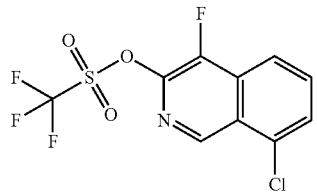 [SMILES: O=S(=O)(Oc1ncc2c(Cl)cccc2c1F)C(F)(F)F]

To a solution of 8-chloro-4-fluoroisoquinolin-3(2H)-one (200 mg, 1.01 mmol) in DCM (4 mL) at 0° C. was added triethylamine (0.42 mL, 3.04 mmol) and trifluoromethanesulfonic anhydride (0.42 mL, 2.53 mmol). The reaction was stirred at room temperature for 12 h and concentrated in vacuo. The crude residue was purified by silica gel chromatography (petroleum ether/EtOAc=10:1) to give the title compound (100 mg, 30%) as a yellow solid. ¹H NMR (400 MHz, DMSO-d₆) δ 9.34 (s, 1H), 8.28 (d, J=8.4 Hz, 1H), 8.13-8.07 (m, 1H), 8.06-8.00 (m, 1H). LCMS M/Z (M+H) 330.

Step 3: 5-(8-chloro-4-fluoroisoquinolin-3-yl)-N-methylpicolinamide

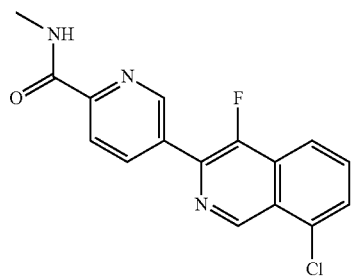 [SMILES: CNC(=O)c1ccc(-c2ncc3c(Cl)cccc3c2F)cn1]

To a solution of 8-chloro-4-fluoroisoquinolin-3-yl trifluoromethanesulfonate (500 mg, 1.52 mmol) in 1,4-dioxane (4 mL) and water (1 mL) was added [1,1'-bis(diphenylphosphino)ferrocene]dichloropalladium(II) (111 mg, 0.15 mmol), Na₂CO₃ (482 mg, 4.55 mmol) and N-methyl-5-(4,4,5,5-tetramethyl-1,3,2-dioxaborolan-2-yl)picolinamide (398 mg, 1.52 mmol). The mixture was irradiated in a microwave at 70° C. for 0.5 h. After cooling the reaction to room temperature, the mixture was filtered and concentrated in vacuo. The crude residue was purified by silica gel chromatography (petroleum ether/EtOAc=3:1) to give the title compound (300 mg, 63%) as a yellow solid. LCMS M/Z (M+H) 316.

Step 4: 5-(4-fluoro-8-(4,4,5,5-tetramethyl-1,3,2-dioxaborolan-2-yl)isoquinolin-3-yl)-N-methylpicolinamide

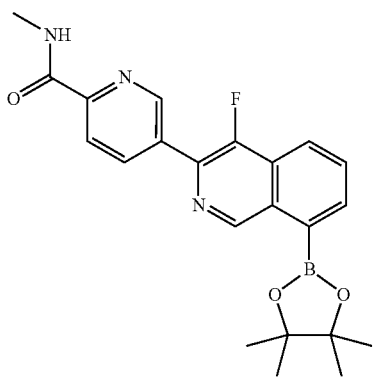 [SMILES: CNC(=O)c1ccc(-c2ncc3c(B4OC(C)(C)C(C)(C)O4)cccc3c2F)cn1]

To a solution of 5-(8-chloro-4-fluoroisoquinolin-3-yl)-N-methylpicolinamide (150 mg, 0.48 mmol) in 1,4-dioxane (3 mL) was added (dicyclohexylphosphino)-2',4',6'-triisopropylbiphenyl (23 mg, 0.05 mmol) and chloro(2-dicyclohexylphosphino-2',4',6'-tri-i-propyl-1,1'-biphenyl)(2'-amino-1,1'-biphenyl-2-yl) palladium(II) (37 mg, 0.05 mmol), 4,4,4',4',5,5,5',5'-octamethyl-2,2'-bi(1,3,2-dioxaborolane) (181 mg, 0.71 mmol) and KOAc (93 mg, 0.95 mmol). The mixture was heated to 80° C. for 1 h under a nitrogen atmosphere. After cooling the reaction to room temperature, the reaction mixture was used to the next step directly without further purification. LCMS M/Z (M+H) 408.

Step 5: 5-(8-(5-acetyl-1-(tetrahydro-2H-pyran-4-yl)-4,5,6,7-tetrahydro-1H-pyrazolo[4,3-c]pyridin-3-yl)-4-fluoroisoquinolin-3-yl)-N-methylpicolinamide

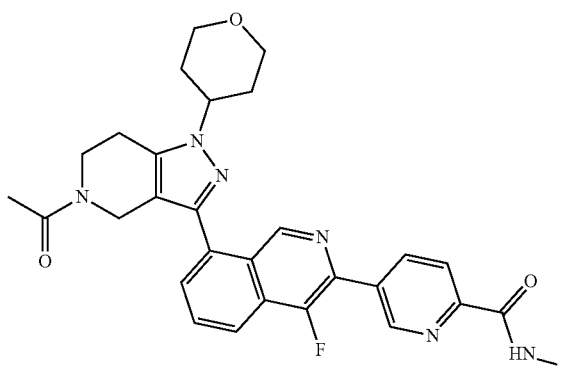 [SMILES: CNC(=O)c1ccc(-c2ncc3c(-c4nn(C5CCOCC5)c5c4CN(C(C)=O)CC5)cccc3c2F)cn1]

To the above step cooled solution was added 1-(3-bromo-1-(tetrahydro-2H-pyran-4-yl)-6,7-dihydro-1H-pyrazolo[4,3-c]pyridin-5(4H)-yl)ethanone (Intermediate H, 118 mg, 0.36 mmol), (dicyclohexylphosphino)-2',4',6'-triisopropylbiphenyl (17 mg, 0.04 mmol) and chloro(2-dicyclohexylphosphino-2',4',6'-tri-i-propyl-1,1'-biphenyl)(2'-amino-1,1'-biphenyl-2-yl) palladium(II) (28 mg, 0.04 mmol) and Na$_2$CO$_3$ (76 mg, 0.72 mmol), 1,4-dioxane (2 mL) and water (1 mL). The reaction mixture was heated to 60° C. for 16 h under a nitrogen atmosphere. After cooling to room temperature, the mixture was filtered and concentrated in vacuo. The crude residue was purified by reverse phase chromatography (acetonitrile 29-59%/0.2% formic acid in water) to give the title compound (28 mg, 11%) as a white solid. $^1$H NMR (400 MHz, DMSO-d$_6$) δ 9.89 (s, 1H), 9.29 (s, 1H), 8.91 (d, J=4.8 Hz, 1H), 8.65 (d, J=8.0 Hz, 1H), 8.27-8.18 (m, 2H), 8.10-7.99 (m, 1H), 7.90-7.76 (m, 1H), 4.60 (s, 2H), 4.54-4.40 (m, 1H), 4.09-3.95 (m, 2H), 3.92-3.75 (m, 2H), 3.53 (t, J=11.6 Hz, 2H), 3.03-2.79 (m, 2H), 2.87 (d, J=4.4 Hz, 3H), 2.17-2.03 (m, 5H), 2.02-1.90 (m, 2H). LCMS M/Z (M+H) 529.

Example 25

3-(6-(difluoromethyl)-7-(1-methyl-1H-pyrazol-4-yl)isoquinolin-4-yl)-N-methyl-1-(tetrahydro-2H-pyran-4-yl)-6,7-dihydro-1H-pyrazolo[4,3-c]pyridine-5(4H)-carboxamide

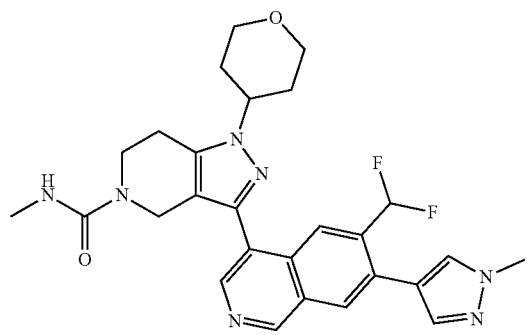

Step 1: N-(3-bromo-4-chlorobenzylidene)-2,2-dimethoxyethanamine

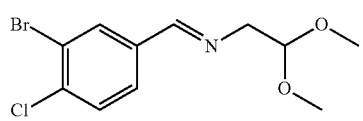 [SMILES: COC(C/N=C/c1ccc(Cl)c(Br)c1)OC]

To a solution of 3-bromo-4-chlorobenzaldehyde (18.0 g, 82.02 mmol) in toluene (200 mL) was added 2,2-dimethoxyethanamine (10.35 g, 98.42 mmol). The mixture was heated to 110° C. for 16 h under a nitrogen atmosphere. After cooling the reaction to room temperature, the mixture was concentrated in vacuo to give the title compound (25.0 g, crude) as yellow oil that required no further purification.

Step 2: N-(3-bromo-4-chlorobenzyl)-2,2-dimethoxyethanamine

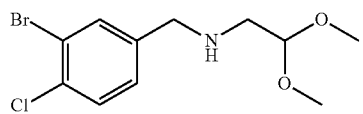 [SMILES: COC(CNCc1ccc(Cl)c(Br)c1)OC]

To a solution of N-(2-bromo-4-chlorobenzylidene)-2,2-dimethoxyethanamine (25.0 g, 81.54 mmol) in MeOH (150 mL) at 0° C. was added sodium borohydride (2.47 g, 65.24 mmol) portionwise. The mixture was stirred at 28° C. for 2 h under a nitrogen atmosphere and concentrated in vacuo. Water (200 mL) was added and extracted with DCM (200 mL×3). The combined organic layers were dried over anhydrous Na$_2$SO$_4$, filtered and concentrated in vacuo to give the title compound (25.0 g, crude) as colorless oil that required no further purification. LCMS M/Z (M+H) 308.

Step 3: N-(3-bromo-4-chlorobenzyl)-N-(2,2-dimethoxyethyl)-4-methylbenzenesulfonamide

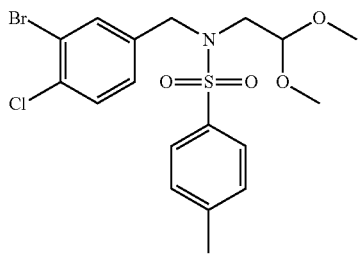 [SMILES: COC(CN(Cc1ccc(Cl)c(Br)c1)S(=O)(=O)c1ccc(C)cc1)OC]

To a solution of N-(3-bromo-4-chlorobenzyl)-2,2-dimethoxyethanamine (27.8 g, 90.08 mmol) in DCM (200 mL) at 0° C. was added 4-methylbenzene-1-sulfonyl chloride (17.17 g, 90.08 mmol), N,N-dimethylpyridin-4-amine (550 mg, 4.5 mmol) and triethylamine (24.97 mL, 180.17 mmol). The mixture was stirred at 28° C. for 16 h under a nitrogen atmosphere. Water (150 mL) was added and extracted with DCM (150 mL×3). The combined organic layers were dried over anhydrous Na$_2$SO$_4$, filtered and concentrated in vacuo. The crude residue was purified by silica gel chromatography (petroleum ether/EtOAc=20:1) to give the title compound (35 g, 84%) as colorless oil. LCMS M/Z (M+H) 462.

Step 4: 7-bromo-6-chloroisoquinoline

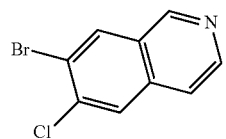 [SMILES: Clc1cc2ccncc2cc1Br]

To a solution of aluminum trichloride (44.66 g, 334.93 mmol) in 1,2-dichloroethane (250 mL) at 0° C. was added N-(3-bromo-4-chlorobenzyl)-N-(2,2-dimethoxyethyl)-4-methylbenzenesulfonamide (31.0 g, 66.99 mmol) in 1,2-dichloroethane (250 mL) dropwise. The mixture was stirred at 28° C. for 16 h under a nitrogen atmosphere. The mixture was quenched with ice-water (130 mL) and extracted with DCM (130 mL×3). The combined organic layers were dried over anhydrous Na$_2$SO$_4$, filtered and concentrated in vacuo. The crude residue was purified by silica gel chromatography (petroleum ether/EtOAc=10:1) to give the title compound (11.0 g, 68%) as a white solid. LCMS M/Z (M+H) 242.

Step 5: 6-chloro-7-(1-methyl-1H-pyrazol-4-yl)isoquinoline

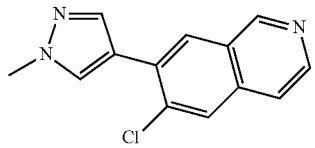 [SMILES: Cn1cc(-c2cc3cnccc3cc2Cl)cn1]

To a solution of 7-bromo-6-chloroisoquinoline (12.1 g, 49.9 mmol) in 1,4-dioxane (100 mL) and water (10 mL) was added [1,1'-bis(diphenylphosphino)ferrocene]dichloropalladium(II) (3.65 g, 4.99 mmol), Na$_2$CO$_3$ (13.22 g, 124.74 mmol) and 1-methyl-4-(4,4,5,5-tetramethyl-1,3,2-dioxaborolan-2-yl)-1H-pyrazole (15.57 g, 74.85 mmol). The mixture was heated to 70° C. for 3 h under a nitrogen atmosphere. After cooling the reaction to room temperature, the mixture was filtered and concentrated in vacuo. The crude residue was purified by silica gel chromatography (petroleum ether/EtOAc=1:1) to give the title compound (11.5 g, 95%) as a brown solid. LCMS M/Z (M+H) 244.

Step 6: 7-(1-methyl-1H-pyrazol-4-yl)isoquinoline-6-carbaldehyde

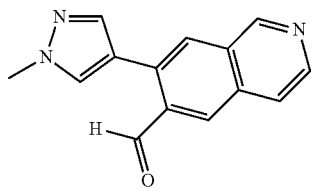 [SMILES: Cn1cc(-c2cc3cnccc3cc2C=O)cn1]

To a solution of 6-chloro-7-(1-methyl-1H-pyrazol-4-yl) isoquinoline (2.0 g, 8.21 mmol) in DMSO (15 mL) was added palladium(II) acetate (92 mg, 0.41 mmol), 1,2-bis (diphenylphosphino)ethane (327 mg, 0.82 mmol), potassium formate (1.38 g, 16.41 mmol) and tert-butyl isocyanide (1.11 mL, 9.85 mmol). The mixture was heated to 120° C. for 6 h under a nitrogen atmosphere. After cooling the reaction to room temperature, sat. aq. NaHCO$_3$ (50 mL) was added and the mixture stirred for an additional 30 min. The solution was extracted with DCM (50 mL×3). The combined organic layers were dried over anhydrous Na$_2$SO$_4$, filtered and concentrated in vacuo. The crude residue was purified by silica gel chromatography (petroleum ether/EtOAc=1:1) to give the title compound (1.0 g, 51%) as a white solid. $^1$H NMR (400 MHz, DMSO-d$_6$) δ 10.31 (s, 1H), 9.41 (s, 1H), 8.57 (d, J=6.0 Hz, 1H), 8.51 (s, 1H), 8.26 (s, 1H), 8.13 (s, 1H), 8.04 (d, J=5.6 Hz, 1H), 7.82 (s, 1H), 3.94 (s, 3H). LCMS M/Z (M+H) 238.

Step 7: 6-(difluoromethyl)-7-(1-methyl-1H-pyrazol-4-yl)isoquinoline

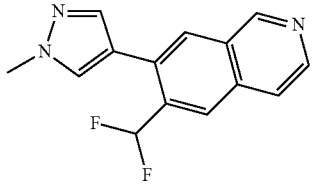 [SMILES: Cn1cc(-c2cc3cnccc3cc2C(F)F)cn1]

To a solution of 7-(1-methyl-1H-pyrazol-4-yl)isoquinoline-6-carbaldehyde (450 mg, 1.9 mmol) in DCM (10 mL) at 0° C. was added diethylaminosulfurtrifluoride (0.75 mL, 5.69 mmol). The mixture was stirred at room temperature for 21 h. The mixture was poured into sat. aq. NaHCO$_3$ (10 mL) at 0° C. and extracted with EtOAc (20 mL×3). The combined organic layers were dried over anhydrous Na$_2$SO$_4$, filtered and concentrated in vacuo. The crude residue was purified by silica gel chromatography (petroleum ether/EtOAc=2:3) to give the title compound (160 mg, 33%) as yellow oil. $^1$H NMR (400 MHz, CDCl$_3$) δ 9.31 (s, 1H), 8.60 (d, J=6.0 Hz, 1H), 8.25 (s, 1H), 7.99 (s, 1H), 7.76 (d, J=5.6 Hz, 1H), 7.72 (s, 1H), 7.63 (s, 1H), 6.79 (d, J=54.8 Hz, 1H), 4.03 (s, 3H).

Step 8: 4-bromo-6-(difluoromethyl)-7-(1-methyl-1H-pyrazol-4-yl)isoquinoline

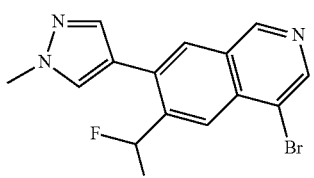

To a solution of 6-(difluoromethyl)-7-(1-methyl-1H-pyrazol-4-yl)isoquinoline (160 mg, 0.6 mmol) in AcOH (1 mL) was added N-bromosuccinimide (109 mg, 0.6 mmol). The mixture was heated to 90° C. for 2 h under a nitrogen atmosphere. After cooling to room temperature, the mixture was concentrated in vacuo. DCM (10 mL) was added and washed with water (10 mL×3) and brine (10 mL). The organic layer was dried over Na$_2$SO$_4$, filtered and concentrated in vacuo. The crude residue was purified by silica gel chromatography (DCM/MeOH=100:1) to give the title compound (95 mg, 45%) as a light yellow solid. LCMS M/Z (M+H) 338.

Step 9: tert-butyl 1-(tetrahydro-2H-pyran-4-yl)-3-(4,4,5,5-tetramethyl-1,3,2-dioxaborolan-2-yl)-6,7-dihydro-1H-pyrazolo[4,3-c]pyridine-5(4H)-carboxylate

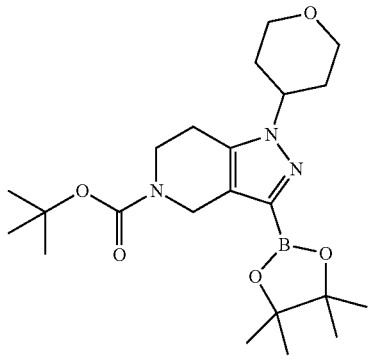 [SMILES: CC(C)(C)OC(=O)N1CCc2c(c(B3OC(C)(C)C(C)(C)O3)nn2C2CCOCC2)C1]

To a solution of tert-butyl 3-bromo-1-(tetrahydro-2H-pyran-4-yl)-6,7-dihydro-1H-pyrazolo[4,3-c]pyridine-5 (4H)-carboxylate (Intermediate G, 500 mg, 1.29 mmol) in 1,4-dioxane (5 mL) was added 2-(dicyclohexylphosphino)-2',4',6'-triisopropylbiphenyl (62 mg, 0.13 mmol), chloro(2-dicyclohexylphosphino-2',4',6'-tri-i-propyl-1,1'-biphenyl) (2'-amino-1,1'-biphenyl-2-yl) palladium(II) (102 mg, 0.13 mmol), KOAc (381 mg, 3.88 mmol) and 4,4,4',4',5,5,5',5'-octamethyl-2,2'-bi(1,3,2-dioxaborolane) (657 mg, 2.59 mmol). The mixture was heated to 80° C. for 3 h under a nitrogen atmosphere. After cooling the reaction to room temperature, the reaction mixture was used to the next step directly without further purification. LCMS M/Z (M+H) 434.

Step 10: tert-butyl 3-(6-(difluoromethyl)-7-(1-methyl-1H-pyrazol-4-yl)isoquinolin-4-yl)-1-(tetrahydro-2H-pyran-4-yl)-6,7-dihydro-1H-pyrazolo[4,3-c]pyridine-5(4H)-carboxylate

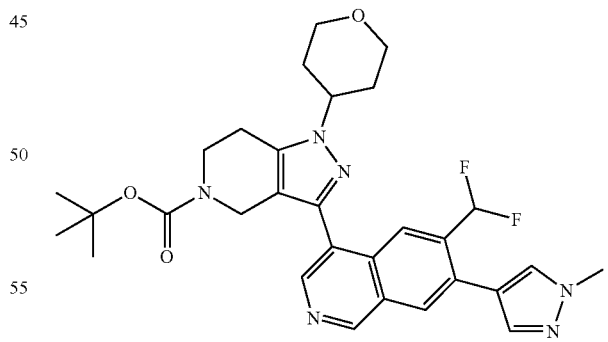

To the above step cooled solution was added 4-bromo-6-(difluoromethyl)-7-(1-methyl-1H-pyrazol-4-yl)isoquinoline (95 mg, 0.28 mmol), 2-(dicyclohexylphosphino)-2',4',6'-triisopropylbiphenyl (13 mg, 0.028 mmol), chloro(2-dicyclohexylphosphino-2',4',6'-tri-i-propyl-1,1'-biphenyl)(2'-amino-1,1'-biphenyl-2-yl) palladium(II) (22 mg, 0.028 mmol), Na$_2$CO$_3$ (89 mg, 0.84 mmol), 1,4-dioxane (5 mL) and water (2 mL). The reaction mixture was heated to 60° C. for 16 h under a nitrogen atmosphere. After cooling to room temperature, the mixture was filtered and concentrated in vacuo. DCM (50 mL) was added and washed with water (30 mL×3) and brine (20 mL). The organic layer was dried over anhydrous $Na_2SO_4$, filtered and concentrated in vacuo. The crude residue was purified by silica gel chromatography (DCM/MeOH=100:1) to give the title compound (70 mg, 10%) as a yellow solid. LCMS M/Z (M+H) 565.

Step 11: 6-(difluoromethyl)-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)isoquinoline

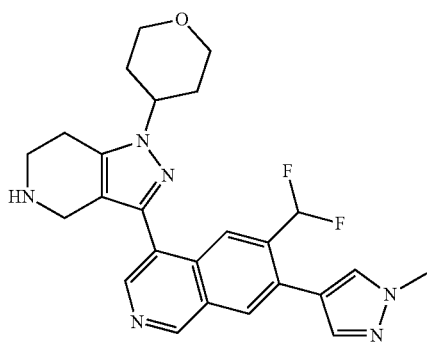 [SMILES: Cn1cc(-c2cc3cncc(-c4nn(C5CCOCC5)c5c4CNCC5)c3cc2C(F)F)cn1]

To a solution of tert-butyl 3-(6-(difluoromethyl)-7-(1-methyl-1H-pyrazol-4-yl)isoquinolin-4-yl)-1-(tetrahydro-2H-pyran-4-yl)-6,7-dihydro-1H-pyrazolo[4,3-c]pyridine-5(4H)-carboxylate (70 mg, 0.12 mmol) in DCM (1 mL) at 0° C. was added trifluoroacetic acid (1 mL, 13.42 mmol). The mixture was stirred at room temperature for 12 h and concentrated in vacuo to give the title compound (50 mg, crude) as brown oil that required no further purification. LCMS M/Z (M+H) 465.

Step 12: 3-(6-(difluoromethyl)-7-(1-methyl-1H-pyrazol-4-yl)isoquinolin-4-yl)-N-methyl-1-(tetrahydro-2H-pyran-4-yl)-6,7-dihydro-1H-pyrazolo[4,3-c]pyridine-5(4H)-carboxamide

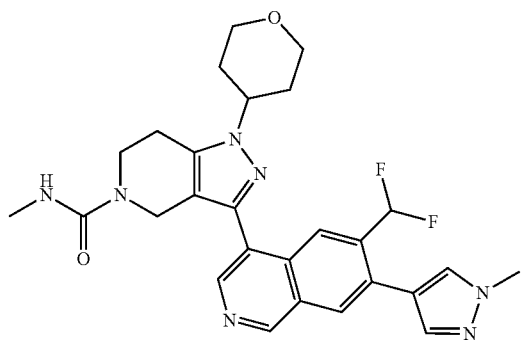

To a solution of 6-(difluoromethyl)-7-(1-methyl-1H-pyrazol-4-yl)-4-(1-(tetrahydro-2H-pyran-4-yl)-4,5,6,7-tetrahydro-1H-pyrazolo[4,3-c]pyridin-3-yl)isoquinoline (50 mg, 0.11 mmol) in DCM (5 mL) was added triethylamine (0.04 mL, 0.32 mmol) and N-methyl-1H-imidazole-1-carboxamide (20 mg, 0.16 mmol). The reaction was stirred at room temperature for 1 h. DCM (50 mL) was added and washed with water (50 mL×3) and brine (20 mL). The organic layer was dried over anhydrous $Na_2SO_4$, filtered and concentrated in vacuo. The crude residue was purified by reverse phase chromatography (acetonitrile 30-60%/0.05% $NH_4OH$ in water) to give the title compound (32 mg, 57%) as a white solid. $^1H$ NMR (400 MHz, DMSO-$d_6$) δ 9.37 (s, 1H), 9.12 (s, 1H), 8.59 (s, 1H), 8.32 (s, 1H), 8.08 (s, 1H), 7.81 (s, 1H), 7.27 (t, J=56.0 Hz, 1H), 6.66-6.60 (m, 1H), 4.51-4.44 (m, 3H), 4.05-3.98 (m, 2H), 3.95 (s, 3H), 3.75-3.67 (m, 2H), 3.57-3.48 (m, 2H), 2.86-2.80 (m, 2H), 2.54 (d, J=4.4 Hz, 3H), 2.20-2.07 (m, 2H), 1.97-1.92 (m, 2H). LCMS M/Z (M+H) 522.

Examples 26 & 27

(S)-1-(3-(3-(1-methyl-1H-pyrazol-4-yl)quinolin-5-yl)-1-(tetrahydrofuran-3-yl)-6,7-dihydro-1H-pyrazolo[4,3-c]pyridin-5(4H)-yl)ethanone and (S)-1-(3-(2-(1-methyl-1H-pyrazol-4-yl)quinolin-5-yl)-1-(tetrahydrofuran-3-yl)-6,7-dihydro-1H-pyrazolo[4,3-c]pyridin-5(4H)-yl)ethanone

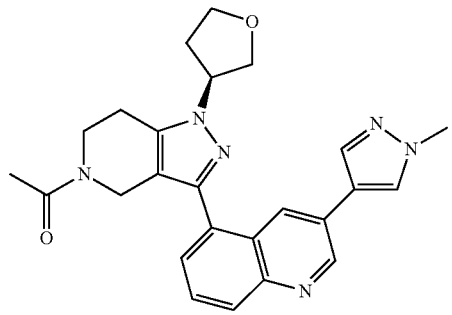

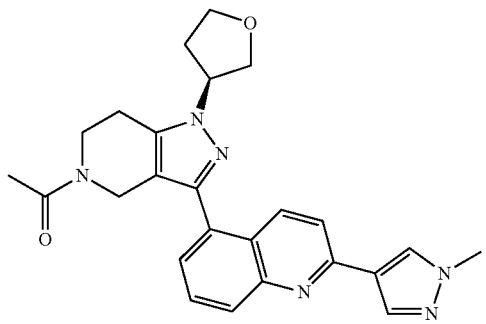

Step 1: (S)-1-(3-(quinolin-5-yl)-1-(tetrahydrofuran-3-yl)-6,7-dihydro-1H-pyrazolo[4,3-c]pyridin-5(4H)-yl)ethanone

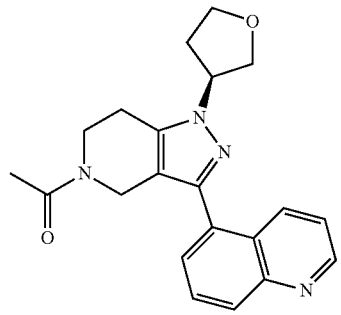 [SMILES: CC(=O)N1CCc2c(c(-c3cccc4ncccc34)nn2[C@H]2CCOC2)C1]

To a solution of (S)-1-(3-bromo-1-(tetrahydrofuran-3-yl)-6,7-dihydro-1H-pyrazolo[4,3-c]pyridin-5(4H)-yl)ethanone (Intermediate E, 500 mg, 1.6 mmol) in 1,4-dioxane (10 mL) and water (2 mL) was added [1,1'-bis(diphenylphosphino)ferrocene]dichloropalladium(II) (116 mg, 0.2 mmol), $K_2CO_3$ (446 mg, 3.2 mmol) and 5-(4,4,5,5-tetramethyl-1,3,2-dioxaborolan-2-yl)quinoline (609 mg, 1.9 mmol). The mixture was heated to 120° C. for 12 h under a nitrogen atmosphere. After cooling the reaction to room temperature, the mixture was filtered and concentrated in vacuo. DCM (50 mL) was added and washed with water (50 mL×2) and brine (50 mL). The organic phase was dried over anhydrous $Na_2SO_4$, filtered and concentrated in vacuo. The crude residue was purified by silica gel chromatography (DCM/MeOH=20:1) to give the title compound (600 mg, 78%) as a yellow solid. LCMS M/Z (M+H) 363.

Step 2: (S)-5-(5-acetyl-1-(tetrahydrofuran-3-yl)-4,5,6,7-tetrahydro-1H-pyrazolo[4,3-c]pyridin-3-yl)quinoline 1-oxide

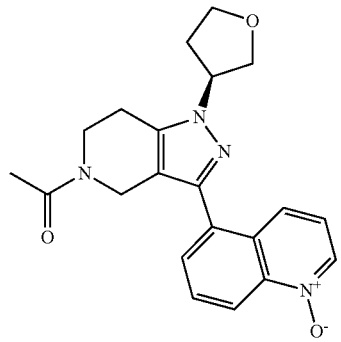 [SMILES: CC(=O)N1CCc2c(c(-c3cccc4c3ccc[n+]4[O-])nn2[C@H]2CCOC2)C1]

To a solution of (S)-1-(3-(quinolin-5-yl)-1-(tetrahydrofuran-3-yl)-6,7-dihydro-1H-pyrazolo[4,3-c]pyridin-5(4H)-yl)ethanone (624 mg, 1.3 mmol) in DCM (10 mL) was added 3-chlorobenzenecarboperoxoic acid (334 mg, 1.9 mmol). The mixture was stirred at 26° C. for 4 h. DCM (80 mL) was added and washed with sat. aq. $Na_2S_2O_3$ (50 mL×3), water (50 mL) and brine (50 mL). The organic phase was dried over anhydrous $Na_2SO_4$, filtered and concentrated in vacuo. The crude residue was purified by silica gel chromatography (DCM/MeOH=20:1) to give the title compound (230 mg, 45%) as a yellow solid. LCMS M/Z (M+H) 379.

Step 3: (S)-1-(3-(3-bromoquinolin-5-yl)-1-(tetrahydrofuran-3-yl)-6,7-dihydro-1H-pyrazolo[4,3-c]pyridin-5(4H)-yl)ethanone and (S)-1-(3-(2-bromoquinolin-5-yl)-1-(tetrahydrofuran-3-yl)-6,7-dihydro-1H-pyrazolo[4,3-c]pyridin-5(4H)-yl)ethanone

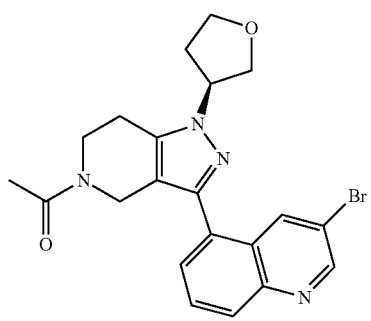

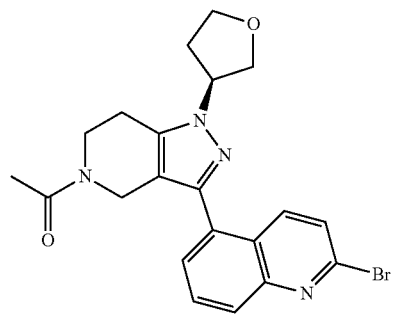

To a solution of (S)-5-(5-acetyl-1-(tetrahydrofuran-3-yl)-4,5,6,7-tetrahydro-1H-pyrazolo[4,3-c]pyridin-3-yl)quinoline 1-oxide (145 mg, 0.4 mmol) and 4 Å molecular sieves in DCM (13 mL) was added tetrabutylammonium bromide (185 mg, 0.6 mmol). The mixture was stirred at room temperature for 10 min and added 4-methylbenzenesulfonic anhydride (187 mg, 0.6 mmol). The mixture was stirred at room temperature for an additional 12 h. The mixture was filtered and concentrated in vacuo. The crude residue was purified by silica gel chromatography (DCM/MeOH=20:1) to give the mixture of title compounds (85 mg, 42%) as a yellow solid. LCMS M/Z (M+H) 441.

Step 4: (S)-1-(3-(3-(1-methyl-1H-pyrazol-4-yl)quinolin-5-yl)-1-(tetrahydrofuran-3-yl)-6,7-dihydro-1H-pyrazolo[4,3-c]pyridin-5(4H)-yl)ethanone and (S)-1-(3-(2-(1-methyl-1H-pyrazol-4-yl)quinolin-5-yl)-1-(tetrahydrofuran-3-yl)-6,7-dihydro-H-pyrazolo[4,3-c]pyridin-5(4H)-yl)ethanone

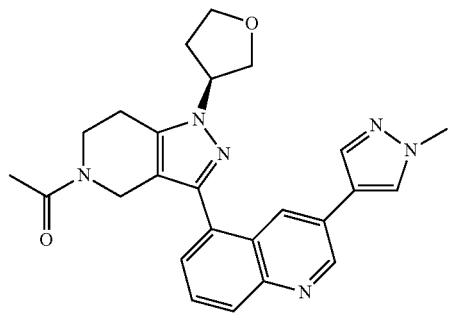

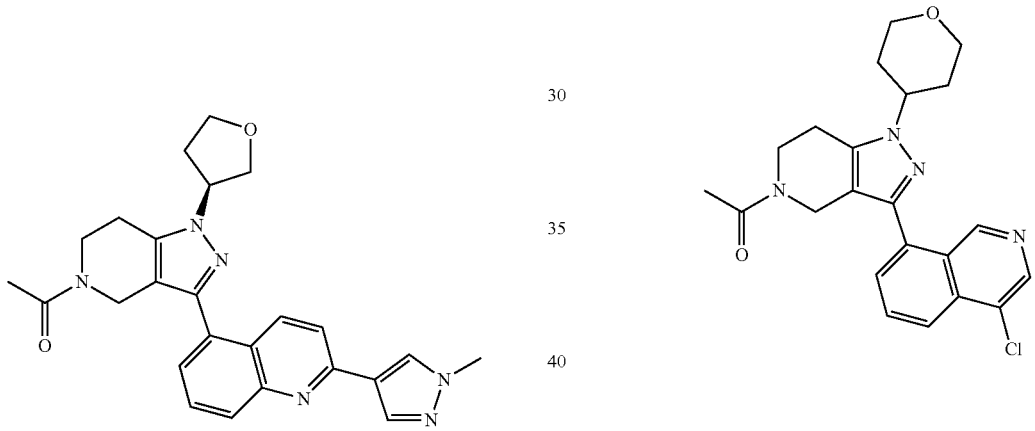

To a solution of (S)-1-(3-(3-bromoquinolin-5-yl)-1-(tetrahydrofuran-3-yl)-6,7-dihydro-1H-pyrazolo[4,3-c]pyridin-5(4H)-yl)ethanone and (S)-1-(3-(2-bromoquinolin-5-yl)-1-(tetrahydrofuran-3-yl)-6,7-dihydro-1H-pyrazolo[4,3-c]pyridin-5(4H)-yl)ethanone (80 mg, 0.15 mmol) in THF (5 mL) and water (1 mL) was added 1-methyl-4-(4,4,5,5-tetramethyl-1,3,2-dioxaborolan-2-yl)-1H-pyrazole (31 mg, 0.15 mmol), 2-(dicyclohexylphosphino)-2',4',6'-triisopropylbiphenyl (7 mg, 0.01 mmol) and chloro(2-dicyclohexylphosphino-2',4',6'-tri-i-propyl-1,1'-biphenyl)(2'-amino-1,1'-biphenyl-2-yl) palladium(II) (12 mg, 0.01 mmol), Na$_2$CO$_3$ (32 mg, 0.3 mmol). The mixture was heated to 60° C. for 16 h under a nitrogen atmosphere. After cooling the reaction to room temperature, the mixture was filtered and concentrated in vacuo. The crude residue was purified by reverse phase chromatography (acetonitrile 30-60%/0.1% NH$_4$OH in water) to give the mixture of title compounds (50 mg, 62%) as a white solid which was separated by using chiral SFC (Chiralpak AD 250×30 mm I.D., 5 um; Supercritical CO$_2$/MEOH+NH$_3$/H$_2$O=45/55; 50 ml/min) to give (S)-1-(3-(3-(1-methyl-1H-pyrazol-4-yl)quinolin-5-yl)-1-(tetrahydrofuran-3-yl)-6,7-dihydro-1H-pyrazolo[4,3-c]pyridin-5 (4H)-yl)etanone (5 mg, first peak) and (S)-1-(3-(2-(1-methyl-1H-pyrazol-4-yl)quinolin-5-yl)-1-(tetrahydrofuran-3-yl)-6,7-dihydro-1H-pyrazolo[4,3-c]pyridin-5(4H)-yl) ethanone (21 mg, second peak). Example 26: $^1$H NMR (400 MHz, DMSO-d$_6$) δ 9.21 (s, 1H), 9.10 (s, 1H), 8.36 (s, 1H), 8.02-7.95 (m, 1H), 7.99 (s, 1H), 7.78-7.73 (m, 1H), 7.63-7.55 (m, 1H), 5.12-5.07 (m, 1H), 4.62-4.50 (m, 2H), 4.12-4.00 (m, 3H), 3.92-3.76 (m, 3H), 3.90 (s, 1H), 2.97-2.84 (m, 2H), 2.44-2.39 (m, 2H), 2.11-2.00 (m, 3H). LCMS M/Z (M+H) 443. Example 27: $^1$H NMR (400 MHz, DMSO-d$_6$) δ 8.79 (d, J=8.8 Hz, 1H), 8.49 (s, 1H), 8.18 (s, 1H), 7.96-7.91 (m, 1H), 7.86 (d, J=8.8 Hz, 1H), 7.80-7.75 (m, 1H), 7.56-7.46 (m, 1H), 5.09-5.03 (m, 1H), 4.50 (s, 2H), 4.12-4.01 (m, 2H), 3.97-3.79 (m, 4H), 3.93 (s, 3H), 2.95-2.82 (m, 2H), 2.42-2.35 (m, 2H), 2.10-2.00 (m, 3H). LCMS M/Z (M+H) 443.

Example 28

1-(3-(4-chloroisoquinolin-8-yl)-1-(tetrahydro-2H-pyran-4-yl)-6,7-dihydro-1H-pyrazolo[4,3-c]pyridin-5(4H)-yl)ethanone Step 1: 8-bromo-4-chloroisoquinoline

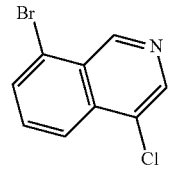 [SMILES: Clc1cncc2c(Br)cccc12]

To a solution of 8-bromoisoquinoline (12.2 g, 58.64 mmol) in AcOH (150 mL) was added 1-chloropyrrolidine-2,5-dione (8.61 g, 64.5 mmol) portionwise. The mixture was heated to 117° C. for 2 h under a nitrogen atmosphere. After cooling the reaction to room temperature, water (150 mL) was added and extracted with EtOAc (150 mL×3). The combined organic layers were washed with sat. aq. NaHCO$_3$ (150 mL×3), dried over anhydrous Na$_2$SO$_4$, filtered and concentrated in vacuo to give the title compound (10.0 g, crude) as a yellow solid that required no further purification. LCMS M/Z (M+H) 242.

Step 2: 4-chloro-8-(4,4,5,5-tetramethyl-1,3,2-dioxaborolan-2-yl)isoquinoline

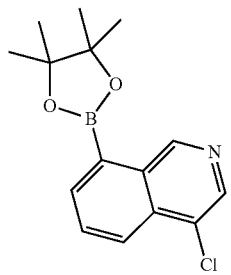 [SMILES: CC1(C)OB(c2cccc3c(Cl)cncc23)OC1(C)C]

To a solution of 8-bromo-4-chloroisoquinoline (500 mg, 2.06 mmol) in 1,4-dioxane (8 mL) was added [1,1'-bis(diphenylphosphino)ferrocene]dichloropalladium(II) (151 mg, 0.21 mmol), KOAc (607 mg, 6.19 mmol) and 4,4,4',4',5,5,5',5'-octamethyl-2,2'-bi(1,3,2-dioxaborolane) (785 mg, 3.09 mmol). The mixture was heated to 80° C. for 4 h under a nitrogen atmosphere. After cooling the reaction to room temperature, the reaction mixture was used to the next step directly without further purification. LCMS M/Z (M+H) 290.

Step 3: 1-(3-(4-chloroisoquinolin-8-yl)-1-(tetrahydro-2H-pyran-4-yl)-6,7-dihydro-1H-pyrazolo[4,3-c]pyridin-5(4H)-yl)ethanone

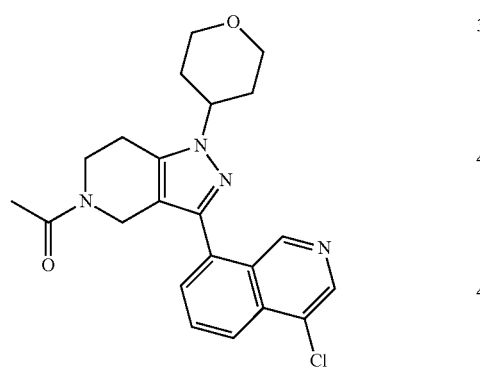

To the above step cooled solution was added 1-(3-bromo-1-(tetrahydro-2H-pyran-4-yl)-6,7-dihydro-1H-pyrazolo[4,3-c]pyridin-5(4H)-yl)ethanone (Intermediate H, 541 mg, 1.65 mmol), [1,1'-bis(diphenylphosphino)ferrocene]dichloropalladium(II) (75 mg, 0.1 mmol) and Na$_2$CO$_3$ (656 mg, 6.19 mmol), 1,4-dioxane (2 mL) and water (2 mL). The reaction mixture was heated to 65° C. for 2 h under nitrogen atmosphere. After cooling to room temperature, the mixture was filtered and concentrated in vacuo. The crude residue was purified by reverse phase chromatography (acetonitrile 20-50%/0.2% formic acid in water) to give the title compound (65 mg, 7%) as a white solid. $^1$H NMR (400 MHz, CDCl$_3$) δ 9.62-9.58 (m, 1H), 8.64-8.60 (m, 1H), 8.29-8.25 (m, 1H), 7.90-7.85 (m, 1H), 7.68-7.63 (m, 1H), 4.62-4.45 (m, 2H), 4.35-4.24 (m, 1H), 4.23-4.13 (m, 2H), 4.06-3.81 (m, 2H), 3.57 (t, J=12.0 Hz, 2H), 2.95-2.85 (m, 2H), 2.44-2.41 (m, 2H), 2.21-2.08 (m, 3H), 1.98-1.94 (m, 2H). LCMS M/Z M+H 411.

Example 29

1-(3-(5-fluoroisoquinolin-8-yl)-1-(tetrahydro-2H-pyran-4-yl)-6,7-dihydro-1H-pyrazolo[4,3-c]pyridin-5(4H)-yl)ethanone

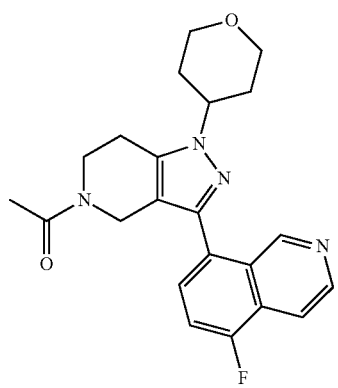 [SMILES: CC(=O)N1CCc2c(c(-c3ccc(F)c4ccncc34)nn2C2CCOCC2)C1]

Step 1: 5-(benzyloxy)isoquinoline

To a stirred solution of isoquinolin-5-ol (1.0 g, 6.89 mmol) in DMF (30 mL) at 0° C. was added NaH (60%, 303 mg, 7.58 mmol) and the mixture was stirred for 30 min. Benzyl bromide (1.0 g, 5.86 mmol) was added dropwise and the mixture stirred for an additional 1 h. The mixture was quenched with water (100 mL) and extracted with EtOAc (50 mL×3). The combined organic layers were washed with brine (50 mL×3), dried over anhydrous Na$_2$SO$_4$, filtered and concentrated in vacuo to give the title compound (900 mg, crude) as yellow oil that required no further purification. LCMS M/Z (M+H) 236.

Step 2: 5-(benzyloxy)-8-bromoisoquinoline

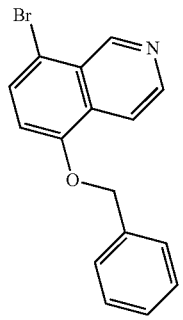 [SMILES: Brc1ccc(OCc2ccccc2)c2ccncc12]

To a solution of 5-(benzyloxy)isoquinoline (1.3 g, 5.53 mmol) and NaOAc (906 mg, 11.05 mmol) in AcOH (50 mL) at 26° C. was added bromine (0.28 mL, 5.53 mmol) dropwise. The mixture was stirred at 26° C. for 16 h. Water (100 mL) was added and extracted with EtOAc (70 mL×3). The combined organic layers were washed with sat. aq. NaHCO$_3$ (100 mL×2), dried over anhydrous Na$_2$SO$_4$, filtered and concentrated in vacuo. The crude residue was purified by silica gel chromatography (petroleum ether/EtOAc=4:1) to give the title compound (300 mg, 17%) as a white solid. LCMS M/Z (M+H) 314.

Step 3: 1-(1-(tetrahydro-2H-pyran-4-yl)-3-(4,4,5,5-tetramethyl-1,3,2-dioxaborolan-2-yl)-6,7-dihydro-1H-pyrazolo[4,3-c]pyridin-5(4H)-yl)ethanone

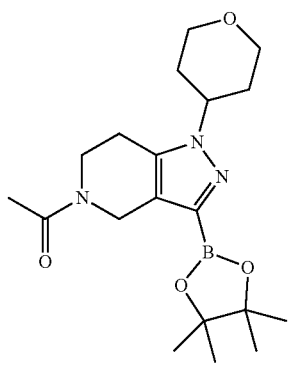 [SMILES: CC(=O)N1CCc2c(c(B3OC(C)(C)C(C)(C)O3)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 2.3 g, 7.0 mmol) in 1,4-dioxane (40 mL) was added 2-(dicyclohexylphosphino)-2',4',6'-triisopropylbiphenyl (200 mg, 0.42 mmol), chloro(2-dicyclohexylphosphino-2',4',6'-tri-i-propyl-1,1'-biphenyl)(2'-amino-1,1'-biphenyl-2-yl) palladium(II) (165 mg, 0.21 mmol), KOAc (2.0 g, 21.0 mmol) and 4,4,4',4',5,5,5',5'-octamethyl-2,2'-bi(1,3,2-dioxaborolane) (3.56 g, 14.0 mmol). The mixture was heated to 80° C. for 3 h under a nitrogen atmosphere. After cooling the reaction to room temperature, the reaction mixture was used to the next step directly without further purification. LCMS M/Z (M+H) 376.

Step 4: 1-(3-(5-(benzyloxy)isoquinolin-8-yl)-1-(tetrahydro-2H-pyran-4-yl)-6,7-dihydro-1H-pyrazolo[4,3-c]pyridin-5(4H)-yl)ethanone

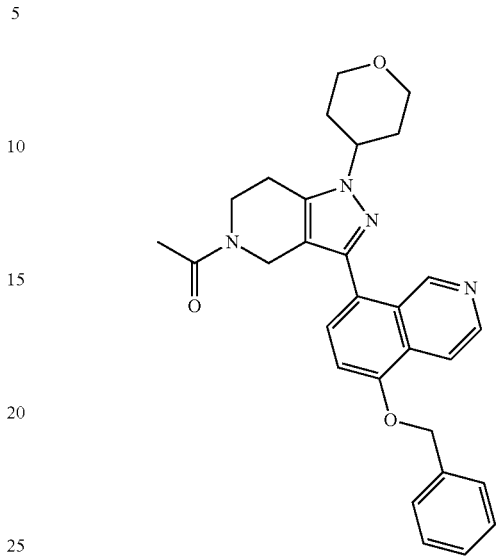

To the above step cooled solution was added 5-(benzyloxy)-8-bromoisoquinoline (1.1 g, 3.5 mmol), chloro(2-dicyclohexylphosphino-2',4',6'-tri-i-propyl-1,1'-biphenyl)(2'-amino-1,1'-biphenyl-2-yl) palladium(II) (185 mg, 0.24 mmol), K$_3$PO$_4$ (1.98 g, 9.3 mmol), 1,4-dioxane (10 mL) and water (10 mL). The reaction mixture was heated to 90° C. for 1 h under a nitrogen atmosphere. After cooling to room temperature, the mixture was filtered and concentrated in vacuo. Water (100 mL) was added and extracted with EtOAc (50 mL×3). The combined organic layers were washed with brine (50 mL×3), dried over anhydrous Na$_2$SO$_4$, filtered and concentrated in vacuo. The crude residue was purified by silica gel chromatography (DCM/MeOH=20:1) to give the title compound (1 g, 30%) as a brown solid. LCMS M/Z (M+H) 483.

Step 5: 1-(3-(5-hydroxyisoquinolin-8-yl)-1-(tetrahydro-2H-pyran-4-yl)-6,7-dihydro-1H-pyrazolo[4,3-c]pyridin-5(4H)-yl)ethanone

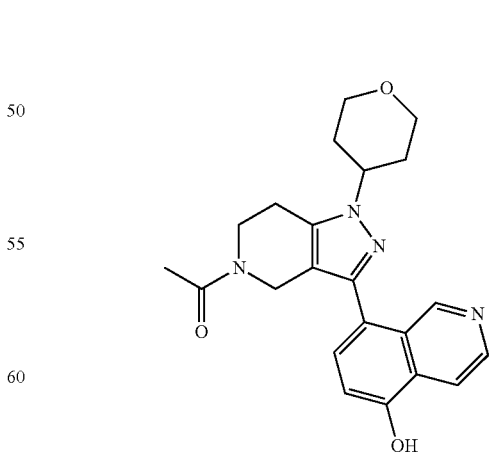

To a solution of 1-(3-(5-(benzyloxy)isoquinolin-8-yl)-1-(tetrahydro-2H-pyran-4-yl)-6,7-dihydro-1H-pyrazolo[4,3-c]pyridin-5(4H)-yl)ethanone (1.0 g, 2.07 mmol) in MeOH (20 mL) was added Pd(OH)$_2$ (100 mg) and AcOH (2 drops). The mixture was stirred at 26° C. for 5 h under a hydrogen atmosphere (15 Psi). The mixture was filtered and concentrated in vacuo. The crude residue was purified by Prep-TLC (DCM/MeOH=20:1) to give the title compound (400 mg, 49%) as a yellow solid. LCMS M/Z (M+H) 393.

Step 6: 1-(3-(5-fluoroisoquinolin-8-yl)-1-(tetrahydro-2H-pyran-4-yl)-6,7-dihydro-1H-pyrazolo[4,3-c]pyridin-5(4H)-yl)ethanone

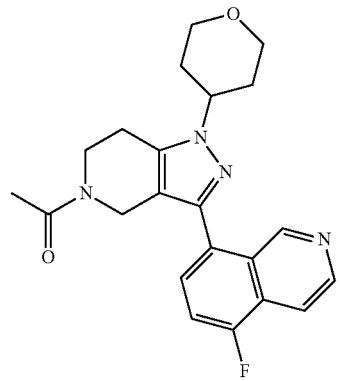 [SMILES: CC(=O)N1CCc2c(c(-c3ccc(F)c4ccncc34)nn2C2CCOCC2)C1]

To a solution of 1-(3-(5-hydroxyisoquinolin-8-yl)-1-(tetrahydro-2H-pyran-4-yl)-6,7-dihydro-1H-pyrazolo[4,3-c]pyridin-5(4H)-yl)ethanone (260 mg, 0.66 mmol) in toluene (7 mL) was added 1,3-bis(2,6-di-i-propylphenyl)-2-chloroimidazolium chloride/cesium fluoride admixture (1.69 g, 2.76 mmol). The mixture was stirred at 26° C. for 0.5 h and then heated to 110° C. for 24 h under a nitrogen atmosphere. After cooling to room temperature, the mixture was filtered and concentrated in vacuo. The crude residue was purified by Prep-TLC (DCM/MeOH=20:1) to give the title compound (3 mg, 1%) as a yellow solid. $^1$H NMR (400 MHz, CDCl$_3$) δ 9.71-9.67 (m, 1H), 8.67-8.53 (m, 1H), 7.96-7.94 (m, 1H), 7.54-7.47 (m, 1H), 7.46-7.35 (m, 1H), 4.61-4.44 (m, 2H), 4.33-4.22 (m, 1H), 4.21-4.12 (m, 2H), 4.02-3.83 (m, 2H), 3.60-3.53 (m, 2H), 2.93-2.84 (m, 2H), 2.44-2.40 (m, 2H), 2.21-2.07 (m, 3H), 1.98-1.94 (m, 2H). LCMS M/Z (M+H) 395.

Example 30

1-(3-(6-chloro-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

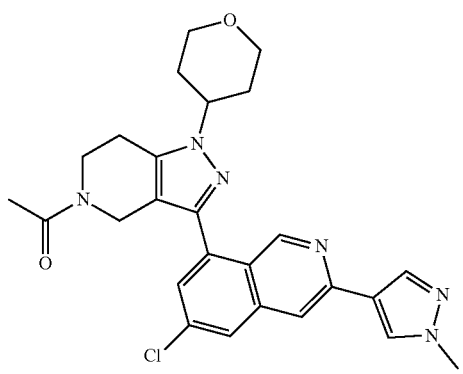 [SMILES: CC(=O)N1CCc2c(c(-c3cc(Cl)cc4cc(-c5cnn(C)c5)ncc34)nn2C2CCOCC2)C1]

Step 1: (2-bromo-4-chlorophenyl)methanamine

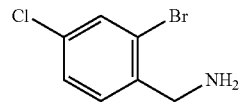

To a stirred solution of 2-bromo-4-chlorobenzonitrile (20.0 g, 138.6 mmol) in anhydrous THF (200 mL) at 0° C. was added borane (277 mL, 277.2 mmol, 1.0 M) in THF dropwise under a nitrogen atmosphere. The resulting mixture was stirred at 22° C. for 1 h and refluxed for 3 h. The reaction was quenched with 2N HCl (300 mL) at 0° C. and then stirred at 70° C. for 1 h. After cooling to room temperature, the solution was extracted with DCM (400 mL) and the aqueous phase was adjusted to pH=8 by using 2N NaOH. The mixture was extracted with DCM (300 mL×3). The organic layer was dried over anhydrous Na$_2$SO$_4$ and concentrated in vacuo to give the title compound (12 g, 59%) as yellow oil. $^1$H NMR (400 MHz, CDCl$_3$) δ 7.55-7.53 (m, 1H), 7.34-7.29 (m, 1H), 7.28-7.23 (m, 1H), 3.86 (s, 2H).

Step 2: N-(2-bromo-4-chlorobenzyl)-2,2-dimethoxyacetamide

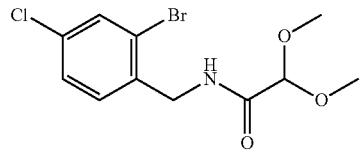 [SMILES: COC(OC)C(=O)NCc1ccc(Cl)cc1Br]

To a solution of (2-bromo-4-chloro-phenyl)methanamine (12 g, 54.4 mmol) in MeOH (80 mL) was added triethylamine (9.5 mL, 68.0 mmol) and methyl dimethoxyacetate (8.0 g, 49.9 mmol). The mixture was heated to 80° C. for 20 h. After cooling to room temperature, the mixture was concentrated in vacuo. The crude residue was dissolved in EtOAc (150 mL), washed with 1N HCl (150 mL), H$_2$O (150 mL), brine (150 mL). The organic phase was dried over anhydrous Na$_2$SO$_4$, filtered and concentrated in vacuo to give the title compound (12 g, 68%) as a light yellow solid. $^1$H-NMR (400 MHz, CDCl$_3$) δ 7.58 (d, J=1.6 Hz, 1H), 7.33 (d, J=8.4 Hz, 1H), 7.29-7.27 (m, 1H), 7.03 (s, 1H), 4.74 (s, 1H), 4.52 (d, J=6.4 Hz, 2H), 3.41 (s, 6H).

Step 3: 8-bromo-6-chloroisoquinolin-3(2H)-one

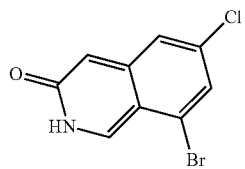 [SMILES: O=c1cc2cc(Cl)cc(Br)c2c[nH]1]

To a solution of sulfuric acid (100 mL) at 0° C. was added N-(2-bromo-4-chlorobenzyl)-2,2-dimethoxyacetamide (12.0 g, 37.2 mmol). The reaction was heated to 50° C. for 16 h. The reaction was poured into ice water (150 mL) and the mixture was basified with ammonium hydroxide to pH 8. The yellow precipitate was filtered off, washed with water, and dried in vacuo. The crude residue was purified by silica gel chromatography (DCM/MeOH=10:1) to give the title compound (3.7 g, 39%) as a yellow solid. $^1$H-NMR (400 MHz, DMSO-d$_6$) δ 9.10 (s, 1H), 7.93 (s, 1H), 7.69 (d, J=2.0 Hz, 1H), 6.94 (s, 1H).

Step 4: 8-bromo-6-chloro-3-((triisopropylsilyl)oxy)isoquinoline

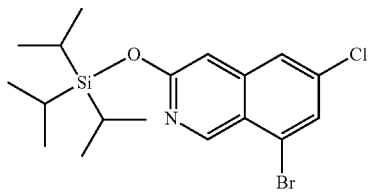 [SMILES: CC(C)[Si](Oc1cc2cc(Cl)cc(Br)c2cn1)(C(C)C)C(C)C]

To a solution of 8-bromo-6-chloroisoquinolin-3(2H)-one (10 g, 38.7 mmol) in DMF (30 mL) at 0° C. was added imidazole (7.9 g, 116.1 mmol) and chlorotriisopropylsilane (12.4 mL, 58.0 mmol). The reaction was stirred at room temperature for 12 h. The reaction mixture was concentrated in vacuo. The crude residue was dissolved in DCM (50 mL) and washed with H$_2$O (50 mL). The organic layer was dried over anhydrous Na$_2$SO$_4$, filtered and concentrated in vacuo. The crude residue was purified by silica gel chromatography (petroleum ether) to give the title compound (10 g, 62%) as yellow oil. $^1$H-NMR (400 MHz, CDCl$_3$) δ 9.15 (s, 1H), 7.59 (s, 1H), 7.54 (s, 1H), 6.88 (s, 1H), 1.51-1.40 (m, 3H), 1.12 (d, J=7.2 Hz, 18H).

Step 5: 6-chloro-8-(4,4,5,5-tetramethyl-1,3,2-dioxaborolan-2-yl)-3-((triisopropylsilyl)oxy)isoquinoline

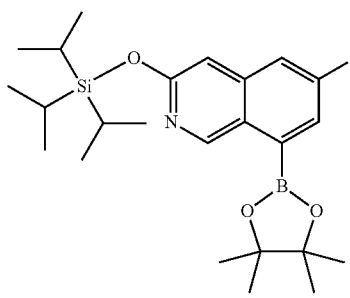

To a solution of 8-bromo-6-chloro-3-((triisopropylsilyl)oxy)isoquinoline (9.0 g, 21.7 mmol) in 1,4-dioxane (9 mL) was added [1,1'-bis(diphenylphosphino)ferrocene]-dichloropalladium(II) (1.6 g, 2.2 mmol), 4,4,4',4',5,5,5',5'-octamethyl-2,2'-bi(1,3,2-dioxaborolane) (8.3 g, 32.5 mmol) and 2-ethylhexanoyloxypotassium (11.9 g, 65.1 mmol). The mixture was heated to 70° C. for 1 h under a nitrogen atmosphere. After cooling the reaction to room temperature, the reaction mixture was used to the next step directly without further purification. LCMS M/Z (M-TIPS+H) 306.

Step 6: 1-(3-(6-chloro-3-((triisopropylsilyl)oxy)isoquinolin-8-yl)-1-(tetrahydro-2H-pyran-4-yl)-6,7-dihydro-1H-pyrazolo[4,3-c]pyridin-5(4H)-yl)ethanone

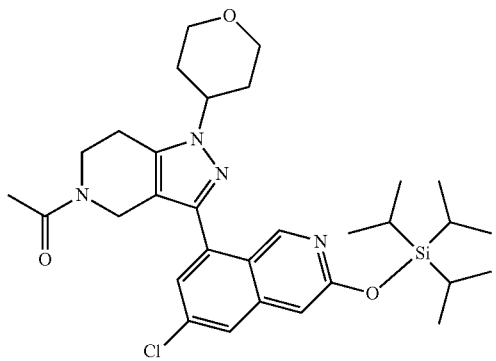 [SMILES: CC(=O)N1CCc2c(c(-c3cc(Cl)cc4cc(O[Si](C(C)C)(C(C)C)C(C)C)ncc34)nn2C2CCOCC2)C1]

To the above step cooled solution in 1,4-dioxane (60 mL) and water (12 mL) was added 1-(3-bromo-1-(tetrahydro-2H-pyran-4-yl)-6,7-dihydro-1H-pyrazolo[4,3-c]pyridin-5(4H)-yl)ethanone (Intermediate H, 6.39 g, 19.49 mmol), [1,1'-bis(diphenylphosphino)ferrocene]-dichloropalladium(II) (1.58 g, 2.16 mmol) and Na$_2$CO$_3$ (6.8 g, 64.9 mmol). The reaction mixture was heated to 70° C. for 4 h under nitrogen atmosphere. After cooling to room temperature, the mixture was filtered and concentrated in vacuo. EtOAc (200 mL) was added and washed with water (120 mL×2). The organic layer was dried over anhydrous Na$_2$SO$_4$, filtered and concentrated in vacuo. The crude residue was purified by silica gel chromatography (DCM/MeOH=10:1) to give the title compound (2.6 g, 38% purity) as a brown solid. LCMS M/Z (M-TIPS+H) 427.

Step 7: 1-(3-(6-chloro-3-hydroxyisoquinolin-8-yl)-1-(tetrahydro-2H-pyran-4-yl)-6,7-dihydro-1H-pyrazolo[4,3-c]pyridin-5(4H)-yl)ethanone

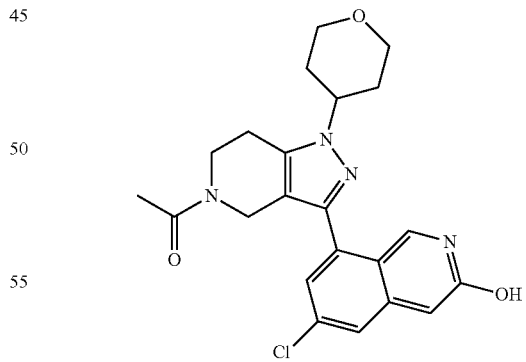

To a solution of 1-(3-(6-chloro-3-((triisopropylsilyl)oxy)isoquinolin-8-yl)-1-(tetrahydro-2H-pyran-4-yl)-6,7-dihydro-1H-pyrazolo[4,3-c]pyridin-5(4H)-yl)ethanone (2.6 g, 38% purity) in THF (10 mL) at 20° C. was added TBAF (22.3 ml, 22.3 mmol, 1 M in THF). The reaction was stirred at room temperature for 12 h. The reaction mixture was concentrated in vacuo. The crude residue was dissolved in DCM (50 mL) and washed with H$_2$O (150 mL×2). The organic layer was dried over anhydrous Na$_2$SO$_4$, filtered and concentrated in vacuo. The crude residue was purified by reverse phase chromatography (acetonitrile 10-40%/0.225% formic acid in water) to give the title compound (120 mg). LCMS M/Z (M+H) 427.

Step 8: 8-(5-acetyl-1-(tetrahydro-2H-pyran-4-yl)-4,5,6,7-tetrahydro-1H-pyrazolo[4,3-c]pyridin-3-yl)-6-chloroisoquinolin-3-yl trifluoromethanesulfonate

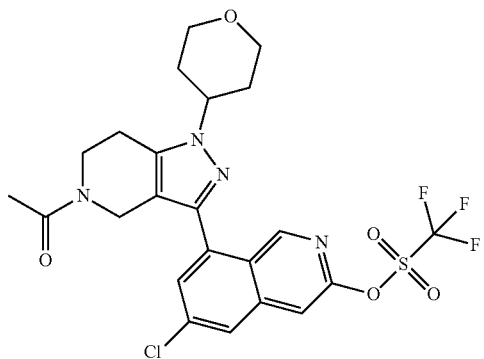 [SMILES: CC(=O)N1CCc2c(c(-c3cc(Cl)cc4cc(OS(=O)(=O)C(F)(F)F)ncc34)nn2C2CCOCC2)C1]

To a solution of 1-(3-(6-chloro-3-hydroxyisoquinolin-8-yl)-1-(tetrahydro-2H-pyran-4-yl)-6,7-dihydro-1H-pyrazolo[4,3-c]pyridin-5(4H)-yl)ethanone (120 mg, 0.28 mmol) in DCM (3 mL) at 0° C. was added triethylamine (0.12 mL, 0.84 mmol) and trifluoromethanesulfonic anhydride (0.06 mL, 0.37 mmol). The reaction was stirred at room temperature for 16 h. DCM (30 mL) was added and washed with water (30 mL×2). The organic layer was dried over anhydrous Na$_2$SO$_4$, filtered and concentrated in vacuo to give the title compound (157 mg, crude) as a brown solid that required no further purification. LCMS M/Z (M+H) 559.

Step 9: 1-(3-(6-chloro-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

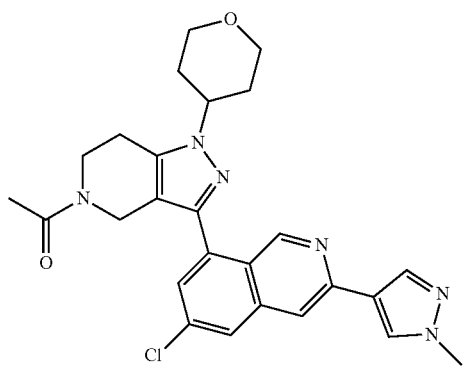 [SMILES: CC(=O)N1CCc2c(c(-c3cc(Cl)cc4cc(-c5cnn(C)c5)ncc34)nn2C2CCOCC2)C1]

To a solution of 8-(5-acetyl-1-(tetrahydro-2H-pyran-4-yl)-4,5,6,7-tetrahydro-1H-pyrazolo[4,3-c]pyridin-3-yl)-6-chloroisoquinolin-3-yl trifluoromethanesulfonate (600 mg, crude) in 1,4-dioxane (10 mL) and water (2 mL) was added [1,1'-bis(diphenylphosphino)-ferrocene]dichloropalladium (II) (79 mg, 0.11 mmol), Na$_2$CO$_3$ (341 mg, 3.21 mmol) and 1-methyl-4-(4,4,5,5-tetramethyl-1,3,2-dioxaborolan-2-yl)-1H-pyrazole (223 mg, 1.07 mmol). The mixture was irradiated in a microwave at 60° C. for 0.5 h. EtOAc (50 mL) was added and washed with water (40 mL), brine (40 mL). The organic layer was dried over anhydrous Na$_2$SO$_4$, filtered and concentrated in vacuo. The crude residue was purified by reverse phase chromatography (acetonitrile 20-50%/0.05% NH$_4$OH in water) to give the title compound (10 mg) as a white solid. $^1$H NMR (400 MHz, CDCl$_3$) δ 9.60 (s, 1H), 8.13-7.93 (m, 2H), 7.79-7.73 (m, 2H), 7.43-7.40 (m, 1H), 4.65-4.49 (m, 2H), 4.33-4.23 (m, 1H), 4.18-4.16 (m, 2H), 4.01-3.83 (m, 2H), 4.00 (s, 3H), 3.60-3.54 (m, 2H), 2.93-2.86 (m, 2H), 2.44-2.41 (m, 2H), 2.21-2.10 (m, 3H), 1.97-1.94 (m, 2H). LCMS M/Z (M+H) 491.

Example 31

1-(3-(6-ethyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

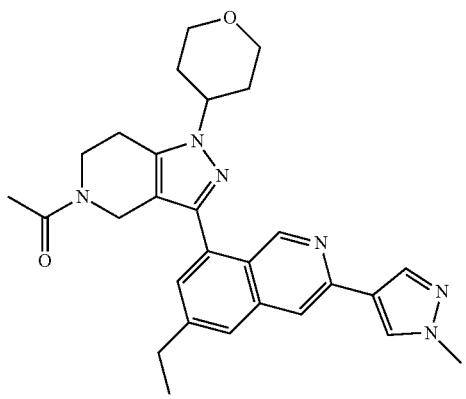 [SMILES: CCc1cc(-c2nn(C3CCOCC3)c3c2CN(C(C)=O)CC3)c2cnc(-c3cnn(C)c3)cc2c1]

Step 1: 1-(3-(3-(1-methyl-1H-pyrazol-4-yl)-6-vinylisoquinolin-8-yl)-1-(tetrahydro-2H-pyran-4-yl)-6,7-dihydro-1H-pyrazolo[4,3-c]pyridin-5(4H)-yl)ethanone

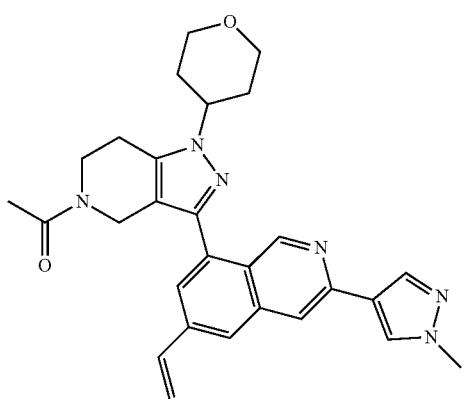 [SMILES: C=Cc1cc(-c2nn(C3CCOCC3)c3c2CN(C(C)=O)CC3)c2cnc(-c3cnn(C)c3)cc2c1]

To a solution of 1-(3-(6-chloro-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5 (4H)-yl)ethanone (Example 30, 110 mg, 0.22 mmol) in THF (3 mL) and water (0.6 mL) was added 2-(dicyclohexylphosphino)-2',4',6'-triisopropylbiphenyl (10 mg, 0.02 mmol) and chloro(2-dicyclohexylphosphino-2',4',6'-tri-i-propyl-1,1'-biphenyl)(2'-amino-1,1'-biphenyl-2-yl) palladium(II) (16 mg, 0.02 mmol), Na₂CO₃ (71 mg, 0.67 mmol) and 4,4,5,5-tetramethyl-2-vinyl-1,3,2-dioxaborolane (345 mg, 2.24 mmol). The mixture was irradiated in a microwave at 60° C. for 0.5 h. EtOAc (50 mL) was added and extracted with water (40 mL), brine (40 mL). The organic layer was dried over anhydrous Na₂SO₄, filtered and concentrated in vacuo. The crude residue was purified by silica gel chromatography (DCM/MeOH=10:1) to give the title compound (70 mg, 65%) as a brown solid. LCMS M/Z (M+H) 483.

Step 2: 1-(3-(6-ethyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

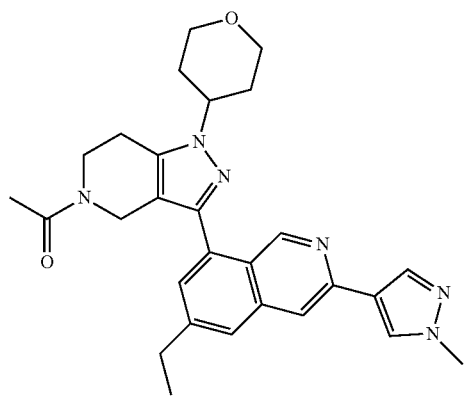 [SMILES: CCc1cc(-c2nn(C3CCOCC3)c3c2CN(C(C)=O)CC3)c2cnc(-c3cnn(C)c3)cc2c1]

To a solution of 1-(3-(3-(1-methyl-1H-pyrazol-4-yl)-6-vinylisoquinolin-8-yl)-1-(tetrahydro-2H-pyran-4-yl)-6,7-dihydro-1H-pyrazolo[4,3-c]pyridin-5(4H)-yl)ethanone (70 mg, 0.15 mmol) in MeOH (5 mL) was added 10% Pd/C (50 mg). The mixture was stirred at room temperature for 1 h under a hydrogen atmosphere (15 Psi). The mixture was filtered and the filtrate was concentrated in vacuo. The crude residue was purified by Prep-TLC (DCM/MeOH=10:1) to give the title compound (6 mg, 9%) as a yellow solid. ¹H NMR (400 MHz, CDCl₃) δ 9.54-9.50 (m, 1H), 8.05-8.02 (m, 2H), 7.78-7.75 (m, 1H), 7.60-7.56 (m, 1H), 7.36-7.34 (m, 1H), 4.66-4.43 (m, 2H), 4.33-4.23 (m, 1H), 4.21-4.12 (m, 2H), 4.04-3.81 (m, 2H), 4.00 (s, 3H), 3.60-3.54 (m, 2H), 2.94-2.81 (m, 4H), 2.53-2.38 (m, 2H), 2.22-2.05 (m, 3H), 1.97-1.94 (m, 2H), 1.40-1.34 (m, 3H). LCMS M/Z (M+H) 485.

Example 32

8-(5-acetyl-1-(tetrahydro-2H-pyran-4-yl)-4,5,6,7-tetrahydro-1H-pyrazolo[4,3-c]pyridin-3-yl)-3-(1-methyl-1H-pyrazol-4-yl)isoquinoline-4-carbonitrile

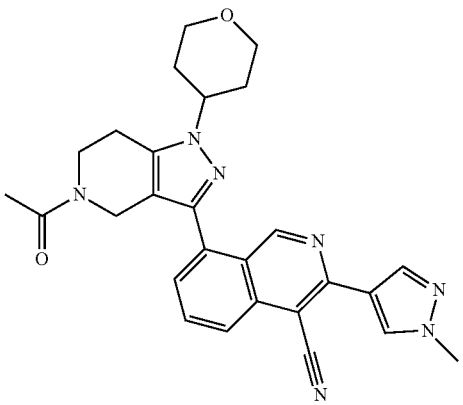 [SMILES: CC(=O)N1CCc2c(c(-c3cccc4c(C#N)c(-c5cnn(C)c5)ncc34)nn2C2CCOCC2)C1]

Step 1: 2-chloro-6-((1-methyl-1H-pyrazol-4-yl)ethynyl)benzaldehyde

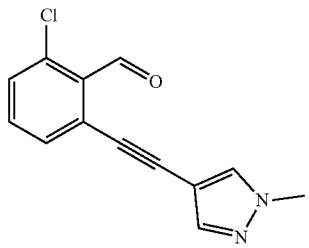 [SMILES: Cn1cc(C#Cc2cccc(Cl)c2C=O)cn1]

a solution of 2-bromo-6-chlorobenzaldehyde (13 g, 59.2 mmol) in triethylamine (650 mL) was added bis(triphenylphosphine)palladium(II) dichloride (2.1 g, 3.0 mmol) and 4-ethynyl-1-methyl-1H-pyrazole (10.4 g, 98 mmol) and copper(I) iodide (650 mg, 3.4 mmol). The mixture was heated to 80° C. for 16 h under a nitrogen atmosphere. After cooling the reaction to room temperature, the mixture was filtered and concentrated in vacuo. The crude residue was purified by silica gel chromatography (petroleum ether/EtOAc=5:1) to give the title compound (6.9 g, 48%) as a yellow solid. ¹H NMR (400 MHz, CDCl₃) δ 10.52 (s, 1H), 7.58 (s, 1H), 7.53 (s, 1H), 7.40 (d, J=7.2 Hz, 1H), 7.35-7.24 (m, 2H), 3.82 (s, 3H). LCMS M/Z (M+H) 245.

Step 2: (2-chloro-6-((1-methyl-1H-pyrazol-4-yl)ethynyl)phenyl)methanol

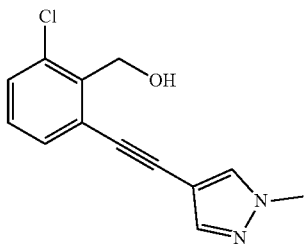 [SMILES: Cn1cc(C#Cc2cccc(Cl)c2CO)cn1]

To a solution of 2-chloro-6-((1-methyl-1H-pyrazol-4-yl)ethynyl)benzaldehyde (6.9 g, 28.2 mmol) in MeOH (60 mL) at 0° C. was added sodium borohydride (1.7 g, 43.9 mmol) portionwise. The mixture was stirred at room temperature for 2 h under a nitrogen atmosphere. The reaction was concentrated in vacuo. Water (50 mL) was added and extracted with EtOAc (50 mL×3). The combined organic layers were dried over anhydrous $Na_2SO_4$, filtered and concentrated in vacuo to give the title compound (8.2 g, crude) as a yellow solid that required no further purification. $^1$H NMR (400 MHz, CDCl$_3$) δ 7.65 (s, 1H), 7.58 (s, 1H), 7.41 (d, J=7.2 Hz, 1H), 7.34 (d, J=8.0 Hz, 1H), 7.23-7.19 (m, 1H), 5.01 (d, J=6.0 Hz, 2H), 3.90 (s, 3H), 2.51 (t, J=6.4 Hz, 1H). LCMS M/Z (M+H) 247.

Step 3: 4-((2-(azidomethyl)-3-chlorophenyl)ethynyl)-1-methyl-1H-pyrazole

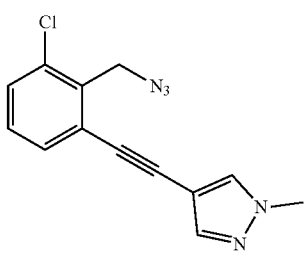 [SMILES: Cn1cc(C#Cc2cccc(Cl)c2CN=[N+]=[N-])cn1]

To a solution of (2-chloro-6-((1-methyl-1H-pyrazol-4-yl)ethynyl)phenyl)methanol (7.2 g, 29 mmol) in toluene (80 mL) was added diphenylphosphoryl azide (9.6 g, 34.8 mmol) and 1,8-diazabicyclo[5.4.0]undec-7-ene (5.7 g, 37.6 mmol). The mixture was stirred at room temperature for 16 h under a nitrogen atmosphere. DCM (30 mL) was added and washed with water (30 mL×2). The organic phase was dried over anhydrous $Na_2SO_4$, filtered and concentrated in vacuo to give the title compound (9 g, crude) as yellow oil that required no further purification. $^1$H NMR (400 MHz, DMSO-d$_6$) δ 8.13 (s, 1H), 7.74 (s, 1H), 7.62-7.52 (m, 1H), 7.46-7.38 (m, 1H), 7.28-7.10 (m, 1H), 4.73 (s, 2H), 3.87 (s, 3H). LCMS M/Z (M+H) 272.

Step 4: 8-chloro-4-iodo-3-(1-methyl-1H-pyrazol-4-yl)isoquinoline

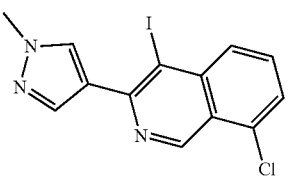

To a solution of 4-((2-(azidomethyl)-3-chlorophenyl)ethynyl)-1-methyl-1H-pyrazole (7.9 g, 28.9 mmol) in DCM (500 mL) was added iodine (36.8 g, 144.9 mmol) and $K_3PO_4$ (30.8 g, 145 mmol). The mixture was stirred at room temperature for 24 h under a nitrogen atmosphere and washed with water (400 mL×2). The organic phase was dried over anhydrous $Na_2SO_4$, filtered and concentrated in vacuo. The crude residue was purified by silica gel chromatography (petroleum ether/EtOAc=1:1) to give the title compound (10 g, 94%) as a brown solid. $^1$H NMR (400 MHz, DMSO-d$_6$) δ 9.43 (s, 1H), 8.47 (s, 1H), 8.18-8.15 (m, 2H), 7.90-1.86 (m, 2H), 3.95 (s, 3H). LCMS M/Z (M+H) 370.

Step 5: 8-chloro-3-(1-methyl-1H-pyrazol-4-yl)isoquinoline-4-carbonitrile

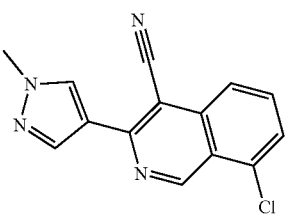 [SMILES: Cn1cc(-c2ncc3c(Cl)cccc3c2C#N)cn1]

To a solution of 8-chloro-4-iodo-3-(1-methylpyrazol-4-yl)isoquinoline (500 mg, 1.35 mmol) in DMF (10 mL) was added copper(I) cyanide (133 mg, 1.49 mmol) and tetrakis(triphenylphosphine)palladium(0) (156 mg, 0.14 mmol). The mixture was heated to 120° C. for 16 h under a nitrogen atmosphere. After cooling the reaction to room temperature, the mixture was filtered and concentrated in vacuo. DCM (50 mL) was added and washed with water (40 mL) and brine (40 mL). The organic phase was dried over anhydrous $Na_2SO_4$, filtered and concentrated in vacuo. The crude residue was purified by silica gel chromatography (petroleum ether/EtOAc=1:1) to give the title compound (300 mg, 83%) as a brown solid. LCMS M/Z (M+H) 269.

Step 6: 3-(1-methyl-1H-pyrazol-4-yl)-8-(4,4,5,5-tetramethyl-1,3,2-dioxaborolan-2-yl)isoquinoline-4-carbonitrile

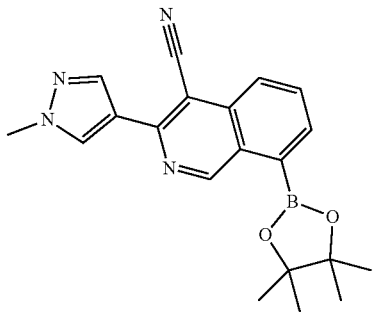

To a solution of 8-chloro-3-(1-methyl-1H-pyrazol-4-yl) isoquinoline-4-carbonitrile (300 mg, 1.12 mmol) in 1,4-dioxane (5 mL) was added 2-(dicyclohexylphosphino)-2',4',6'-triisopropylbiphenyl (52 mg, 0.11 mmol) and chloro(2-dicyclohexylphosphino-2',4',6'-tri-i-propyl-1,1'-biphenyl)(2'-amino-1,1'-biphenyl-2-yl) palladium(II) (87 mg, 0.11 mmol), KOAc (328 mg, 3.35 mmol) and 4,4,4',4',5,5,5',5'-octamethyl-2,2'-bi(1,3,2-dioxaborolane) (850 mg, 3.35 mmol). The mixture was heated to 90° C. for 12 h under a nitrogen atmosphere. After cooling the reaction to room temperature, the reaction mixture was used to the next step directly without further purification.

Step 7: 8-(5-acetyl-1-(tetrahydro-2H-pyran-4-yl)-4,5,6,7-tetrahydro-1H-pyrazolo[4,3-c]pyridin-3-yl)-3-(1-methyl-1H-pyrazol-4-yl)isoquinoline-4-carbonitrile

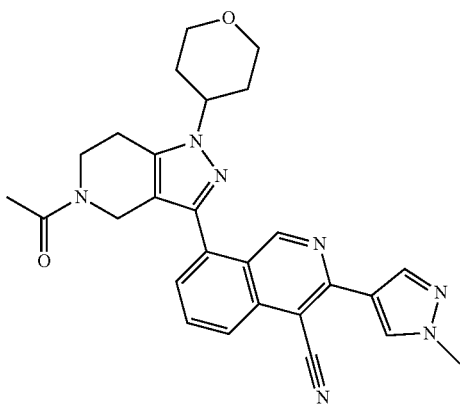 [SMILES: CC(=O)N1CCc2c(c(-c3cccc4c(C#N)c(-c5cnn(C)c5)ncc34)nn2C2CCOCC2)C1]

To the above reaction mixture was added 1-(3-bromo-1-(tetrahydro-2H-pyran-4-yl)-6,7-dihydro-1H-pyrazolo[4,3-c]pyridin-5(4H)-yl)ethanone (Intermediate H, 300 mg, 0.92 mmol), 2-(dicyclohexylphosphino)-2',4',6'-triisopropylbiphenyl (38 mg, 0.08 mmol) and chloro(2-dicyclohexylphosphino-2',4',6'-tri-i-propyl-1,1'-biphenyl)(2'-amino-1,1'-biphenyl-2-yl) palladium(II) (63 mg, 0.08 mmol), Na₂CO₃ (266 mg, 2.5 mmol) and water (1 mL). The mixture was heated to 60° C. for 12 h under a nitrogen atmosphere. After cooling the reaction to room temperature, DCM (50 mL) was added and washed with water (40 mL), brine (40 mL). The organic phase was dried over anhydrous $Na_2SO_4$, filtered and concentrated in vacuo. The crude residue was purified by reverse phase chromatography (acetonitrile 23-53%/0.2% formic acid in water) to give the title compound (11 mg, 3%) as a white solid. $^1$H NMR (400 MHz, CDCl₃) δ 9.90 (d, J=6.0 Hz, 1H), 8.52-8.38 (m, 2H), 8.22-8.17 (m, 1H), 7.96-7.84 (m, 1H), 7.66-7.54 (m, 1H), 4.68-4.51 (m, 2H), 4.32-4.27 (m, 1H), 4.19-4.16 (m, 2H), 4.04 (s, 3H), 4.02-3.84 (m, 2H), 3.61-3.55 (m, 2H), 2.99-2.81 (m, 2H), 2.48-2.39 (m, 2H), 2.27-2.06 (m, 3H), 1.98-1.95 (m, 2H). LCMS M/Z (M+H) 482.

Example 33

1-(3-(4-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

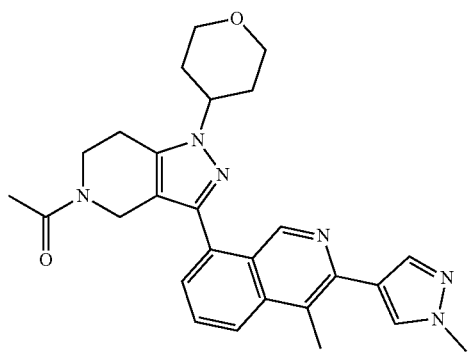 [SMILES: CC(=O)N1CCc2c(c(-c3cccc4c(C)c(-c5cnn(C)c5)ncc34)nn2C2CCOCC2)C1]

Step 1: 8-chloro-4-methyl-3-(1-methyl-1H-pyrazol-4-yl)isoquinoline

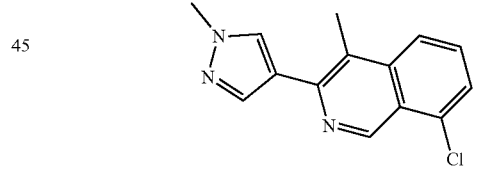

To a solution of 8-chloro-4-iodo-3-(1-methylpyrazol-4-yl)isoquinoline (300 mg, 0.81 mmol) in DMF (15 mL) and water (3 mL) was added potassium methyltrifluoroborate (495 mg, 4.1 mmol), butyl di-1-adamantylphosphine (30 mg, 0.08 mmol), palladium(II) acetate (18 mg, 0.08 mmol) and Cs₂CO₃ (795 mg, 2.4 mmol). The mixture was heated to 80° C. for 20 h under a nitrogen atmosphere. After cooling the reaction to room temperature, EtOAc (50 mL) was added and washed with water (40 mL×2) and brine (40 mL). The organic phase was dried over anhydrous Na₂SO₄, filtered and concentrated in vacuo. The crude residue was purified by silica gel chromatography (petroleum ether/EtOAc=1:1) to give the title compound (200 mg, 95%) as a yellow solid. $^1$H NMR (400 MHz, CDCl₃) δ 9.57 (s, 1H), 7.98 (d, J=8.0 Hz, 1H), 7.95-7.90 (m, 2H), 7.67-7.57 (m, 2H), 4.02 (s, 3H), 2.79 (s, 3H). LCMS M/Z (M+H) 258.

Step 2: 4-methyl-3-(1-methyl-1H-pyrazol-4-yl)-8-(4,4,5,5-tetramethyl-1,3,2-dioxaborolan-2-yl)isoquinoline

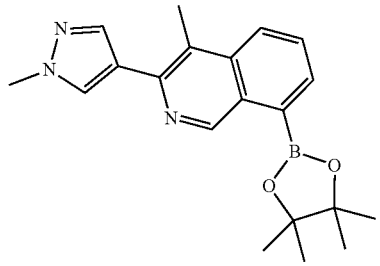

To a solution of 8-chloro-4-methyl-3-(1-methyl-1H-pyrazol-4-yl)isoquinoline (200 mg, 0.78 mmol) in 1,4-dioxane (5 mL) was added 2-(dicyclohexylphosphino)-2',4',6'-triisopropylbiphenyl (38 mg, 0.08 mmol) and chloro(2-dicyclohexylphosphino-2',4',6'-tri-i-propyl-1,1'-biphenyl)(2'-amino-1,1'-biphenyl-2-yl) palladium(II) (64 mg, 0.08 mmol), KOAc (228 mg, 2.33 mmol) and 4,4,4',4',5,5,5',5'-octamethyl-2,2'-bi(1,3,2-dioxaborolane) (591 mg, 2.33 mmol). The mixture was heated to 90° C. for 16 h under a nitrogen atmosphere. After cooling the reaction to room temperature, the mixture was filtered and concentrated in vacuo. EtOAc (50 mL) was added and washed with water (40 mL×2) and brine (40 mL). The organic phase was dried over anhydrous Na$_2$SO$_4$, filtered and concentrated in vacuo. The crude residue was purified by silica gel chromatography (petroleum ether/EtOAc=3:1) to give the title compound (100 mg, 37%) as a brown solid. LCMS M/Z (M+H) 350.

Step 3: 1-(3-(4-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

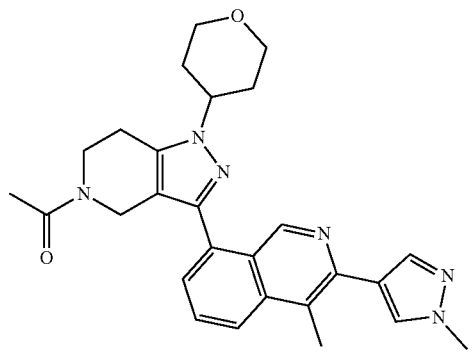 [SMILES: CC(=O)N1CCc2c(c(-c3cccc4c(C)c(-c5cnn(C)c5)ncc34)nn2C2CCOCC2)C1]

To a solution of 4-methyl-3-(1-methyl-1H-pyrazol-4-yl)-8-(4,4,5,5-tetramethyl-1,3,2-dioxaborolan-2-yl)isoquinoline (100 mg, 0.29 mmol) in THF (3 mL) and water (0.6 mL) was added 1-(3-bromo-1-(tetrahydro-2H-pyran-4-yl)-6,7-dihydro-1H-pyrazolo[4,3-c]pyridin-5 (4H)-yl)ethanone (Intermediate H, 103 mg, 0.31 mmol), 2-(dicyclohexylphosphino)-2',4',6'-triisopropylbiphenyl (14 mg, 0.03 mmol) and chloro(2-dicyclohexylphosphino-2',4',6'-tri-i-propyl-1,1'-biphenyl)(2'-amino-1,1'-biphenyl-2-yl) palladium(II) (24 mg, 0.03 mmol), Na$_2$CO$_3$ (91 mg, 0.86 mmol). The mixture was heated to 60° C. for 16 h under a nitrogen atmosphere. After cooling the reaction to room temperature, EtOAc (50 mL) was added and washed with water (40 mL), brine (40 mL). The organic phase was dried over anhydrous Na$_2$SO$_4$, filtered and concentrated in vacuo. The crude residue was purified by reverse phase chromatography (acetonitrile 20-50%/0.05% NH$_4$OH in water) to give the title compound (14 mg, 10%) as a white solid. $^1$H NMR (400 MHz, CDCl$_3$) δ 9.61-9.48 (m, 1H), 8.14-8.04 (m, 1H), 7.95-7.90 (m, 2H), 7.84-7.74 (m, 1H), 7.61-7.50 (m, 1H), 4.63-4.44 (m, 2H), 4.31-4.25 (m, 1H), 4.20-4.12 (m, 2H), 4.01 (s, 3H), 4.00-3.83 (m, 2H), 3.59-3.54 (m, 2H), 2.96-2.82 (m, 2H), 2.81 (s, 3H), 2.48-2.39 (m, 2H), 2.21-2.05 (m, 3H), 1.98-1.95 (m, 2H). LCMS M/Z (M+H) 471.

Example 34

N-methyl-3-(4-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxamide

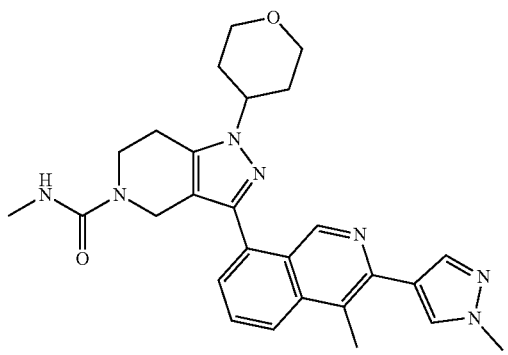

Step 1: tert-butyl 3-(4-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxylate

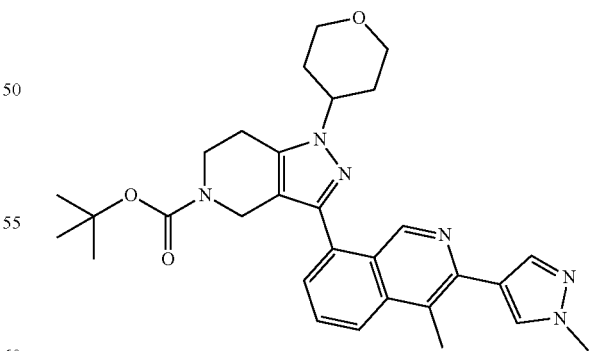

To a solution of 4-methyl-3-(1-methyl-1H-pyrazol-4-yl)-8-(4,4,5,5-tetramethyl-1,3,2-dioxaborolan-2-yl)isoquinoline (300 mg, 0.86 mmol) in THF (10 mL) and water (2 mL) was added tert-butyl 3-bromo-1-(tetrahydro-2H-pyran-4-yl)-6,7-dihydro-1H-pyrazolo[4,3-c]pyridine-5(4H)-carboxylate (Intermediate G, 398 mg, 1.03 mmol), 2-(dicyclohexylphosphino)-2',4',6'-triisopropylbiphenyl (43 mg, 0.09 mmol) and chloro(2-dicyclohexylphosphino-2',4',6'-tri-i-propyl-1,1'-biphenyl)(2'-amino-1,1'-biphenyl-2-yl) palladium(II) (71 mg, 0.09 mmol), Na₂CO₃ (273 mg, 2.58 mmol). The mixture was heated to 60° C. for 16 h under a nitrogen atmosphere. After cooling the reaction to room temperature, DCM (70 mL) was added and washed with water (50 mL), brine (50 mL). The organic phase was dried over anhydrous Na₂SO₄, filtered and concentrated in vacuo. The crude residue was purified by silica gel chromatography (DCM/MeOH=50:1) to give the title compound (200 mg, 44%) as a brown solid. LCMS M/Z (M+H) 529.

Step 2: 4-methyl-3-(1-methyl-1H-pyrazol-4-yl)-8-(1-(tetrahydro-2H-pyran-4-yl)-4,5,6,7-tetrahydro-1H-pyrazolo[4,3-c]pyridin-3-yl)isoquinoline

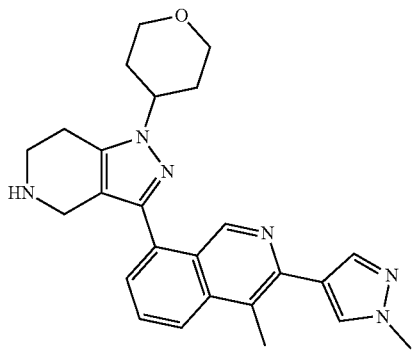 [SMILES: Cc1c(-c2cnn(C)c2)ncc2c(-c3nn(C4CCOCC4)c4c3CNCC4)cccc12]

To a solution of tert-butyl 3-(4-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxylate (200 mg, 0.38 mmol) in DCM (3 mL) at 0° C. was added trifluoroacetic acid (0.28 mL, 3.78 mmol). The mixture was stirred at room temperature for 12 h. DCM (20 mL) was added and washed with sat. aq. NaHCO₃ (10 mL×3), dried over anhydrous Na₂SO₄, filtered and concentrated in vacuo to give the title compound (180 mg, crude) as brown oil that required no further purification. LCMS M/Z (M+H) 429.

Step 3: N-methyl-3-(4-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxamide

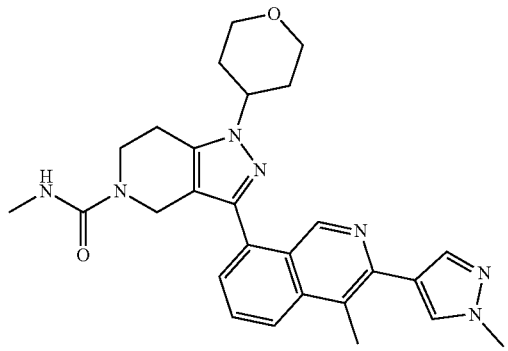

To a solution of 4-methyl-3-(1-methyl-1H-pyrazol-4-yl)-8-(1-(tetrahydro-2H-pyran-4-yl)-4,5,6,7-tetrahydro-1H-pyrazolo[4,3-c]pyridin-3-yl)isoquinoline (180 mg, 0.42 mmol) in DCM (5 mL) was added triethylamine (0.23 mL, 1.68 mmol) and N-methyl-1H-imidazole-1-carboxamide (105 mg, 0.84 mmol). The mixture was stirred at room temperature for 12 h. DCM (40 mL) was added, washed with water (40 mL×2) and brine (40 mL). The organic layer was dried over anhydrous Na₂SO₄, filtered and concentrated in vacuo. The crude residue was purified by reverse phase chromatography (acetonitrile 20-50%/0.05% NH₄OH in water) to give the title compound (53 mg, 24%) as a white solid. ¹H NMR (400 MHz, CDCl₃) 9.44 (s, 1H), 8.01 (d, J=8.4 Hz, 1H), 7.86 (s, 1H), 7.80 (s, 1H), 7.72-7.68 (m, 1H), 7.49 (d, J=7.2 Hz, 1H), 4.85-4.72 (m, 1H), 4.35-4.21 (m, 3H), 4.13-4.10 (m, 2H), 3.96 (s, 3H), 3.85-3.82 (m, 2H), 3.56-3.50 (m, 2H), 2.84-2.81 (m, 2H), 2.78-2.67 (m, 6H), 2.48-2.32 (m, 2H), 1.96-1.87 (m, 2H). LCMS M/Z (M+H) 486.

Example 35

1-(3-(1-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone

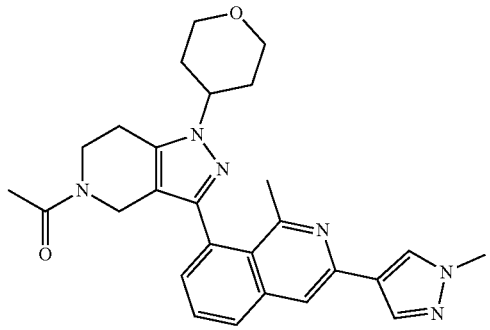 [SMILES: CC(=O)N1CCc2c(c(-c3cccc4cc(-c5cnn(C)c5)nc(C)c34)nn2C2CCOCC2)C1]

Step 1: 8-chloro-3-(1-methyl-1H-pyrazol-4-yl)isoquinoline

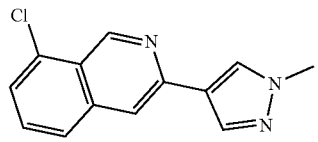 [SMILES: Cn1cc(-c2cc3cccc(Cl)c3cn2)cn1]

To a solution of 3-bromo-8-chloroisoquinoline (500 mg, 2.1 mmol) in 1,4-dioxane (10 mL) and water (2 mL) was added [1,1'-bis(diphenylphosphino)ferrocene]dichloropalladium(II) (75 mg, 0.1 mmol), Na₂CO₃ (437 mg, 4.1 mmol) and 1-methyl-4-(4,4,5,5-tetramethyl-1,3,2-dioxaborolan-2-yl)-1H-pyrazole (472 mg, 2.3 mmol). The mixture was heated to 90° C. for 16 h under a nitrogen atmosphere. After cooling the reaction to room temperature, EtOAc (30 mL) was added and washed with water (20 mL×2). The organic layer was dried over anhydrous Na₂SO₄, filtered and concentrated in vacuo. The crude residue was purified by silica gel chromatography (DCM/MeOH=20:1) to give the title compound (430 mg, 85%) as a yellow solid. H NMR (400

MHz, DMSO-d$_6$) δ 9.49 (s, 1H), 8.37 (s, 1H), 8.14 (s, 1H), 8.10 (s, 1H), 7.89-7.86 (m, 1H), 7.72-7.70 (m, 2H), 3.92 (s, 3H).

Step 2: 8-chloro-3-(1-methyl-1H-pyrazol-4-yl)isoquinoline 2-oxide

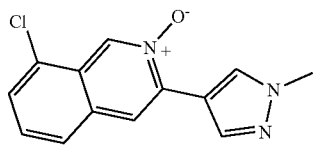

To a solution of 8-chloro-3-(1-methyl-1H-pyrazol-4-yl)isoquinoline (1.38 g, 5.66 mmol) in DCM (100 mL) was added 3-chloroperoxybenzoic acid (3.45 g, 16.99 mmol). The mixture was stirred at 16° C. for 3 h. DCM (200 mL) was added and washed with sat. aq. NaHCO$_3$ (100 mL×3). The organic layer was dried over anhydrous Na$_2$SO$_4$, filtered and concentrated in vacuo. The crude residue was purified by Prep-TLC (DCM/MeOH=20:1) to give the title compound (600 mg, 41%) as a white solid.

Step 3: 8-chloro-1-methyl-3-(1-methyl-1H-pyrazol-4-yl)isoquinoline

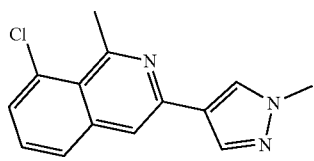 [SMILES: Cc1nc(-c2cnn(C)c2)cc2cccc(Cl)c12]

To a solution of 8-chloro-3-(1-methyl-1H-pyrazol-4-yl)isoquinoline 2-oxide (750 mg, 2.89 mmol), magnesium chloride (825 mg, 8.66 mmol) and copper(I) chloride (14 mg, 0.15 mmol) in diethyl ether (50 mL) at 0° C. was added methylmagnesium bromide (3 M, 3.85 mL, 11.55 mmol). The mixture was stirred at room temperature for 16 h. Sat. aq. NH$_4$Cl (100 mL) was added and extracted with DCM (50 mL×3). The combined organic layers were washed with brine (50 mL), dried over anhydrous Na$_2$SO$_4$, filtered and concentrated in vacuo. The crude residue was purified by Prep-TLC (DCM/MeOH=50:1) to give the title compound (40 mg, 5%) as a yellow solid. LCMS M/Z (M+H) 258.

Step 4: 1-(1-(tetrahydro-2H-pyran-4-yl)-3-(4,4,5,5-tetramethyl-1,3,2-dioxaborolan-2-yl)-6,7-dihydro-1H-pyrazolo[4,3-c]pyridin-5(4H)-yl)ethanone To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 200 mg, 0.61 mmol) in 1,4-dioxane (4 mL) was added 2-(dicyclohexylphosphino)-2',4',6'-triisopropylbiphenyl (17 mg, 0.04 mmol), chloro(2-dicyclohexylphosphino-2',4',6'-tri-i-propyl-1,1'-biphenyl)(2'-amino-1,1'-biphenyl-2-yl) palladium(II) (14 mg, 0.02 mmol), KOAc (179 mg, 1.83 mmol) and 4,4,4',4',5,5,5',5'-octamethyl-2,2'-bi(1,3,2-dioxaborolane) (309 mg, 1.22 mmol). The mixture was heated to 80° C. for 3 h under a nitrogen atmosphere. After cooling the reaction to room temperature, the reaction mixture was used to the next step directly without further purification. LCMS M/Z (M+H) 376.

Step 5: 1-(3-(1-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone To the above step cooled solution was added 8-chloro-1-methyl-3-(1-methyl-1H-pyrazol-4-yl)isoquinoline (40 mg, 0.16 mmol), 2-(dicyclohexylphosphino)-2',4',6'-triisopropylbiphenyl (8 mg, 0.02 mmol), chloro(2-dicyclohexylphosphino-2',4',6'-tri-i-propyl-1,1'-biphenyl)(2'-amino-1,1'-biphenyl-2-yl) palladium(II) (6 mg, 0.01 mmol), K$_3$PO$_4$ (117 mg, 0.55 mmol), 1,4-dioxane (1 mL) and water (1 mL). The reaction mixture was heated to 90° C. for 2 h under a nitrogen atmosphere. After cooling to room temperature, the mixture was filtered and concentrated in vacuo. Water (50 mL) was added and extracted with EtOAc (30 mL×3). The combined organic layers were washed with brine (30 mL×2), dried over anhydrous Na₂SO₄, filtered and concentrated in vacuo. The crude residue was purified by reverse phase chromatography (acetonitrile 18-48%/0.05% NH₄OH in water) to give the title compound (1 mg, 1%) as a white solid. ¹H NMR (400 MHz, CDCl₃) δ 8.03-8.00 (m, 2H), 7.84-7.82 (m, 1H), 7.69-7.61 (m, 2H), 7.42-7.40 (m, 1H), 4.45-4.35 (m, 1H), 4.26-4.22 (m, 2H), 4.15-4.12 (m, 2H), 4.00-3.75 (m, 2H), 3.97 (s, 3H), 3.58-3.52 (m, 2H), 2.93-2.86 (m, 2H), 2.39-2.36 (m, 5H), 2.21-2.04 (m, 3H), 1.94-1.91 (m, 2H). LCMS M/Z (M+H) 471.

Example 36

(S)-1-(3-(6-(1-methyl-1H-pyrazol-4-yl)naphthalen-1-yl)-1-(tetrahydrofuran-3-yl)-6,7-dihydro-1H-pyrazolo[4,3-c]pyridin-5(4H)-yl)ethanone

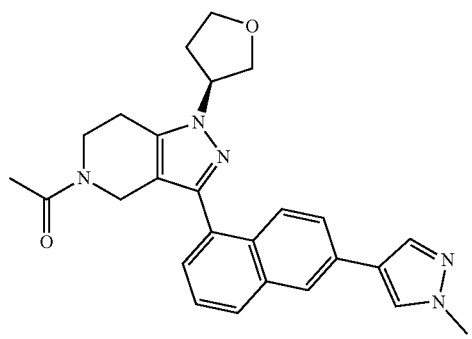 [SMILES: CC(=O)N1CCc2c(c(-c3cccc4cc(-c5cnn(C)c5)ccc34)nn2[C@H]2CCOC2)C1]

Step 1:
6-(1-methyl-1H-pyrazol-4-yl)naphthalen-1-amine

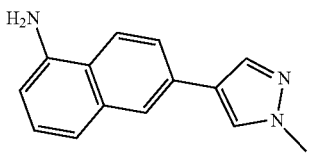 [SMILES: Cn1cc(-c2ccc3c(N)cccc3c2)cn1]

To a solution of 6-bromonaphthalen-1-amine (470 mg, 2.12 mmol) in 1,4-dioxane (25 mL) and water (5 mL) was added [1,1'-bis(diphenylphosphino)ferrocene]dichloropalladium(II) (155 mg, 0.21 mmol), Na₂CO₃ (449 mg, 4.24 mmol) and 1-methyl-4-(4,4,5,5-tetramethyl-1,3,2-dioxaborolan-2-yl)-1H-pyrazole (528 mg, 2.54 mmol). The mixture was heated to 120° C. for 3 h under a nitrogen atmosphere. After cooling the reaction to room temperature, water (100 mL) was added and extracted with EtOAc (50 mL×3). The combined organic layers were dried over anhydrous Na₂SO₄, filtered and concentrated in vacuo. The crude residue was purified by silica gel chromatography (DCM/MeOH=30:1) to give the title compound (300 mg, 63%) as yellow solid. LCMS M/Z (M+H) 224.

Step 2:
4-(5-bromonaphthalen-2-yl)-1-methyl-1H-pyrazole

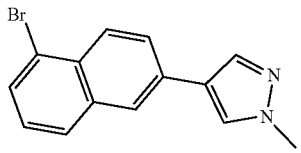 [SMILES: Cn1cc(-c2ccc3c(Br)cccc3c2)cn1]

To a solution of 6-(1-methyl-1H-pyrazol-4-yl)naphthalen-1-amine (150 mg, 0.67 mmol) in HCl (2.0 M, 6 mL) at 0° C. was added sodium nitrite (51 mg, 0.74 mmol) in water (4 mL) slowly. The mixture was stirred at 0° C. for 1 h. Copper (I) bromide (350 mg, 2.44 mmol) in water (5 mL) at 0° C. was added by dropwise. The mixture was stirred at 0° C. for an additional 1 h. Water (50 mL) was added and extracted with EtOAc (30 mL×3). The combined organic layers were dried over anhydrous Na₂SO₄, filtered and concentrated in vacuo. The crude residue was purified by Prep-TLC (DCM/MeOH=20:1) to give the title compound (40 mg, 17%) as a yellow solid. LCMS M/Z (M+H) 287.

Step 3: 1-methyl-4-(5-(4,4,5,5-tetramethyl-1,3,2-dioxaborolan-2-yl)naphthalen-2-yl)-1H-pyrazole

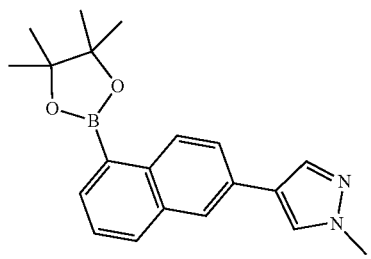

To a solution of 4-(5-bromonaphthalen-2-yl)-1-methyl-1H-pyrazole (40 mg, 0.14 mmol), KOAc (27 mg, 0.28 mmol) and 4,4,5,5-tetramethyl-2-(4,4,5,5-tetramethyl-1,3,2-dioxaborolan-2-yl)-1,3,2-dioxaborolane (70 mg, 0.28 mmol) in 1,4-dioxane (10 mL) was added [1,1'-bis(diphenylphosphino)ferrocene]dichloropalladium(II) (11 mg, 0.01 mmol). The mixture was heated to 80° C. for 16 h under a nitrogen atmosphere. After cooling the reaction to room temperature, water (30 mL) was added and extracted with EtOAc (20 mL×3). The combined organic layers were dried over anhydrous Na₂SO₄, filtered and concentrated in vacuo. The crude residue was purified by Prep-TLC (petroleum ether/EtOAc=3:1) to give the title compound (30 mg, 64%) as a yellow solid.

Step 4: (S)-1-(3-(6-(1-methyl-1H-pyrazol-4-yl)naphthalen-1-yl)-1-(tetrahydrofuran-3-yl)-6,7-dihydro-1H-pyrazolo[4,3-c]pyridin-5(4H)-yl)ethanone

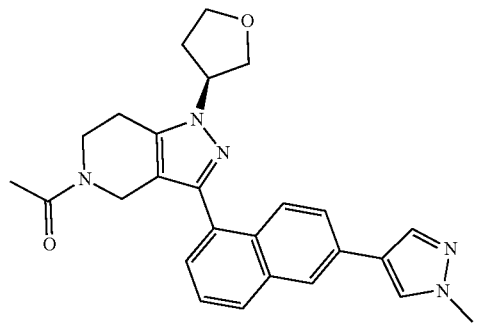 [SMILES: CC(=O)N1CCc2c(c(-c3cccc4cc(-c5cnn(C)c5)ccc34)nn2[C@H]2CCOC2)C1]

To a solution of (S)-1-(3-bromo-1-(tetrahydrofuran-3-yl)-6,7-dihydro-1H-pyrazolo[4,3-c]pyridin-5(4H)-yl)ethanone (Intermediate E, 28 mg, 0.09 mmol) in THF (5 mL) and water (1 mL) was added 1-methyl-4-(5-(4,4,5,5-tetramethyl-1,3,2-dioxaborolan-2-yl)naphthalen-2-yl)-1H-pyrazole (30 mg, 0.09 mmol), 2-(dicyclohexylphosphino)-2',4',6'-triisopropylbiphenyl (4 mg, 0.01 mmol) and chloro(2-dicyclohexylphosphino-2',4',6'-tri-i-propyl-1,1'-biphenyl)(2'-amino-1,1'-biphenyl-2-yl) palladium(II) (7 mg, 0.01 mmol), $Na_2CO_3$ (19 mg, 0.18 mmol). The mixture was heated to 60° C. for 16 h under a nitrogen atmosphere. After cooling the reaction to room temperature, water (50 mL) was added and extracted with EtOAc (30 mL×3). The combined organic layers were dried over anhydrous $Na_2SO_4$, filtered and concentrated in vacuo. The crude residue was purified by reverse phase chromatography (acetonitrile 23-53%/0.05% $NH_4OH$ in water) to give the title compounds (4 mg, 11%) as a white solid. $^1$H NMR (400 MHz, $CDCl_3$) δ 8.16-8.14 (m, 1H), 7.98-7.85 (m, 3H), 7.76-7.74 (m, 1H), 7.66-7.57 (m, 1H), 7.55-7.47 (m, 1H), 7.45-7.40 (m, 1H), 4.93-4.91 (m, 1H), 4.56-4.39 (m, 2H), 4.23-4.18 (m, 2H), 4.16-4.01 (m, 2H), 4.00 (s, 3H), 3.99-3.82 (m, 2H), 2.91-2.85 (m, 2H), 2.61-2.43 (m, 2H), 2.20-2.04 (m, 3H). LCMS M/Z (M+H) 442.

Example 37

N-methyl-3-(2-(1-methyl-1H-pyrazol-4-yl)-3-oxo-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxamide

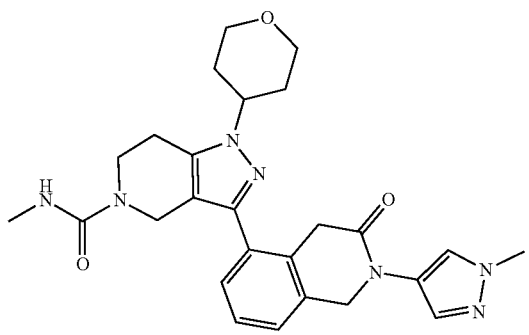

Step 1: 5-chloro-1,2-dihydroisoquinolin-3(4H)-one

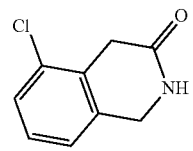 [SMILES: O=C1Cc2c(Cl)cccc2CN1]

A mixture of 2-(2-chlorophenyl)acetonitrile (5 g, 32.98 mmol), paraformaldehyde (1.09 g, 36.28 mmol) and pyrophosphoric acid (29.35 g, 164.92 mmol) was heated to 180° C. for 15 min. The reaction mixture was poured into ice water (200 mL), neutralized with $Na_2CO_3$, and then extracted with DCM (100 mL×3). The combined organic layers were dried over anhydrous $Na_2SO_4$, filtered and concentrated in vacuo. The crude residue was purified by silica gel chromatography (DCM/MeOH=20:1) to give the title compound (400 mg, 7%) as a yellow solid. $^1$H NMR (400 MHz, $CDCl_3$) δ 7.35 (d, J=8.0 Hz, 1H), 7.24-7.18 (m, 1H), 7.09 (d, J=8.0 Hz, 1H), 4.57 (s, 2H), 3.70 (s, 2H). LCMS M/Z (M+H) 182.

Step 2: 5-chloro-2-(1-methyl-1H-pyrazol-4-yl)-1,2-dihydroisoquinolin-3(4H)-one

To a solution of 5-chloro-1,2-dihydroisoquinolin-3(4H)-one (500 mg, 2.75 mmol) in 1,4-dioxane (10 mL) was added copper(I) iodide (26 mg, 0.14 mmol), (1R,2R)-cyclohexane-1,2-diamine (63 mg, 0.55 mmol), $K_3PO_4$ (1.75 g, 8.26 mmol) and 4-iodo-1-methyl-1H-pyrazole (859 mg, 4.13 mmol). The reaction mixture was heated to 120° C. for 12 h under a nitrogen atmosphere. After cooling to room temperature, the mixture was filtered and concentrated in vacuo. Water (100 mL) was added and extracted with EtOAc (50 mL×3). The combined organic layers were dried over anhydrous $Na_2SO_4$, filtered and concentrated in vacuo. The crude residue was purified by silica gel chromatography (DCM/MeOH=20:1) to give the title compound (80 mg, 11%) as a yellow solid. LCMS M/Z (M+H) 262.

Step 3: tert-butyl 1-(tetrahydro-2H-pyran-4-yl)-3-(4,4,5,5-tetramethyl-1,3,2-dioxaborolan-2-yl)-6,7-dihydro-1H-pyrazolo[4,3-c]pyridine-5(4H)-carboxylate

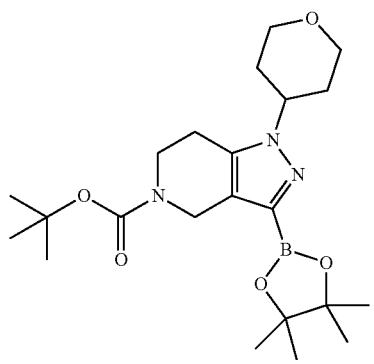 [SMILES: CC(C)(C)OC(=O)N1CCc2c(c(B3OC(C)(C)C(C)(C)O3)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 400 mg, 1.04 mmol) in 1,4-dioxane (8 mL) was added 2-(dicyclohexylphosphino)-2',4',6'-triisopropylbiphenyl (30 mg, 0.06 mmol), chloro(2-dicyclohexylphosphino-2',4',6'-tri-i-propyl-1,1'-biphenyl)(2'-amino-1,1'-biphenyl-2-yl) palladium(II) (25 mg, 0.03 mmol), KOAc (300 mg, 3.12 mmol) and 4,4,4',4',5,5,5',5'-octamethyl-2,2'-bi(1,3,2-dioxaborolane) (526 mg, 2.08 mmol). The mixture was heated to 80° C. for 2 h under a nitrogen atmosphere. After cooling the reaction to room temperature, the reaction mixture was used to the next step directly without further purification. LCMS M/Z (M+H) 434.

Step 4: tert-butyl 3-(2-(1-methyl-1H-pyrazol-4-yl)-3-oxo-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxylate

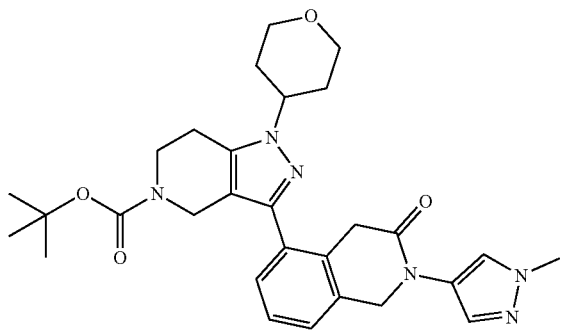 [SMILES: Cn1cc(N2Cc3cccc(-c4nn(C5CCOCC5)c5c4CN(C(=O)OC(C)(C)C)CC5)c3CC2=O)cn1]

To the above step cooled solution was added 5-chloro-2-(1-methyl-1H-pyrazol-4-yl)-1,2-dihydroisoquinolin-3(4H)-one (100 mg, 0.38 mmol), chloro(2-dicyclohexylphosphino-2',4',6'-tri-i-propyl-1,1'-biphenyl)(2'-amino-1,1'-biphenyl-2-yl) palladium(II) (25 mg, 0.03 mmol), K₃PO₄ (244 mg, 1.15 mmol), 1,4-dioxane (2 mL) and water (2 mL). The reaction mixture was heated to 90° C. for 1 h under a nitrogen atmosphere. After cooling to room temperature, the mixture was filtered and concentrated in vacuo. Water (100 mL) was added and extracted with EtOAc (50 mL×3). The combined organic layers were washed with brine (50 mL×2), dried over anhydrous Na₂SO₄, filtered and concentrated in vacuo. The crude residue was purified by silica gel chromatography (DCM/MeOH=20:1) to give the title compound (60 mg, 12%) as a yellow solid. LCMS M/Z (M+H) 533.

Step 5: 2-(1-methyl-1H-pyrazol-4-yl)-5-(1-(tetrahydro-2H-pyran-4-yl)-4,5,6,7-tetrahydro-1H-pyrazolo[4,3-c]pyridin-3-yl)-1,2-dihydroisoquinolin-3(4H)-one

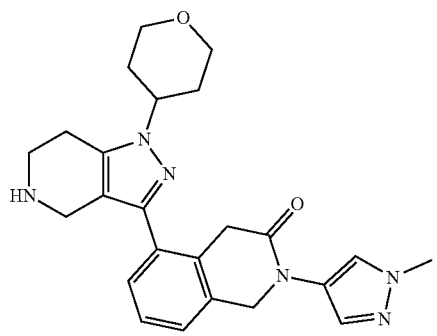 [SMILES: Cn1cc(N2Cc3cccc(-c4nn(C5CCOCC5)c5c4CNCC5)c3CC2=O)cn1]

To a solution of tert-butyl 3-(2-(1-methyl-1H-pyrazol-4-yl)-3-oxo-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxylate (60 mg, 0.11 mmol) in DCM (10 mL) at 0° C. was added trifluoroacetic acid (3 mL, 40 mmol). The mixture was stirred at 0° C. for 2 h and concentrated in vacuo to give the title compound (50 mg, crude) as brown oil that required no further purification. LCMS M/Z (M+H) 433.

Step 6: N-methyl-3-(2-(1-methyl-1H-pyrazol-4-yl)-3-oxo-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxamide

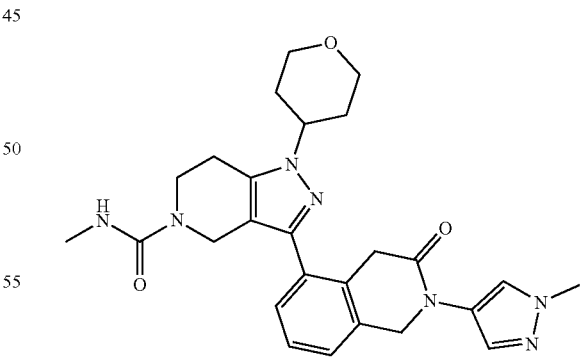

To a solution of 2-(1-methyl-1H-pyrazol-4-yl)-5-(1-(tetrahydro-2H-pyran-4-yl)-4,5,6,7-tetrahydro-1H-pyrazolo[4,3-c]pyridin-3-yl)-1,2-dihydroisoquinolin-3(4H)-one (50 mg, 0.12 mmol) in DCM (15 mL) was added triethylamine (0.10 mL, 0.70 mmol) and N-methyl-1H-imidazole-1-carboxamide (43 mg, 0.35 mmol). The reaction was stirred at room temperature for 16 h. DCM (40 mL) was added and washed with brine (30 mL×3). The organic layer was dried over anhydrous Na₂SO₄, filtered and concentrated in vacuo. The crude residue was purified by reverse phase chromatography (acetonitrile 23-53%/0.2% formic acid in water) to give the title compound (14 mg, 24%) as a white solid. ¹H NMR (400 MHz, CDCl₃) δ 7.98 (s, 2H), 7.58 (s, 1H), 7.35-7.27 (m, 3H), 4.88 (s, 2H), 4.87-4.80 (m, 1H), 4.26 (s, 2H), 4.25-4.17 (m, 1H), 4.16-4.10 (m, 2H), 3.91 (s, 3H), 3.87-3.80 (m, 4H), 3.55 (t, J=11.6 Hz, 2H), 2.85-2.77 (m, 5H), 2.40-2.29 (m, 2H), 1.95-1.87 (m, 2H). LCMS M/Z (M+H) 490.

Example 38

N-methyl-3-(3-methyl-2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxamide

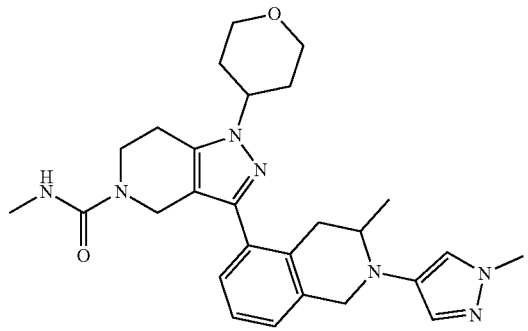

Step 1: N-(1-(2-chlorophenyl)propan-2-yl)-1-methyl-1H-pyrazol-4-amine

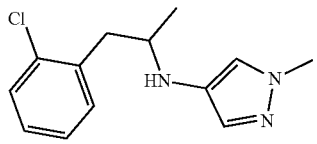 [SMILES: CC(Cc1ccccc1Cl)Nc1cnn(C)c1]

To a solution of 1-(2-chlorophenyl)propan-2-one (4.0 g, 23.7 mmol) in MeOH (50 mL) was added 1-methyl-1H-pyrazol-4-amine (3.49 g, 26.09 mmol) and NaHCO₃ (3.99 g, 47.44 mmol). The reaction mixture was heated to 50° C. for 2 h under a nitrogen atmosphere. After cooling to 0° C., sodium borohydride (916 mg, 24.22 mmol) was added portionwise. The mixture was stirred at room temperature for 2 h under a nitrogen atmosphere. The reaction was concentrated in vacuo. Water (100 mL) was added and extracted with EtOAc (50 mL×3). The combined organic layers were dried over anhydrous Na₂SO₄, filtered and concentrated in vacuo. The crude residue was purified by silica gel chromatography (DCM/MeOH=20:1) to give the title compound (2.2 g, 55%) as brown oil. ¹H NMR (400 MHz, CDCl₃) δ 7.38-7.35 (m, 1H), 7.25-7.15 (m, 3H), 7.14 (s, 1H), 6.95 (s, 1H), 3.81 (s, 3H), 3.51-3.41 (m, 1H), 3.14-3.07 (m, 1H), 2.77-2.69 (m, 1H), 1.16 (d, J=6.4 Hz, 3H). LCMS M/Z (M+H) 250.

Step 2: 5-chloro-3-methyl-2-(1-methyl-1H-pyrazol-4-yl)-1,2,3,4-tetrahydroisoquinoline

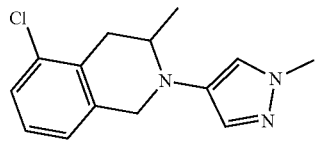 [SMILES: CC1Cc2c(Cl)cccc2CN1c1cnn(C)c1]

To a solution of N-(1-(2-chlorophenyl)propan-2-yl)-1-methyl-1H-pyrazol-4-amine (1.0 g, 4 mmol) in AcOH (1 mL) was added paraformaldehyde (240 mg, 8.01 mmol). The mixture was stirred at room temperature for 5 min under a nitrogen atmosphere. After cooling to 0° C., H₂SO₄ (3.2 mL 1) was added. The mixture was stirred at room temperature for 16 h under a nitrogen atmosphere. The reaction mixture was poured into water (100 mL), basified with solid NaHCO₃ to pH 8 and then extracted with EtOAc (50 mL×3). The combined organic layers were dried over anhydrous Na₂SO₄, filtered and concentrated in vacuo. The crude residue was purified by silica gel chromatography (DCM/MeOH=20:1) to give the title compound (300 mg, 29%) as yellow oil. ¹H NMR (400 MHz, CDCl₃) δ 7.25-7.09 (m, 4H), 7.05-6.97 (m, 1H), 4.22-4.02 (m, 2H), 3.85-3.81 (m, 3H), 3.76-3.66 (m, 1H), 3.08-3.00 (m, 1H), 2.78-2.72 (m, 1H), 1.08 (d, J=6.4 Hz, 3H). LCMS M/Z (M+H) 262.

Step 3: tert-butyl 1-(tetrahydro-2H-pyran-4-yl)-3-(4,4,5,5-tetramethyl-1,3,2-dioxaborolan-2-yl)-6,7-dihydro-1H-pyrazolo[4,3-c]pyridine-5(4H)-carboxylate

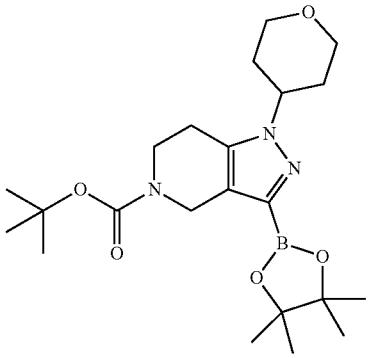 [SMILES: CC(C)(C)OC(=O)N1CCc2c(c(B3OC(C)(C)C(C)(C)O3)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 1.0 g, 2.59 mmol) in 1,4-dioxane (20 mL) was added 2-(dicyclohexylphosphino)-2',4',6'-triisopropylbiphenyl (74 mg, 0.16 mmol), chloro(2-dicyclohexylphosphino-2',4',6'-tri-i-propyl-1,1'-biphenyl) (2'-amino-1,1'-biphenyl-2-yl) palladium(II) (61 mg, 0.08 mmol), KOAc (762 mg, 7.77 mmol) and 4,4,4',4',5,5,5',5'-octamethyl-2,2'-bi(1,3,2-dioxaborolane) (1.32 g, 5.18 mmol). The mixture was heated to 80° C. for 5 h under a nitrogen atmosphere. After cooling the reaction to room temperature, the reaction mixture was used to the next step directly without further purification. LCMS M/Z (M+H) 434.

Step 4: tert-butyl 3-(3-methyl-2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxylate

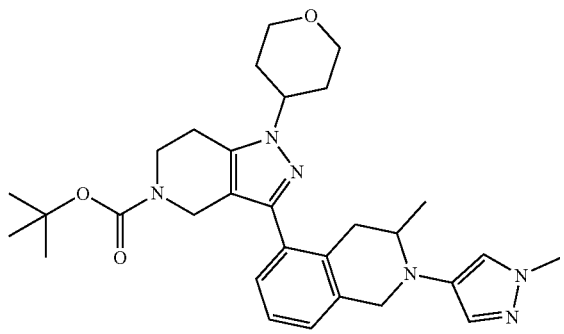 [SMILES: CC1Cc2c(cccc2-c2nn(C3CCOCC3)c3c2CN(C(=O)OC(C)(C)C)CC3)CN1c1cnn(C)c1]

To the above step cooled solution was added 5-chloro-3-methyl-2-(1-methyl-1H-pyrazol-4-yl)-1,2,3,4-tetrahydroisoquinoline (300 mg, 1.15 mmol), chloro(2-dicyclohexylphosphino-2',4',6'-tri-i-propyl-1,1'-biphenyl)(2'-amino-1,1'-biphenyl-2-yl) palladium(II) (57 mg, 0.07 mmol), $K_3PO_4$ (612 mg, 2.88 mmol), 1,4-dioxane (4 mL) and water (6 mL). The reaction mixture was heated to 90° C. for 1 h under a nitrogen atmosphere. After cooling to room temperature, the mixture was filtered and concentrated in vacuo. Water (50 mL) was added and extracted with EtOAc (30 mL×3). The combined organic layers were washed with brine (30 mL×3), dried over anhydrous $Na_2SO_4$, filtered and concentrated in vacuo. The crude residue was purified by silica gel chromatography (DCM/MeOH=20:1) to give the title compound (70 mg, 11%) as a yellow solid. LCMS M/Z (M+H) 533.

Step 5: 3-methyl-2-(1-methyl-1H-pyrazol-4-yl)-5-(1-(tetrahydro-2H-pyran-4-yl)-4,5,6,7-tetrahydro-1H-pyrazolo[4,3-c]pyridin-3-yl)-1,2,3,4-tetrahydroisoquinoline

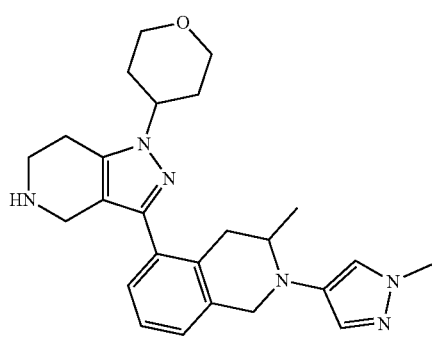 [SMILES: CC1Cc2c(cccc2-c2nn(C3CCOCC3)c3c2CNCC3)CN1c1cnn(C)c1]

To a solution of tert-butyl 3-(3-methyl-2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxylate (70 mg, 0.12 mmol) in DCM (10 mL) at 0° C. was added trifluoroacetic acid (0.11 mL, 1.2 mmol). The mixture was stirred at 0° C. for 2 h and concentrated in vacuo to give the title compound (50 mg, crude) as a brown oil that required no further purification. LCMS M/Z (M+H) 433.

Step 6: N-methyl-3-(3-methyl-2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxamide

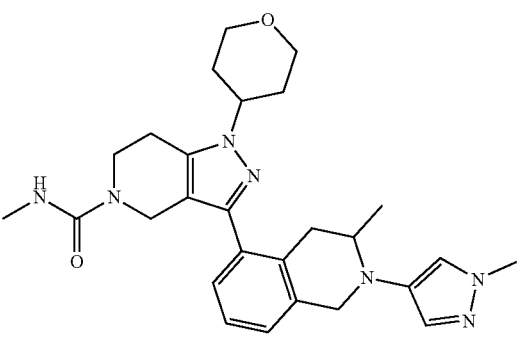

To a solution of 3-methyl-2-(1-methyl-1H-pyrazol-4-yl)-5-(1-(tetrahydro-2H-pyran-4-yl)-4,5,6,7-tetrahydro-1H-pyrazolo[4,3-c]pyridin-3-yl)-1,2,3,4-tetrahydroisoquinoline (50 mg, 0.12 mmol) in DCM (10 mL) was added triethylamine (0.10 mL, 0.70 mmol) and N-methyl-1H-imidazole-1-carboxamide (43 mg, 0.35 mmol). The reaction was stirred at room temperature for 16 h. DCM (40 mL) was added and washed with brine (30 mL×3). The organic layer was dried over anhydrous $Na_2SO_4$, filtered and concentrated in vacuo. The crude residue was purified by reverse phase chromatography (acetonitrile 23-53%/0.2% formic acid in water) to give the title compound (2 mg, 3%) as a white solid. $^1$H NMR (400 MHz, $CDCl_3$) δ 7.24-7.08 (m, 4H), 7.02 (s, 1H), 4.48-4.39 (m, 1H), 4.30-4.07 (m, 7H), 3.97-3.88 (m, 1H), 3.86 (s, 3H), 3.80-3.65 (m, 3H), 3.55 (t, J=11.6 Hz, 2H), 3.20-3.12 (m, 1H), 2.80 (d, J=4.4 Hz, 3H), 2.75-2.62 (m, 1H), 2.39-2.29 (m, 2H), 1.95-1.86 (m, 2H), 1.03 (d, J=6.4 Hz, 3H). LCMS M/Z (M+H) 490.

Example 39

N-methyl-3-(2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxamide

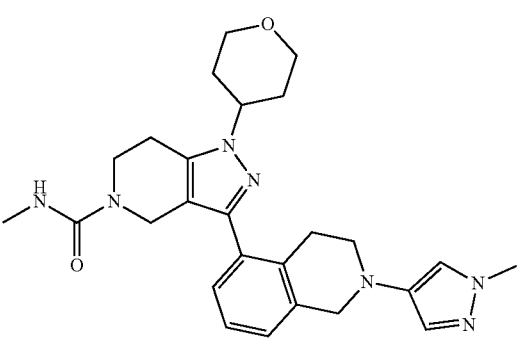

Step 1: 5-bromo-2-(1-methyl-1H-pyrazol-4-yl)-1,2,3,4-tetrahydroisoquinoline

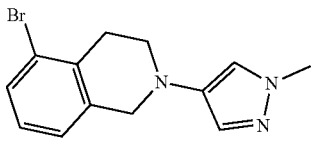 [SMILES: Cn1cc(N2CCc3c(Br)cccc3C2)cn1]

o a solution of 5-bromo-1,2,3,4-tetrahydroisoquinoline (1.0 g, 4.72 mmol) in ethylene glycol (15 mL) was added copper(I) iodide (898 mg, 4.72 mmol), $K_3PO_4$ (3.0 g, 14.15 mmol) and 4-iodo-1-methyl-1H-pyrazole (1.96 g, 9.43 mmol). The reaction mixture was heated to 120° C. for 3 h under a nitrogen atmosphere. After cooling to room temperature, the mixture was filtered and concentrated in vacuo. Water (50 mL) was added and extracted with DCM (30 mL×3). The combined organic layers were dried over anhydrous $Na_2SO_4$, filtered and concentrated in vacuo. The crude residue was purified by silica gel chromatography (petroleum ether/EtOAc=1:1) to give the title compound (0.28 g, 42% purity) as a brown solid which was further purified by reverse phase chromatography (acetonitrile 5-35/0.05% HCl in water) to give the title compound (0.05 g, 4%, HCl salt) as a light yellow solid. $^1$H NMR (400 MHz, DMSO-$d_6$) δ 9.77 (s, 1H), 8.65 (s, 1H), 8.26 (s, 1H), 8.11 (d, J=8.0 Hz, 1H), 7.99 (d, J=7.2 Hz, 1H), 7.60-7.54 (m, 1H), 4.55 (t, J=8.0 Hz, 2H), 3.95 (s, 3H), 3.38 (t, J=8.0 Hz, 2H), 2.54 (s, 2H). LCMS M/Z (M+H) 292.

Step 2: tert-butyl 1-(tetrahydro-2H-pyran-4-yl)-3-(4,4,5,5-tetramethyl-1,3,2-dioxaborolan-2-yl)-6,7-dihydro-1H-pyrazolo[4,3-c]pyridine-5(4H)-carboxylate

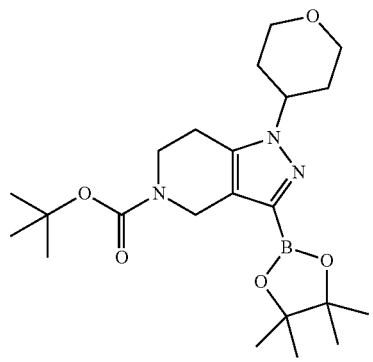 [SMILES: CC(C)(C)OC(=O)N1CCc2c(c(B3OC(C)(C)C(C)(C)O3)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 100 mg, 0.26 mmol) in 1,4-dioxane (4 mL) was added 2-(dicyclohexylphosphino)-2',4',6'-triisopropylbiphenyl (14 mg, 0.03 mmol), chloro(2-dicyclohexylphosphino-2',4',6'-tri-i-propyl-1,1'-biphenyl)(2'-amino-1,1'-biphenyl-2-yl) palladium(II) (24 mg, 0.03 mmol), KOAc (76 mg, 0.78 mmol) and 4,4,4',4',5,5,5',5'-octamethyl-2,2'-bi(1,3,2-dioxaborolane) (131 mg, 0.52 mmol). The mixture was heated to 80° C. for 2 h under a nitrogen atmosphere. After cooling the reaction to room temperature, the reaction mixture was used to the next step directly without further purification. LCMS M/Z (M+H) 434.

Step 3: tert-butyl 3-(2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxylate

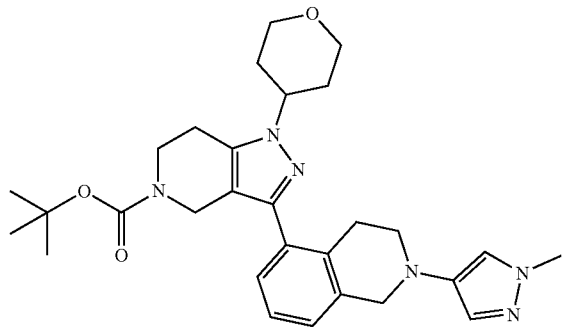 [SMILES: Cn1cc(N2CCc3c(cccc3-c3nn(C4CCOCC4)c4c3CN(C(=O)OC(C)(C)C)CC4)C2)cn1]

To the above step cooled solution was added 5-bromo-2-(1-methyl-1H-pyrazol-4-yl)-1,2,3,4-tetrahydroisoquinoline (25 mg, 0.09 mmol), 2-(dicyclohexylphosphino)-2',4',6'-triisopropylbiphenyl (5 mg, 0.01 mmol), chloro(2-dicyclohexylphosphino-2',4',6'-tri-i-propyl-1,1'-biphenyl)(2'-amino-1,1'-biphenyl-2-yl) palladium(II) (8 mg, 0.01 mmol), $K_3PO_4$ (59 mg, 0.28 mmol), 1,4-dioxane (1 mL) and water (1 mL). The reaction mixture was heated to 90° C. for 1 h under a nitrogen atmosphere. After cooling to room temperature, the mixture was filtered and concentrated in vacuo. DCM (50 mL) was added and washed with water (40 mL), brine (40 mL). The organic layer was dried over anhydrous $Na_2SO_4$, filtered and concentrated in vacuo. The crude residue was purified by silica gel chromatography (DCM/MeOH=20:1) to give the title compound (50 mg, 52%) as brown oil. LCMS M/Z (M+H) 519.

Step 4: 2-(1-methyl-1H-pyrazol-4-yl)-5-(1-(tetrahydro-2H-pyran-4-yl)-4,5,6,7-tetrahydro-1H-pyrazolo[4,3-c]pyridin-3-yl)-1,2,3,4-tetrahydroisoquinoline

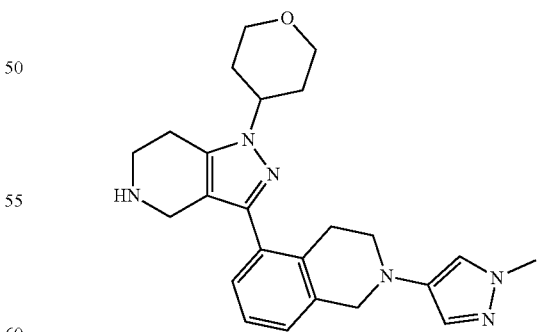

To a solution of tert-butyl 3-(2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxylate (50 mg, 0.1 mmol) in DCM (1 mL) at 0° C. was added trifluoroacetic acid (0.07 mL, 0.96 mmol). The mixture was stirred at room temperature for 1 h and concentrated in vacuo to give the title compound (43 mg, crude) as brown oil that required no further purification. LCMS M/Z (M+H) 419.

Step 5: N-methyl-3-(2-(1-methyl-1H-pyrazol-4-yl)-1,2,3,4-tetrahydroisoquinolin-5-yl)-1-(tetrahydro-2H-pyran-4-yl)-6,7-dihydro-1H-pyrazolo[4,3-c]pyridine-5(4H)-carboxamide

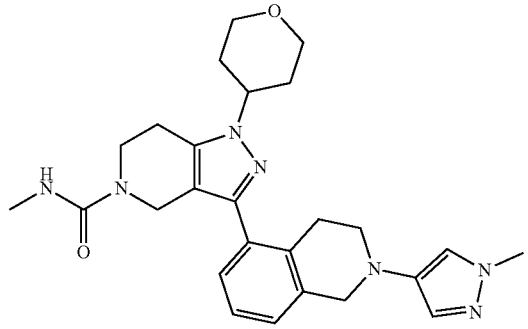

To a solution of 2-(1-methyl-1H-pyrazol-4-yl)-5-(1-(tetrahydro-2H-pyran-4-yl)-4,5,6,7-tetrahydro-1H-pyrazolo[4,3-c]pyridin-3-yl)-1,2,3,4-tetrahydroisoquinoline (43 mg, 0.10 mmol) in DCM (3 mL) was added triethylamine (0.07 mL, 0.5 mmol) and N-methyl-1H-imidazole-1-carboxamide (25 mg, 0.2 mmol). The reaction was stirred at room temperature for 12 h. DCM (50 mL) was added and washed with water (40 mL), brine (40 mL). The organic layer was dried over anhydrous Na₂SO₄, filtered and concentrated in vacuo. The crude residue was purified by reverse phase chromatography (acetonitrile 15-45%/0.05% NH₄OH in water) to give the title compound (7 mg, 14%) as a white solid. ¹H NMR (400 MHz, CDCl₃) δ 7.30 (s, 1H), 7.22 (d, J=7.6 Hz, 1H), 7.17-7.11 (m, 2H), 7.04 (s, 1H), 4.46-4.37 (m, 1H), 4.25-4.09 (m, 6H), 3.90-3.80 (m, 4H), 3.58-3.45 (m, 4H), 3.26-3.21 (m, 2H), 3.04-3.01 (m, 2H), 2.85-2.77 (m, 4H), 2.41-2.25 (m, 2H), 1.91-1.87 (m, 2H). LCMS M/Z (M+H) 476.

Example 40

N-methyl-3-(2-methyl-5-(1-methyl-1H-pyrazol-4-yl)-1H-pyrrolo[2,3-c]pyridin-1-yl)-1-(tetrahydro-2H-pyran-4-yl)-6,7-dihydro-1H-pyrazolo[4,3-c]pyridine-5(4H)-carboxamide

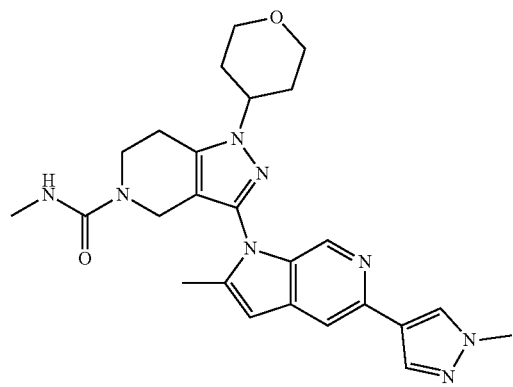

Step 1: tert-butyl 3-(2-methyl-5-(1-methyl-1H-pyrazol-4-yl)-1H-pyrrolo[2,3-c]pyridin-1-yl)-1-(tetrahydro-2H-pyran-4-yl)-6,7-dihydro-1H-pyrazolo[4,3-c]pyridine-5(4H)-carboxylate

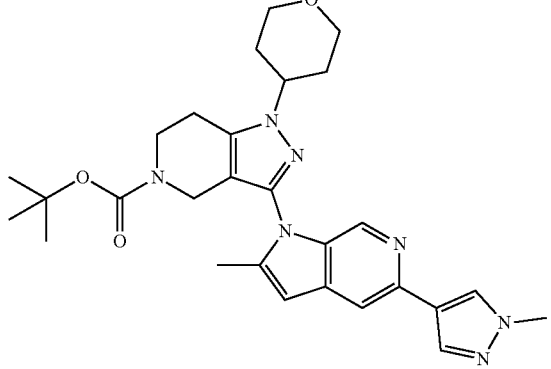

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 1.0 g, 2.59 mmol) in toluene (20 mL) was added copper(I) iodide (25 mg, 0.13 mmol), K₃PO₄ (2.2 g, 10.36 mmol), (1R,2R)-cyclohexane-1,2-diamine (59 mg, 0.52 mmol) and 2-methyl-5-(1-methyl-1H-pyrazol-4-yl)-1H-pyrrolo[2,3-c]pyridine (500 mg, 2.36 mmol). The mixture was heated to 120° C. for 12 h under a nitrogen atmosphere. After cooling the reaction to room temperature, the mixture was filtered and concentrated in vacuo. Water (100 mL) was added and extracted with EtOAc (50 mL×3). The combined organic layers were washed with brine (50 mL), dried over anhydrous Na₂SO₄, filtered and concentrated in vacuo. The crude residue was purified by silica gel chromatography (DCM/MeOH=20:1) to give the title compound (90 mg, 7%) as a yellow solid. LCMS M/Z (M+H) 518.

Step 2: 3-(2-methyl-5-(1-methyl-1H-pyrazol-4-yl)-1H-pyrrolo[2,3-c]pyridin-1-yl)-1-(tetrahydro-2H-pyran-4-yl)-4,5,6,7-tetrahydro-1H-pyrazolo[4,3-c]pyridine

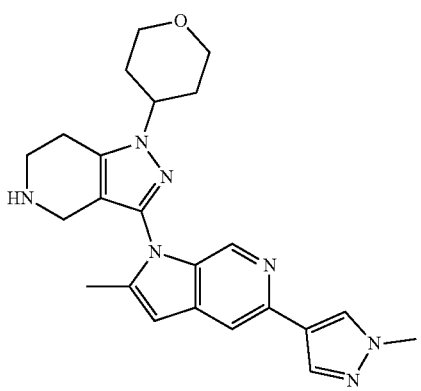 [SMILES: Cc1cc2cc(-c3cnn(C)c3)ncc2n1-c1nn(C2CCOCC2)c2c1CNCC2]

To a solution of tert-butyl 3-(2-methyl-5-(1-methyl-1H-pyrazol-4-yl)-1H-pyrrolo[2,3-c]pyridin-1-yl)-1-(tetrahydro-2H-pyran-4-yl)-6,7-dihydro-1H-pyrazolo[4,3-c]pyridine-5

(4H)-carboxylate (90 mg, 0.17 mmol) in DCM (10 mL) at 0° C. was added trifluoroacetic acid (0.06 mL, 0.87 mmol). The mixture was stirred at 0° C. for 2 h and concentrated in vacuo to give the title compound (60 mg, crude) as a yellow solid that required no further purification. LCMS M/Z (M+H) 418.

Step 3: N-methyl-3-(2-methyl-5-(1-methyl-1H-pyrazol-4-yl)-H-pyrazol-4-yl)-H-pyrrolo[2,3-c]pyridin-1-yl)-1-(tetrahydro-2H-pyran-4-yl)-6,7-dihydro-1H-pyrazolo[4,3-c]pyridine-5(4H)-carboxamide

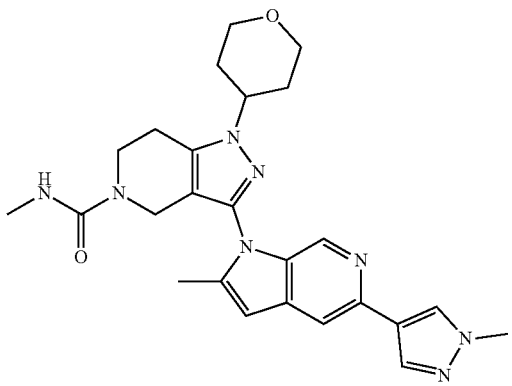

To a solution of 3-(2-methyl-5-(1-methyl-1H-pyrazol-4-yl)-1H-pyrrolo[2,3-c]pyridin-1-yl)-1-(tetrahydro-2H-pyran-4-yl)-4,5,6,7-tetrahydro-1H-pyrazolo[4,3-c]pyridine (60 mg, 0.14 mmol) in DCM (10 mL) at 0° C. was added triethylamine (0.04 mL, 0.29 mmol) and N-methyl-1H-imidazole-1-carboxamide (36 mg, 0.29 mmol). The reaction was stirred at room temperature for 16 h. DCM (40 mL) was added and washed with brine (30 mL×3). The organic layer was dried over anhydrous Na$_2$SO$_4$, filtered and concentrated in vacuo. The crude residue was purified by reverse phase chromatography (acetonitrile 28-58%/0.2% formic acid in water) to give the title compound (9 mg, 13%) as a yellow solid. $^1$H NMR (400 MHz, CDCl$_3$) δ 8.59 (s, 1H), 8.08 (s, 1H), 7.95 (s, 1H), 7.68 (s, 1H), 6.46 (s, 1H), 5.10-5.02 (m, 1H), 4.31-4.18 (m, 1H), 4.16-4.11 (m, 4H), 3.97 (s, 3H), 3.86 (t, J=5.6 Hz, 2H), 3.56 (t, J=11.6 Hz, 2H), 2.91-2.80 (m, 2H), 2.77 (d, J=3.6 Hz, 3H), 2.42 (s, 3H), 2.36-2.25 (m, 2H), 1.98-1.87 (m, 2H). LCMS M/Z (M+H) 475.

Example 41

1-(5-acetyl-1-(tetrahydro-2H-pyran-4-yl)-4,5,6,7-tetrahydro-1H-pyrazolo[4,3-c]pyridin-3-yl)-2-methyl-5-(1-methyl-1H-pyrazol-4-yl)-1H-indole-6-carbonitrile

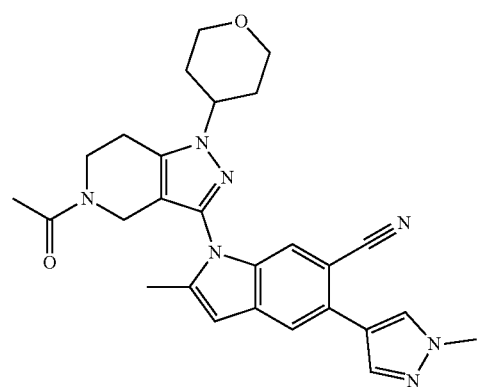 [SMILES: CC(=O)N1CCc2c(c(-n3c(C)cc4cc(-c5cnn(C)c5)c(C#N)cc43)nn2C2CCOCC2)C1]

Step 1:
5-bromo-6-chloro-1-(phenylsulfonyl)-1H-indole

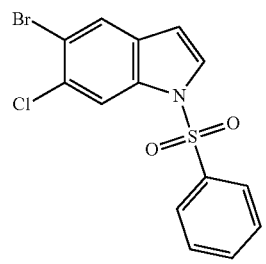 [SMILES: O=S(=O)(c1ccccc1)n1ccc2cc(Br)c(Cl)cc21]

To a stirred solution of 5-bromo-6-chloro-1H-indole (5.0 g, 21.69 mmol) in DMF (50 mL) at 0° C. was added NaH (60%, 1.3 g, 32.54 mmol) and the mixture was stirred at room temperature for 30 min. Benzenesulfonyl chloride (3.33 mL, 26.03 mmol) was added dropwise and the mixture stirred for an additional 2 h. The mixture was quenched with sat. aq. NH$_4$Cl (100 mL) and extracted with EtOAc (100 mL×3). The combined organic layers were washed with brine (50 mL×3), dried over anhydrous Na$_2$SO$_4$, filtered and concentrated in vacuo. The crude residue was recrystallized with DCM (20 mL) and TBME (200 mL) to give the title compound (6.0 g, 75%) as a yellow solid. $^1$H NMR (400 MHz, CD$_3$OD) δ 8.13 (s, 1H), 7.98-7.93 (m, 2H), 7.90 (s, 1H), 7.74 (d, J=4.0 Hz, 1H), 7.69-7.63 (m, 1H), 7.60-7.51 (m, 2H), 6.73 (d, J=4.0 Hz, 1H).

Step 2: 5-bromo-6-chloro-2-methyl-1-(phenylsulfonyl)-1H-indole

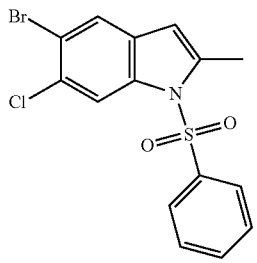 [SMILES: Cc1cc2cc(Br)c(Cl)cc2n1S(=O)(=O)c1ccccc1]

To a solution of 5-bromo-6-chloro-1-(phenylsulfonyl)-1H-indole (1.0 g, 2.56 mmol) in THF (10 mL) was added LDA (1.92 mL, 3.84 mmol, 2 M in THF). The reaction was stirred at −78° C. for 2 h under a nitrogen atmosphere. Iodomethane (0.24 mL, 3.84 mmol) was added drop wise, the cooling bath was removed and the mixture was stirred at room temperature for 1 h. The mixture was quenched with sat. aq. NH$_4$Cl (20 mL) and extracted with EtOAc (100 mL×3). The combined organic layers were dried over anhydrous Na$_2$SO$_4$, filtered and concentrated in vacuo to give the title compound (0.8 g, crude) as a yellow solid that required no further purification. $^1$H NMR (400 MHz, CDCl$_3$) δ 8.33 (s, 1H), 7.81-7.75 (m, 2H), 7.65 (s, 1H), 7.64-7.57 (m, 1H), 7.54-7.46 (m, 2H), 6.27 (s, 1H), 2.57 (s, 3H).

Step 3: 6-chloro-2-methyl-5-(1-methyl-1H-pyrazol-4-yl)-1-(phenylsulfonyl)-1H-indole

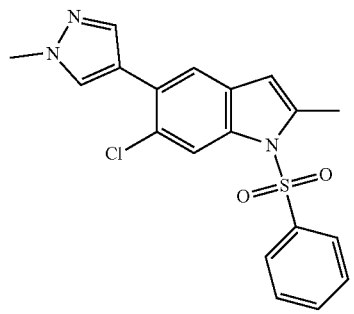 [SMILES: Cc1cc2cc(-c3cnn(C)c3)c(Cl)cc2n1S(=O)(=O)c1ccccc1]

To a solution of 5-bromo-6-chloro-2-methyl-1-(phenylsulfonyl)-1H-indole (11.76 g, 26 mmol) in 1,4-dioxane (100 mL) and water (25 mL) was added [1,1'-bis(diphenylphosphino)ferrocene]dichloropalladium(II) (1.9 g, 2.6 mmol), Na$_2$CO$_3$ (5.51 g, 51.99 mmol) and 1-methyl-4-(4,4,5,5-tetramethyl-1,3,2-dioxaborolan-2-yl)-1H-pyrazole (6.49 g, 31.19 mmol). The mixture was heated to 90° C. for 12 h under a nitrogen atmosphere. After cooling the reaction to room temperature, water (200 mL) was added and extracted with EtOAc (200 mL×3). The combined organic layers were dried over anhydrous Na$_2$SO$_4$, filtered and concentrated in vacuo. The crude residue was purified by silica gel chromatography (petroleum ether/EtOAc=2:1) to give the title compound (4.6 g, 46%) as a yellow solid. LCMS M/Z (M+H) 386.

Step 4: 6-chloro-2-methyl-5-(1-methyl-1H-pyrazol-4-yl)-1H-indole

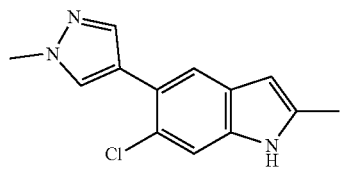

To a solution of 6-chloro-2-methyl-5-(1-methyl-1H-pyrazol-4-yl)-1-(phenylsulfonyl)-1H-indole (1.8 g, 4.66 mmol) in THF (30 mL) was added TBAF (9.33 ml, 9.33 mmol, 1 M in THF). The mixture was heated to 65° C. for 2 h under a nitrogen atmosphere. The reaction mixture was concentrated in vacuo. The crude residue was dissolved in EtOAc (100 mL) and washed with water (100 mL×3). The organic layer was dried over anhydrous Na$_2$SO$_4$, filtered and concentrated in vacuo. The crude residue was purified by silica gel chromatography (petroleum ether/EtOAc=6:1) to give the title compound (1.1 g, 86%) as a yellow solid. LCMS M/Z (M+H) 246.

Step 5: 1-(3-(6-chloro-2-methyl-5-(1-methyl-1H-pyrazol-4-yl)-1H-indol-1-yl)-1-(tetrahydro-2H-pyran-4-yl)-6,7-dihydro-1H-pyrazolo[4,3-c]pyridin-5(4H)-yl)ethanone

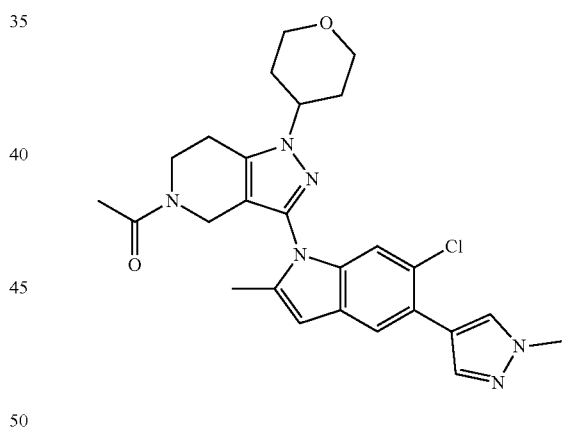

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 1.1 g, 3.35 mmol) in toluene (8 mL) was added copper(I) iodide (32 mg, 0.17 mmol), K$_3$PO$_4$ (2.85 g, 13.41 mmol), (1R,2R)-cyclohexane-1,2-diamine (77 mg, 0.67 mmol) and 6-chloro-2-methyl-5-(1-methyl-1H-pyrazol-4-yl)-1H-indole (906 mg, 3.69 mmol). The mixture was heated to 120° C. for 12 h under a nitrogen atmosphere. After cooling the reaction to room temperature, the mixture was filtered and concentrated in vacuo. The crude residue was dissolved in EtOAc (100 mL) and washed with water (100 mL×3). The organic layer was dried over anhydrous Na$_2$SO$_4$, filtered and concentrated in vacuo. The crude residue was purified by silica gel chromatography (DCM/MeOH=100:1) to give the title compound (1.0 g, 55%) as a yellow solid. LCMS M/Z (M+H) 493.

Step 6: 1-(5-acetyl-1-(tetrahydro-2H-pyran-4-yl)-4, 5,6,7-tetrahydro-1H-pyrazolo[4,3-c]pyridin-3-yl)-2-methyl-5-(1-methyl-1H-pyrazol-4-yl)-1H-indole-6-carbonitrile

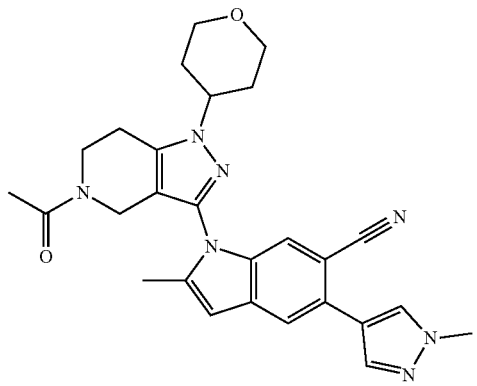 [SMILES: CC(=O)N1CCc2c(c(-n3c(C)cc4cc(-c5cnn(C)c5)c(C#N)cc43)nn2C2CCOCC2)C1]

To a solution of 1-(3-(6-chloro-2-methyl-5-(1-methyl-1H-pyrazol-4-yl)-1H-indol-1-yl)-1-(tetrahydro-2H-pyran-4-yl)-6,7-dihydro-1H-pyrazolo[4,3-c]pyridin-5 (4H)-yl)ethanone (154 mg, 0.31 mmol) in 1,4-dioxane (1.5 mL) and water (1.5 mL) was added potassium hexacyanoferrate(II) trihydrate (92 mg, 0.16 mmol), KOAc (4 mg, 0.04 mmol), methanesulfonato(2-di-t-butylphosphino-2',4',6'-tri-i-propyl-1,1'-biphenyl)(2'-amino-1,1'-biphenyl-2-yl)palladium(II) (25 mg, 0.03 mmol) and 2-di-tert-butylphosphino-2',4',6'-triisopropylbiphenyl (13 mg, 0.03 mmol). The mixture was heated to 120° C. for 12 h under a nitrogen atmosphere. After cooling the reaction to room temperature, the mixture was filtered and concentrated in vacuo. The crude residue was purified by reverse phase chromatography (acetonitrile 18-48%/ 0.2% formic acid in water) to give the title compound (15 mg, 10%) as a white solid. $^1$H NMR (400 MHz, DMSO-d$_6$) δ 8.13 (s, 1H), 7.84 (s, 1H), 7.77 (s, 1H), 7.53-7.43 (m, 1H), 6.58 (s, 1H), 4.51-4.42 (m, 1H), 4.28-4.18 (m, 2H), 4.02-3.96 (m, 2H), 3.91 (s, 3H), 3.87-3.78 (m, 2H), 3.56-3.45 (m, 2H), 3.03-2.87 (m, 2H), 2.34-2.30 (m, 3H), 2.10-1.87 (m, 7H). LCMS M/Z (M+H) 484.

Example 42

1-(3-(6-(difluoromethyl)-2-methyl-5-(1-methyl-1H-pyrazol-4-yl)-1H-indol-1-yl)-1-(tetrahydro-2H-pyran-4-yl)-6,7-dihydro-1H-pyrazolo[4,3-c]pyridin-5(4H)-yl)ethanone

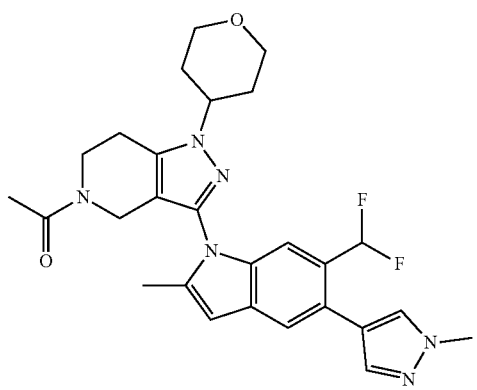 [SMILES: CC(=O)N1CCc2c(c(-n3c(C)cc4cc(-c5cnn(C)c5)c(C(F)F)cc43)nn2C2CCOCC2)C1]

Step 1: 2,2-difluoro-2-(2-methyl-5-(1-methyl-1H-pyrazol-4-yl)-1-(phenylsulfonyl)-1H-indol-6-yl)-1-phenylethanone

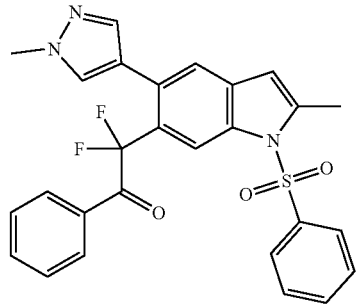 [SMILES: Cc1cc2cc(-c3cnn(C)c3)c(C(F)(F)C(=O)c3ccccc3)cc2n1S(=O)(=O)c1ccccc1]

To a solution of 6-chloro-2-methyl-5-(1-methyl-1H-pyrazol-4-yl)-1-(phenylsulfonyl)-1H-indole (4.0 g, 9.85 mmol) in toluene (40 mL) was added 2,2-difluoro-1-phenyl-ethanone (3.08 g, 19.7 mmol), chloro[(tricyclohexylphosphine)-2-(2'-aminobiphenyl)]palladium(II) (505 mg, 0.98 mmol) and K$_3$PO$_4$ (8.36 g, 39.39 mmol). The reaction mixture was heated to 120° C. for 16 h under a nitrogen atmosphere. After cooling the reaction to room temperature, water (100 mL) was added and extracted with DCM (100 mL×2). The combined organic layers were dried over anhydrous Na$_2$SO$_4$, filtered and concentrated in vacuo to give the title compound (3 g, crude) as a yellow solid that required no further purification. LCMS M/Z (M+H) 506.

Step 2: 6-(difluoromethyl)-2-methyl-5-(1-methyl-1H-pyrazol-4-yl)-1-(phenylsulfonyl)-1H-indole

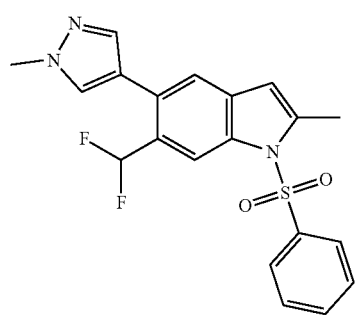 [SMILES: Cc1cc2cc(-c3cnn(C)c3)c(C(F)F)cc2n1S(=O)(=O)c1ccccc1]

To a solution of 2,2-difluoro-2-(2-methyl-5-(1-methyl-1H-pyrazol-4-yl)-1-(phenylsulfonyl)-1H-indol-6-yl)-1-phenylethanone (0.5 g, 0.30 mmol) in toluene (5 mL) and water (0.08 mL) was added KOH (50 mg, 0.89 mmol). The reaction mixture was heated to 100° C. for 6 h. After cooling the reaction to room temperature, EtOAc (100 mL) was added and washed with water (50 mL×3). The combined organic layers were dried over anhydrous Na$_2$SO$_4$, filtered and concentrated in vacuo. The crude residue was purified by silica gel chromatography (petroleum ether/EtOAc=2/1) to give the title compound (0.2 g, 50%) as a yellow solid. LCMS M/Z (M+H) 402.

Step 3: 6-(difluoromethyl)-2-methyl-5-(1-methyl-1H-pyrazol-4-yl)-1H-indole

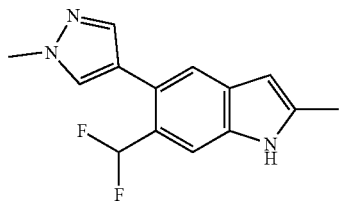

To a solution of 6-(difluoromethyl)-2-methyl-5-(1-methyl-1H-pyrazol-4-yl)-1-(phenylsulfonyl)-1H-indole (400 mg, 1.0 mmol) in THF (4 mL) was added TBAF (2.0 ml, 2.0 mmol, 1 M in THF). The mixture was heated to 65° C. for 8 h under a nitrogen atmosphere. The reaction mixture was concentrated in vacuo. The crude residue was dissolved in EtOAc (100 mL) and washed with water (100 mL×3). The organic layer was dried over anhydrous $Na_2SO_4$, filtered and concentrated in vacuo. The crude residue was purified by silica gel chromatography (petroleum ether/EtOAc=2:1) to give the title compound (150 mg, 58%) as a yellow solid. LCMS M/Z (M+H) 262.

Step 4: 1-(3-(6-(difluoromethyl)-2-methyl-5-(1-methyl-1H-pyrazol-4-yl)-1H-indol-1-yl)-1-(tetrahydro-2H-pyran-4-yl)-6,7-dihydro-1H-pyrazolo[4,3-c]pyridin-5(4H)-yl)ethanone

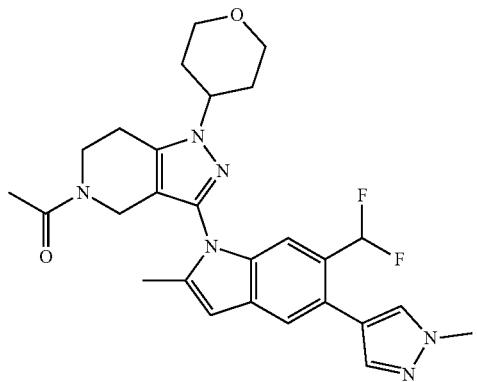 [SMILES: CC(=O)N1CCc2c(c(-n3c(C)cc4cc(-c5cnn(C)c5)c(C(F)F)cc43)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 130 mg, 0.40 mmol) in toluene (2 mL) was added copper(I) iodide (4 mg, 0.02 mmol), $K_3PO_4$ (336 mg, 1.58 mmol), (1R,2R)-cyclohexane-1,2-diamine (9 mg, 0.08 mmol) and 6-(difluoromethyl)-2-methyl-5-(1-methyl-1H-pyrazol-4-yl)-1H-indole (114 mg, 0.44 mmol). The mixture was heated to 120° C. for 12 h under a nitrogen atmosphere. After cooling the reaction to room temperature, the mixture was filtered and concentrated in vacuo. The crude residue was purified by reverse phase chromatography (acetonitrile 25-55%/0.2% formic acid in water) to give the title compound (31 mg, 15%) as a white solid. $^1$H NMR (400 MHz, DMSO-$d_6$) δ 7.84 (s, 1H), 7.58 (s, 1H), 7.57 (s, 1H), 7.30-7.26 (m, 1H), 6.96 (t, J=55.2 Hz, 1H), 6.51 (s, 1H), 4.51-4.42 (m, 1H), 4.25-4.18 (m, 2H), 4.02-3.96 (m, 2H), 3.90 (s, 3H), 3.87-3.78 (m, 2H), 3.56-3.45 (m, 2H), 3.03-2.87 (m, 2H), 2.34-2.30 (m, 3H), 2.10-1.95 (m, 7H). LCMS M/Z (M+H) 509.

Example 43

1-(1-methyl-3-(4-(1-methyl-1H-pyrazol-4-yl)benzoyl)-6,7-dihydro-1H-pyrazolo[4,3-c]pyridin-5(4H)-yl)ethanone

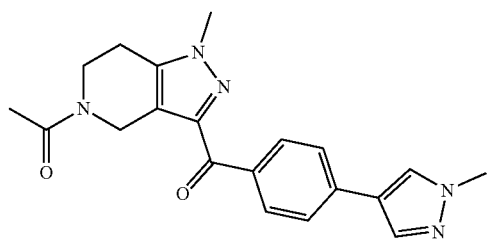 [SMILES: CC(=O)N1CCc2c(c(C(=O)c3ccc(-c4cnn(C)c4)cc3)nn2C)C1]

Step 1: methyl 4-(1-methyl-1H-pyrazol-4-yl)benzoate

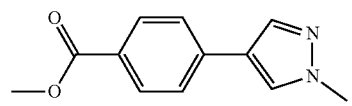

To a solution of methyl 4-bromobenzoate (10 g, 46.5 mmol) in 1,4-dioxane (75 mL) and water (25 mL) was added [1,1'-bis(diphenylphosphino)ferrocene]dichloropalladium (II) (3.4 g, 4.65 mmol), $Na_2CO_3$ (14.8 g, 139.5 mmol) and 1-methyl-4-(4,4,5,5-tetramethyl-1,3,2-dioxaborolan-2-yl)-1H-pyrazole (14.5 g, 69.8 mmol). The mixture was heated to 120° C. for 12 h under a nitrogen atmosphere. After cooling the reaction to room temperature, the mixture was filtered and concentrated in vacuo. The crude residue was purified by silica gel chromatography (petroleum ether/EtOAc=5:1) to give the title compound (4.6 g, 46%) as yellow oil.

Step 2: 4-(1-methyl-1H-pyrazol-4-yl)benzoic acid

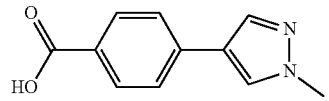

To a solution of methyl 4-(1-methyl-1H-pyrazol-4-yl)benzoate (4.6 g, 21.3 mmol) in MeOH (50 mL) was added sodium hydroxide (5M, 42.6 mL). The mixture was heated to 50° C. for 5 h. After cooling the reaction to room temperature, the mixture was washed with EtOAc (100 mL). The aqueous layer was acidified with HCl (2 N) to pH 2-3 and then extracted with EtOAc (100 mL×3). The combined organic layers were dried over anhydrous $Na_2SO_4$, filtered and concentrated in vacuo to give the title compound (3.5 g, crude) as a white solid that required no further purification.

Step 3: N-methoxy-N-methyl-4-(1-methyl-1H-pyrazol-4-yl)benzamide

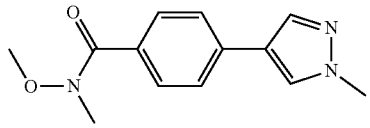

To a solution of 4-(1-methyl-1H-pyrazol-4-yl)benzoic acid (3.5 g, 17.3 mmol) in DCM (100 mL) was added N,O-dimethylhydroxylamine hydrochloride (2.0 g, 20.8 mmol), (dimethylamino)-N,N-dimethyl(3H-[1,2,3]triazolo[4,5-b]pyridin-3-yloxy)-methaniminium hexafluorophosphate (7.9 g, 20.8 mmol) and N,N-diisopropylethylamine (8.58 mL, 51.9 mmol). The mixture was stirred at room temperature for 8 h. The reaction mixture was washed with 1 N HCl (100 mL×2), dried over anhydrous $Na_2SO_4$, filtered and concentrated in vacuo. The crude residue was purified by silica gel chromatography (petroleum ether/EtOAc=3:1) to give the title compound (3.2 g, 75%) as a yellow solid.

Step 4: tert-butyl 1-methyl-3-(4-(1-methyl-1H-pyrazol-4-yl)benzoyl)-6,7-dihydro-1H-pyrazolo[4,3-c]pyridine-5(4H)-carboxylate

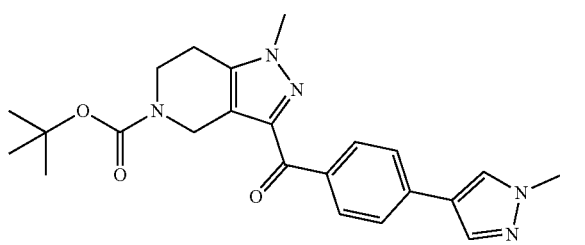 [SMILES: Cn1cc(-c2ccc(C(=O)c3nn(C)c4c3CN(C(=O)OC(C)(C)C)CC4)cc2)cn1]

To a solution of tert-butyl 3-bromo-1-methyl-6,7-dihydro-1H-pyrazolo[4,3-c]pyridine-5(4H)-carboxylate (300 mg, 0.95 mmol) in THF (6 mL) at −78° C. was slowly added n-BuLi (2.5 M, 0.46 mL, 1.14 mmol) under a nitrogen atmosphere. After stirred at −78° C. for 30 min, the mixture was added a solution of N-methoxy-N-methyl-4-(1-methyl-1H-pyrazol-4-yl)benzamide (279 mg, 1.14 mmol) in THF (0.5 mL) by dropwise. The mixture was stirred at −78° C. for an additional 2 h. The reaction mixture was quenched with water (20 mL) and extracted with EtOAc (20 mL×2). The combined organic layers were dried over anhydrous $Na_2SO_4$, filtered and concentrated in vacuo. The crude residue was purified by reverse phase chromatography (acetonitrile 45-75%/0.2% formic acid in water) to give the title compound (50 mg, 13%) as a white solid.

Step 5: (4-(1-methyl-1H-pyrazol-4-yl)phenyl)(1-methyl-4,5,6,7-tetrahydro-1H-pyrazolo[4,3-c]pyridin-3-yl)methanone

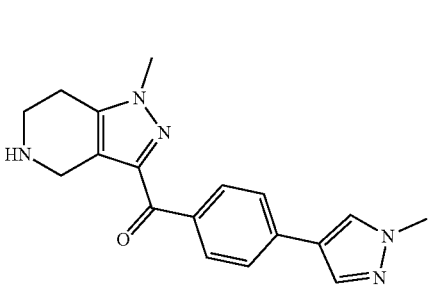 [SMILES: Cn1cc(-c2ccc(C(=O)c3nn(C)c4c3CNCC4)cc2)cn1]

A mixture of tert-butyl 1-methyl-3-(4-(1-methyl-1H-pyrazol-4-yl)benzoyl)-6,7-dihydro-1H-pyrazolo[4,3-c]pyridine-5(4H)-carboxylate (50 mg, 0.12 mmol) and trifluoroacetic acid (2 mL) in DCM (2 mL) was stirred at room temperature for 3 h. The mixture was concentrated in vacuo to give the title compound (30 mg, crude) as brown oil that required no further purification.

Step 6: 1-(1-methyl-3-(4-(1-methyl-1H-pyrazol-4-yl)benzoyl)-6,7-dihydro-1H-pyrazolo[4,3-c]pyridin-5(4H)-yl)ethanone

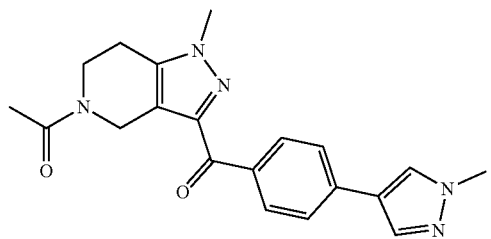 [SMILES: CC(=O)N1CCc2c(c(C(=O)c3ccc(-c4cnn(C)c4)cc3)nn2C)C1]

To a solution of (4-(1-methyl-1H-pyrazol-4-yl)phenyl)(1-methyl-4,5,6-tetrahydro-1H-pyrazolo[4,3-c]pyridin-3-yl)methanone (30 mg, 0.09 mmol) in DCM (1 mL) was added triethylamine (0.026 mL, 0.19 mmol) and acetic anhydride (0.018 mL, 0.19 mmol). The mixture was stirred at room temperature for 2 h. DCM (5 mL) was added and washed with water (5 mL×2). The organic layer was dried over anhydrous $Na_2SO_4$, filtered and concentrated in vacuo. The crude residue was purified by reverse phase chromatography (acetonitrile 32-62%/0.2% formic acid in water) to give the title compound (6 mg, 18%) as a white solid. $^1$H NMR (400 MHz, $CD_3OD$) δ 8.33-8.28 (m, 2H), 8.11 (s, 1H), 7.94 (s, 1H), 7.71-7.68 (m, 2H), 4.82 (s, 2H), 3.96 (s, 3H), 3.95-3.84 (m, 2H), 4.90 (s, 3H), 3.91-3.74 (m, 2H), 2.23-2.21 (m, 3H). LCMS M/Z (M+H) 364.

Example 44

(S)-1-(3-(6-(1-methyl-1H-pyrazol-4-yl)-3,4-dihydronaphthalen-1-yl)-1-(tetrahydrofuran-3-yl)-6,7-dihydro-1H-pyrazolo[4,3-c]pyridin-5(4H)-yl)ethanone

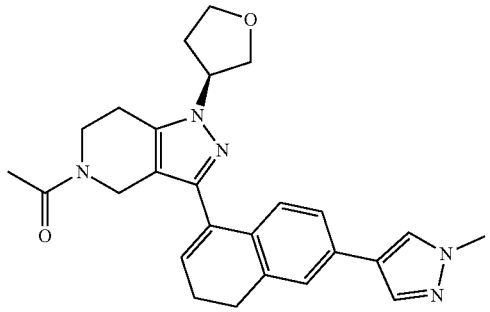

Step 1: 6-(1-methyl-1H-pyrazol-4-yl)-3,4-dihydronaphthalen-1(2H)-one

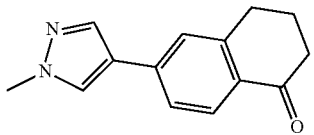 [SMILES: Cn1cc(-c2ccc3c(c2)CCCC3=O)cn1]

To a solution of 6-bromo-3,4-dihydronaphthalen-1(2H)-one (0.9 g, 4.0 mmol) in 1,4-dioxane (8 mL) and water (2 mL) was added [1,1'-bis(diphenylphosphino)ferrocene]-dichloropalladium(II) (146 mg, 0.20 mmol), $K_2CO_3$ (1.38 mg, 10.0 mmol) and 1-methyl-4-(4,4,5,5-tetramethyl-1,3,2-dioxaborolan-2-yl)-1H-pyrazole (915 mg, 4.4 mmol). The mixture was heated to 120° C. for 16 h under a nitrogen atmosphere. After cooling the reaction to room temperature, the mixture was filtered and concentrated in vacuo. The crude residue was purified by silica gel chromatography (petroleum ether/EtOAc=5:1) to give the title compound (800 mg, 88%) as yellow oil. LCMS M/Z (M+H) 227.

Step 2: 4-methyl-N'-(6-(1-methyl-1H-pyrazol-4-yl)-3,4-dihydronaphthalen-1(2H)-ylidene)benzenesulfonohydrazide

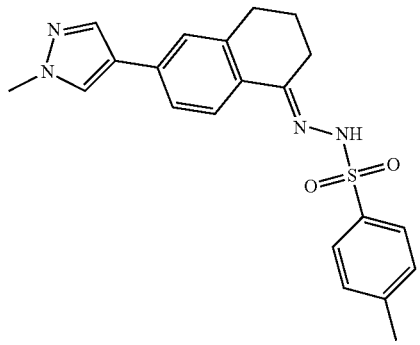 [SMILES: Cc1ccc(S(=O)(=O)N/N=C2\CCCc3cc(-c4cnn(C)c4)ccc32)cc1]

To a solution of 6-(1-methyl-1H-pyrazol-4-yl)-3,4-dihydronaphthalen-1(2H)-one (0.8 g, 3.54 mmol) in MeOH (10 mL) was added 4-methylbenzenesulfonohydrazide (725 mg, 3.89 mmol). The mixture was heated to 70° C. for 3 h under a nitrogen atmosphere. After cooling the reaction to room temperature, the mixture was filtered to give the title compound (1.2 g, 86%) as a white solid.

Step 3: (S)-1-(3-(6-(1-methyl-1H-pyrazol-4-yl)-3,4-dihydronaphthalen-1-yl)-1-(tetrahydrofuran-3-yl)-6,7-dihydro-1H-pyrazolo[4,3-c]pyridin-5(4H)-yl)ethanone

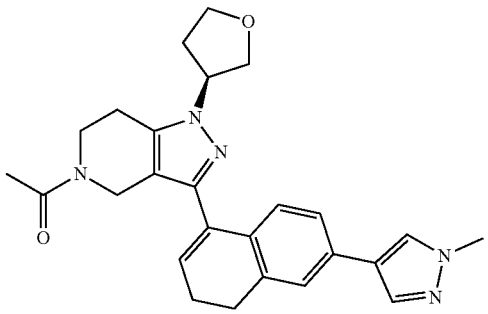 [SMILES: CC(=O)N1CCc2c(c(C3=CCCc4cc(-c5cnn(C)c5)ccc43)nn2[C@H]2CCOC2)C1]

To a solution of (S)-1-(3-bromo-1-(tetrahydrofuran-3-yl)-6,7-dihydro-1H-pyrazolo[4,3-c]pyridin-5(4H)-yl)ethanone (Intermediate E, 670 mg, 2.13 mmol) in 1,4-dioxane (5 mL) was added [1,1'-bis(diphenylphosphino)ferrocene]dichloropalladium(II) (65 mg, 0.09 mmol), t-BuOLi (312 mg, 3.9 mmol) and 4-methyl-N-(6-(1-methyl-1H-pyrazol-4-yl)-3,4-dihydronaphthalen-1(2H)-ylidene)benzenesulfonohydrazide (0.7 g, 1.77 mmol). The mixture was heated to 100° C. for 3 h under a nitrogen atmosphere. After cooling the reaction to room temperature, the mixture was filtered and concentrated in vacuo. The crude residue was purified by silica gel chromatography (DCM/MeOH=20:1) to give the title compound (680 mg, 86%) as a brown solid. $^1$H NMR (400 MHz, $CDCl_3$) δ 7.70-7.68 (m, 1H), 7.55-7.53 (m, 1H), 7.23-7.10 (m, 3H), 6.13-6.10 (m, 1H), 4.77-4.74 (m, 1H), 4.38-4.20 (m, 2H), 4.11-4.06 (m, 2H), 4.00-3.66 (m, 4H), 3.87 (s, 3H), 2.82-2.71 (m, 4H), 2.40-2.29 (m, 4H), 2.11-1.99 (m, 3H). LCMS M/Z (M+H) 444.

Example 45

N-methyl-3-(3-(2-methylthiazol-5-yl)isoquinolin-8-yl)-1-(1-oxidotetrahydro-2H-thiopyran-4-yl)-6,7-dihydro-1H-pyrazolo[4,3-c]pyridine-5(4H)-carboxamide

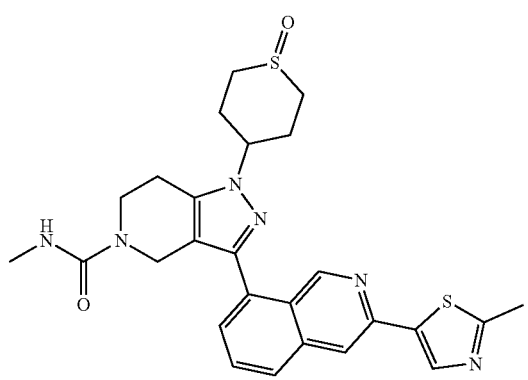

Step 1: tetrahydro-2H-thiopyran-4-yl methanesulfonate

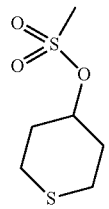

To a solution of tetrahydro-2H-thiopyran-4-ol (10 g, 84.6 mmol) and triethylamine (35.4 mL, 253.8 mmol) in DCM (150 mL) at 0° C. was added methanesulfonyl chloride (10.7 mL, 138.8 mmol) dropwise under a nitrogen atmosphere. The mixture was stirred at 25° C. for 16 h. Water (100 mL) was added and extracted with DCM (100 mL×2). The combined organic layers were dried over anhydrous $Na_2SO_4$, filtered and concentrated in vacuo to give the title compound (17 g, crude) as yellow oil that required no further purification. $^1$H NMR (400 MHz, DMSO-$d_6$) δ 4.73-4.69 (m, 1H), 3.19 (s, 3H), 2.76-2.63 (m, 4H), 2.17-2.16 (m, 2H), 1.87-1.84 (m, 2H).

Step 2: tert-butyl 3-bromo-1-(tetrahydro-2H-thiopyran-4-yl)-6,7-dihydro-1H-pyrazolo[4,3-c]pyridine-5(4H)-carboxylate

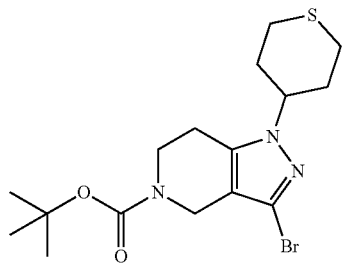 [SMILES: CC(C)(C)OC(=O)N1CCc2c(c(Br)nn2C2CCSCC2)C1]

To a solution of tert-butyl 3-bromo-6,7-dihydro-1H-pyrazolo[4,3-c]pyridine-5(4H)-carboxylate (Intermediate A, 10 g, 33.1 mmol) in DMF (50 mL) was added $Cs_2CO_3$ (27 g, 82.7 mmol) and tetrahydro-2H-thiopyran-4-yl methanesulfonate (8.4 g, 43.0 mmol). The mixture was heated to 80° C. for 16 h under a nitrogen atmosphere. After cooling the reaction to room temperature, the mixture was filtered. The mixture was diluted with EtOAc (100 mL) and washed with brine (100 mL×2). The organic layer was dried over anhydrous $Na_2SO_4$, filtered and concentrated in vacuo. The crude residue was purified by silica gel chromatography (petroleum ether:tert-butyl methyl ether:THF=from 10:1:1 to 3:1:1) to give the title compound (5.9 g, 44%) as a white solid. $^1$H NMR (400 MHz, DMSO-$d_6$) δ 4.17 (s, 2H), 4.09-4.04 (m, 1H), 3.62-3.59 (m, 2H), 2.83-2.77 (m, 2H), 2.71-2.68 (m, 4H), 2.13-2.10 (m, 2H), 2.03-1.93 (m, 2H), 1.44 (s, 9H).

Step 3: tert-butyl 3-bromo-1-(1-oxidotetrahydro-2H-thiopyran-4-yl)-6,7-dihydro-1H-pyrazolo[4,3-c]pyridine-5(4H)-carboxylate

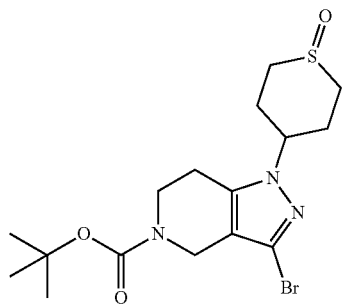 [SMILES: CC(C)(C)OC(=O)N1CCc2c(c(Br)nn2C2CCS(=O)CC2)C1]

To a solution of tert-butyl 3-bromo-1-(tetrahydro-2H-thiopyran-4-yl)-6,7-dihydro-1H-pyrazolo[4,3-c]pyridine-5(4H)-carboxylate (500 mg, 1.24 mmol) in THF (4 mL) and water (1 mL) at 0° C. was added Oxone (382 mg, 0.62 mmol) portionwise. The mixture was stirred at 25° C. for 1 h. The reaction was quenched by sat. aq. $Na_2SO_3$ (5 mL) and extracted with DCM (5 mL×3). The combined organic layers were dried over anhydrous $Na_2SO_4$, filtered and concentrated in vacuo to give the title compound (511 mg, crude) as a white solid that required no further purification. LCMS M/Z (M+H) 418.

Step 4: 5-(8-chloroisoquinolin-3-yl)-2-methylthiazole

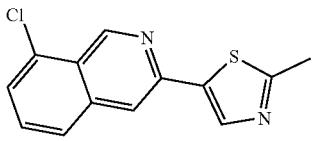 [SMILES: Cc1ncc(-c2cc3cccc(Cl)c3cn2)s1]

To a solution of 8-chloroisoquinolin-3-yl trifluoromethanesulfonate (3.0 g, 9.6 mmol) in 1,4-dioxane (10 mL) and water (2 mL) was added [1,1'-bis(diphenylphosphino)ferrocene]-dichloropalladium(II) (0.7 g, 0.96 mmol), Na$_2$CO$_3$ (3.1 g, 28.9 mmol) and 2-methyl-5-(4,4,5,5-tetramethyl-1,3,2-dioxaborolan-2-yl)thiazole (2.2 g, 9.6 mmol). The mixture was heated to 90° C. for 12 h under a nitrogen atmosphere. After cooling the reaction to room temperature, DCM (80 mL) was added and washed with water (50 mL×2), brine (30 mL). The organic layer was dried over anhydrous Na$_2$SO$_4$, filtered and concentrated in vacuo. The crude residue was purified by silica gel chromatography (petroleum ether/EtOAc=2:1) to give the title compound (0.8 g, 32%) as a yellow solid. LCMS M/Z (M+H) 261.

Step 5: 2-methyl-5-(8-(4,4,5,5-tetramethyl-1,3,2-dioxaborolan-2-yl)isoquinolin-3-yl)thiazole

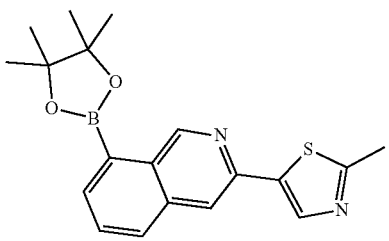

To a solution of 5-(8-chloroisoquinolin-3-yl)-2-methylthiazole (300 mg, 1.1 mmol) in 1,4-dioxane (4 mL) was added 2-(dicyclohexylphosphino)-2',4',6'-triisopropylbiphenyl (55 mg, 0.1 mmol), chloro(2-dicyclohexylphosphino-2',4',6'-tri-i-propyl-1,1'-biphenyl)(2'-amino-1,1'-biphenyl-2-yl) palladium(II) (90 mg, 0.1 mmol), KOAc (282 mg, 2.9 mmol) and 4,4,4',4',5,5,5',5'-octamethyl-2,2'-bi(1,3,2-dioxaborolane) (876 mg, 3.5 mmol). The mixture was heated to 90° C. for 1 h under a nitrogen atmosphere. After cooling the reaction to room temperature, the reaction mixture was used to the next step directly without further purification. LCMS M/Z (M+H) 353.

Step 6: tert-butyl 3-(3-(2-methylthiazol-5-yl)isoquinolin-8-yl)-1-(1-oxidotetrahydro-2H-thiopyran-4-yl)-6,7-dihydro-1H-pyrazolo[4,3-c]pyridine-5(4H)-carboxylate

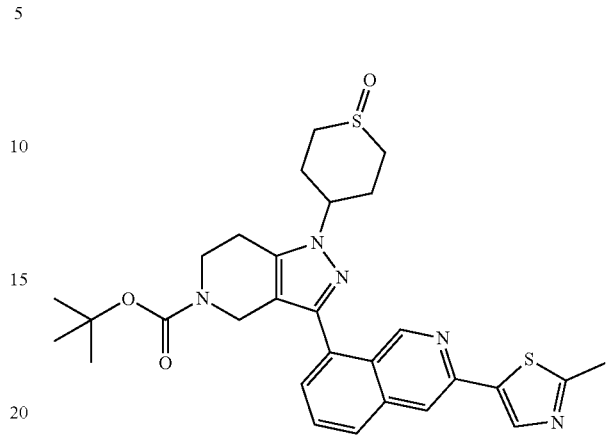

To the above step cooled solution was added tert-butyl 3-bromo-1-(1-oxidotetrahydro-2H-thiopyran-4-yl)-6,7-dihydro-1H-pyrazolo[4,3-c]pyridine-5 (4H)-carboxylate (100 mg, 0.2 mmol), chloro(2-dicyclohexylphosphino-2',4',6'-tri-i-propyl-1,1'-biphenyl)(2'-amino-1,1'-biphenyl-2-yl) palladium(II) (19 mg, 0.02 mmol), K$_3$PO$_4$ (152 mg, 0.7 mmol), 1,4-dioxane (4 mL) and water (2 mL). The reaction mixture was heated to 90° C. for 4 h under a nitrogen atmosphere. After cooling to room temperature, the mixture was filtered and concentrated in vacuo. DCM (60 mL) was added and washed with water (50 mL×2), brine (50 mL). The organic layer was dried over anhydrous Na$_2$SO$_4$, filtered and concentrated in vacuo. The crude residue was purified by silica gel chromatography (DCM/MeOH=50:1) to give the title compound (55 mg, 41%) as a brown solid. LCMS M/Z (M+H) 564.

Step 7: 4-(3-(3-(2-methylthiazol-5-yl)isoquinolin-8-yl)-4,5,6,7-tetrahydro-1H-pyrazolo[4,3-c]pyridin-1-yl)tetrahydro-2H-thiopyran 1-oxide

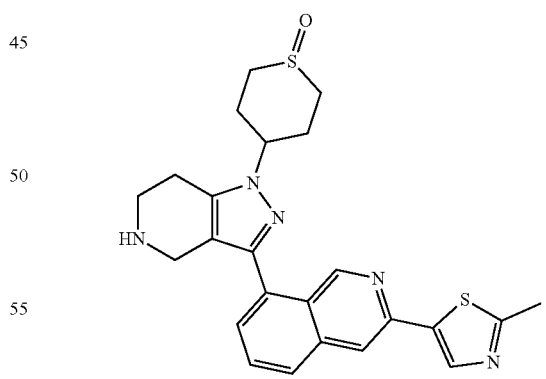

To a solution of tert-butyl 3-(3-(2-methylthiazol-5-yl)isoquinolin-8-yl)-1-(1-oxidotetrahydro-2H-thiopyran-4-yl)-6,7-dihydro-1H-pyrazolo[4,3-c]pyridine-5 (4H)-carboxylate (55 mg, 0.1 mmol) in DCM (2 mL) was added trifluoroacetic acid (1.0 mL, 12 mmol). The mixture was stirred at room temperature for 2 h and concentrated in vacuo to give the title compound (40 mg, crude) as a yellow solid that required no further purification. LCMS M/Z (M+H) 464.

Step 8: N-methyl-3-(3-(2-methylthiazol-5-yl)isoquinolin-8-yl)-1-(1-oxidotetrahydro-2H-thiopyran-4-yl)-6,7-dihydro-1H-pyrazolo[4,3-c]pyridine-5(4H)-carboxamide

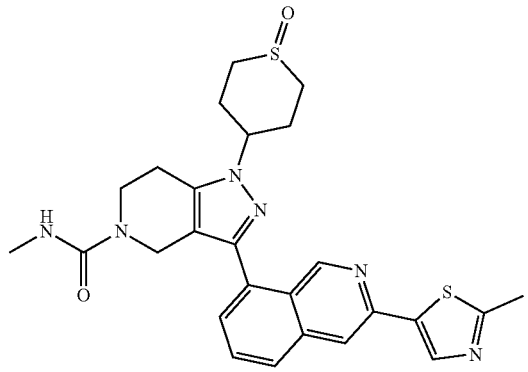

To a solution of 4-(3-(3-(2-methylthiazol-5-yl)isoquinolin-8-yl)-4,5,6,7-tetrahydro-1H-pyrazolo[4,3-c]pyridin-1-yl)tetrahydro-2H-thiopyran 1-oxide (40 mg, 0.09 mmol) in DCM (3 mL) was added triethylamine (0.06 mL, 0.43 mmol) and N-methyl-1H-imidazole-1-carboxamide (54 mg, 0.4 mmol). The reaction was stirred at room temperature for 5 h and concentrated in vacuo. DCM (30 mL) was added and washed with water (10 mL×3), brine (10 mL). The organic layer was dried over anhydrous Na$_2$SO$_4$, filtered and concentrated in vacuo. The crude residue was purified by reverse phase chromatography (acetonitrile 20-50%/0.05% NH$_4$OH in water) to give the title compound (0.7 mg, 2%) as a yellow solid. $^1$H NMR (400 MHz, DMSO-d$_6$) δ 9.74 (s, 1H), 8.42 (s, 1H), 8.38 (s, 1H), 7.98 (d, J=8.0 Hz, 1H), 7.90-7.83 (m, 1H), 7.62 (d, J=7.2 Hz, 1H), 6.65-6.56 (m, 1H), 4.65-4.54 (m, 1H), 4.42 (s, 2H), 3.76-3.67 (m, 2H), 2.95-2.89 (m, 2H), 2.86-2.67 (m, 2H), 2.71 (s, 3H), 2.51-2.12 (m, 9H). LCMS M/Z (M+H) 521.

Example 46

1-(1-acetylpiperidin-4-yl)-N-methyl-3-(3-(2-methylthiazol-5-yl)isoquinolin-8-yl)-6,7-dihydro-1H-pyrazolo[4,3-c]pyridine-5(4H)-carboxamide

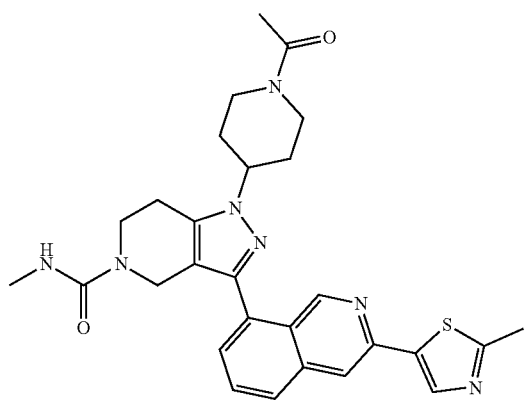

Step 1: 1-acetylpiperidin-4-yl methanesulfonate

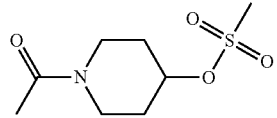

To a solution of 1-(4-hydroxy-1-piperidyl)ethanone (200 mg, 1.4 mmol) in DCM (5 mL) at 0° C. was added triethylamine (212 mg, 2.1 mmol) and methanesulfonyl chloride (480 mg, 4.19 mmol). The mixture was stirred at 25° C. for 2 h. Water (50 mL) was added and the mixture was extracted with DCM (50 mL×3). The combined organic layers were dried over anhydrous Na$_2$SO$_4$, filtered and concentrated in vacuo to give the title compound (300 mg, crude) as yellow oil that required no further purification. $^1$H NMR (400 MHz, CDCl$_3$) δ 4.98-4.92 (m, 1H), 3.83-3.81 (m, 1H), 3.67-3.65 (m, 1H), 3.58-3.56 (m, 1H), 3.43-3.41 (m, 1H), 3.06 (s, 3H), 2.01 (s, 3H), 2.00-1.88 (m, 4H).

Step 2: tert-butyl 1-(1-acetylpiperidin-4-yl)-3-bromo-6,7-dihydro-1H-pyrazolo[4,3-c]pyridine-5(4H)-carboxylate

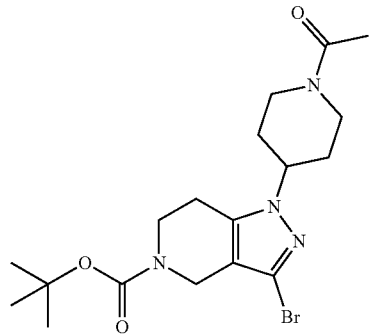 [SMILES: CC(=O)N1CCC(n2nc(Br)c3c2CCN(C(=O)OC(C)(C)C)C3)CC1]

To a solution of tert-butyl 3-bromo-6,7-dihydro-1H-pyrazolo[4,3-c]pyridine-5(4H)-carboxylate (Intermediate A, 5.0 g, 16.6 mmol) in DMF (40 mL) was added Cs$_2$CO$_3$ (19.5 g, 59.6 mmol) and 1-acetylpiperidin-4-yl methanesulfonate (5.5 g, 24.8 mmol). The mixture was heated to 90° C. for 12 h under a nitrogen atmosphere. After cooling to room temperature, the mixture was filtered and concentrated in vacuo. DCM (100 mL) was added and washed with brine (80 mL×2). The organic layer was dried over anhydrous Na$_2$SO$_4$, filtered and concentrated in vacuo. The crude residue was purified by silica gel chromatography (petroleum ether:tert-butyl methyl ether:THF=from 10:1:1 to 2:1:1) to give the title compound (2.0 g, 28%) as clear oil. $^1$H NMR (400 MHz, DMSO-d$_6$) δ 4.50-4.41 (m, 1H), 4.38-4.29 (m, 1H), 4.16 (s, 2H), 3.94-3.85 (m, 1H), 3.64-3.57 (m, 2H), 3.21-3.09 (m, 1H), 2.75-2.58 (m, 3H), 2.03 (s, 3H), 1.91-1.80 (m, 3H), 1.73-1.61 (m, 1H), 1.41 (s, 9H).

Step 3: tert-butyl 1-(1-acetylpiperidin-4-yl)-3-(4,4,5,5-tetramethyl-1,3,2-dioxaborolan-2-yl)-6,7-dihydro-1H-pyrazolo[4,3-c]pyridine-5(4H)-carboxylate

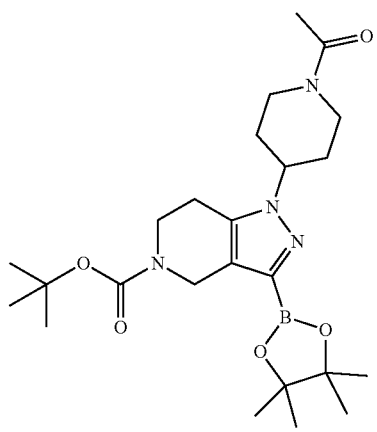 [SMILES: CC(=O)N1CCC(n2nc(B3OC(C)(C)C(C)(C)O3)c3c2CCN(C(=O)OC(C)(C)C)C3)CC1]

To a solution of tert-butyl 1-(1-acetylpiperidin-4-yl)-3-bromo-6,7-dihydro-1H-pyrazolo[4,3-c]pyridine-5(4H)-carboxylate (500 mg, 1.17 mmol) in 1,4-dioxane (10 mL) was added 2-(dicyclohexylphosphino)-2',4',6'-triisopropylbiphenyl (56 mg, 0.12 mmol), chloro(2-dicyclohexylphosphino-2',4',6'-tri-i-propyl-1,1'-biphenyl)(2'-amino-1,1'-biphenyl-2-yl) palladium(II) (92 mg, 0.12 mmol), KOAc (345 mg, 3.51 mmol) and 4,4,4',4',5,5,5',5'-octamethyl-2,2'-bi(1,3,2-dioxaborolane) (740 mg, 2.93 mmol). The mixture was heated to 80° C. for 2 h under a nitrogen atmosphere. After cooling the reaction to room temperature, the reaction mixture was used to the next step directly without further purification. LCMS M/Z (M+H) 475.

Step 4: tert-butyl 1-(1-acetylpiperidin-4-yl)-3-(3-(2-methylthiazol-5-yl)isoquinolin-8-yl)-6,7-dihydro-1H-pyrazolo[4,3-c]pyridine-5(4H)-carboxylate

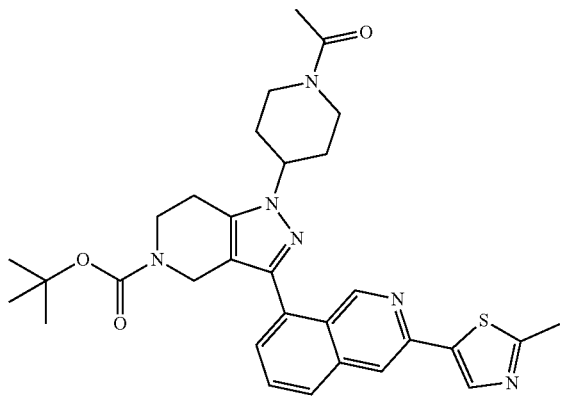 [SMILES: CC(=O)N1CCC(n2nc(-c3cccc4cc(-c5cnc(C)s5)ncc34)c3c2CCN(C(=O)OC(C)(C)C)C3)CC1]

To the above step cooled solution was added 5-(8-chloroisoquinolin-3-yl)-2-methylthiazole (302 mg, 1.16 mmol), chloro(2-dicyclohexylphosphino-2',4',6'-tri-i-propyl-1,1'-biphenyl)(2'-amino-1,1'-biphenyl-2-yl) palladium(II) (45 mg, 0.06 mmol), K₃PO₄ (738 mg, 3.48 mmol), 1,4-dioxane (5 mL) and water (3 mL). The reaction mixture was heated to 90° C. for 12 h under a nitrogen atmosphere. After cooling to room temperature, the mixture was filtered and concentrated in vacuo. DCM (20 mL) was added and washed with water (15 mL×2), brine (20 mL). The organic layer was dried over anhydrous Na₂SO₄, filtered and concentrated in vacuo. The crude residue was purified by silica gel chromatography (DCM/MeOH=20:1) to give the title compound (200 mg, 30%) as a yellow solid. LCMS M/Z (M+H) 573.

Step 5: 1-(4-(3-(3-(2-methylthiazol-5-yl)isoquinolin-8-yl)-4,5,6,7-tetrahydro-1H-pyrazolo[4,3-c]pyridin-1-yl)piperidin-1-yl)ethanone

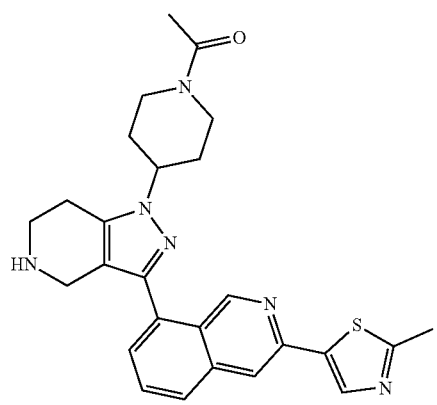 [SMILES: CC(=O)N1CCC(n2nc(-c3cccc4cc(-c5cnc(C)s5)ncc34)c3c2CCNC3)CC1]

To a solution of tert-butyl 1-(1-acetylpiperidin-4-yl)-3-(3-(2-methylthiazol-5-yl)isoquinolin-8-yl)-6,7-dihydro-1H-pyrazolo[4,3-c]pyridine-5(4H)-carboxylate (200 mg, 0.35 mmol) in DCM (3 mL) was added trifluoroacetic acid (0.27 mL, 3.6 mmol). The mixture was stirred at room temperature for 2 h and concentrated in vacuo to give the title compound (100 mg, crude) as yellow oil that required no further purification. LCMS M/Z (M+H) 473.

Step 6: 1-(1-acetylpiperidin-4-yl)-N-methyl-3-(3-(2-methylthiazol-5-yl)isoquinolin-8-yl)-6,7-dihydro-1H-pyrazolo[4,3-c]pyridine-5(4H)-carboxamide

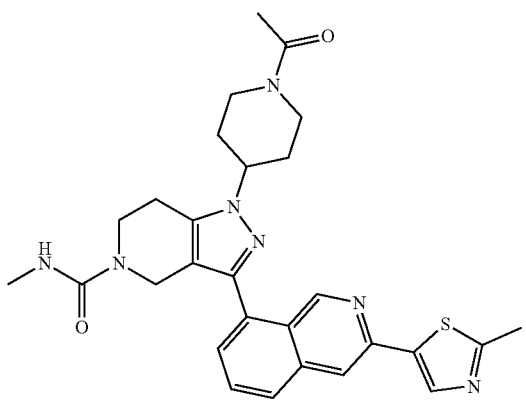

To a solution of 1-(4-(3-(3-(2-methylthiazol-5-yl)isoquinolin-8-yl)-4,5,6,7-tetrahydro-1H-pyrazolo[4,3-c]pyridin-1-yl)piperidin-1-yl)ethanone (100 mg, 0.21 mmol) in DCM (2 mL) was added triethylamine (0.1 mL, 0.70 mmol) and N-methyl-1H-imidazole-1-carboxamide (58 mg, 0.47 mmol). The reaction was stirred at room temperature for 12 h and concentrated in vacuo. The crude residue was purified by reverse phase chromatography (acetonitrile 30-60%/0.05% NH₄OH in water) to give the title compound (62 mg, 55%) as a white solid. ¹H NMR (400 MHz, CDCl₃) δ 9.58 (s, 1H), 8.16 (s, 1H), 7.93 (s, 1H), 7.81 (d, J=8.4 Hz, 1H), 7.73-7.68 (m, 1H), 7.51 (d, J=7.2 Hz, 1H), 4.83-4.78 (m, 1H), 4.65-4.59 (m, 1H), 4.34 (s, 2H), 4.32-4.22 (m, 1H), 4.07-4.00 (m, 1H), 3.94-3.82 (m, 2H), 3.30-3.21 (m, 1H), 2.88-2.83 (m, 2H), 2.78 (d, J=4.8 Hz, 1H), 2.76 (s, 3H), 2.42-2.30 (m, 1H), 2.21-2.00 (m, 6H). LCMS M/Z (M+H) 530.

Example 47

3-isopropyl-N-methyl-1-(3-(1-methyl-1H-pyrazol-4-yl)isoquinolin-8-yl)-4,5-dihydro-1H-pyrazolo[3,4-c]pyridine-6(7H)-carboxamide

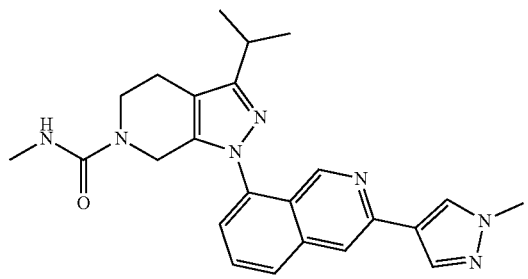

Step 1: ethyl 2-(benzyl(3-cyanopropyl)amino)acetate

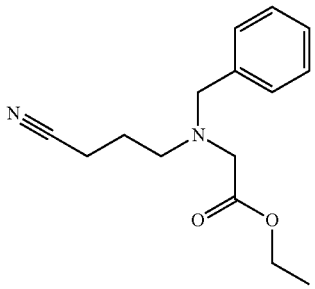 [SMILES: CCOC(=O)CN(CCCC#N)Cc1ccccc1]

To a solution of ethyl 2-(benzylamino)acetate (50 g, 258.7 mmol) and K₂CO₃ (71.5 g, 517.5 mmol) in MeCN (500 mL) was added 4-bromobutyronitrile (28.7 mL, 284.6 mmol) dropwise. The mixture was heated to 80° C. for 12 h under a nitrogen atmosphere. After cooling to room temperature, the mixture was filtered and concentrated in vacuo. The crude residue was purified by silica gel chromatography (petroleum ether/EtOAc=5:1) to give the title compound (56 g, 83%) as light yellow oil. ¹H NMR (400 MHz, CDCl₃) δ 7.37-7.28 (m, 5H), 4.18 (q, J=7.2 Hz, 2H), 3.80 (s, 2H), 3.32 (s, 2H), 2.80 (t, J=6.4 Hz, 2H), 2.47 (t, J=7.2 Hz, 2H), 1.87-1.77 (m, 2H), 1.29 (t, J=7.2 Hz, 3H).

Step 2: ethyl 2-((tert-butoxycarbonyl)(3-cyanopropyl)amino)acetate

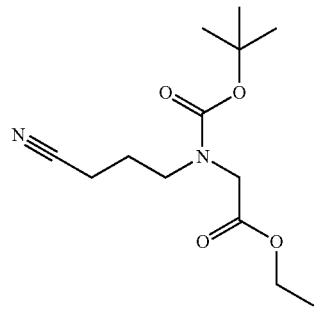 [SMILES: CCOC(=O)CN(CCCC#N)C(=O)OC(C)(C)C]

To a solution of ethyl 2-(benzyl(3-cyanopropyl)amino)acetate (22 g, 84.5 mmol) and Boc₂O (38.8 mL, 169 mmol) in EtOH (150 mL) was added 10% Pd/C (2.3 g). The mixture was stirred at room temperature for 6 h under a hydrogen atmosphere (40 Psi). The mixture was filtered and the filtrate was concentrated in vacuo. The crude residue was purified by silica gel chromatography (petroleum ether/EtOAc=3:1) to give the title compound (17 g, 74%) as colorless oil. ¹H NMR (400 MHz, CDCl₃) δ 4.25-4.14 (m, 2H), 3.94-3.82 (m, 2H), 3.43-3.39 (m, 2H), 2.49-2.41 (m, 2H), 1.96-1.84 (m, 2H), 1.51-1.37 (m, 9H), 1.30-1.27 (m, 2H).

Step 3: tert-butyl 4-cyano-3-oxopiperidine-1-carboxylate

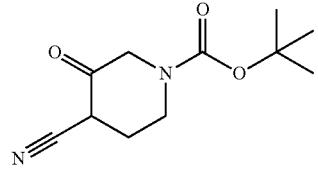 [SMILES: CC(C)(C)OC(=O)N1CCC(C#N)C(=O)C1]

To a solution of t-BuOK (8.5 g, 75.5 mmol) in toluene (100 mL) at 0° C. was added ethyl 2-((tert-butoxycarbonyl)(3-cyanopropyl)amino)acetate (17 g, 62.9 mmol). The mixture was stirred at room temperature for 30 min under a nitrogen atmosphere. Sat. aq. NH₄Cl (200 mL) was added and washed with hexanes (200 mL). The aqueous phase was acidified with HCl (2 N) to pH 6 and then extracted with EtOAc (200 mL×2). The combined organic layers were dried over anhydrous Na₂SO₄, filtered and concentrated in vacuo to give the title compound (13 g, 92%) as yellow oil that required no further purification.

Step 4: tert-butyl 3-amino-4,5-dihydro-1H-pyrazolo[3,4-c]pyridine-6(7H)-carboxylate

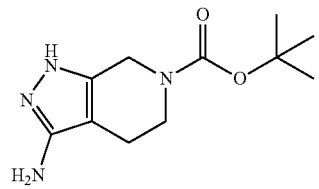 [SMILES: CC(C)(C)OC(=O)N1CCc2c(N)n[nH]c2C1]

A mixture of tert-butyl 4-cyano-3-oxopiperidine-1-carboxylate (13 g, 57.9 mmol) and hydrazine mono-hydrate (85%, 6.6 mL, 116 mmol) in EtOH (100 mL) was heated to 60° C. for 3 h. The mixture was concentrated in vacuo to give the crude product that was dissolved in EtOAc (150 mL) and washed with sat. aq. Na$_2$CO$_3$ (100 mL), water (100 mL). The organic layer was dried over anhydrous Na$_2$SO$_4$, filtered and concentrated in vacuo. The crude residue was purified by silica gel chromatography (DCM/MeOH=20:1) to give the title compound (10 g, 72%) as a white solid. $^1$H NMR (400 MHz, DMSO-d$_6$) δ 4.28 (s, 2H), 3.48 (d, J=5.6 Hz, 2H), 2.27 (d, J=5.6 Hz, 2H), 1.40 (s, 9H).

Step 5: tert-butyl 3-bromo-4,5-dihydro-1H-pyrazolo[3,4-c]pyridine-6(7H)-carboxylate

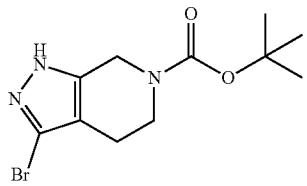 [SMILES: CC(C)(C)OC(=O)N1CCc2c(Br)n[nH]c2C1]

To a stirred mixture of tert-butyl 3-amino-4,5-dihydro-1H-pyrazolo[3,4-c]pyridine-6(7H)-carboxylate (10 g, 42 mmol), CuBr$_2$ (10.3 g, 46.2 mmol) in MeCN (80 mL) at 0° C. was added isopentyl nitrite (7.4 mL, 54.6 mmol) dropwise and the reaction mixture stirred for 20 min. The temperature was raised to 60° C. and the reaction mixture was stirred for an additional 5 h. After cooling the reaction to room temperature, the reaction mixture was quenched with water (200 mL) and the mixture was extracted with EtOAc (200 mL×2). The combined organic layers were dried over anhydrous Na$_2$SO$_4$, filtered and concentrated in vacuo. The crude residue was purified by silica gel chromatography (petroleum ether/EtOAc=1:1) to give the title compound (6 g, 47%) as a white solid. $^1$H NMR (400 MHz, DMSO-d$_6$) δ 4.45 (s, 2H), 3.55 (d, J=5.6 Hz, 2H), 2.35 (d, J=5.6 Hz, 2H), 1.41 (s, 9H).

Step 6: tert-butyl 3-(prop-1-en-2-yl)-4,5-dihydro-1H-pyrazolo[3,4-c]pyridine-6(7H)-carboxylate

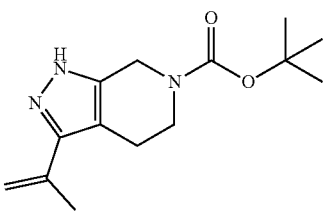 [SMILES: C=C(C)c1n[nH]c2c1CCN(C(=O)OC(C)(C)C)C2]

To a solution of tert-butyl 3-bromo-4,5-dihydro-1H-pyrazolo[3,4-c]pyridine-6(7H)-carboxylate (2 g, 6.6 mmol) in 1,4-dioxane (25 mL) and water (5 mL) was added [1,1'-bis(diphenylphosphino)ferrocene]dichloropalladium(II) (484 mg, 0.7 mmol), Na$_2$CO$_3$ (2.1 g, 19.9 mmol) and 4,4,5,5-tetramethyl-2-(prop-1-en-2-yl)-1,3,2-dioxaborolane (5.6 g, 33.1 mmol). The mixture was heated to 100° C. for 12 h under a nitrogen atmosphere. After cooling the reaction to room temperature, the mixture was filtered and concentrated in vacuo. EtOAc (150 mL) was added and washed with water (140 mL×2). The organic layer was dried over anhydrous Na$_2$SO$_4$, filtered and concentrated in vacuo. The crude residue was purified by silica gel chromatography (petroleum ether/EtOAc=3:1) to give the title compound (1.3 g, 73%) as a yellow solid. $^1$H NMR (400 MHz, DMSO-d$_6$) δ 12.72-12.35 (m, 1H), 5.23 (s, 1H), 5.08 (s, 1H), 4.41 (s, 2H), 3.60-3.49 (m, 2H), 2.67-2.55 (m, 2H), 2.05 (s, 3H), 1.41 (s, 9H).

Step 7: tert-butyl 3-isopropyl-4,5-dihydro-1H-pyrazolo[3,4-c]pyridine-6(7H)-carboxylate

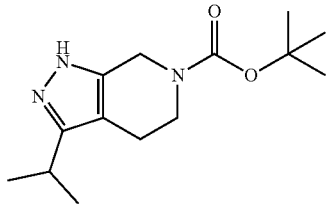 [SMILES: CC(C)c1n[nH]c2c1CCN(C(=O)OC(C)(C)C)C2]

a solution of tert-butyl 3-(prop-1-en-2-yl)-4,5-dihydro-1H-pyrazolo[3,4-c]pyridine-6(7H)-carboxylate (1.2 g, 4.6 mmol) in MeOH (8 mL) was added 10% Pd/C (485 mg). The mixture was stirred at room temperature for 12 h under a hydrogen atmosphere (15 Psi). The mixture was filtered and the filtrate was concentrated in vacuo to give the title compound (860 mg, 71%) as a white solid. $^1$H NMR (400 MHz, DMSO-d$_6$) δ 12.24 (s, 1H), 4.37 (s, 2H), 3.52 (d, J=6.0 Hz, 2H), 2.98-2.85 (m, 1H), 2.48 (d, J=6.0 Hz, 2H), 1.41 (s, 9H), 1.18 (d, J=7.2 Hz, 6H).

Step 8: tert-butyl 3-isopropyl-1-(3-(1-methyl-1H-pyrazol-4-yl)isoquinolin-8-yl)-4,5-dihydro-1H-pyrazolo[3,4-c]pyridine-6(7H)-carboxylate

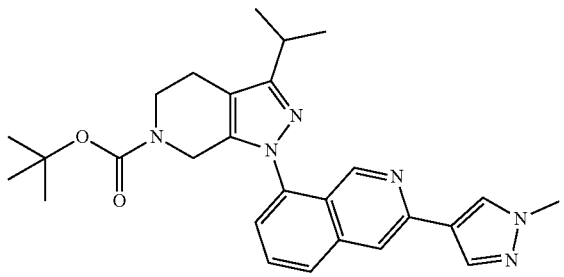 [SMILES: CC(C)c1nn(-c2cccc3cc(-c4cnn(C)c4)ncc23)c2c1CCN(C(=O)OC(C)(C)C)C2]

To a solution of tert-butyl 3-isopropyl-4,5-dihydro-1H-pyrazolo[3,4-c]pyridine-6(7H)-carboxylate (240 mg, 0.9 mmol) in toluene (8 mL) was added tris(dibenzylideneacetone)-dipalladium (83 mg, 0.09 mmol), 2-di-tert-butylphosphino-2',4',6'-triisopropylbiphenyl (38 mg, 0.09 mmol), t-BuONa (261 mg, 2.7 mmol) and 8-chloro-3-(1-methyl-1H-pyrazol-4-yl)isoquinoline (286 mg, 1.2 mmol). The mixture was heated to 110° C. for 12 h under a nitrogen atmosphere. After cooling the reaction to room temperature, the mixture was filtered and concentrated in vacuo. EtOAc (50 mL) was added and washed with water (40 mL) and brine (40 mL). The organic phase was dried over anhydrous Na$_2$SO$_4$, filtered and concentrated in vacuo. The crude residue was purified by silica gel chromatography (petroleum ether/EtOAc=2:1) to give the title compound (150 mg, 35%) as a yellow solid. ¹H NMR (400 MHz, CDCl₃) δ 9.02 (s, 1H), 8.05 (s, 1H), 8.01 (s, 1H), 7.89-7.76 (m, 2H), 7.73-7.59 (m, 1H), 7.44 (d, J=7.6 Hz, 1H), 4.36 (s, 2H), 3.99 (s, 3H), 3.76-3.67 (m, 2H), 3.12-3.05 (m, 1H), 2.76-2.67 (m, 2H), 1.44 (s, 9H), 1.37 (d, J=6.4 Hz, 6H).

Step 9: 8-(3-isopropyl-4,5,6,7-tetrahydro-1H-pyrazolo[3,4-c]pyridin-1-yl)-3-(1-methyl-1H-pyrazol-4-yl)isoquinoline

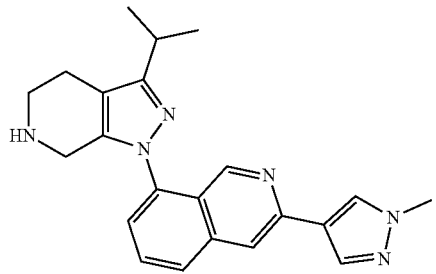 [SMILES: CC(C)c1nn(-c2cccc3cc(-c4cnn(C)c4)ncc23)c2c1CCNC2]

To a solution of tert-butyl 3-isopropyl-1-(3-(1-methyl-1H-pyrazol-4-yl)isoquinolin-8-yl)-4,5-dihydro-1H-pyrazolo[3,4-c]pyridine-6(7H)-carboxylate (150 mg, 0.32 mmol) in DCM (0.5 mL) was added trifluoroacetic acid (0.46 mL, 6.35 mmol). The mixture was stirred at room temperature for 12 h and concentrated in vacuo to give the title compound (120 mg, crude) as brown oil that required no further purification. LCMS M/Z (M+H) 373.

Step 10: 3-isopropyl-N-methyl-1-(3-(1-methyl-1H-pyrazol-4-yl)isoquinolin-8-yl)-4,5-dihydro-1H-pyrazolo[3,4-c]pyridine-6(7H)-carboxamide

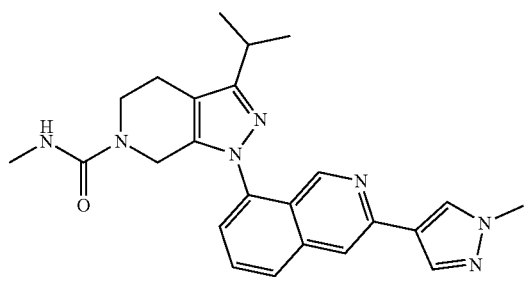

To a solution of 8-(3-isopropyl-4,5,6,7-tetrahydro-1H-pyrazolo[3,4-c]pyridin-1-yl)-3-(1-methyl-1H-pyrazol-4-yl)isoquinoline (120 mg, 0.32 mmol) in DCM (2 mL) was added triethylamine (0.09 mL, 0.64 mmol) and N-methyl-1H-imidazole-1-carboxamide (81 mg, 0.64 mmol). The reaction was stirred at room temperature for 12 h and concentrated in vacuo. DCM (50 mL) was added and washed with water (40 mL), brine (40 mL). The organic layer was dried over anhydrous Na₂SO₄, filtered and concentrated in vacuo. The crude residue was purified by Prep-TLC (DCM/MeOH=10:1) to give the title compound (62 mg, 45%) as a white solid. ¹H NMR (400 MHz, CDCl₃) δ 8.99 (s, 1H), 8.03 (s, 1H), 8.00 (s, 1H), 7.83 (d, J=8.4 Hz, 1H), 7.80 (s, 1H), 7.70-7.66 (m, 1H), 7.43 (d, J=7.6 Hz, 1H), 4.62-4.46 (m, 1H), 4.35 (s, 2H), 3.97 (s, 3H), 3.65 (d, J=5.6 Hz, 2H), 3.12-3.02 (m, 1H), 2.77 (d, J=4.4 Hz, 3H), 2.74 (d, J=5.6 Hz, 2H), 1.35 (d, J=6.8 Hz, 6H). LCMS M/Z (M+H) 430.

Example 48

N-methyl-1-(3-(1-methyl-1H-pyrazol-4-yl)isoquinolin-8-yl)-3-morpholino-4,5-dihydro-1H-pyrazolo[3,4-c]pyridine-6(7H)-carboxamide

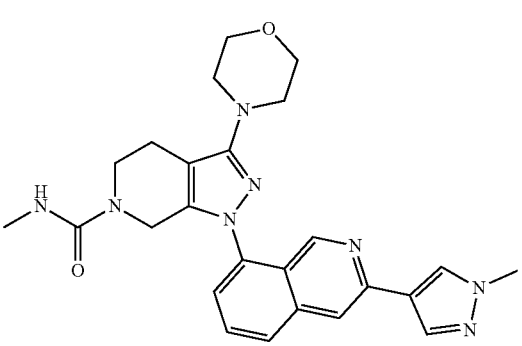

Step 1: 3-(1-methyl-1H-pyrazol-4-yl)-8-(4,4,5,5-tetramethyl-1,3,2-dioxaborolan-2-yl)isoquinoline

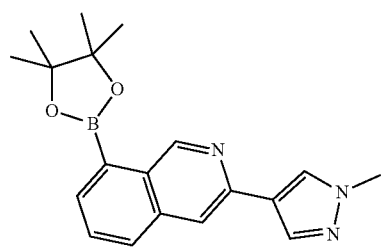

To a solution of 8-chloro-3-(1-methyl-1H-pyrazol-4-yl)isoquinoline (10.0 g, 41.04 mmol) in 1,4-dioxane (220 mL) was added 2-(dicyclohexylphosphino)-2',4',6'-triisopropylbiphenyl (1.96 g, 4.1 mmol) and chloro(2-dicyclohexylphosphino-2',4',6'-tri-i-propyl-1,1'-biphenyl)(2'-amino-1,1'-biphenyl-2-yl) palladium(II) (3.23 g, 4.1 mmol), KOAc (10.1 g, 102.59 mmol) and 4,4,4',4',5,5,5',5'-octamethyl-2,2'-bi(1,3,2-dioxaborolane) (31.26 g, 123.11 mmol). The mixture was heated to 90° C. for 1 h under a nitrogen atmosphere. After cooling to room temperature, EtOAc (400 mL) was added and washed with water (200 mL×2). The organic layer was dried over anhydrous Na₂SO₄, filtered and concentrated in vacuo. The crude residue was purified by silica gel chromatography (petroleum ether/EtOAc=1:1) to give the title compound (11.0 g, 22% purity) as a brown solid that required no further purification. LCMS M/Z (M+H) 336.

Step 2: (3-(1-methyl-1H-pyrazol-4-yl)isoquinolin-8-yl)boronic acid

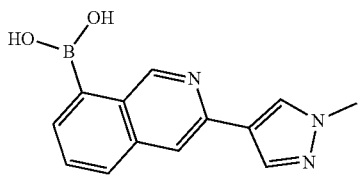 [SMILES: Cn1cc(-c2cc3cccc(B(O)O)c3cn2)cn1]

To a solution of 3-(1-methyl-1H-pyrazol-4-yl)-8-(4,4,5,5-tetramethyl-1,3,2-dioxaborolan-2-yl)isoquinoline (10 g, crude) in acetone (50 mL) and water (50 mL) was added NaIO₄ (16.0 g, 74.6 mmol) and NH₄OAc (5.7 g, 74.6 mmol). The mixture was stirred at room temperature for 48 h. The reaction was filtered and concentrated in vacuo. EtOAc (100 mL) was added and washed with water (70 mL), brine (70 mL). The organic layer was dried over anhydrous Na₂SO₄, filtered and concentrated in vacuo. The crude residue was purified by silica gel chromatography (DCM/MeOH=10:1) to give the title compound (440 mg, 4% over 2 steps) as a yellow solid. ¹H NMR (400 MHz, DMSO-d₆) δ 9.64 (s, 1H), 8.57-8.51 (m, 2H), 8.31 (s, 1H), 8.06 (s, 1H), 8.01 (s, 1H), 7.87 (d, J=8.4 Hz, 1H), 7.78 (d, J=5.6 Hz, 1H), 7.73-7.63 (m, 1H), 3.91 (s, 3H).

Step 3: tert-butyl 3-bromo-1-(3-(1-methyl-1H-pyrazol-4-yl)isoquinolin-8-yl)-4,5-dihydro-1H-pyrazolo[3,4-c]pyridine-6(7H)-carboxylate

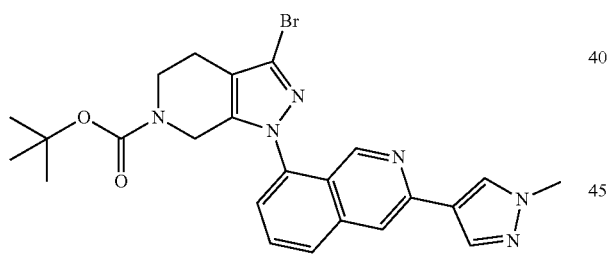

To a solution of tert-butyl 3-bromo-4,5-dihydro-1H-pyrazolo[3,4-c]pyridine-6(7H)-carboxylate (400 mg, 1.3 mmol) in THF (10 mL) was added (3-(1-methyl-1H-pyrazol-4-yl)isoquinolin-8-yl)boronic acid (469 mg, 1.6 mmol), triethylamine (0.92 mL, 6.6 mmol), pyridine (1.43 mL, 13.2 mmol) and copper(II) acetate (721 mg, 4.0 mmol). The mixture was heated to 60° C. for 12 h under an oxygen atmosphere. After cooling to room temperature, the mixture was filtered and concentrated in vacuo. EtOAc (100 mL) was added and washed with water (80 mL×2), brine (80 mL). The organic layer was dried over anhydrous Na₂SO₄, filtered and concentrated in vacuo. The crude residue was purified by silica gel chromatography (petroleum ether/EtOAc=1:1) to give the title compound (100 mg, 15%) as a yellow solid. LCMS M/Z (M+H) 511.

Step 4: tert-butyl 1-(3-(1-methyl-1H-pyrazol-4-yl)isoquinolin-8-yl)-3-morpholino-4,5-dihydro-1H-pyrazolo[3,4-c]pyridine-6(7H)-carboxylate

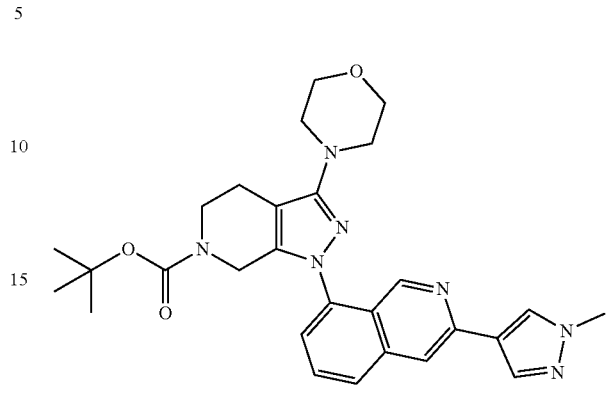

To a solution of tert-butyl 3-bromo-1-(3-(1-methyl-1H-pyrazol-4-yl)isoquinolin-8-yl)-4,5-dihydro-1H-pyrazolo[3,4-c]pyridine-6(7H)-carboxylate (100 mg, 0.2 mmol) in 1,4-dioxane (4 mL) was dichloro[1,3-bis(2,6-di-3-pentylphenyl)imidazol-2-ylidene](3-chloropyridyl)palladium(II), t-BuONa (57 mg, 0.6 mmol) and morpholine (0.035 mL, 0.4 mmol). The mixture was heated to 110° C. for 16 h under an argon atmosphere. After cooling to room temperature, DCM (50 mL) was added and washed with water (40 mL×2), brine (40 mL). The organic layer was dried over anhydrous Na₂SO₄, filtered and concentrated in vacuo. The crude residue was purified by silica gel chromatography (petroleum ether/EtOAc=1:1) to give the title compound (42 mg, 41%) as a yellow solid. LCMS M/Z (M+H) 516.

Step 5: 4-(1-(3-(1-methyl-1H-pyrazol-4-yl)isoquinolin-8-yl)-4,5,6,7-tetrahydro-1H-pyrazolo[3,4-c]pyridin-3-yl)morpholine

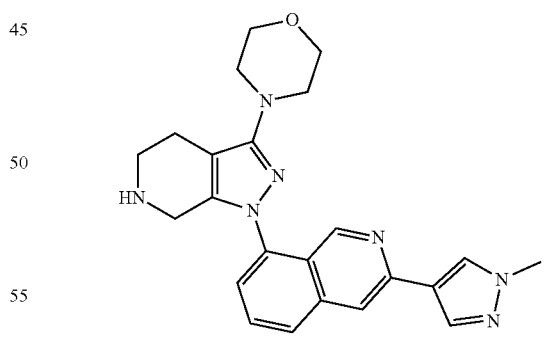

To a solution of tert-butyl 1-(3-(1-methyl-1H-pyrazol-4-yl)isoquinolin-8-yl)-3-morpholino-4,5-dihydro-1H-pyrazolo[3,4-c]pyridine-6(7H)-carboxylate (42 mg, 0.08 mmol) in DCM (1 mL) was added trifluoroacetic acid (0.06 mL, 0.8 mmol). The mixture was stirred at room temperature for 3 h and concentrated in vacuo to give the title compound (35 mg, crude) as brown oil that required no further purification. LCMS M/Z (M+H) 416.

Step 6: N-methyl-1-(3-(1-methyl-1H-pyrazol-4-yl)isoquinolin-8-yl)-3-morpholino-4,5-dihydro-1H-pyrazolo[3,4-c]pyridine-6(7H)-carboxamide

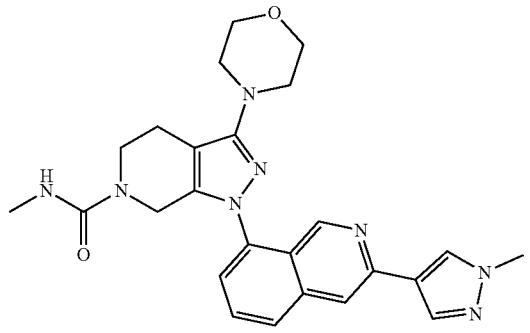

To a solution of 4-(1-(3-(1-methyl-1H-pyrazol-4-yl)isoquinolin-8-yl)-4,5,6,7-tetrahydro-1H-pyrazolo[3,4-c]pyridin-3-yl)morpholine (35 mg, 0.08 mmol) in DCM (3 mL) was added triethylamine (0.04 mL, 0.25 mmol) and N-methyl-1H-imidazole-1-carboxamide (16 mg, 0.13 mmol). The reaction was stirred at room temperature for 12 h and concentrated in vacuo. EtOAc (50 mL) was added and washed with water (40 mL×2). The organic layer was dried over anhydrous Na$_2$SO$_4$, filtered and concentrated in vacuo. The crude residue was purified by reverse phase chromatography (acetonitrile 17-47%/0.05% HCl in water) to give the title compound (6 mg, 15%) as a yellow solid. $^1$H NMR (400 MHz, DMSO-d$_6$) δ 9.38 (s, 1H), 8.49 (s, 1H), 8.40 (s, 1H), 8.22 (s, 1H), 8.01 (d, J=8.4 Hz, 1H), 7.98-7.90 (m, 1H), 7.62 (d, J=6.8 Hz, 1H), 6.61 (s, 1H), 4.43 (s, 2H), 3.94 (s, 3H), 3.76-3.70 (m, 4H), 3.65-3.55 (m, 2H), 3.23-3.13 (m, 4H), 2.65-2.55 (m, 2H), 2.52 (s, 3H). LCMS M/Z (M+H) 473.

Example 49

2-cyano-N-methyl-3-(3-(1-methyl-1H-pyrazol-4-yl)isoquinolin-8-yl)-1-(tetrahydro-2H-pyran-4-yl)-6,7-dihydro-1H-pyrrolo[3,2-c]pyridine-5(4H)-carboxamide

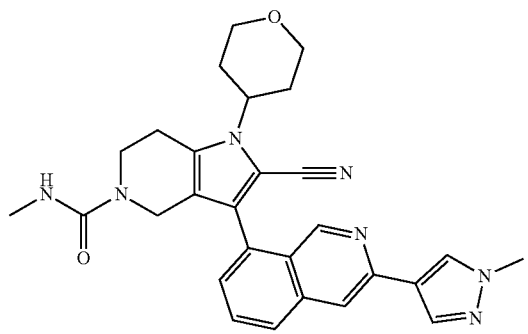

Step 1: 2-((tetrahydro-2H-pyran-4-yl)amino)acetonitrile

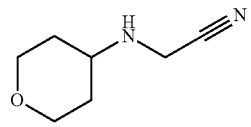

To a solution of tetrahydro-2H-pyran-4-amine hydrochloride (45 g, 327 mmol) and K$_2$CO$_3$ (135.6 g, 981 mmol) in MeCN (300 mL) was added 2-chloroacetonitrile (24.9 mL, 392 mmol) dropwise. The mixture was heated to 80° C. for 16 h under a nitrogen atmosphere. After cooling to room temperature, the mixture was filtered and concentrated in vacuo. The crude residue was purified by silica gel chromatography (petroleum ether/EtOAc=1:1) to give the title compound (26 g, 57%) as brown oil. $^1$H NMR (400 MHz, CDCl$_3$) δ 3.95-3.88 (m, 2H), 3.59 (s, 2H), 3.42-3.35 (m, 2H), 2.95-2.82 (m, 1H), 1.82-1.68 (m, 2H), 1.42-1.29 (m, 2H).

Step 2: tert-butyl 3-cyano-4-(((trifluoromethyl)sulfonyl)oxy)-5,6-dihydropyridine-1(2H)-carboxylate

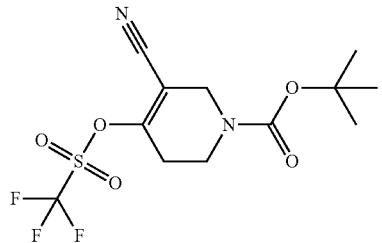 [SMILES: CC(C)(C)OC(=O)N1CCC(OS(=O)(=O)C(F)(F)F)=C(C#N)C1]

To a solution of tert-butyl 3-cyano-4-oxopiperidine-1-carboxylate (21 g, 93.6 mmol) in DCM (200 mL) at 0° C. was added triethylamine (17 mL, 121 mmol), N,N-dimethylpyridin-4-amine (2.3 g, 18.7 mmol) and trifluoromethanesulfonic anhydride (20.4 mL, 121 mmol). The reaction was stirred at room temperature for 6 h. DCM (100 mL) was added and washed with water (200 mL), brine (200 mL). The organic layer was dried over anhydrous Na$_2$SO$_4$, filtered and concentrated in vacuo. The crude residue was purified by silica gel chromatography (petroleum ether/EtOAc=3:1) to give the title compound (20 g, 60%) as a yellow solid. $^1$H NMR (400 MHz, DMSO-d$_6$) δ 4.26 (s, 2H), 3.62-3.56 (m, 2H), 2.73-2.62 (m, 2H), 1.42 (s, 9H).

Step 3: tert-butyl 3-amino-2-cyano-1-(tetrahydro-2H-pyran-4-yl)-6,7-dihydro-1H-pyrrolo[3,2-c]pyridine-5(4H)-carboxylate

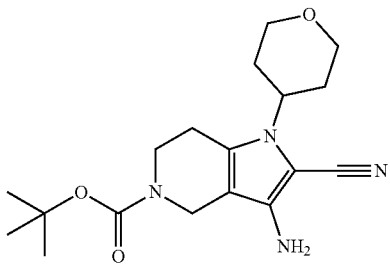 [SMILES: CC(C)(C)OC(=O)N1CCc2c(c(N)c(C#N)n2C2CCOCC2)C1]

To a solution of tert-butyl 3-cyano-4-(((trifluoromethyl)sulfonyl)oxy)-5,6-dihydropyridine-1(2H)-carboxylate (5 g, 14 mmol) in t-BuOH (70 mL) was added 2-((tetrahydro-2H-pyran-4-yl)amino)acetonitrile (2.4 g, 16.8 mmol) and $Cs_2CO_3$ (13.7 g, 42 mmol). The mixture was heated to 90° C. for 16 h under a nitrogen atmosphere. After cooling to room temperature, the mixture was filtered and concentrated in vacuo. EtOAc (250 mL) was added and washed with water (200 mL×2), brine (200 mL). The organic layer was dried over anhydrous $Na_2SO_4$, filtered and concentrated in vacuo. The crude residue was purified by silica gel chromatography (petroleum ether/EtOAc=1:1) to give the title compound (270 mg, 6%) as a yellow solid. $^1$H NMR (400 MHz, $CDCl_3$) δ 4.23 (s, 2H), 4.15-4.09 (m, 2H), 4.06-4.00 (m, 1H), 3.75-3.65 (m, 2H), 3.55-3.41 (m, 4H), 2.70-2.58 (m, 2H), 2.41-2.30 (m, 2H), 1.84-1.74 (m, 2H), 1.48 (s, 9H). LCMS M/Z (M+H) 347.

Step 4: tert-butyl 3-bromo-2-cyano-1-(tetrahydro-2H-pyran-4-yl)-6,7-dihydro-1H-pyrrolo[3,2-c]pyridine-5(4H-carboxylate

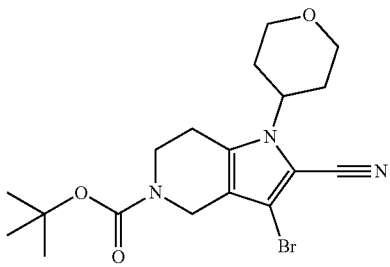 [SMILES: CC(C)(C)OC(=O)N1CCc2c(c(Br)c(C#N)n2C2CCOCC2)C1]

To a stirred mixture of tert-butyl 3-amino-2-cyano-1-(tetrahydro-2H-pyran-4-yl)-6,7-dihydro-1H-pyrrolo[3,2-c]pyridine-5(4H)-carboxylate (510 mg, 1.47 mmol), $CuBr_2$ (428 mg, 1.91 mmol) in MeCN (30 mL) at 0° C. was added isopentyl nitrite (0.26 mL, 1.91 mmol) dropwise and the reaction mixture stirred for 20 min. The temperature was raised to 60° C. and the reaction mixture was stirred for an additional 5 h. After cooling the reaction to room temperature, the reaction mixture was quenched with water (60 mL) and the mixture was extracted with EtOAc (60 mL×2). The combined organic layers were washed with brine (40 mL), dried over anhydrous $Na_2SO_4$, filtered and concentrated in vacuo. The crude residue was purified by silica gel chromatography (petroleum ether/EtOAc=3:2) to give the title compound (170 mg, 28%) as a white solid. $^1$H NMR (400 MHz, $CDCl_3$) δ 4.28 (s, 2H), 4.24-4.18 (m, 1H), 4.16-4.12 (m, 2H), 3.80-3.68 (m, 2H), 3.51-3.45 (m, 2H), 2.78-2.68 (m, 2H), 2.51-2.33 (m, 2H), 1.87-1.80 (m, 2H), 1.50 (s, 9H).

Step 5: tert-butyl 2-cyano-3-(3-(1-methyl-1H-pyrazol-4-yl)isoquinolin-8-yl)-1-(tetrahydro-2H-pyran-4-yl)-6,7-dihydro-1H-pyrrolo[3,2-c]pyridine-5(4H)-carboxylate

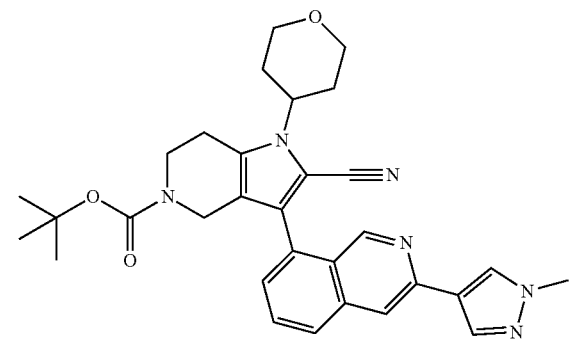 [SMILES: Cn1cc(-c2cc3cccc(-c4c5c(n(C6CCOCC6)c4C#N)CCN(C(=O)OC(C)(C)C)C5)c3cn2)cn1]

To a solution of tert-butyl 3-bromo-2-cyano-1-(tetrahydro-2H-pyran-4-yl)-6,7-dihydro-1H-pyrrolo[3,2-c]pyridine-5(4H)-carboxylate (170 mg, 0.41 mmol) in THF (15 mL) and water (3 mL) was added 2-(dicyclohexylphosphino)-2',4',6'-triisopropylbiphenyl (20 mg, 0.041 mmol), chloro(2-dicyclohexylphosphino-2',4',6'-tri-i-propyl-1,1'-biphenyl)(2'-amino-1,1'-biphenyl-2-yl) palladium(II) (33 mg, 0.041 mmol), $Na_2CO_3$ (134 mg, 1.24 mmol) and 3-(1-methyl-1H-pyrazol-4-yl)-8-(4,4,5,5-tetramethyl-1,3,2-dioxaborolan-2-yl)isoquinoline (181 mg, 0.54 mmol). The mixture was heated to 60° C. for 12 h under a nitrogen atmosphere. After cooling to room temperature, the mixture was filtered and concentrated in vacuo. EtOAc (55 mL) was added and washed with water (40 mL×2). The organic layer was dried over anhydrous $Na_2SO_4$, filtered and concentrated in vacuo. The crude residue was purified by silica gel chromatography (petroleum ether/EtOAc=3:2) to give the title compound (192 mg, 86%) as a yellow solid. $^1$H NMR (400 MHz, $CDCl_3$) δ 9.07 (s, 1H), 8.06 (s, 1H), 8.00 (s, 1H), 7.86-7.78 (m, 2H), 7.71-7.66 (m, 1H), 7.46 (d, J=6.8 Hz, 1H), 4.46-4.32 (m, 1H), 4.29-4.08 (m, 4H), 4.05-3.65 (m, 5H), 3.58-3.52 (m, 2H), 2.93-2.80 (m, 2H), 2.58-2.49 (m, 2H), 2.01-1.94 (m, 2H), 1.62 (s, 9H). LCMS M/Z (M+H) 539.

Step 6: 3-(3-(1-methyl-1H-pyrazol-4-yl)isoquinolin-8-yl)-1-(tetrahydro-2H-pyran-4-yl)-4,5,6,7-tetrahydro-1H-pyrrolo[3,2-c]pyridine-2-carbonitrile

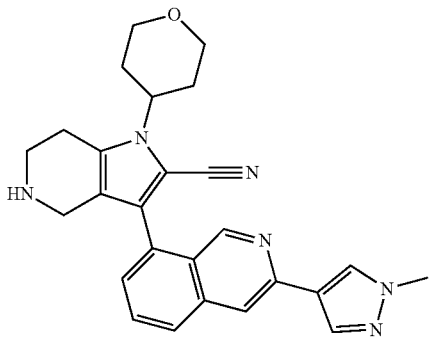 [SMILES: Cn1cc(-c2cc3cccc(-c4c5c(n(C6CCOCC6)c4C#N)CCNC5)c3cn2)cn1]

To a solution of tert-butyl 2-cyano-3-(3-(1-methyl-1H-pyrazol-4-yl)isoquinolin-8-yl)-1-(tetrahydro-2H-pyran-4-yl)-6,7-dihydro-1H-pyrrolo[3,2-c]pyridine-5 (4H)-carboxylate (192 mg, 0.36 mmol) in DCM (0.5 mL) was added trifluoroacetic acid (0.52 mL, 7.12 mmol). The mixture was stirred at room temperature for 3 h and concentrated in vacuo to give the title compound (145 mg, crude) as brown oil that required no further purification. LCMS M/Z (M+H) 439.

Step 7: 2-cyano-N-methyl-3-(3-(1-methyl-1H-pyrazol-4-yl)isoquinolin-8-yl)-1-(tetrahydro-2H-pyran-4-yl)-6,7-dihydro-1H-pyrrolo[3,2-c]pyridine-5(4H)-carboxamide

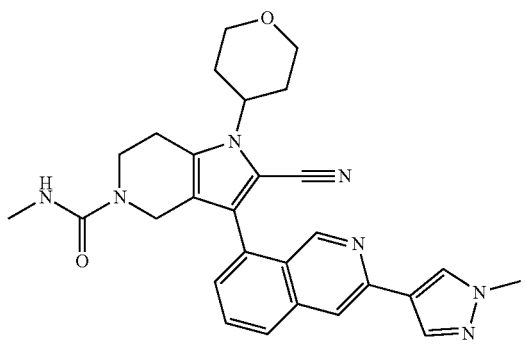

To a solution of 3-(3-(1-methyl-1H-pyrazol-4-yl)isoquinolin-8-yl)-1-(tetrahydro-2H-pyran-4-yl)-4,5,6,7-tetrahydro-1H-pyrrolo[3,2-c]pyridine-2-carbonitrile (145 mg, 0.33 mmol) in DCM (3 mL) was added triethylamine (0.1 mL, 0.66 mmol) and N-methyl-1H-imidazole-1-carboxamide (83 mg, 0.66 mmol). The reaction was stirred at room temperature for 12 h and concentrated in vacuo. DCM (30 mL) was added and washed with water (30 mL×2). The organic layer was dried over anhydrous Na$_2$SO$_4$, filtered and concentrated in vacuo. The crude residue was purified by Prep-TLC (DCM/MeOH=10:1) to give the title compound (73 mg, 55%) as a white solid. $^1$H NMR (400 MHz, CDCl$_3$) δ 9.05 (s, 1H), 8.04 (s, 1H), 7.99 (s, 1H), 7.86-7.80 (m, 2H), 7.73-7.68 (m, 1H), 7.46 (d, J=6.4 Hz, 1H), 4.46-4.32 (m, 2H), 4.25-4.15 (m, 2H), 4.12-3.95 (m, 6H), 3.75-3.64 (m, 1H), 3.55 (t, J=12.0 Hz, 2H), 2.96-2.84 (m, 2H), 2.73 (d, J=3.6 Hz, 3H), 2.62-2.45 (m, 2H), 2.03-1.93 (m, 2H). LCMS M/Z (M+H) 496.

Example 50

8-(5-acetyl-1-(tetrahydro-2H-pyran-4-yl)-4,5,6,7-tetrahydro-1H-pyrazolo[4,3-c]pyridin-3-yl)imidazo[1,2-a]pyridine-2-carboxylic acid

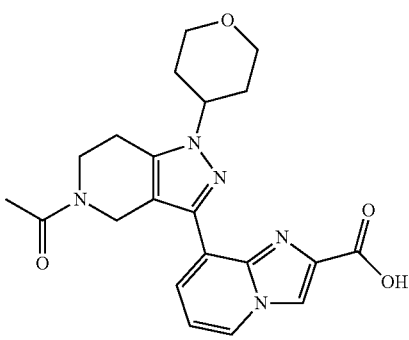 [SMILES: CC(=O)N1CCc2c(c(-c3cccn4cc(C(=O)O)nc34)nn2C2CCOCC2)C1]

To a solution of methyl 8-(5-acetyl-1-tetrahydropyran-4-yl-6,7-dihydro-4H-pyrazolo[4,3-c]pyridin-3-yl)imidazo[1,2-a]pyridine-2-carboxylate (50 mg, 0.15 mmol), obtained in a similar fashion as procedure S, in THF (0.35 mL) was added lithium chloride (3.3 mg, 0.078 mmol) and sodium hydroxide 3.7 mol/L in water (77 μL). The mixture was stirred at 55° C. for 3 h. The reaction mixture was then cooled to room temperature, concentrated HCl was added (20 μL) and the solution was concentrated in vacuo. The mixture obtained was purified by reverse phase chromatography (acetonitrile 2-20%/0.1% ammonium hydroxide in water) to give the title compound (5.0 mg, 17%) as a white solid. $^1$H NMR (400 MHz, DMSO-d$_6$, 22/23 H) δ 8.58 (dt, J=6.9, 1.5 Hz, 1H), 8.47 (s, 1H), 7.53-7.40 (m, 1H), 7.03 (td, J=6.9, 3.8 Hz, 1H), 4.89 (s, 1H), 4.60 (s, 1H), 4.39 (tq, J=11.9, 4.2 Hz, 1H), 3.98 (dt, J=10.1, 4.6 Hz, 2H), 3.79 (t, J=6.0 Hz, 2H), 3.55-3.43 (m, 2H), 2.95-2.75 (m, 2H), 2.19-2.01 (m, 5H), 1.87 (dt, J=13.5, 3.3 Hz, 2H). LCMS M/Z (M+H) 410.

Example 51

1-(3-(2-(pyridin-3-yl)-1H-benzo[d]imidazol-4-yl)-1-(tetrahydro-2H-pyran-4-yl)-1,4,6,7-tetrahydro-5H-pyrazolo[4,3-c]pyridin-5-yl)ethan-1-one

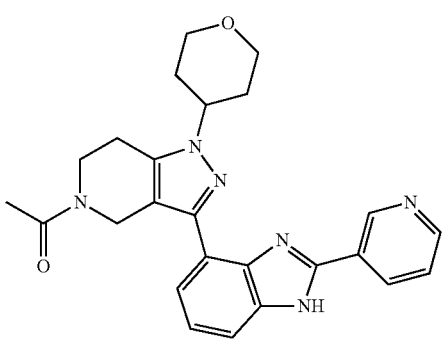 [SMILES: CC(=O)N1CCc2c(c(-c3cccc4[nH]c(-c5cccnc5)nc34)nn2C2CCOCC2)C1]

Step 1: 4-chloro-2-(pyridin-3-yl)-1H-benzo[d]imidazole

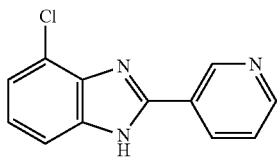 [SMILES: Clc1cccc2[nH]c(-c3cccnc3)nc12]

To a solution of pyridine-3-carbonyl chloride hydrochloride (157 mg, 0.884 mmol) and trimethylamine (224 mg, 2.21 mmol) in DCM (5.3 mL) was added 3-chlorobenzene-1,2-diamine (105 mg, 0.736 mmol). The mixture was stirred at room temperature for 16 h. The reaction mixture was then cooled to room temperature and saturated aqueous NaHCO$_3$ solution (20 mL) and brine solution (5 mL) were added and the two layers were separated. The aqueous layer was washed with DCM (2×10 mL). The combined organic layers were dried over anhydrous MgSO$_4$, filtered and concentrated in vacuo. The residue obtained was dissolved in acetic acid (1.8 mL) and concentrated HCl was added (60 μL, 0.74 mmol). The mixture was stirred at 100° C. for 2 h. The reaction mixture was then cooled to room temperature and concentrated in vacuo. The crude residue was partitioned between DCM (20 mL) and saturated aqueous NaHCO$_3$ solution (20 mL). The two phases were separated and the aqueous layer was extracted with DCM (2×15 mL). The combined organic layers were washed with brine, dried over anhydrous MgSO$_4$, filtered and concentrated in vacuo. The mixture obtained was purified by silica gel chromatography (acetone/heptane=1:19 to 2:3) to give the title compound (97.4 mg, 58%) as a beige solid. $^1$H NMR (400 MHz, DMSO-d$_6$, 7/8 H) δ 8.75 (dd, J=4.8, 1.7 Hz, 1H), 7.53-7.45 (m, 1H), 7.39-7.27 (m, 2H), 9.30 (dd, J=2.3, 1.0 Hz, 1H), 8.42 (dt, J=8.0, 2.0 Hz, 1H), 7.74 (d, J=7.8 Hz, 1H). LCMS M/Z (M+H) 230.

Step 2: 1-(3-(2-(pyridin-3-yl)-1H-benzo[d]imidazol-4-yl)-1-(tetrahydro-2H-pyran-4-yl)-1,4,6,7-tetrahydro-5H-pyrazolo[4,3-c]pyridin-5-yl)ethan-1-one

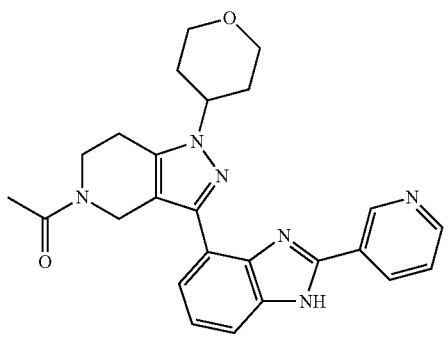 [SMILES: CC(=O)N1CCc2c(c(-c3cccc4[nH]c(-c5cccnc5)nc34)nn2C2CCOCC2)C1]

To a solution of 1-(3-bromo-1-(tetrahydro-2H-pyran-4-yl)-6,7-dihydro-1H-pyrazolo[4,3-c]pyridin-5(4H)-yl)ethanone (Intermediate H, 50 mg, 0.15 mmol) and bis(pinacolato)diboron (77 mg, 0.30 mmol) in dioxane (0.76 mL) was added KOAc (45 mg, 0.46 mmol), (2-dicyclohexylphosphino-2',4',6'-triisopropyl-1,1'-biphenyl)[2-(2'-amino-1,1'-biphenyl)]palladium(II) methanesulfonate (3.7 mg, 0.0046 mmol) and 2-(dicyclohexylphosphino)-2',4',6'-triisopropylbiphenyl (4.4 mg, 0.0091 mmol). The mixture was stirred at 80° C. for 16 h under a nitrogen atmosphere. The reaction mixture was cooled to room temperature and 4-chloro-2-(3-pyridyl)-1H-benzimidazole (30 mg, 0.13 mmol), K$_3$PO$_4$.H$_2$O (40 mg, 0.19 mmol), water (0.3 mL) and (2-dicyclohexylphosphino-2',4',6'-triisopropyl-1,1'-biphenyl)[2-(2'-amino-1,1'-biphenyl)]palladium(II) methanesulfonate (3.7 mg, 0.0046 mmol) were added. The reaction mixture was stirred at 90° C. for 4 h under a nitrogen atmosphere. The reaction mixture was then cooled to room temperature and concentrated in vacuo. The crude residue was dissolved in dichloromethane (5 mL), dried over anhydrous MgSO$_4$, filtered through celite and concentrated in vacuo. The mixture obtained was purified by reverse phase chromatography (acetonitrile 5-50%/0.1% ammonium hydroxide in water) to give the title compound (30.4 mg, 45%) as a white solid. $^1$H NMR (400 MHz, DMSO-d$_6$) δ 13.49-12.78 (m, 1H), 9.52-9.31 (m, 1H), 8.68 (dt, J=3.9, 1.6 Hz, 1H), 8.60 (s, 1H), 7.60 (dt, J=8.1, 4.3 Hz, 2H), 7.45 (s, 1H), 7.34-7.29 (m, 1H), 4.85 (s, 2H), 4.41 (s, 1H), 4.04-3.97 (m, 2H), 3.88-3.77 (m, 2H), 3.51 (t, J=11.8 Hz, 2H), 3.39-3.33 (m, 2H), 2.99-2.79 (m, 2H), 2.25-2.07 (m, 2H), 2.01 (s, 1H), 1.91 (d, J=12.7 Hz, 2H). LCMS M/Z (M+H) 443.

Example 52

N-methyl-3-(2-(1-methyl-1H-pyrazol-4-yl)-2,3,4,5-tetrahydro-1H-benzo[c]azepin-6-yl)-1-(tetrahydro-2H-pyran-4-yl)-6,7-dihydro-1H-pyrazolo[4,3-c]pyridine-5(4H)-carboxamide

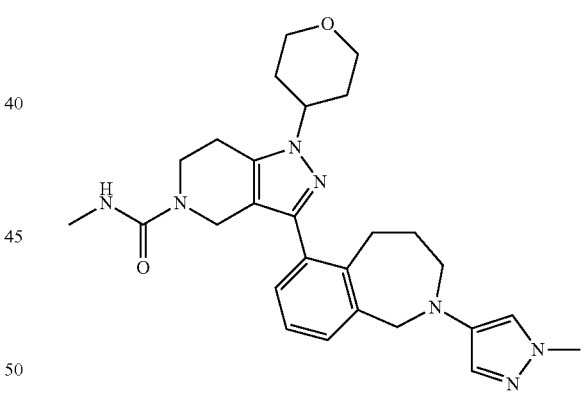

Step 1: 6-bromo-2,3,4,5-tetrahydro-1H-benzo[c]azepin-1-one

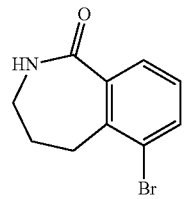 [SMILES: O=C1NCCCc2c(Br)cccc21]

To a solution of 5-bromo-1-tetralone (3.0 g, 13.33 mmol) in conc. HCl (30 mL) at 0° C. was added sodium azide (1.79 g, 27.53 mmol) portionwise. The reaction mixture was heated to 50° C. for 16 h under a nitrogen atmosphere. After cooling to room temperature, the mixture was basified with $K_2CO_3$ (1 M) to pH 10 and then extracted with EtOAc (100 mL×2). The combined organic layers were washed with sat. aq. $NaHCO_3$ (50 mL), dried over anhydrous $Na_2SO_4$, filtered and concentrated in vacuo. The crude residue was purified by silica gel chromatography (petroleum ether/EtOAc=3:2) to give the title compound (1.2 g, 37%) as a white solid. $^1$H NMR (400 MHz, DMSO-$d_6$) δ 8.22-8.13 (m, 1H), 7.75-7.71 (m, 1H), 7.48 (d, J=6.8 Hz, 1H), 7.29-7.25 (m, 1H), 2.93 (t, J=6.8 Hz, 2H), 2.90-2.84 (m, 2H), 1.90-1.82 (m, 2H).

Step 2: 6-bromo-2-(1-methyl-1H-pyrazol-4-yl)-2,3,4,5-tetrahydro-1H-benzo[c]azepin-1-one

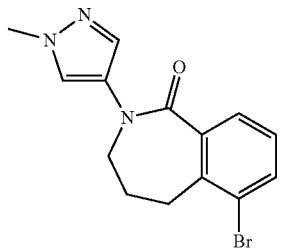 [SMILES: Cn1cc(N2CCCc3c(Br)cccc3C2=O)cn1]

To a solution of 6-bromo-2,3,4,5-tetrahydro-1H-benzo[c]azepin-1-one (1.5 g, 6.25 mmol) in 1,4-dioxane (50 mL) was added copper(I) iodide (119 mg, 0.62 mmol), (1R,2R)-cyclohexane-1,2-diamine (142 mg, 1.25 mmol), $K_3PO_4$ (3.9 g, 18.74 mmol) and 4-iodo-1-methyl-1H-pyrazole (1.95 g, 9.37 mmol). The reaction mixture was heated to 120° C. for 48 h under a nitrogen atmosphere. After cooling to room temperature, the mixture was filtered and concentrated in vacuo. Water (100 mL) was added and extracted with EtOAc (50 mL×3). The combined organic layers were dried over anhydrous $Na_2SO_4$, filtered and concentrated in vacuo. The crude residue was purified by silica gel chromatography (DCM/MeOH=20:1) to give the title compound (900 mg, 45%) as a yellow solid. LCMS M/Z (M+H) 320.

Step 3: 6-bromo-2-(1-methyl-1H-pyrazol-4-yl)-2,3,4,5-tetrahydro-1H-benzo[c]azepine

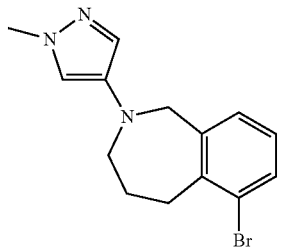 [SMILES: Cn1cc(N2CCCc3c(Br)cccc3C2)cn1]

To a solution of 6-bromo-2-(1-methyl-1H-pyrazol-4-yl)-2,3,4,5-tetrahydro-1H-benzo[c]azepin-1-one (900 mg, 2.81 mmol) in THF (50 mL) was added borane dimethyl sulfide complex (1.41 mL, 14.1 mmol, 10 M). The reaction mixture was heated to 70° C. for 16 h under a nitrogen atmosphere. After cooling to room temperature, the reaction was quenched with MeOH (20 mL) and heated to 70° C. for an additional 1 h. After cooling to room temperature, the mixture was filtered and concentrated in vacuo. The crude residue was purified by silica gel chromatography (DCM/MeOH=10:1) to give the title compound (700 mg, 81%) as gray oil. LCMS M/Z (M+H) 306.

Step 4: tert-butyl 1-(tetrahydro-2H-pyran-4-yl)-3-(4,4,5,5-tetramethyl-1,3,2-dioxaborolan-2-yl)-6,7-dihydro-1H-pyrazolo[4,3-c]pyridine-5(4H)-carboxylate

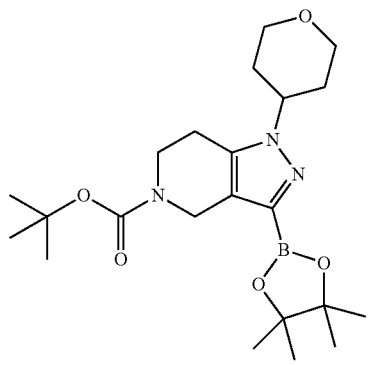 [SMILES: CC(C)(C)OC(=O)N1CCc2c(c(B3OC(C)(C)C(C)(C)O3)nn2C2CCOCC2)C1]

To a solution of tert-butyl 3-bromo-1-(tetrahydro-2H-pyran-4-yl)-6,7-dihydro-1H-pyrazolo[4,3-c]pyridine-5(4H)-carboxylate (Intermediate G, 400 mg, 1.04 mmol) in 1,4-dioxane (8 mL) was added 2-(dicyclohexylphosphino)-2',4',6'-triisopropylbiphenyl (30 mg, 0.06 mmol), chloro(2-dicyclohexylphosphino-2',4',6'-tri-i-propyl-1,1'-biphenyl)(2'-amino-1,1'-biphenyl-2-yl) palladium(II) (25 mg, 0.03 mmol), KOAc (300 mg, 3.12 mmol) and 4,4,4',4',5,5,5',5'-octamethyl-2,2'-bi(1,3,2-dioxaborolane) (526 mg, 2.08 mmol). The mixture was heated to 80° C. for 2 h under a nitrogen atmosphere. After cooling the reaction to room temperature, the reaction mixture was used to the next step directly without further purification. LCMS M/Z (M+H) 434.

Step 5: tert-butyl 3-(2-(1-methyl-1H-pyrazol-4-yl)-2,3,4,5-tetrahydro-1H-benzo[c]azepin-6-yl)-1-(tetrahydro-2H-pyran-4-yl)-6,7-dihydro-1H-pyrazolo[4,3-c]pyridine-5(4H)-carboxylate

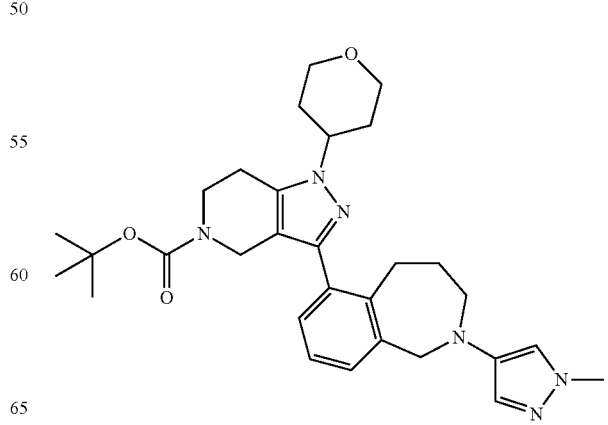

To the above step cooled solution was added 6-bromo-2-(1-methyl-1H-pyrazol-4-yl)-2,3,4,5-tetrahydro-1H-benzo[c]azepine (141 mg, 0.46 mmol), chloro(2-dicyclohexylphosphino-2',4',6'-tri-i-propyl-1,1'-biphenyl)(2'-amino-1,1'-biphenyl-2-yl) palladium(II) (25 mg, 0.03 mmol), K₃PO₄ (244 mg, 1.15 mmol), 1,4-dioxane (2 mL) and water (2 mL). The reaction mixture was heated to 90° C. for 1 h under a nitrogen atmosphere. After cooling to room temperature, the mixture was filtered and concentrated in vacuo. Water (50 mL) was added and extracted with EtOAc (30 mL×3). The combined organic layers were washed with brine (30 mL×3), dried over anhydrous Na₂SO₄, filtered and concentrated in vacuo. The crude residue was purified by silica gel chromatography (DCM/MeOH=20:1) to give the title compound (150 mg, 27%) as a yellow solid. LCMS M/Z (M+H) 533.

Step 6: 2-(1-methyl-1H-pyrazol-4-yl)-6-(1-(tetrahydro-2H-pyran-4-yl)-4,5,6,7-tetrahydro-1H-pyrazolo[4,3-c]pyridin-3-yl)-2,3,4,5-tetrahydro-1H-benzo[c]azepine

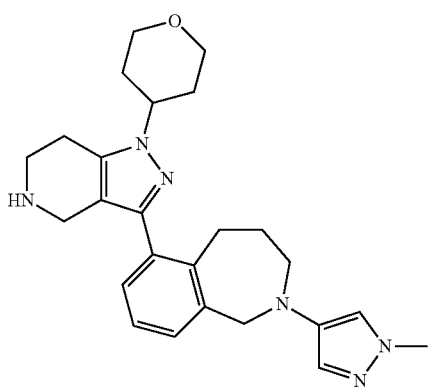 [SMILES: Cn1cc(N2CCCc3c(cccc3-c3nn(C4CCOCC4)c4c3CNCC4)C2)cn1]

To a solution of tert-butyl 3-(2-(1-methyl-1H-pyrazol-4-yl)-2,3,4,5-tetrahydro-1H-benzo[c]azepin-6-yl)-1-(tetrahydro-2H-pyran-4-yl)-6,7-dihydro-1H-pyrazolo[4,3-c]pyridine-5(4H)-carboxylate (150 mg, 0.28 mmol) in DCM (10 mL) at 0° C. was added trifluoroacetic acid (0.42 mL, 5.63 mmol). The mixture was stirred at 0° C. for 2 h and concentrated in vacuo to give the title compound (120 mg, crude) as brown oil that required no further purification. LCMS M/Z (M+H) 433.

Step 7: N-methyl-3-(2-(1-methyl-1H-pyrazol-4-yl)-2,3,4,5-tetrahydro-1H-benzo[c]azepin-6-yl)-1-(tetrahydro-2H-pyran-4-yl)-6,7-dihydro-1H-pyrazolo[4,3-c]pyridine-5(4H)-carboxamide

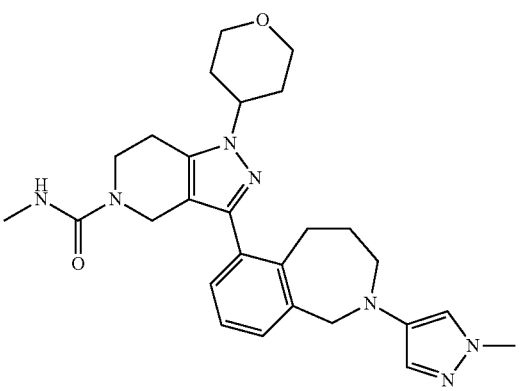

To a solution of 2-(1-methyl-1H-pyrazol-4-yl)-6-(1-(tetrahydro-2H-pyran-4-yl)-4,5,6,7-tetrahydro-1H-pyrazolo[4,3-c]pyridin-3-yl)-2,3,4,5-tetrahydro-1H-benzo[c]azepine (120 mg, 0.28 mmol) in DCM (15 mL) was added triethylamine (0.12 mL, 0.83 mmol) and N-methyl-1H-imidazole-1-carboxamide (69 mg, 0.55 mmol). The reaction was stirred at room temperature for 16 h. DCM (40 mL) was added and washed with brine (30 mL×3). The organic layer was dried over anhydrous Na₂SO₄, filtered and concentrated in vacuo. The crude residue was purified by reverse phase chromatography (acetonitrile 8-38%/0.2% formic acid in water) to give the title compound (38 mg, 28%) as a white solid. ¹H NMR (400 MHz, CDCl₃) δ 7.26-7.21 (m, 1H), 7.17-7.07 (m, 3H), 6.79 (s, 1H), 4.42 (s, 2H), 4.25-4.08 (m, 5H), 3.83 (t, J=5.2 Hz, 2H), 3.76 (s, 3H), 3.58-3.48 (m, 4H), 3.02-2.95 (m, 2H), 2.85-2.75 (m, 5H), 2.39-2.25 (m, 2H), 1.92-1.84 (m, 2H), 1.82-1.74 (m, 2H). LCMS M/Z (M+H) 490.

Example 53

1-(3-(3-(1-methyl-1H-pyrazol-4-yl)isoquinolin-8-yl)-1-(tetrahydro-2H-pyran-4-yl)-1,4,6,7-tetrahydro-5H-pyrrolo[3,2-c]pyridin-5-yl)ethan-1-one

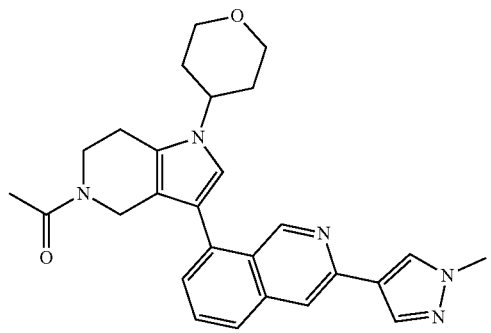

Step 1: 5-benzyl-1-(triisopropylsilyl)-4,5,6,7-tetrahydro-1H-pyrrolo[3,2-c]pyridine

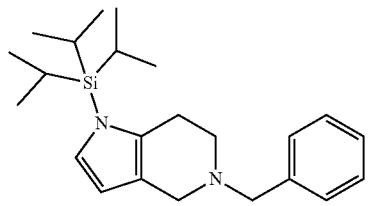 [SMILES: CC(C)[Si](C(C)C)(C(C)C)n1ccc2c1CCN(Cc1ccccc1)C2]

To a solution of 5-benzyl-4,5,6,7-tetrahydro-1H-pyrrolo[3,2-c]pyridine (1.50 g, 7.06 mmol) in THF (18 mL) at 0° C. was added sodium hydride 60% in mineral oil (424 mg, 10.6 mmol). The solution was stirred at 0° C. for 30 min, followed by the addition of triisopropylsilyl chloride (1.82 mL, 8.48 mmol). The mixture was stirred at 0° C. for 15 min and then heated at 60° C. for 2 h. The reaction mixture was then cooled to room temperature and concentrated in vacuo. Water (50 mL) and iPrOAc (50 mL) were added and the two layers were separated. The aqueous layer was extracted with iPrOAc (40 mL). The combined organic layers were dried over anhydrous MgSO$_4$, filtered and concentrated in vacuo. The residue obtained was purified by silica gel chromatography (iPrOAc/heptane=1:9) to give the title compound (2.60 g, quant.) as a pale yellow oil. $^1$H NMR (400 MHz, CDCl$_3$) δ 7.43-7.20 (m, 5H), 6.67 (d, J=2.9 Hz, 1H), 6.00 (d, J=2.8 Hz, 1H), 3.69 (s, 2H), 3.54 (s, 2H), 2.73 (s, 4H), 1.60-1.54 (m, 2H), 1.51-1.39 (m, 3H), 1.10 (d, J=7.5 Hz, 18H). LCMS M/Z (M+H) 369.

Step 2: 1-(triisopropylsilyl)-4,5,6,7-tetrahydro-1H-pyrrolo[3,2-c]pyridine

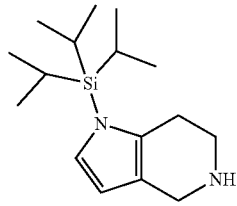 [SMILES: CC(C)[Si](C(C)C)(C(C)C)n1ccc2c1CCNC2]

To a 100 mL round bottom flask was added 5-benzyl-1-(triisopropylsilyl)-4,5,6,7-tetrahydro-1H-pyrrolo[3,2-c]pyridine (1.00 g, 2.71 mmol) and palladium 10% on carbon (433 mg, 0.407 mmol) in EtOH (9.0 mL) and AcOH (2.7 mL). The solution was purged three times with hydrogen gas and stirred at 30° C. for 4 h under 1 atm of hydrogen. The hydrogen was removed in vacuo, the reaction mixture was filtered through celite and the solvent was concentrated in vacuo to afford the title compound (870 mg, quant.) as an orange oil. $^1$H NMR (400 MHz, CDCl$_3$) δ 6.73 (d, J=2.9 Hz, 1H), 6.06 (d, J=2.8 Hz, 1H), 4.15 (s, 2H), 3.39 (t, J=6.0 Hz, 2H), 2.96 (t, J=5.8 Hz, 2H), 1.51-1.39 (m, 3H), 1.10 (d, J=7.4 Hz, 18H). LCMS M/Z (M+H) 279.

Step 3: 1-(1-(triisopropylsilyl)-1,4,6,7-tetrahydro-5H-pyrrolo[3,2-c]pyridin-5-yl)ethan-1-one

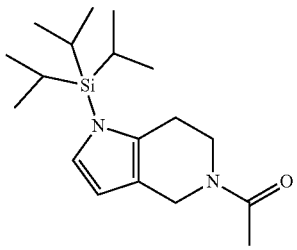 [SMILES: CC(=O)N1CCc2c(ccn2[Si](C(C)C)(C(C)C)C(C)C)C1]

To a solution of 1-(triisopropylsilyl)-4,5,6,7-tetrahydro-1H-pyrrolo[3,2-c]pyridine (1.50 g, 7.06 mmol) in DCM (6.2 mL) at 0° C. was added triethylamine (947 mg, 9.36 mmol) followed by acetic anhydride (382 mg, 3.74 mmol). The solution was stirred at room temperature for 2 h. To the reaction mixture was then added saturated aqueous NaHCO$_3$ solution (40 mL) and DCM (10 mL) and the two layers were separated. The aqueous layer was washed with DCM (2×30 mL). The combined organic layers were washed with brine, dried over anhydrous MgSO$_4$, filtered and concentrated in vacuo. The residue obtained was purified by silica gel chromatography (iPrOAc/heptane=3:7) to give the title compound (837 mg, 84%) as a white solid. $^1$H NMR (400 MHz, CDCl$_3$) δ 6.76-6.68 (m, 1H), 6.07 (d, J=2.8 Hz, 1H), 4.63-4.46 (m, 2H), 3.90-3.63 (m, 2H), 2.82-2.68 (m, 2H), 2.19-2.11 (m, 3H), 1.56-1.39 (m, 3H), 1.13-1.07 (m, 18H). LCMS M/Z (M+H) 321.

Step 4: 1-(3-bromo-1-(triisopropylsilyl)-1,4,6,7-tetrahydro-5H-pyrrolo[3,2-c]pyridin-5-yl)ethan-1-one

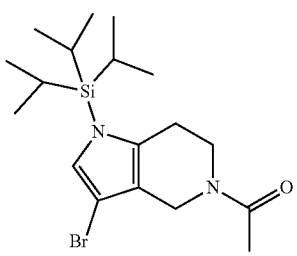 [SMILES: CC(=O)N1CCc2c(c(Br)cn2[Si](C(C)C)(C(C)C)C(C)C)C1]

To a solution of 1-(1-(triisopropylsilyl)-1,4,6,7-tetrahydro-5H-pyrrolo[3,2-c]pyridin-5-yl)ethan-1-one (400 mg, 1.25 mmol) in THF (4.2 mL) at −78° C. under a nitrogen atmosphere was added N-bromosuccinimide (244 mg, 1.37 mmol). The reaction mixture was stirred at −78° C. for 2 h30. The reaction mixture was then added to stirring MeOH (30 mL) at −78° C. and the the mixture was concentrated in vacuo. Water (40 mL) and iPrOAc (40 mL) and the two layers were separated. The aqueous layer was washed with iPrOAc (40 mL). The combined organic layers were washed with brine, dried over anhydrous MgSO$_4$, filtered and concentrated in vacuo. The residue obtained was purified by silica gel chromatography (iPrOAc/heptane=3:7 to 7:3) to give the title compound (239 mg, 48%) as a pale yellow oil. $^1$H NMR (400 MHz, CDCl$_3$) δ 6.74-6.66 (m, 1H), 4.55-4.32

(m, 2H), 3.88-3.61 (m, 2H), 2.78-2.65 (m, 2H), 2.25-2.15 (m, 3H), 1.53-1.36 (m, 3H), 1.13-1.07 (m, 18H). LCMS M/Z (M+H) 399.

Step 5: 1-(3-(3-(1-methyl-1H-pyrazol-4-yl)isoquinolin-8-yl)-1-(triisopropylsilyl)-1,4,6,7-tetrahydro-5H-pyrrolo[3,2-c]pyridin-5-yl)ethan-1-one

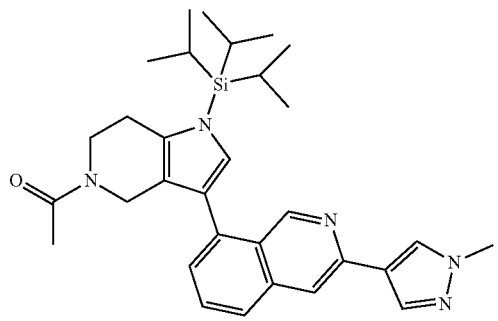 [SMILES: CC(=O)N1CCc2c(c(-c3cccc4cc(-c5cnn(C)c5)ncc34)cn2[Si](C(C)C)(C(C)C)C(C)C)C1]

To a solution of 1-(3-bromo-1-(triisopropylsilyl)-1,4,6,7-tetrahydro-5H-pyrrolo[3,2-c]pyridin-5-yl)ethan-1-one (225 mg, 0.563 mmol) and 3-(1-methyl-1H-pyrazol-4-yl)-8-(4,4,5,5-tetramethyl-1,3,2-dioxaborolan-2-yl)isoquinoline (227 mg, 0.676 mmol) in 1,4-dioxane (1.9 mL) and water (0.47 mL) was added $K_3PO_4 \cdot H_2O$ (334 mg, 1.41 mmol), chloro(2-dicyclohexylphosphino-2',4',6'-triisopropyl-1,1'-biphenyl)[2-(2'-amino-1,1'-biphenyl)]palladium(II) (23 mg, 0.028 mmol) and 2-(dicyclohexylphosphino)-2',4',6'-triisopropylbiphenyl (13 mg, 0.028 mmol). The mixture was stirred at 140° C. for 12 min in a microwave under a nitrogen atmosphere. The crude mixture was diluted in DCM (30 mL), filtered through celite and concentrated in vacuo. The residue obtained was purified by silica gel chromatography (MeOH/DCM=1:9 to 3:7) to give the title compound (149 mg, 50%) as a brown-orange solid. $^1$H NMR (400 MHz, CDCl$_3$) δ 9.31 (s, 1H), 8.07-7.84 (m, 2H), 7.86-7.56 (m, 3H), 7.39 (dt, J=6.9, 1.3 Hz, 1H), 6.86 (d, J=2.3 Hz, 1H), 4.52-4.44 (m, 1H), 4.33 (s, 1H), 3.98 (s, 3H), 3.94 (t, J=5.7 Hz, 1H), 3.76 (t, J=5.7 Hz, 1H), 2.77-2.95 (m, 2H), 2.03-1.98 (m, 3H), 1.58-1.46 (m, 3H), 1.17 (dd, J=7.6, 2.6 Hz, 18H). LCMS M/Z (M+H) 528.

Step 6: 1-(3-(3-(1-methyl-1H-pyrazol-4-yl)isoquinolin-8-yl)-1,4,6,7-tetrahydro-5H-pyrrolo[3,2-c]pyridin-5-yl)ethan-1-one

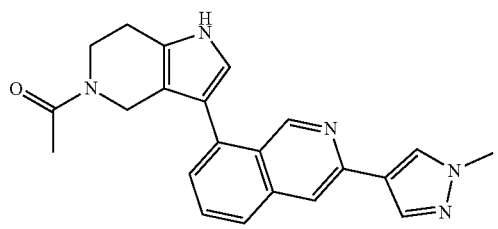 [SMILES: CC(=O)N1CCc2[nH]cc(-c3cccc4cc(-c5cnn(C)c5)ncc34)c2C1]

To a solution of 1-(3-(3-(1-methyl-1H-pyrazol-4-yl)isoquinolin-8-yl)-1-(triisopropylsilyl)-1,4,6,7-tetrahydro-5H-pyrrolo[3,2-c]pyridin-5-yl)ethan-1-one (145 mg, 0.275 mmol) in THF (0.92 mL) was added tetrabutylammonium fluoride 1 M in THF (0.330 mL, 0.330 mmol). The reaction mixture was stirred at room temperature for 3 h. Water (2 mL) was added and the mixture was concentrated in vacuo. The crude residue obtained was dissolved in DMSO (2 mL), filtered and purified by reverse phase chromatography (acetonitrile 30-70%/0.1% formic acid in water) to give the title compound (77 mg, 75%) as a yellow oil. $^1$H NMR (400 MHz, CDCl$_3$) δ 9.46 (d, J=13.6 Hz, 1H), 8.08-8.01 (m, 2H), 7.83 (d, J=5.3 Hz, 1H), 7.78-7.62 (m, 2H), 7.41 (t, J=10.1, 6.7 Hz, 1H), 6.89 (s, 1H), 4.54 (s, 1H), 4.37 (s, 1H), 3.99 (d, J=2.1 Hz, 4H), 3.81 (t, J=5.6 Hz, 1H), 2.91-2.77 (m, 2H), 2.17 (s, 1H), 2.05-1.98 (m, 3H). LCMS M/Z (M+H) 372.

Step 7: tetrahydro-2H-pyran-4-yl trifluoromethanesulfonate

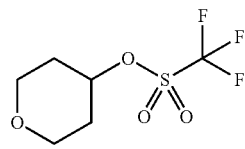 [SMILES: O=S(=O)(OC1CCOCC1)C(F)(F)F]

To a solution of tetrahydropyran-4-ol (270 mg, 2.64 mmol) in DCM (2.9 mL) was added pyridine (230 mg, 2.91 mmol) followed by trifluoromethanesulfonic anhydride (810 mg, 2.87 mmol) at 0° C. The reaction mixture was stirred at 0° C. for 20 min. The reaction mixture was filtered and the solid was washed with DCM (2 mL). The filtrate was washed with water, 1.0 N HCl, water and brine. The organic layer was dried over anhydrous MgSO$_4$, filtered and concentrated in vacuo to afford the title compound (462 mg, 76%) as a black liquid which was used directly in the next step. $^1$H NMR (400 MHz, CDCl$_3$) δ 1.99 (m, 2H), 2.11 (m, 2H), 3.58 (m, 2H), 3.96 (m, 2H), 5.17 (m, 1H).

Step 8: 1-(3-(3-(1-methyl-1H-pyrazol-4-yl)isoquinolin-8-yl)-1-(tetrahydro-2H-pyran-4-yl)-1,4,6,7-tetrahydro-5H-pyrrolo[3,2-c]pyridin-5-yl)ethan-1-one

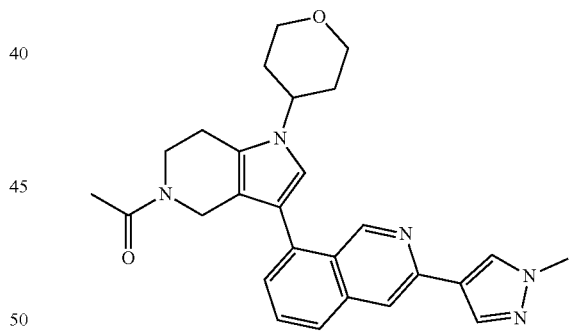

To a solution of 1-(3-(3-(1-methyl-1H-pyrazol-4-yl)isoquinolin-8-yl)-1,4,6,7-tetrahydro-5H-pyrrolo[3,2-c]pyridin-5-yl)ethan-1-one (75 mg, 0.202 mmol) in DMF (1.0 mL) was added sodium hydride 60% in mineral oil (9.7 mg, 0.24 mmol) at 0° C. followed by tetrahydro-2H-pyran-4-yl trifluoromethanesulfonate (200 mg, 0.854 mmol). The reaction mixture was slowly warmed up and stirred at room temperature for 2 h. Then, the reaction mixture was stirred at 150° C. for 10 min. The reaction mixture was cooled down to room temperature, diluted with DCM (10 mL), filtered through celite and concentrated in vacuo. The crude residue obtained was dissolved in DMSO (2 mL), filtered and purified by reverse phase chromatography (acetonitrile 20-60%/0.1% ammonium hydroxide in water) to give the title compound (1.5 mg, 2%) as a yellow oil. LCMS M/Z (M+H) 456.

The following were prepared in a similar fashion to the above compounds:

| Example | Compound Name and Structure | NMR; m/z | Procedure |
| --- | --- | --- | --- |
| Example 54 | 1-(3-(1H-indazol-4-yl)-1-methyl-6,7-dihydro-1H-pyrazolo[4,3-c]pyridin-5(4H)-yl)ethanone 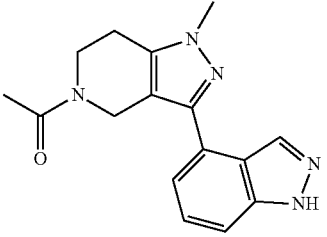 | $^1$H NMR (400 MHz, CD$_3$OD) δ 8.53 (s, 1H), 7.55-7.48 (m, 2H), 7.22-7.19 (m, 1H), 4.79-4.75 (m, 2H), 3.99-3.68 (m, 5H), 2.93-2.81 (m, 2H), 2.24-2.16 (m, 3H); m/z 296. | A |
| Example 55 | 1-(3-(1H-indol-4-yl)-1-methyl-6,7-dihydro-1H-pyrazolo[4,3-c]pyridin-5(4H)-yl)ethanone 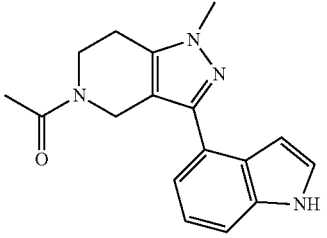 | $^1$H NMR (400 MHz, CD$_3$OD) δ 7.44-7.42 (m, 1H), 7.30 (d, J = 6.0 Hz, 1H), 7.20-7.16 (m, 1H), 7.09 (d, J = 7.2 Hz, 1H), 4.60-4.66 (m, 2H), 3.99-3.88 (m, 2H), 3.86 (s, 3H), 2.95-2.82 (m, 2H), 2.21-2.08 (m, 3H); m/z 295. | A |
| Example 56 | 1-(1-(cyclopropylmethyl)-3-(1H-indol-3-yl)-6,7-dihydro-1H-pyrazolo[4,3-c]pyridin-5(4H)-yl)ethanone 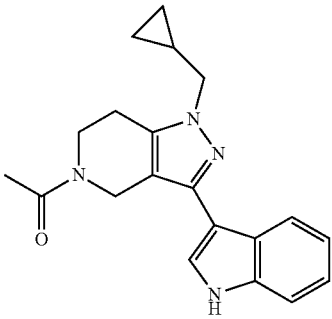 | $^1$H NMR (400 MHz, CDCl$_3$) δ 8.08-8.03 (m, 1H), 7.43-7.40 (m, 2H), 7.17-7.09 (m, 2H), 4.68-4.64 (m, 2H), 4.01-3.99 (m, 2H), 3.95-3.85 (m, 2H), 2.93-3.82 (m, 2H), 2.23-2.17 (m, 3H), 1.35-1.32 (m, 1H), 0.62-0.59 (m, 2H), 0.47-0.43 (m, 2H); m/z 335. | A |

-continued

| Example | Compound Name and Structure | NMR; m/z | Procedure |
|---|---|---|---|
| Example 57 | 1-(3-(1H-indol-3-yl)-1-(tetrahydro-2H-pyran-4-yl)-6,7-dihydro-1H-pyrazolo[4,3-c]pyridin-5(4H)-yl)ethanone 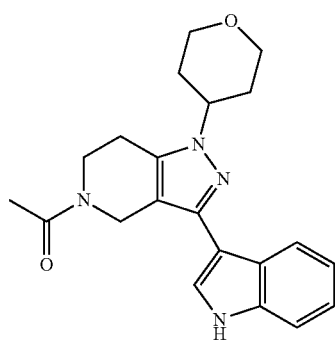 | $^1$H NMR (400 MHz, DMSO-$d_6$) δ 11.23 (s, 1H), 8.31-8.20 (m, 1H), 7.56-7.35 (m, 2H), 7.17-7.05 (m, 2H), 4.59 (s, 2H), 4.39-4.23 (m, 1H), 4.08-3.95 (m, 2H), 3.80-3.74 (m, 2H), 3.50 (t, J = 12.0 Hz, 2H), 2.91-2.71 (m, 2H), 2.22-2.09 (m, 5H), 1.90-1.78 (m, 2H); m/z 365. | A |
| Example 58 | 1-(3-(1-isopropyl-1H-indol-3-yl)-1-methyl-6,7-dihydro-1H-pyrazolo[4,3-c]pyridin-5(4H)-yl)ethanone 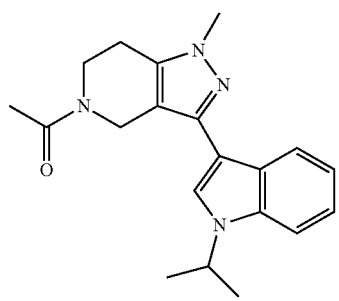 | $^1$H NMR (400 MHz, DMSO-$d_6$) δ 8.24-8.19 (m, 1H), 7.54-7.47 (m, 2H), 7.20-7.16 (m, 1H), 7.10-7.06 (m, 1H), 4.84-4.77 (m, 1H), 4.60 (s, 2H), 3.80-3.73 (m, 5H), 2.82-2.68 (m, 2H), 2.12 (s, 3H), 1.53-1.51 (m, 6H); m/z 337. | B |
| Example 59 | 1-(3-(1-methyl-1H-indol-3-yl)-1-(tetrahydro-2H-pyran-4-yl)-6,7-dihydro-1H-pyrazolo[4,3-c]pyridin-5(4H)-yl)ethanone 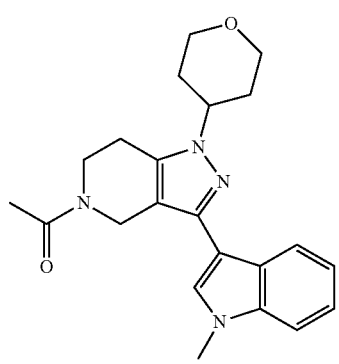 | $^1$H NMR (400 MHz, DMSO-$d_6$) δ 8.33-8.23 (m, 1H), 7.58-7.38 (m, 2H), 7.23-7.17 (m, 1H), 7.15-7.07 (m, 1H), 4.59 (s, 2H), 4.40-4.27 (m, 1H), 4.07-3.95 (m, 2H), 3.85 (s, 3H), 3.83-3.71 (m, 2H), 3.50 (t, J = 12.0 Hz, 2H), 2.90-2.71 (m, 2H), 2.23-2.08 (m, 5H), 1.93-1.79 (m, 2H); m/z 379. | B |

-continued

| Example | Compound Name and Structure | NMR; m/z | Procedure |
|---|---|---|---|
| Example 60 | 1-(1-methyl-3-(5-(1-methyl-1H-pyrazol-4-yl)-1H-indol-3-yl)-6,7-dihydro-1H-pyrazolo[4,3-c]pyridin-5(4H)-yl)ethanone | $^1$H NMR (400 MHz, CD$_3$OD): δ 8.22 (s, 1H), 7.91 (s, 1H), 7.81 (s, 1H), 7.43-7.38 (m, 3H), 4.69-4.65 (m, 2H), 3.99-3.85 (m, 2H), 3.93 (s, 3H), 3.84 (s, 3H), 2.90-2.78 (m, 2H), 2.24-2.16 (m, 3H); m/z 375. | C |
| Example 61 | methyl 4-(5-acetyl-1-methyl-4,5,6,-tetrahydro-1H-pyrazolo[4,3-c]pyridin-3-yl)-1H-indole-6-carboxylate | $^1$H NMR (400 MHz, DMSO-d$_6$) δ 11.60 (s, 1H), 8.04 (s, 1H), 7.65-7.63 (m, 2H), 7.06-7.02 (m, 1H), 4.64-4.61 (m, 2H), 3.88 (s, 3H), 3.81-3.77 (m, 5H), 2.86-2.73 (m, 2H), 2.11-2.02 (m, 3H); m/z 353. | C |
| Example 62 | 1-(3-(7-chloro-1H-indol-4-yl)-1-methyl-6,7-dihydro-1H-pyrazolo[4,3-c]pyridin-5(4H)-yl)ethanone | $^1$H NMR (400 MHz, DMSO-d$_6$) δ 11.50 (s, 1H), 7.42 (s, 1H), 7.25-7.21 (m, 1H), 7.08-7.00 (m, 2H), 4.61 (s, 2H), 3.80-3.75 (m, 5H), 2.86-2.71 (m, 2H), 2.11-2.04 (m, 3H); m/z 329. | C |

| Example | Compound Name and Structure | NMR; m/z | Procedure |
|---|---|---|---|
| Example 63 | 1-(3-(6-methoxy-1H-indol-4-yl)-1-methyl-6,7-dihydro-1H-pyrazolo[4,3-c]pyridin-5(4H)-yl)ethanone | $^1$H NMR (400 MHz, DMSO-$d_6$) δ 10.94 (s, 1H), 7.19 (s, 1H), 6.88-6.84 (m, 1H), 6.64-6.61 (m, 1H), 4.60 (s, 2H), 3.80-3.75 (m, 8H), 284-2.70 (m, 2H), 2.10-2.04 (m, 3H); m/z 325. | C |
| Example 64 | 1-(1-methyl-3-(7-methyl-1H-indol-4-yl)-6,7-dihydro-1H-pyrazolo[4,3-c[pyridin-5(4H)-yl)ethanone | $^1$H NMR (400 MHz, DMSO-$d_6$) δ 11.10 (s, 1H), 7.34-7.32 (m, 1H), 6.97-6.89 (m, 3H), 4.58 (s, 2H), 3.81-3.74 (m, 5H), 2.84-2.69 (m, 2H), 2.10-2.02 (m, 3H); m/z 309. | C |
| Example 65 | 1-(1-methyl-3-(3-(1-methyl-1H-pyrazol-4-yl)phenyl)-6,7-dihydro-1H-pyrazolo[4,3-c]pyridin-5(4H)-yl)ethanone | $^1$H NMR (400 MHz, CDCl$_3$) δ 7.81-7.79 (m, 2H), 7.67 (s, 1H), 7.45-7.27 (m, 3H), 4.83-4.66 (m, 2H), 3.99 (s, 3H), 3.95-3.75 (m, 2H), 3.82 (s, 3H), 2.80-2.72 (m, 2H), 2.21-2.15 (m, 3H); m/z 336. | C |

-continued

| Example | Compound Name and Structure | NMR; m/z | Procedure |
|---|---|---|---|
| Example 66 | 1-(1-(cyclopropylmethyl)-3-(7-methyl-1H-indol-4-yl)-6,7-dihydro-1H-pyrazolo[4,3-c]pyridin-5(4H)-yl)ethanone | $^1$H NMR (400 MHz, DMSO-$d_6$) δ 11.10 (s, 1H), 7.33 (s, 1H), 7.01 (s, 1H), 6.95-6.91 (m, 2H), 4.60 (s, 2H), 3.96 (d, J = 6.8 Hz), 3.81-3.74 (m, 2H), 2.87-2.74 (m, 2H), 2.11-2.04 (m, 3H), 1.29-1.25 (m, 1H), 0.55-0.52 (m, 2H), 0.42-0.40 (m, 2H); m/z 349. | C |
| Example 67 | 1-(1-(cyclopropylmethyl)-3-(1H-indol-4-yl)-6,7-dihydro-1H-pyrazolo[4,3-c]pyridin-5(4H)-yl)ethanone | $^1$H NMR (400 MHz, DMSO-$d_6$) δ 11.15 (s, 1H), 7.39-7.36 (m, 2H), 7.18-7.14 (m, 1H), 7.06-7.00 (m, 2H), 4.64 (s, 2H), 3.98 (d, J = 7.2 Hz), 3.82-3.76 (m, 2H), 2.89-2.76 (m, 2H), 2.12-2.07 (m, 3H), 1.29-1.25 (m, 1H), 0.55-0.52 (m, 2H), 0.45-0.41 (m, 2H); m/z 335. | C |
| Example 68 | 1-(3-(6-(1-methyl-1H-pyrazol-4-yl)-1H-indol-3-yl)-1-(oxetan-3-yl)-6,7-dihydro-1H-pyrazolo[4,3-c]pyridin-5(4H)-yl)ethanone | $^1$H NMR (400 MHz, DMSO-$d_6$) δ 11.25 (s, 1H), 8.29-8.23 (m, 1H), 8.07 (s, 1H), 7.81 (s, 1H), 7.52 (s, 1H), 7.41 (s, 1H), 7.32-7.30 (m, 1H), 5.52-5.48 (m, 1H), 5.08-5.04 (m, 2H), 4.91-4.87 (m, 2H), 4.56 (s, 2H), 3.85 (s, 3H), 3.75-3.69 (m, 2H), 2.77-2.64 (m, 2H), 2.09-1.94 (m, 3H); m/z 417. | C |

-continued

| Example | Compound Name and Structure | NMR; m/z | Procedure |
|---|---|---|---|
| Example 69 | 1-(3-(6-(1-methyl-1H-pyrazol-4-yl)-1H-indol-3-yl)-1-(tetrahydrofuran-3-yl)-6,7-dihydro-1H-pyrazolo[4,3-c]pyridin-5(4H)-yl)ethanone | $^1$H NMR (400 MHz, DMSO-$d_6$) δ 11.29 (s, 1H), 8.17-8.12 (m, 1H), 8.06 (s, 1H), 7.81 (s, 1H), 7.50 (s, 1H), 7.48-7.36 (m, 1H), 7.29-7.26 (m, 1H), 5.02-4.91 (m, 1H), 4.56 (s, 2H), 4.12-4.03 (m, 2H), 3.92-3.87 (m, 2H), 3.85 (s, 3H), 3.79-3.68 (m, 2H), 2.89-2.68 (m, 2H), 2.41-2.23 (m, 2H), 2.10 (s, 3H); m/z 431. | C |
| Example 70 | 1-(3-(2-methyl-6-(1-methyl-1H-pyrazol-4-yl)-1H-indol-3-yl)-1-((S)-tetrahydrofuran-3-yl)-6,7-dihydro-1H-pyrazolo[4,3-c]pyridin-5(4H)-yl)ethanone | $^1$H NMR (400 MHz, DMSO-$d_6$) δ 11.11 (s, 1H), 8.07 (s, 1H), 7.81 (s, 1H), 7.43 (s, 1H), 7.42-7.37 (m, 1H), 7.20-7.17 (m, 1H), 4.98-4.94 (m, 1H), 4.38-4.35 (m, 2H), 4.07-4.03 (m, 2H), 3.92-3.71 (m, 4H), 3.88 (s, 3H), 2.89-2.77 (m, 2H), 2.50-2.32 (m, 5H), 2.08-1.97 (m, 3H); m/z 445. | C |
| Example 71 | 1-(3-(2-methyl-6-(1-methyl-1H-pyrazol-4-yl)-1H-indol-3-y)-1-(tetrahydrofuran-3-yl)-6,7-dihydro-1H-pyrazolo[4,3-c]pyridin-5(4H)-yl)ethanone | $^1$H NMR (400 MHz, DMSO-$d_6$) δ 11.11 (s, 1H), 8.06 (s, 1H), 7.81 (s, 1H), 7.44 (s, 1H), 7.40-7.37 (m, 1H), 7.20-7.17 (m, 1H), 4.98-4.94 (m, 1H), 4.37-4.35 (m, 2H), 4.07-4.02 (m, 2H), 3.92-3.71 (m, 4H), 3.88 (s, 3H), 2.88-2.77 (m, 2H), 2.50-2.32 (m, 5H), 2.08-1.97 (m, 3H); m/z 445. | C |

| Example | Compound Name and Structure | NMR; m/z | Procedure |
|---|---|---|---|
| Example 72 | 1-(3-(2-methyl-1H-indol-3-yl)-1-(tetrahydro-2H-pyran-4-yl)-6,7-dihydro-1H-pyrazolo[4,3-c]pyridin-5(4H)-yl)ethanone 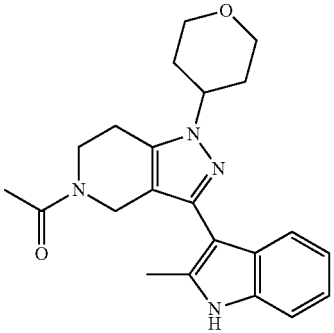 | $^1$H NMR (400 MHz, DMSO-$d_6$) δ 11.10 (s, 1H), 7.48-7.36 (m, 1H), 7.29 (d, J = 8.0 Hz, 1H), 7.05-6.99 (m, 1H), 6.98-6.87 (m, 1H), 4.37-4.24 (m, 3H), 3.98-3.95 (m, 2H), 3.85-3.71 (m, 2H), 3.54-3.44 (m, 2H), 2.93-2.71 (m, 2H), 2.40-2.33 (m, 3H), 2.15-1.93 (m, 5H), 1.87-1.83 (m, 2H); m/z 379. | C |
| Example 73 | 1-(3-(1H-indol-7-yl)-1-(tetrahydro-2H-pyran-4-yl)-6,7-dihydro-1H-pyrazolo[4,3-c]pyridin-5(4H)-yl)ethanone 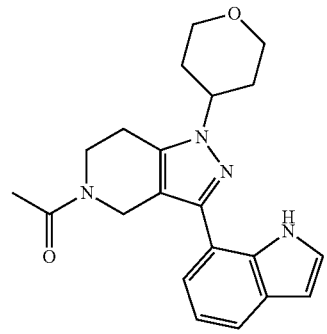 | $^1$H NMR (400 MHz, DMSO-$d_6$) δ 10.74 (s, 1H), 7.54 (d, J = 8.0 Hz, 1H), 7.45 (s, 1H), 7.24-7.17 (m, 1H), 7.15-7.07 (m, 1H), 6.50 (s, 1H), 4.75 (s, 2H), 4.48-4.40 (m, 1H), 4.04-4.00 (m, 2H), 3.84-3.77 (m, 2H), 3.53 (t, J = 12.0 Hz, 2H), 2.97-2.75 (m, 2H), 2.40-2.28 (m, 2H), 2.17-2.09 (m, 3H), 1.87-1.83 (m, 2H); m/z 365. | C |
| Example 74 | 1-(3-(5-chloroisoquinolin-8-yl)-1-(tetrahydro-2H-pyran-4-yl)-6,7-dihydro-1H-pyrazolo[4,3-c]pyridin-5(4H)-yl)ethanone 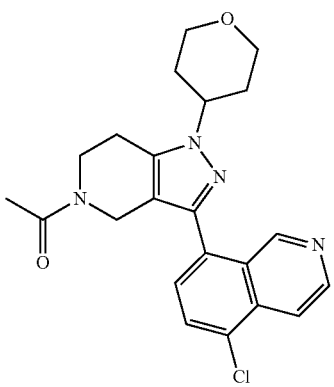 | $^1$H NMR (400 MHz, CDCl$_3$) δ 9.71-9.67 (m, 1H), 8.71-8.64 (m, 1H), 8.13-8.06 (m, 1H), 7.86-7.79 (m, 1H), 7.55-7.47 (m, 1H), 4.63-4.40 (m, 2H), 4.33-4.23 (m, 1H), 4.19-4.12 (m, 2H), 4.04-3.81 (m, 2H), 3.59-3.52 (m, 2H), 2.96-2.82 (m, 2H), 2.49-2.35 (m, 2H), 2.23-2.04 (m, 3H), 2.00-1.92 (m, 2H); m/z 411. | D |

| Example | Compound Name and Structure | NMR; m/z | Procedure |
|---|---|---|---|
| Example 75 | 1-(3-(5-methylisoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.77 (s, 1H), 8.62-8.52 (m, 1H), 7.97-7.88 (m, 1H), 7.72-7.64 (m, 1H), 7.60-7.49 (m, 1H), 4.49 (s, 2H), 4.48-4.38 (m, 1H), 4.05-3.95 (m, 2H), 3.88-3.74 (m, 2H), 3.51 (t, J = 11.2 Hz, 2H), 3.00-2.78 (m, 2H), 2.69 (s, 3H), 2.20-2.03 (m, 5H), 2.00-1.87 (m, 2H); m/z 391. | D |
| Example 76 | 1-(3-(5-methoxyisoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, CDCl$_3$) δ 9.64-9.55 (m, 1H), 8.61-8.52 (m, 1H), 8.11-8.04 (m, 1H), 7.54-7.45 (m, 1H), 7.09-7.02 (m, 1H), 4.63-4.40 (m, 2H), 4.31-4.21 (m, 1H), 4.20-4.13 (m, 2H), 4.06 (s, 3H), 3.98-3.80 (m, 2H), 3.57 (t, J = 12.0 Hz, 2H), 2.95-2.82 (m, 2H), 2.50-2.37 (m, 2H), 2.24-2.03 (m, 3H), 2.00-1.93 (m, 2H); m/z 407. | E |
| Example 77 | 1-(3-(4-methoxyisoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.41 (s, 1H), 8.22 (s, 1H), 8.17 (d, J = 8.4 Hz, 1H), 7.87-7.80 (m, 1H), 7.73-7.61 (m, 1H), 4.50 (s, 2H), 4.49-4.39 (m, 1H), 4.08 (s, 3H), 4.04-3.95 (m, 2H), 3.86-3.76 (m, 2H), 3.51 (t, J = 12.0 Hz, 2H), 3.02-2.79 (m, 2H), 2.15-2.02 (m, 5H), 2.01-1.89 (m, 2H); m/z 407. | E |

-continued

| Example | Compound Name and Structure | NMR; m/z | Procedure |
|---|---|---|---|
| Example 78 | 1-(1-(tetrahydro-2H-pyran-4-yl)-3-(4-vinylisoquinolin-8-yl)-6,7-dihydro-1H-pyrazolo[4,3-c]pyridin-5(4H)-yl)ethanone | $^1$H NMR (400 MHz, DMSO-$d_6$) δ 9.69 (s, 1H), 8.69 (s, 1H), 8.21 (d, J = 8.4 Hz, 1H), 7.93-7.84 (m, 1H), 7.74-7.62 (m, 1H), 7.55-7.48 (m, 1H), 5.98 (d, J = 17.6 Hz, 1H), 5.60 (d, J = 12.4 Hz, 1H), 4.50 (s, 2H), 4.49-4.39 (m, 1H), 4.05-3.95 (m, 2H), 3.86-3.77 (m, 2H), 3.51 (t, J = 12.0 Hz, 2H), 2.98-2.80 (m, 2H), 2.20-2.04 (m, 5H), 2.02-1.92 (m, 2H); m/z 403. | F |
| Example 79 | 1-(3-(5-ethylisoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, CDCl$_3$) δ 9.66-9.55 (m, 1H), 8.61-8.52 (m, 1H), 7.88-7.84 (m, 1H), 7.63-7.56 (m, 1H), 7.55-7.48 (m, 1H), 4.62-4.40 (m, 2H), 4.32-4.23 (m, 1H), 4.21-4.07 (m, 2H), 4.04-3.82 (m, 2H), 3.56 (t, J = 12.0 Hz, 2H), 3.09 (q, J = 7.2 Hz, 2H), 2.96-2.82 (m, 2H), 2.49-2.36 (m, 2H), 2.23-2.04 (m, 3H), 2.00-1.92 (m, 2H), 1.41 (t, J = 7.2 Hz, 3H); m/z 405. | G |
| Example 80 | 1-(3-(4-ethylisoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.60 (s, 1H), 8.41 (s, 1H), 8.13 (d, J = 8.8 Hz, 1H), 7.92-7.83 (m, 1H), 7.72-7.57 (m, 1H), 4.50 (s, 2H), 4.49-4.39 (m, 1H), 4.06-3.92 (m, 2H), 3.89-3.75 (m, 2H), 3.52 (t, J = 12.0 Hz, 2H), 3.09 (q, J = 7.6 Hz, 2H), 3.00-2.81 (m, 2H), 2.19-2.05 (m, 5H), 2.04-1.89 (m, 2H), 1.33 (t, J = 7.6 Hz, 3H); m/z 405. | G |

| Example | Compound Name and Structure | NMR; m/z | Procedure |
|---|---|---|---|
| Example 81 | 1-(3-(5-(hydroxymethyl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.78 (s, 1H), 8.55 (d, J = 6.0 Hz, 1H), 7.97 (d, J = 6.4 Hz, 1H), 7.85 (d, J = 7.6 Hz, 1H), 7.67-7.56 (m, 1H), 5.50-5.41 (m, 1H), 4.99 (d, J = 5.6 Hz, 2H), 4.50 (s, 2H), 4.49-4.39 (m, 1H), 4.05-3.95 (m, 2H), 3.87-3.76 (m, 2H), 3.51 (t, J = 12.0 Hz, 2H), 2.98-2.82 (m, 2H), 2.14-2.02 (m, 5H), 2.00-1.88 (m, 2H); m/z 407. | H |
| Example 82 | 1-(3-(4-(hydroxymethyl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.67 (s, 1H), 8.51 (s, 1H), 8.15 (d, J = 8.4 Hz, 1H), 7.91-7.83 (m, 1H), 7.72-7.60 (m, 1H), 5.42 (s, 1H), 4.98 (s, 2H), 4.49 (s, 2H), 4.48-4.41 (m, 1H), 4.06-3.92 (m, 2H), 3.87-3.77 (m, 2H), 3.51 (t, J = 12.0 Hz, 2H), 3.00-2.81 (m, 2H), 2.18-2.02 (m, 5H), 2.01-1.88 (m, 2H); m/z 407. | H |
| Example 83 | 1-(3-(6-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, CDCl$_3$) δ 9.54-9.48 (m, 1H), 8.10-7.96 (m, 2H), 7.75-7.72 (m, 1H), 7.59-7.54 (m, 1H), 7.34-7.32 (m, 1H), 4.63-4.44 (m, 2H), 4.30-4.22 (m, 1H), 4.20-4.12 (m, 2H), 4.07-3.79 (m, 2H), 4.00 (s, 3H), 3.60-3.54 (m, 2H), 2.94-2.83 (m, 2H), 2.65-2.52 (m, 3H), 2.51-2.36 (m, 2H), 2.22-2.04 (m, 3H), 1.97-1.94 (m, 2H); m/z 471. | I |

-continued

| Example | Compound Name and Structure | NMR; m/z | Procedure |
|---|---|---|---|
| Example 84 | 1-(3-(7-methyl-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, CDCl$_3$) δ 8.86-8.84 (m, 1H), 8.03 (s, 1H), 7.98-7.96 (m, 1H), 7.78-7.72 (m, 2H), 7.61-7.57 (m, 1H), 4.31-4.25 (m, 1H), 4.16-4.07 (m, 4H), 3.98 (s, 3H), 3.96-3.66 (m, 2H), 3.57 (t, J = 12.0 Hz, 2H), 2.94-2.86 (m, 2H), 2.41-2.35 (m, 2H), 3.37 (s, 3H), 2.19-2.00 (m, 3H), 1.97-1.93 (m, 2H); m/z 471. | I |
| Example 85 | 1-(3-(7-fluoro-3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-d$_6$) δ 9.39-9.36 (m, 1H), 8.34 (s, 1H), 8.14 (s, 1H), 8.07 (s, 1H), 8.05-8.00 (m, 1H), 7.80-7.75 (m, 1H), 4.49-4.46 (m, 1H), 4.37 (s, 2H), 4.05-3.97 (m, 2H), 3.91 (s, 3H), 3.85-3.79 (m, 2H), 3.52 (t, J = 12.0 Hz, 2H), 3.02-2.85 (m, 2H), 2.16-1.93 (m, 7H); m/z 475. | I |
| Example 86 | 5-(8-(5-acetyl-1-(tetrahydro-2H-pyran-4-yl)-4,5,6,7-tetrahydro-1H-pyrazolo[4,3-c]pyridin-3-yl)-7-fluoroisoquinolin-3-yl)-N-methylpicolinamide | $^1$H NMR (400 MHz, DMSO-d$_6$) δ 9.58-9.55 (m, 1H), 9.43 (s, 1H), 8.88-8.83 (m, 1H), 8.77 (s, 1H), 8.76-8.74 (m, 1H), 8.25-8.21 (m, 1H), 8.20-8.17 (m, 1H), 7.94-7.89 (m, 1H), 4.53-4.50 (m, 1H), 4.39 (s, 2H), 4.05-3.97 (m, 2H), 3.90-3.78 (m, 2H), 3.53 (t, J = 12.4 Hz, 2H), 3.02-2.85 (m, 2H), 2.86 (d, J = 5.2 Hz, 3H), 2.16-1.93 (m, 7H); m/z 529. | I |

| Example | Compound Name and Structure | NMR; m/z | Procedure |
|---|---|---|---|
| Example 87 | 5-(8-(5-acetyl-1-(tetrahydro-2H-pyran-4-yl)-4,5,6,7-tetrahydro-1H-pyrazolo[4,3-c]pyridin-3-yl)isoquinolin-3-yl)-N-methylpicolinamide 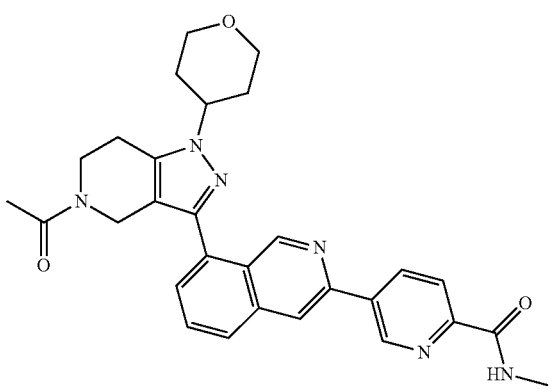 | $^1$H NMR (400 MHz, DMSO-$d_6$) δ 10.00 (s, 1H), 9.45 (s, 1H), 8.87 (s, 1H), 8.79-8.76 (m, 1H), 8.71 (s, 1H), 8.17 (d, J = 8.0 Hz, 1H), 8.08 (d, J = 8.0 Hz, 1H), 7.94-7.89 (m, 1H), 7.75-7.66 (m, 1H), 4.58 (s, 2H), 4.53-4.42 (m, 1H), 4.07-3.97 (m, 2H), 3.89-3.79 (m, 2H), 3.56-3.50 (m, 2H), 3.00-2.80 (m, 2H), 2.86 (s, 3H), 2.22-1.90 (m, 7H); m/z 411. | I |
| Example 88 | 1-(3-(3-(1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone 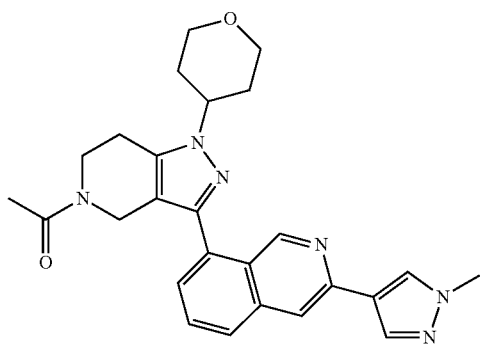 | $^1$H NMR (400 MHz, DMSO-$d_6$) δ 9.81 (s, 1H), 8.36 (s, 1H), 8.12-8.07 (m, 1H), 7.90-7.86 (m, 1H), 7.81-7.76 (m, 1H), 7.59-7.50 (m, 1H), 4.55 (s, 2H), 4.48-4.43 (m, 1H), 4.03-4.00 (m, 2H), 3.91 (s, 3H), 3.85-3.80 (m, 2H), 3.55-3.49 (m, 2H), 2.96-2.82 (m, 2H), 2.20-2.02 (m, 5H), 1.99-1.91 (m, 2H); m/z 457. | I |
| Example 89 | (S)-1-(3-(3-(1-methyl-1H-pyrazol-4-yl)isoquinolin-8-yl)-1-(tetrahydrofuran-3-yl)-6,7-dihydro-1H-pyrazolo[4,3-c]pyridin-5(4H)-yl)ethanone 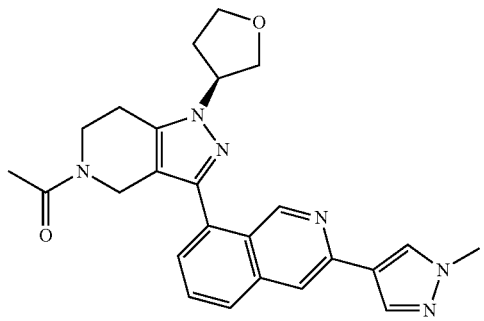 | $^1$H NMR (400 MHz, DMSO-$d_6$) δ 9.76 (s, 1H), 8.36 (s, 1H), 8.13-8.05 (m, 1H), 7.90-7.87 (m, 1H), 7.81-7.76 (m, 1H), 7.58-7.50 (m, 1H), 5.10-5.06 (m, 1H), 4.54 (s, 2H), 4.11-4.05 (m, 2H), 3.98-3.78 (m, 4H), 3.95 (s, 3H), 2.98-2.78 (m, 2H), 2.42-2.37 (m, 2H), 2.10-2.01 (m, 3H); m/z 443. | I |

-continued

| Example | Compound Name and Structure | NMR; m/z | Procedure |
|---|---|---|---|
| Example 90 | 1-(3-(3-(1,5-dimethyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, CDCl$_3$) δ 9.72-9.65 (m, 1H), 7.92 (s, 1H), 7.85-7.64 (m, 3H), 7.54-7.46 (m, 1H), 4.65-4.47 (m, 2H), 4.37-4.23 (m, 1H), 4.21-4.15 (m, 2H), 4.07-3.82 (m, 2H), 3.89 (s, 3H), 3.63-3.54 (m, 2H), 2.96-2.84 (m, 2H), 2.67 (s, 3H), 2.54-2.39 (m, 2H), 2.21-2.08 (m, 3H), 2.01-1.93 (m, 2H); m/z 471. | I |
| Example 91 | 3-(7-fluoro-3-(1-methyl-1H-pyrazol-4-yl)isoquinolin-8-yl)-N-methyl-1-(tetrahydro-2H-pyran-4-yl)-6,7-dihydro-1H-pyrazolo[4,3-c]pyridine-5(4H)-carboxamide | $^1$H NMR (400 MHz, DMSO-d$_6$) δ 9.35 (s, 1H), 8.33 (s, 1H), 8.14 (s, 1H), 8.07 (s, 1H), 8.06-8.00 (m, 1H), 7.80-7.75 (m, 1H), 6.55-6.47 (m, 1H), 4.50-4.43 (m, 1H), 4.22 (s, 2H), 4.02-3.98 (m, 2H), 3.91 (s, 3H), 3.73-3.67 (m, 2H), 3.55-3.48 (m, 2H), 2.87-2.79 (m, 2H), 2.55-2.53 (m, 3H), 2.18-2.08 (m, 2H), 1.97-1.91 (m, 2H); m/z 490. | J |
| Example 92 | N-methyl-3-(3-(6-(methylcarbamoyl)pyridin-3-yl)isoquinolin-8-yl)-1-(tetrahydro-2H-pyran-4-yl)-6,7-dihydro-1H-pyrazolo[4,3-c]pyridine-5(4H)-carboxamide | $^1$H NMR (400 MHz, CDCl$_3$) δ 9.84 (s, 1H), 9.29 (s, 1H), 8.54-8.51 (m, 1H), 8.27 (d, J = 8.4 Hz, 1H), 8.15 (s, 1H), 8.12-8.05 (m, 1H), 7.90 (d, J = 8.4 Hz, 1H), 7.80-7.75 (m, 1H), 7.61 (d, J = 7.2 Hz, 1H), 4.61-4.50 (m, 1H), 4.40 (s, 2H), 4.34-4.27 (m, 1H), 4.19-4.15 (m, 2H), 3.90-3.87 (m, 2H), 3.62-3.55 (m, 2H), 3.08 (d, J = 5.2 Hz, 3H), 2.90-2.87 (m, 2H), 2.80 (d, J = 4.4 Hz, 3H), 2.50-2.40 (m, 2H), 2.04-1.93 (m, 2H); m/z 526. | J |

-continued

| Example | Compound Name and Structure | NMR; m/z | Procedure |
|---|---|---|---|
| Example 93 | N-methyl-3-(3-(1-methyl-1H-pyrazol-4-yl)isoquinolin-8-yl)-1-(tetrahydro-2H-pyran-4-yl)-6,7-dihydro-1H-pyrazolo[4,3-c]pyridine-5(4H)-carboxamide 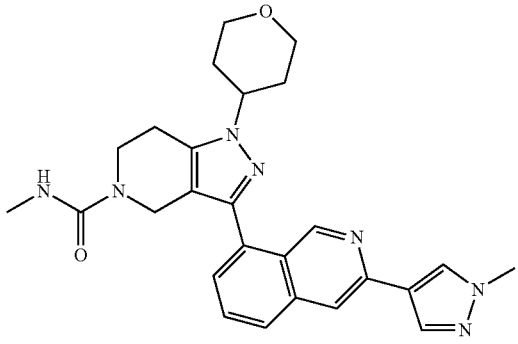 | $^1$H NMR (400 MHz, DMSO-d$_6$) δ 9.87 (s, 1H), 8.38 (s, 1H), 8.16-8.13 (m, 1H), 8.11 (s, 1H), 7.90 (d, J = 8.0 Hz, 1H), 7.86-7.80 (m, 1H), 7.56 (d, J = 8.0 Hz, 1H), 6.65-6.53 (m, 1H), 4.52-4.42 (m, 3H), 4.05-3.98 (m, 2H), 3.92 (s, 3H), 3.73-3.67 (m, 2H), 3.55-3.48 (m, 2H), 2.87-2.79 (m, 2H), 2.55-2.53 (m, 3H), 2.18-2.08 (m, 2H), 1.97-1.91 (m, 2H); m/z 472. | J |
| Example 94 | N-methyl-3-(3-(2-methylthiazol-5-yl)isoquinolin-8-yl)-1-(tetrahydro-2H-pyran-4-yl)-6,7-dihydro-1H-pyrazolo[4,3-c]pyridine-5(4H)-carboxamide 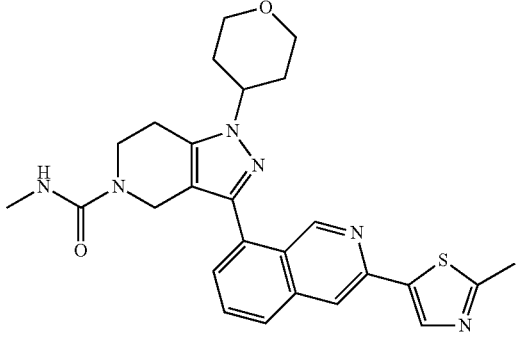 | $^1$H NMR (400 MHz, CDCl$_3$) δ 9.65 (s, 1H), 8.19 (s, 1H), 7.96 (s, 1H), 7.83 (d, J = 8.4 Hz, 1H), 7.75-7.70 (m, 1H), 7.54 (d, J = 7.2 Hz, 1H), 4.52-4.44 (m, 1H), 4.34 (s, 2H), 4.30-4.26 (m, 1H), 4.21-4.13 (m, 2H), 3.89-3.86 (m, 2H), 3.60-2.64 (m, 2H), 2.88-2.86 (m, 2H), 2.80-2.77 (m, 6H), 2.48-2.38 (m, 2H), 1.97-1.94 (m, 2H); m/z 489. | J |
| Example 95 | N-methyl-3-(3-phenoxyphenyl)-1-(tetrahydro-2H-pyran-4-yl)-6,7-dihydro-1H-pyrazolo[4,3-c]pyridine-5(4H)-carboxamide 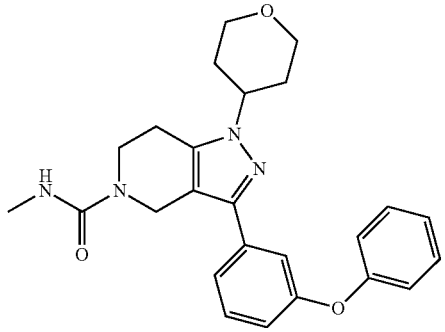 | $^1$H NMR (400 MHz, CDCl$_3$) δ 7.57-7.23 (m, 5H), 7.22-6.83 (m, 3H), 6.75-6.57 (m, 1H), 4.48 (s, 2H), 4.41-4.24 (m, 1H), 4.07-3.83 (m, 2H), 3.75-3.50 (m, 4H), 2.85-2.65 (m, 2H), 2.59 (s, 3H), 2.17-1.92 (m, 2H), 1.90-1.71 (m, 2H); m/z 433. | J |

-continued

| Example | Compound Name and Structure | NMR; m/z | Procedure |
|---|---|---|---|
| Example 96 | 4-(8-(5-acetyl-1-(tetrahydro-2H-pyran-4-yl)-4,5,6,7-tetrahydro-1H-pyrazolo[4,3-c]pyridin-3-yl)isoquinolin-3-yl)-1-methyl-1H-pyrazole-5-carbonitrile | $^1$H NMR (400 MHz, DMSO-$d_6$) δ 9.89-9.80 (m, 1H), 8.40 (s, 1H), 8.34 (s, 1H), 7.99 (d, J = 8.0 Hz, 1H), 7.93-7.82 (m, 1H), 7.71-7.59 (m, 1H), 4.55 (s, 2H), 4.54-4.41 (m, 1H), 4.09 (s, 3H), 4.06-3.98 (m, 2H), 3.88-3.77 (m, 2H), 3.52 (t, J = 12.0 Hz, 2H), 3.01-2.80 (m, 2H), 2.19-2.02 (m, 5H), 2.01-1.88 (m, 2H); m/z 482. | K |
| Example 97 | 1-(3-(3-(3-(difluoromethyl)-1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.83-9.76 (m, 1H), 8.50 (s, 1H), 8.11 (s, 1H), 7.93 (d, J = 8.0 Hz, 1H), 7.86-7.79 (m, 1H), 7.65-7.54 (m, 1H), 7.58 (t, J = 54.0 Hz, 1H), 4.54 (s, 2H), 4.52-4.41 (m, 1H), 4.07-3.93 (m, 2H), 3.97 (s, 3H), 3.88-3.77 (m, 2H), 3.52 (t, J = 12.0 Hz, 2H), 3.01-2.81 (m, 2H), 2.20-2.01 (m, 5H), 2.00-1.88 (m, 2H); m/z 507. | K |
| Example 98 | 1-(3-(3-(5-(difluoromethyl)-1-methyl-1H-pyrazol-4-yl)isoquinolin-8-yl)-1-(tetrahydro-2H-pyran-4-yl)-6,7-dihydro-1H-pyrazolo[4,3-c]pyridin-5(4H)-yl)ethanone | $^1$H NMR (400 MHz, DMSO-$d_6$) δ 9.81 (s, 1H), 8.30 (s, 1H), 8.22 (s, 1H), 8.13 (t, J = 54.0 Hz, 1H), 8.04-7.93 (m, 1H), 7.90-7.82 (m, 1H), 7.69-7.56 (m, 1H), 4.54 (s, 2H), 4.53-4.41 (m, 1H), 4.06 (s, 3H), 4.05-4.00 (m, 2H), 3.89-3.73 (m, 2H), 3.52 (t, J = 12.0 Hz, 2H), 3.02-2.81 (m, 2H), 2.23-2.01 (m, 5H), 2.00-1.88 (m, 2H); m/z 507. | K |

-continued

| Example | Compound Name and Structure | NMR; m/z | Procedure |
|---|---|---|---|
| Example 99 | 5-(5-acetyl-1-(tetrahydro-2H-pyran-4-yl)-4,5,6,7-tetrahydro-1H-pyrazolo[4,3-c]pyridin-3-yl)-1,2-dihydroisoquinolin-3(4H)-one | $^1$H NMR (400 MHz, CDCl$_3$) δ 7.35-7.27 (m, 1H), 7.25-7.12 (m, 2H), 6.71-6.59 (m, 1H), 4.60-4.38 (m, 4H), 4.26-4.07 (m, 3H), 3.96-3.75 (m, 2H), 3.74-3.67 (m, 2H), 3.60-3.48 (m, 2H), 2.86-2.76 (m, 2H), 2.40-2.29 (m, 2H), 2.20-2.10 (m, 3H), 1.99-1.82 (m, 2H); m/z 395. | L |
| Example 100 | 5-(5-acetyl-1-(tetrahydro-2H-pyran-4-yl)-4,5,6,7-tetrahydro-1H-pyrazolo[4,3-c]pyridin-3-yl)isoquinolin-3(2H)-one | $^1$H NMR (400 MHz, CDCl$_3$) δ 8.83-8.72 (m, 1H), 7.92-7.78 (m, 1H), 7.57 (d, J = 6.4 Hz, 1H), 7.45-7.34 (m, 2H), 4.62-4.40 (m, 2H), 4.31-4.23 (m, 1H), 4.21-4.12 (m, 2H), 4.04-3.82 (m, 2H), 3.58 (t, J = 12.0 Hz, 2H), 2.95-2.84 (m, 2H), 2.49-2.38 (m, 2H), 2.24-2.05 (m, 3H), 2.01-1.91 (m, 2H); m/z 393. | L |
| Example 101 | 5-(5-acetyl-1-(tetrahydro-2H-pyran-4-yl)-4,5,6,7-tetrahydro-1H-pyrazolo[4,3-c]pyridin-3-yl)-2-(1-methyl-1H-pyrazol-4-yl)-1,2-dihydroisoquinolin-3(4H)-one | $^1$H NMR (400 MHz, CDCl$_3$) δ 7.99 (d, J = 8.4 Hz, 1H), 7.58 (s, 1H), 7.40-7.17 (m, 3H), 4.90-4.87 (m, 2H), 4.57-4.42 (m, 2H), 4.27-4.08 (m, 3H), 4.00-3.75 (m, 4H), 3.91 (s, 3H), 3.57 (t, J = 12.0 Hz, 2H), 2.90-2.76 (m, 2H), 2.43-2.25 (m, 2H), 2.20-2.11 (m, 3H), 1.95-1.85 (m, 2H); m/z 475. | L |

-continued

| Example | Compound Name and Structure | NMR; m/z | Procedure |
|---|---|---|---|
| Example 102 | 5-(5-acetyl-1-(tetrahydro-2H-pyran-4-yl)-4,5,6,7-tetrahydro-1H-pyrazolo[4,3-c]pyridin-3-yl)-2-(1,5-dimethyl-1H-pyrazol-4-yl)-1,2-dihydroisoquinolin-3(4H)-one | $^1$H NMR (400 MHz, CDCl$_3$) δ 7.44-7.42 (m, 1H), 7.35-7.31 (m, 2H), 7.23-7.17 (m, 1H), 4.78-4.76 (m, 2H), 4.57-4.45 (m, 2H), 4.25-4.13 (m, 3H), 3.98-3.79 (m, 7H), 3.55 (t, J = 12.0 Hz, 2H), 2.87-2.80 (m, 2H), 2.43-2.28 (m, 2H), 2.21-2.10 (m, 6H), 1.97-1.76 (m, 2H); m/z 489. | L |
| Example 103 | 5-(5-acetyl-1-(tetrahydro-2H-pyran-4-yl)-4,5,6,7-tetrahydro-1H-pyrazolo[4,3-c]pyridin-3-yl)-2-(6-(methylamino)pyridin-3-yl)-1,2-dihydroisoquinolin-3(4H)-one | $^1$H NMR (400 MHz, DMSO-d$_6$) δ 7.92 (d, J = 2.8 Hz, 1H), 7.37-7.24 (m, 4H), 6.58-6.52 (m, 1H), 6.48-6.41 (m, 1H), 4.83 (s, 2H), 4.46 (s, 2H), 4.42-4.33 (m, 1H), 4.30-3.94 (m, 2H), 3.85 (s, 2H), 3.83-3.73 (m, 4H), 3.55-3.40 (m, 2H), 2.92-2.77 (m, 2H), 2.76 (d, J = 5.2 Hz, 3H), 2.14-1.99 (m, 5H), 1.92-1.82 (m, 2H); m/z 501. | L |
| Example 104 | 5-(5-acetyl-1-(tetrahydro-2H-pyran-4-yl)-4,5,6,7-tetrahydro-1H-pyrazolo[4,3-c]pyridin-3-yl)-2-(6-(dimethylamino)pyridin-3-yl)-1,2-dihydroisoquinolin-3(4H)-one | $^1$H NMR (400 MHz, DMSO-d$_6$) δ 8.04 (d, J = 2.4 Hz, 1H), 7.49-7.45 (m, 1H), 7.39-7.24 (m, 3H), 6.65 (d, J = 9.2 Hz, 1H), 4.86 (s, 2H), 4.47 (s, 2H), 4.43-7.31 (m, 1H), 4.06-3.95 (m, 2H), 3.89-3.84 (m, 2H), 3.83-3.72 (m, 2H), 3.46 (d, J = 11.6 Hz, 2H), 3.02 (s, 6H), 2.94-2.75 (m, 2H), 2.12-2.01 (m, 5H), 1.93-1.82 (m, 2H); m/z 515. | L |

-continued

| Example | Compound Name and Structure | NMR; m/z | Procedure |
|---|---|---|---|
| Example 105 | 5-(5-(5-acetyl-1-(tetrahydro-2H-pyran-4-yl)-4,5,6,7-tetrahydro-1H-pyrazolo[4,3-c]pyridin-3-yl)-3-oxo-3,4-dihydroisoquinolin-2(1H)-yl)-N-methylpicolinamide | $^1$H NMR (400 MHz, CDCl$_3$) δ 8.64 (s, 1H), 8.26 (d, J = 8.8 Hz, 2H), 8.00-7.91 (m, 1H), 7.84 (d, J = 8.4 Hz, 1H), 7.39-7.33 (m, 2H), 4.97-4.93 (m, 2H), 4.60-4.48 (m, 2H), 4.25-4.10 (m, 3H), 4.02-3.82 (m, 4H), 3.56 (t, J = 12.0 Hz, 2H), 3.05 (d, J = 5.2 Hz, 3H), 2.89-2.80 (m, 2H), 2.45-2.30 (m, 2H), 2.22-2.14 (m, 3H), 1.97-1.87 (m, 2H); m/z 529. | L |
| Example 106 | 1-(1-methyl-3-(5-(1-methyl-1H-pyraozl-4-yl)-1H-indol-1-yl)-6,7-dihydro-1H-pyrazolo[4,3-c]pyridin-5(4H)-yl)ethanone | $^1$H NMR (400 MHz, DMSO-d$_6$) δ 8.09 (s, 1H), 7.84 (s, 1H), 7.80-7.71 (m, 2H), 7.55-7.41 (m, 2H), 6.66 (s, 1H), 4.50-4.47 (m, 2H), 3.87 (s, 3H), 3.82-3.72 (m, 5H), 2.88-2.73 (m, 2H), 2.11-2.05 (m, 3H); m/z 375. | M |
| Example 107 | 1-(1-methyl-3-(5-(1-methyl-1H-pyrazol-4-yl)-1H-benzo[d]imidazol-1-yl)-6,7-dihydro-1H-pyrazolo[4,3-c]pyridin-5(4H)-yl)ethanone | $^1$H NMR (400 MHz, DMSO-d$_6$) δ 8.46-8.40 (m, 1H), 8.17 (s, 1H), 7.96 (s, 1H), 7.92 (s, 1H), 7.81-7.69 (m, 1H), 7.56 (d, J = 8.4 Hz, 1H), 4.57-4.51 (m, 2H), 3.88 (s, 3H), 3.83-3.72 (m, 5H), 2.90-2.74 (m, 2H), 2.11-2.06 (m, 3H); m/z 376. | M |

-continued

| Example | Compound Name and Structure | NMR; m/z | Procedure |
|---|---|---|---|
| Example 108 | 1-(1-methyl-3-(6-(1-methyl-1H-pyrazol-4-yl)-1H-benzo[d]imidazol-1-yl)-6,7-dihydro-1H-pyrazolo[4,3-c]pyridin-5(4H)-yl)ethanone | ¹H NMR (400 MHz, DMSO-d₆) δ 8.42-8.36 (m, 1H), 8.18 (s, 1H), 7.91-7.73 (m, 3H), 7.53 (d, J = 8.4 Hz, 1H), 4.54-4.49 (m, 2H), 3.87 (s, 3H), 3.85-3.75 (m, 5H), 2.92-2.76 (m, 2H), 2.13-2.04 (m, 3H); m/z 376. | M |
| Example 109 | 1-(3-(1H-indol-1-yl)-1-(tetrahydro-2H-pyran-4-yl)-6,7-dihydro-1H-pyrazolo[4,3-c]pyridin-5(4H)-yl)ethanone | ¹H NMR (400 MHz, DMSO-d₆) δ 7.88-7.76 (m, 1H), 7.64 (d, J = 7.6 Hz, 1H), 7.60-7.47 (m, 1H), 7.26-7.18 (m, 1H), 7.17-7.09 (m, 1H), 6.69 (s, 1H), 4.54-4.46 (m, 2H), 4.45-4.34 (m, 1H), 4.08-3.94 (m, 2H), 3.80-3.76 (m, 2H), 3.49 (t, J = 12.0 Hz, 2H), 2.98-2.77 (m, 2H), 2.14-2.02 (m, 5H), 1.96-1.82 (m, 2H); m/z 365. | M |
| Example 110 | 1-(3-(3-methyl-1H-indol-1-yl)-1-(tetrahydro-2H-pyran-4-yl)-6,7-dihydro-1H-pyrazolo[4,3-c]pyridin-5(4H)-yl)ethanone | H NMR (400 MHz, DMSO-d₆) δ 7.85-7.75 (m, 1H), 7.57 (d, J = 8.0 Hz, 1H), 7.38-7.26 (m, 1H), 7.25-7.18 (m, 1H), 7.17-7.09 (m, 1H), 4.57-4.45 (m, 2H), 4.44-4.30 (m, 1H), 4.02-3.9 (m, 2H), 3.86-3.72 (m, 2H), 3.49 (t, J = 12.0 Hz, 2H), 2.95-2.73 (m, 2H), 2.33 (s, 3H), 2.16-1.99 (m, 5H), 1.93-1.81 (m, 2H); m/z 379. | M |

| Example | Compound Name and Structure | NMR; m/z | Procedure |
| --- | --- | --- | --- |
| Example 111 | 1-[3-[3-(3R)-methoxypyrrolidin-1-yl)-8-isoquinolyl]-1-tetrahydropyran-4-yl-6,7-dihydro-4H-pyrazolo[4,3-c]pyridin-5-yl]ethanone (single unknown stereoisomer) | $^1$H NMR (400 MHz, DMSO-$d_6$) δ 9.46 (t, J = 0.9 Hz, 1H), 7.61 (dt, J = 8.5, 1.0 Hz, 1H), 7.57-7.47 (m, 1H), 7.22-7.04 (m, 1H), 6.69-6.57 (m, 1H), 4.51 (s, 2H), 4.43 (d, J = 4.2 Hz, 1H), 4.16-4.08 (m, 1H), 4.08-3.97 (m, 2H), 3.87-3.75 (m, 2H), 3.61-3.40 (m, 6H), 3.29 (s, 3H), 2.98-2.77 (m, 2H), 2.18-1.97 (m, 7H), 1.93 (d, J = 9.3 Hz, 2H); m/z 476.3. | N |
| Example 112 | 1-[3-[3-(3S)-methoxypyrrolidin-1-yl)-8-isoquinolyl]-1-tetrahydropyran-4-yl-6,7-dihydro-4H-pyrazolo[4,3-c]pyridin-5-yl]ethanone (single unknown stereoisomer) | $^1$H NMR (400 MHz, DMSO-$d_6$) δ 9.46 (t, J = 0.9 Hz, 1H), 7.61 (dt, J = 8.5, 1.0 Hz, 1H), 7.57-7.47 (m, 1H), 7.22-7.04 (m, 1H), 6.69-6.57 (m, 1H), 4.51 (s, 2H), 4.43 (d, J = 4.2 Hz, 1H), 4.16-4.08 (m, 1H), 4.08-3.97 (m, 2H), 3.87-3.75 (m, 2H), 3.61-3.40 (m, 6H), 3.29 (s, 3H), 2.98-2.77 (m, 2H), 2.18-1.97 (m, 7H), 1.93 (d, J = 9.3 Hz, 2H); m/z 476.4. | N |

| Example | Compound Name and Structure | NMR; m/z | Procedure |
|---|---|---|---|
| Example 113 | 1-[3-[3-(2R)-methylpyrrolidin-1-yl)-8-isoquinolyl]-1-tetrahydropyran-4-yl-6,7-dihydro-4H-pyrazolo[4,3-c]pyridin-5-yl]ethanone (single unknown stereoisomer) | $^1$H NMR (400 MHz, DMSO-$d_6$) δ 9.42 (t, J = 0.8 Hz, 1H), 7.60 (dt, J = 8.4, 0.9 Hz, 1H), 7.51 (ddd, J = 8.9, 6.9, 2.1 Hz, 1H), 7.20-7.03 (m, 1H), 6.60 (s, 1H), 4.49 (d, J = 1.3 Hz, 2H), 4.43 (td, J = 11.3, 9.6, 5.7 Hz, 1H), 4.30-4.20 (m, 1H), 4.06-3.97 (m, 2H), 3.82 (dt, J = 17.8, 6.1 Hz, 2H), 3.59-3.47 (m, 3H), 3.37-3.32 (m, 1H), 2.88 (dt, J = 48.5, 5.8 Hz, 1H), 2.14-1.90 (m, 10H), 1.70 (d, J = 5.1 Hz, 1H), 1.20 (d, J = 6.2 Hz, 3H); m/z 460.2. | N |
| Example 114 | 1-[3-[3-(2S)-methylpyrrolidin-1-yl)-8-isoquinolyl]-1-tetrahydropyran-4-yl-6,7-dihydro-4H-pyrazolo[4,3-c]pyridin-5-yl]ethanone (single unknown stereoisomer) | $^1$H NMR (400 MHz, DMSO-$d_6$) δ 9.42 (t, J = 0.8 Hz, 1H), 7.60 (dt, J = 8.4, 0.9 Hz, 1H), 7.51 (ddd, J = 8.9, 6.9, 2.1 Hz, 1H), 7.20-7.03 (m, 1H), 6.60 (s, 1H), 4.49 (d, J = 1.3 Hz, 2H), 4.43 (td, J = 11.3, 9.6, 5.7 Hz, 1H), 4.30-4.20 (m, 1H), 4.06-3.97 (m, 2H), 3.82 (dt, J = 17.8, 6.1 Hz, 2H), 3.59-3.47 (m, 3H), 3.37-3.32 (m, 1H), 2.88 (dt, J = 48.5, 5.8 Hz, 2H), 2.14-1.90 (m, 10H), 1.70 (d, J = 5.1 Hz, 1H), 1.20 (d, J = 6.2 Hz, 3H); m/z 460.2. | N |
| Example 115 | 1-[3-[3-(3-fluoropyrrolidin-1-yl)-8-isoquinolyl]-1-tetrahydropyran-4-yl-6,7-dihydro-4H-pyrazolo[4,3-c]pyridin-5-yl]ethanone (mixture of enantiomers) | $^1$H NMR (400 MHz, DMSO-$d_6$) δ 9.48 (t, J = 0.9 Hz, 1H), 8.53 (s, 1H), 7.68-7.58 (m, 1H), 7.55 (ddd, J = 9.0, 7.0, 2.3 Hz, 1H), 7.23-7.10 (m, 1H), 6.70 (s, 1H), 4.51 (s, 2H), 4.43 (d, J = 4.0 Hz, 1H), 4.04-3.98 (m, 2H), 3.83-3.68 (m, 4H), 3.56-3.46 (m, 4H), 2.97-2.81 (m, 2H), 2.31-2.08 (m, 7H), 1.96-1.90 (m, 2H); m/z 464.2. | N |

-continued

| Example | Compound Name and Structure | NMR; m/z | Procedure |
|---|---|---|---|
| Example 116 | 1-[3-[3-[(3S)-3-(dimethylamino)pyrrolidin-1-yl]-8-isoquinolyl]-1-tetrahydropyran-4-yl-6,7-dihydro-4H-pyrazolo[4,3-c]pyridin-5-yl]ethanone (single known stereoisomer) | ¹H NMR (400 MHz, DMSO-d₆) δ 9.46 (t, J = 0.8 Hz, 1H), 7.60 (dt, J = 8.5, 1.0 Hz, 1H), 7.53 (ddd, J = 8.8, 6.9, 2.1 Hz, 1H), 7.21-7.04 (m, 1H), 6.64 (d, J = 0.9 Hz, 1H), 4.50 (s, 2H), 4.47-4.39 (m, 1H), 4.07-3.94 (m, 2H), 3.85-3.72 (m, 3H), 3.66 (t, J = 9.2 Hz, 1H), 3.57-3.46 (m, 2H), 3.41 (td, J = 10.1, 6.8 Hz, 1H), 3.19 (dd, J = 10.0, 8.2 Hz, 1H), 2.94 (t, J = 5.8 Hz, 1H), 2.81 (t, J = 8.2 Hz, 2H), 2.23 (s, 6H), 2.21-1.99 (m, 6H), 1.92 (dd, J = 11.9, 6.4 Hz, 2H), 1.89-1.81 (m, 1H); m/z 489.3. | N |
| Example 117 | 1-[3-[3-[3-(difluoromethyl)pyrrolidin-1-yl]-8-isoquinolyl]-1-tetrahydropyran-4-yl-6,7-dihydro-4H-pyrazolo[4,3-c]pyridin-5-yl]ethanone (mixture of enantiomers) 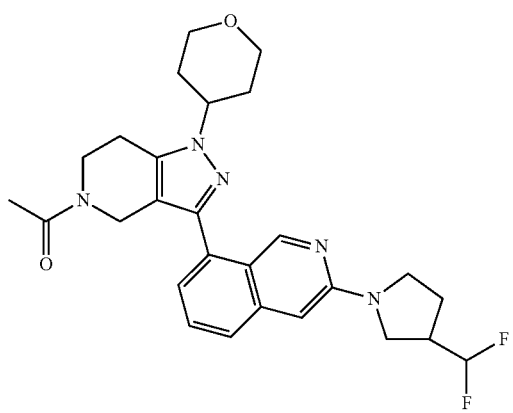 | Not Determined; m/z 496.2. | N |

| Example | Compound Name and Structure | NMR; m/z | Procedure |
|---|---|---|---|
| Example 118 | 1-[3-[3-[(3S)-3-methylpyrrolidin-1-yl]-8-isoquinolyl]-1-tetrahydropyran-4-yl-6,7-dihydro-4H-pyrazolo[4,3-c]pyridin-5-yl]ethanone (single known stereoisomer) | $^1$H NMR (400 MHz, DMSO-d$_6$) δ 9.43 (d, J = 0.8 Hz, 1H), 7.59 (dt, J = 8.6, 1.0 Hz, 1H), 7.56-7.47 (m, 1H), 7.20-7.04 (m, 1H), 6.59 (d, J = 0.9 Hz, 1H), 4.50 (d, J = 2.2 Hz, 2H), 4.47-4.38 (m, 1H), 4.01 (dt, J = 9.5, 4.5 Hz, 2H), 3.81 (dt, J = 15.2, 5.8 Hz, 2H), 3.69 (dd, J = 10.1, 7.2 Hz, 1H), 3.59 (dd, J = 3.7, 2.3 Hz, 1H), 3.55-3.49 (m, 2H), 3.47-3.41 (m, 1H), 3.01 (dd, J = 10.1, 7.5 Hz, 1H), 2.98-2.78 (m, 2H), 2.43-2.33 (m, 1H), 2.21-2.01 (m, 6H), 1.93 (d, J = 12.6 Hz, 2H), 1.63 (dq, J = 12.0, 8.2 Hz, 1H), 1.11 (d, J = 6.6 Hz, 3H); m/z 460.3. | N |
| Example 119 | 1-[3-[3-[(3S)-3-methylpyrrolidin-1-yl]-8-isoquinolyl]-1-tetrahydropyran-4-yl-6,7-dihydro-4H-pyrazolo[4,3-c]pyridin-5-yl]ethanone (single known stereoisomer) | $^1$H NMR (400 MHz, DMSO-d$_6$) δ 9.49-9.37 (m, 1H), 7.59 (dt, J = 8.6, 1.0 Hz, 1H), 7.51 (ddd, J = 8.8, 6.9, 2.0 Hz, 1H), 7.17-7.05 (m, 1H), 6.59 (d, J = 0.9 Hz, 1H), 4.50 (d, J = 2.1 Hz, 2H), 4.43 (q, J = 5.6, 4.2 Hz, 1H), 4.04-3.97 (m, 2H), 3.85-3.76 (m, 2H), 3.72-3.65 (m, 1H), 3.58 (ddd, J = 4.5, 3.8, 1.3 Hz, 1H), 3.55-3.48 (m, 2H), 3.47-3.41 (m, 1H), 3.06-2.97 (m, 1H), 2.97-2.77 (m, 2H), 2.45-2.33 (m, 1H), 2.16-2.00 (m, 6H), 1.93 (d, J = 12.2 Hz, 2H), 1.69-1.57 (m, 1H), 1.11 (d, J = 6.6 Hz, 3H); m/z 460.3. | N |

| Example | Compound Name and Structure | NMR; m/z | Procedure |
|---|---|---|---|
| Example 120 | 1-[8-(5-acetyl-1-tetrahydropyran-4-yl-6,7-dihydro-4H-pyrazolo[4,3-c]pyridin-3-yl)-3-isoquinolyl]-N,N-dimethyl-pyrrolidine-3-carboxamide (mixture of enantiomers)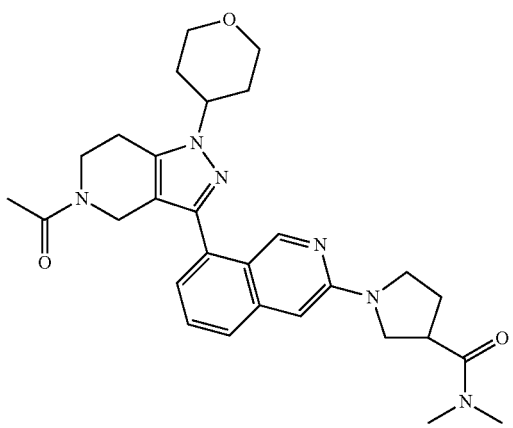 | $^1$H NMR (400 MHz, DMSO-$d_6$, 34/36 H) δ 9.51-9.41 (m, 1H), 7.61 (dt, J = 8.5, 1.0 Hz, 1H), 7.53 (ddd, J = 8.8, 6.9, 2.1 Hz, 1H), 7.22-7.07 (m, 1H), 6.64 (d, J = 0.9 Hz, 1H), 4.51 (d, J = 1.7 Hz, 2H), 4.48-4.37 (m, 1H), 4.08-3.96 (m, 2H), 3.88-3.71 (m, 3H), 3.65-3.45 (m, 6H), 3.10 (s, 3H), 2.98-2.78 (m, 5H), 2.10 (s, 5H), 1.97-1.88 (m, 2H); m/z 517.3. | N |
| Example 121 | 1-[3-[3-(3,3-dimethylpyrrolidin-1-yl)-8-isoquinolyl]-1-tetrahydropyran-4-yl-6,7-dihydro-4H-pyrazolo[4,3-c]pyridin-5-yl]ethanone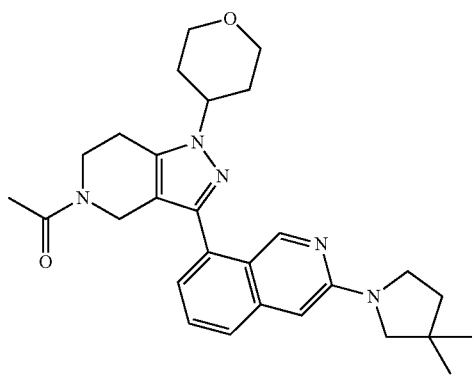 | $^1$H NMR (400 MHz, DMSO-$d_6$) δ 9.43 (t, J = 0.9 Hz, 1H), 7.59 (dt, J = 8.5, 1.0 Hz, 1H), 7.55-7.48 (m, 1H), 7.17-7.06 (m, 1H), 6.62-6.55 (m, 1H), 4.50 (s, 2H), 4.46-4.39 (m, 1H), 4.01 (d, J = 11.5 Hz, 2H), 3.86-3.78 (m, 2H), 3.57-3.51 (m, 4H), 2.94 (t, J = 5.7 Hz, 2H), 2.14-2.06 (m, 5H), 1.96-1.91 (m, 2H), 1.13 (s, 6H), 1.06-1.01 (m, 2H), 0.90 (dd, J = 4.9, 2.0 Hz, 2H); m/z 474.3. | N |

-continued

| Example | Compound Name and Structure | NMR; m/z | Procedure |
|---|---|---|---|
| Example 122 | 1-[3-[3-[(3R,4S)-3,4-difluoropyrrolidin-1-yl]-8-isoquinolyl]-1-tetrahydropyran-4-yl-6,7-dihydro-4H-pyrazolo[4,3-c]pyridin-5-yl]ethanone (single meso isomer) 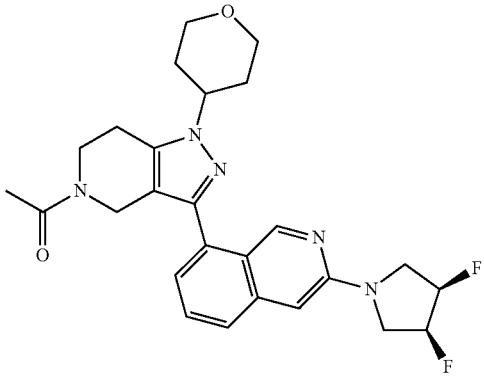 | $^1$H NMR (400 MHz, DMSO-$d_6$) δ 9.51 (t, J = 0.8 Hz, 1H), 7.66 (dt, J = 8.5, 1.0 Hz, 1H), 7.58 (ddd, J = 8.3, 6.9, 2.5 Hz, 1H), 7.27-7.11 (m, 1H), 6.76 (d, J = 1.0 Hz, 1H), 5.61-5.48 (m, 1H), 5.48-5.34 (m, 1H), 4.51 (s, 2H), 4.44 (dt, J = 8.3, 4.2 Hz, 1H), 4.07-3.97 (m, 2H), 3.97-3.87 (m, 2H), 3.85-3.78 (m, 2H), 3.73-3.63 (m, 2H), 3.57-3.46 (m, 2H), 2.98-2.77 (m, 2H), 2.16-2.00 (m, 5H), 1.93 (d, J = 11.5 Hz, 2H); m/z 482.2. | N |
| Example 123 | 1-[3-[3-(2,2-dimethylpyrrolidin-1-yl)-8-isoquinolyl]-1-tetrahydropyran-4-yl-6,7-dihydro-4H-pyrazolo[4,3-c]pyridin-5-yl]ethanone 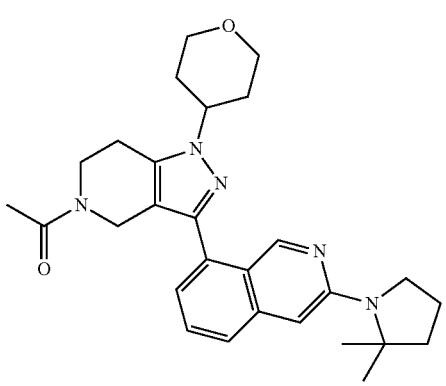 | Not Determined; m/z 474.3. | N |
| Example 124 | 1-[3-[3-(2,5-dihydropyrrol-1-yl)-8-isoquinolyl]-1-tetrahydropyran-4-yl-6,7-dihydro-4H-pyrazolo[4,3-c]pyridin-5-yl]ethanone 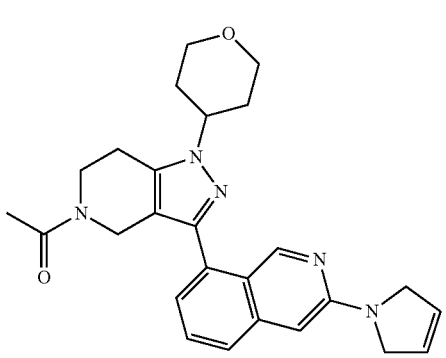 | $^1$H NMR (400 MHz, DMSO-$d_6$) δ 9.49 (t, J = 0.8 Hz, 1H), 7.69-7.59 (m, 1H), 7.55 (ddd, J = 8.9, 7.0, 2.3 Hz, 1H), 7.24-6.96 (m, 1H), 6.65 (d, J = 0.9 Hz, 1H), 6.08 (s, 2H), 4.51 (d, J = 1.7 Hz, 2H), 4.48-4.38 (m, 1H), 4.28 (s, 4H), 4.07-3.97 (m, 2H), 3.87-3.77 (m, 2H), 3.57-3.50 (m, 2H), 2.98-2.77 (m, 2H), 2.16-2.00 (m, 5H), 1.93 (d, J = 9.4 Hz, 2H); m/z 444.2. | N |

-continued

| Example | Compound Name and Structure | NMR; m/z | Procedure |
|---------|----------------------------|----------|-----------|
| Example 125 | 1-[3-[3-(3,3-difluoropyrrolidin-1-yl)-8-isoquinolyl]-1-tetrahydropyran-4-yl-6,7-dihydro-4H-pyrazolo[4,3-c]pyridin-5-yl]ethanone | Not Determined; m/z 482.2. | N |
| Example 126 | 1-[8-(5-acetyl-1-tetrahydropyran-4-yl-6,7-dihydro-4H-pyrazolo[4,3-c]pyridin-3-yl)-3-isoquinolyl]pyrrolidine-3-carbonitrile (mixture of enantiomers) | Not Determined; m/z 471.2. | N |
| Example 127 | 1-[3-[3-(4-methylpiperazin-1-yl)-8-isoquinolyl]-1-tetrahydropyran-4-yl-6,7-dihydro-4H-pyrazolo[4,3-c]pyridin-5-yl]ethanone | $^1$H NMR (400 MHz, DMSO-d$_6$) δ 9.50 (d, J = 1.0 Hz, 1H), 7.70-7.63 (m, 1H), 7.63-7.51 (m, 1H), 7.31-7.17 (m, 1H), 7.02 (d, J = 0.9 Hz, 1H), 4.52 (d, J = 2.7 Hz, 2H), 4.44 (dd, J = 11.3, 4.1 Hz, 1H), 4.07-3.95 (m, 2H), 3.88-3.75 (m, 2H), 3.53 (ddd, J = 8.9, 7.4, 3.4 Hz, 6H), 3.01-2.77 (m, 2H), 2.46 (t, J = 5.0 Hz, 4H), 2.24 (s, 3H), 2.15-2.00 (m, 5H), 1.93 (d, J = 11.4 Hz, 2H); m/z 475.3. | N |

-continued

| Example | Compound Name and Structure | NMR; m/z | Procedure |
|---|---|---|---|
| Example 128 | 1-[3-[3-(1-piperidyl)-8-isoquinolyl]-1-tetrahydropyran-4-l-6,7-dihydro-4H-pyrazolo[4,3-c]pyridin-5-yl]ethanone | $^{1}$H NMR (400 MHz, DMSO-$d_6$) δ 9.47 (d, J = 0.8 Hz, 1H), 7.76-7.48 (m, 2H), 7.19 (ddd, J = 26.4, 7.1, 1.2 Hz, 1H), 6.99 (d, J = 1.0 Hz, 1H), 4.51 (d, J = 2.5 Hz, 2H), 4.43 (td, J = 11.2, 5.4 Hz, 1H), 4.09-3.95 (m, 2H), 3.81 (dt, J = 14.5, 5.8 Hz, 2H), 3.66-3.45 (m, 6H), 3.01-2.77 (m, 2H), 2.22-1.98 (m, 5H), 1.98-1.85 (m, 2H), 1.61 (d, J = 7.6 Hz, 6H); m/z 460.3. | N |
| Example 129 | 1-[3-(3-pyrrolidin-1-yl-8-isoquinolyl)-1-tetrahydropyran-4-yl-6,7-dihydro-4H-pyrazolo[4,3-c]pyridin-5-yl]ethanone | $^{1}$H NMR (400 MHz, DMSO-$d_6$) δ 9.44 (t, J = 0.8 Hz, 1H), 7.60 (dt, J = 8.5, 1.0 Hz, 1H), 7.52 (ddd, J = 8.8, 6.9, 2.1 Hz, 1H), 7.12 (ddd, J = 26.7, 6.9, 1.2 Hz, 1H), 6.67-6.47 (m, 1H), 4.50 (s, 2H), 4.47-4.35 (m, 1H), 4.10-3.92 (m, 2H), 3.81 (dt, J = 15.2, 5.8 Hz, 2H), 3.57-3.41 (m, 6H), 2.88 (dt, J = 48.6, 5.9 Hz, 2H), 2.19-2.04 (m, 4H), 2.02-1.96 (m, 5H), 1.97-1.89 (m, 2H); m/z 446.2. | N |
| Example 130 | 1-[3-(3-morpholino-8-isoquinolyl)-1-tetrahydropyran-4-yl-6,7-dihydro-4H-pyrazolo[4,3-c]pyridin-5-yl]ethanone | $^{1}$H NMR (400 MHz, DMSO-$d_6$) δ 9.53 (d, J = 0.9 Hz, 1H), 7.73-7.65 (m, 1H), 7.65-7.56 (m, 1H), 7.39-7.19 (m, 1H), 7.04 (d, J = 0.9 Hz, 1H), 4.52 (d, J = 3.2 Hz, 2H), 4.49-4.36 (m, 1H), 4.09-3.93 (m, 2H), 3.88-3.72 (m, 6H), 3.52 (q, J = 6.8, 5.2 Hz, 6H), 2.99-2.77 (m, 2H), 2.16-1.99 (m, 5H), 1.93 (d, J = 11.0 Hz, 2H); m/z 462.2. | N |

| Example | Compound Name and Structure | NMR; m/z | Procedure |
|---|---|---|---|
| Example 131 | 1-(3-(quinolin-5-yl)-1-(tetrahydro-2H-pyran-4-yl)-1,4,6,7-tetrahydro-5H-pyrazolo[4,3-c]pyridin-5-yl)ethan-1-one | ¹H NMR (400 MHz, DMSO-d₆) δ 8.93 (dd, J = 4.1, 1.7 Hz, 1H), 8.87 (ddt, J = 9.0, 2.5, 1.2 Hz, 1H), 8.04 (dt, J = 8.5, 1.0 Hz, 1H), 7.83 (ddd, J = 8.4, 7.1, 3.2 Hz, 1H), 7.61-7.53 (m, 2H), 4.49 (s, 2H), 4.44 (ddd, J = 11.3, 7.4, 4.0 Hz, 1H), 4.05-3.96 (m, 2H), 3.82 (dt, J = 13.9, 5.8 Hz, 2H), 3.59-3.46 (m, 2H), 2.95 (t, J = 6.9 Hz, 1H), 2.89-2.77 (m, 1H), 2.20-206 (m, 4H), 2.00 (s, 1H), 1.97-1.88 (m, 2H); m/z 377. | O |
| Example 132 | 1-(3-(2-methyl-2H-indazol-4-yl)-1-(tetrahydro-2H-pyran-4-yl)-1,4,6,7-tetrahydro-5H-pyrazolo[4,3-c]pyridin-5-yl)ethan-1-one | ¹H NMR (400 MHz, DMSO-d₆) δ 8.67 (d, J = 2.8 Hz, 1H), 7.54 (d, J = 8.6 Hz, 1H), 7.30 (ddd, J = 8.5, 6.9, 3.4 Hz, 1H), 7.12-7.01 (m, 1H), 4.71 (s, 2H), 4.39 (tt, J = 11.5, 4.2 Hz, 1H), 4.23 (s, 3H), 4.03 (dd, J = 11.4, 4.3 Hz, 2H), 3.85-3.74 (m, 2H), 3.53 (td, J = 11.9, 1.8 Hz, 2H), 2.94-2.74 (m, 2H), 2.29-2.15 (m, 2H), 2.15-2.08 (m, 3H), 1.89 (dd, J = 12.2, 4.9 Hz, 2H); m/z 380. | O |
| Example 133 | 1-(3-(naphthalen-1-yl)-1-(tetrahydro-2H-pyran-4-yl)-1,4,6,7-tetrahydro-5H-pyrazolo[4,3-c]pyridin-5-yl)ethan-1-one | ¹H NMR (400 MHz, DMSO-d₆) δ 8.36-8.28 (m, 1H), 8.02-7.91 (m, 2H), 7.62-7.43 (m, 4H), 4.41 (s, 3H), 4.01 (dd, J = 10.6, 4.8 Hz, 2H), 3.87-3.75 (m, 2H), 3.57-3.46 (m, 2H), 2.99-2.79 (m, 2H), 2.20-2.03 (m, 4H), 2.00-1.88 (m, 3H); m/z 376. | O |

-continued

| Example | Compound Name and Structure | NMR; m/z | Procedure |
|---|---|---|---|
| Example 134 | 1-(3-(1H-indol-6-yl)-1-(tetrahydro-2H-pyran-4-yl)-1,4,6,7-tetrahydro-5H-pyrazolo[4,3-c]pyridin-5-yl)ethan-1-one | $^{1}$H NMR (400 MHz, DMSO-$d_6$) δ 11.09 (d, J = 10.7 Hz, 1H), 7.69-7.60 (m, 1H), 7.57 (d, J = 8.2 Hz, 1H), 7.41-7.28 (m, 2H), 6.42 (ddd, J = 2.9, 1.9, 0.9 Hz, 1H), 4.69 (d, J = 8.4 Hz, 2H), 4.33 (ddt, J = 11.3, 7.3, 4.1 Hz, 1H), 4.05-3.94 (m, 2H), 3.78 (dt, J = 19.0, 5.9 Hz, 2H), 3.57-3.43 (m, 2H), 2.91-2.71 (m, 2H), 2.18-2.05 (m, 5H), 1.85 (d, J = 12.9 Hz, 2H); m/z 365. | O |
| Example 135 | 1-(3-(benzo[b]thiophen-3-yl)-1-(tetrahydro-2H-pyran-4-yl)-1,4,6,7-tetrahydro-5H-pyrazolo[4,3-c]pyridin-5-yl)ethan-1-one | $^{1}$H NMR (400 MHz, DMSO-$d_6$) δ 8.77-8.63 (m, 1H), 8.17-7.99 (m, 1H), 7.88-7.63 (m, 1H), 7.50-7.34 (m, 2H), 4.66 (d, J = 4.4 Hz, 2H), 4.41 (td, J = 11.3, 5.6 Hz, 1H), 4.07-3.97 (m, 2H), 3.80 (dt, J = 13.7, 5.8 Hz, 2H), 3.58-3.46 (m, 2H), 2.91-2.70 (m, 2H), 2.22-2.07 (m, 5H), 1.91 (d, J = 13.3 Hz, 2H); m/z 382. | O |
| Example 136 | 1-(3-(quinolin-4-yl)-1-(tetrahydro-2H-pyran-4-yl)-1,4,6,7-tetrahydro-5H-pyrazolo[4,3-c]pyridin-5-yl)ethan-1-one | $^{1}$H NMR (400 MHz, DMSO-$d_6$) δ 8.95 (dd, J = 4.5, 2.4 Hz, 1H), 8.61 (dt, J = 8.7, 2.0 Hz, 1H), 8.11-8.03 (m, 1H), 7.79 (ddd, J = 8.4, 6.8, 1.4 Hz, 1H), 7.65 (dddd, J = 8.3, 6.8, 2.4, 1.3 Hz, 1H), 7.61-7.38 (m, 1H), 4.56 (d, J = 5.2 Hz, 2H), 4.47 (ddt, J = 11.3, 7.3, 4.1 Hz, 1H), 4.10-3.95 (m, 2H), 3.82 (dt, J = 11.9, 5.8 Hz, 2H), 3.58-3.47 (m, 2H), 3.01-2.79 (m, 2H), 2.20-2.05 (m, 4H), 2.01 (s, 1H), 1.95 (td, J = 6.1, 3.7 Hz, 2H); m/z 377. | O |

-continued

| Example | Compound Name and Structure | NMR; m/z | Procedure |
|---|---|---|---|
| Example 137 | 1-(3-(5-fluoro-1H-indol-4-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 11.21 (d, J = 2.9 Hz, 1H), 7.45-7.34 (m, 2H), 7.01 (ddd, J = 11.2, 8.8, 3.1 Hz, 1H), 6.71-6.58 (m, 1H), 4.39 (d, J = 2.1 Hz, 3H), 4.06-3.96 (m, 2H), 3.86-3.74 (m, 2H), 3.57-3.45 (m, 2H), 2.97-2.75 (m, 2H), 2.17-2.04 (m, 4H), 1.99 (s, 1H), 1.96-1.86 (m, 2H); m/z 383. | O |
| Example 138 | 5-(5-acetyl-1-(tetrahydro-2H-pyran-4-yl)-4,5,6,7-tetrahydro-1H-pyrazolo[4,3-c]pyridin-3-yl)isoquinolin-1(2H)-one | $^1$H NMR (400 MHz, DMSO-$d_6$) δ 11.30 (d, J = 5.6 Hz, 1H), 8.24 (dd, J = 8.0, 1.3 Hz, 1H), 7.74-7.60 (m, 1H), 7.54 (td, J = 7.7, 1.8 Hz, 1H), 7.17 (dt, J = 7.3, 5.1 Hz, 1H), 6.93 (t, J = 8.1 Hz, 1H), 4.47-4.34 (m, 3H), 3.99 (dd, J = 10.4, 4.7 Hz, 2H), 3.79 (dt, J = 12.0, 5.7 Hz, 2H), 3.50 (td, J = 12.0, 2.3 Hz, 2H), 2.96-2.76 (m, 2H), 2.12-2.05 (m, 3H), 2.00 (s, 1H), 1.94-1.85 (m, 3H); m/z 393. | O |
| Example 139 | 1-(1-(tetrahydro-2H-pyran-4-yl)-3-(5,6,7,8-tetrahydronaphthalen-1-yl)-1,4,6,7-tetrahydro-5H-pyrazolo[4,3-c]pyridin-5-yl)ethan-1-one | $^1$H NMR (400 MHz, DMSO-$d_6$) δ 7.12 (d, J = 7.6 Hz, 1H), 7.06 (d, J = 8.0 Hz, 1H), 7.02-6.96 (m, 1H), 4.34 (d, J = 3.3 Hz, 2H), 3.96 (d, J = 12.3 Hz, 2H), 3.76 (dt, J = 16.8, 5.8 Hz, 2H), 3.47 (tt, J = 12.0, 2.2 Hz, 2H), 2.87 (dd, J = 10.0, 4.3 Hz, 1H), 2.81-2.60 (m, 5H), 2.08 (s, 2H), 2.06-1.98 (m, 3H), 1.84 (dd, J = 12.8, 5.2 Hz, 2H), 1.78-1.61 (m, 5H); m/z 380. | O |

| Example | Compound Name and Structure | NMR; m/z | Procedure |
|---|---|---|---|
| Example 140 | 1-(3-(1H-indazol-4-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 13.09 (s, 1H), 8.54 (d, J = 6.2 Hz, 1H), 7.49 (d, J = 8.3 Hz, 1H), 7.47-7.37 (m, 1H), 7.14 (ddd, J = 18.2, 7.1, 0.8 Hz, 1H), 4.71 (s, 2H), 4.41 (ddd, J = 11.3, 8.9, 4.3 Hz, 1H), 4.08-3.98 (m, 2H), 3.85-2.74 (m, 2H), 3.59-3.47 (m, 2H), 2.96-2.76 (m, 2H), 2.25-2.03 (m, 5H), 1.92 (d, J = 13.0 Hz, 2H); m/z 366. | O |
| Example 141 | 1-(3-(1H-indol-4-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 10.74 (s, 1H), 7.54 (d, J = 7.7 Hz, 1H), 7.45 (t, J = 2.8 Hz, 1H), 7.26-7.15 (m, 1H), 7.11 (td, J = 7.6, 1.4 Hz, 1H), 6.50 (dd, J = 3.1, 2.1 Hz, 1H), 4.75 (d, J = 3.2 Hz, 2H), 4.41 (ddt, J = 11.6, 7.6, 4.0 Hz, 1H), 4.10-3.97 (m, 2H), 3.81 (dt, J = 15.5, 5.8 Hz, 2H), 3.60-3.44 (m, 2H), 2.97-2.74 (m, 2H), 2.37 (tq, J = 12.2, 6.1, 5.5 Hz, 2H), 2.13 (d, J = 5.2 Hz, 3H), 1.87 (t, J = 8.3 Hz, 2H); m/z 365. | O |
| Example 142 | 1-(1-(tetrahydro-2H-pyran-4-yl)-3-(5-(trifluoromethyl)-1H-pyrrolo[2,3-b]pyridin-3-yl)-1,4,6,7-tetrahydro-5H-pyrazolo[4,3-c]pyridin-5-yl)ethan-1-one | $^1$H NMR (400 MHz, DMSO-$d_6$) δ 8.84 (dd, J = 12.2, 2.3 Hz, 1H), 8.63 (d, J = 2.1 Hz, 1H), 7.95-7.75 (m, 1H), 4.64 (s, 2H), 4.37 (ddq, J = 11.2, 7.8, 4.0 Hz, 1H), 4.03 (dd, J = 10.6, 4.3 Hz, 2H), 3.78 (dt, J = 15.3, 5.7 Hz, 2H), 3.51 (t, J = 11.7 Hz, 2H), 2.92-2.71 (m, 2H), 2.20-2.04 (m, 6H), 1.94-1.84 (m, 2H); m/z 434. | O |

| Example | Compound Name and Structure | NMR; m/z | Procedure |
|---------|----------------------------|----------|-----------|
| Example 143 | 1-(3-(2-aminoquinazolin-5-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 9.59 (d, J = 4.5 Hz, 1H), 7.73 (ddd, J = 8.5, 7.2, 3.6 Hz, 1H), 7.41 (d, J = 8.4 Hz, 1H), 7.28-7.10 (m, 1H), 6.82 (s, 2H), 4.55 (s, 2H), 4.43 (tq, J = 11.4, 4.2 Hz, 1H), 4.01 (dd, J = 10.7, 4.7 Hz, 2H), 3.81 (dt, J = 12.1, 5.8 Hz, 2H), 3.51 (tt, J = 11.7, 2.1 Hz, 2H), 2.94-2.74 (m, 2H), 2.18-2.00 (m, 5H), 1.98-1.87 (m, 2H); m/z 393. | P |
| Example 144 | 1-(3-(isoquinolin-8-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 9.81 (d, J = 1.0 Hz, 1H), 85.4 (d, J = 5.6 Hz, 1H), 7.99 (d, J = 8.2 Hz, 1H), 7.92-7.80 (m, 2H), 7.73-7.59 (m, 1H), 4.57-4.40 (m, 3H), 4.05-3.96 (m, 2H), 3.83 (dt, J = 12.0, 5.8 Hz, 2H), 3.58-3.46 (m, 2H), 3.02-2.80 (m, 2H), 2.20-2.05 (m, 4H), 2.01 (s, 1H), 1.96 (t, J = 8.3 Hz, 2H); m/z 377. | P |
| Example 145 | 4-(5-acetyl-1-(tetrahydro-2H-pyran-4-yl)-4,5,6,7-tetrahydro-1H-pyrazolo[4,3-c]pyridin-3-yl)-2-(4-methoxyphenyl)isoindolin-1-one | $^1$H NMR (400 MHz, DMSO-$d_6$) δ 7.81-7.61 (m, 5H), 7.10-7.01 (m, 2H), 5.19-5.13 (m, 2H), 4.75 (s, 2H), 4.42 (td, J = 11.1, 5.5 Hz, 1H), 4.02 (d, J = 11.7 Hz, 2H), 3.85-3.74 (m, 2H), 3.79 (s, 3H), 3.57-3.47 (m, 2H), 2.95-2.75 (m, 2H), 2.18-2.05 (m, 4H), 1.91 (d, J = 13.0 Hz, 3H); m/z 487. | Q |

| Example | Compound Name and Structure | NMR; m/z | Procedure |
|---|---|---|---|
| Example 146 | 4-(5-acetyl-1-(tetrahydro-1H-pyran-4-yl)-4,5,6,7-tetrahydro-1H-pyrazolo[4,3-c]pyridin-3-yl)-2-(1-methyl-1H-pyrazol-4-yl)isoindolin-1-one | $^1$H NMR (400 MHz, DMSO-$d_6$) δ 8.14 (d, J = 1.7 Hz, 1H), 7.76-7.60 (m, 4H), 5.06-5.00 (m, 2H), 4.74 (s, 2h), 4.43 (td, J = 11.3, 5.4 Hz, 1H), 4.09-4.01 (m, 2H), 3.89 (s, 3H), 3.85-3.74 (m, 2H), 3.53 (dd, J = 12.8, 10.6 Hz, 2H), 2.96-2.75 (m, 2H), 2.19-2.09 (m, 5H), 1.92 (d, J = 12.9 Hz, 2H); m/z 461. | Q |
| Example 147 | 1-(3-(6-(1-methyl-1H-pyrazol-4-yl)-1H-indol-1-yl)-1-(tetrahydro-2H-pyran-4-yl)-1,4,6,7-tetrahydro-5H-pyrazolo[4,3-c]pyridin-5-yl)ethan-1-one | Not Determined; m/z 445. | R |
| Example 148 | 1-(3-(2-(4-(pyrrolidin-1-yl)phenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one | Not Determined; m/z 511. | S |

| Example | Compound Name and Structure | NMR; m/z | Procedure |
| --- | --- | --- | --- |
| Example 149 | 1-(1-(tetrahydro-2H-pyran-4-yl)-3-(2-(3-(trifluoromethyl)phenyl)imidazo[1,2-a]pyridin-8-yl)-1,4,6,7-tetrahydro-5H-pyrazolo[4,3-c]pyridin-5-yl)ethan-1-one | $^1$H NMR (400 MHz, DMSO-d$_6$) δ 8.69 (d, J = 1.3 Hz, 1H), 8.57 (td, J = 6.9, 1.3 Hz, 1H), 8.45-8.26 (m, 2H), 7.69 (ddd, J = 8.8, 4.9, 2.5 Hz, 2H), 7.48 (ddd, J = 14.9, 7.1, 1.2 Hz, 1H), 7.01 (q, J = 7.1 Hz, 1H), 4.83 (d, J = 14.2 Hz, 2H), 4.40 (ddt, J = 15.4, 11.0, 5.4 Hz, 1H), 4.05-3.96 (m, 2H), 3.81 (q, J = 5.9 Hz, 2H), 3.51 (dd, J = 12.8, 10.8 Hz, 2H), 2.94-2.74 (m, 2H), 2.20-2.04 (m, 4H), 1.98 (s, 1H), 1.95-1.85 (m, 2H); m/z 510. | S |
| Example 150 | 1-(3-(2-(2-fluoro-4-methoxyphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-d$_6$) δ 8.61 (dd, J = 6.6, 2.4 Hz, 1H), 8.40-8.11 (m, 2H), 7.46 (dd, J = 10.3, 6.9 Hz, 1H), 7.02-6.85 (m, 3H), 4.84 (s, 2H), 4.40 (tq, J = 10.4, 4.7 Hz, 1H), 4.00 (dd, J = 11.1, 4.2 Hz, 2H), 3.87-3.77 (m, 5H), 3.50 (t, J = 11.7 Hz, 2H), 2.94-2.75 (m, 2H), 2.19-2.03 (m, 4H), 1.97 (s, 1H), 1.89 (dd, J = 11.8, 3.3 Hz, 2H); m/z 490. | S |
| Example 151 | 1-(3-(2-(3-methoxyphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-d$_6$) δ 8.58-8.52 (m, 1H), 8.51 (s, 1H), 7.66-7.50 (m, 2H), 7.51-7.40 (m, 1H), 7.36 (q, J = 8.1 Hz, 1H), 6.97 (q, J = 6.7 Hz, 1H), 6.93-6.85 (m, 1H), 4.89-4.76 (m, 2H), 4.40 (dq, J = 11.3, 6.1 Hz, 1H), 4.03-3.96 (m, 2H), 3.87-3.76 (m, 5H), 3.50 (t, J = 11.9 Hz, 2H), 2.98-2.78 (m, 2H), 2.18-2.04 (m, 4H), 1.98 (s, 1H), 1.89 (d, J = 13.0 Hz, 2H); m/z 472. | S |

-continued

| Example | Compound Name and Structure | NMR; m/z | Procedure |
| --- | --- | --- | --- |
| Example 152 | 1-(3-(2-(3-fluoro-4-methoxyphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 8.53 (ddd, J = 6.7, 4.4, 1.3 Hz, 1H), 8.44 (d, J = 1.9 Hz, 1H), 7.92-7.82 (m, 1H), 7.82-7.75 (m, 1H), 7.45 (ddd, J = 13.0, 7.1, 1.2 Hz, 1H), 7.24 (dt, J = 14.5, 9.0 Hz, 1H), 6.97 (q, J = 6.8 Hz, 1H), 4.84 (d, J = 5.1 Hz, 2H), 4.39 (dt, J = 11.2, 6.0 Hz, 1H), 4.00 (d, J = 11.4 Hz, 2H), 3.88 (s, 3H), 3.82 (dt, J = 11.6, 5.8 Hz, 2H), 3.55-3.43 (m, 2H), 2.97-2.75 (m, 2H), 2.17-2.05 (m, 4H), 1.99 (s, 1H), 1.89 (d, J = 12.6 Hz, 2H); m/z 490. | S |
| Example 153 | 1-(3-(2-(1H-indol-3-yl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 11.42-11.29 (m, 1H), 8.54 (td, J = 6.6, 6.2, 1.3 Hz, 1H), 8.42 (s, 1H), 8.20-7.81 (m, 2H), 7.49-7.37 (m, 2H), 7.21-7.08 (m, 2H), 6.93 (q, J = 7.1 Hz, 1H), 4.98-4.85 (m, 2H), 4.40 (tt, J = 10.4, 4.7 Hz, 1H), 4.05-3.96 (m, 2H), 3.82 (dt, J = 12.1, 5.7 Hz, 2H), 3.51 (td, J = 11.9, 2.0 Hz, 2H), 3.01-2.79 (m, 2H), 2.21-2.05 (m, 4H), 1.98-1.86 (m, 3H); m/z 481. | S |
| Example 154 | 1-(3-(2-(3-hydroxyphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)than-1-one | $^1$H NMR (400 MHz, DMSO-$d_6$) δ 9.44 (s, 1H), 8.54 (ddd, J = 6.7, 2.8, 1.2 Hz, 1H), 8.40 (d, J = 3.1 Hz, 1H), 7.49-7.35 (m, 3H), 7.22 (td, J = 7.8, 3.0 Hz, 1H), 7.01-6.91 (m, 1H), 6.76-6.68 (m, 1H), 4.86 (s, 1H), 4.76 (s, 1H), 4.44-4.34 (m, 1H), 4.00 (d, J = 11.3 Hz, 2H), 3.83 (q, J = 5.6 Hz, 2H), 3.50 (dd, J = 12.6, 10.8 Hz, 2H), 2.94 (d, J = 5.8 Hz, 1H), 2.83 (d, J = 5.9 Hz, 1H), 2.20-2.04 (m, 4H), 1.99 (s, 1H), 1.89 (d, J = 12.7 Hz, 2H); m/z 458. | S |

-continued

| Example | Compound Name and Structure | NMR; m/z | Procedure |
|---|---|---|---|
| Example 155 | 1-(3-(2-(4-methoxyphenyl)imidazo[1,2-a]pyridin-8-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 8.53 (ddd, J = 6.7, 4.0, 1.3 Hz, 1H), 8.37 (d, J = 1.8 Hz, 1H), 8.03-7.96 (m, 1H), 7.95-7.88 (m, 1H), 7.43 (ddd, J = 13.4, 7.1, 1.3 Hz, 1H), 7.08-6.98 (m, 2H), 6.95 (q, J = 6.8 Hz, 1H), 4.85 (d, J = 13.8 Hz, 2H), 4.39 (tt, J = 10.5, 5.1 Hz, 1H), 4.00 (d, J = 11.7 Hz, 2H), 3.87-3.77 (m, 5H), 3.50 (t, J = 11.7 Hz, 2H), 2.98-2.77 (m, 2H), 2.19-2.04 (m, 4H), 1.99 (s, 1H), 1.94-1.85 (m, 2H); m/z 472. | S |
| Example 156 | 1-(1-(tetrahydro-2H-pyran-4-yl)-3-(2-(4-(trifluoromethoxy)phenyl)imidazo[1,2-a]pyridin-8-yl)-1,4,6,7-tetrahydro-5H-pyrazolo[4,3-c]pyridin-5-yl)ethan-1-one | $^1$H NMR (400 MHz, DMSO-$d_6$) δ 8.61-8.55 (m, 1H), 8.54 (s, 1H), 8.24-8.15 (m, 1H), 8.15-8.07 (m, 1H), 7.52-7.38 (m, 3H), 6.99 (q, J = 6.6 Hz, 1H), 4.84 (s, 2H), 4.40 (tt, J = 10.7, 4.8 Hz, 1H), 4.00 (dd, J = 11.3, 4.4 Hz, 2H), 3.82 (dt, J = 11.8, 5.8 Hz, 2H), 3.50 (td, J = 12.1, 2.1 Hz, 2H), 2.98-2.74 (m, 2H), 2.19-2.03 (m, 4H), 1.97 (s, 1H), 1.89 (d, J = 13.6 Hz, 2H); m/z 526. | S |
| Example 157 | 1-(3-(2-(4-methoxyphenyl)imidazo[1,2-a]pyridin-5-yl)-1-(tetrahydro-2H-pyran-4-yl)-1,4,6,7-tetrahydro-5H-pyrazolo[4,3-c]pyridin-5-yl)ethan-1-one | $^1$H NMR (400 MHz, DMSO-$d_6$) δ 9.01 (d, J = 4.7 Hz, 1H), 7.93-7.85 (m, 2H), 7.62 (d, J = 8.9 Hz, 1H), 7.38 (dt, J = 9.0, 6.9 Hz, 1H), 7.09-6.93 (m, 3H), 4.67 (s, 2H), 4.53 (tt, J = 11.2, 4.0 Hz, 1H), 4.06 (dd, J = 10.8, 4.7 Hz, 2H), 3.88-3.77 (m, 5H), 3.55 (tt, J = 11.6, 2.1 Hz, 2H), 2.97-2.78 (m, 2H), 2.24-2.04 (m, 5H), 2.05-1.94 (m, 2H); m/z 472. | S |

| Example | Compound Name and Structure | NMR; m/z | Procedure |
|---|---|---|---|
| Example 158 | 1-(3-(2-(pyridin-3-yl)benzo[d]oxazol-7-yl)-1-(tetrahydro-2H-pyran-4-yl)-1,4,6,7-tetrahydro-5H-pyrazolo[4,3-c]pyridin-5-yl)ethan-1-one | ¹H NMR (400 MHz, DMSO-d₆) δ 9.51-9.37 (m, 1H), 8.82 (dt, J = 4.9, 1.6 Hz, 1H), 8.72-8.54 (m, 1H), 7.84 (dd, J = 7.9, 1.1 Hz, 1H), 7.73-7.63 (m, 2H), 7.52 (t, J = 7.8 Hz, 1H), 4.86-4.72 (m, 2H), 4.44 (ddt, J = 11.3, 8.3, 4.2 Hz, 1H), 4.07-3.98 (m, 2H), 3.92-3.79 (m, 2H), 3.52 (td, J = 11.9, 2.1 Hz, 2H), 3.03-2.79 (m, 2H), 2.22-2.04 (m, 4H), 2.01 (s, 1H), 1.97-1.88 (m, 2H); m/z 444. | T |
| Example 159 | 1-(3-(2-(4-methoxyphenyl)benzo[d]oxazol-7-yl)-1-(tetrahydro-2H-pyran-4-yl)-1,4,6,7-tetrahydro-5H-pyrazolo[4,3-c]pyridin-5-yl)than-1-one | ¹H NMR (400 MHz, DMSO-d₆) δ 8.32-8.11 (m, 2H), 7.74 (dd, J = 8.0, 1.1 Hz, 1H), 7.62 (dd, J = 7.6, 1.2 Hz, 1H), 7.45 (t, J = 7.8 Hz, 1H), 7.23-7.12 (m, 2H), 4.80-4.70 (m, 2H), 4.49-4.37 (m, 1H), 4.07-3.98 (m, 2H), 3.91-3.79 (m ,5H), 3.52 (td, J = 1.9, 2.1 Hz, 2H), 2.95-2.75 (m, 2H), 2.22-2.06 (m, 4H), 2.01 (s, 1H), 1.92 (dd, J = 13.1, 3.8 Hz, 2H); m/z 473. | T |
| Example 160 | 3-(5-acetyl-1-tetrahydrofuran-3-yl-6,7-dihydro-4H-pyrazolo[4,3-c]pyridin-3-yl)-N-(1-methylpyrazol-4-yl)benzamide | ¹H NMR (400 MHz, DMSO-d₆, 24/26 H) δ 10.50 (d, J = 3.6 Hz, 1H), 8.29-8.10 (m, 1H), 8.04 (d, J = 0.8 Hz, 1H), 7.95-7.84 (m, 1H), 7.84-7.71 (m, 1H), 7.68-7.51 (m, 2H), 5.00 (dd, J = 6.7, 4.7 Hz, 1H), 4.70 (s, 2H), 4.16-3.99 (m, 2H), 3.98-3.67 (m, 6H), 3.00-2.84 (m, 1H), 2.44-2.26 (m, 2H), 2.18-1.97 (m, 3H); m/z 435.2. | U |

| Example | Compound Name and Structure | NMR; m/z | Procedure |
|---|---|---|---|
| Example 161 | 3-(5-acetyl-1-tetrahydrofuran-3-yl-6,7-dihydro-4H-pyrazolo[4,3-c]pyridin-3-yl)-N-(4-cyanophenyl)benzamide | $^1$H NMR (400 MHz, DMSO-d$_6$) δ 10.76 (s, 1H), 8.25-8.09 (m, 1H), 8.01 (dd, J = 8.8, 1.7 Hz, 2H), 7.96-7.76 (m, 4H), 7.63 (td, J = 7.7, 3.3 Hz, 1H), 5.15-4.86 (m, 1H), 4.70 (s, 2H), 4.24-3.99 (m, 2H), 3.99-3.82 (m, 4H), 3.77 (dt, J = 11.3, 4.2 Hz, 4H), 2.11 (d, J = 9.7 Hz, 3H); m/z 456.2. | U |
| Example 162 | 3-(5-acetyl-1-tetrahydrofuran-3-yl-6,7-dihydro-4H-pyrazolo[4,3-c]pyridin-3-yl)-N-(6-quinolyl)benzamide. | $^1$H NMR (400 MHz, DMSO-d$_6$) δ 10.68 (d, J = 4.4 Hz, 1H), 8.82 (dd, J = 4.2, 1.7 Hz, 1H), 8.66-8.49 (m, 1H), 8.40-8.29 (m, 1H), 8.29-8.14 (m, 1H), 8.12-7.91 (m, 3H), 7.84 (dd, J = 7.9, 1.5 Hz, 1H), 7.64 (td, J = 7.7, 2.7 Hz, 1H), 7.51 (dd, J = 8.3, 4.2 Hz, 1H), 5.01 (qd, J = 6.7, 4.6 Hz, 1H), 4.73 (d, J = 3.0 Hz, 2H), 4.19-4.00 (m, 2H), 4.00-3.84 (m, 3H), 3.78 (d, J = 5.9 Hz, 3H), 2.36 (qd, J = 7.1, 2.9 Hz, 2H), 2.21-1.98 (m, 3H); m/z 482.2. | U |
| Example 163 | 3-(5-acetyl-1-tetrahydrofuran-3-yl-6,7-dihydro-4H-pyrazolo[4,3-c]pyridin-3-yl)-N-(4-imidazol-1-ylphenyl)benzamide | $^1$H NMR (400 MHz, DMSO-d$_6$, 26/28 H) δ 10.53 (d, J = 3.6 Hz, 1H), 8.29 (dt, J = 1.9, 1.0 Hz, 1H), 8.19 (dt, J = 11.5, 1.8 Hz, 1H), 8.05-7.91 (m, 2H), 7.91-7.78 (m, 1H), 7.71 (dd, J = 8.6, 0.9 Hz, 1H), 7.63 (t, J = 7.7 Hz, 1H), 7.40 (ddd, J = 8.7, 2.9, 1.7 Hz, 1H), 5.08-4.90 (m, 1H), 4.72 (t, J = 2.3 Hz, 2H), 4.23-3.97 (m, 5H), 3.98-3.82 (m, 2H), 3.78 (d, J = 5.9 Hz, 1H), 2.42-2.29 (m, 3H), 2.12 (d, J = 7.5 Hz, 3H); m/z 485.2. | U |

-continued

| Example | Compound Name and Structure | NMR; m/z | Procedure |
|---|---|---|---|
| Example 164 | 3-(5-acetyl-1-tetrahydrofuran-3-yl-6,7-dihydro-4H-pyrazolo[4,3-c]pyridin-3-yl)-N-(4-imidazol-1-ylphenyl)benzamide | $^1$H NMR (400 MHz, DMSO-$d_6$) δ 10.51 (d, J = 3.6 Hz, 1H), 8.31-8.10 (m, 2H), 8.06-7.89 (m, 3H), 7.86-7.77 (m, 1H), 7.72 (t, J = 1.3 Hz, 2H), 7.71-7.56 (m, 3H), 5.09-4.91 (m, 1H), 4.71 (s, 2H), 4.08 (tt, J = 9.0, 7.0 Hz, 2H), 3.97-3.82 (m, 2H), 3.77 (q, J = 6.4, 5.5 Hz, 2H), 2.43-2.25 (m, 4H), 2.11 (d, J = 7.9 Hz, 3H); m/z 497.2. | U |
| Example 165 | 3-(5-acetyl-1-tetrahydrofuran-3-yl-6,7-dihydro-4H-pyrazolo[4,3-c]pyridin-3-yl)-N-[4-(1,2,4-triazol-1-ylmethyl)phenyl]benzamide | $^1$H NMR (400 MHz, DMSO-$d_6$) δ 10.39 (d, J = 3.6 Hz, 1H), 8.64 (s, 1H), 8.14 (dt, J = 9.2, 1.8 Hz, 1H), 7.98 (s, 1H), 7.95-7.84 (m, 2H), 7.77 (dd, J = 8.6, 1.9 Hz, 2H), 7.60 (td, J = 7.8, 2.5 Hz, 1H), 7.36-7.25 (m, 2H), 5.38 (s, 2H), 4.99 (qd, J = 6.6, 4.6 Hz, 1H), 4.70 (d, J = 3.7 Hz, 2H), 4.16-3.97 (m, 2H), 3.97-3.82 (m, 4H), 3.77 (q, J = 7.0, 6.0 Hz, 2H), 2.34 (qd, J = 6.8, 2.7 Hz, 2H), 2.16-2.02 (m, 3H); m/z 512.2. | U |
| Example 166 | 3-(5-acetyl-1-tetrahydrofuran-3-yl-6,7-dihydro-4H-pyrazolo[4,3-c]pyridin-3-yl)-N-(1-methyl-5-phenyl-imidazol-2-yl)benzamide | Not Determined; m/z 511.2. | U |

-continued

| Example | Compound Name and Structure | NMR; m/z | Procedure |
|---|---|---|---|
| Example 167 | 3-(5-acetyl-1-tetrahydrofuran-3-yl-6,7-dihydro-4H-pyrazolo[4,3-c]pyridin-3-yl)-N-(1-methylbenzimidazol-2-yl)benzamide | $^1$H NMR (400 MHz, DMSO-$d_6$) δ 12.77 (s, 1H), 8.57 (s, 1H), 8.36-8.07 (m, 1H), 8.00-7.68 (m, 1H), 7.68-7.39 (m, 3H), 7.25 (dqd, J = 8.8, 7.4, 1.3 Hz, 2H), 5.18-4.89 (m, 1H), 4.76 (d, J = 14.1 Hz, 2H), 4.27-3.98 (m, 2H), 3.99-3.84 (m, 2H), 2.97-2.83 (m, 1H), 2.77 (s, 3H), 2.42-2.28 (m, 5H), 2.13 (d, J = 11.2 Hz, 3H); m/z 485.2. | U |
| Example 168 | 3-(5-acetyl-1-tetrahydrofuran-3-yl-6,7-dihydro-4H-pyrazolo[4,3-c]pyridin-3-yl)-N-(3-quinolyl)benzamide | $^1$H NMR (400 MHz, DMSO-$d_6$, 26/27 H) δ 10.82 (s, 1H), 9.16 (dd, J = 2.5, 0.8 Hz, 1H), 8.87 (dt, J = 2.5, 1.3 Hz, 1H), 8.42-8.10 (m, 1H), 8.16-7.97 (m, 3H), 7.93-7.79 (m, 1H), 7.76-7.53 (m, 2H), 5.01 (qd, J = 6.7, 4.6 Hz, 1H), 4.73 (d, J = 3.7 Hz, 2H), 4.20-3.98 (m, 2H), 3.98-3.84 (m, 2H), 2.89 (t, J = 5.9 Hz, 1H), 2.78 (d, J = 6.2 Hz, 1H), 2.44-2.27 (m, 4H), 2.12 (d, J = 6.3 Hz, 3H); m/z 482.2. | U |
| Example 169 | 3-(5-acetyl-1-tetrahydrofuran-3-yl-6,7-dihydro-4H-pyrazolo[4,3-c]pyridin-3-yl)-N-(2-methyl-4-pyridyl)benzamide | Not Determined; m/z 446.2. | U |

| Example | Compound Name and Structure | NMR; m/z | Procedure |
|---|---|---|---|
| Example 170 | 3-(5-acetyl-1-tetrahydrofuran-3-yl-6,7-dihydro-4H-pyrazolo[4,3-c]pyiridn-3-yl)-N-pyrimidin-5-yl-benzamide | $^1$H NMR (400 MHz, DMSO-$d_6$) δ 10.76 (s, 1H), 9.18 (d, J = 1.4 Hz, 2H), 8.93 (s, 1H), 8.21 (dt, J = 12.9, 1.7 Hz, 1H), 8.07-7.78 (m, 2H), 7.64 (td, J = 7.8, 3.4 Hz, 1H), 5.00 (qd, J = 6.7, 4.7 Hz, 1H), 4.21-3.98 (m, 2H), 3.98-3.66 (m, 6H), 2.35 (qd, J = 6.8, 2.3 Hz, 4H), 2.11 (d, J = 8.9 Hz, 3H); m/z 433.2. | U |
| Example 171 | 3-(5-acetyl-1-tetrahydrofuran-3-yl-6,7-dihydro-4H-pyrazolo[4,3-c]pyridin-3-yl)-N-(3-pyridyl)benzamide | $^1$H NMR (400 MHz, DMSO-$d_6$) δ 10.56 (s, 1H), 8.94 (dd, J = 2.5, 0.9 Hz, 1H), 8.32 (dd, J = 4.6, 1.5 Hz, 1H), 8.27-8.12 (m, 2H), 8.02-7.88 (m, 1H), 7.88-7.77 (m, 1H), 7.62 (td, J = 7.7, 2.9 Hz, 1H), 7.41 (ddt, J = 8.4, 4.8, 0.8 Hz, 1H), 5.00 (qd, J = 6.6, 4.6 Hz, 1H), 4.71 (d, J = 3.6 Hz, 2H), 4.19-3.99 (m, 2H), 3.99-3.81 (m, 3H), 3.77 (q, J = 6.9, 5.7 Hz, 2H), 2.98-2.85 (m, 1H), 2.35 (qd, J = 6.7, 2.4 Hz, 2H), 2.18-1.98 (m, 3H); m/z 432.2. | U |
| Example 172 | 3-(5-acetyl-1-tetrahydrofuran-3-yl-6,7-dihydro-4H-pyrazolo[4,3-c]pyridin-3-yl)-N-(1-methylindazol-5-yl)benzamide | $^1$H NMR (400 MHz, DMSO-$d_6$) δ 10.38 (d, J = 4.7 Hz, 1H), 8.30-8.22 (m, 1H), 8.18 (dt, J = 10.6, 1.7 Hz, 1H), 8.03 (dd, J = 1.9, 0.9 Hz, 1H), 7.92 (dq, J = 7.8, 1.6 Hz, 1H), 7.87-7.76 (m, 1H), 7.69 (d, J = 1.9 Hz, 1H), 7.66-7.54 (m, 2H), 5.00 (qd, J = 6.6, 4.7 Hz, 1H), 4.72 (d, J = 3.8 Hz, 2H), 4.17-3.97 (m, 5H), 3.99-3.82 (m, 2H), 3.77 (q, J = 7.0, 5.7 Hz, 2H), 2.89 (t, J = 5.8 Hz, 1H), 2.77 (s, 1H), 2.43-2.25 (m, 2H), 2.11 (d, J = 7.6 Hz, 3H); m/z 485.2. | U |

| Example | Compound Name and Structure | NMR; m/z | Procedure |
|---|---|---|---|
| Example 173 | 5-(5-acetyl-1-(tetrahydro-2H-pyran-4-yl)-4,5,6,7-tetrahydro-1H-pyrazolo[4,3-c]pyridin-3-yl)-2-isopropyl-1,2-dihydroisoquinolin-3(4H)-one | $^1$H NMR (400 MHz, CDCl$_3$) δ 7.34-7.20 (m, 3H), 4.99-4.87 (m, 1H), 4.55-4.27 (m, 4H), 4.24-4.04 (m, 3H), 4.00-3.75 (m, 2H), 3.74-3.65 (m, 2H), 3.54 (t, J = 12.0 Hz, 2H), 2.89-2.72 (m, 2H), 2.42-2.26 (m, 2H), 2.20-2.11 (m, 3H), 1.95-1.83 (m, 2H), 1.19-(t, J = 6.8 Hz, 6H); m/z 437. | V |
| Example 174 | 5-(5-acetyl-1-(tetrahydro-2H-pyran-4-yl)-4,5,6,7-tetrahydro-1H-pyrazolo[4,3-c]pyridin-3-yl)-2-cyclohexyl-1,2-dihydroisoquinolin-3(4H)-one | $^1$H NMR (400 MHz, CDCl$_3$) δ 7.34-7.18 (m, 3H), 4.54 (s, 2H), 4.53-4.45 (m, 1H), 4.43-4.34 (m, 2H), 4.25-4.07 (m, 3H), 3.99-3.76 (m, 2H), 3.75-3.66 (m, 2H), 3.54 (t, J = 12.0 Hz, 2H), 2.90-2.73 (m, 2H), 2.42-2.27 (m, 2H), 2.20-2.11 (m, 3H), 1.94-1.77 (m, 4H), 1.74-1.58 (m, 4H), 1.56-1.36 (m, 4H); m/z 477. | V |
| Example 175 | 5-(5-acetyl-1-(tetrahydro-2H-pyran-4-yl)-4,5,6,7-tetrahydro-1H-pyrazolo[4,3-c]pyridin-3-yl)-2-cyclobutyl-1,2-dihydroisoquinolin-3(4H)-one | $^1$H NMR (400 MHz, CDCl$_3$) δ 7.30-7.15 (m, 3H), 5.09-4.95 (m, 1H), 4.49-4.32 (m, 1H), 4.16-4.02 (m, 3H), 3.91-3.69 (m, 2H), 3.65-3.61 (m, 2H), 3.49 (t, J = 12.0 Hz, 2H), 2.80-2.68 (m, 2H), 2.35-2.20 (m, 2H), 2.18-2.03 (m, 7H), 1.88-1.79 (m, 2H), 1.75-1.59 (m, 2H); m/z 449. | V |

Example 176

IC$_{50}$ Measurements for Inhibitors Using CBP TR-FRET Binding Assay

His/Flag epitope tagged CBP was cloned, expressed, and purified to homogeneity. CBP binding and inhibition was assessed by monitoring the engagement of a biotinylated small molecule compound with the target using the TR-FRET assay technology (Perkin-Elmer). Specifically, in a 384 well ProxiPlate CBP (4 nM final) was combined with biotin-ligand (60 nM final) in 50 mM HEPES (pH 7.5), 50 mM NaCl, 1 mM TCEP, 0.01% (w/v) BSA, and 0.008% (w/v) Brij-35 either in the presence of DMSO (final 0.2% DMSO) or compound dilution series in DMSO. After 10 minutes incubation at room temperature, a mixture Eu-W1024 Anti-6xHis antibody ("6xHis" is disclosed as SEQ ID NO: 3) (Perkin Elmer ADO 110) and SureLight™ Allophycocyanin-Streptavidin (APC-SA, Perkin Elmer CR130-100) were added to a final concentrations of 0.2 nMolar antibody and 50 nMolar APC-SA, respectively. After twenty minutes of equilibration, the plates were read on an Envision instrument and IC50s calculated using a four parameter non-linear curve fit.

MYC_RPL19 QuantiGene Assay in MV-4-11 Cells

QuantiGene 2.0 Reagent system, Affymetrix: HUMAN MYCN; V-myc myelocytomatosis viral related oncogene, neuroblastoma derived (avian); NM_005378 SA-15008. 10,000 MV-4-11 cells (GNE in-house) were plated in 75 ul complete media: RPMI-1640 (GNE in-house), 10% FBS (Life Technologies, cat. no. 10082), 1% Pen-strep (GNE in-house), in 96 well clear flat bottom plates (Costar, cat. no. 3595). 25 ul compound was added for 4 hours at 37 deg C. in a 1:3 serial dilution 10-point dose response, with a final DMSO concentration=0.2%. The cells were then lysed according to the assay kit's protocol and frozen at −80 deg C. The following day, an appropriate volume of Working Probe Set was prepared by combining the following reagents in the order listed: Nuclease-free water, Lysis Mixture, Blocking Reagent, and 2.0 Probe Set (MYC or RPL19). 20 ul of the working probe set was added into each assay well on the capture plate, and then 80 ul of the lysates were transferred into the assay plates. The capture plate was placed in a 55 deg C. incubator for overnight hybridization (16-20 hours). The following day, wash buffer was prepared according to manufacturer's recommendations. The capture plates were washed with 300 ul per well of 1× wash buffer three times. Then 100 ul Pre-Amplifier was added to the plate for a 60 minute incubation at 55 deg C. After the incubation, the capture plate was washed with 300 ul per well of 1× wash buffer three times, and 100 ul Amplifier was added to the plate for a 60 minute incubation at 55 deg C. The capture plate was again washed with 300 ul per well of 1× wash buffer three times, and 100 ul Label Probe was added to the plate for a 60 minute incubation at 50 deg C. Then the capture plate was washed with 300 ul per well of 1× wash buffer three times, and 100 ul 2.0 Substrate was added to each well of the plate. The plates were incubated at RT for 5 minutes in the dark and read on the Envision using the luminescence protocol, with an integration time set at 0.2 seconds.

Data for representative compounds from the assays described above is provided in the following table.

| Example | Compound | CBP HTRF IC$_{50}$ (μM) | Myc IC$_{50}$ (μM) |
|---|---|---|---|
| 1 | 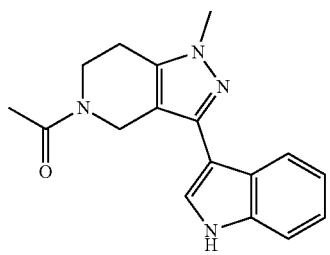 [SMILES: CC(=O)N1CCc2c(c(-c3c[nH]c4ccccc34)nn2C)C1] | | 0.0935 |
| 2 | 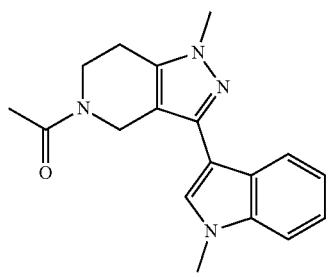 [SMILES: CC(=O)N1CCc2c(c(-c3cn(C)c4ccccc34)nn2C)C1] | | 0.0972 |

-continued

| Example | Compound | CBP HTRF IC$_{50}$ (μM) | Myc IC$_{50}$ (μM) |
|---|---|---|---|
| 3 | | 0.0174 | |
| 4 | | 0.0581 | |
| 5 | | 0.0687 | |
| 6 | | 0.0493 | |

-continued

| Example | Compound | CBP HTRF IC$_{50}$ (μM) | Myc IC$_{50}$ (μM) |
|---|---|---|---|
| 7 | | 0.0240 | |
| 8 | | 0.0687 | |
| 9 | | 0.00113 | 0.0321 |
| 10 | | 0.00115 | 0.0153 |

-continued

| Example | Compound | CBP HTRF IC$_{50}$ (μM) | Myc IC$_{50}$ (μM) |
|---|---|---|---|
| 11 | | 0.00238 | 0.114 |
| 12 | | 0.123 | |
| 13 | | 0.0598 | |
| 14 | | 0.00342 | 0.203 |

| Example | Compound | CBP HTRF IC$_{50}$ (μM) | Myc IC$_{50}$ (μM) |
|---|---|---|---|
| 15 | | 0.00232 | 0.0540 |
| 16 | | 0.0899 | |
| 17 | | 0.0553 | |
| 18 | | 0.0676 | |

-continued

| Example | Compound | CBP HTRF IC$_{50}$ (μM) | Myc IC$_{50}$ (μM) |
|---|---|---|---|
| 19 | | 0.00674 | 1.09 |
| 20 | | 0.0813 | |
| 21 | | 0.0263 | 6.16 |
| 22 | | 0.0248 | |

-continued
| Example | Compound | CBP HTRF IC$_{50}$ (μM) | Myc IC$_{50}$ (μM) |
|---|---|---|---|
| 23 | 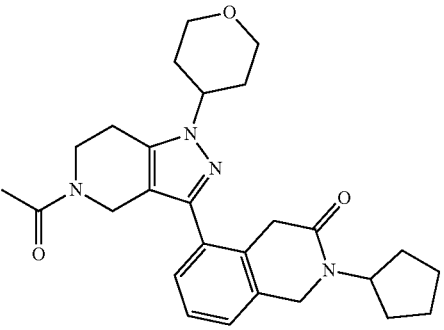 | 0.0167 | |
| 24 | 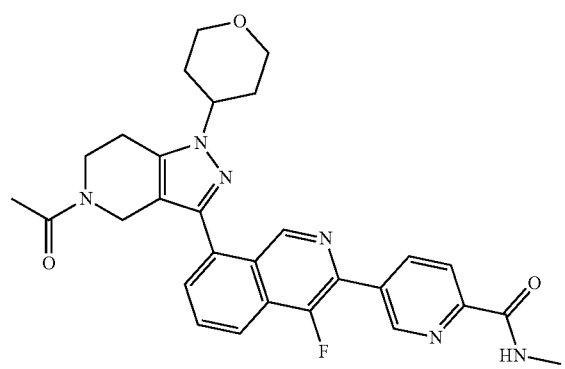 | 0.00205 | 0.0263 |
| 25 | 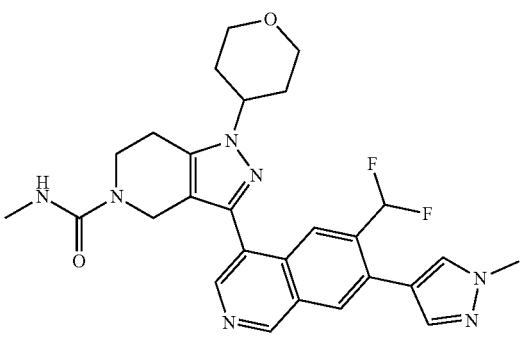 | 0.00107 | 0.00596 |
| 26 | 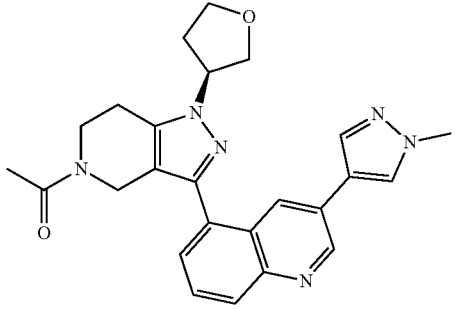 | 0.00643 | |

-continued
| Example | Compound | CBP HTRF IC$_{50}$ (μM) | Myc IC$_{50}$ (μM) |
|---|---|---|---|
| 27 | 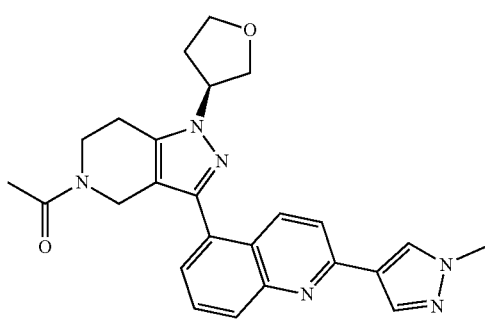 | 0.0167 | |
| 28 | 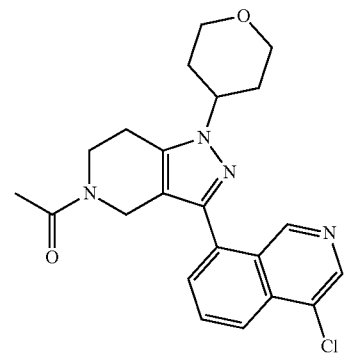 | 0.0416 | |
| 29 | 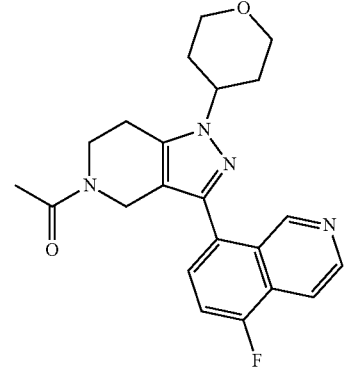 | 0.0595 | |
| 30 | 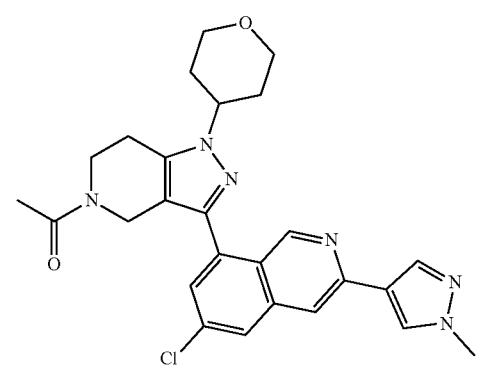 | 0.00502 | 0.198 |

| Example | Compound | CBP HTRF IC$_{50}$ (μM) | Myc IC$_{50}$ (μM) |
|---|---|---|---|
| 31 | | 0.00171 | 0.0646 |
| 32 | | 0.00564 | 0.0728 |
| 33 | | 0.00237 | 0.0988 |
| 34 | | 0.00145 | 0.0592 |

-continued

| Example | Compound | CBP HTRF IC$_{50}$ (μM) | Myc IC$_{50}$ (μM) |
|---|---|---|---|
| 35 | | 0.0182 | |
| 36 | | 0.00139 | 0.0465 |
| 37 | | 0.00242 | 0.164 |
| 38 | | 0.0165 | 1.43 |

-continued

| Example | Compound | CBP HTRF IC$_{50}$ (μM) | Myc IC$_{50}$ (μM) |
|---|---|---|---|
| 39 | | 0.00577 | 0.617 |
| 40 | | 0.0176 | 0.727 |
| 41 | | 0.0265 | |
| 42 | | 0.0104 | |

-continued

| Example | Compound | CBP HTRF IC$_{50}$ (μM) | Myc IC$_{50}$ (μM) |
|---|---|---|---|
| 43 | | 0.0547 | |
| 44 | | 0.00629 | |
| 45 | | 0.00154 | 0.481 |
| 46 | | 0.00097 | 0.00903 |

-continued

| Example | Compound | CBP HTRF IC$_{50}$ (μM) | Myc IC$_{50}$ (μM) |
|---|---|---|---|
| 47 | | 0.00191 | 0.0619 |
| 48 | | 0.00961 | 0.568 |
| 49 | | 0.00142 | 0.0559 |
| 50 | | 0.124 | |

-continued

| Example | Compound | CBP HTRF IC$_{50}$ (μM) | Myc IC$_{50}$ (μM) |
|---------|----------|-------------------------|---------------------|
| 51 | | 0.121 | |
| 52 | | | |
| 53 | | 0.00238 | 0.0520 |
| 54 | | 0.124 | |
| 55 | | 0.0999 | |

-continued

| Example | Compound | CBP HTRF IC$_{50}$ (μM) | Myc IC$_{50}$ (μM) |
|---|---|---|---|
| 56 | | 0.0308 | |
| 57 | | 0.0431 | |
| 58 | | 0.109 | |
| 59 | | 0.0525 | |

-continued

| Example | Compound | CBP HTRF IC$_{50}$ (μM) | Myc IC$_{50}$ (μM) |
|---|---|---|---|
| 60 | | 0.0080 | |
| 61 | | 0.103 | |
| 62 | | 0.0430 | |
| 63 | | 0.0999 | |
| 64 | | 0.0378 | |

-continued

| Example | Compound | CBP HTRF IC$_{50}$ (μM) | Myc IC$_{50}$ (μM) |
|---|---|---|---|
| 65 | | | 0.0849 |
| 66 | | | 0.0205 |
| 67 | | | 0.0300 |
| 68 | | | 0.0159 |

-continued
| Example | Compound | CBP HTRF IC$_{50}$ (μM) | Myc IC$_{50}$ (μM) |
|---|---|---|---|
| 69 | 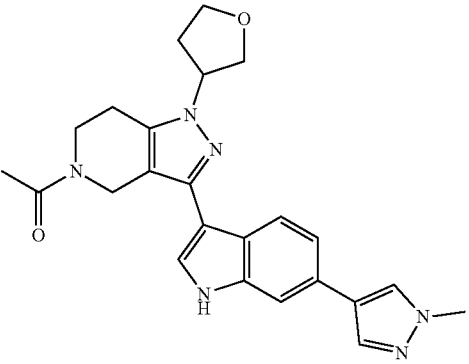 | 0.0155 | |
| 70 | 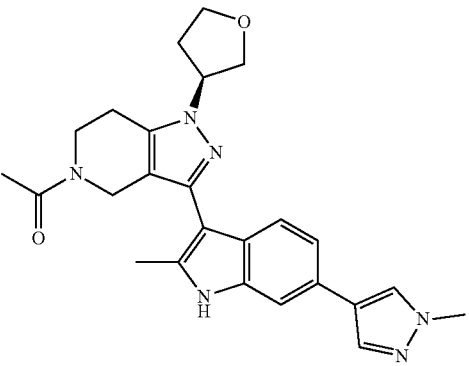 | 0.00514 | |
| 71 | 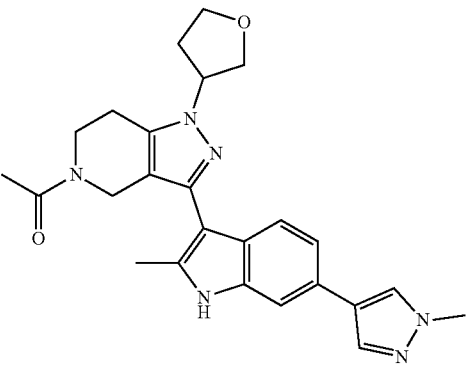 | 0.00657 | |
| 72 | 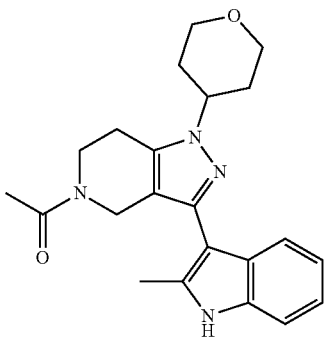 | 0.125 | |

-continued

| Example | Compound | CBP HTRF IC$_{50}$ (μM) | Myc IC$_{50}$ (μM) |
|---|---|---|---|
| 73 | | 0.141 | |
| 74 | | 0.0902 | |
| 75 | | 0.0134 | 0.523 |
| 76 | | 0.0272 | |

-continued

| Example | Compound | CBP HTRF IC$_{50}$ (μM) | Myc IC$_{50}$ (μM) |
|---------|----------|-------------------------|---------------------|
| 77 | | 0.0233 | |
| 78 | | 0.0294 | |
| 79 | | 0.0308 | |
| 80 | | 0.0378 | |

-continued
| Example | Compound | CBP HTRF IC$_{50}$ (µM) | Myc IC$_{50}$ (µM) |
|---|---|---|---|
| 81 | 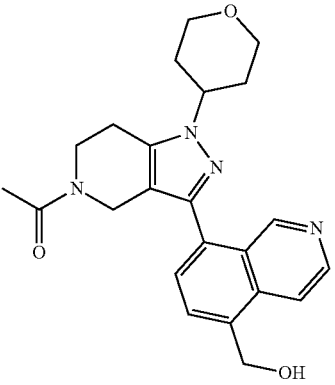 | 0.0648 | |
| 82 | 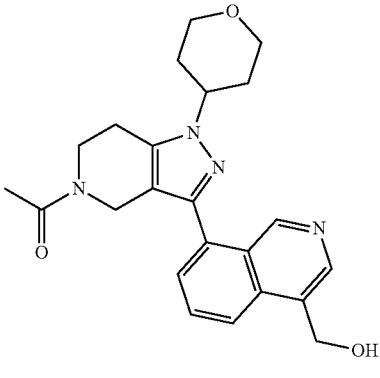 | 0.0805 | |
| 83 | 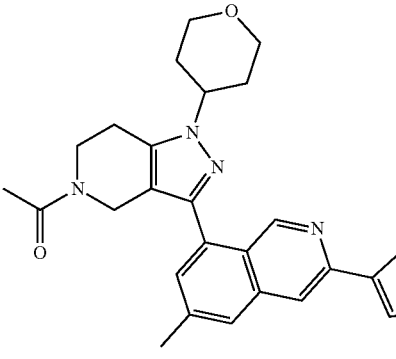 | 0.00270 | 0.0662 |
| 84 | 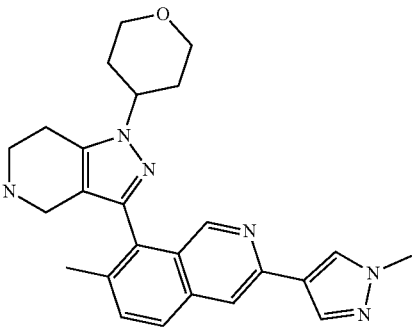 | 0.0222 | 8.87 |

-continued

| Example | Compound | CBP HTRF IC$_{50}$ (μM) | Myc IC$_{50}$ (μM) |
|---|---|---|---|
| 85 | | 0.00212 | 0.052 |
| 86 | | 0.00233 | 0.0305 |
| 87 | | 0.000997 | 0.0180 |
| 88 | | 0.00116 | 0.0319 |

-continued

| Example | Compound | CBP HTRF IC$_{50}$ (µM) | Myc IC$_{50}$ (µM) |
|---|---|---|---|
| 89 | | 0.00192 | |
| 90 | | 0.00110 | 0.0168 |
| 91 | | 0.00117 | 0.0283 |
| 92 | | 0.000760 | 0.00735 |

-continued

| Example | Compound | CBP HTRF IC$_{50}$ (μM) | Myc IC$_{50}$ (μM) |
|---------|----------|-------------------------|--------------------|
| 93 | | 0.000910 | |
| 94 | | 0.00100 | 0.00722 |
| 95 | | 0.0357 | |
| 96 | | 0.00294 | 0.0755 |

-continued
| Example | Compound | CBP HTRF IC$_{50}$ (μM) | Myc IC$_{50}$ (μM) |
|---|---|---|---|
| 97 | 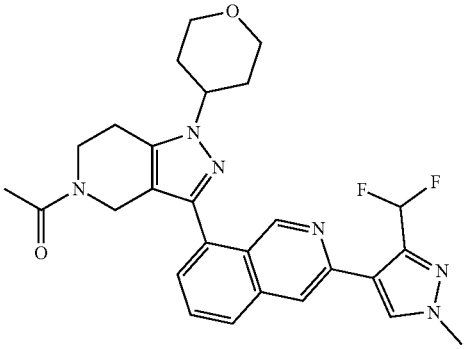 | 0.00334 | 0.221 |
| 98 | 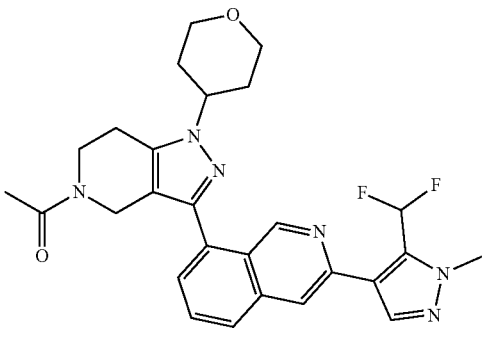 | 0.00278 | 0.109 |
| 99 | 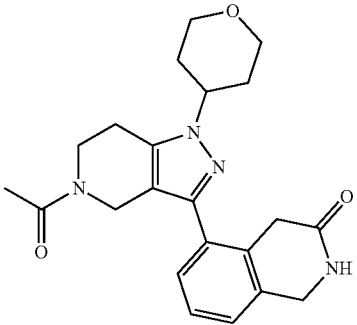 | 0.0814 | |
| 100 | 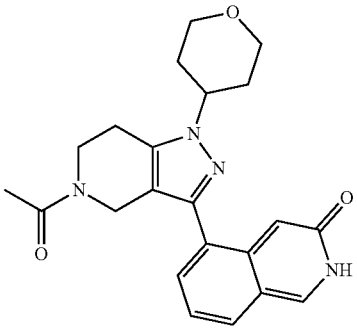 | 0.0788 | |

-continued

| Example | Compound | CBP HTRF IC$_{50}$ (μM) | Myc IC$_{50}$ (μM) |
|---------|----------|-------------------------|---------------------|
| 101 | | 0.00641 | 0.330 |
| 102 | | 0.0568 | |
| 103 | | 0.0410 | |
| 104 | | 0.0345 | |

-continued

| Example | Compound | CBP HTRF IC$_{50}$ (μM) | Myc IC$_{50}$ (μM) |
|---|---|---|---|
| 105 | | 0.0338 | |
| 106 | | 0.0111 | |
| 107 | | 0.0954 | |
| 108 | | 0.0576 | |
| 109 | | 0.0912 | |

-continued

| Example | Compound | CBP HTRF IC$_{50}$ (μM) | Myc IC$_{50}$ (μM) |
|---|---|---|---|
| 110 | | 0.0677 | |
| 111 | | 0.00362 | 0.152 |
| 112 | | 0.00349 | 0.249 |
| 113 | | 0.00299 | 0.863 |

-continued

| Example | Compound | CBP HTRF IC$_{50}$ (μM) | Myc IC$_{50}$ (μM) |
|---|---|---|---|
| 114 | | 0.00349 | 1.15 |
| 115 | | 0.00898 | 0.942 |
| 116 | | 0.0245 | |
| 117 | | 0.0128 | 1.51 |

-continued

| Example | Compound | CBP HTRF IC$_{50}$ (μM) | Myc IC$_{50}$ (μM) |
|---|---|---|---|
| 118 | | 0.00281 | 0.850 |
| 119 | | 0.00282 | 1.18 |
| 120 | | 0.00369 | 0.119 |
| 121 | | 0.00582 | 1.12 |

-continued

| Example | Compound | CBP HTRF IC$_{50}$ (μM) | Myc IC$_{50}$ (μM) |
|---|---|---|---|
| 122 | | 0.00408 | 0.563 |
| 123 | | 0.0132 | 2.49 |
| 124 | | 0.00215 | 0.491 |
| 125 | | 0.00417 | 0.925 |

-continued

| Example | Compound | CBP HTRF IC$_{50}$ (μM) | Myc IC$_{50}$ (μM) |
|---------|----------|-------------------------|---------------------|
| 126 | | 0.00771 | 0.374 |
| 127 | | 0.0145 | |
| 128 | | 0.00244 | 0.280 |
| 129 | | 0.00185 | 0.605 |

-continued
| Example | Compound | CBP HTRF IC$_{50}$ (μM) | Myc IC$_{50}$ (μM) |
|---|---|---|---|
| 130 | 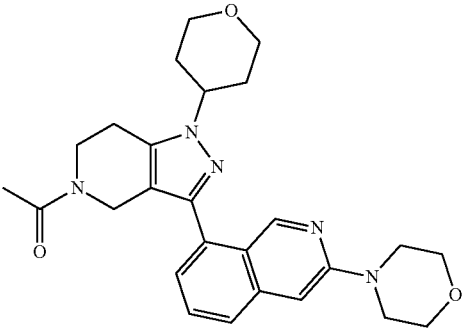 | 0.00725 | 0.285 |
| 131 | 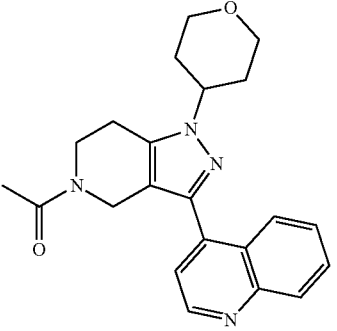 | 0.094 | |
| 132 | 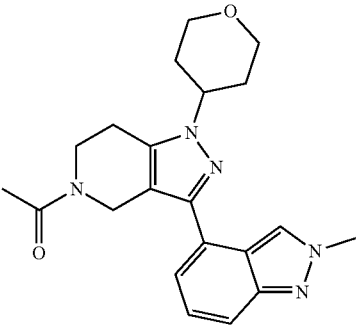 | 0.133 | |
| 133 | 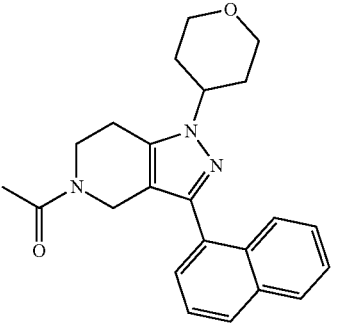 | 0.0168 | 0.623 |

-continued

| Example | Compound | CBP HTRF IC$_{50}$ (μM) | Myc IC$_{50}$ (μM) |
|---|---|---|---|
| 134 | | 0.123 | |
| 135 | | 0.0354 | 1.01 |
| 136 | | 0.133 | |
| 137 | | 0.054 | |

-continued
| Example | Compound | CBP HTRF IC$_{50}$ (μM) | Myc IC$_{50}$ (μM) |
|---|---|---|---|
| 138 | 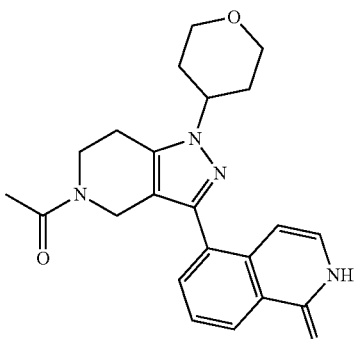 | 0.132 | |
| 139 | 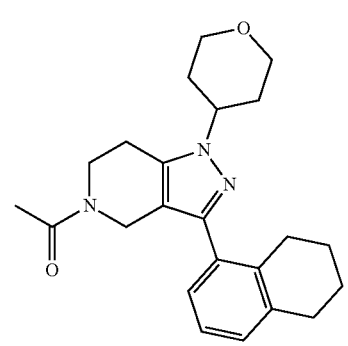 | 0.131 | |
| 140 | 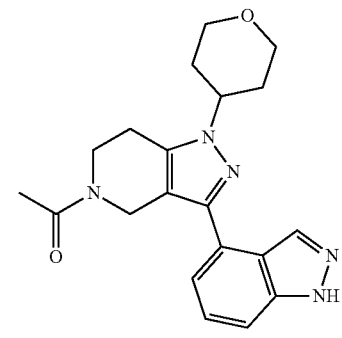 | 0.0445 | 2.71 |
| 141 | 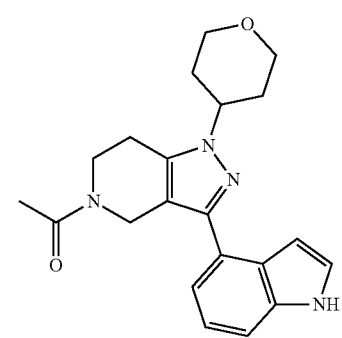 | 0.115 | |

-continued
| Example | Compound | CBP HTRF IC$_{50}$ (μM) | Myc IC$_{50}$ (μM) |
|---------|----------|--------------------------|---------------------|
| 142 | 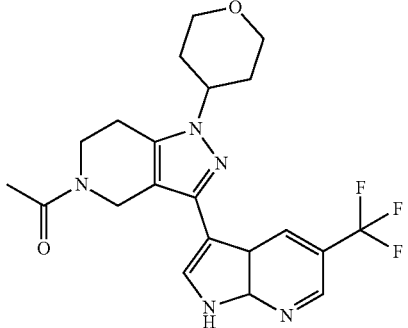 | 0.0423 | 0.504 |
| 143 | 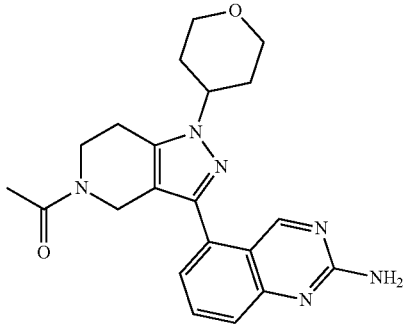 | 0.0581 | |
| 144 | 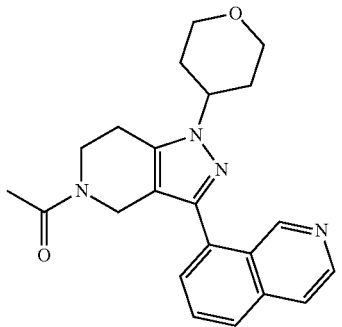 | 0.0295 | 0.761 |
| 145 | 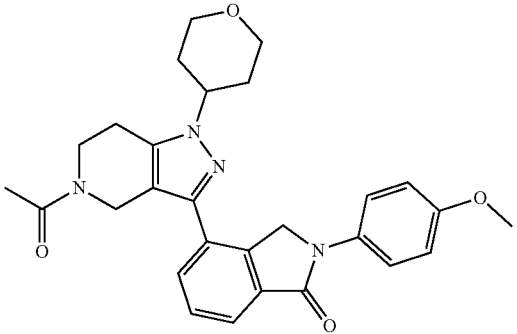 | 0.013 | 4.42 |

-continued

| Example | Compound | CBP HTRF IC$_{50}$ (μM) | Myc IC$_{50}$ (μM) |
|---|---|---|---|
| 146 | | 0.0298 | |
| 147 | | 0.00609 | 0.263 |
| 148 | | 0.0797 | |
| 149 | | 0.123 | |

-continued

| Example | Compound | CBP HTRF IC$_{50}$ (μM) | Myc IC$_{50}$ (μM) |
|---|---|---|---|
| 150 | | 0.0667 | |
| 151 | | 0.128 | |
| 152 | | 0.0461 | >10 |
| 153 | | 0.0957 | |

-continued

| Example | Compound | CBP HTRF IC$_{50}$ (μM) | Myc IC$_{50}$ (μM) |
|---|---|---|---|
| 154 | | 0.101 | |
| 155 | | 0.0691 | |
| 156 | | 0.107 | |
| 157 | | 0.00446 | 1.04 |

-continued

| Example | Compound | CBP HTRF IC$_{50}$ (μM) | Myc IC$_{50}$ (μM) |
|---|---|---|---|
| 158 | | 0.0193 | 5.32 |
| 159 | | 0.00411 | 1.58 |
| 160 | | 0.0737 | |
| 161 | | 0.082 | |

-continued
| Example | Compound | CBP HTRF IC$_{50}$ (μM) | Myc IC$_{50}$ (μM) |
|---|---|---|---|
| 162 | 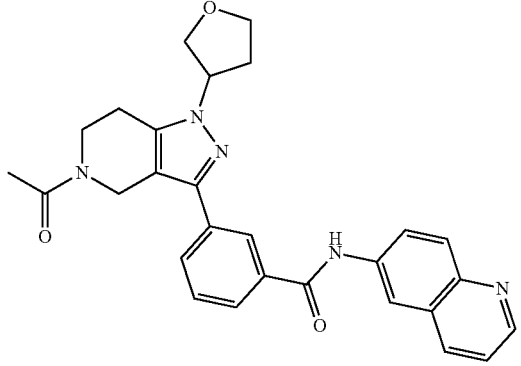 | 0.0329 | |
| 163 | 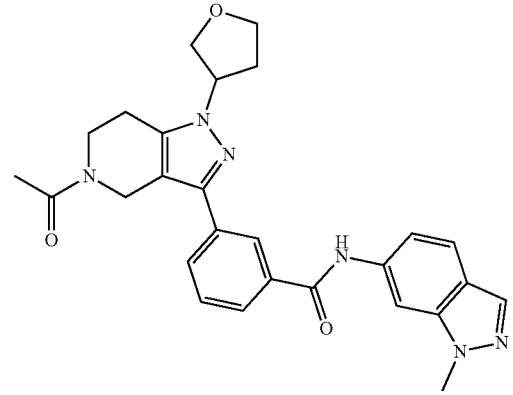 | 0.0497 | |
| 164 | 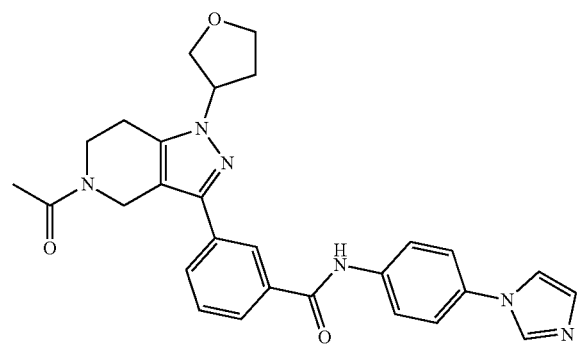 | 0.0831 | |
| 165 | 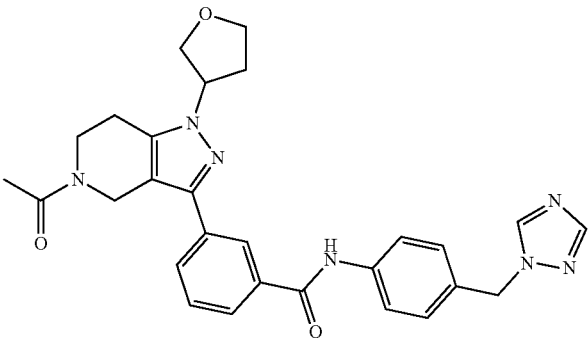 | 0.0442 | |

-continued

| Example | Compound | CBP HTRF IC$_{50}$ (µM) | Myc IC$_{50}$ (µM) |
|---|---|---|---|
| 166 | | 0.0365 | |
| 167 | | 0.011 | |
| 168 | | 0.0326 | |
| 169 | | 0.0592 | |

-continued

| Example | Compound | CBP HTRF IC$_{50}$ (μM) | Myc IC$_{50}$ (μM) |
|---------|----------|------------------------|--------------------|
| 170 | | 0.123 | |
| 171 | | 0.104 | |
| 172 | | 0.0392 | |
| 173 | | 0.0305 | |

-continued

| Example | Compound | CBP HTRF IC$_{50}$ (μM) | Myc IC$_{50}$ (μM) |
|---------|----------|------------------------|--------------------|
| 174 | | 0.0119 | |
| 175 | | 0.0104 | 0.122 |

Exemplification of CBP/EP300 Inhibitors for the Treatment of Fibrotic Disease

Cell Culture:

Collagen 1-coated 384-well plates (BD Biosciences cat #356667) were seeded with Normal Human Lung Fibroblasts (Lonza cat #CC-2512) at 2000 cells per well in 50 μl DMEM (Genentech) containing 0.5% fetal bovine serum (Sigma cat #F2442). After 16 hours, the indicated compounds were added to cells at final concentrations ranging from 10 μM to 0.005 nM in an 8-fold dilution series. After one hour, TGF beta (Genentech) was added to cells to a final concentration of 10 ng/ml. All treatments were performed in duplicate.

Animal Study:

Bleomycin was administered to mice via subcutaneous implantation of an osmotic pump (Alzet cat #1007D). After bleomycin administration, mice were treated with compounds by oral gavage. Mice received either MCT vehicle (0.5% w/v methylcellulose, 0.2% w/v polysorbate 80), G0272 in MCT at 5 mg/kg twice daily, G0272 in MCT at 15 mg/kg twice daily, G5049 in MCT at 5 mg/kg twice daily, G5049 in MCT at 15 mg/kg twice daily, G3486 in MCT at 15 mg/kg twice daily, or G3486 in MCT at 45 mg/kg twice daily. To label newly synthesized collagen, mice were injected intraperitoneally with 35 ml/kg heavy water (Sigma Aldrich, cat #151882) in two doses and heavy water was provided in drinking water. At study termination, blood samples were collected by retro-orbital bleed under isoflurane anesthesia and mice were euthanized. Upper right lung lobes were placed in glass vials and snap frozen in liquid nitrogen for mass spectrometry. The lower right lung lobe was placed in RNAlater for expression analysis, and frozen at −20° C.

Lung Hydroxyproline Determination:

Lungs were thawed, dried overnight at 80° C., then hydrolyzed at 110° C. overnight in 6N HCl. The remainder of this paragraph was performed by KineMed, Emeryville Calif.). A 100 μl aliquot of tissue hydrolysate received a spike containing 1 μg $^2$H3-labeled hydroxyproline (D3-OHP; trans-4-Hydroxy-L-proline-2,5,5-d3; CDN), and then dried under vacuum and re-suspended in a solution of 50% acetonitrile, 50 mM K$_2$HPO$_4$ and pentafluorobenzyl bromide before incubation. Derivatives were extracted into ethyl acetate, and the top layer was removed and dried by vacuum centrifugation. In order to acetylate the hydroxyl moiety of hydroxyproline, samples were incubated with a solution of acetonitrile, N-Methyl-N-[tert-butyldimethyl-silyl]trifluoroacetamide and methylimidizole. This material was extracted in petroleum ether and dried with Na$_2$SO$_4$. The derivatized hydroxyproline was analyzed by GC/MS, performed in the negative chemical ionization mode. Selected ion monitoring was performed on ions with mass-to-charge ratios (m/z) 445, 446, 447, and 448 which include all of the carbon-hydrogen bonds from hydroxyproline. Incorporation of $^2$H into hydroxyproline was calculated as the molar fraction of molecules with one excess mass unit above the natural abundance fraction (EM1). Fractional collagen synthesis (f) was calculated as the ratio of the EM1 value in protein-bound hydroxyproline to the maximal value possible at the body water enrichment present. This method has previously been described (Gardner, J. L., et al., Measurement of liver collagen synthesis by heavy water labeling: effects of profibrotic toxicants and antifibrotic interventions. *Am J Physiol Gastrointest Liver Physiol*, 2007. 292 (6): p. G1695-705). Additionally, hydroxyproline content in each tissue sample was determined by comparing the abundance in the m3 448 m/z channel representing the D3-OHP internal standard in each sample with that the m0 445 m/z ion. A set of standards with known OHP/D3-OHP concentration ratios was analyzed alongside the samples. $^2H_2O$ enrichment in plasma was determined using a previously described method (Previs S F, Hazey J W, Diraison F, Beylot M, David F, Brunengraber H (1996) Assay of the deuterium enrichment of water via acetylene. *J Mass Spectrom* 31:639-642). Briefly body water is evaporated from plasma by overnight incubation at 80° C. Samples are then mixed in 10M NaOH and acetone followed by a second overnight incubation. This material was extracted in hexane and dried with $Na_2SO_4$ prior to GCMS analysis.

RNA Isolation:

For cultured cells, after 24 hours of treatment with TGF beta and CBP/p300 inhibitor, mRNA was isolated with the Turbocapture 384 mRNA kit (Qiagen cat #72271) according to the manufacturers' instructions and eluted with 30 µl elution buffer. For lungs, tissues were thawed, removed from RNAlater, homogenized in GentleMACS M tubes (Miltenyi Biotec cat #130-093-236) and RNA extracted with the RNeasy 96 kit (Qiagen cat #74182) according to the manufacturers instructions.

Expression Analysis:

First-strand cDNA was synthesized using 14 µl mRNA for cultured cells and 150 ng RNA for lung. The High Capacity cDNA Reverse Transcription Kit (Life Technologies cat #4368814) was used according to the manufacturers protocol. Specific target amplification was performed using 1.25 µl cDNA, Taqman assays (Life Technologies cat #4331182) at a final concentration of 0.2×, and Taqman Preamp Master Mix (Life Technologies cat #4488593) and subsequently diluted according to the protocol for Fluidigm qPCR (Fluidigm Corp). Samples and assays were mixed with loading buffers and loaded onto 192.24 IFCs (Fluidigm cat #100-6266) according to the manufacturers instructions. Reactions were mixed using the IFC controller RX (Fluidigm) then amplified and measured using the Biomark system (Fluidigm). For cultured cells, relative expression of each target gene was determined using the ΔCt method, normalizing to the Ct for HPRT1 using Excel software (Microsoft). To generate heat maps, TGF beta-mediated expression increase for each gene in the presence of CBP/p300 inhibitor was divided by the increase in the absence of CBP/p300 inhibitor using Excel (i.e. $(2^{-\Delta Ct,\ SMI+TGFb} - 2^{-\Delta Ct,\ SMI,\ no\ TGFb})/(2^{-\Delta Ct,\ TGFb} - 2^{-\Delta Ct,\ no\ TGFb})$). Line graphs of $2^{-\Delta Ct}$ values were generated using Prism software (Graphpad). For lung, relative expression of each target gene was determined using the ΔΔCt method, normalizing to the Ct for GAPDH and the vehicle control group. Heat maps were generated with Excel software (Microsoft).

While a number of embodiments have been described, these examples may be altered to provide other embodiments that utilize the compounds and methods described herein. Therefore, the scope of this invention is to be defined by the appended claims rather than by the specific embodiments that have been represented by way of example.

---

We claim:
1. A compound of formula (Ia):
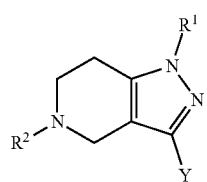
(Ia)
or a salt thereof, wherein:
$R^1$ is
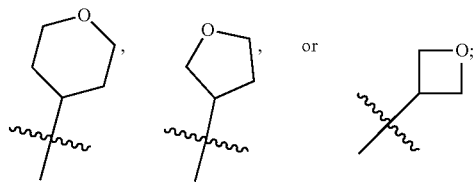
$R^2$ is —C(O)—N($R^e$)$_2$, or —C(O)—$R^e$;
Y is selected from the group consisting of:
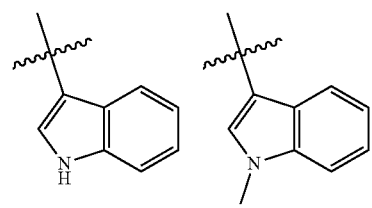
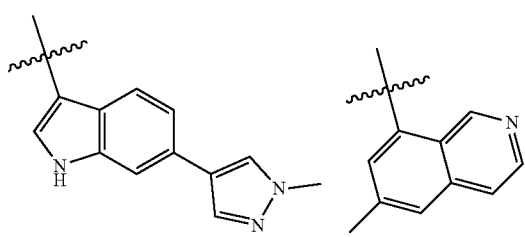
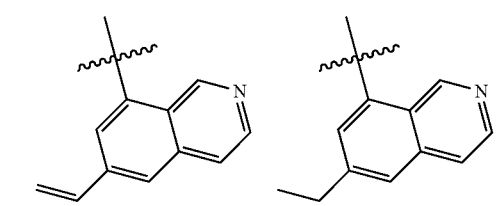
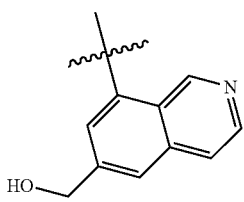
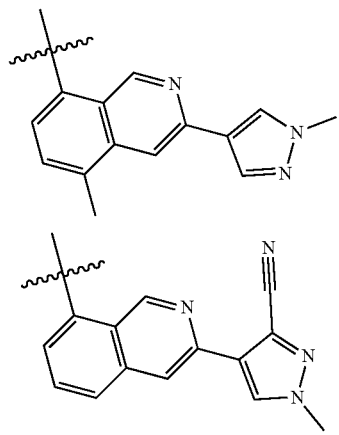
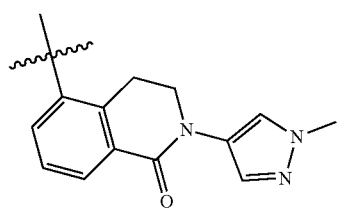
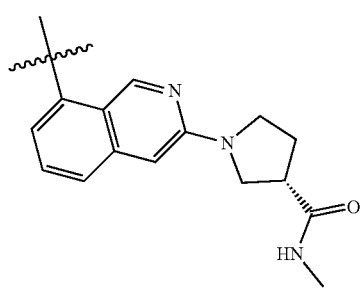
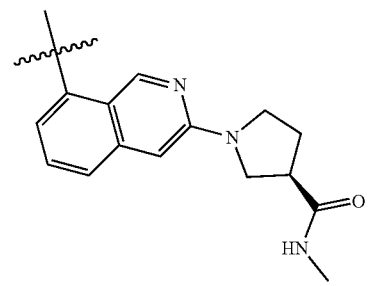
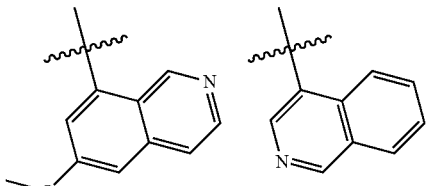
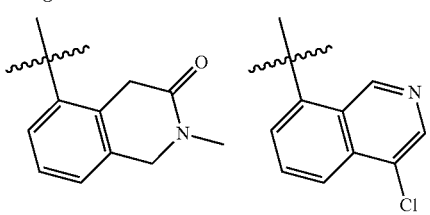

463
-continued
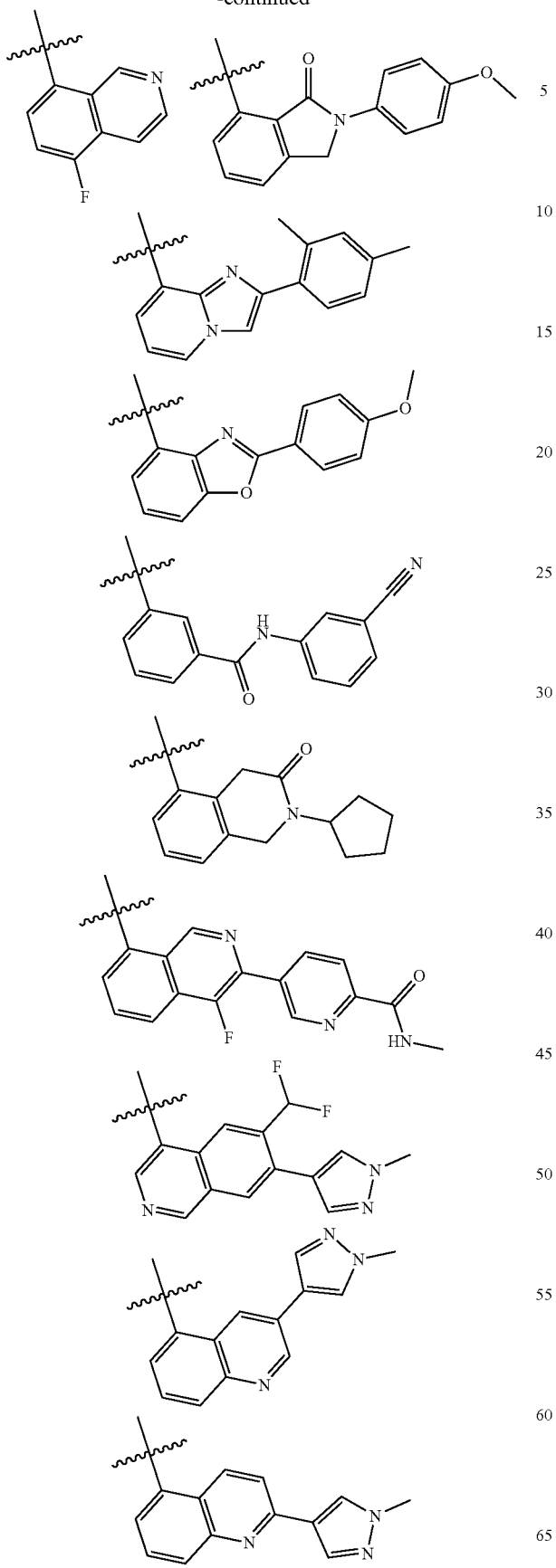
464
-continued
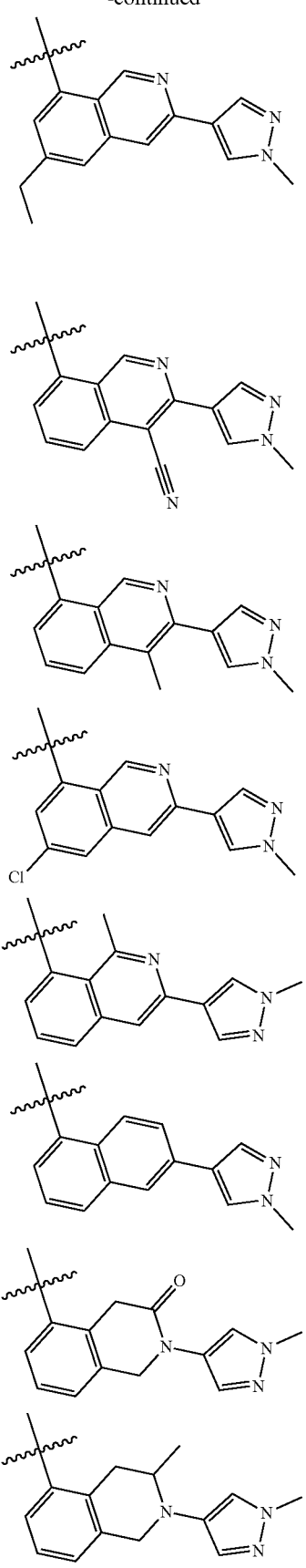

465
-continued
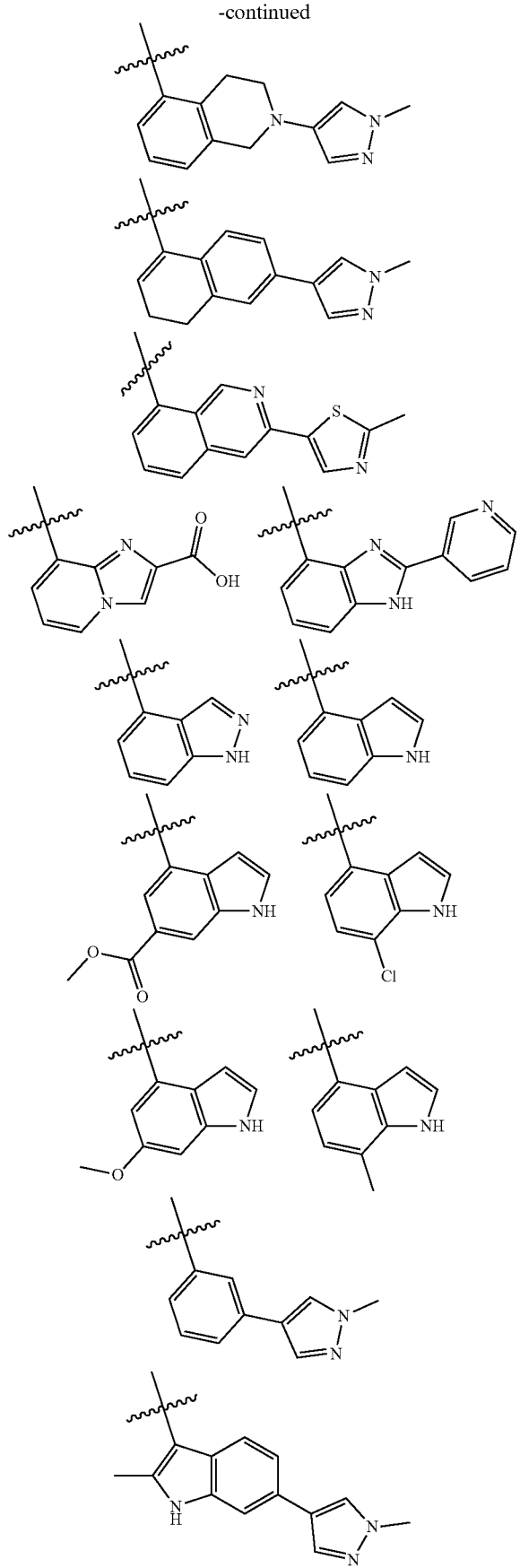
466
-continued
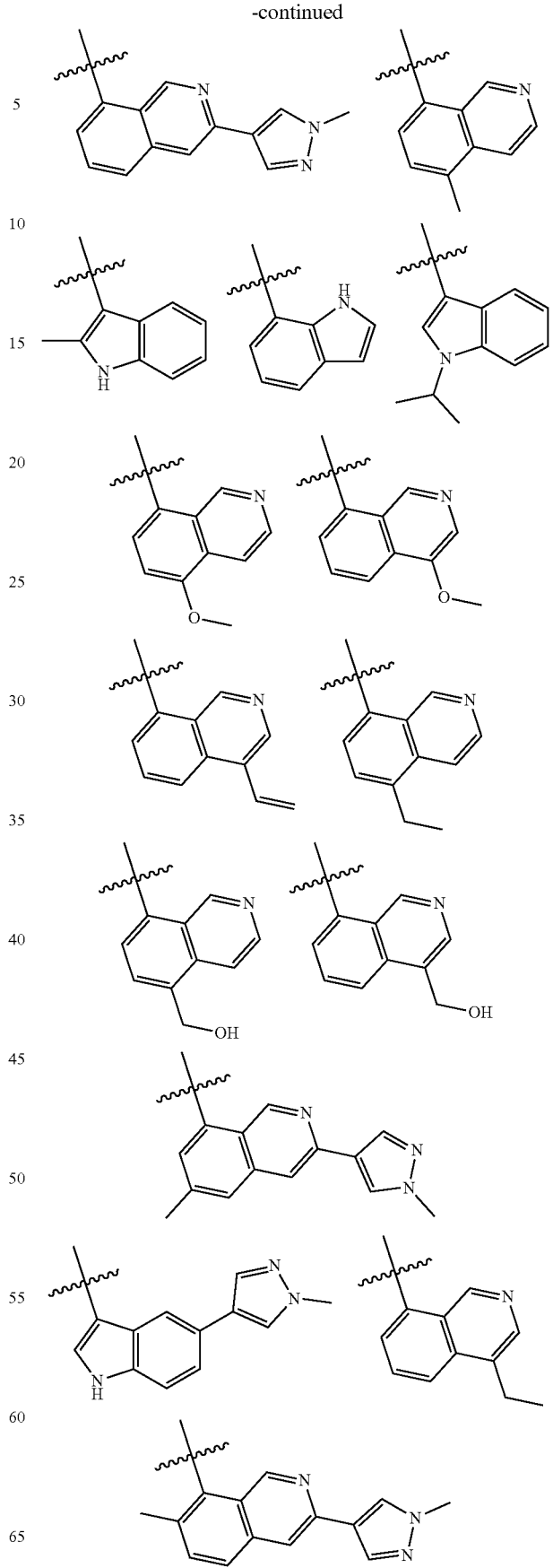

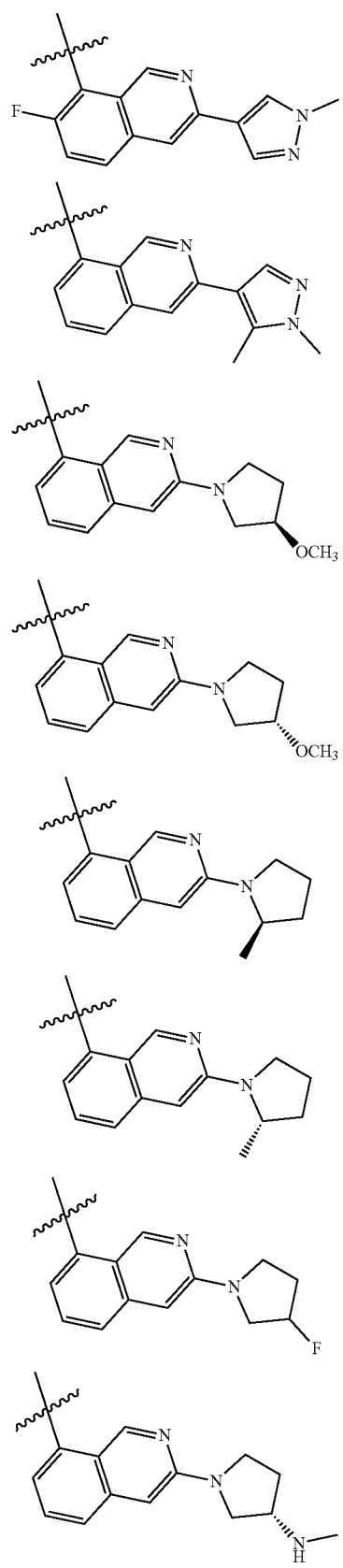
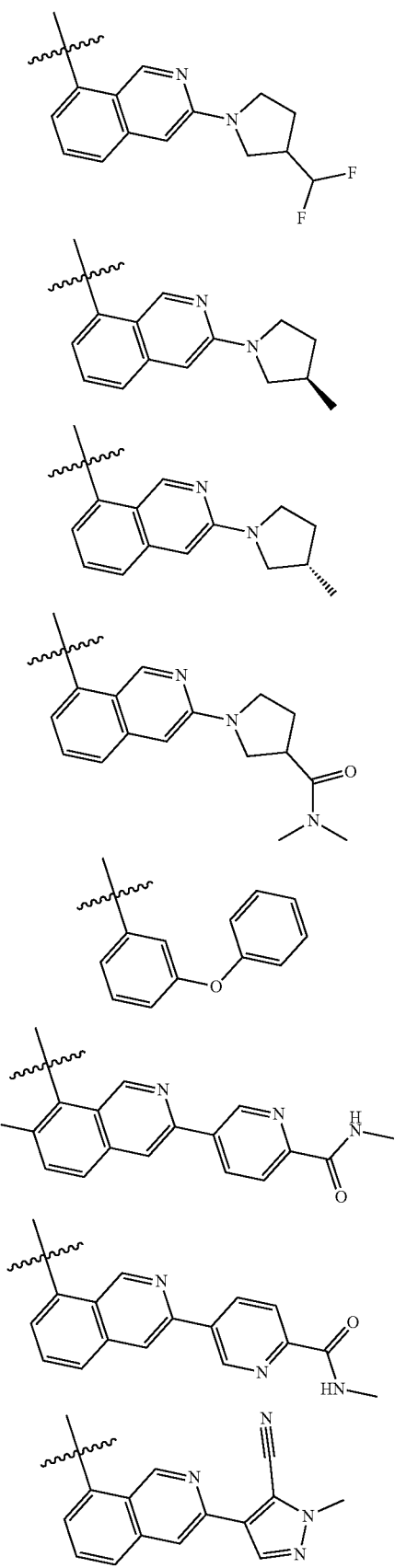

469
-continued
470
-continued
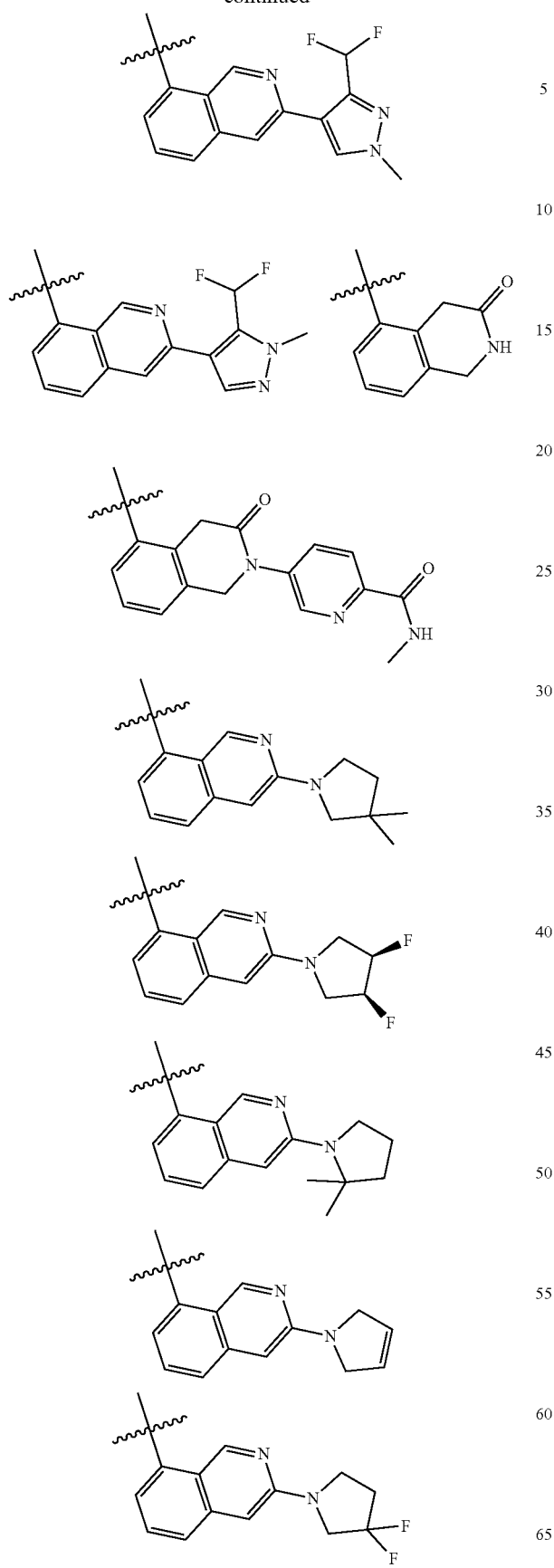
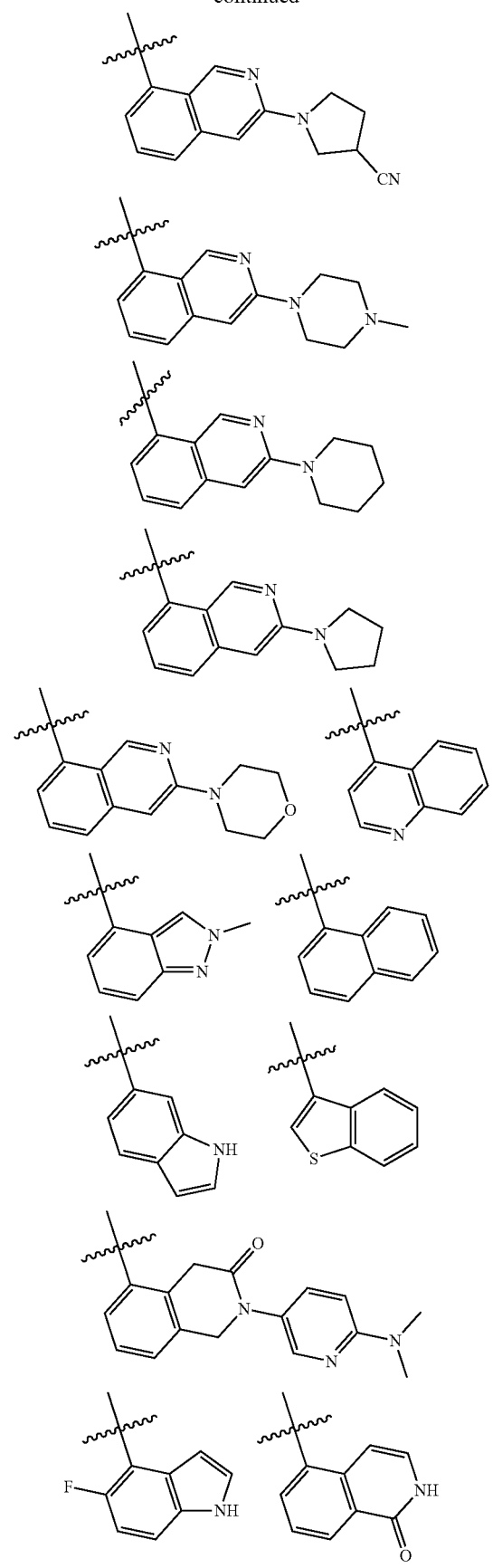

471
-continued
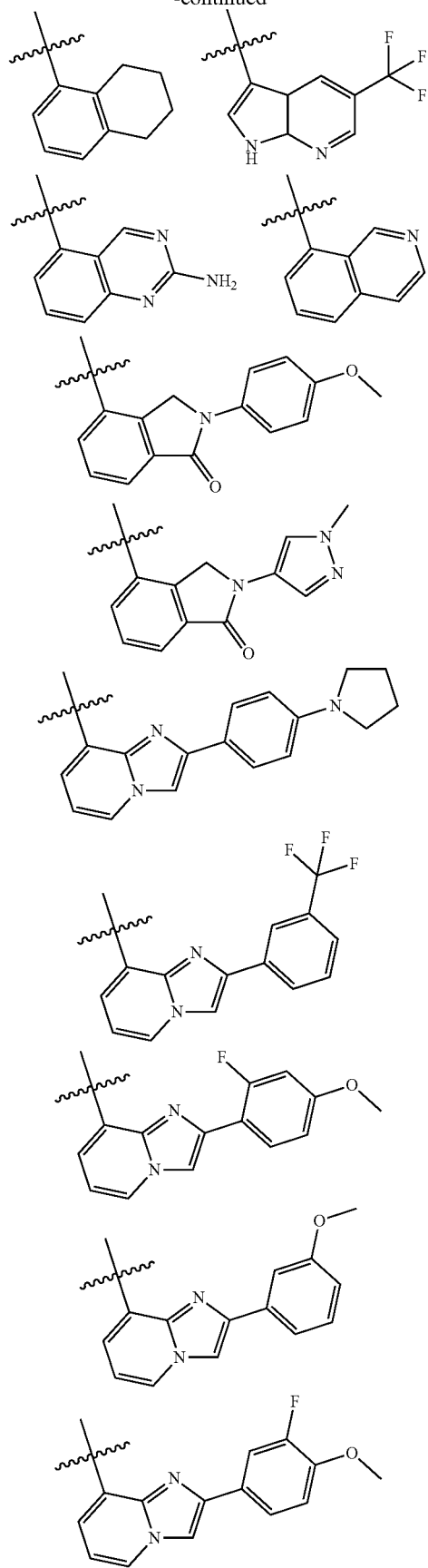
472
-continued
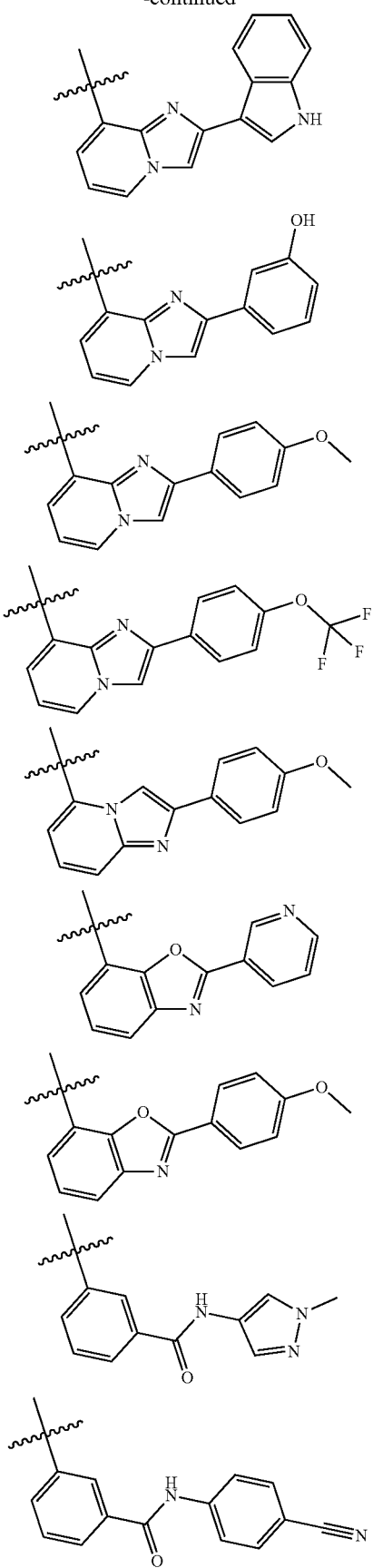

473
-continued
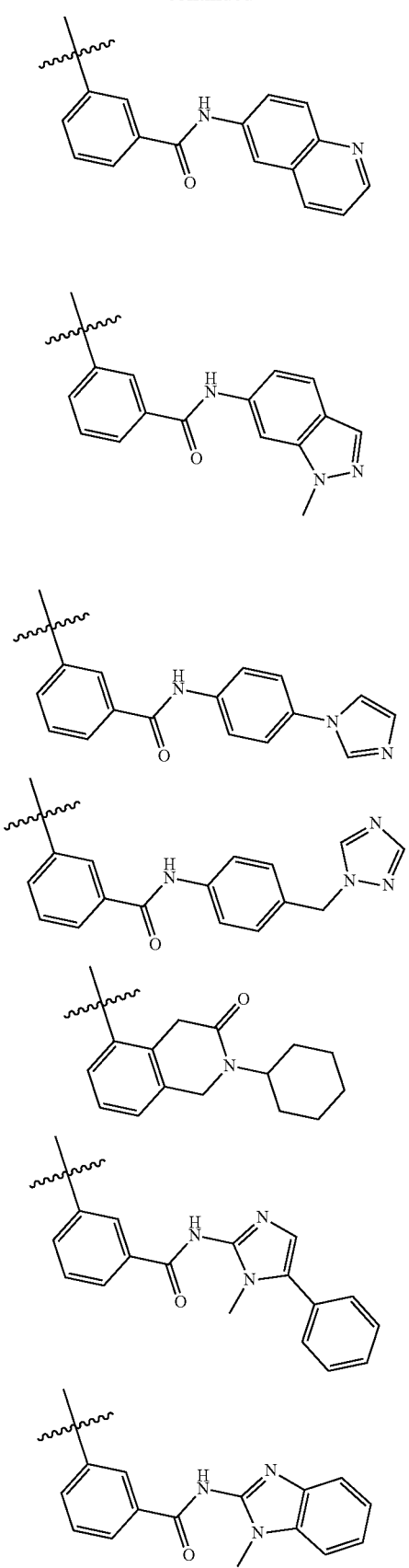
474
-continued
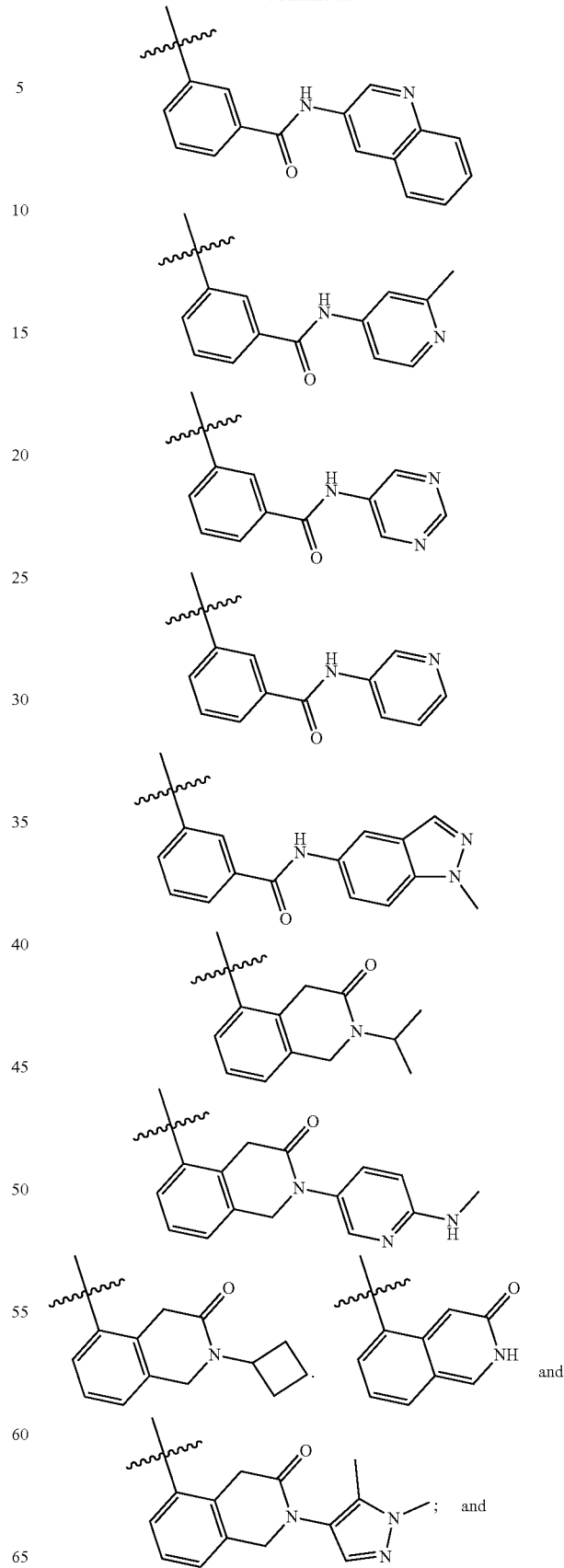

each $R^e$ is independently selected from hydrogen, $C_{1-4}$alkyl, $C_{2-4}$alkenyl, $C_{2-4}$alkynyl, and $C_{2-5}$cycloalkyl, wherein each $C_{1-4}$alkyl, $C_{2-4}$alkenyl, $C_{2-4}$alkynyl, and $C_{2-5}$cycloalkyl is optionally substituted with one or more groups independently selected from oxo, halo, amino, hydroxyl, $C_{1-3}$alkoxy, and $C_1$-$C_3$ alkyl that is optionally substituted with one or more groups independently selected from halo.

2. The compound or salt of claim 1 wherein $R^1$ is

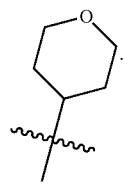

3. The compound or salt of claim 1 wherein Y is selected from the group consisting of:

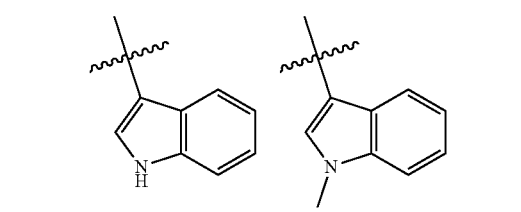

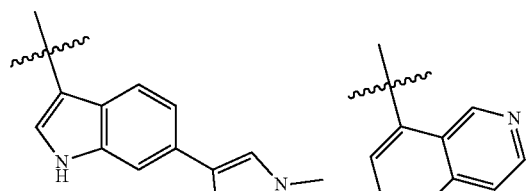

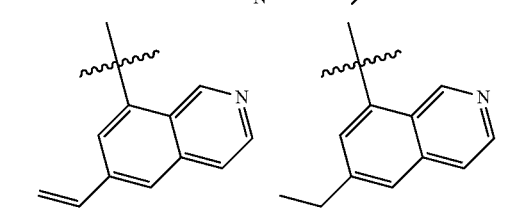

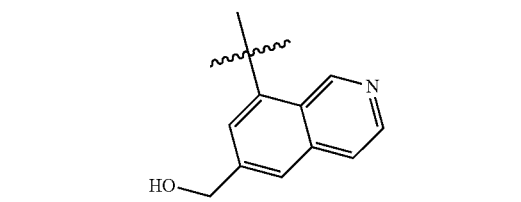

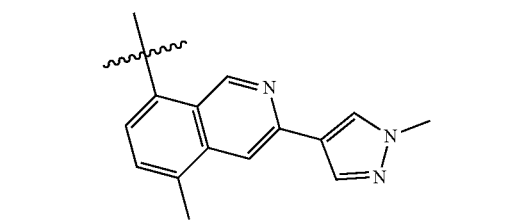

-continued

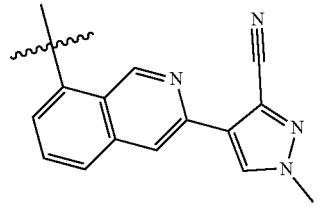

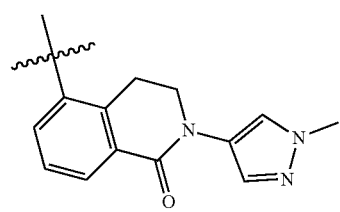

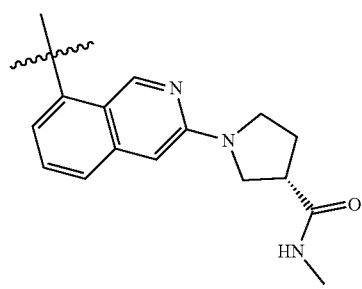

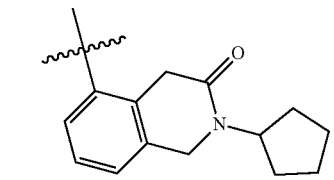

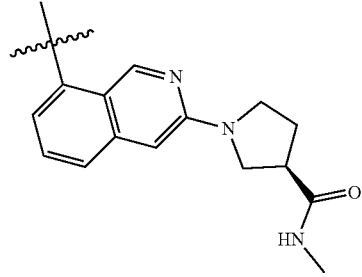

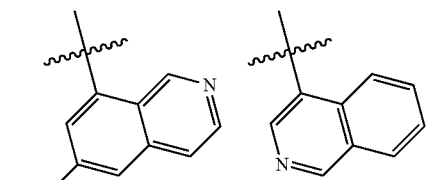

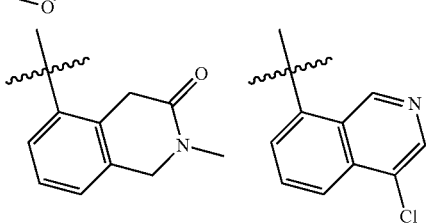

477
-continued
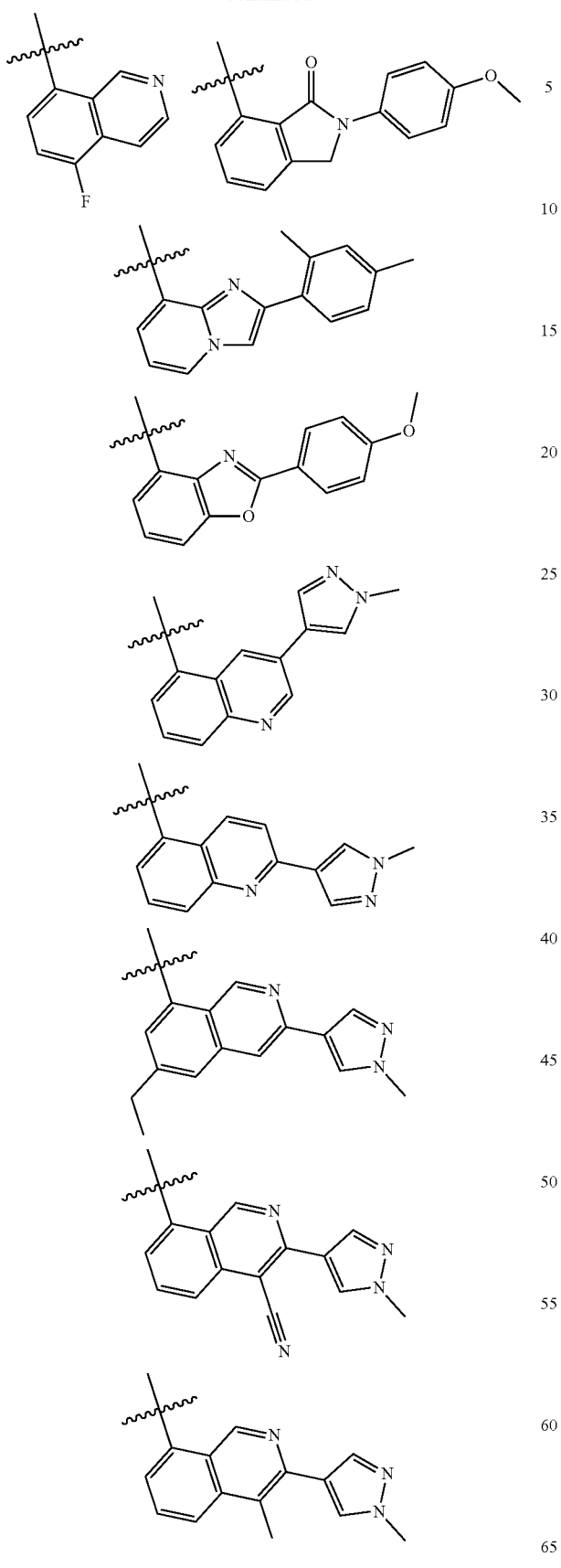
478
-continued
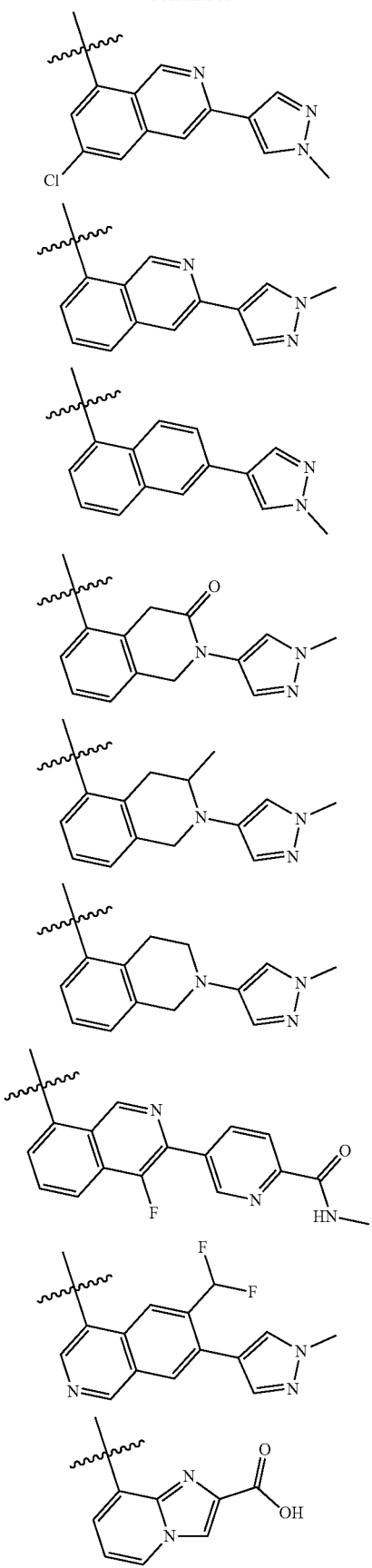

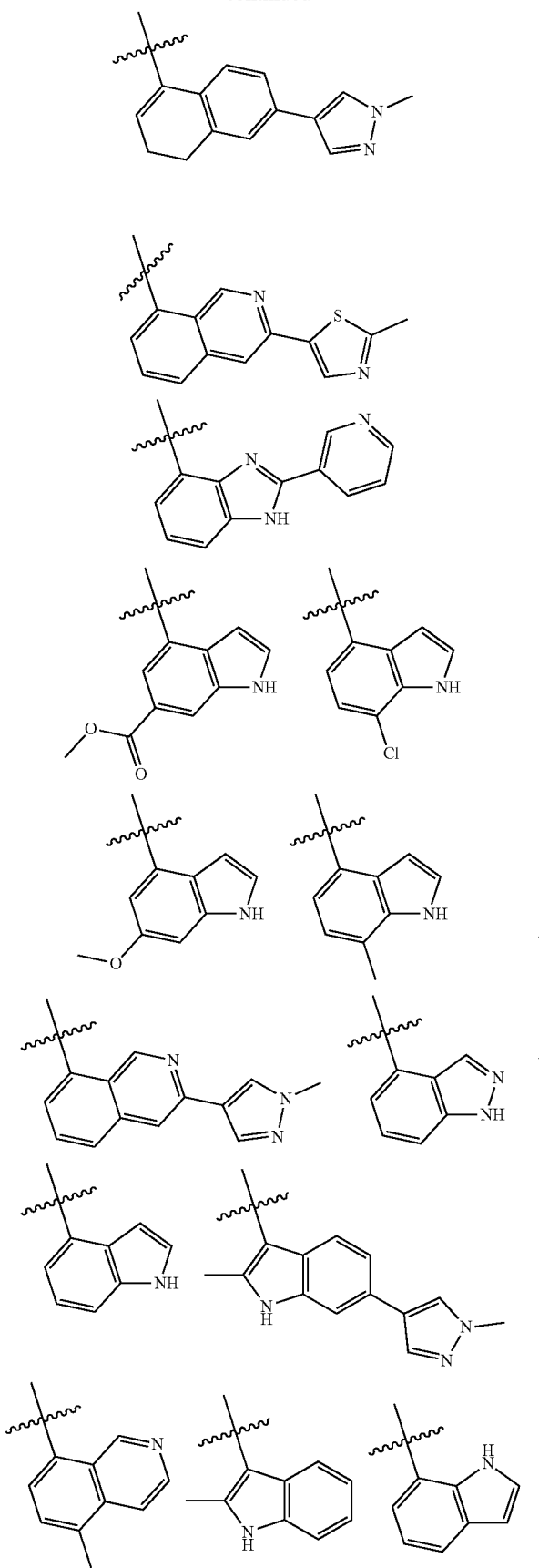
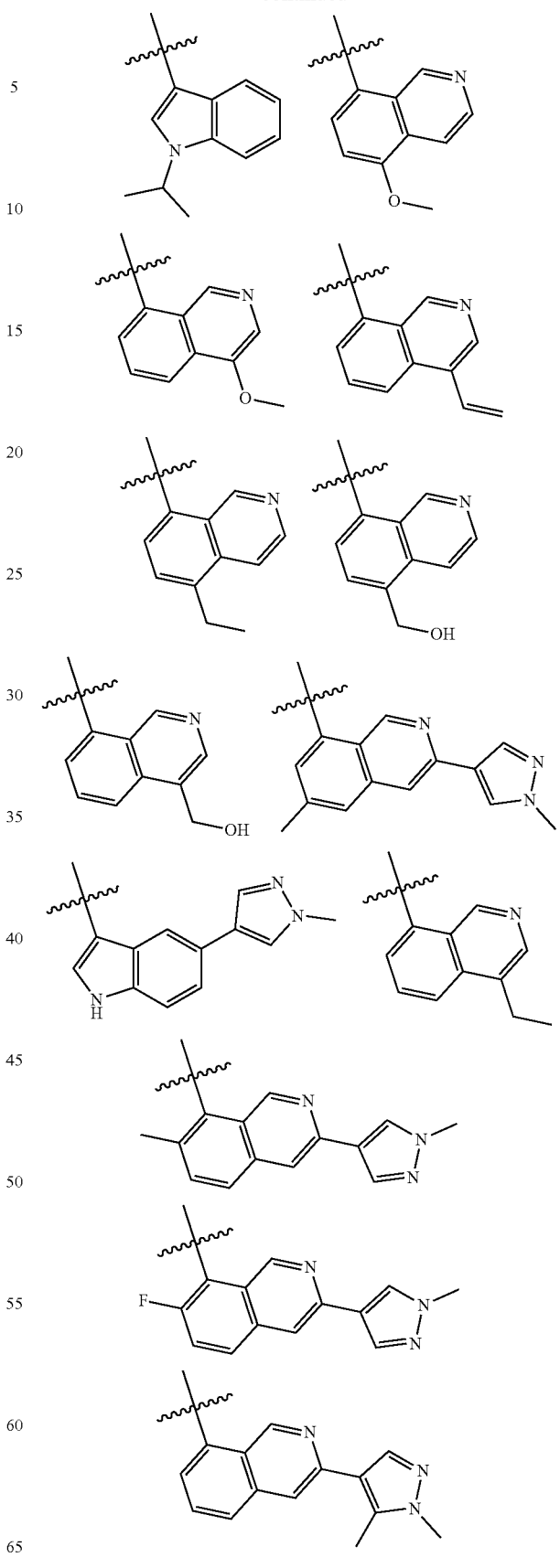

481
-continued
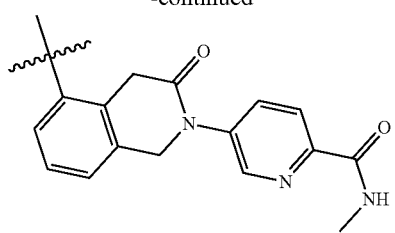
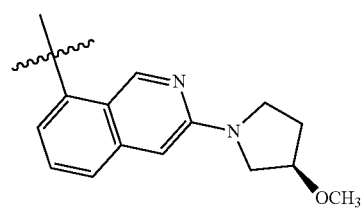
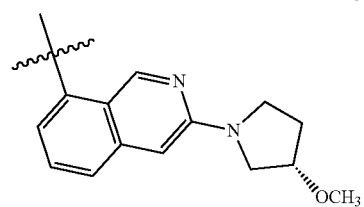
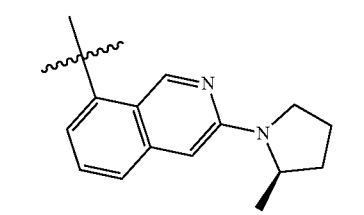
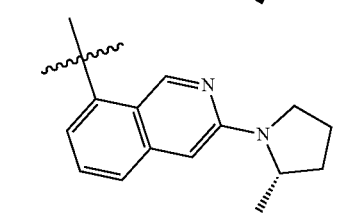
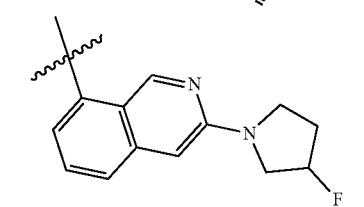
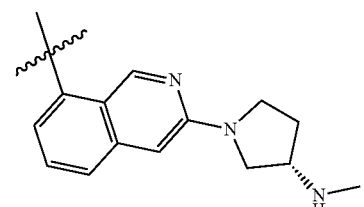
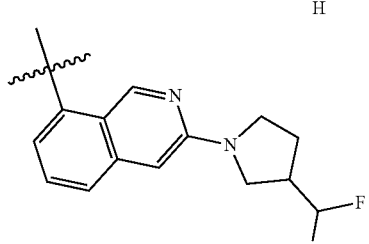
482
-continued
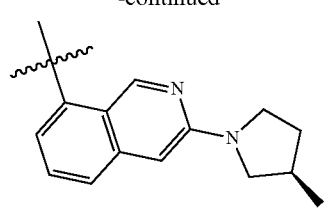
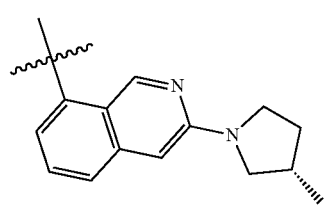
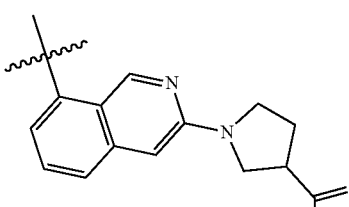
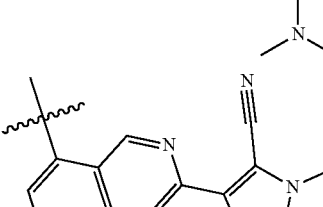
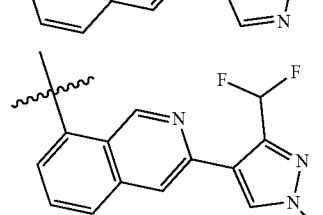
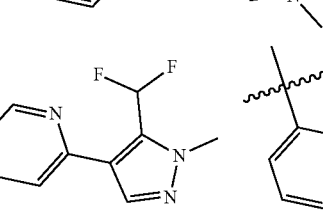
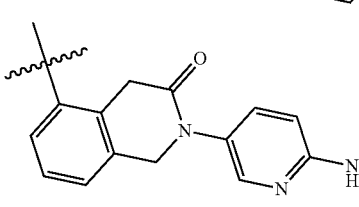
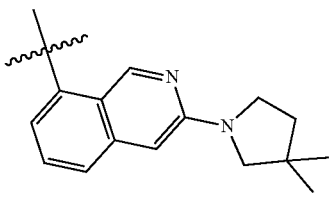

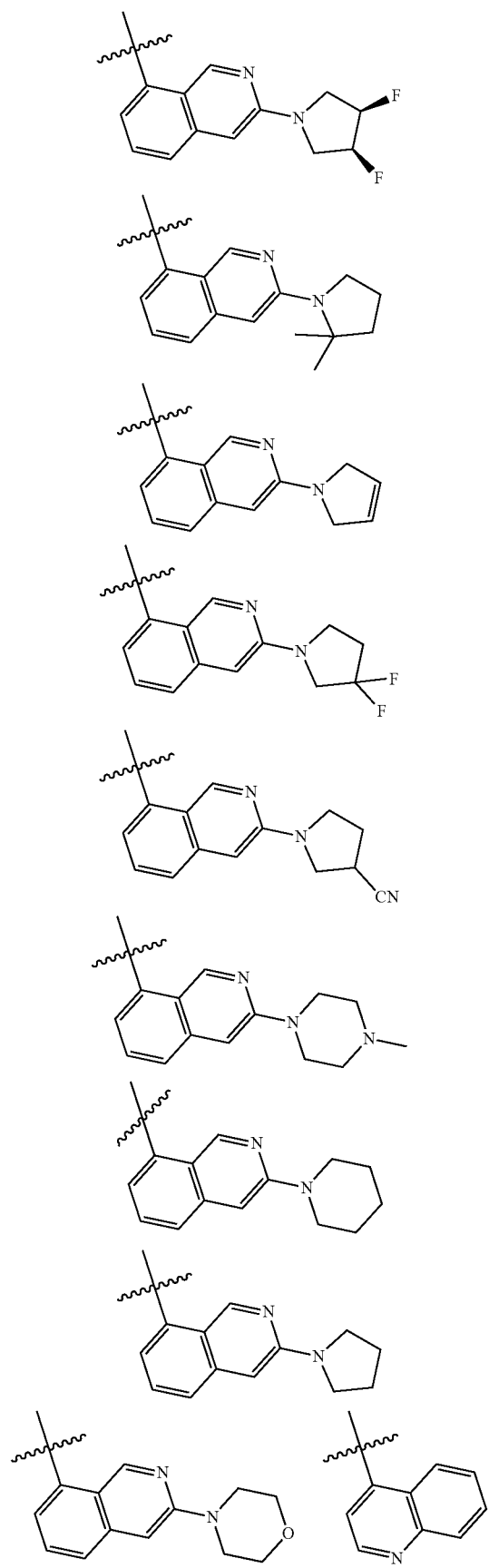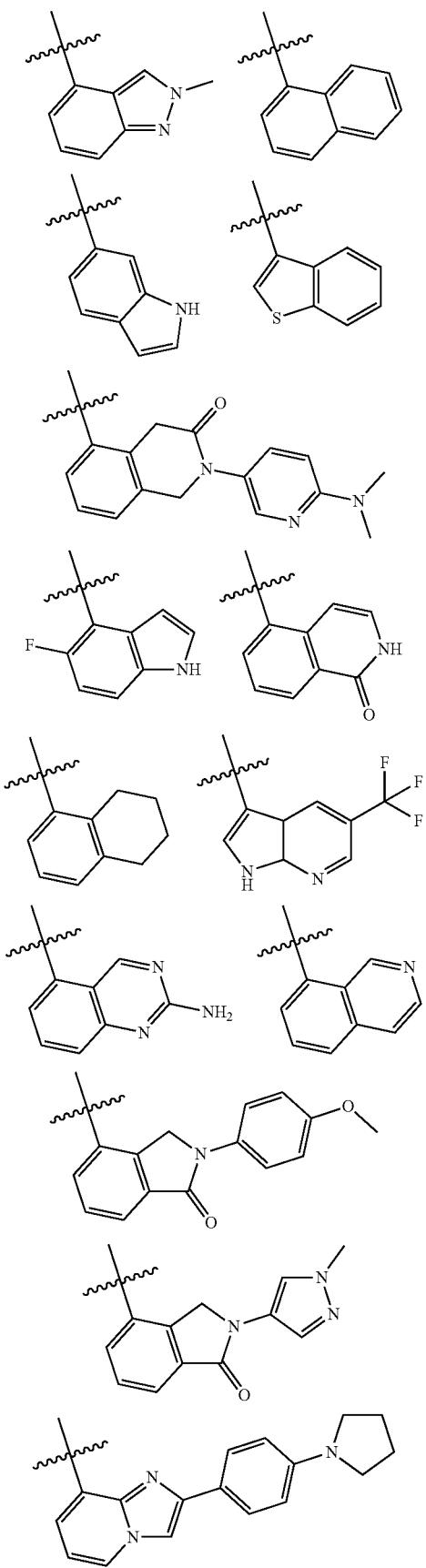

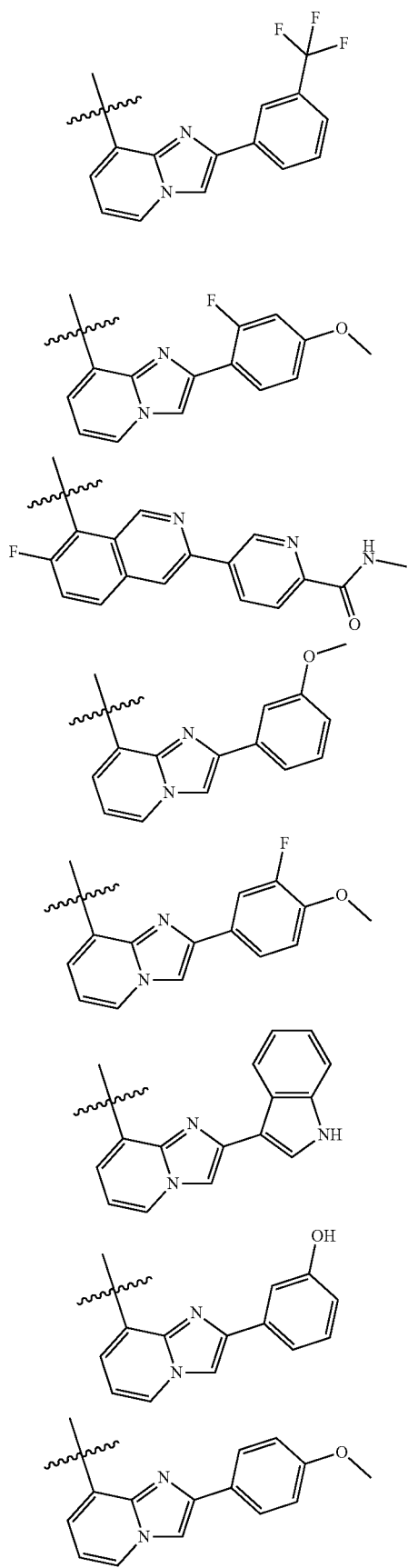
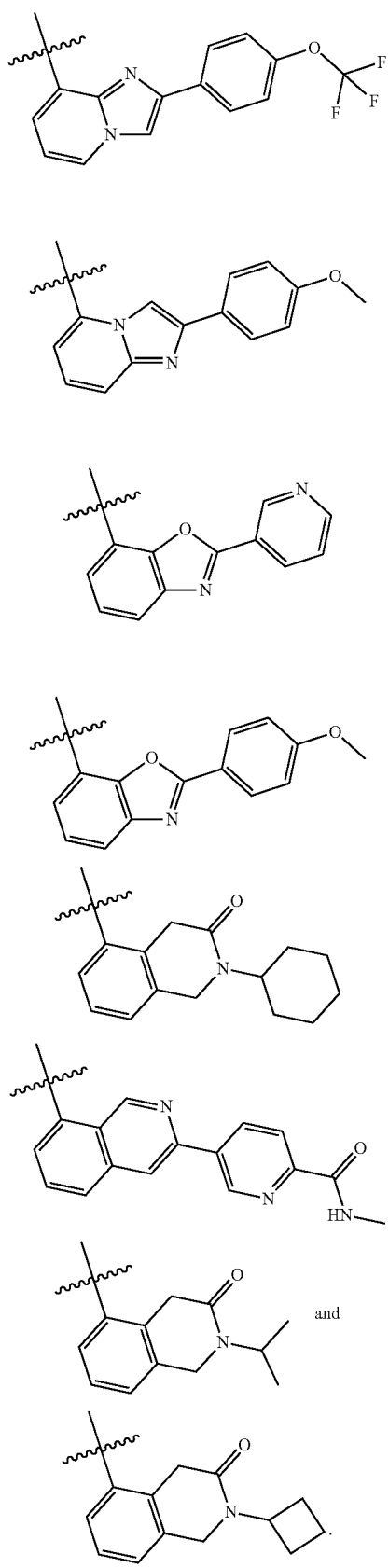

4. The compound or salt of claim 1 wherein Y is selected from the group consisting of:
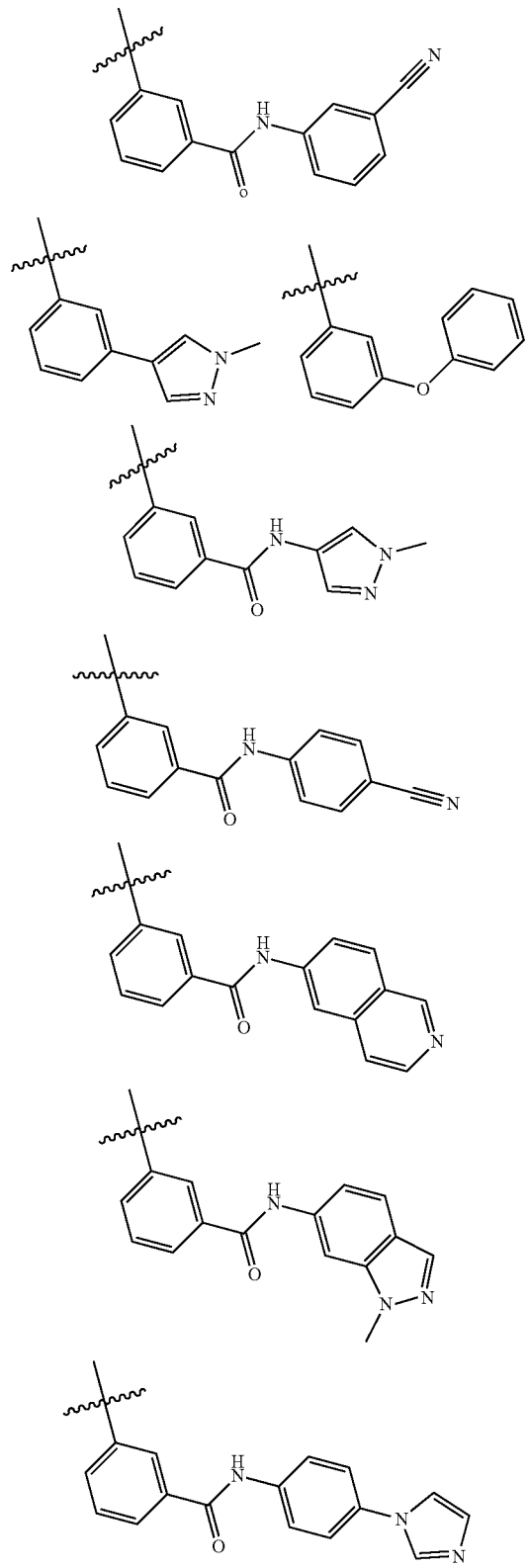
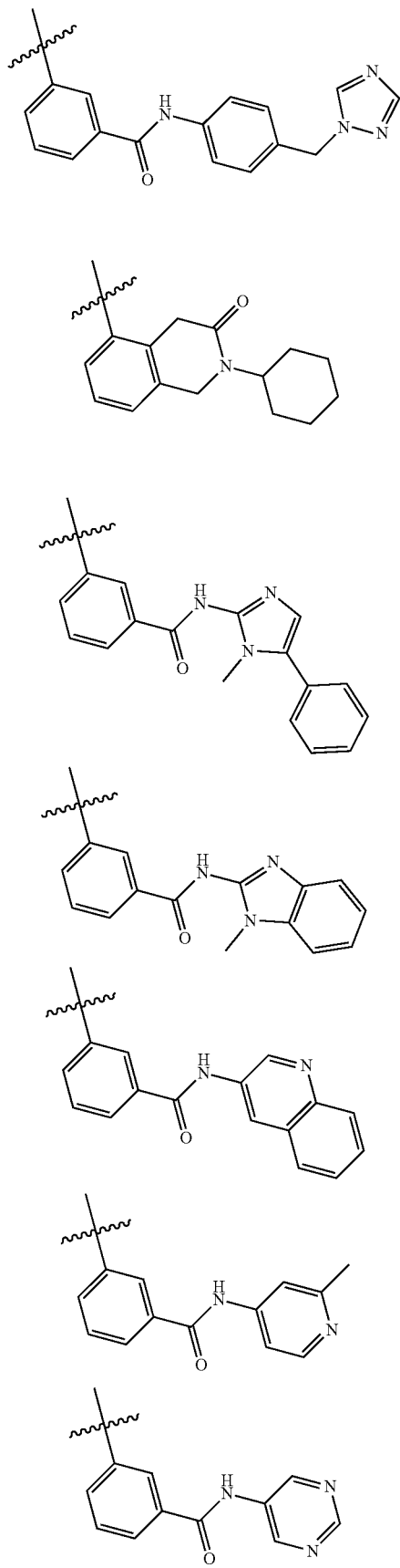

489
-continued
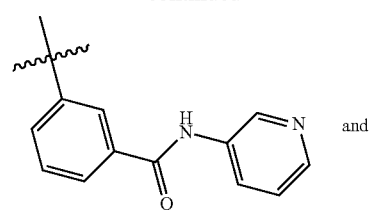
and
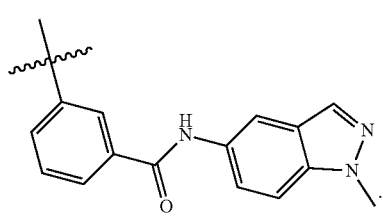
5. A compound or salt thereof selected from the group consisting of:
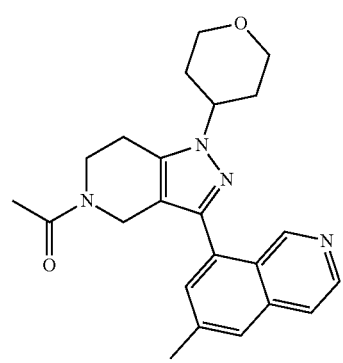 [SMILES: CC(=O)N1CCc2c(c(-c3cc(C)cc4ccncc34)nn2C2CCOCC2)C1]
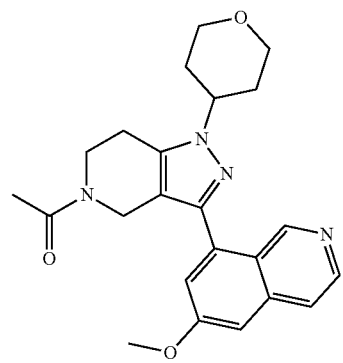 [SMILES: COc1cc(-c2nn(C3CCOCC3)c3c2CN(C(C)=O)CC3)c2cnccc2c1]
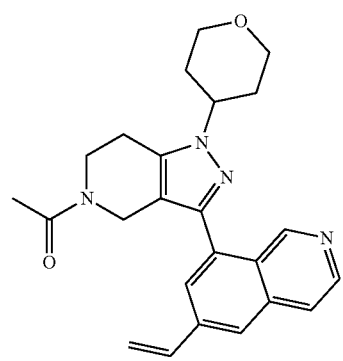 [SMILES: C=Cc1cc(-c2nn(C3CCOCC3)c3c2CN(C(C)=O)CC3)c2cnccc2c1]
490
-continued
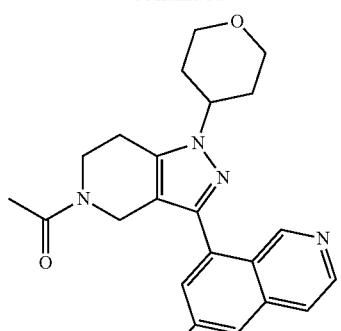
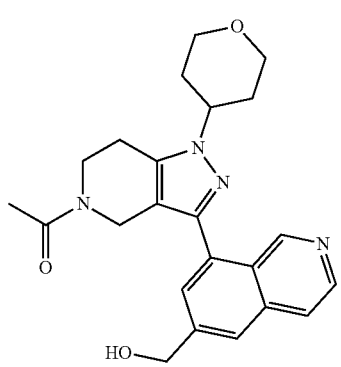 [SMILES: CC(=O)N1CCc2c(c(-c3cc(CO)cc4ccncc34)nn2C2CCOCC2)C1]
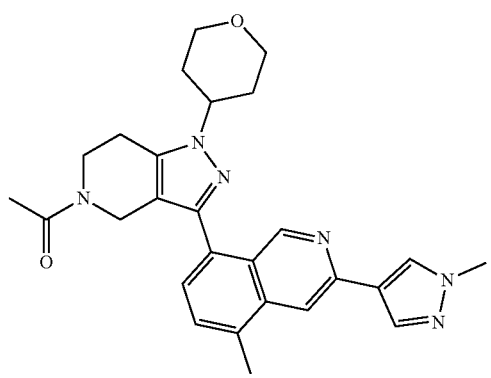 [SMILES: CC(=O)N1CCc2c(c(-c3ccc(C)c4cc(-c5cnn(C)c5)ncc34)nn2C2CCOCC2)C1]
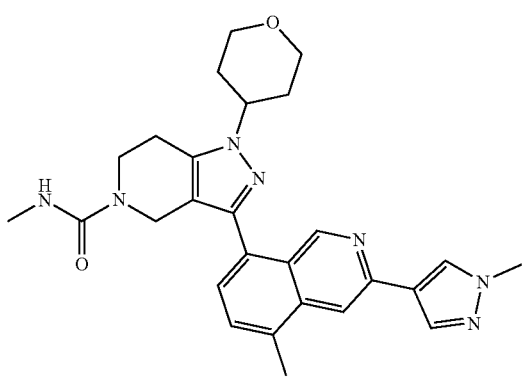

491
-continued
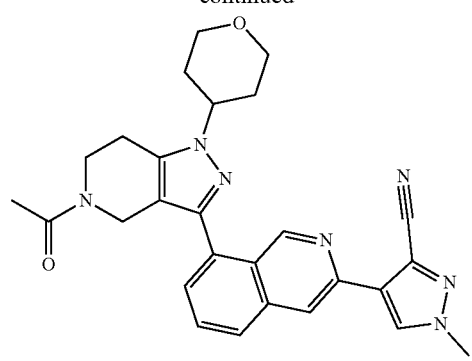
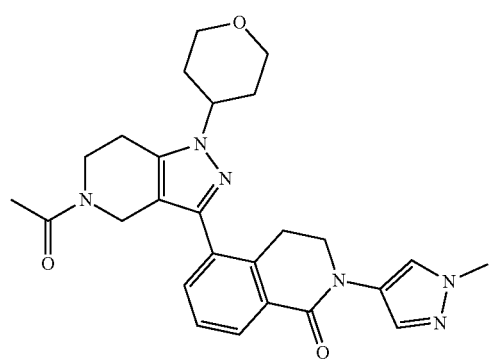 [SMILES: CC(=O)N1CCc2c(c(-c3cccc4c3CCN(c3cnn(C)c3)C4=O)nn2C2CCOCC2)C1]
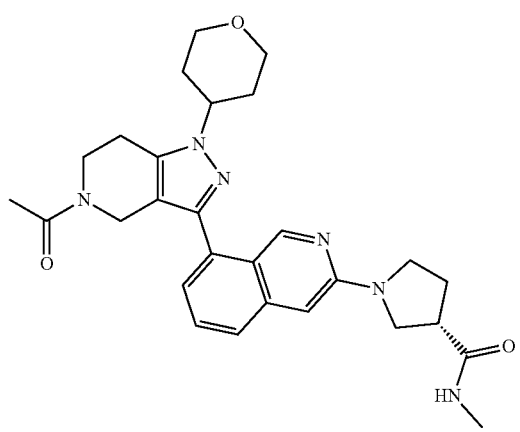 [SMILES: CNC(=O)[C@H]1CCN(c2cc3cccc(-c4nn(C5CCOCC5)c5c4CN(C(C)=O)CC5)c3cn2)C1]
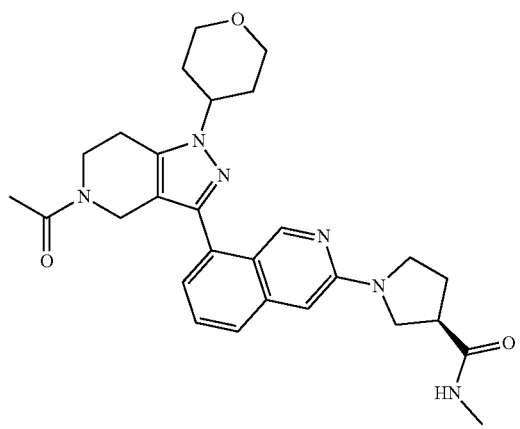 [SMILES: CNC(=O)[C@@H]1CCN(c2cc3cccc(-c4nn(C5CCOCC5)c5c4CN(C(C)=O)CC5)c3cn2)C1]
492
-continued
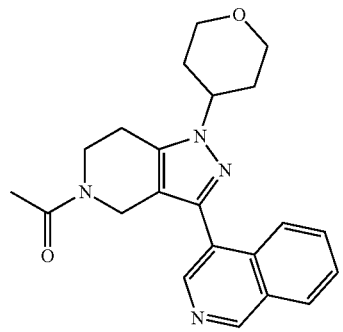 [SMILES: CC(=O)N1CCc2c(c(-c3cncc4ccccc34)nn2C2CCOCC2)C1]
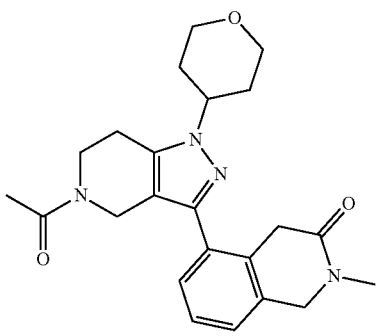 [SMILES: CC(=O)N1CCc2c(c(-c3cccc4c3CC(=O)N(C)C4)nn2C2CCOCC2)C1]
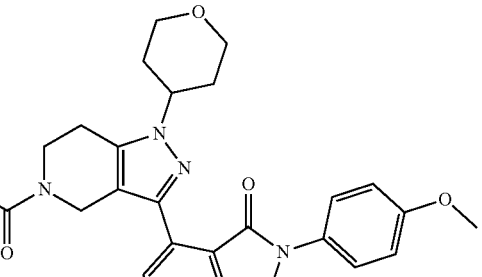
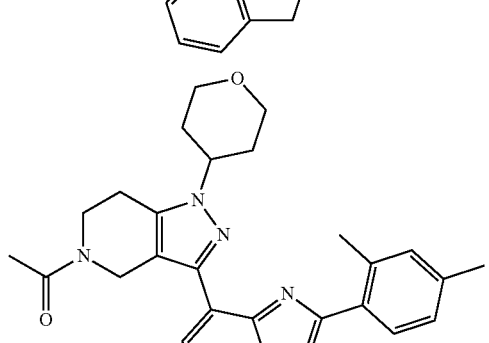
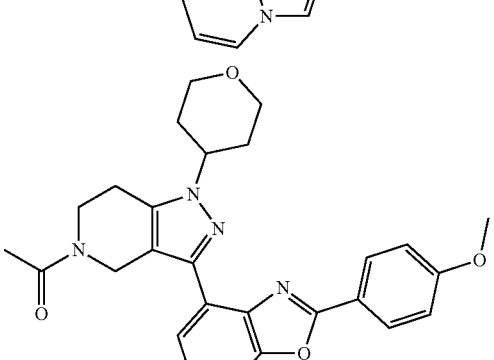

493
-continued
494
-continued
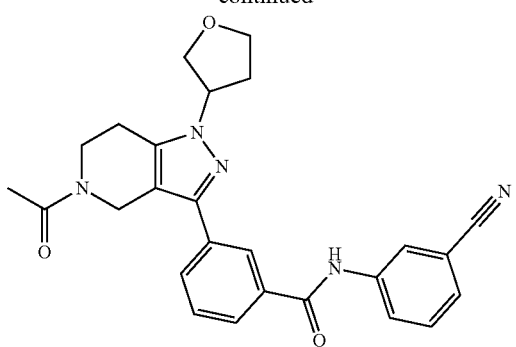
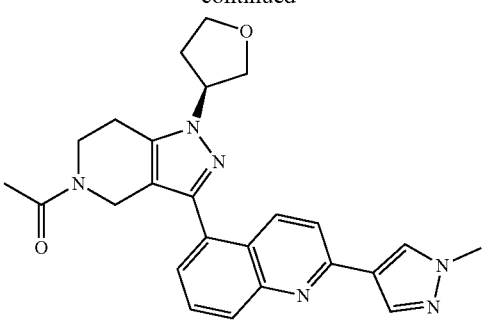
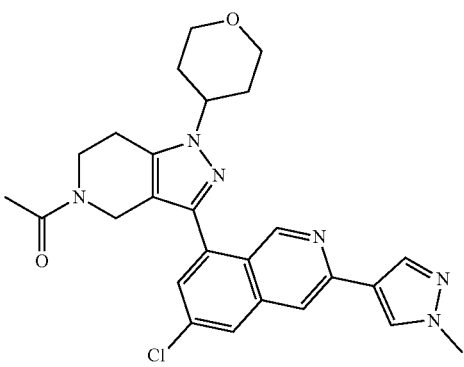 [SMILES: CC(=O)N1CCc2c(c(-c3cc(Cl)cc4cc(-c5cnn(C)c5)ncc34)nn2C2CCOCC2)C1]

495
-continued
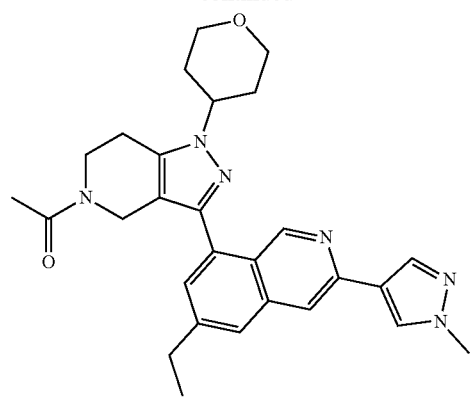 [SMILES: CCc1cc(-c2nn(C3CCOCC3)c3c2CN(C(C)=O)CC3)c2cnc(-c3cnn(C)c3)cc2c1]
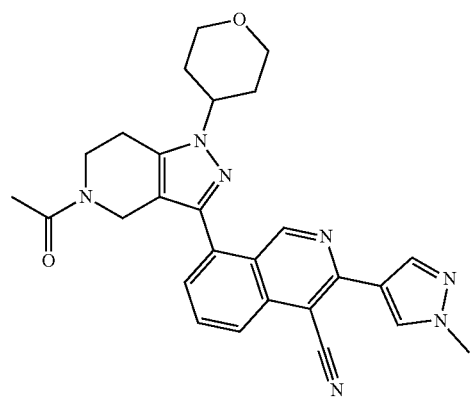 [SMILES: CC(=O)N1CCc2c(c(-c3cccc4c(C#N)c(-c5cnn(C)c5)ncc34)nn2C2CCOCC2)C1]
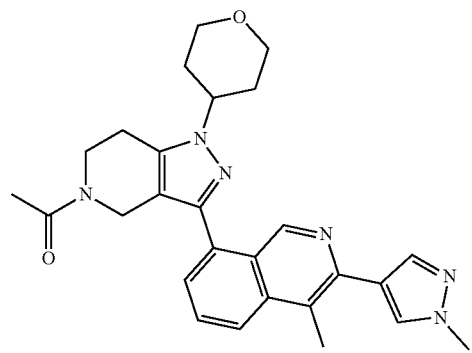 [SMILES: CC(=O)N1CCc2c(c(-c3cccc4c(C)c(-c5cnn(C)c5)ncc34)nn2C2CCOCC2)C1]
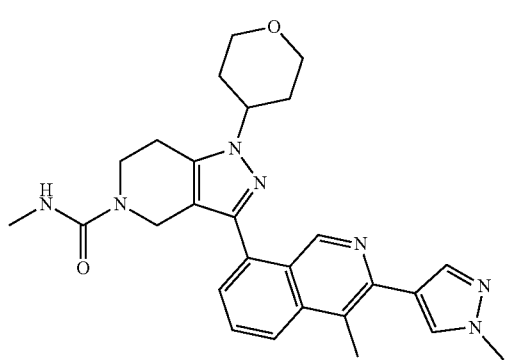
496
-continued
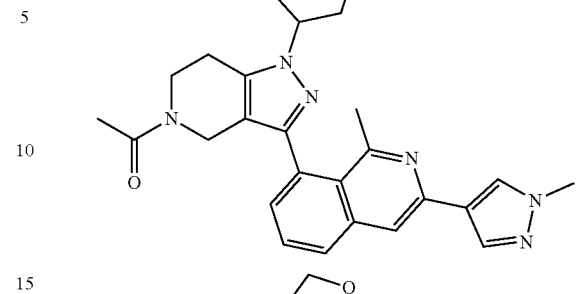
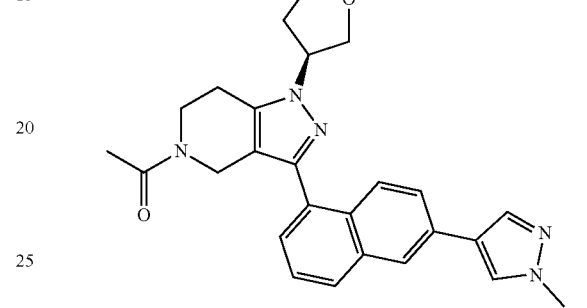
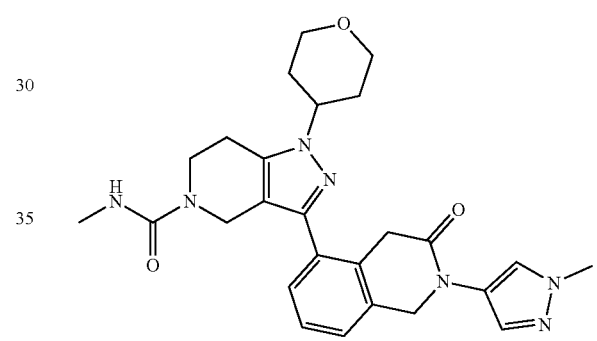
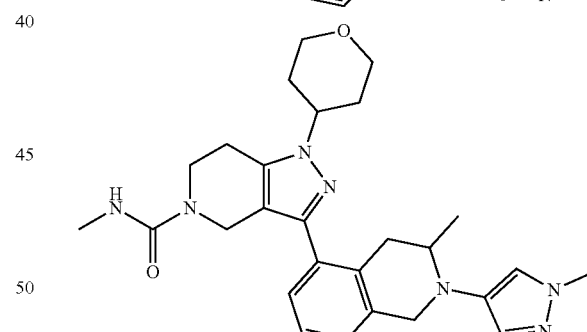
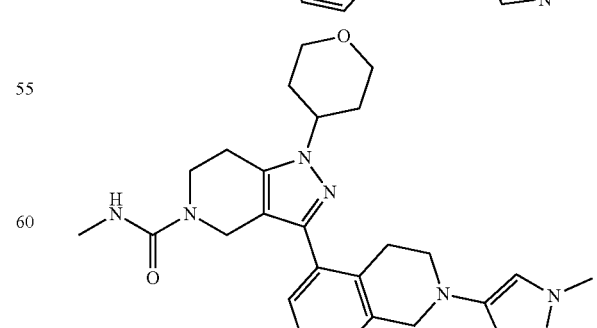

497
-continued
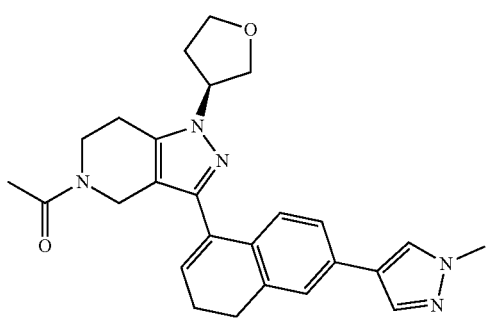 [SMILES: CC(=O)N1CCc2c(c(C3=CCCc4cc(-c5cnn(C)c5)ccc43)nn2[C@H]2CCOC2)C1]
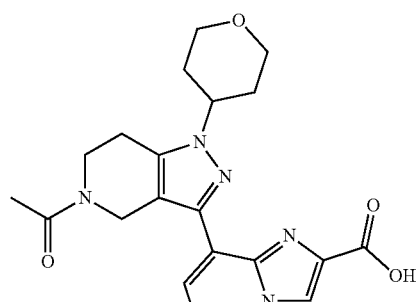
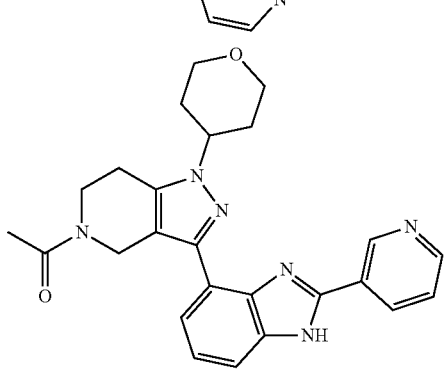
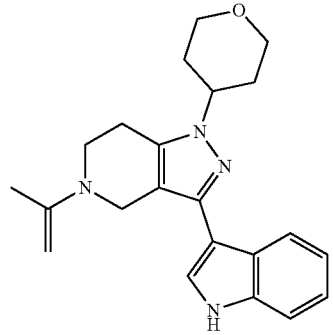 [SMILES: CC(=O)N1CCc2c(c(-c3c[nH]c4ccccc34)nn2C2CCOCC2)C1]
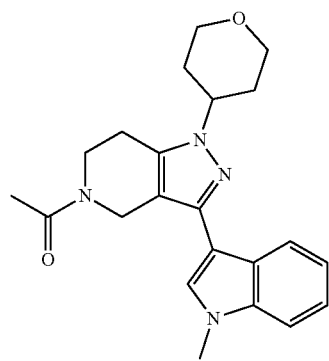 [SMILES: CC(=O)N1CCc2c(c(-c3cn(C)c4ccccc34)nn2C2CCOCC2)C1]
498
-continued
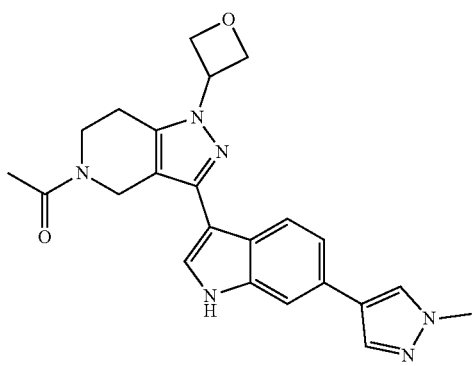 [SMILES: CC(=O)N1CCc2c(c(-c3c[nH]c4cc(-c5cnn(C)c5)ccc34)nn2C2COC2)C1]
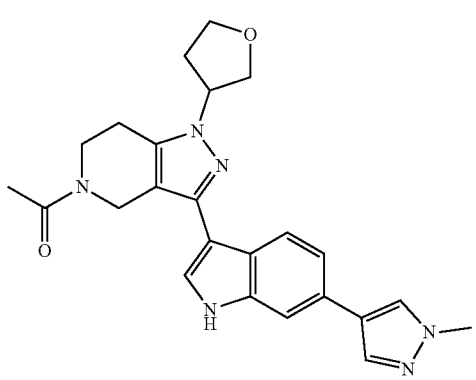 [SMILES: CC(=O)N1CCc2c(c(-c3c[nH]c4cc(-c5cnn(C)c5)ccc34)nn2C2CCOC2)C1]
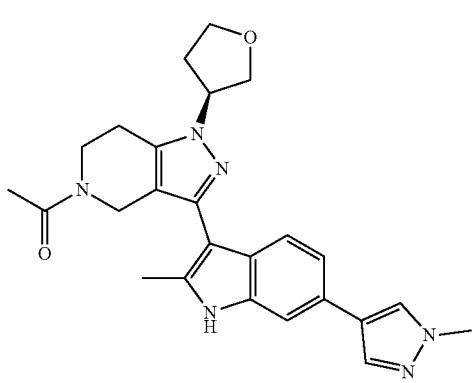 [SMILES: CC(=O)N1CCc2c(c(-c3c(C)[nH]c4cc(-c5cnn(C)c5)ccc34)nn2[C@H]2CCOC2)C1]
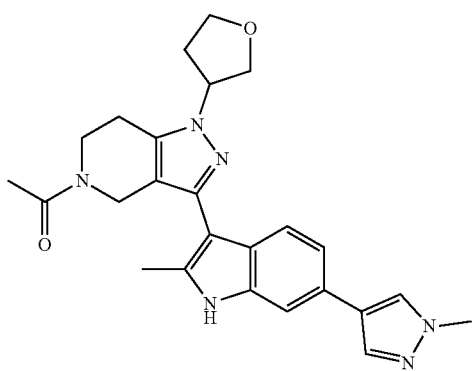 [SMILES: CC(=O)N1CCc2c(c(-c3c(C)[nH]c4cc(-c5cnn(C)c5)ccc34)nn2C2CCOC2)C1]

US 11,247,989 B2

499
-continued

500
-continued

| 501 -continued | 502 -continued |
|---|---|
| 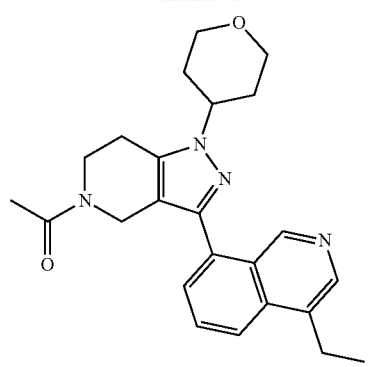 [SMILES: CCc1cncc2c(-c3nn(C4CCOCC4)c4c3CN(C(C)=O)CC4)cccc12] | 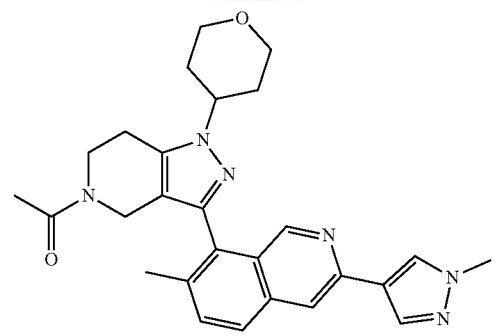 |
| 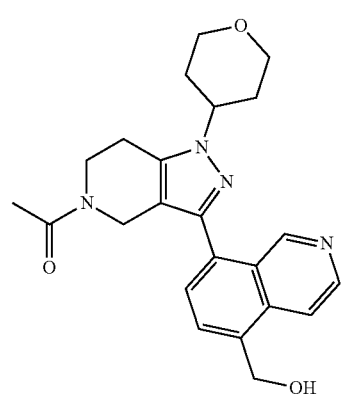 [SMILES: CC(=O)N1CCc2c(c(-c3ccc(CO)c4ccncc34)nn2C2CCOCC2)C1] | 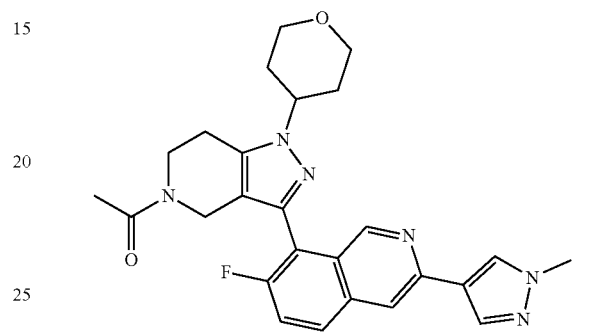 |
| 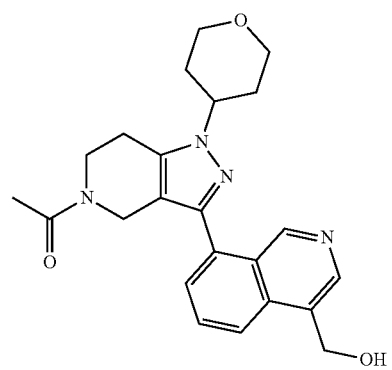 [SMILES: CC(=O)N1CCc2c(c(-c3cccc4c(CO)cncc34)nn2C2CCOCC2)C1] | 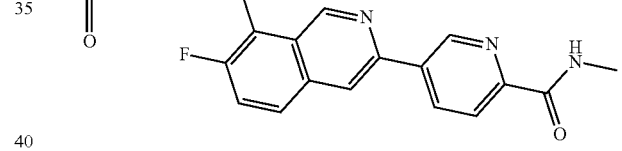 |
| 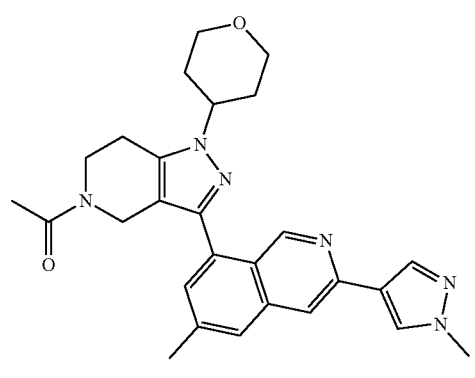 [SMILES: CC(=O)N1CCc2c(c(-c3cc(C)cc4cc(-c5cnn(C)c5)ncc34)nn2C2CCOCC2)C1] | 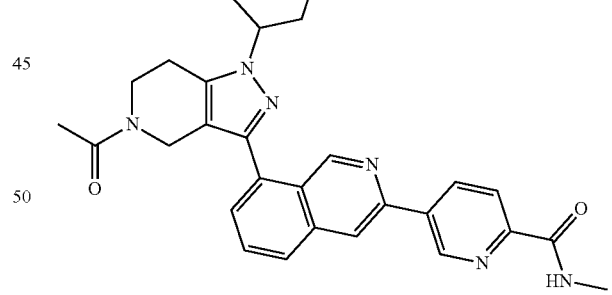 |
|  | 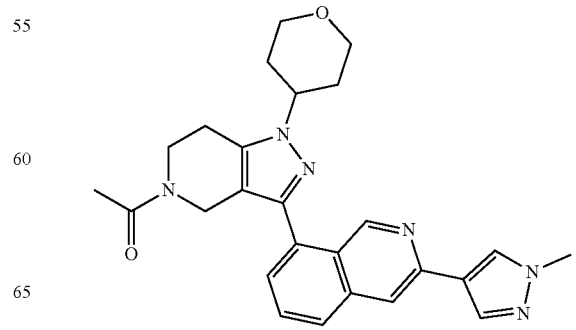 |

503
-continued
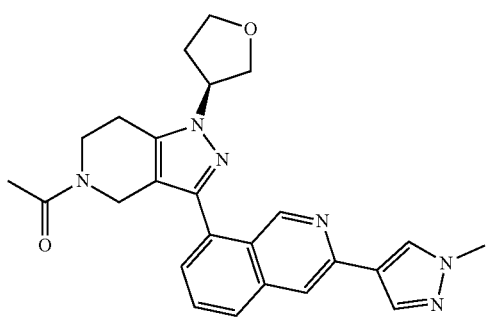 [SMILES: CC(=O)N1CCc2c(c(-c3cccc4cc(-c5cnn(C)c5)ncc34)nn2[C@H]2CCOC2)C1]
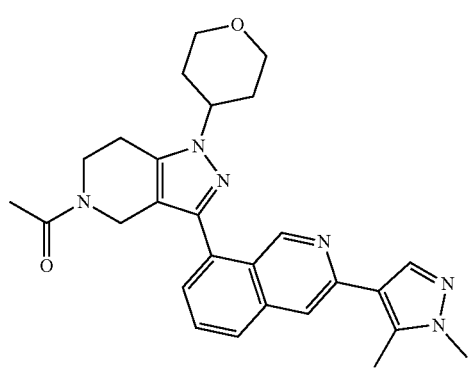 [SMILES: CC(=O)N1CCc2c(c(-c3cccc4cc(-c5cnn(C)c5C)ncc34)nn2C2CCOCC2)C1]
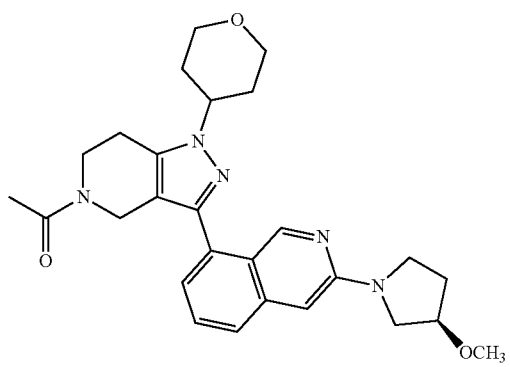 [SMILES: CO[C@@H]1CCN(c2cc3cccc(-c4nn(C5CCOCC5)c5c4CN(C(C)=O)CC5)c3cn2)C1]
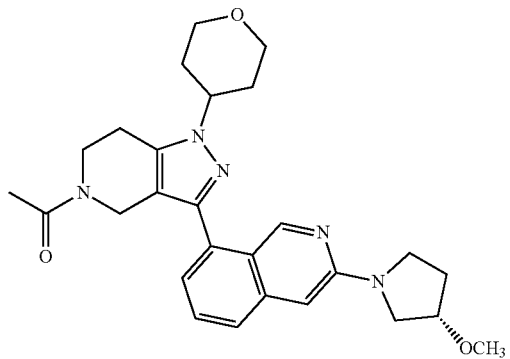 [SMILES: CO[C@H]1CCN(c2cc3cccc(-c4nn(C5CCOCC5)c5c4CN(C(C)=O)CC5)c3cn2)C1]
504
-continued
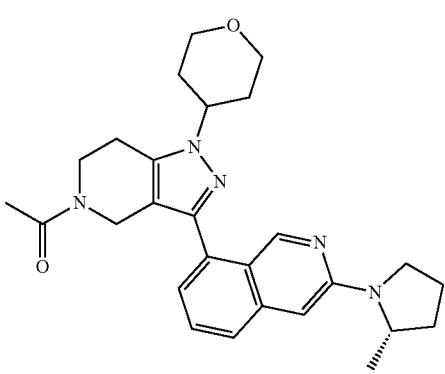 [SMILES: CC(=O)N1CCc2c(c(-c3cccc4cc(N5CCC[C@@H]5C)ncc34)nn2C2CCOCC2)C1]
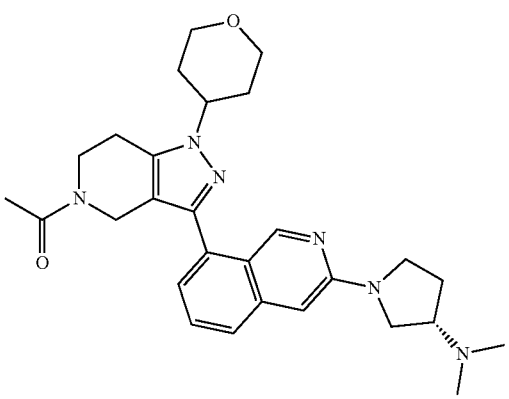 [SMILES: CC(=O)N1CCc2c(c(-c3cccc4cc(N5CC[C@H](N(C)C)C5)ncc34)nn2C2CCOCC2)C1]

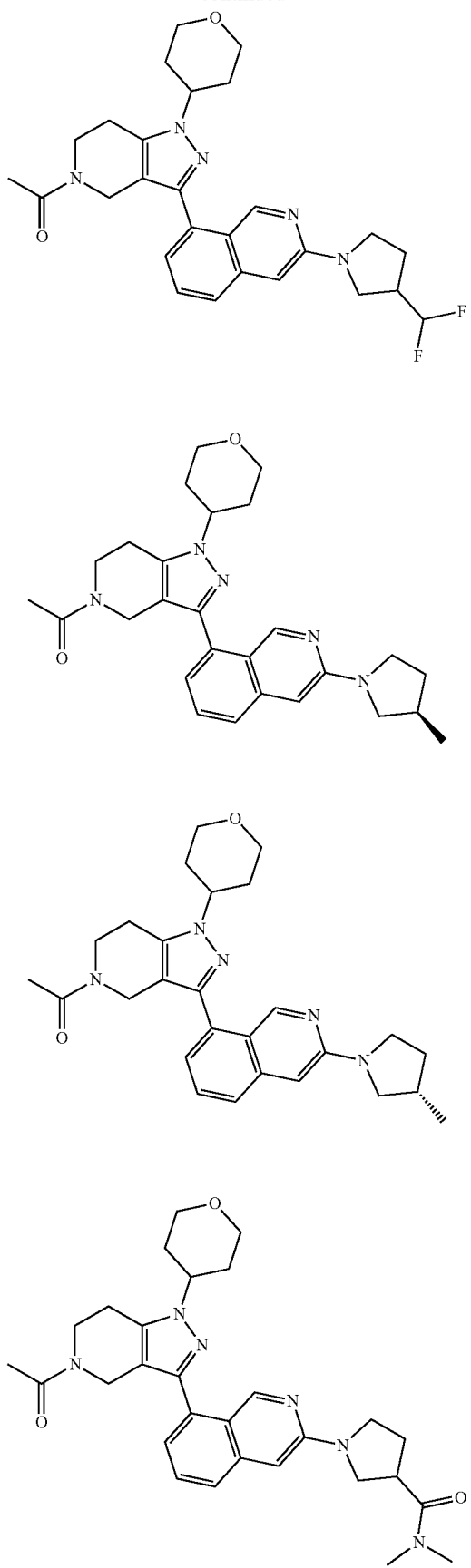
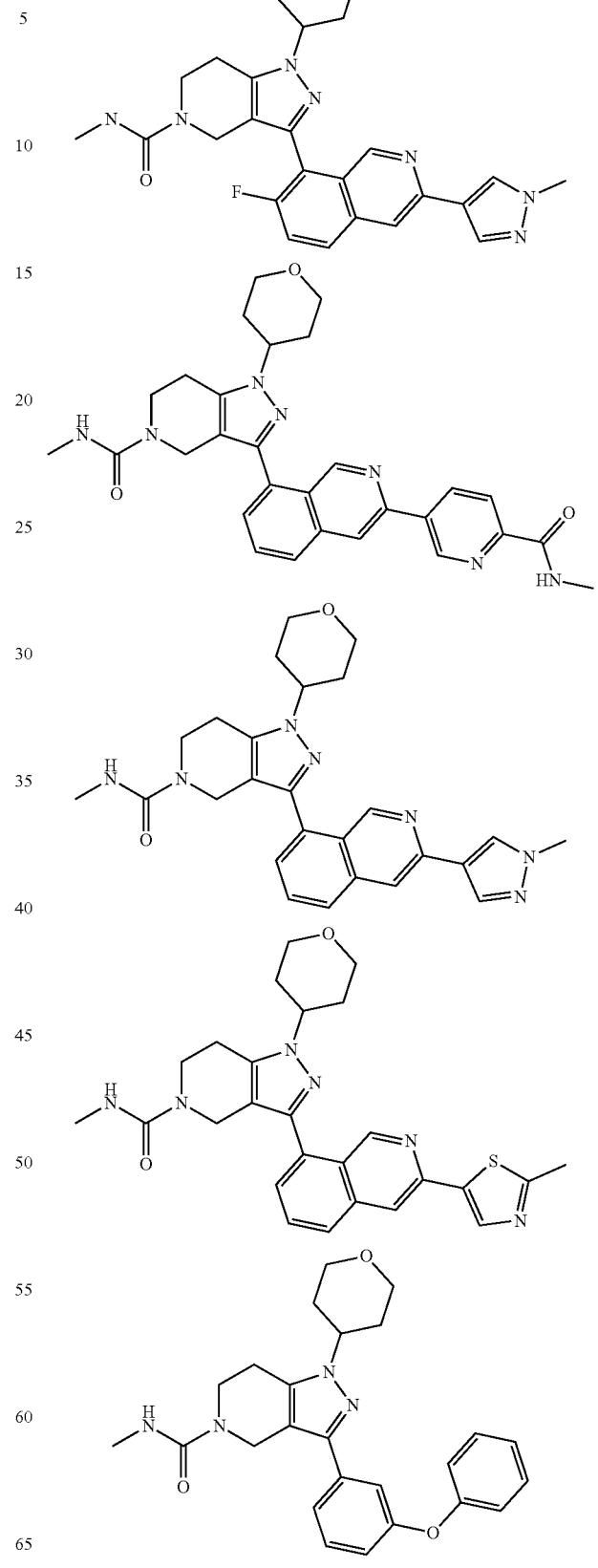

507
-continued
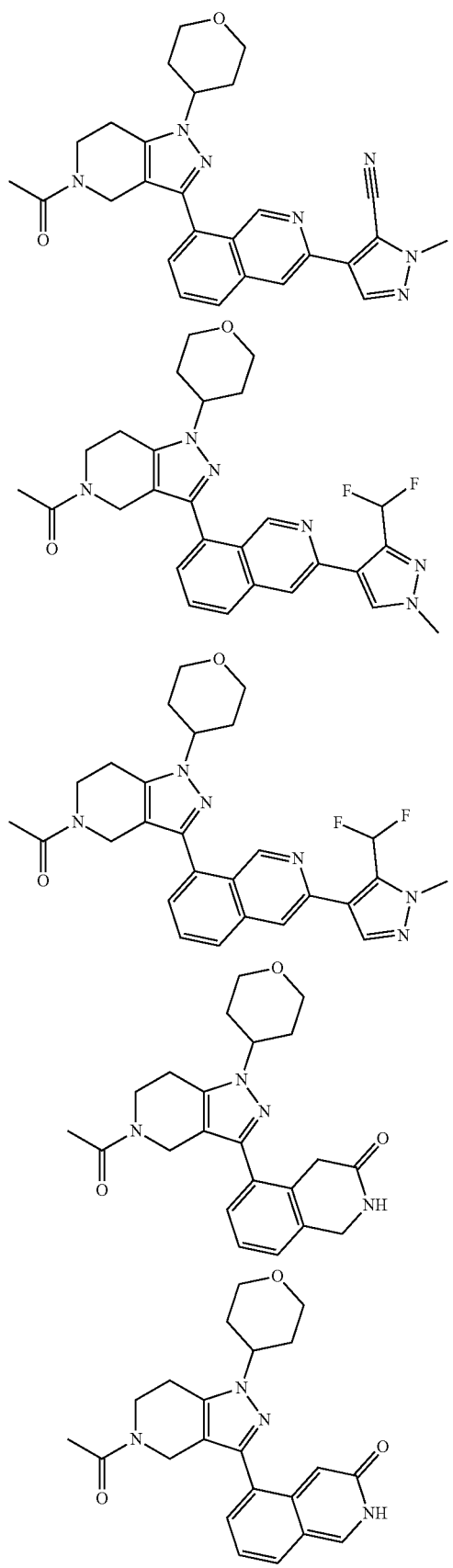
508
-continued
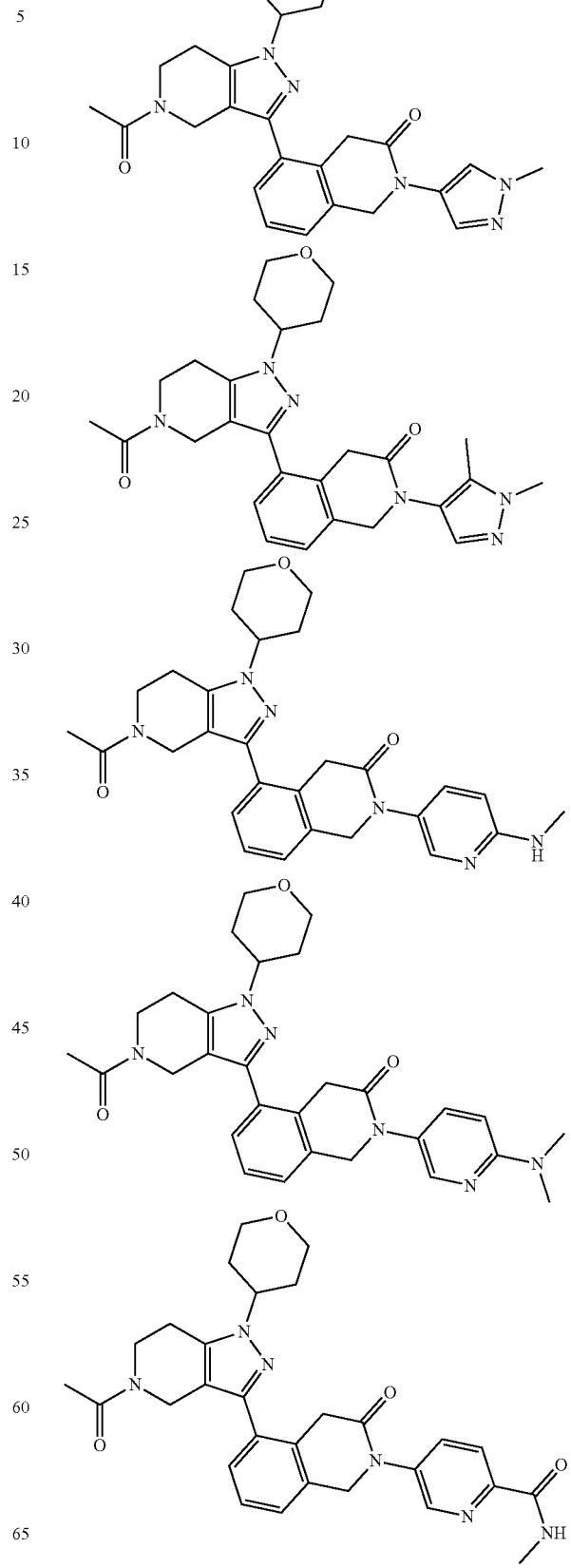

509
-continued
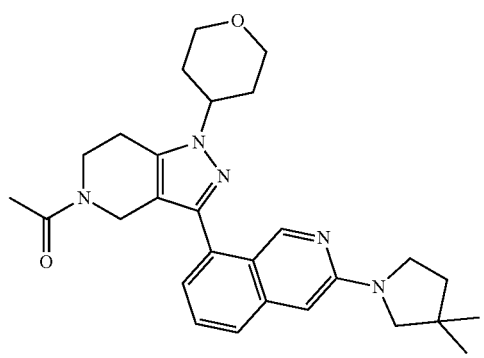 [SMILES: CC(=O)N1CCc2c(c(-c3cccc4cc(N5CCC(C)(C)C5)ncc34)nn2C2CCOCC2)C1]
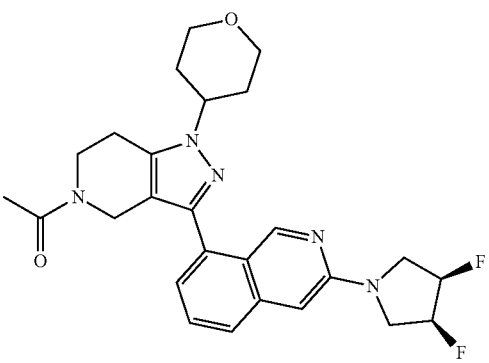 [SMILES: CC(=O)N1CCc2c(c(-c3cccc4cc(N5C[C@@H](F)[C@@H](F)C5)ncc34)nn2C2CCOCC2)C1]
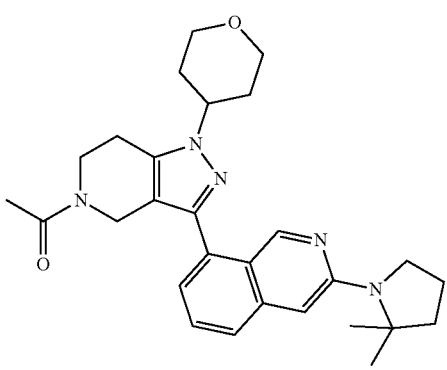 [SMILES: CC(=O)N1CCc2c(c(-c3cccc4cc(N5CCCC5(C)C)ncc34)nn2C2CCOCC2)C1]
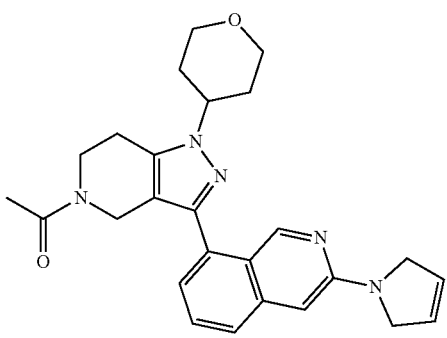 [SMILES: CC(=O)N1CCc2c(c(-c3cccc4cc(N5CC=CC5)ncc34)nn2C2CCOCC2)C1]
510
-continued
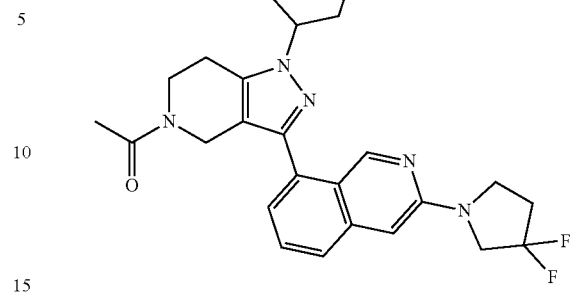
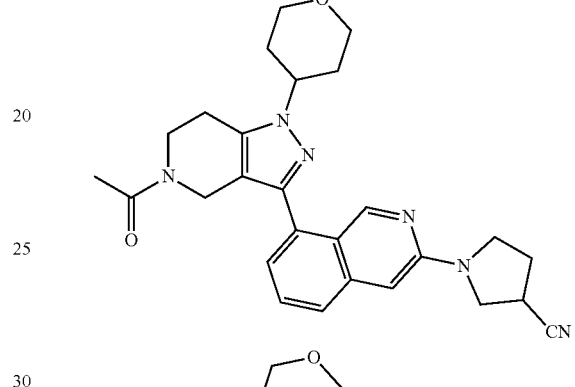
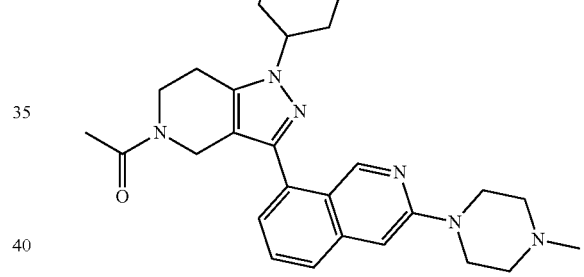
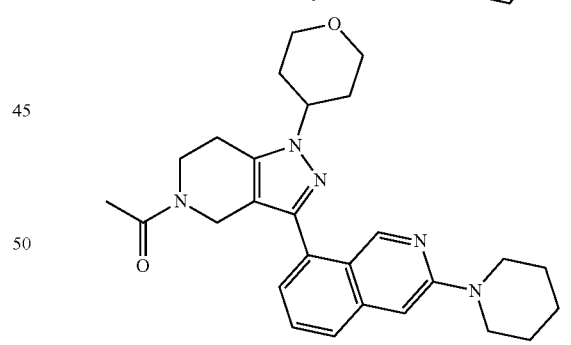
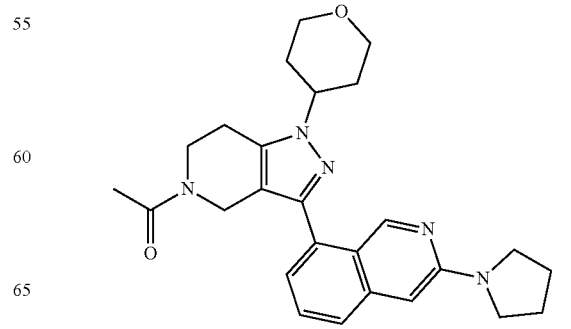

511
-continued
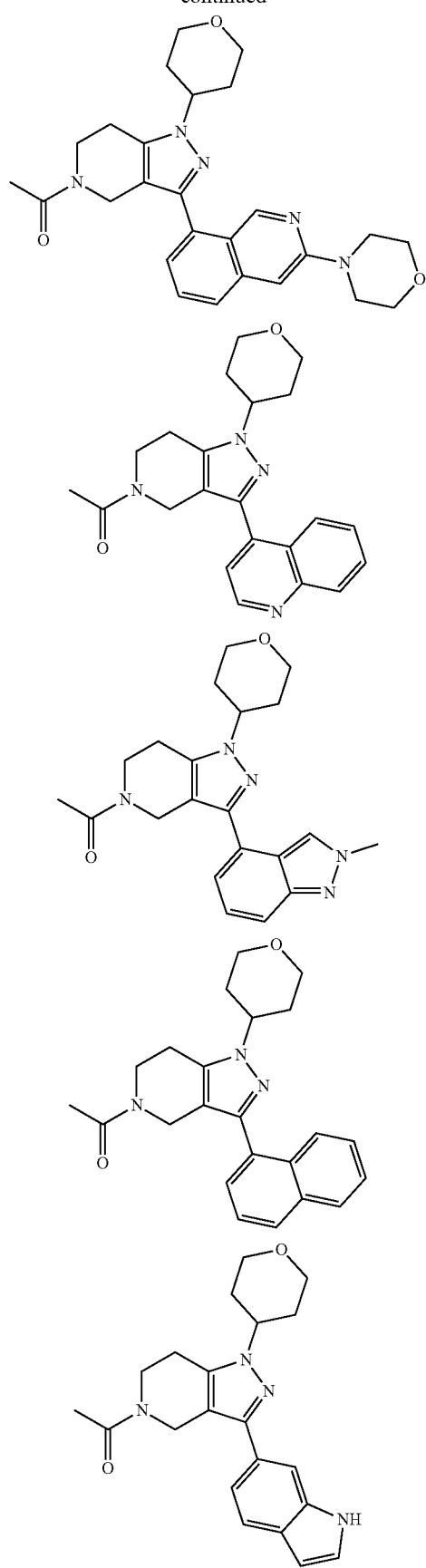
512
-continued
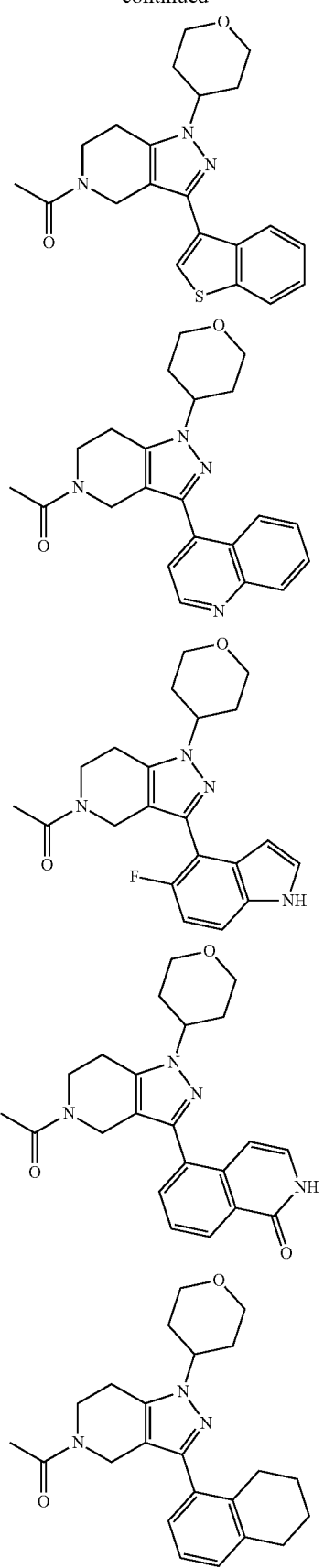

513
-continued
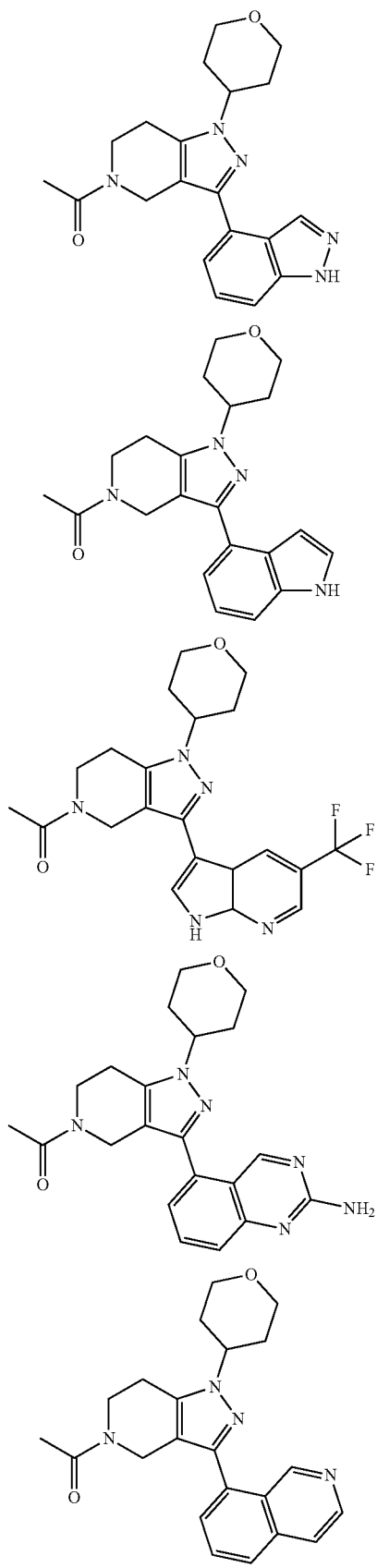
514
-continued
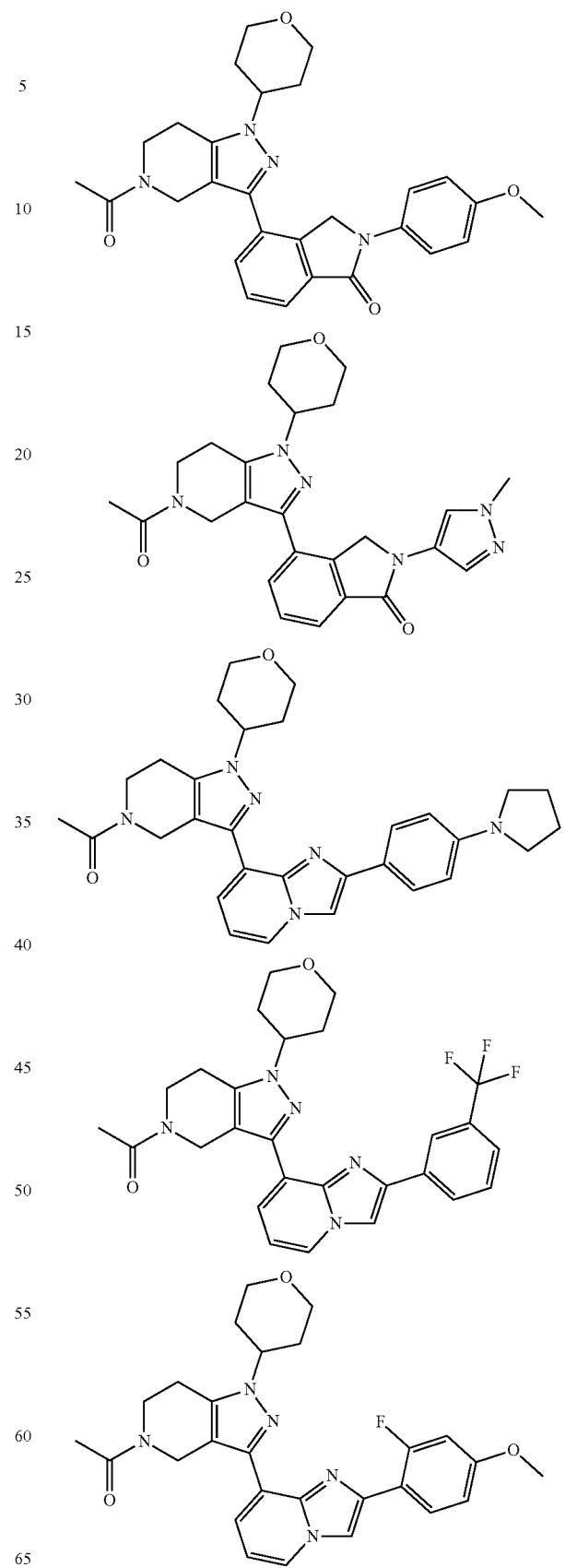

515
-continued
516
-continued
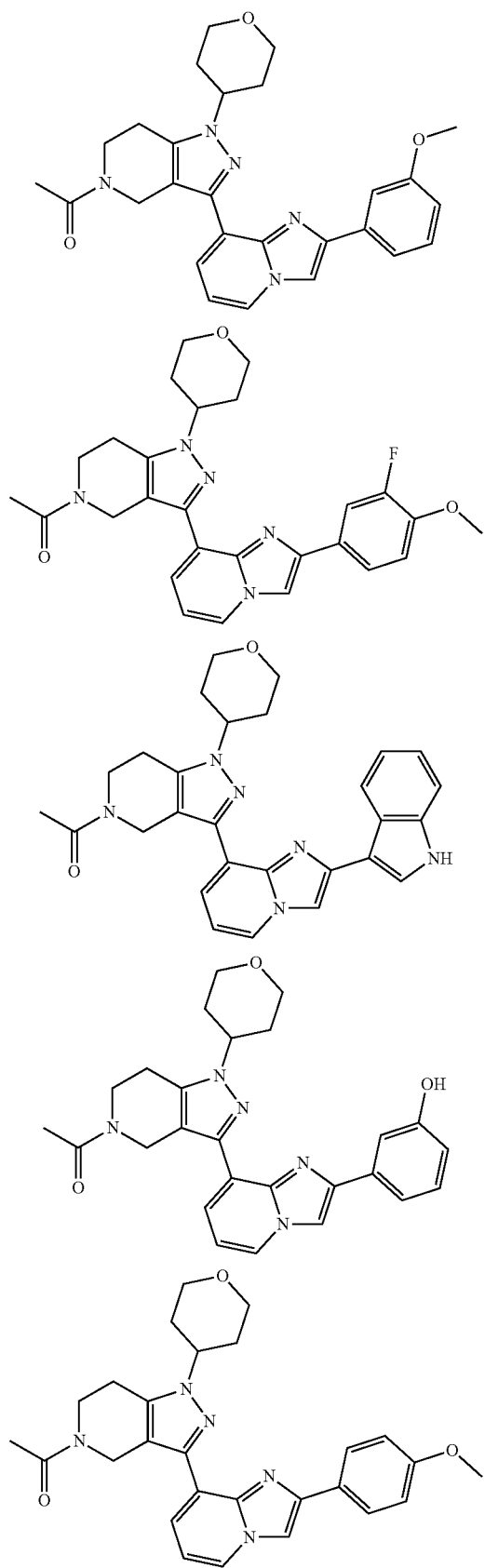
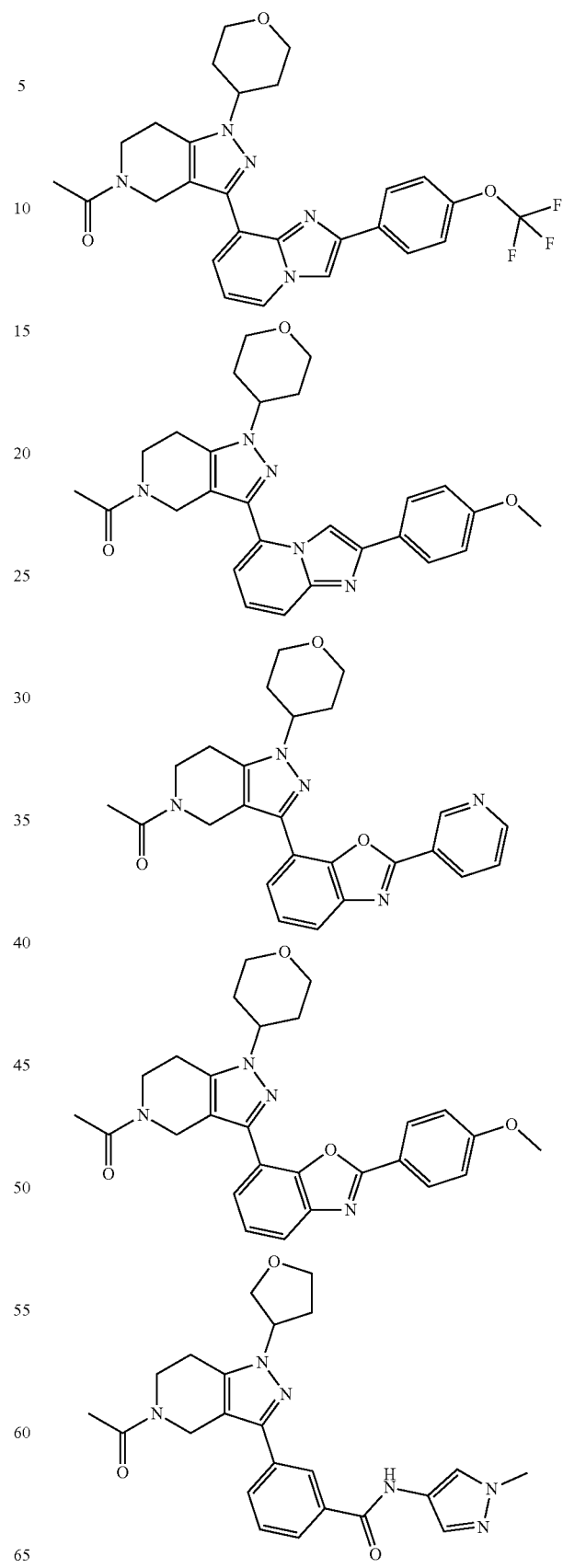

517
-continued
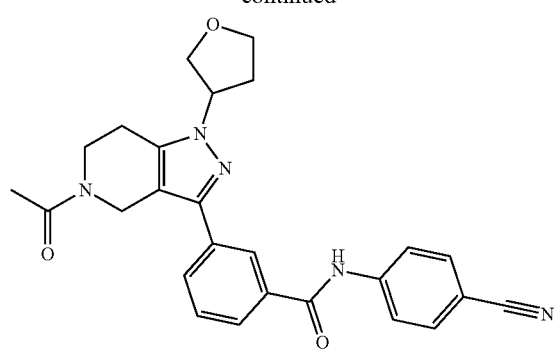
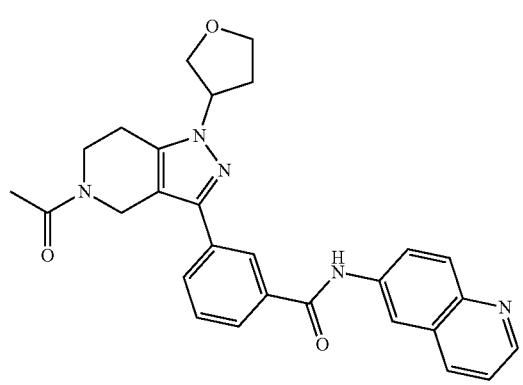 [SMILES: CC(=O)N1CCc2c(c(-c3cccc(C(=O)Nc4ccc5ncccc5c4)c3)nn2C2CCOC2)C1]
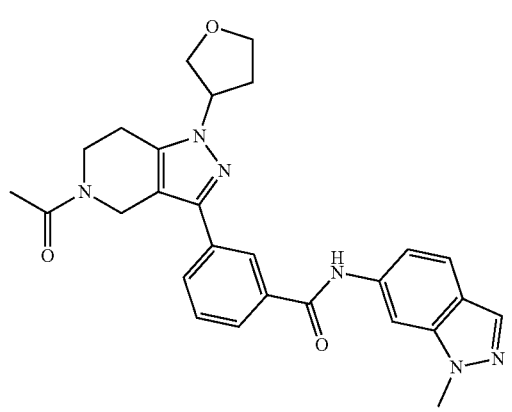 [SMILES: CC(=O)N1CCc2c(c(-c3cccc(C(=O)Nc4ccc5cnn(C)c5c4)c3)nn2C2CCOC2)C1]
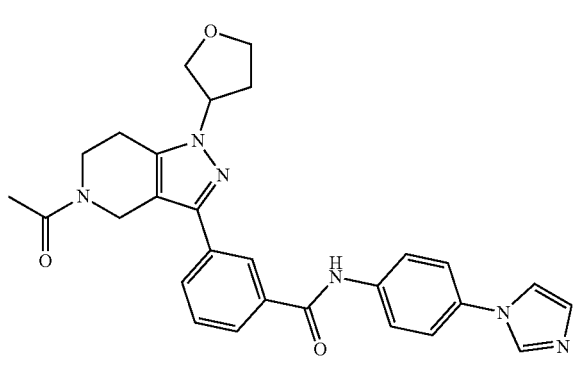 [SMILES: CC(=O)N1CCc2c(c(-c3cccc(C(=O)Nc4ccc(-n5ccnc5)cc4)c3)nn2C2CCOC2)C1]
518
-continued
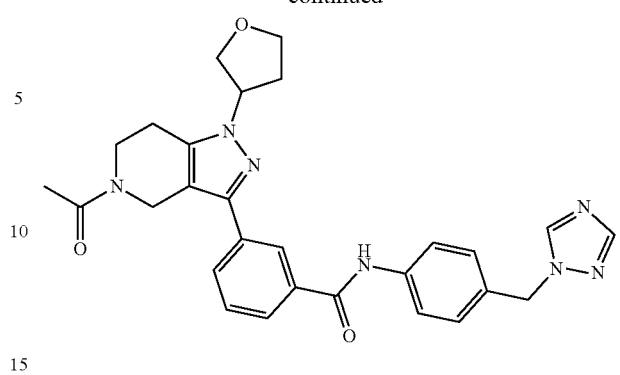
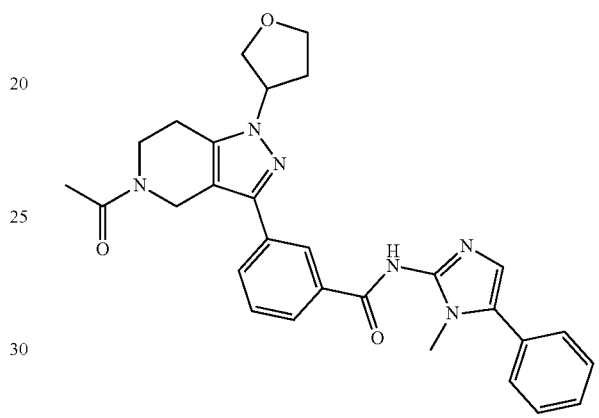
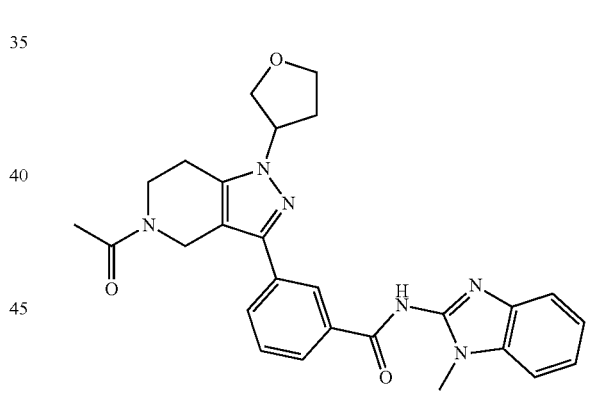
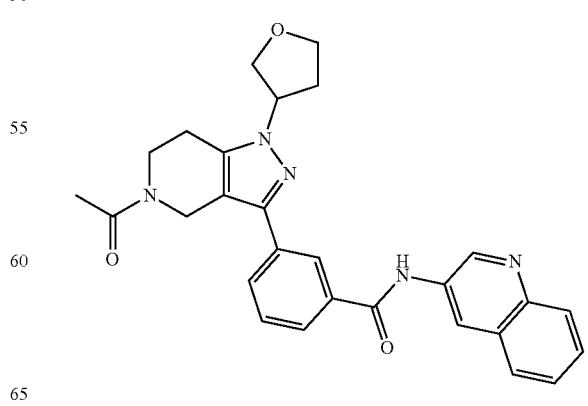

519
-continued

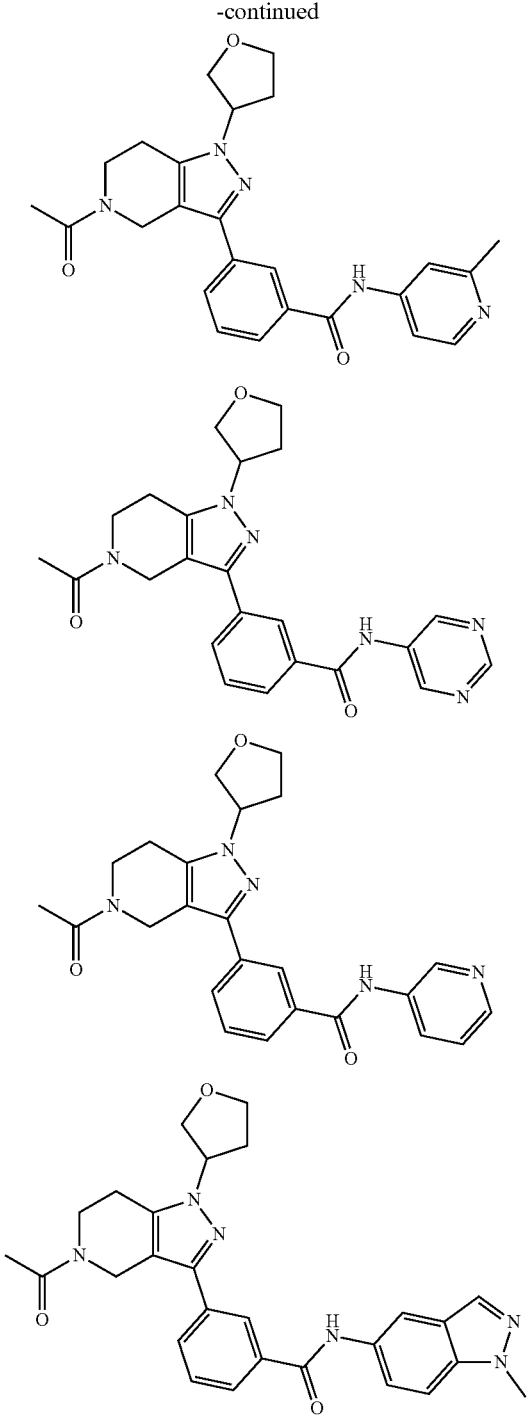

520
-continued

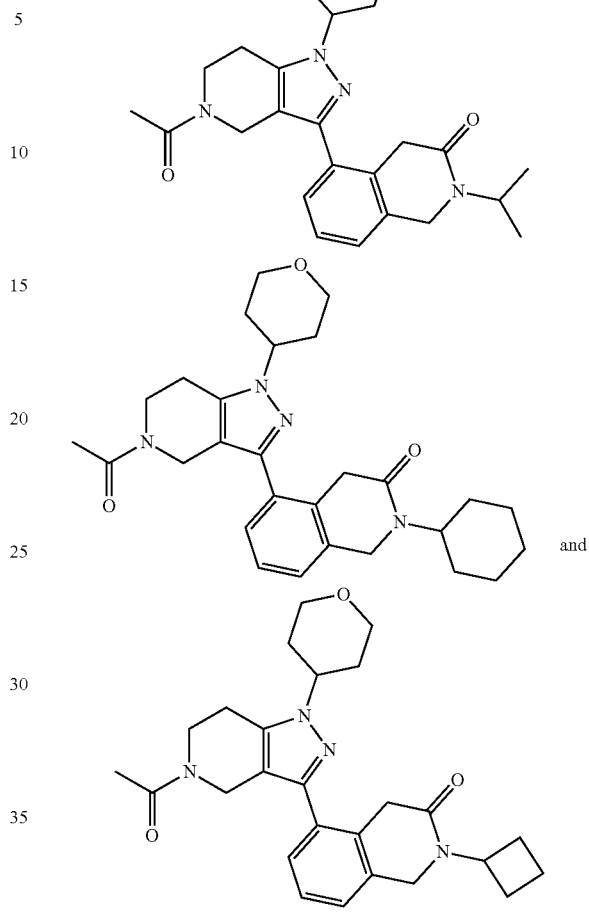

or a salt thereof.

6. A composition comprising a compound as described in claim 1 or a pharmaceutically acceptable salt thereof, and a pharmaceutically acceptable adjuvant, carrier, or vehicle.

7. A method for treating a CBP and/or EP300-mediated cancer in an animal by selectively inhibiting a bromodomain of the CBP and/or EP300 in the animal, comprising administering an effective amount of a compound or a pharmaceutically acceptable salt thereof, as described in claim 1, to the animal, wherein the animal has a mutation in the CBP and/or EP300, and wherein the cancer is selected from lung cancer, breast cancer, pancreatic cancer, colorectal cancer, or melanoma.

8. A composition comprising a compound as described in claim 5 or a pharmaceutically acceptable salt thereof, and a pharmaceutically acceptable adjuvant, carrier, or vehicle.

* * * * *

UNITED STATES PATENT AND TRADEMARK OFFICE
CERTIFICATE OF CORRECTION

PATENT NO. : 11,247,989 B2  
APPLICATION NO. : 16/198581  
DATED : February 15, 2022  
INVENTOR(S) : Patrick Cyr et al.

Page 1 of 1

It is certified that error appears in the above-identified patent and that said Letters Patent is hereby corrected as shown below:

In the Claims

Column 487, Lines 36-46, Claim 4, please delete "

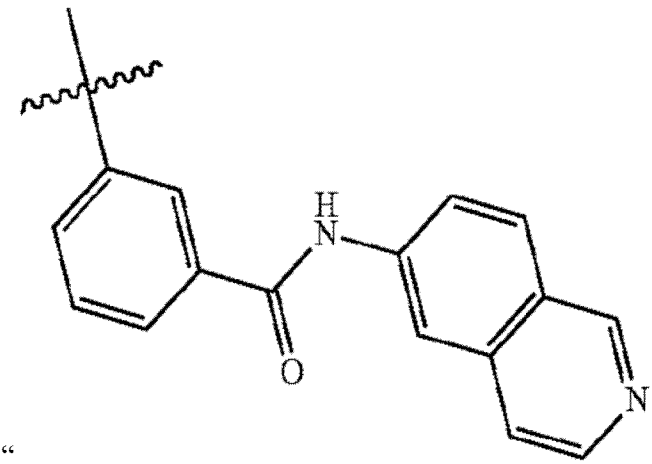

" and insert

--

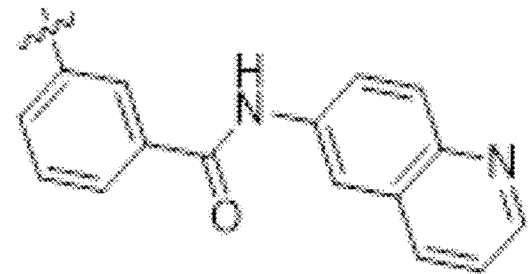

-- therefor.

Signed and Sealed this  
Second Day of August, 2022

Katherine Kelly Vidal  
*Director of the United States Patent and Trademark Office*